US012187720B2

(12) United States Patent
Li et al.

(10) Patent No.: US 12,187,720 B2
(45) Date of Patent: Jan. 7, 2025

(54) COMPOUNDS FOR TREATMENT OF CANCER

(71) Applicants: ONCTERNAL THERAPEUTICS, INC., San Diego, CA (US); UNIVERSITY OF TENNESSEE RESEARCH FOUNDATION, Knoxville, TN (US)

(72) Inventors: Wei Li, Germantown, TN (US); Duane D Miller, Collierville, TN (US); Kinsie E. Arnst, Gulf Breeze, FL (US); Dong-Jin Hwang, Arlington, TN (US)

(73) Assignee: UNIVERSITY OF TENNESSEE RESEARCH FOUNDATION, Knoxville, TN (US)

( * ) Notice: Subject to any disclaimer, the term of this patent is extended or adjusted under 35 U.S.C. 154(b) by 0 days.

(21) Appl. No.: 17/370,201

(22) Filed: Jul. 8, 2021

(65) Prior Publication Data

US 2022/0024912 A1    Jan. 27, 2022

Related U.S. Application Data

(63) Continuation of application No. 16/281,291, filed on Feb. 21, 2019, now Pat. No. 11,084,811, which is a continuation-in-part of application No. 15/270,359, filed on Sep. 20, 2016, now Pat. No. 11,465,987, which is a continuation of application No. 13/676,650, filed on Nov. 14, 2012, now Pat. No. 9,447,049, which is a continuation-in-part of application No. 13/216,927, filed on Aug. 24, 2011, now Pat. No. 8,822,513, which is a continuation-in-part of application No. 12/981,233, filed on Dec. 29, 2010, now Pat. No. 9,334,242.

(60) Provisional application No. 61/376,675, filed on Aug. 24, 2010, provisional application No. 61/315,790, filed on Mar. 19, 2010, provisional application No. 61/309,360, filed on Mar. 1, 2010.

(51) Int. Cl.
| | | |
|---|---|---|
| *C07D 417/14* | (2006.01) |
| *A61P 35/00* | (2006.01) |
| *C07C 49/786* | (2006.01) |
| *C07D 211/14* | (2006.01) |
| *C07D 213/76* | (2006.01) |
| *C07D 217/04* | (2006.01) |
| *C07D 233/64* | (2006.01) |
| *C07D 277/24* | (2006.01) |
| *C07D 405/06* | (2006.01) |
| *C07D 417/04* | (2006.01) |
| *C07D 417/12* | (2006.01) |

(52) U.S. Cl.
CPC ............ *C07D 417/14* (2013.01); *A61P 35/00* (2018.01); *C07C 49/786* (2013.01); *C07D 211/14* (2013.01); *C07D 213/76* (2013.01); *C07D 217/04* (2013.01); *C07D 233/64* (2013.01); *C07D 277/24* (2013.01); *C07D 405/06* (2013.01); *C07D 417/04* (2013.01); *C07D 417/12* (2013.01)

(58) Field of Classification Search
None
See application file for complete search history.

(56) References Cited

U.S. PATENT DOCUMENTS

| | | |
|---|---|---|
| 4,814,470 A | 3/1989 | Colin et al. |
| 5,362,334 A | 11/1994 | Adams |
| 6,706,717 B2 | 3/2004 | Barrish et al. |
| 7,538,113 B2 | 5/2009 | Pelletier |
| 7,863,288 B2 | 1/2011 | Ibrahim et al. |
| 8,592,465 B2 | 11/2013 | Miller et al. |
| 8,822,513 B2 | 9/2014 | Lu et al. |
| 9,029,408 B2 | 5/2015 | Miller et al. |
| 9,334,242 B2 | 5/2016 | Lu et al. |
| 9,447,049 B2 | 9/2016 | Li et al. |
| 10,022,356 B2 | 7/2018 | Wang et al. |
| 10,301,285 B2 | 5/2019 | Miller et al. |
| 10,525,037 B2 | 1/2020 | Wang et al. |
| 2003/0069238 A1 | 4/2003 | Barrish et al. |
| 2004/0192743 A1 | 9/2004 | Mjalli et al. |
| 2004/0248957 A1 | 12/2004 | Lockhart et al. |
| 2006/0189618 A1 | 8/2006 | Pelletier |
| 2006/0211603 A1 | 9/2006 | Raju et al. |
| 2006/0252793 A1 | 11/2006 | Ameriks et al. |
| 2008/0125418 A1 | 5/2008 | Babin et al. |
| 2009/0246291 A1 | 10/2009 | Burger et al. |
| 2009/0275575 A1 | 11/2009 | Choi et al. |

(Continued)

FOREIGN PATENT DOCUMENTS

| | | |
|---|---|---|
| AU | 2009330686 | 7/2010 |
| AU | 2010347233 | 9/2011 |

(Continued)

OTHER PUBLICATIONS

Database Registry Chemical Abstracts Service, Columbus, Ohio, Accession No. RN 223671-35-0. Entered STN: May 28, 1999.*
Database Registry Chemical Abstracts Service, Columbus, Ohio, Accession No. RN 863665-55-8. Entered STN: Sep. 22, 2005.*
Database Registry Chemical Abstracts Service, Columbus, Ohio, Accession No. RN 1332881-31-8. Entered STN: Sep. 20, 2011.*
Database Registry Chemical Abstracts Service, Columbus, Ohio, Accession No. RN 110032- 89-8, Entered STN: Aug. 29, 1987.
Final Office Action dated Jul. 22, 2021 in respect of U.S. Appl. No. 15/270,359.
Notice of Allowance dated Oct. 14, 2021 in respect of Russian Patent Application No. 2017102002.

(Continued)

*Primary Examiner* — Samantha L Shterengarts
(74) *Attorney, Agent, or Firm* — Mark S. Cohen; PEARL COHEN ZEDEK LATZER BARATZ LLP

(57) ABSTRACT

The present invention relates to novel compounds having anti-cancer activity, methods of making these compounds, and their use for treating cancer and drug-resistant tumors, e.g. melanoma, metastatic melanoma, drug resistant melanoma, prostate cancer and drug resistant prostate cancer.

16 Claims, 61 Drawing Sheets

(56) References Cited

U.S. PATENT DOCUMENTS

| | | |
|---|---|---|
| 2009/0326020 A1 | 12/2009 | Miller et al. |
| 2011/0257196 A1 | 10/2011 | Lu et al. |
| 2012/0022121 A1 | 1/2012 | Dalton et al. |
| 2012/0071524 A1 | 3/2012 | Lu et al. |
| 2012/0196879 A1 | 8/2012 | Dumble et al. |
| 2013/0197049 A1 | 8/2013 | Li et al. |

FOREIGN PATENT DOCUMENTS

| | | |
|---|---|---|
| AU | 2011293353 | 3/2012 |
| AU | 2015227531 | 9/2015 |
| CA | 2728118 | 7/2010 |
| CA | 2962524 | 7/2010 |
| CA | 2809256 | 3/2012 |
| EP | 2959900 | 12/2015 |
| EP | 3064204 | 9/2016 |
| EP | 2303021 | 12/2018 |
| EP | 2608671 | 12/2018 |
| RU | 2008 105 663 | 8/2009 |
| WO | WO-1995/04724 | 2/1995 |
| WO | WO-1999/24048 | 5/1999 |
| WO | WO-2003/016338 | 2/2003 |
| WO | WO-2003/035644 | 5/2003 |
| WO | WO-2003/074516 | 9/2003 |
| WO | WO-2007/011962 | 1/2007 |
| WO | WO-2007/096259 | 8/2007 |
| WO | WO-2010/074776 | 7/2010 |
| WO | WO-2011/047238 | 4/2011 |
| WO | WO-2011-109059 | 9/2011 |
| WO | WO-2012/027481 | 3/2012 |
| WO | WO-2012/027482 | 3/2012 |
| WO | WO-2012/135781 | 10/2012 |
| WO | WO-2012/136776 | 10/2012 |
| WO | WO-2014/138279 | 9/2014 |

OTHER PUBLICATIONS

Office Action dated Jan. 4, 2022 in respect of EP Patent Application No. 15202743.9.
Office Action dated Jan. 19, 2022 in respect of U.S. Appl. No. 15/270,359.
Amaria, et al., "Therapeutic options in cutaneous melanoma: latest developments", Therapeutic Advances in Medical Oncology 2011, 3(5), pp. 245-251.
Bellina, et al., Novel imidazole-based combretastatin A-4 analogues: Evaluation of their in vitro antitumor activity and molecular modeling study of their binding to the colchicine site of tubulin; Bioorganic & American Medicinal Chemistry Letters 2006; vol. 16, Iss. 22, pp. 5757-5762.
Chen et al., "Discovery of Novel 2-Aryl-4-benzoyl-imidazole (ABI-III) Analogues Targeting Tubulin Polymerization As Antiproliferative Agents", J. Med. Chem. 2012, 55, pp. 7285-7289.
Chen et al., "Discovery of novel 2-aryl-4-benzoyl-imidazoles targeting the colchicines binding site in tubulin as potential anticancer agents", J. Med. Chem. 2010, 53(20), pp. 7414-7427.
Cheng, et al., Aerobic Visible-Light Photoredox Radical C—H Functionalizaiton: Catalytic Synthesis of 2-Substituted Benzothiazoles; Organic Letters 2012; vol. 14, No. 1, pp. 98-101.
Gilchrist, et al., Ring Contraction of 1,2,4-Benzodiazines to Benzoxales; J. Chem. Soc. Chem. Comm., 1975, pp. 962-963.
Giles et al., "Synthesis of 2-Thio-and 2-Oxoimidazoles via Cascade Addition—Cycloisomerization Reactions of Propargylcyanamides", J. Org. Chem. 2010, 75, pp. 261-264.
Haass et al., "The Mitogen-Activated Protein/Extracellular Signal-Regulated Kinase Kinase Inhiitor AZD6244 9ARRY-142886) Induces Growth Arrest in Melanoma Cells and Tumor Regression When Combined with Docetaxel", Clin. Cancer Res. 2008, vol. 14(1), pp. 230-239.
Kayagil et al. "Synthesis of some 2,3,6,8-tetraarylimidazo[1,2-a]pyrazine derivatives by using either reflux or microwave irradiation method, and investigation their anticancer activities", Turk J. Chem. 2011, 35, pp. 13-24.
Lee et al., "The Safety, Tolerability, Pharmacokinetics, and Pharmacodynamics of Single Oral Doses of RO5068760, an MEK Inhibitor, in Healty Volunteers: Assessment of Target Suppression", The Journal of Clinical Pharmacology 2010, vol. 50, Iss. 12, pp. 1397-1405.
Li et al., "Orally Bioavailable Tubulin Antagonists for Paclitaxel-Refractory Cancer", Pharm Res. 2012, 29, pp. 3053-3063.
Lu et al., "An Overview of Tubulin Inhibitors That Interact with the Colchicine Binding Site", Pharm Res 2012, 29, pp. 2943-2971.
Lu et al., "Design, Synthesis, and SAR Studies of 4-Substituted Methoxylbenzoyl-aryl-thiazoles Analogues as Potent and Orally Bioavailable Anticancer Agents", J Med. Chem. 2011, 54(13), pp. 4678-4693.
Mahboobi et al., "Synthesis of Naturally Occurring Pyrazine and Imidazole Alkaloids from Botryllus Leachi", Monatshefte für Chemie 2004, vol. 135, No. 3, pp. 333-342.
Patel et al., "Clinical Responses to Selumetinib (AZD6244; ARRY-142886)-Based Combination Therapy Stratified by Gene Mutations in Patients With Metastatic Melanoma", Cancer 2013, 119(4), pp. 799-805.
Rowe et al., Handbook of Pharmaceutical excipients 2006.
STN International File Registry [online] ED Entered STN: Nov. 6, 2008, CAS Registry No. 1071016-37-9.
STN International File Registry [online] ED Entered STN: Aug. 5, 2011, searched—Sep. 19, 2019, CAS Registry No. 1315246-54-8.
STN International File Registry [online] ED Entered STN: Aug. 5, 2011, searched—Sep. 19, 2019, CAS Registry No. 1315246-52-6.
STN International File Registry [online] ED Entered STN: Apr. 7, 2003, searched—Nov. 29, 2018, CAS Registry No. 501917-71-1.
Terasawa et al., "Cytotoxic Activity of 5-Benzoylimidazole and Related Compounds against Human Oral Tumor Cell Lines", AntiCancer Research 2001, 21: pp. 1081-1086.
Tesei et al., "Low-dose Taxotere enhances the ability of sorafenib to induce apoptosis in gastric cancer models", J. Cell. Mol. Med. 2011, vol. 15, No. 2, pp. 316-326.
Tucker et al., "Structure-Activity Relationships of Acyloxyamidine Cytomegalovirus DNA Polymerase Inhibitors", Bioorganic & Medicinal Chemistry 2000, vol. 8, No. 8, pp. 601-615.
Wang et al., "Novel Tubulin Polymerization Inhibitors Overcome Multidrug Resistance and Reduce Melanoma Lung Metastasis", Pharm. Res. 2012, 29, pp. 3040-3052.
Zarganes-Tzitzikas et al., "Synthesis of 2-Keto-imidazoles Utilizing N-Arylamino-Substituted N-Heterocyclic Carbenes", J. Org. Chem. 2011, 76, pp. 1468-1471.
Office Action dated May 8, 2019 from corresponding Canadian Application No. 2,791,738.
Office Action dated Sep. 11, 2019 from corresponding Indian Application No. 201818027795.
Office Action dated Mar. 11, 2020 from corresponding Canadian Application No. 2,904,338.
Office Action dated Mar. 13, 2020 from corresponding Canadian Application No. 3,030,689.
Office Action dated Sep. 27, 2018 from corresponding Chinese Application No. 201580036882.X (English translation).
Office Action dated Jan. 8, 2019 from corresponding Japanese Application No. 2016-567005 (English translation).
Office Action dated Feb. 28, 2019 from corresponding Israeli Application No. 241232.
Office Action dated Dec. 25, 2019 from corresponding Russian Application No. 2016147654.
Office Action dated Mar. 14, 2019 from corresponding Indian Application No. 8964/DELNP/2015.
Office Action dated Aug. 6, 2019 from corresponding Indian Application No. 1672/DELNP/2013.
Office Action dated Feb. 1, 2021 from corresponding Indian Application No. 201818027795.
Office Action dated Mar. 7, 2019 from corresponding Israeli Application No. 261852.
Office Action dated Mar. 31, 2019 from corresponding Israeli Application No. 248767.
Office Action dated Mar. 14, 2019 from corresponding Mexican Application No. MX/a/2015/011713.

(56) References Cited

OTHER PUBLICATIONS

Office Action dated Oct. 1, 2019 from corresponding Japanese Application No. 2016-567005 (English translation).
Office Action dated Nov. 21, 2019 from corresponding Indian Application No. 201617037830.

* cited by examiner

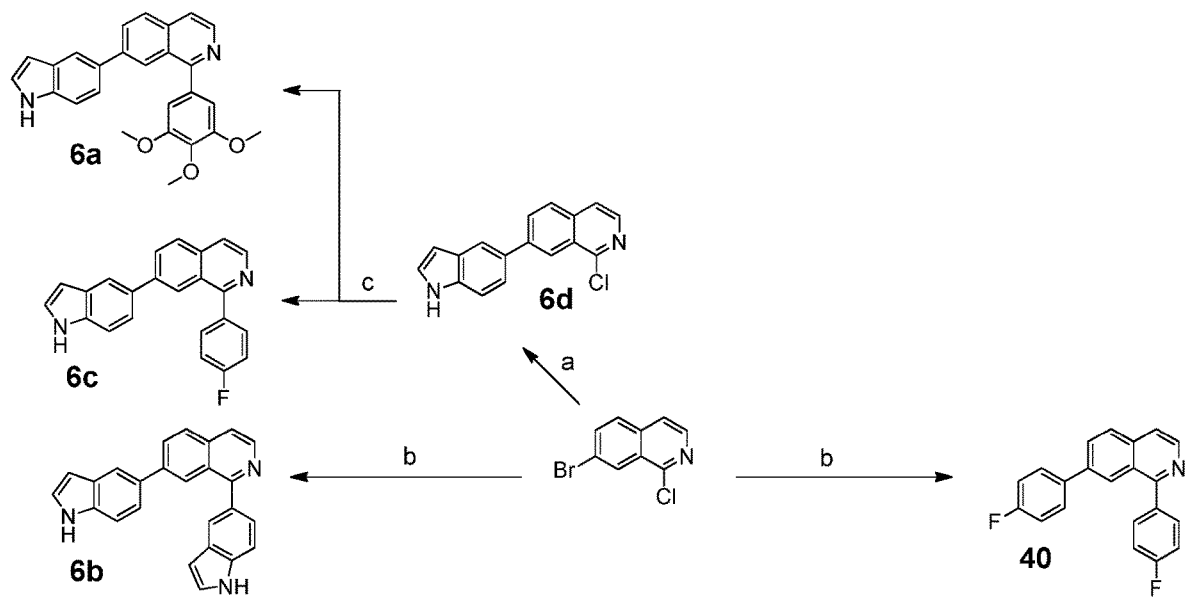
*Figure 16A*
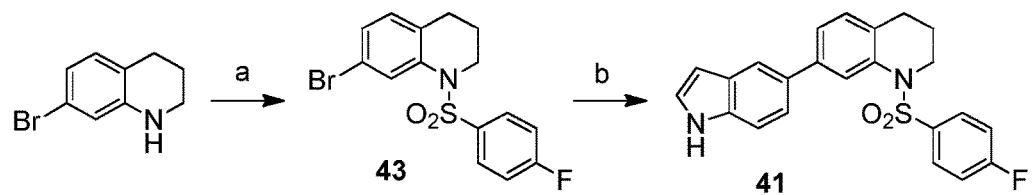
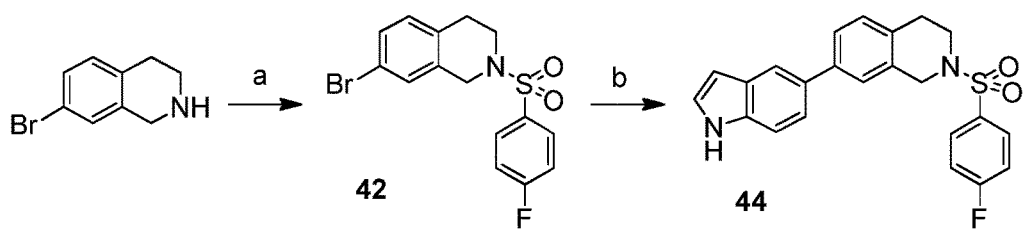
*Figure 16B*
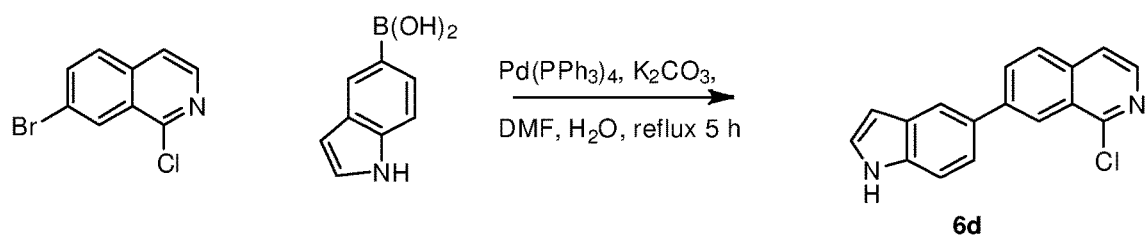
*Figure 16C*

R= -H,1h
R= -F,2k
R= -OH,2l

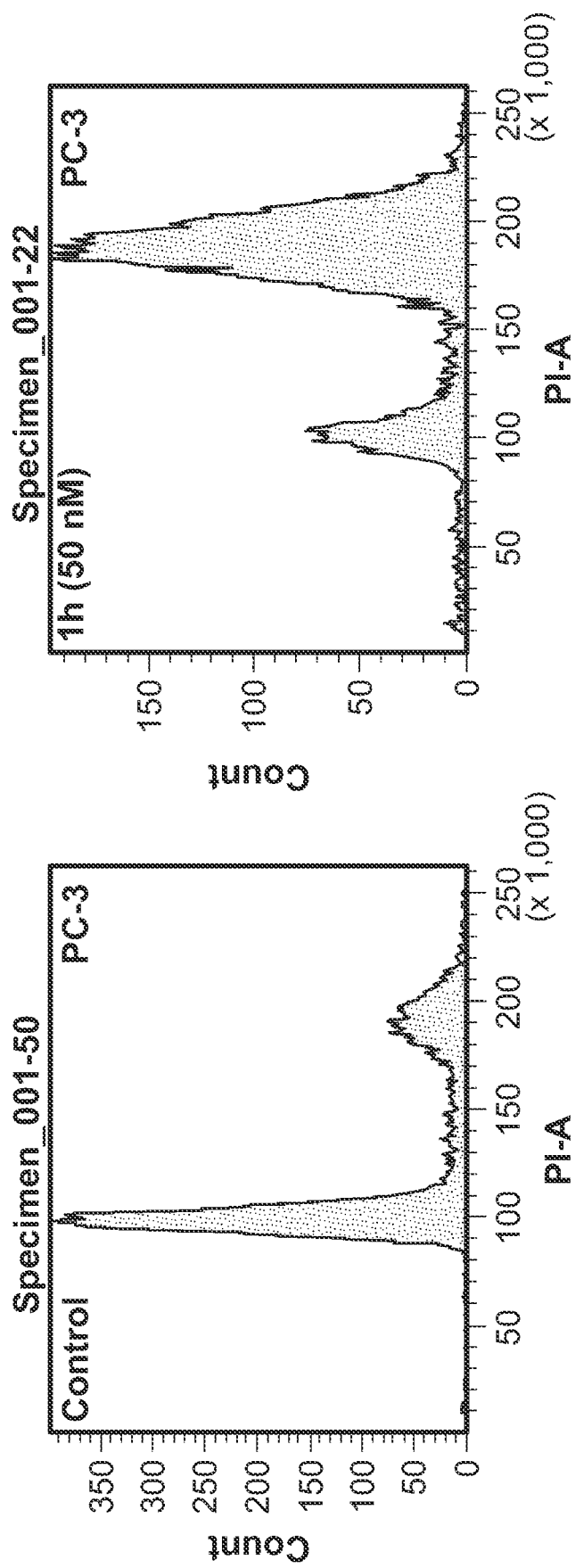
FIGURES 29A(i)    FIGURES 29A(ii)

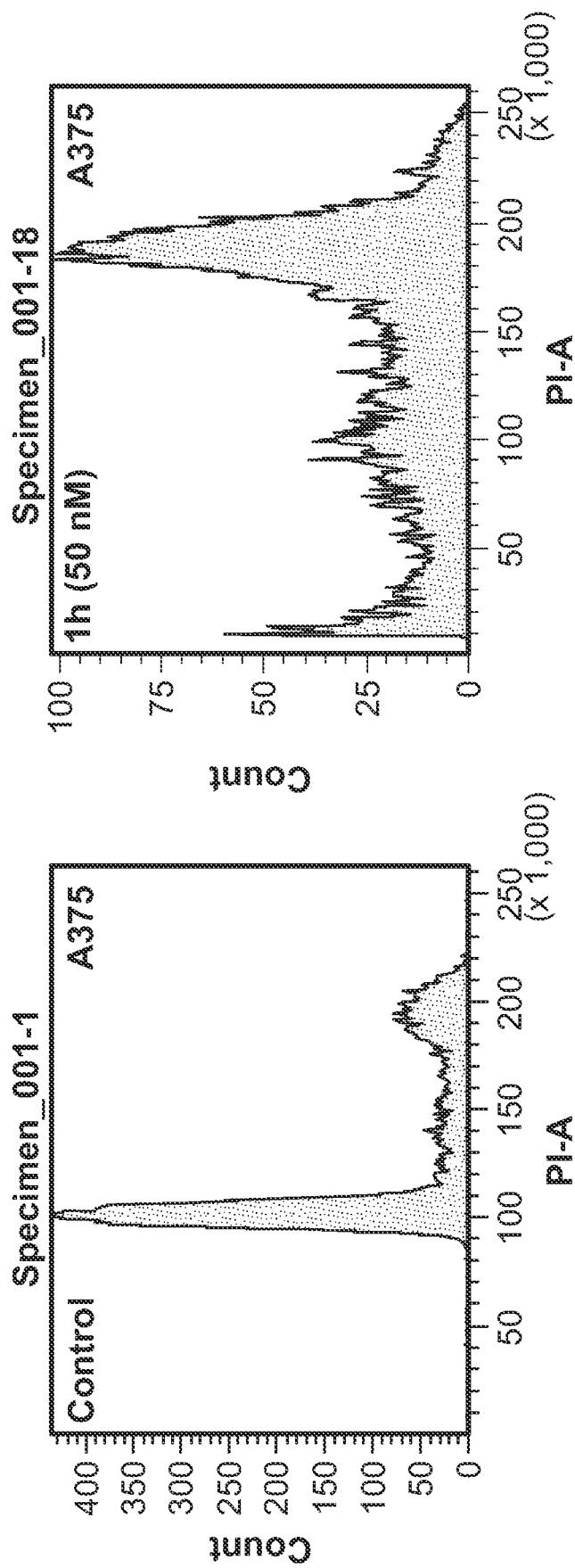
FIGURES 29A(iii)
FIGURES 29A(iv)

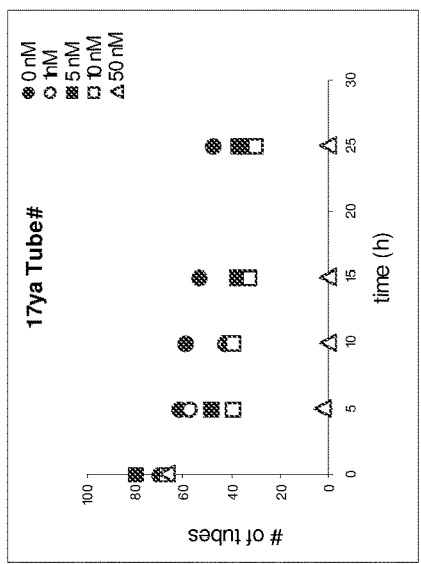
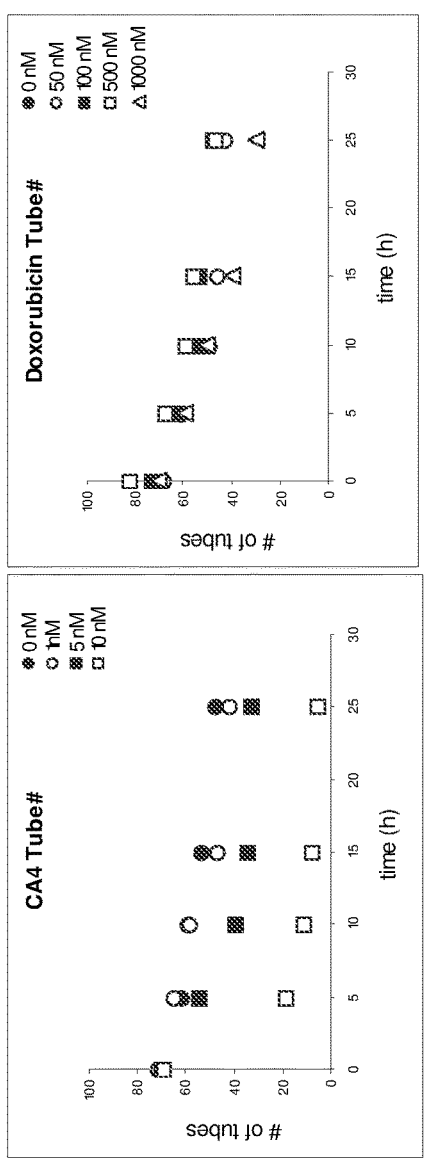
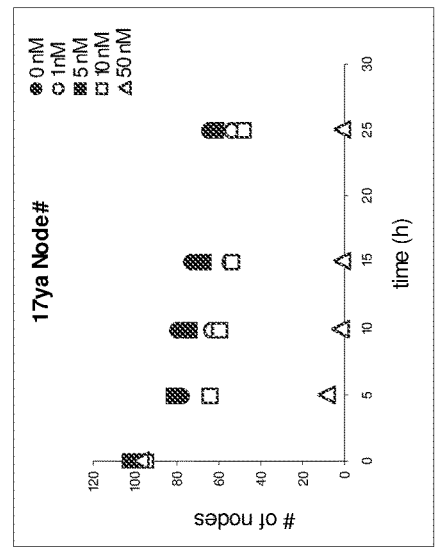
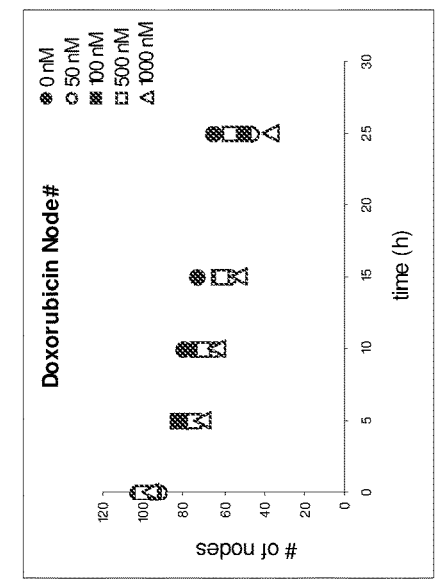
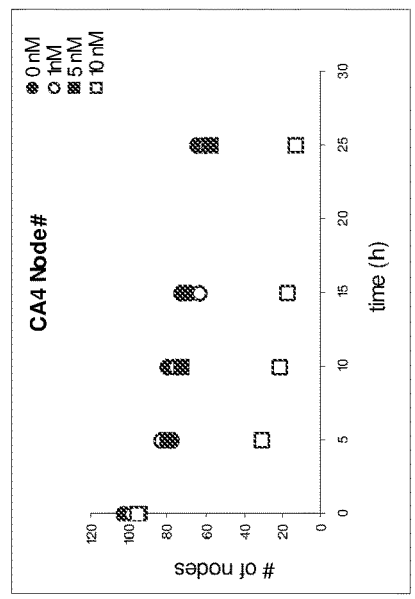
*Figure 36A*  *Figure 36B*  *Figure 36C*
*Figure 36D*  *Figure 36E*  *Figure 36F*

Compound 12q
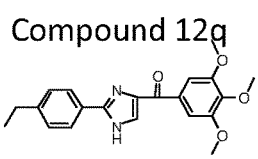
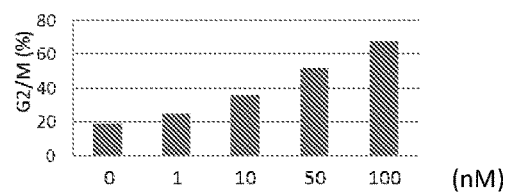
Compound 70a
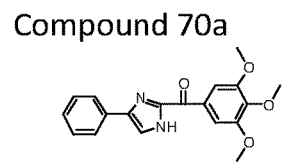
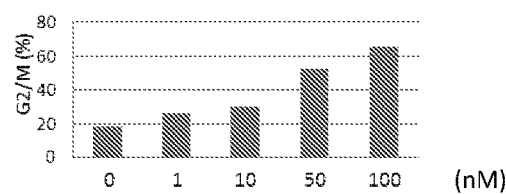
Compound 70f
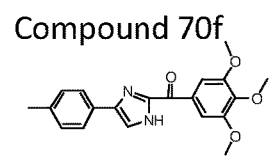
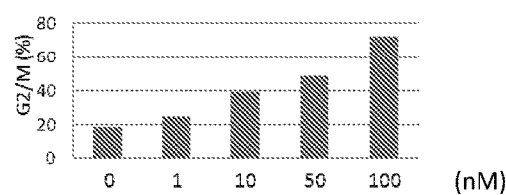
Compound 70m
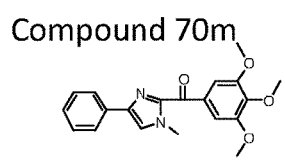
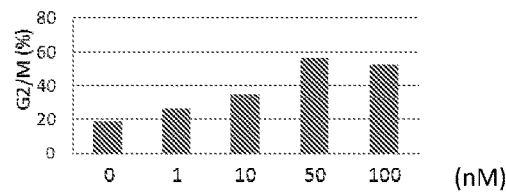
*Figure 39*

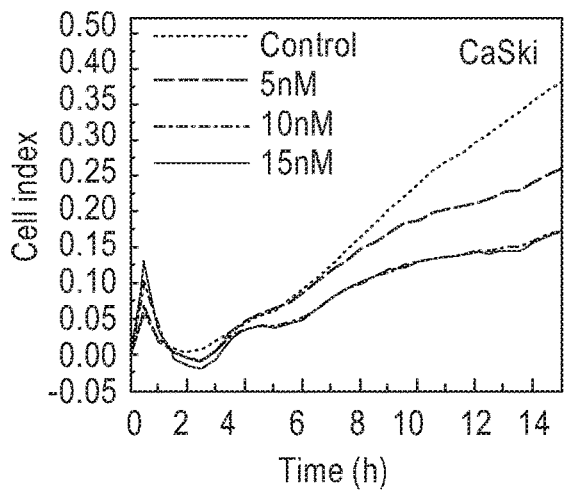
*Figure 52A*
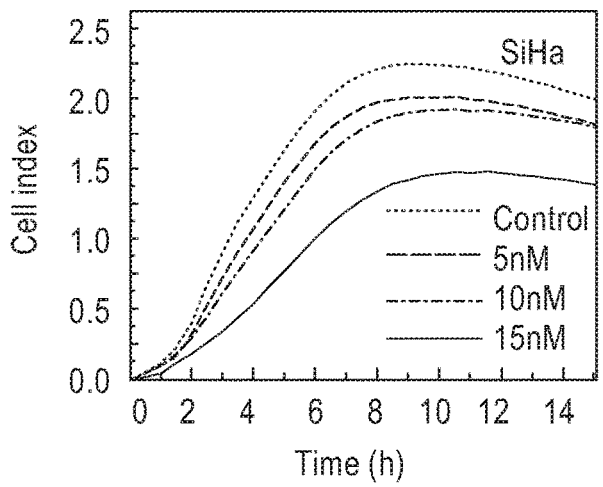
*Figure 52B*
*Figure 53A*
*Figure 53B*
*Figure 53C*
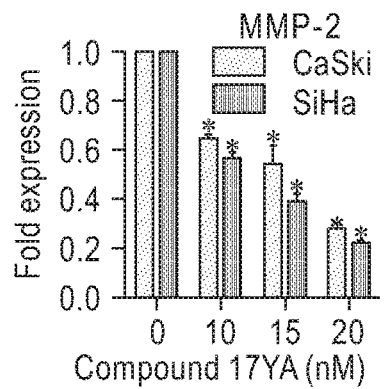
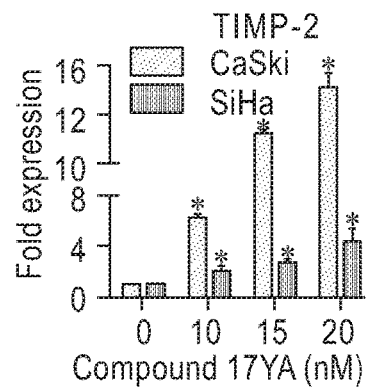
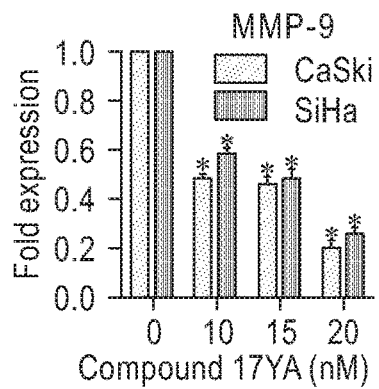
*Figure 53D*
*Figure 53E*
*Figure 53F*
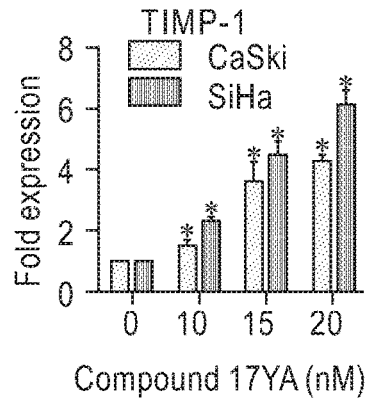
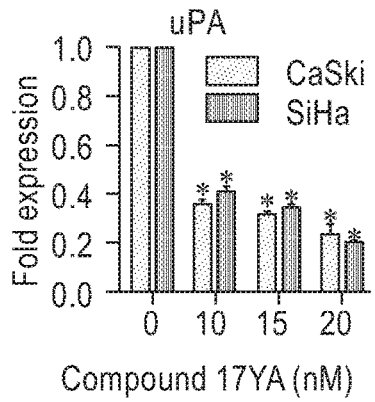
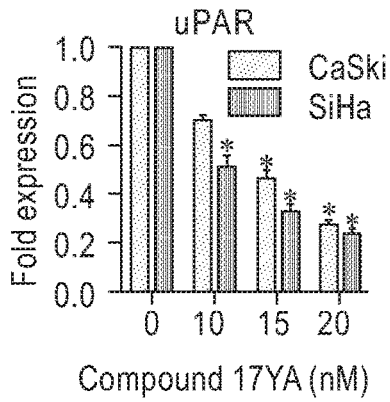

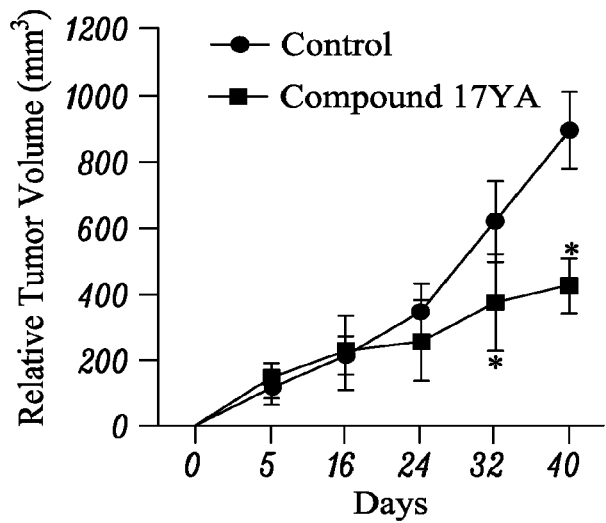
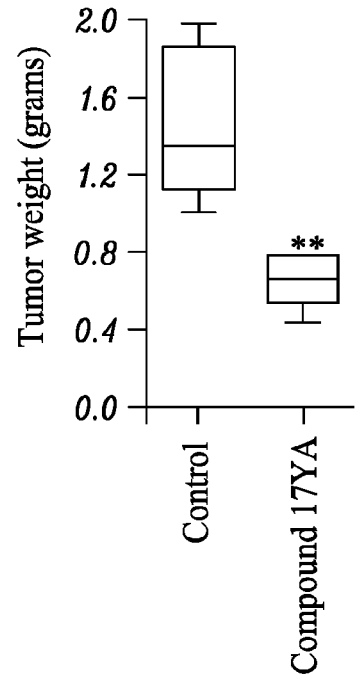
*FIG. 54A*  *FIG. 54B*
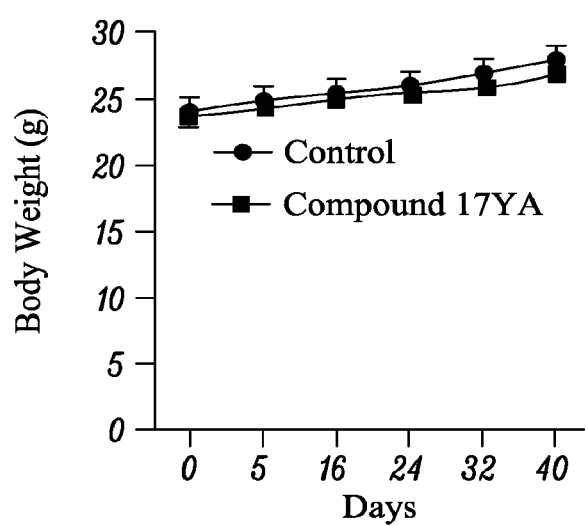
*FIG. 54C*

COMPOUNDS FOR TREATMENT OF CANCER

CROSS-REFERENCE TO RELATED APPLICATIONS

This application is a continuation of U.S. application Ser. No. 16/281,291 filed Feb. 21, 2019, which is a continuation-in-part application of U.S. application Ser. No. 15/270,359, filed on Sep. 20, 2016, which is a continuation application of U.S. application Ser. No. 13/676,650, filed on Nov. 14, 2012, now U.S. Pat. No. 9,447,049, issued Sep. 20, 2016, which is a continuation-in-part application of U.S. application Ser. No. 13/216,927, filed on Aug. 24, 2011, now U.S. Pat. No. 8,822,513, issued Sep. 2, 2014, which is a continuation-in-part application of U.S. application Ser. No. 12/981,233, filed on Dec. 29, 2010, now U.S. Pat. No. 9,334,242, issued May 10, 2016, which claims priority to U.S. Provisional Patent Application Nos. 61/376,675 filed Aug. 24, 2010, 61/315,790, filed Mar. 19, 2010 and 61/309,360 filed Mar. 1, 2010; all of which are hereby incorporated by reference in their entireties.

GOVERNMENT INTEREST STATEMENT

This invention was made in whole or in part with government support under Grant Number 1R15CA125623-01A2 and 1R01CA148706-01A1 awarded by the National Institutes of Health and Grant RO1CA148706 from the National Cancer Institute. The government has certain rights in the invention.

FIELD OF THE INVENTION

The present invention relates to novel compounds having anti-cancer activity, methods of making these compounds, and their use for treating cancer, treating drug-resistant tumors, drug-resistant cancer, metastatic cancer, metastatic melanoma, drug resistant melanoma, prostate cancer and drug resistant prostate cancer.

BACKGROUND OF THE INVENTION

Cancer is the second most common cause of death in the United States, exceeded only by heart disease. In the United States, cancer accounts for 1 of every 4 deaths. The 5-year relative survival rate for all cancer patients diagnosed in 1996-2003 is 66%, up from 50% in 1975-1977 (*Cancer Facts & Figures* American Cancer Society: Atlanta, GA (2008)). This improvement in survival reflects progress in diagnosing at an earlier stage and improvements in treatment. Discovering highly effective anticancer agents with low toxicity is a primary goal of cancer research.

Microtubules are cytoskeletal filaments consisting of aX-tubulin heterodimers and are involved in a wide range of cellular functions, including shape maintenance, vesicle transport, cell motility, and division. Tubulin is the major structural component of the microtubules and a well verified target for a variety of highly successful anti-cancer drugs. Compounds that are able to interfere with microtubule-tubulin equilibrium in cells are effective in the treatment of cancers. Anticancer drugs like taxol and vinblastine that are able to interfere with microtubule-tubulin equilibrium in cells are extensively used in cancer chemotherapy. There are three major classes of antimitotic agents. Microtubule-stabilizing agents, which bind to fully formed microtubules and prevent the depolymerization of tubulin subunits, are represented by taxanes and epothilones. The other two classes of agents are microtubule-destabilizing agents, which bind to tubulin dimers and inhibit their polymerization into microtubules. Vina alkaloids such as vinblastine bind to the vinca site and represent one of these classes. Colchicine and colchicine-site binders interact at a distinct site on tubulin and define the third class of antimitotic agents.

Both the taxanes and vinca alkaloids are widely used to treat human cancers, while no colchicine-site binders are currently approved for cancer chemotherapy yet. However, colchicine binding agents like combretastatin A-4 (CA-4) and ABT-751 (FIG. 19), are now under clinical investigation as potential new chemotherapeutic agents (Luo, Y.; Hradil, V. P.; Frost, D. J.; Rosenberg, S. H.; Gordon, G. B.; Morgan, S. J.; Gagne, G. D.; Cox, B. F.; Tahir, S. K.; Fox, G. B., ABT-751, "A novel tubulin-binding agent, decreases tumor perfusion and disrupts tumor vasculature". *Anticancer Drugs* 2009, 20(6), 483-92.; Mauer, A. M.; Cohen, E. E.; Ma, P. C.; Kozloff, M. F.; Schwartzberg, L.; Coates, A. I.; Qian, J.; Hagey, A. E.; Gordon, G. B., "A phase II study of ABT-751 in patients with advanced non-small cell lung cancer". *J Thorac Oncol* 2008, 3(6), 631-6.; Rustin, G. J.; Shreeves, G.; Nathan, P. D.; Gaya, A.; Ganesan, T. S.; Wang, D.; Boxall, J.; Poupard, L.; Chaplin, D. J.; Stratford, M. R.; Balkissoon, J.; Zweifel, M., "A Phase Ib trial of CA4P (combretastatin A-4 phosphate), carboplatin, and paclitaxel in patients with advanced cancer". *Br J Cancer* 2010, 102(9), 1355-60.).

Unfortunately, microtubule-interacting anticancer drugs in clinical use share two major problems, resistance and neurotoxicity. A common mechanism of multidrug resistance (MDR), namely ATP binding cassette (ABC) transporter protein-mediated drug efflux, limits their efficacy (Green, H.; Rosenberg, P.; Soderkvist, P.; Horvath, G.; Peterson, C., "beta-Tubulin mutations in ovarian cancer using single strand conformation analysis-risk of false positive results from paraffin embedded tissues". *Cancer Letters* 2006, 236(1), 148-54.; Wang, Y.; Cabral, F., "Paclitaxel resistance in cells with reduced beta-tubulin". *Biochimica et Biophysica Acta, Molecular Cell Research* 2005, 1744(2), 245-255.; Leslie, E. M.; Deeley, R. G.; Cole, S. P. C., "Multidrug resistance proteins: role of P-glycoprotein, MRP1, MRP2, and BCRP (ABCG2) in tissue defense". *Toxicology and Applied Pharmacology* 2005, 204(3), 216-237.).

P-glycoproteins (P-gp, encoded by the MDR1 gene) are important members of the ABC superfamily. P-gp prevents the intracellular accumulation of many cancer drugs by increasing their efflux out of cancer cells, as well as contributing to hepatic, renal, or intestinal clearance pathways. Attempts to co-administer P-gp modulators or inhibitors to increase cellular availability by blocking the actions of P-gp have met with limited success (Gottesman, M. M.; Pastan, I., "The multidrug transporter, a double-edged sword". *J Biol Chem* 1988, 263(25), 12163-6.; Fisher, G. A.; Sikic, B. I., "Clinical studies with modulators of multidrug resistance". *Hematology/Oncology Clinics of North America* 1995, 9(2), 363-82).

The other major problem with taxanes, as with many biologically active natural products, is its lipophilicity and lack of solubility in aqueous systems. This leads to the use of emulsifiers like Cremophor EL and Tween 80 in clinical preparations. A number of biologic effects related to these drug formulation vehicles have been described, including acute hypersensitivity reactions and peripheral neuropathies (Hennenfent, K. L.; Govindan, R., "Novel formulations of taxanes: a review. Old wine in a new bottle?" *Ann Oncol*

2006, 17(5), 735-49.; ten Tije, A. J.; Verweij, J.; Loos, W. J.; Sparreboom, A., "Pharmacological effects of formulation vehicles: implications for cancer chemotherapy". *Clin Pharmacokinet* 2003, 42(7), 665-85).

Compared to compounds binding the paclitaxel- or vinca alkaloid binding site, colchicine-binding agents usually exhibit relatively simple structures. Thus, providing a better opportunity for oral bioavailability via structural optimization to improve solubility and pharmacokinetic (PK) parameters. In addition, many of these drugs appear to circumvent P-gp-mediated MDR. Therefore, these novel colchicine binding site targeted compounds hold great promise as therapeutic agents, particularly since they have improved aqueous solubility and overcome P-gp mediated MDR.

Prostate cancer is one of the most frequently diagnosed noncutaneous cancers among men in the US and is the second most common cause of cancer deaths with over 180,000 new cases and almost 29,000 deaths expected this year. Patients with advanced prostate cancer undergo androgen deprivation therapy (ADT), typically either by luteinizing hormone releasing hormone (LHRH) agonists or by bilateral orchiectomy. Androgen deprivation therapy not only reduces testosterone, but estrogen levels are also lower since estrogen is derived from the aromatization of testosterone, which levels are depleted by ADT. Androgen deprivation therapy-induced estrogen deficiency causes significant side effects which include hot flushes, gynecomastia and mastalgia, bone loss, decreases in bone quality and strength, osteoporosis and life-threatening fractures, adverse lipid changes and higher cardiovascular disease and myocardial infarction, and depression and other mood changes.

Leuprolide acetate (Lupron®) is a synthetic nonapeptide analog of naturally occurring gonadotropin-releasing hormone (GnRH or LHRH). Leuprolide acetate is an LHRH superagonist that eventually suppresses LH secretion by the pituitary. Leuprolide acetate acts as a potent inhibitor of gonadotropin secretion, resulting in suppression of ovarian and testicular steroidogenesis. In humans, administration of leuprolide acetate results in an initial increase in circulating levels of luteinizing hormone (LH) and follicle stimulating hormone (FSH), leading to a transient increase in levels of the gonadal steroids (testosterone and dihydrotestosterone in males, and estrone and estradiol in premenopausal females). However, continuous administration of leuprolide acetate results in decreased levels of LH and FSH. In males, testosterone is reduced to castrate levels (below 50 ng/dL). In premenopausal females, estrogens are reduced to postmenopausal levels. Testosterone is a known stimulus for cancerous cells of the prostate. Suppressing testosterone secretion or inhibiting the actions of testosterone is thus a necessary component of prostate cancer therapy. Leuprolide acetate can be used for LH suppression, which is the reduction and lowering of serum testosterone to castrate levels to treat prostate cancer.

Malignant melanoma is the most dangerous form of skin cancer, accounting for about 75% of skin cancer deaths. The incidence of melanoma is rising steadily in Western populations. The number of cases has doubled in the past 20 years. Around 160,000 new cases of melanoma are diagnosed worldwide each year, and it is more frequent in males and Caucasians. According to a WHO Report, about 48,000 melanoma-related deaths occur worldwide per year.

Currently there is no effective way to treat metastatic melanoma. It is highly resistant to current chemotherapy, radiotherapy, and immunotherapy. Metastatic melanoma has a very poor prognosis, with a median survival rate of 6 months and a 5-year survival rate of less than 5%. In the past 30 years, dacarbazine (DTIC) is the only FDA-approved drug for metastatic melanoma. However, it provides only less than 5% of complete remission in patients. In recent years, great efforts have been attempted in fighting metastatic melanoma. Neither combinations of DTIC with other chemotherapy drugs (e.g., cisplatin, vinblastine, and carmustine) nor adding interferon-α2b to DTIC have shown a survival advantage over DTIC treatment alone. Most recently, clinical trials with antibodies and vaccines to treat metastatic melanoma also failed to demonstrate satisfactory efficacy. Ipilimumab (Yervoy) is such drug that uses your immune system to fight melanoma. Ipilimumab is used to treat advanced melanoma that has spread beyond its original location. Targeted therapy uses medications designed to target specific vulnerabilities in cancer cells. Vemurafenib (Zelboraf) is a targeted therapy approved to treat advanced melanoma that can't be treated with surgery or melanoma that has spread through the body. Vemurafenib only treats melanoma that has a certain genetic mutation.

Melanoma cells have low levels of spontaneous apoptosis in vivo compared with other tumor cell types, and they are relatively resistant to drug-induced apoptosis in vitro. The natural role of melanocytes is to protect inner organs from UV light, a potent DNA damaging agent. Therefore, it is not surprising that melanoma cells may have special DNA damage repair systems and enhanced survival properties. Moreover, recent studies showed that, during melanoma progression, it acquired complex genetic alterations that led to hyperactivation of efflux pumps, detoxification enzymes, and a multifactorial alteration of survival and apoptotic pathways. All these have been proposed to mediate the multidrug-resistant (MDR) phenotype of melanoma. With the rapidly rising incidence of this disease and the high resistance to current therapeutic agents, developing more effective drugs for advanced melanoma and other cancer types that can effectively circumvent MDR will provide significant benefits to cancer patients.

Cervical cancer (CxCa) is the second leading cause of female cancer deaths worldwide. High-risk human papillomaviruses (HPV) plays a central role in the development of 99.5% of cervical cancers. HPV acts through infecting the genital mucosa, and is integrated into the host genome, leading to overexpression of E6 and E7 oncoproteins, then immortalizeation to the host cells by disrupting p53 and pRb function, respectively. Oncoprotein E6 binds to p53 and targets it for ubiquitin-mediated degradation. Activation of p53 further induces downstream target gene involved in cell cycle arrest, apoptosis, or attempts to repair the damaged DNA. Cyclin-dependent kinase (cdk) inhibitor p2cip1/waf1 and Bax mediate the cytotoxic and apoptotic effect of p53 respectively. Thus, activation of the p53 function represents a viable option for the effective therapeutic targeting and management of CxCa. Reactivation of p53 is regulated either via inhibition of viral oncoproteins expression and function or in prevention of proteasomal degradation of p53. To activate p53 in cervical cancer, several different strategies like small molecule compounds, direct anti-E6 approaches, gamma-irradiation, certain cytotoxic drugs, and ribozyme techniques have been adopted. As current treatment modalities are rather ineffective against metastatic cervical cancer, there is an urgent need to find affordable and new therapeutic approaches with low systemic toxicity.

SUMMARY OF THE INVENTION

The invention encompasses methods of treating cervical cancer in a subject in need thereof comprising administering a therapeutically effective amount of a compound having the structure of formula XI:

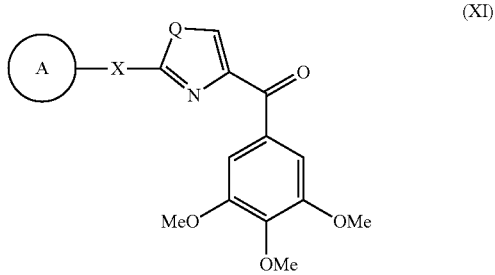

(XI)

wherein X is a bond; Q is NH; A is substituted or unsubstituted single-, fused- or multiple-ring, (hetero) cyclic ring systems; substituted or unsubstituted, saturated or unsaturated N-heterocycles; substituted or unsubstituted, saturated or unsaturated S-heterocycles; substituted or unsubstituted, saturated or unsaturated O-heterocycles; substituted or unsubstituted, saturated or unsaturated cyclic hydrocarbons; or substituted or unsubstituted or saturated or unsaturated mixed heterocycles; wherein the A ring is optionally substituted by 1-5 substituents independently selected from O-alkyl, O-haloalkyl, F, Cl, Br, I, CN, —CH$_2$CN, NH$_2$, hydroxyl, —OC(O)CF$_3$, C$_1$-C$_5$ linear or branched alkyl, haloalkyl, alkylamino, aminoalkyl, —OCH$_2$Ph, —NHCO-alkyl, COOH, —C(O)Ph, C(O)O-alkyl, C(O)H, —C(O)NH$_2$ or NO$_2$, or an isomer, pharmaceutically acceptable salt, pharmaceutical product, tautomer, hydrate, N-oxide, or combinations thereof.

In another embodiment, the invention encompasses methods of treating cervical cancer by administering a therapeutically effective amount of a compound that has a structure of formula XI(e):

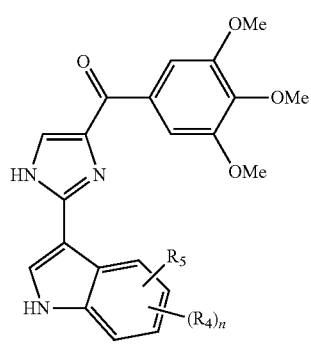

XI(e)

wherein, R$_4$ and R$_5$ are independently hydrogen, O-alkyl, O-haloalkyl, F, Cl, Br, I, haloalkyl, CN, —CH$_2$CN, NH$_2$, hydroxyl, —OC(O)CF$_3$, C$_1$-C$_5$ linear or branched alkyl, haloalkyl, alkylamino, aminoalkyl, —OCH$_2$Ph, —NHCO-alkyl, COOH, —C(O)Ph, C(O)O— alkyl, C(O)H, —C(O)NH$_2$ or NO$_2$; and n is an integer between 1-4.

In yet another embodiment, the invention encompasses methods of treating cervical cancer by administering a therapeutically effective amount of compound 17ya represented by the structure:

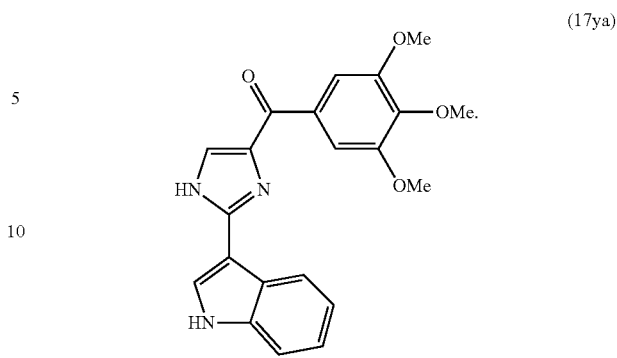

(17ya)

One embodiment of the invention encompasses methods of treating cervical cancer wherein the compound is administered in a pharmaceutical composition with a pharmaceutically acceptable carrier. In another embodiment, the methods of treating cervical cancer with the compounds of formula XI further comprise administering another cancer therapy.

In yet another embodiment, the methods of treating cervical cancer in a subject in need thereof comprise administering a therapeutically effective amount of a compound having the structure of formula XI:

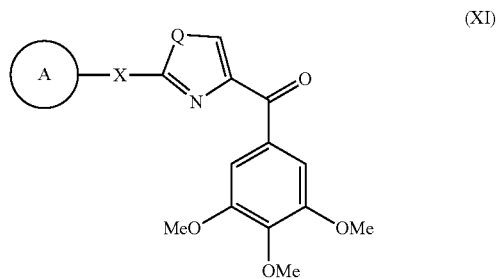

(XI)

wherein X is a NH; Q is NH; A is substituted or unsubstituted single-, fused- or multiple-ring (hetero)cyclic ring systems; substituted or unsubstituted, saturated or unsaturated N-heterocycles; substituted or unsubstituted, saturated or unsaturated S-heterocycles; substituted or unsubstituted, saturated or unsaturated O-heterocycles; substituted or unsubstituted, saturated or unsaturated cyclic hydrocarbons; or substituted or unsubstituted or saturated or unsaturated mixed heterocycles; wherein the A ring is optionally substituted by 1-5 substituents which are independently O-alkyl, O-haloalkyl, F, Cl, Br, I, CN, —CH$_2$CN, NH$_2$, hydroxyl, —(CH$_2$)$_i$NHCH$_3$, —(CH$_2$)$_i$NH$_2$, —(CH$_2$)$_i$N (CH$_3$)$_2$, —OC(O)CF$_3$, C$_1$-C$_5$ linear or branched alkyl, haloalkyl, alkylamino, aminoalkyl, —OCH$_2$Ph, —NHCO-alkyl, COOH, —C(O)Ph, C(O)O-alkyl, C(O)H, —C(O)NH$_2$ or NO$_2$; and i is an integer between 0-5, or an isomer, pharmaceutically acceptable salt, pharmaceutical product, tautomer, hydrate, N-oxide, or combinations thereof.

One embodiment of the invention encompasses methods of treating cervical cancer by administering a therapeutically effective amount of a compound that has a structure of formula VIII:

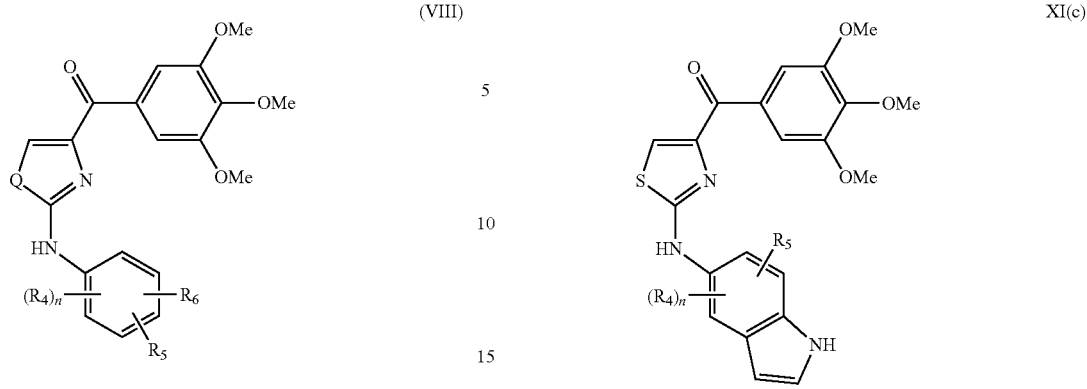

(VIII)

$R_4$, $R_5$ and $R_6$ are independently hydrogen, O-alkyl, O-haloalkyl, F, Cl, Br, I, haloalkyl, $CF_3$, CN, —$CH_2CN$, $NH_2$, hydroxyl, —$(CH_2)_iNHCH_3$, —$(CH_2)_iNH_2$, —$(CH_2)_iN(CH_3)_2$, —$OC(O)CF_3$, $C_1$-$C_5$ linear or branched alkyl, haloalkyl, alkylamino, aminoalkyl, —$OCH_2Ph$, —NHCO-alkyl, COOH, —C(O)Ph, C(O)O-alkyl, C(O)H, —$C(O)NH_2$ or $NO_2$; Q is S, O or NH; i is an integer between 0-5; and n is an integer between 1-3.

Another embodiment of the invention encompasses methods of treating cervical cancer by administering a therapeutically effective amount of a compound that has a structure of formula XI(b):

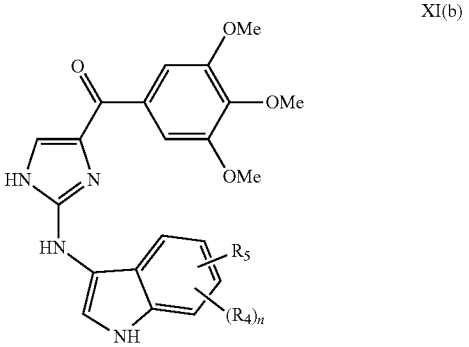

(XI(b))

wherein $R_4$ and $R_5$ are independently hydrogen, O-alkyl, O-haloalkyl, F, Cl, Br, I, haloalkyl, $CF_3$, CN, —$CH_2CN$, $NH_2$, hydroxyl, —$(CH_2)_iNHCH_3$, —$(CH_2)_iNH_2$, —$(CH_2)_iN(CH_3)_2$, —$OC(O)CF_3$, $C_1$-$C_5$ linear or branched alkyl, haloalkyl, alkylamino, aminoalkyl, —$OCH_2Ph$, —NHCO-alkyl, COOH, —C(O)Ph, C(O)O-alkyl, C(O)H, —$C(O)NH_2$ or $NO_2$; i is an integer from 0-5; and n is an integer between 1-4.

Yet another embodiment of the invention encompasses methods of treating cervical cancer by administering a therapeutically effective amount of a compound has the structure of formula XI(c):

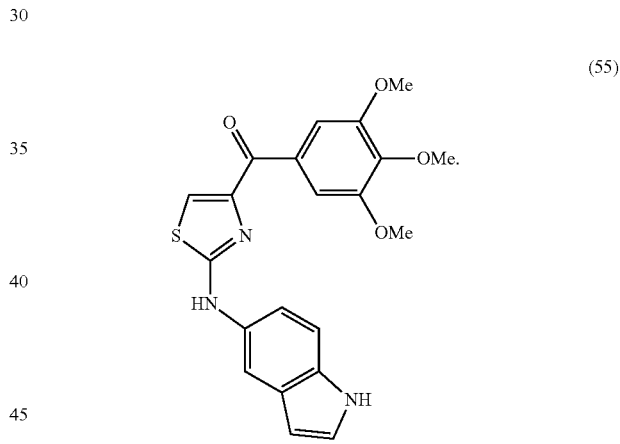

XI(c)

wherein $R_4$ and $R_5$ are independently hydrogen, O-alkyl, O-haloalkyl, F, Cl, Br, I, haloalkyl, $CF_3$, CN, —$CH_2CN$, $NH_2$, hydroxyl, —$(CH_2)_iNHCH_3$, —$(CH_2)_iNH_2$, —$(CH_2)_iN(CH_3)_2$, —$OC(O)CF_3$, $C_1$-$C_5$ linear or branched alkyl, haloalkyl, alkylamino, aminoalkyl, —$OCH_2Ph$, —NHCO-alkyl, COOH, —C(O)Ph, C(O)O-alkyl, C(O)H, —$C(O)NH_2$ or $NO_2$; i is an integer from 0-5; and n is an integer between 1-4.

One embodiment of the invention encompasses methods of treating cervical cancer by administering a therapeutically effective amount of compound 55, represented by the structure:

(55)

Another embodiment of the invention encompasses methods of treating cervical cancer with compounds of formula XI further comprise administering another cancer therapy.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIGS. 16A-E depict a synthetic scheme of isoquinoline and quinoline based compounds. FIG. 16A depicts the synthetic scheme of isoquinoline derivatives. Reagents and conditions: a) arylboronic acid (1 equiv.), Pd(PPh$_3$)$_4$(0.01 equiv.), K$_2$CO$_3$, H$_2$O, DMF, 5 h; b) arylboronic acid (2.4 equiv.), Pd(PPh$_3$)$_4$(0.04 equiv.), K$_2$CO$_3$, H$_2$O, DMF, 16 h; c) arylboronic acid (1.2 equiv.), Pd(PPh$_3$)$_4$(0.04 equiv.), K$_2$CO$_3$, H$_2$O, DMF, 16 h. FIG. 16B depicts the synthetic scheme of compounds 41 and 44. Reagents and conditions: a) p-fluorobenzenesulfonyl chloride, pyridine, pyridine, 80° C., 3 h; b) 5-indoleboronic acid (1.2 equiv.), Pd(PPh$_3$)$_4$(0.02 equiv.), K$_2$CO$_3$, H$_2$O, DMF, 16 h. FIG. 16C depicts synthetic scheme of isoquinoline derivative 6d. FIG. 16D depicts the synthetic scheme of isoquinoline derivative 6c. FIG. 16E depicts the synthetic scheme of isoquinoline derivative 6b.

FIG. 21E-12da; FIG. 21F-12cb) indicate that the ABI compounds were not substrates for P-gp and overcame multidrug resistance.

FIG. 23A depicts representative pictures of control and each tested compound (12cb, 12da, and 12fb) at 100 nM. The diameter of each well was 35 mm. FIG. 23B depicts a quantified representation of assay results for each tested compound (12cb, 12da, and 12fb). P value was calculated comparing with control using Student's t test by GraphPad Prism software. Columns, means of three replicates; bars, SD.

FIG. 24A depicts the in vivo activity of 12cb against B16-F1 melanoma tumors in C57/BL mice. FIG. 24B depicts the in vivo activity of 12fb against B16-F1 melanoma in C57BL/6 mice and SHO nude mice. Results showed that 12fb inhibited melanoma tumor growth in a dose-dependent manner. C57BL/6 mice bearing B16-F1 melanoma allograft (n=5 per group). Each mouse received $0.5 \times 10^6$ cells by s.c. injection into the flank. 30 μL i.p. daily treatments were started when tumor size reached ~100 nun³. FIG. 24C depicts the in vivo activity of 12fb against an A375 human melanoma xenograft. SHO nude mice bearing an A375 human melanoma xenograft (n=5 per group). Each mouse received $2.5 \times 10^6$ cells by s.c. injection into the flank. 30 μL i.p. daily treatments were started when the tumor size reached ~150 mm³. Control, vehicle solution only; points, means; bars, SD. DTIC, (5-(3,3,-dimethyl-1-triazenyl)-imidazole-4-carboxamide, dacarbazine.

FIG. 25A depicts a [$^3$H]-colchicine competition-binding scintillation proximity assay which showed that 12cb competitively bound to tubulin colchicine binding site. FIG. 25B depicts representative graphs of cell cycle analysis using flow cytometry which showed that ABI compounds (examples shown for 12da and 12fb) arrested A375 cells in the G2/M phase after 24 h incubation. The effect and potency were similar to those of colchicine. FIG. 25C shows quantified graphic depictions of cell cycle analysis. All tested compounds (examples shown for 12cb, 12da, and 12fb) arrested A375 cells in the G2/M phase in a dose-dependent manner. ABI 12da showed greater potency than did colchicine. FIG. 25D depicts a cell cycle analysis using flow cytometry of A375 cells after being incubated with 12cb, 12da, and 12fb at different concentrations for 24 h. Colchicine arrested most cells in the G2/M phase starting from 50 nM. 12cb, 12da, and 12fb also arrested most cells in the G2/M phase starting from 200, 50, and 200 nM respectively.

FIG. 26A, competitive mass binding. Tubulin (1 mg/mL) and colchicine (1.2 μM) were incubated with various concentrations of podophylltoxin, vinblastine, compounds 17ya, and 55. N=3; mean±SD. Podophylltoxin and vinblastine were used as positive and negative controls, respectively. FIG. 26B, effect on tubulin polymerization. Tubulin (0.4 mg) was exposed to test compounds (5 μM). Colchicine was used as positive control. FIGS. 26C and 26D, ability of 17ya and 55 to enhance cytoplasmic DNA-Histone complex formation (apoptosis) at 24 h in PC-3 (C) and PC-3/TxR (D) cells (N=3); mean±SD. Docetaxel was used as positive control.

FIG. 27A, Nude mice bearing PC-3 tumors were treated with docetaxel (i.v., 10 or 20 mg/kg) on day 1 and 9. (N=5-6). Bars, SE. FIG. 27B, Nude mice bearing PC-3/TxR tumors were treated with docetaxel (i.v., 10 or 20 mg/kg) on day 1 and 9, compound 17ya treatments (p.o., 6.7 mg/kg) once daily, five days a week. (N=4–5). Bars, SE. FIG. 27C, Nude mice bearing PC-3/TxR tumors were treated with compound 17ya (PO, 3.3 mg/kg) twice a day for four days in the first week, and then dosed once a day, five days a week for weeks 2-4 (N=7), with compound 55 treatments (p.o., 10 or 30 mg/kg) twice a day, five days a week for four weeks (N=7). Bars, SE. FIG. 27D, Nude mice bearing PC-3/TxR tumors were treated with compound 17ya (PO, 10 mg/kg) three times a week for four weeks (N=5). Bars, SE.

(FIG. 28A) Structures of 1h (—H), 2k (—F), and 21 (—OH). (FIG. 28B) Effect of the compounds on tubulin polymerization. Tubulin (0.4 mg) was exposed to compounds 1h, 2k, and 21 (10 μM). Absorbance at 340 nm was monitored every min for 15 min. (FIG. 28C) Ability of 1h to compete for colchicine, vinblastine and paclitaxel binding sites on tubulin using mass spectrometry competitive binding assay (n=3); bars, SD.

FIGS. 29A-E depict that compounds 1h, 2k and 21 arrested cells into G2/M phase and induced apoptosis. (FIGS. 29A($i$)-29A($iv$)) Representative graphs of cell cycle analysis after compounds treatment for 24 h on PC-3 and A375 cells. (FIG. 29B) The changes in G2/M proportion induced by 1h, 2k, and 21 in PC-3 and (FIG. 29C) A375 cells after 24 h treatment. (FIGS. 29D, and 29E) Ability of 1h, 2k, and 21 to enhance cytoplasmic DNA-Histone complex formation in 24 h (n=3); bars, SD. Colchicine and vinblastine were used as positive controls.

(FIG. 30A) Concentration-time curve of SMART compounds in ICR mice (n=3); bars, SD. SMART compounds were administrated 15 mg/kg i.v. by tail vein injection. (FIG. 30B) Concentration-time curve of 1h and 2k in SD rats (n=4); bars, SD. Spague-Dawley rats were dosed 2.5 mg/kg i.v. with the formulation DMSO/PEG300 (¼).

(FIG. 31A) SMART compounds efficacy for PC-3 prostate tumor xenografted on nude mice (n=6-8). (FIG. 31B) Vinblastine efficacy for PC-3 prostate tumor xenografted on nude mice (n=8). This served as the positive control. (FIG. 31C) In vivo efficacy of 1h and 2k in nude mice bearing A375 melanoma xenografts (n=10). Nude mice were inoculated with $2.5 \times 10^6$ PC-3 or A375 cells and dosed i.p. daily (SMART compounds) and q2d (vinblastine) after tumor formation (150-200 mm³). Each point represents mean tumor volume for animals in each group. (FIG. 31D) In vivo neurotoxicity (rotarod test) of 1h in ICR mice (n=7 or 8). 1h (5 and 15 mg/kg), vinblastine (0.5 mg/kg) and vehicle were given i.p. daily, and vinblastine was used as the positive control. The dosing was stopped on day 31. *, p<0.05. Bars, SE.

FIGS. 32A and 32B depict molecular modeling of compound 12cb and 11cb, respectively.

FIG. 33 depicts microscopic images of immunofluorescence-labeled microtubules in WM-164 melanoma cells, which showed microtubule modality was dramatically changed after compound treatment for 18 h. This provides visual proof that ABI compounds target tubulin and disrupt functional microtubule formation.

FIG. 34C illustrates the liver size (g) of each nude mouse that was measured after 3 weeks treatment. FIG. 34D illustrates the number of white blood cells that was counted in whole blood collected from animal after 3 weeks treatment.

FIGS. 36A-F illustrate the disruption of preformed capillary by 17ya. HUVEC cells loaded on Matrigel were allowed to make tube for 16 h and the test compound was treated to the preformed tubes. The number of tubes (Figure A, Figure B, and Figure_C) and nodes (Figure D, Figure E, and Figure F) were counted up to 25 h after drug treatment. Panels A and D are conditions in the presence of CA4, panels B and E are conditions in the presence of doxorubicin and panels C and F are conditions in the presence of 17ya.

FIG. 38-17*ya* and 55 increased the permeability of endothelial cell monolayers. Confluent HUVEC monolayers were exposed to test compound. The leakage of FITC-conjugated dextran through the monolayer was assessed by relative fluorescence measurements at λ=485 nm excitation and λ=530 nm emission in a receiver to determine changes in monolayer permeability following exposure.

FIG. 39 depicts PC3 cell cycle distribution for 24 hours treatment of compounds of this invention (12q, 70a, 70f and 70m)

FIG. 46A illustrates that compund 17ya had a significant downregulation of both HPV16 E6 and E7 transcripts in a dose dependent in CaSki. FIG. 46B illustrates that compound 17ya had a significant downregulation of both HPV16 E6 and E7 transcripts in a dose dependent in SiHa.

FIG. 47A illustrates the effect of compound 17ya on expression of p21 levels (CaSki cell line) as it significantly increased the mRNA. FIG. 47B illustrates the effect of compound 17ya on expression of p53 levels (CaSki cell line) as the protein level indicated the involvement of p53 dependent apoptosis in these cells. FIG. 47C illustrates the effect of compound 17ya on expression of p21 levels (SiHa cell line) as it significantly increased the mRNA. FIG. 47D illustrates the effect of compound 17ya on expression of p53 levels (SiHa cell line) as the protein level indicated the involvement of p53 dependent apoptosis in these cells.

FIGS. 48A-D illustrate the effect fo compound 17ya on miR-23b and miR-34a. FIGS. 48A-B illustrate the effect of compound 17ya on the expression of miR-23b and miR-34a by qRT-PCR in CxCa cells that illustrated an 8- and 14-fold induction of miR-23b expression in treated (20 nM) CaSki and SiHa cells, respectively, as compared to the untreated control. While FIGS. 48C-D illustrate that MiR-34a was also significantly upregulated in dose dependent compared to untreated cells when treated with compound 17ya.

FIGS. 52A-B illustrate the effect of compound 17ya on cell invasion by treating CxCa cells with 2.5-5 nM compound 17ya followed by allowing cells to invade in Matrigel-coated Transwell for 24 h.

FIG. 53A-F illustrate the effect of compound 17ya on the expression of proteolytic enzymes matrix metalloproteinases (MMPs) MMP-2, MMP-9, uPA, uPAR, TIMP-1 and TIMP-2 in CxCa cells compared to the untreated group by use of RT-qPCR.

FIGS. 54A-C illustrate that intra-tumoral administration of compound 17ya (50 µg/mice, three times in week) significantly (p<0.01) inhibited CaSki cell-derived orthotopic xenograft tumors in athymic nude mice compared to an untreated control.

Figure 1:
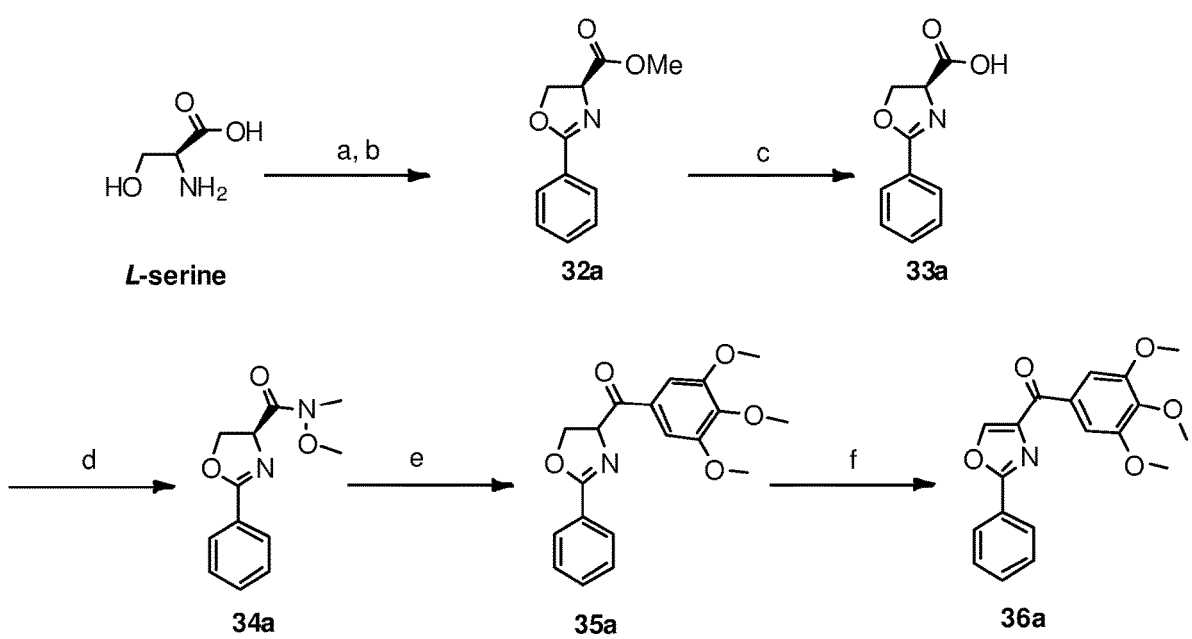
FIG. 1 depicts the synthesis of the diverse B-ring template: oxazole. Reagents and conditions: (a) MeOH, $CH_3COCl$, 83%; (b) Benzimidic acid ethyl ester, $CH_2Cl_2$, $Et_3N$, 96%; (c) LiOH, MeCOH, $H_2O$, 65%; (d) EDCI, HOBt, NMM, $CH_3OCH_3NH \cdot HCl$, 61%; (e) 3,4,5-trimethoxyphenylmagnesium bromide, THF, 48%-71%; (f) $CBrCl_3$, DBU, $CH_2Cl_2$, 56%.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

To address the need in the art, the activities of compound 17ya was evaluated to determine the ability to inhibit CxCa in vitro and in vivo and investigate its underlying molecular mechanisms of action. Mechanistically, it is believed that the mechanism through repression of HPV E6 and E7 oncoproteins and restoration of p53 levels by Compound 17ya, leads to sequential reactivation of p53-dependent tumor suppressor activity by downstream modulation of proteins involved in cell proliferation, cell cycle progression and apoptosis. In addition, treatment with compound 17ya also regulates the JAK2/STAT3 signalling pathways. Evaluation in vivo of the anti-tumor activities of compound 17ya in CxCa tumor models in nude mice confirmed the postulation. Compound 17 ya showed good safety profiles in the sub-acute toxicity test. This indicated that compound 17ya significantly down-regulated expression of HPV E6/E7 oncogenes, restored the p53 pathway, and induced apoptosis of CxCa cells. The results showed that compound 17ya is a potential novel anti-tumor drug candidate for CxCa treatment.

In one embodiment, this invention is directed to a compound of formula (I)

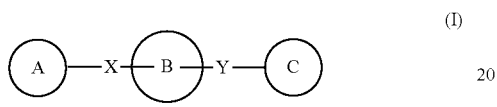

(I)

wherein

A and C are each independently substituted or unsubstituted single-, fused- or multiple-ring aryl or (hetero) cyclic ring systems; substituted or unsubstituted, saturated or unsaturated N-heterocycles; substituted or unsubstituted, saturated or unsaturated S-heterocycles; substituted or unsubstituted, saturated or unsaturated O-heterocycles; substituted or unsubstituted, saturated or unsaturated cyclic hydrocarbons; or substituted or unsubstituted, saturated or unsaturated mixed heterocycles;

B is

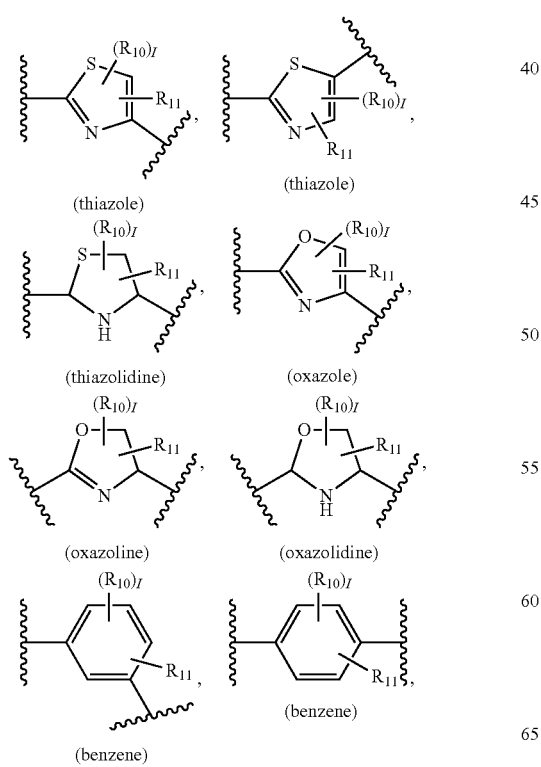

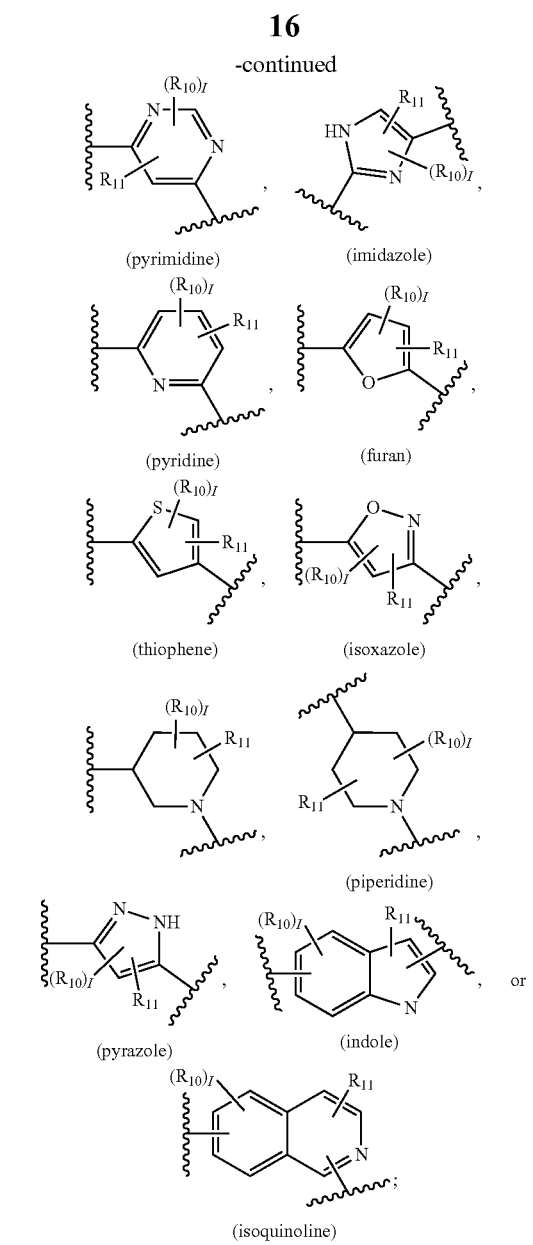

$R_{10}$ and $R_{11}$ are independently hydrogen, O-alkyl, O-haloalkyl, F, Cl, Br, I, haloalkyl, $CF_3$, CN, —$CH_2CN$, $NH_2$, hydroxyl, —$(CH_2)_iNHCH_3$, —$(CH_2)_iNH_2$, —$(CH_2)_iN(CH_3)_2$, —$OC(O)CF_3$, $C_1$-$C_5$ linear or branched alkyl, haloalkyl, alkylamino, aminoalkyl, —$OCH_2Ph$, —NHCO— alkyl, COOH, —C(O)Ph, C(O)O-alkyl, C(O)H, —$C(O)NH_2$ or $NO_2$;

X is a bond, NH, $C_1$ to $C_5$ hydrocarbon, O, or S;

Y is a bond, —C=O, —C=S, —C=N—$NH_2$, —C=N—OH, —CH—OH, —C=CH—CN, —C=N—CN, —CH=CH—, —C=C(CH_3)_2, —C=N—OMe, —(C=O)—NH, —NH—(C=O), —(C=O)—O, —O—(C=O), —$(CH_2)_{1-5}$—(C=O), (C=O)—$(CH_2)_{1-5}$, —$(SO_2)$—NH—, —NH—$(SO_2)$—, $SO_2$, SO or S;

wherein said A and C rings are optionally substituted by 1-5 substituents which are independently O-alkyl, O-haloalkyl, F, Cl, Br, I, haloalkyl, $CF_3$, CN, —$CH_2CN$, $NH_2$, hydroxyl, —$(CH_2)_iNHCH_3$, —$(CH_2)_iNH_2$, —$(CH_2)_iN(CH_3)_2$, —$OC(O)CF_3$, $C_1$-$C_5$ linear or branched alkyl, haloalkyl, alkylamino, aminoalkyl, —OCH$_2$Ph, —NHCO-alkyl, COOH, —C(O)Ph, C(O) O-alkyl, C(O)H, —C(O)NH$_2$ or NO$_2$;

i is an integer between 0-5;

l in an integer between 1-2;

wherein if B is a benzene ring, a thiophene ring, a furan ring or an indole ring then X is not a bond or CH$_2$, and A is not indole;

if B is indole then X is not 0; and or its pharmaceutically acceptable salt, hydrate, polymorph, metabolite, tautomer or isomer.

In one embodiment, if B of formula I is a thiazole ring then X is not a bond.

In one embodiment, A in compound of Formula I is indolyl. In another embodiment A is 2-indolyl. In another embodiment A is phenyl. In another embodiment A is pyridyl. In another embodiment A is naphthyl. In another embodiment A is isoquinoline. In another embodiment, C in compound of Formula I is indolyl. In another embodiment C is 2-indolyl. In another embodiment C is 5-indolyl. In another embodiment, B in compound of Formula I is thiazole. In another embodiment, B in compound of Formula I is thiazole; Y is CO and X is a bond. Non limiting examples of compound of formula I are selected from: (2-(1H-Indol-2-yl)thiazol-4-yl)(1H-indol-2-yl)methanone (8) and (2-(1H-indol-2-yl)thiazol-4-yl)(1H-indol-5-yl)methanone (21).

In one embodiment, this invention is directed to a compound of formula (Ia)

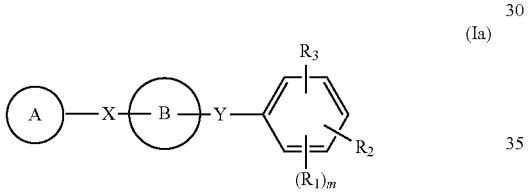

(Ia)

wherein

A is substituted or unsubstituted single-, fused- or multiple-ring, aryl or (hetero)cyclic ring systems; substituted or unsubstituted, saturated or unsaturated N-heterocycles; substituted or unsubstituted, saturated or unsaturated S-heterocycles; substituted or unsubstituted, saturated or unsaturated O-heterocycles; substituted or unsubstituted, saturated or unsaturated cyclic hydrocarbons; or substituted or unsubstituted, saturated or unsaturated mixed heterocycles;

B is

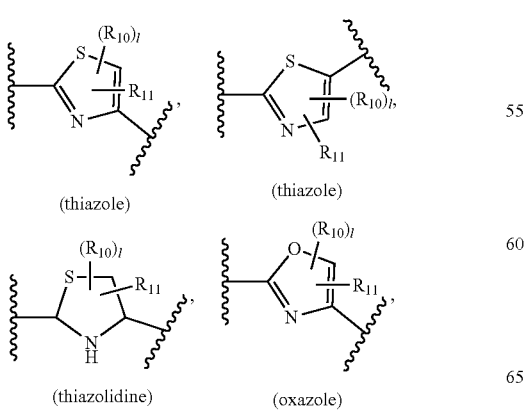

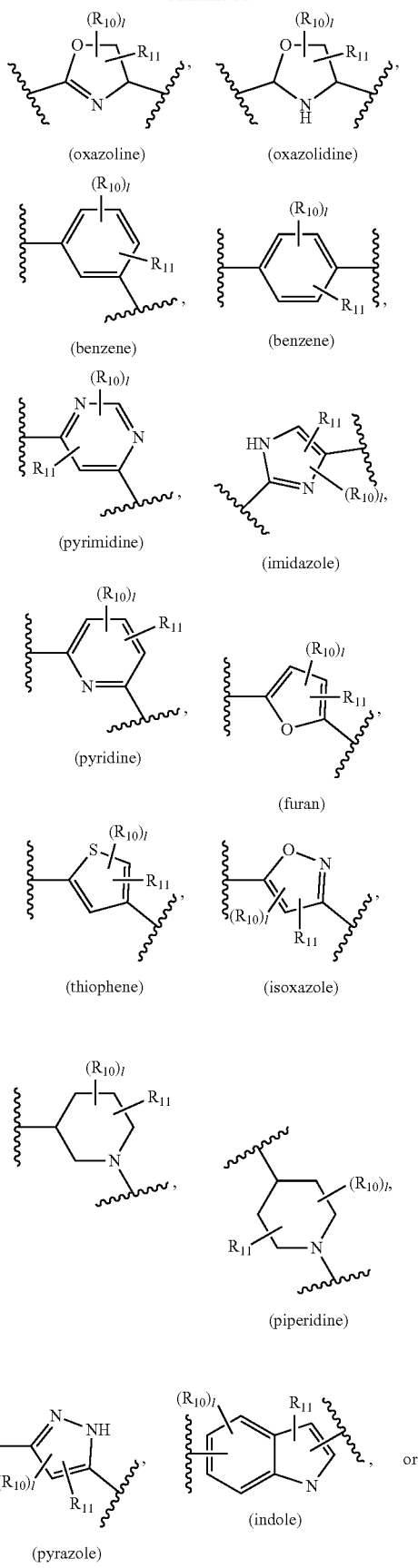

-continued

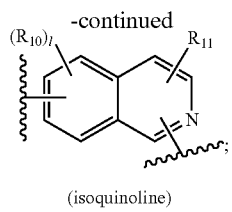
(isoquinoline)

$R_1$, $R_2$ and $R_3$ are independently hydrogen, O-alkyl, O-haloalkyl, F, Cl, Br, I, haloalkyl, $CF_3$, CN, —$CH_2CN$, $NH_2$, hydroxyl, —$(CH_2)_iNHCH_3$, —$(CH_2)_iNH_2$, —$(CH_2)_iN(CH_3)_2$, —$OC(O)CF_3$, $C_1$-$C_5$ linear or branched alkyl, haloalkyl, alkylamino, aminoalkyl, —$OCH_2Ph$, —NHCO-alkyl, COOH, —C(O)Ph, C(O)O-alkyl, C(O)H, —$C(O)NH_2$ or $NO_2$;

$R_{10}$ and $R_{11}$ are independently hydrogen, O-alkyl, O-haloalkyl, F, Cl, Br, I, haloalkyl, $CF_3$, CN, —$CH_2CN$, $NH_2$, hydroxyl, —$(CH_2)_iNHCH_3$, —$(CH_2)_iNH_2$, —$(CH_2)_iN(CH_3)_2$, —$OC(O)CF_3$, $C_1$-$C_5$ linear or branched alkyl, haloalkyl, alkylamino, aminoalkyl, —$OCH_2Ph$, —NHCO- alkyl, COOH, —C(O)Ph, C(O)O-alkyl, C(O)H, —$C(O)NH_2$ or $NO_2$;

X is a bond, NH, $C_1$ to $C_5$ hydrocarbon, O, or S;

Y is a bond, —C=O, —C=S, —C=N—$NH_2$, —C=N—OH, —CH—OH, —C=CH—CN, —C=N—CN, —CH=CH—, —C=C($CH_3$)_2, —C=N—OMe, —(C=O)—NH, —NH—(C=O), —(C=O)—O, —O—(C=O), —$(CH_2)_{1-5}$—(C=O), (C=O)—$(CH_2)_{1-5}$, —$(SO_2)$—NH—, —NH—$(SO_2)$—, $SO_2$, SO or S;

wherein said A ring is optionally substituted by 1-5 substituents which are independently O-alkyl, O-haloalkyl, F, Cl, Br, I, haloalkyl, $CF_3$, CN, —$CH_2CN$, $NH_2$, hydroxyl, —$(CH_2)_iNHCH_3$, —$(CH_2)_iNH_2$, —$(CH_2)_iN(CH_3)_2$, —$OC(O)CF_3$, $C_1$-$C_5$ linear or branched alkyl, haloalkyl, alkylamino, aminoalkyl, —$OCH_2Ph$, —NHCO-alkyl, COOH, —C(O)Ph, C(O)O— alkyl, C(O)H, —$C(O)NH_2$ or $NO_2$;

i is an integer between 0-5;
l is an integer between 1-2;
m is an integer between 1-3;
wherein
if B is a benzene ring, a thiophene ring, a furan ring or an indole ring then X is not a bond or $CH_2$ and A is not indole;
if B is indole then X is not 0;
or its pharmaceutically acceptable salt, hydrate, polymorph, metabolite, tautomer or isomer.

In one embodiment, if B of formula Ia is a thiazole ring then X is not a bond.

In one embodiment, this invention is directed to a compound of formula (II):

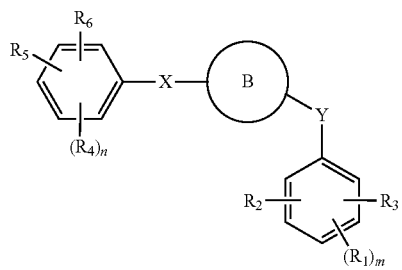

II wherein
B is

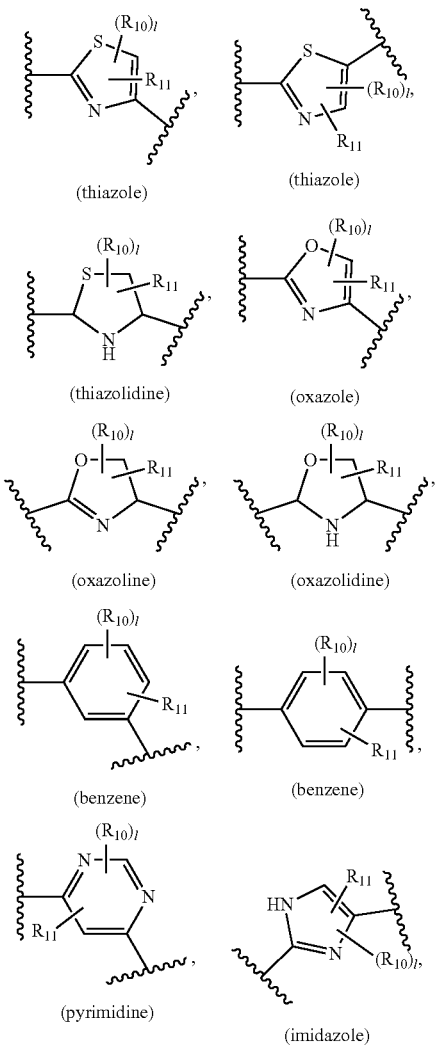

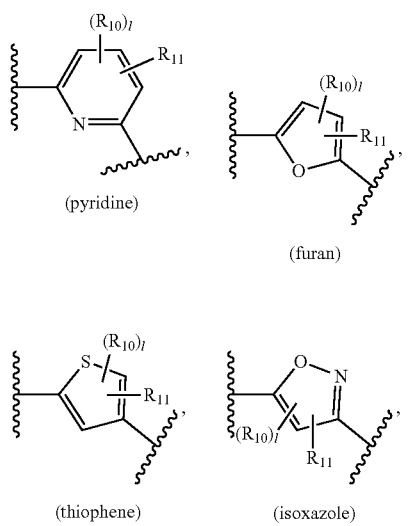

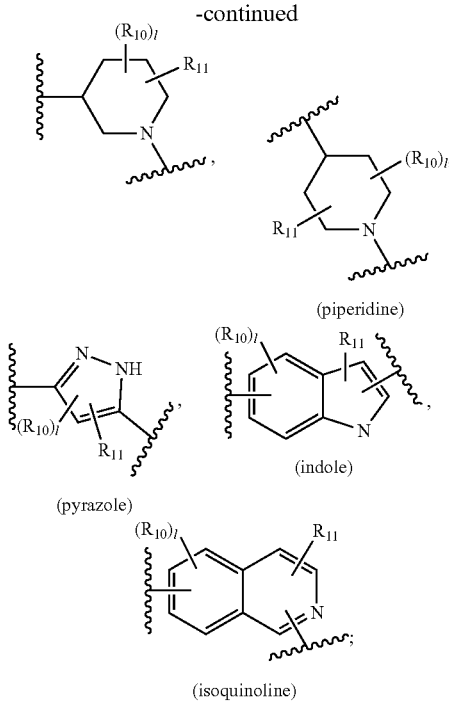

(piperidine)

(pyrazole)

(indole) or (isoquinoline)

R₁, R₂, R₃, R₄, R₅ and R₆ are independently hydrogen, O-alkyl, O-haloalkyl, F, Cl, Br, I, haloalkyl, CF₃, CN, —CH₂CN, NH₂, hydroxyl, —(CH₂)ᵢNHCH₃, —(CH₂)ᵢNH₂, —(CH₂)ᵢN(CH₃)₂, —OC(O)CF₃, C₁-C₅ linear or branched alkyl, haloalkyl, alkylamino, aminoalkyl, —OCH₂Ph, —NHCO-alkyl, COOH, —C(O)Ph, C(O)O-alkyl, C(O)H, —C(O)NH₂ or NO₂;

R₁₀ and R₁₁ are independently hydrogen, O-alkyl, O-haloalkyl, F, Cl, Br, I, haloalkyl, CF₃, CN, —CH₂CN, NH₂, hydroxyl, —(CH₂)ᵢNHCH₃, —(CH₂)ᵢNH₂, —(CH₂)ᵢN(CH₃)₂, —OC(O)CF₃, C₁-C₅ linear or branched alkyl, haloalkyl, alkylamino, aminoalkyl, —OCH₂Ph, —NHCO— alkyl, COOH, —C(O)Ph, C(O)O-alkyl, C(O)H, —C(O)NH₂ or NO₂;

X is a bond, NH, C₁ to C₅ hydrocarbon, O, or S;

Y is a bond, —C=O, —C=S, —C=N—NH₂, —C=N—OH, —CH—OH, —C=CH—CN, —C=N—CN, —CH=CH—, C=C(CH₃)₂, —C=N—OMe, —(C=O)—NH, —NH—(C=O), —(C=O)—O, —O—(C=O), —(CH₂)₁₋₅—(C=O), (C=O)—(CH₂)₁₋₅, —(SO₂)—NH—, —NH—(SO₂)—, SO₂, SO or S;

i is an integer between 0-5;

l is an integer between 1-2;

n is an integer between 1-3; and m is an integer between 1-3;

wherein if B is indole then X is not O;

or its pharmaceutically acceptable salt, hydrate, polymorph, metabolite, tautomer or isomer.

In one embodiment, if B of formula II is a thiazole ring then X is not a bond.

In one embodiment, this invention is directed to a compound of formula (III)

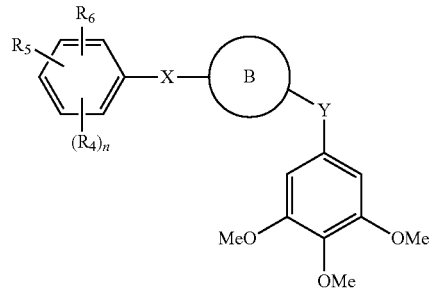

(III)

wherein

B is

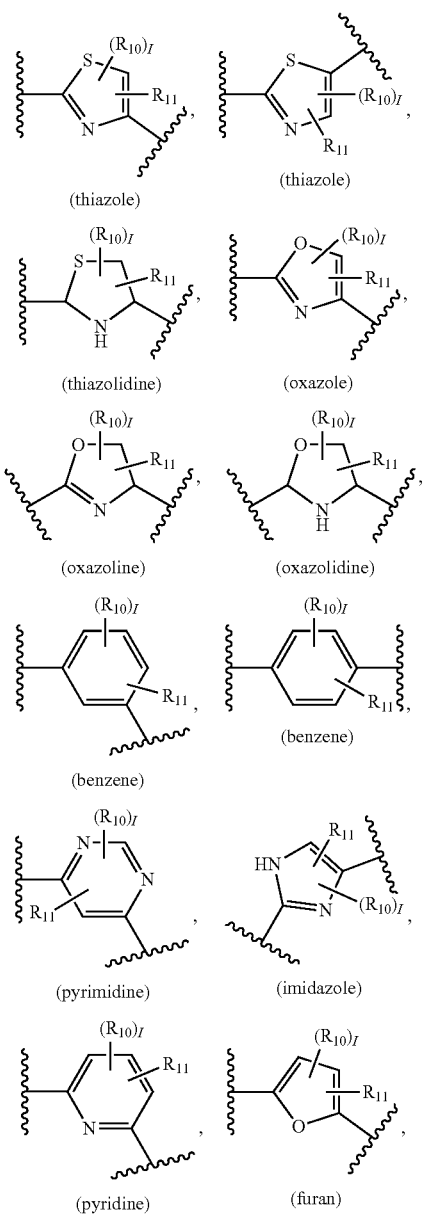

-continued

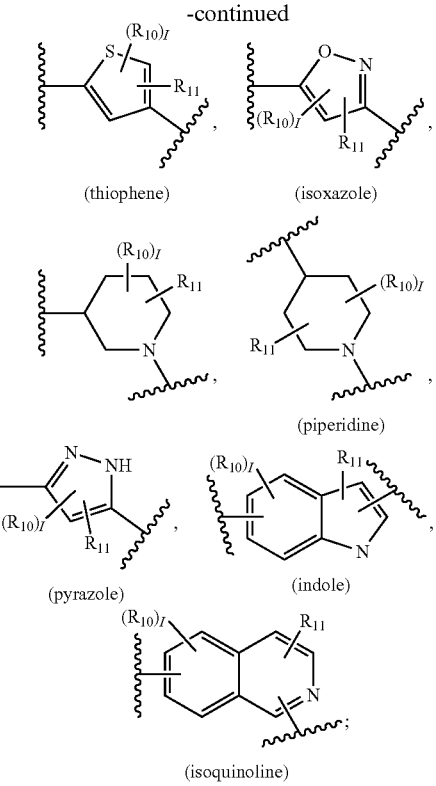

R$_4$, R$_5$ and R$_6$ are independently hydrogen, O-alkyl, O-haloalkyl, F, Cl, Br, I, haloalkyl, CF$_3$, CN, —CH$_2$CN, NH$_2$, hydroxyl, —(CH$_2$)$_i$NHCH$_3$, —(CH$_2$)$_i$NH$_2$, —(CH$_2$)$_i$N(CH$_3$)$_2$, —OC(O)CF$_3$, C$_1$-C$_5$ linear or branched alkyl, haloalkyl, alkylamino, aminoalkyl, —OCH$_2$Ph, —NHCO-alkyl, COOH, —C(O)Ph, C(O)O-alkyl, C(O)H, —C(O)NH$_2$ or NO$_2$; and R$_{10}$ and R$_{11}$ are independently hydrogen, O-alkyl, O-haloalkyl, F, Cl, Br, I, haloalkyl, CF$_3$, CN, —CH$_2$CN, NH$_2$, hydroxyl, —(CH$_2$)$_i$NHCH$_3$, —(CH$_2$)$_i$NH$_2$, —(CH$_2$)$_i$N(CH$_3$)$_2$, —OC(O)CF$_3$, C$_1$-C$_5$ linear or branched alkyl, haloalkyl, alkylamino, aminoalkyl, —OCH$_2$Ph, —NHCO— alkyl, COOH, —C(O)Ph, C(O)O-alkyl, C(O)H, —C(O)NH$_2$ or NO$_2$;

X is a bond, NH, C$_1$ to C$_5$ hydrocarbon, O, or S;

Y is a bond, —C=O, —C=S, —C=N—NH$_2$, —C=N—OH, —CH—OH, —C=CH—CN, —C=N—CN, —CH=CH—, C=C(CH$_3$)$_2$, —C=N—OMe, —(C=O)—NH, —NH—(C=O), —(C=O)—O, —O—(C=O), —(CH$_2$)$_{1-5}$—(C=O), (C=O)—(CH$_2$)$_{1-5}$, —(SO$_2$)—NH—, —NH—(SO$_2$)—, SO$_2$, SO or S;

i is an integer between 0-5;

l is an integer between 1-2; and n is an integer between 1-3;

wherein if B is indole then X is not O;

or its pharmaceutically acceptable salt, hydrate, polymorph, metabolite, tautomer or isomer.

In one embodiment, if B of formula III is a thiazole ring then X is not a bond.

In one embodiment, this invention is directed to a compound of formula (IV)

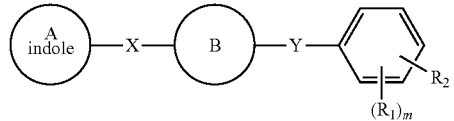

wherein ring A is an indolyl;

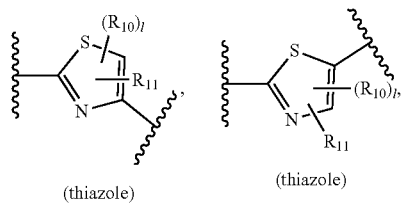

(thiazole)　(thiazole)

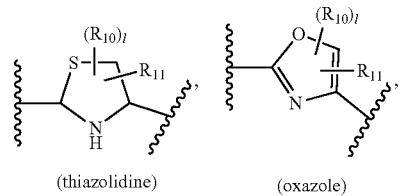

(thiazolidine)　(oxazole)

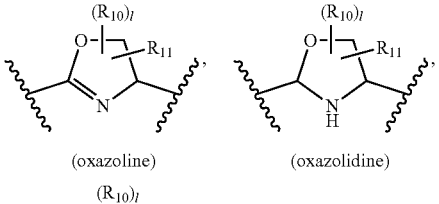

(oxazoline)　(oxazolidine)

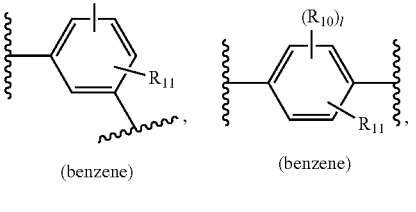

(benzene)　(benzene)

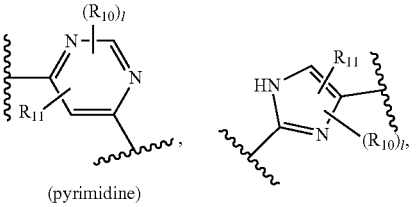

(pyrimidine)　(imidazole)

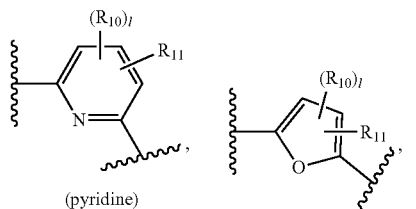

(pyridine)　(furan)

-continued

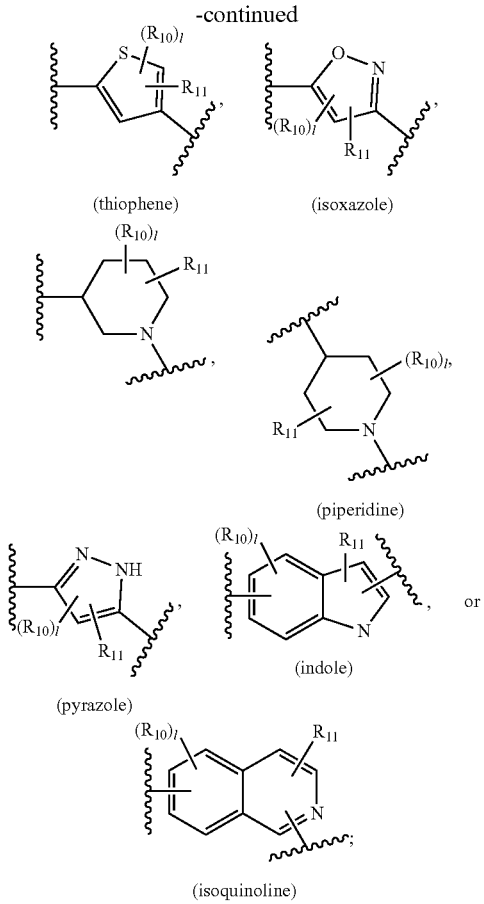

(thiophene)
(isoxazole)
(piperidine)
(pyrazole)
(indole)
(isoquinoline)

B is
$R_1$ and $R_2$ are independently hydrogen, O-alkyl, O-haloalkyl, F, Cl, Br, I, haloalkyl, $CF_3$, CN, —$CH_2CN$, $NH_2$, hydroxyl, —$(CH_2)_iNHCH_3$, —$(CH_2)_iNH_2$, —$(CH_2)_iN(CH_3)_2$, —$OC(O)CF_3$, $C_1$-$C_5$ linear or branched alkyl, haloalkyl, alkylamino, aminoalkyl, —$OCH_2Ph$, —NHCO— alkyl, COOH, —C(O)Ph, C(O)O-alkyl, C(O)H, —$C(O)NH_2$ or $NO_2$;

$R_{10}$ and $R_{11}$ are independently hydrogen, O-alkyl, O-haloalkyl, F, Cl, Br, I, haloalkyl, $CF_3$, CN, —$CH_2CN$, $NH_2$, hydroxyl, —$(CH_2)_iNHCH_3$, —$(CH_2)_iNH_2$, —$(CH_2)_iN(CH_3)_2$, —$OC(O)CF_3$, $C_1$-$C_5$ linear or branched alkyl, haloalkyl, alkylamino, aminoalkyl, —$OCH_2Ph$, —NHCO— alkyl, COOH, —C(O)Ph, C(O)O-alkyl, C(O)H, —$C(O)NH_2$ or $NO_2$;

X is a bond, NH, $C_1$ to $C_5$ hydrocarbon, O, or S;

Y is a bond, C=O, —C=S, —C=N—$NH_2$, —C=N—OH, —CH—OH, —C=CH—CN, —C=N—CN, —CH=CH—, C=$C(CH_3)_2$, —C=N—OMe, —(C=O)—NH, —NH—(C=O), —(C=O)—O, —O—(C=O), —$(CH_2)_{1-5}$—(C=O), (C=O)—$(CH_2)_{1-5}$, —$(SO_2)$—NH—, —NH—$(SO_2)$—, $SO_2$, SO or S;

wherein said A is optionally substituted by O-alkyl, O-haloalkyl, F, Cl, Br, I, haloalkyl, $CF_3$, CN, —$CH_2CN$, $NH_2$, hydroxyl, —$(CH_2)_iNHCH_3$, —$(CH_2)_iNH_2$, —$(CH_2)_iN(CH_3)_2$, —$OC(O)CF_3$, $C_1$-$C_5$ linear or branched alkyl, haloalkyl, alkylamino, aminoalkyl, —$OCH_2Ph$, —NHCO-alkyl, COOH, —C(O)Ph, C(O)O-alkyl, C(O)H, —$C(O)NH_2$ or $NO_2$; and i is an integer between 0-5;
l is an integer between 1-2; and
m is an integer between 1-4;

wherein
if B is a benzene ring, a thiophene ring, a furan ring or an indole ring then X is not a bond or $CH_2$;
or its pharmaceutically acceptable salt, hydrate, polymorph, metabolite, tautomer or isomer.

In one embodiment, if B of formula IV is a thiazole ring then X is not a bond.

In another embodiment, the indolyl of ring A of formula IV is attached to one of its 1-7 positions to X or direct to B if X is a bond (i.e nothing).

In one embodiment, this invention is directed to a compound of formula IV(a)

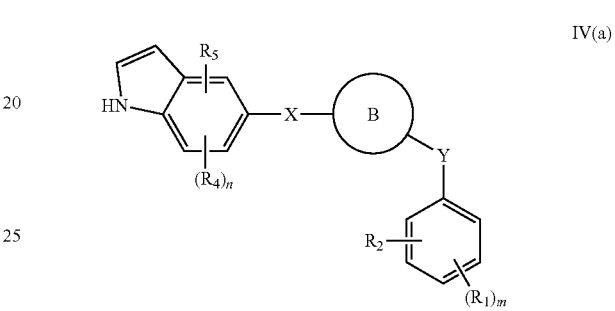

IV(a)

B is

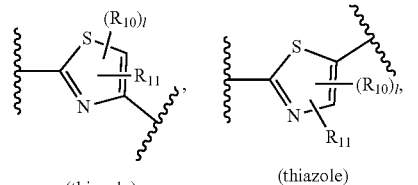

(thiazole)    (thiazole)

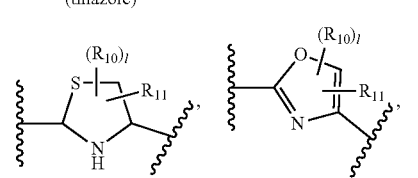

(thiazolidine)    (oxazole)

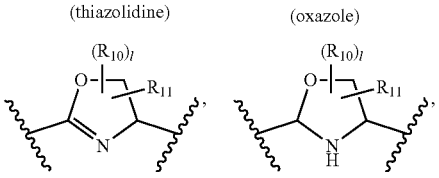

(oxazoline)    (oxazolidine)

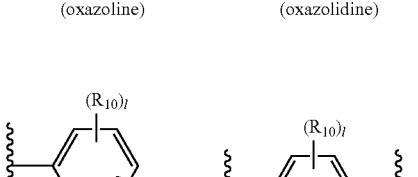

(benzene)    (benzene)

-continued

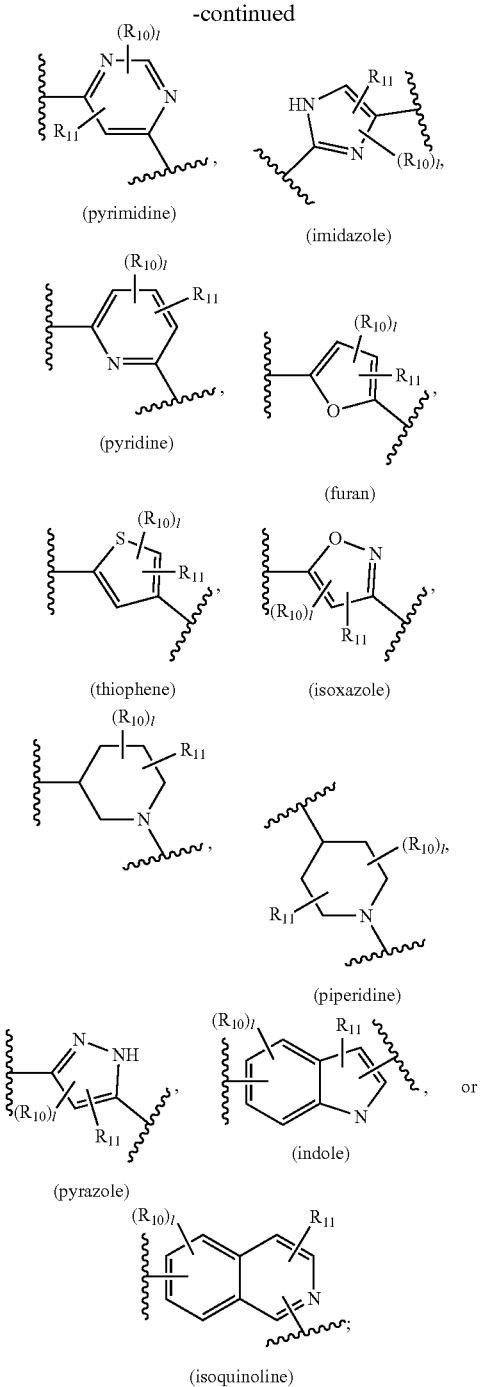

(pyrimidine)
(imidazole)
(pyridine)
(furan)
(thiophene)
(isoxazole)
(piperidine)
(pyrazole)
(indole)
(isoquinoline)

$R_1$, $R_2$, $R_4$ and $R_5$ are independently hydrogen, O-alkyl, O-haloalkyl, F, Cl, Br, I, haloalkyl, $CF_3$, CN, —$CH_2CN$, $NH_2$, hydroxyl, —$(CH_2)_iNHCH_3$, —$(CH_2)_i$ $NH_2$, —$(CH_2)_iN(CH_3)_2$, —$OC(O)CF_3$, $C_1$-$C_5$ linear or branched alkyl, haloalkyl, alkylamino, aminoalkyl, —$OCH_2Ph$, —NHCO-alkyl, COOH, —C(O)Ph, C(O)O-alkyl, C(O)H, —$C(O)NH_2$ or $NO_2$; and $R_{10}$ and $R_{11}$ are independently hydrogen, O-alkyl, O-haloalkyl, F, Cl, Br, I, haloalkyl, $CF_3$, CN, —$CH_2CN$, $NH_2$, hydroxyl, —$(CH_2)_iNHCH_3$, —$(CH_2)_iNH_2$, —$(CH_2)_iN(CH_3)_2$, —$OC(O)CF_3$, $C_1$-$C_5$ linear or branched alkyl, haloalkyl, alkylamino, aminoalkyl, —$OCH_2Ph$, —NHCO— alkyl, COOH, —C(O)Ph, C(O)O-alkyl, C(O)H, —$C(O)NH_2$ or $NO_2$;

X is a bond, NH, $C_1$ to $C_5$ hydrocarbon, O, or S;

Y is a bond or C=O, —C=S, —C=N—$NH_2$, —C=N—OH, —CH—OH, —C=CH—CN, —C=N—CN, —CH=CH—, C=C($CH_3$)$_2$, —C=N—OMe, —(C=O)—NH, —NH—(C=O), —(C=O)—O—, —O—(C=O), —$(CH_2)_{1-5}$—(C=O), (C=O)—$(CH_2)_{1-5}$, —$(SO_2)$—NH—, —NH—$(SO_2)$—, $SO_2$, SO or S;

i is an integer between 0-5;

l is an integer between 1-2;

n is an integer between 1-2; and m is an integer between 1-4;

wherein if B is a benzene ring, a thiophene ring, a furan ring or an indole ring then X is not a bond or $CH_2$;

or its pharmaceutically acceptable salt, hydrate, polymorph, metabolite, tautomer or isomer.

In one embodiment, if B of formula IVa is a thiazole ring then X is not a bond.

In one embodiment, this invention is directed to a compound of formula (V)

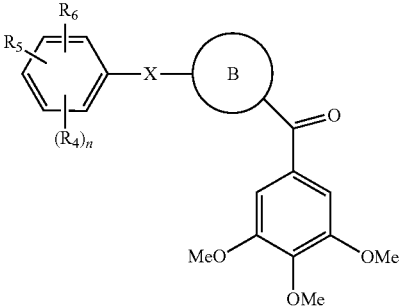

(V)

B is

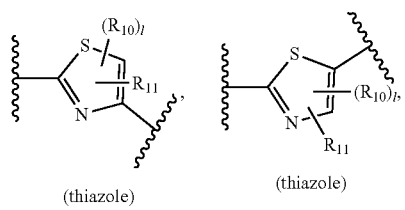

(thiazole)       (thiazole)

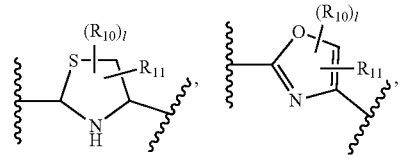

(thiazolidine)   (oxazole)

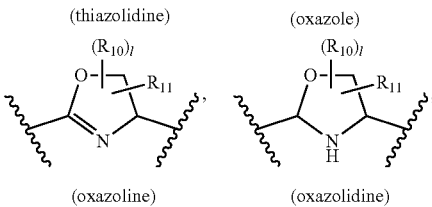

(oxazoline)      (oxazolidine)

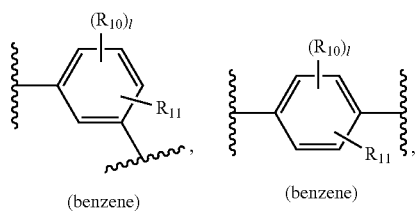

(benzene) (benzene)

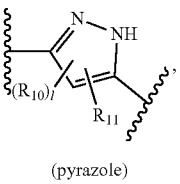

(pyrazole)

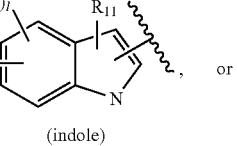

(indole)

, or

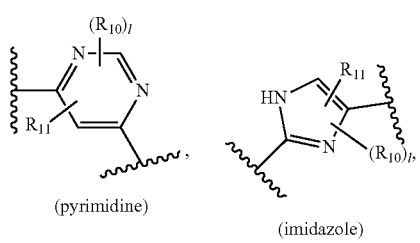

(pyrimidine) (imidazole)

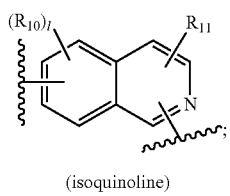

(isoquinoline)

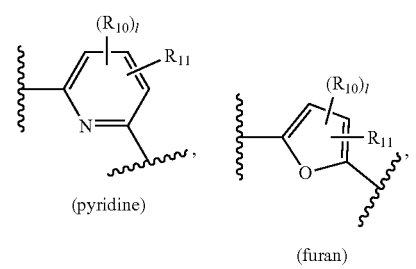

(pyridine) (furan)

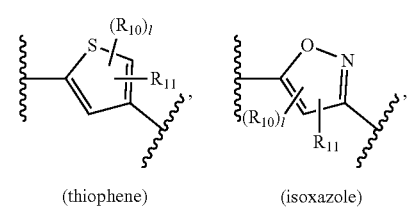

(thiophene) (isoxazole)

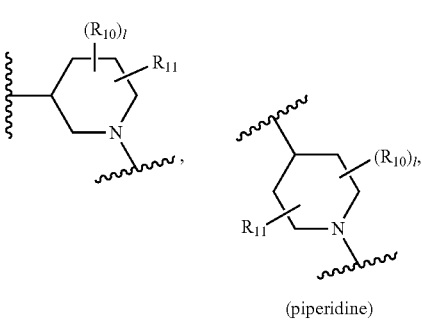

(piperidine)

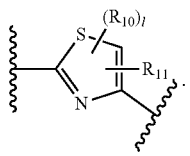

$R_4$, $R_5$ and $R_6$ are independently hydrogen, O-alkyl, O-haloalkyl, F, Cl, Br, I, haloalkyl, $CF_3$, CN, —$CH_2CN$, $NH_2$, hydroxyl, —$(CH_2)_iNHCH_3$, —$(CH_2)_iNH_2$, —$(CH_2)_iN(CH_3)_2$, —$OC(O)CF_3$, $C_{1-5}$ linear or branched alkyl, haloalkyl, alkylamino, aminoalkyl, —$OCH_2Ph$, —NHCO-alkyl, COOH, —C(O)Ph, C(O)O-alkyl, C(O)H, —$C(O)NH_2$ or $NO_2$;

$R_{10}$ and $R_{11}$ are independently hydrogen, O-alkyl, O-haloalkyl, F, Cl, Br, I, haloalkyl, $CF_3$, CN, —$CH_2CN$, $NH_2$, hydroxyl, —$(CH_2)_iNHCH_3$, —$(CH_2)_iNH_2$, —$(CH_2)_iN(CH_3)_2$, —$OC(O)CF_3$, $C_{1-5}$ linear or branched alkyl, haloalkyl, alkylamino, aminoalkyl, —$OCH_2Ph$, —NHCO— alkyl, COOH, —C(O)Ph, C(O)O-alkyl, C(O)H, —$C(O)NH_2$ or $NO_2$;

i is an integer between 1-5;

l is an integer between 1-2; and n is an integer between 1-3;

or its pharmaceutically acceptable salt, hydrate, polymorph, metabolite, tautomer or isomer.

In another embodiment, B of formula V is not a thiazole

In another embodiment, B of formula V is not an oxazole.
In another embodiment, B of formula V is not an oxazoline.
In another embodiment, B of formula V is not an imidazole.
In another embodiment, B of formula V is not a thiazole, oxazole, oxazoline or imidazole.

In one embodiment, this invention is directed to the following compounds

Formula V
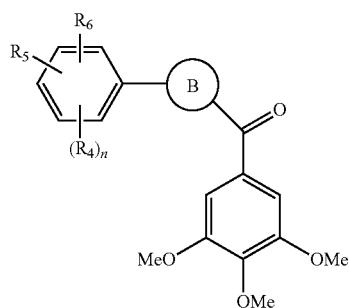
| Compound B | | $R_4$, $R_5$ and $R_6$ |
|---|---|---|
| 1a | 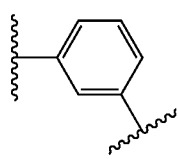 [SMILES: *c1cccc(*)c1] | H |
| 1b | 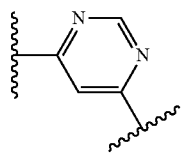 [SMILES: *c1cc(*)ncn1] | H |
| 1c | 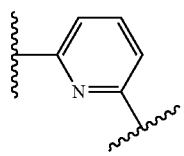 [SMILES: *c1cccc(*)n1] | H |
| 1d | 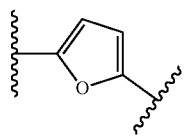 [SMILES: *c1ccc(*)o1] | H |
| 1e | 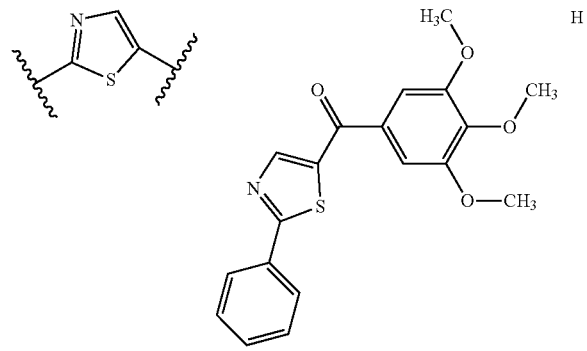 | H |

-continued
Formula V
| Compound | B | | $R_4$, $R_5$ and $R_6$ |
|---|---|---|---|
| 1f | 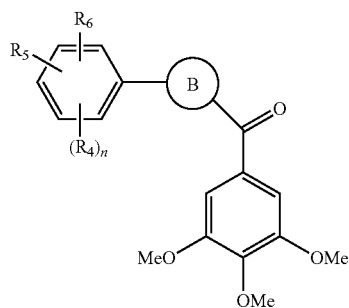 | 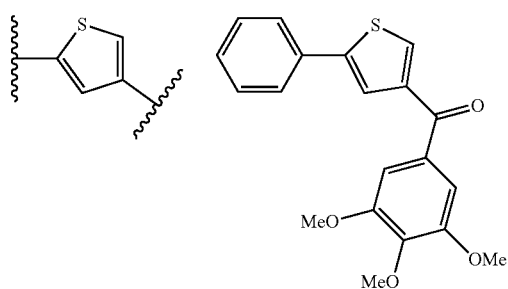 | H |
| 1g | | 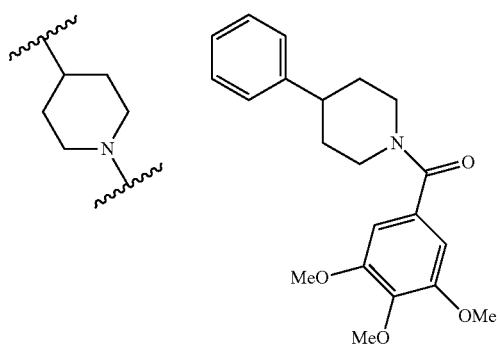 | H |
| 1h | 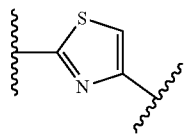 [SMILES: *c1csc(*)n1] | | H |
| 1i | 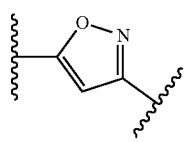 [SMILES: *c1cc(*)on1] | | H |

-continued
Formula V
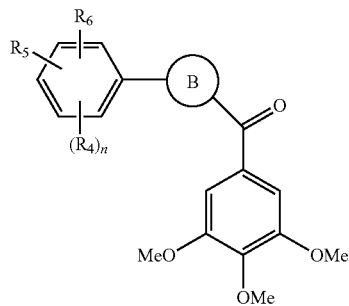
| Compound | B | | R4, R5 and R6 |
|---|---|---|---|
| 1k | 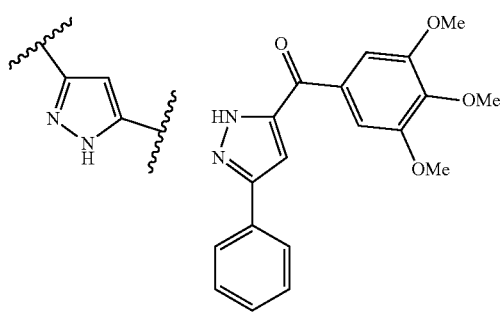 | | H |
| 1l | 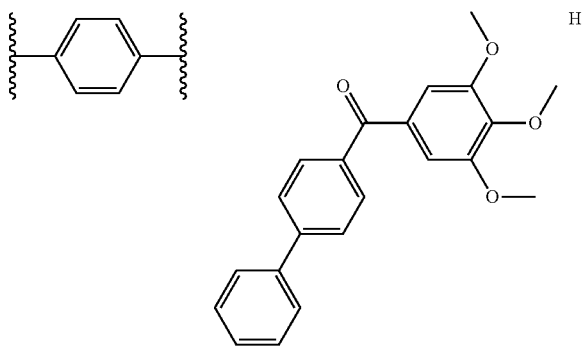 | | H |
| 35a | 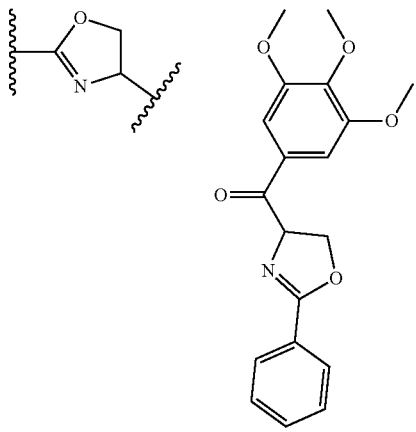 | | H |

| | Formula V |
|---|---|
| 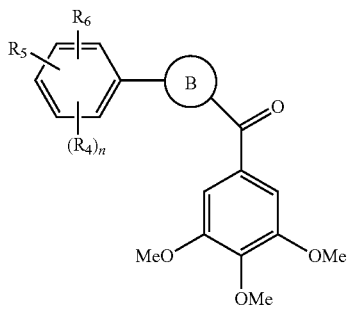 | |

| Compound | B | R₄, R₅ and R₆ |
|---|---|---|
| 36a | 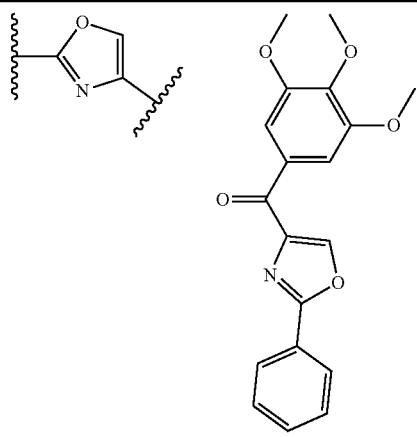 | H |

In one embodiment, this invention is directed to a compound of formula (VI)

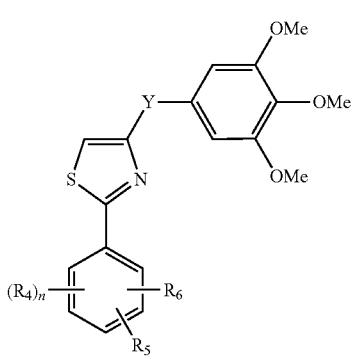
(VI)

wherein
R₄, R₅ and R₆ are independently hydrogen, O-alkyl, O-haloalkyl, F, Cl, Br, I, haloalkyl, CF₃, CN, —CH₂CN, NH₂, hydroxyl, —(CH₂)ᵢNHCH₃, —(CH₂)ᵢNH₂, —(CH₂)ᵢN(CH₃)₂, —OC(O)CF₃, C₁-C₅ linear or branched alkyl, haloalkyl, alkylamino, aminoalkyl, —OCH₂Ph, —NHCO-alkyl, COOH, —C(O)Ph, C(O)O-alkyl, C(O)H, —C(O)NH₂ or NO₂; and
Y is a bond or C=O, —C=S, —C=N—NH₂, —C=N—OH, —C=CH—CN, —C=N—CN, —CH=CH—, C=C(CH₃)₂, —C=N—OMe, —(C=O)—NH, —NH—(C=O), —(C=O)—O, —O—(C=O), —(CH₂)₁₋₅—(C=O), (C=O)—(CH₂)₁₋₅, —(SO₂)—NH—, —NH—(SO₂)—, SO₂, SO or S;
n is an integer between 1-3; and
i is an integer from 1-5;
or its pharmaceutically acceptable salt, hydrate, polymorph, metabolite, tautomer or isomer.

In one embodiment, this invention is directed to the following compounds:

| | Formula VI |
|---|---|
| 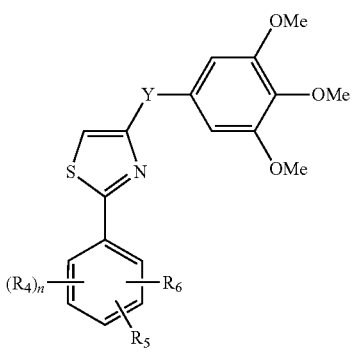 | |

| Compound | Y | R₄, R₅ and R₆ |
|---|---|---|
| 1h | —C=O | H |
| 2a | —C=C(CH₃)₂ | H |

Formula VI

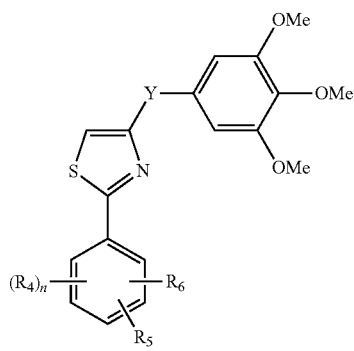

| Compound | Y | $R_4$, $R_5$ and $R_6$ |
|---|---|---|
| 2b | —CH—OH | H |
| 2c | —C=CH—CN (cis and trans) | H |
| 2d | —C=N—NH$_2$ (cis and trans) | H |
| 2e | —C=N—OH (cis and trans) | H |
| 2f | —C=N—OMe (cis and trans) | H |
| 2g | —(C=O)—NH— | H |
| 2h | —NH—(C=O)— | H |
| 2i | nothing | H |
| 2j | —C=N—CN (cis and trans) | H |
| 2k | C=O | $R_4 = R_6 = H$; $R_5 = $ p-F |
| 2l | C=O | $R_4 = R_6 = H$; $R_5 = $ p-OH |
| 2m | C=O | $R_4 = R_6 = H$; $R_5 = $ p-CH$_3$ |
| 2n | C=O | $R_4 = R_6 = H$; $R_5 = $ p-CH$_2$—CN |
| 2o | C=O | $R_4 = R_6 = H$; $R_5 = $ p-N(CH$_3$)$_2$ |
| 2p | C=O | $R_4 = $ m-F; $R_5 = $ p-F; $R_6 = $ m-F; n = 1 |
| 2q | C=O | $R_4 = R_6 = H$; $R_5 = $ p-CH$_2$—(C=O)NH$_2$ |
| 2r | C=O | $R_4 = R_6 = H$; $R_5 = $ p-CH$_2$NH$_2$ |
| 2s | C=O | $R_4 = R_6 = H$; $R_5 = $ p-CH$_2$NH—CH$_3$ |
| 2t | C=O | $R_4 = $ m-OMe; $R_5 = $ p-OMe; $R_6 = $ m-OMe; n = 1 |
| 2u | C=O | $R_4 = R_6 = H$; $R_5 = $ p-CH$_2$NMe$_2$ |

In one embodiment, this invention is directed to compound 3a:

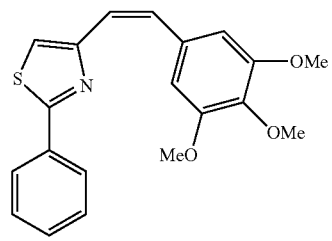

3a

In one embodiment, this invention is directed to compound 3b:

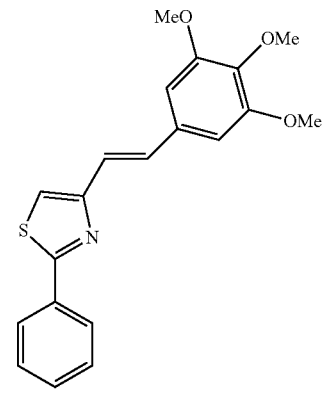

3b

In one embodiment, this invention is directed to a compound of formula (VII)

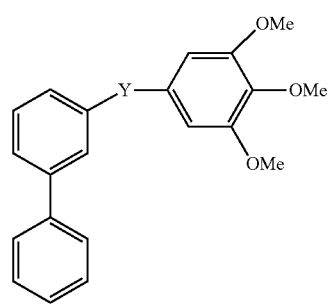

(VII)

wherein

Y is a bond or C=O, —C=S, —C=N—NH$_2$, —C=N—OH, —CH—OH, —C=CH—CN, —C=N—CN, —CH=CH—, C=C(CH$_3$)$_2$, —C=N—OMe, —(C=O)—NH, —NH—(C=O), —(C=O)—O, —O—(C=O), —(CH$_2$)$_{1-5}$—(C=O), (C=O)—(CH$_2$)$_{1-5}$, —(SO$_2$)—NH—, —NH—(SO$_2$)—, SO$_2$, SO or S;

or its pharmaceutically acceptable salt, hydrate, polymorph, metabolite, tautomer or isomer.

In one embodiment, this invention is directed to the following compounds:

Formula VII

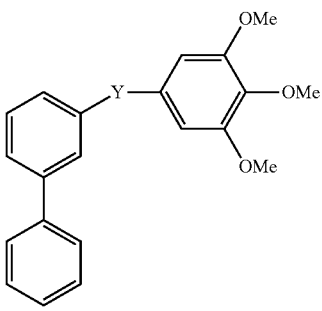

| Compound | Y |
|---|---|
| 4a | S |
| 4b | SO$_2$ |
| 4c | SO |
| 4d | —(SO$_2$)—NH— |

In one embodiment, this invention is directed to a compound of formula (VIII)

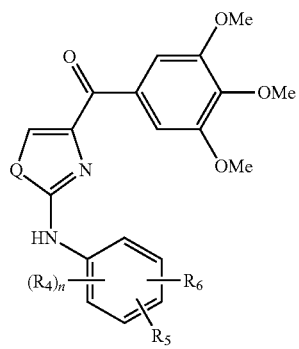

wherein

R$_4$, R$_5$ and R$_6$ are independently hydrogen, O-alkyl, O-haloalkyl, F, Cl, Br, I, haloalkyl, CF$_3$, CN, —CH$_2$CN, NH$_2$, hydroxyl, —(CH$_2$)$_i$NHCH$_3$, —(CH$_2$)$_i$NH$_2$, —(CH$_2$)$_i$N(CH$_3$)$_2$, —OC(O)CF$_3$, C$_1$-C$_5$ linear or branched alkyl, haloalkyl, alkylamino, aminoalkyl, —OCH$_2$Ph, —NHCO-alkyl, COOH, —C(O)Ph, C(O)O-alkyl, C(O)H, —C(O)NH$_2$ or NO$_2$;

Q is S, O or NH;

i is an integer between 0-5; and n is an integer between 1-3;

or its pharmaceutically acceptable salt, hydrate, polymorph, metabolite, tautomer or isomer.

In one embodiment, this invention is directed to the following compounds:

Formula VIII

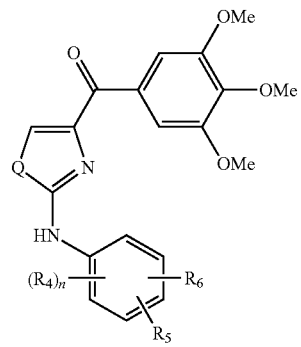

| Compound | R$_4$ | R$_5$ | R$_6$ | Q |
|---|---|---|---|---|
| 5a | H, n = 1 | H | H | S |
| 5b | H, n = 1 | p-CH$_3$ | H | S |
| 5c | H, n = 1 | p-F | H | S |
| 5d | H, n = 1 | p-Cl | H | S |
| 5e | H, n = 1 | H | H | N |

In one embodiment, this invention is directed to a compound of formula (IX)

(IX)

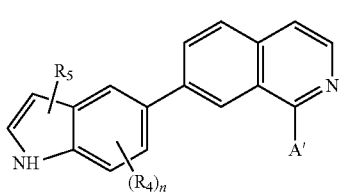

wherein

R$_4$ and R$_5$ are independently hydrogen, O-alkyl, O-haloalkyl, F, Cl, Br, I, haloalkyl, CF$_3$, CN, —CH$_2$CN, NH$_2$, hydroxyl, —(CH$_2$)$_i$NHCH$_3$, —(CH$_2$)$_i$NH$_2$, —(CH$_2$)$_i$N(CH$_3$)$_2$, —OC(O)CF$_3$, C$_1$-C$_5$ linear or branched alkyl, haloalkyl, alkylamino, aminoalkyl, —OCH$_2$Ph, —NHCO-alkyl, COOH, —C(O)Ph, C(O)O-alkyl, C(O)H, —(O)NH$_2$ or NO$_2$;

A' is halogen; substituted or unsubstituted single-, fused- or multiple-ring, aryl or (hetero)cyclic ring systems; substituted or unsubstituted, saturated or unsaturated N-heterocycles; substituted or unsubstituted, saturated or unsaturated S-heterocycles; substituted or unsubstituted, saturated or unsaturated O-heterocycles; substituted or unsubstituted, saturated or unsaturated cyclic hydrocarbons; or substituted or unsubstituted, saturated or unsaturated mixed heterocycles; wherein said A' ring is optionally substituted by 1-5 substituents which are independently O-alkyl, O-haloalkyl, F, Cl, Br, I, haloalkyl, CF$_3$, CN, —CH$_2$CN, NH$_2$, hydroxyl, —(CH$_2$)$_i$NHCH$_3$, —(CH$_2$)$_i$NH$_2$, —(CH$_2$)$_i$N(CH$_3$)$_2$, —OC(O)CF$_3$, C$_1$-C$_5$ linear or branched alkyl, haloalkyl, alkylamino, aminoalkyl, —OCH$_2$Ph, —NHCO-alkyl, COOH, —C(O)Ph, C(O)O-alkyl, C(O)H, —C(O)NH$_2$ or NO$_2$;

i is an integer between 1-5; and n is an integer between 1-3;

or its pharmaceutically acceptable salt, hydrate, polymorph, metabolite, tautomer or isomer.

In one embodiment, a compound of Formula IX is represented by the structures of the following compounds:

Formula IX

| Compound | A' | R₄, R₅ |
|---|---|---|
| 6a | 3,4,5-trimethoxyphenyl (H₃CO, OCH₃, OCH₃) | H |
| 6b | 5-indolyl | H |
| 6c | 4-fluorophenyl | H |
| 6d | Cl | H |

In another embodiment A' of formula IX is a halogen. In one embodiment A' of formula IX is a phenyl. In another embodiment A' of formula IX is substituted phenyl. In another embodiment the substitution of A' is halogen. In another embodiment the substitution is 4-F. In another embodiment the substitution is 3,4,5-(OCH₃)₃. In another embodiment, A' of formula IX is substituted or unsubstituted 5-indolyl. In another embodiment, A' of formula IX is substituted or unsubstituted 2-indolyl. In another embodiment, A' of formula IX is substituted or unsubstituted 3-indolyl. In another embodiment, compounds of formula IX are presented in FIG. 16A.

In one embodiment, this invention is directed to a compound of formula (IXa)

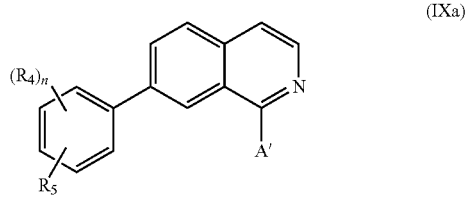

(IXa)

wherein

R₄ and R₅ are independently hydrogen, O-alkyl, O-haloalkyl, F, Cl, Br, I, haloalkyl, CF₃, CN, —CH₂CN, NH₂, hydroxyl, —(CH₂)ᵢNHCH₃, —(CH₂)ᵢNH₂, —(CH₂)ᵢN(CH₃)₂, —OC(O)CF₃, C₁-C₅ linear or branched alkyl, haloalkyl, alkylamino, aminoalkyl, —OCH₂Ph, —NHCO-alkyl, COOH, —C(O)Ph, C(O)O-alkyl, C(O)H, —(O)NH₂ or NO₂;

A' is halogen; substituted or unsubstituted single-, fused- or multiple-ring, aryl or (hetero)cyclic ring systems; substituted or unsubstituted, saturated or unsaturated N-heterocycles; substituted or unsubstituted, saturated or unsaturated S-heterocycles; substituted or unsubstituted, saturated or unsaturated O-heterocycles; substituted or unsubstituted, saturated or unsaturated cyclic hydrocarbons; or substituted or unsubstituted, saturated or unsaturated mixed heterocycles; wherein said A' ring is optionally substituted by 1-5 substituents which are independently O-alkyl, O-haloalkyl, F, Cl, Br, I, haloalkyl, CF₃, CN, —CH₂CN, NH₂, hydroxyl, —(CH₂)ᵢNHCH₃, —(CH₂)ᵢNH₂, —(CH₂)ᵢN(CH₃)₂, —OC(O)CF₃, C₁-C₅ linear or branched alkyl, haloalkyl, alkylamino, aminoalkyl, —OCH₂Ph, —NHCO-alkyl, COOH, —C(O)Ph, C(O)O-alkyl, C(O)H, —C(O)NH₂ or NO₂;

i is an integer between 1-5; and n is an integer between 1-3;

or its pharmaceutically acceptable salt, hydrate, polymorph, metabolite, tautomer or isomer.

In another embodiment A' of formula IXa is a halogen. In one embodiment A' of formula IXa is a phenyl. In another embodiment A' of formula IXa is substituted phenyl. In another embodiment the substitution of A' is halogen. In another embodiment the substitution is 4-F. In another embodiment the substitution is 3,4,5-(OCH₃)₃. In another embodiment, A' of formula IXa is substituted or unsubstituted 5-indolyl. In another embodiment, A' of formula IXa is substituted or unsubstituted 2-indolyl. In another embodiment, A' of formula IXa is substituted or unsubstituted 3-indolyl.

In another embodiment, a compound of formula IXa is 1-chloro-7-(4-fluorophenyl)isoquinoline. In another embodiment, a compound of formula IXa is 7-(4-fluorophenyl)-1-(1H-indol-5-yl)isoquinoline. In another embodiment, a compound of formula IXa is 7-(4-fluorophenyl)-1-(3,4,5-trimethoxyphenyl)isoquinoline. In another embodiment, a compound of formula IXa is 1,7-bis(4-fluorophenyl)isoquinoline (40). In another embodiment, a compound of formula IXa is 1,7-bis(3,4,5-trimethoxyphenyl)isoquinoline. In another embodiment, a compound of formula IXa is 1-(4-fluorophenyl)-7-(3,4,5-trimethoxyphenyl)isoquinoline. In another embodiment, a compound of formula IXa is 1-(1H-indol-5-yl)-7-(3,4,5-trimethoxyphenyl)isoquinoline. In another embodiment, a compound of formula IXa is 1-chloro-7-(3,4,5-trimethoxyphenyl)isoquinoline.

In one embodiment, this invention is directed to a compound represented by the structure of formula XI:

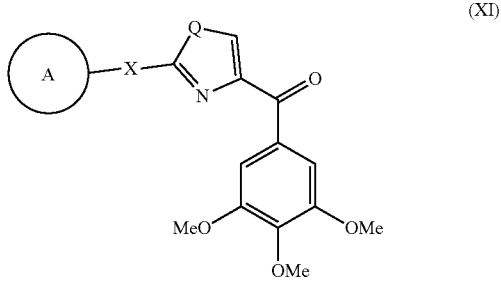

(XI)

wherein

X is a bond, NH or S;

Q is O, NH or S; and

A is substituted or unsubstituted single-, fused- or multiple-ring aryl or (hetero)cyclic ring systems; substituted or unsubstituted, saturated or unsaturated N-heterocycles; substituted or unsubstituted, saturated or unsaturated S-heterocycles; substituted or unsubstituted, saturated or unsaturated O-heterocycles; substituted or unsubstituted, saturated or unsaturated cyclic hydrocarbons; or substituted or unsubstituted, saturated or unsaturated mixed heterocycles; wherein said A ring is optionally substituted by 1-5 1-5 substituents which are independently O-alkyl, O-haloalkyl, F, Cl, Br, I, haloalkyl, $CF_3$, CN, —$CH_2CN$, $NH_2$, hydroxyl, —$(CH_2)_iNHCH_3$, —$(CH_2)_iNH_2$, —$(CH_2)_iN(CH_3)_2$, —$OC(O)CF_3$, $C_1$-$C_5$ linear or branched alkyl, haloalkyl, alkylamino, aminoalkyl, —$OCH_2Ph$, —NHCO-alkyl, COOH, —C(O)Ph, C(O)O-alkyl, C(O)H, —$C(O)NH_2$ or $NO_2$; and i is an integer from 0-5;

or its pharmaceutically acceptable salt, hydrate, polymorph, metabolite, tautomer or isomer.

In one embodiment if Q of Formula XI is S, then X is not a bond.

In one embodiment, A of compound of Formula XI is Ph. In another embodiment, A of compound of Formula XI is substituted Ph. In another embodiment, the substitution is 4-F. In another embodiment, the substitution is 4-Me. In another embodiment, Q of compound of Formula XI is S. In another embodiment, X of compound of Formula XI is NH. Non limiting examples of compounds of Formula XI are selected from: (2-(phenylamino)thiazol-4-yl)(3,4,5-trimethoxyphenyl)methanone (5a), (2-(p-tolylamino)thiazol-4-yl)(3,4,5-trimethoxyphenyl)methanone (5b), (2-(p-fluorophenylamino)thiazol-4-yl)(3,4,5-trimethoxyphenyl)methanone (5c), (2-(4-chlorophenylamino)thiazol-4-yl)(3,4,5-trimethoxyphenyl)methanone (5d), (2-(phenylamino)-1H-imidazol-4-yl)(3,4,5-trimethoxyphenyl)methanone (5e), (2-(phenylamino)thiazol-4-yl)(3,4,5-trimethoxyphenyl)methanone hydrochloride salt (5Ha), (2-(p-tolylamino)thiazol-4-yl)(3,4,5-trimethoxyphenyl)methanone hydrochloride salt (5Hb), (2-(p-fluorophenylamino)thiazol-4-yl)(3,4,5-trimethoxyphenyl)methanone hydrochloride salt (5Hc), (2-(4-chlorophenylamino)thiazol-4-yl)(3,4,5-trimethoxyphenyl)methanone hydrochloride salt (5Hd), (2-(phenylamino)-1H-imidazol-4-yl)(3,4,5-trimethoxyphenyl)methanone hydrochloride salt (5He).

In one embodiment, this invention is directed to a compound represented by the structure of formula XI(a):

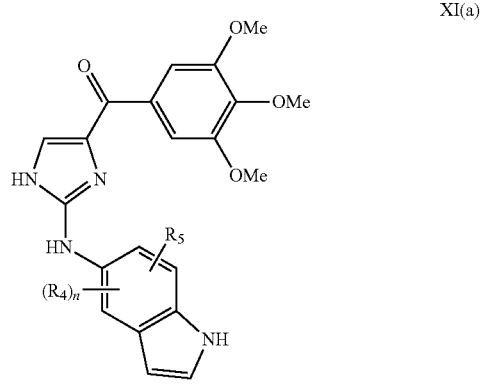

XI(a)

wherein $R_4$ and $R_5$ are independently hydrogen, O-alkyl, O-haloalkyl, F, Cl, Br, I, haloalkyl, $CF_3$, CN, —$CH_2CN$, $NH_2$, hydroxyl, —$(CH_2)_iNHCH_3$, —$(CH_2)_iNH_2$, —$(CH_2)_iN(CH_3)_2$, —$OC(O)CF_3$, $C_1$-$C_5$ linear or branched alkyl, haloalkyl, alkylamino, aminoalkyl, —$OCH_2Ph$, —NHCO-alkyl, COOH, —C(O)Ph, C(O)O-alkyl, C(O)H, —$C(O)NH_2$ or $NO_2$;

i is an integer from 0-5; and n is an integer between 1-4;

or its pharmaceutically acceptable salt, hydrate, polymorph, metabolite, tautomer or isomer.

In one embodiment, this invention is directed to a compound represented by the structure of formula XI(b):

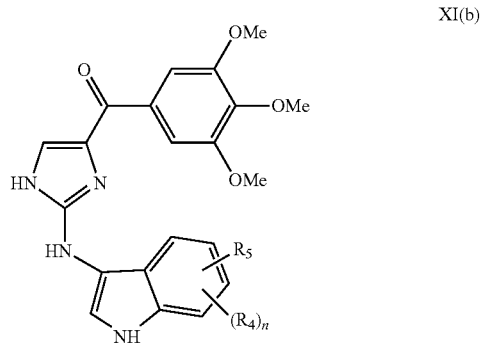

XI(b)

wherein $R_4$ and $R_5$ are independently hydrogen, O-alkyl, O-haloalkyl, F, Cl, Br, I, haloalkyl, $CF_3$, CN, —$CH_2CN$, $NH_2$, hydroxyl, —$(CH_2)_iNHCH_3$, —$(CH_2)_iNH_2$, —$(CH_2)_iN(CH_3)_2$, —$OC(O)CF_3$, $C_1$-$C_5$ linear or branched alkyl, haloalkyl, alkylamino, aminoalkyl, —$OCH_2Ph$, —NHCO-alkyl, COOH, —C(O)Ph, C(O)O-alkyl, C(O)H, —$C(O)NH_2$ or $NO_2$;

i is an integer from 0-5; and n is an integer between 1-4;

or its pharmaceutically acceptable salt, hydrate, polymorph, metabolite, tautomer or isomer.

In one embodiment, this invention is directed to a compound represented by the structure of formula XI(c):

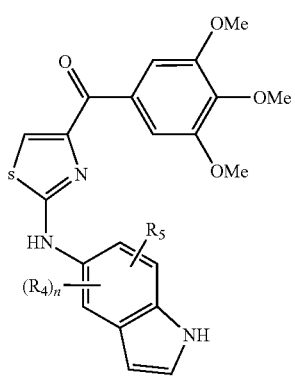

XI(c)

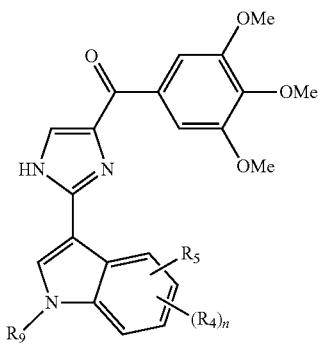

XI(e)

wherein $R_4$ and $R_5$ are independently hydrogen, O-alkyl, O-haloalkyl, F, Cl, Br, I, haloalkyl, $CF_3$, CN, —$CH_2CN$, $NH_2$, hydroxyl, —$(CH_2)_iNHCH_3$, —$(CH_2)_iNH_2$, —$(CH_2)_iN(CH_3)_2$, —$OC(O)CF_3$, $C_1$-$C_5$ linear or branched alkyl, haloalkyl, alkylamino, aminoalkyl, —$OCH_2Ph$, —NHCO-alkyl, COOH, —C(O)Ph, C(O)O-alkyl, C(O)H, —$C(O)NH_2$ or $NO_2$;

i is an integer from 0-5; and n is an integer between 1-4;

or its pharmaceutically acceptable salt, hydrate, polymorph, metabolite, tautomer or isomer.

In one embodiment, this invention is directed to a compound represented by the structure of formula XI(d):

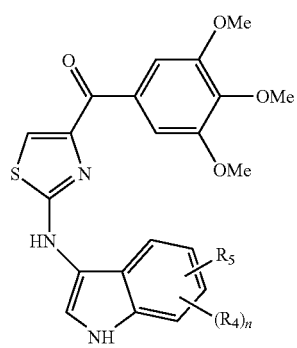

XI(d)

wherein $R_4$ and $R_5$ are independently hydrogen, O-alkyl, O-haloalkyl, F, Cl, Br, I, haloalkyl, $CF_3$, CN, —$CH_2CN$, $NH_2$, hydroxyl, —$(CH_2)_iNHCH_3$, —$(CH_2)_iNH_2$, —$(CH_2)_iN(CH_3)_2$, —$OC(O)CF_3$, $C_1$-$C_5$ linear or branched alkyl, haloalkyl, alkylamino, aminoalkyl, —$OCH_2Ph$, —NHCO-alkyl, COOH, —C(O)Ph, C(O)O-alkyl, C(O)H, —$C(O)NH_2$ or $NO_2$;

i is an integer from 0-5; and n is an integer between 1-4;

or its pharmaceutically acceptable salt, hydrate, polymorph, metabolite, tautomer or isomer.

In one embodiment, this invention is directed to a compound represented by the structure of formula XI(e):

wherein $R_4$ and $R_5$ are independently hydrogen, O-alkyl, O-haloalkyl, F, Cl, Br, I, haloalkyl, $CF_3$, CN, —$CH_2CN$, $NH_2$, hydroxyl, —$(CH_2)_iNHCH_3$, —$(CH_2)_iNH_2$, —$(CH_2)_iN(CH_3)_2$, —$OC(O)CF_3$, $C_1$-$C_5$ linear or branched alkyl, haloalkyl, alkylamino, aminoalkyl, —$OCH_2Ph$, —NHCO-alkyl, COOH, —C(O)Ph, C(O)O-alkyl, C(O)H, —$C(O)NH_2$ or $NO_2$;

$R_9$ is H, linear or branched, substituted or unsubstituted alkyl, substituted or unsubstituted aryl, —$CH_2Ph$, substituted benzyl, haloalkyl, aminoalkyl, —$OCH_2Ph$, substituted or unsubstituted $SO_2$-aryl, substituted or unsubstituted —(C=O)-aryl or OH;

i is an integer from 0-5; and n is an integer between 1-4;

or its pharmaceutically acceptable salt, hydrate, polymorph, metabolite, tautomer or isomer.

In another embodiment, a compound of formula XI is represented by the structure of compound 55:

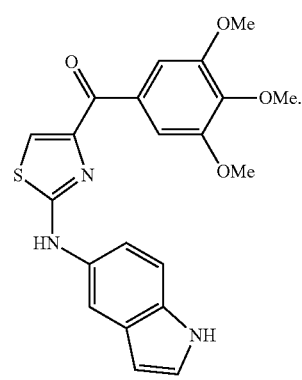

(55)

In another embodiment, a compound of formula XI (e) is represented by the structure of compound 17ya:

| Compound | Structure |
|---|---|
| | (17ya) 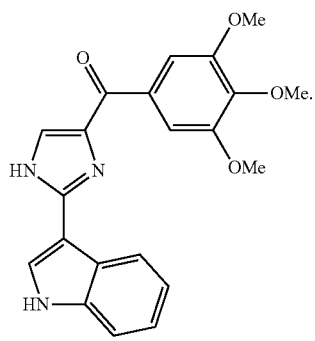 |
| 8 | 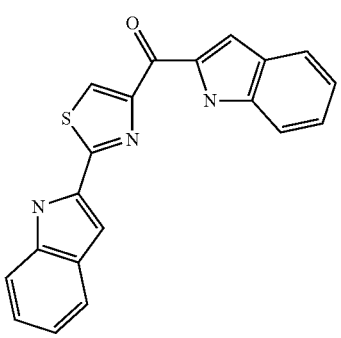 [SMILES: O=C(c1csc(-c2cc3ccccc3[nH]2)n1)c1cc2ccccc2[nH]1] |
In another embodiment, a compound of formula XI (e) is represented by the structure of compound 17yab:
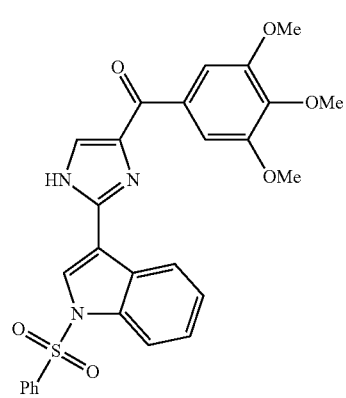
17yab
| 9 | 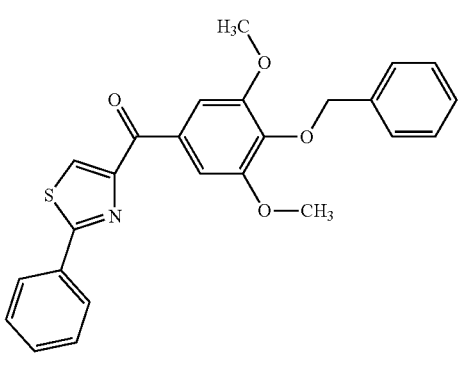 [SMILES: COc1cc(C(=O)c2csc(-c3ccccc3)n2)cc(OC)c1OCc1ccccc1] |
| 10 | 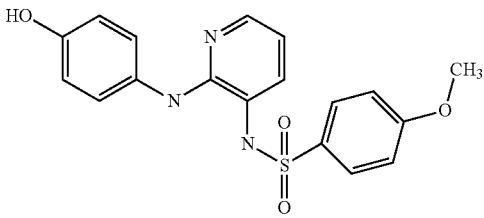 [SMILES: COc1ccc(S(=O)(=O)Nc2cccnc2Nc2ccc(O)cc2)cc1] |
| 11 | |
In another embodiment, a compound of formula XI (e) is represented by the structure of compound 17yac:
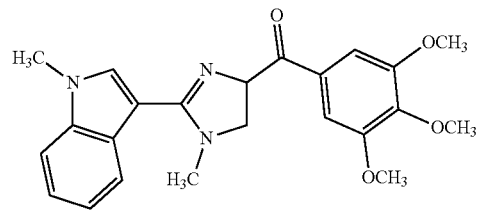
17yac
| 12 | 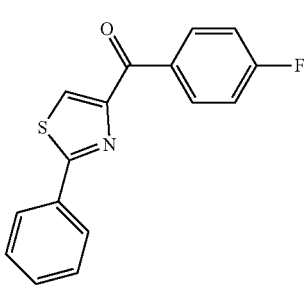 [SMILES: O=C(c1ccc(F)cc1)c1csc(-c2ccccc2)n1] |
In one embodiment, this invention provides a compound represented by the following structures:

| Compound | Structure |
|---|---|
| 13 | 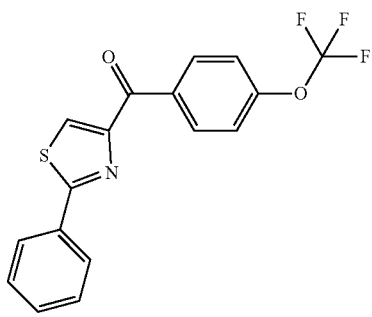 [SMILES: O=C(c1ccc(OC(F)(F)F)cc1)c1csc(-c2ccccc2)n1] |
| 14 | 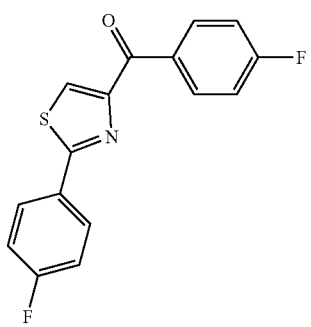 [SMILES: O=C(c1ccc(F)cc1)c1csc(-c2ccc(F)cc2)n1] |
| 16 | 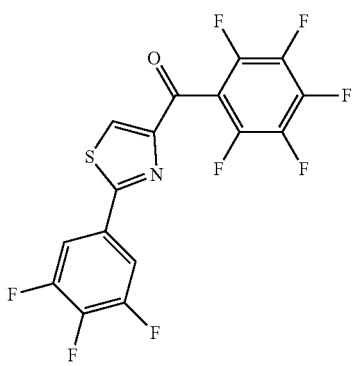 [SMILES: O=C(c1csc(-c2cc(F)c(F)c(F)c2)n1)c1c(F)c(F)c(F)c(F)c1F] |
| 17 | 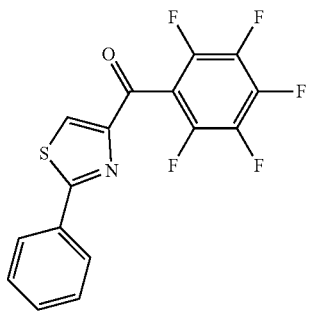 [SMILES: O=C(c1csc(-c2ccccc2)n1)c1c(F)c(F)c(F)c(F)c1F] |
| 18 | 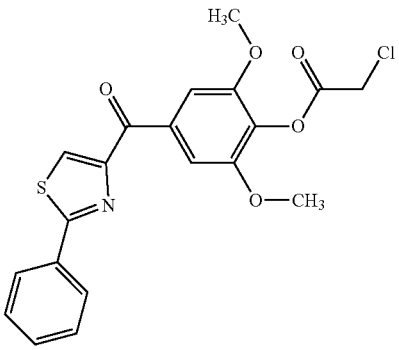 [SMILES: COc1cc(C(=O)c2csc(-c3ccccc3)n2)cc(OC)c1OC(=O)CCl] |
| 19 | 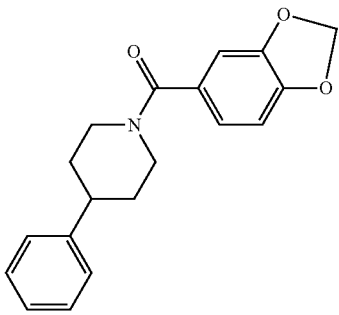 [SMILES: O=C(c1ccc2c(c1)OCO2)N1CCC(c2ccccc2)CC1] |
| 20 | 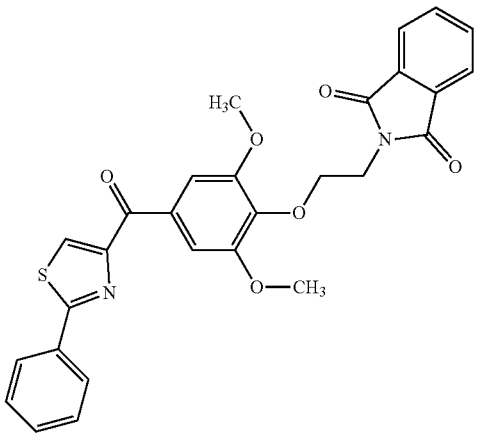 [SMILES: COc1cc(C(=O)c2csc(-c3ccccc3)n2)cc(OC)c1OCCN1C(=O)c2ccccc2C1=O] |
| 21 | 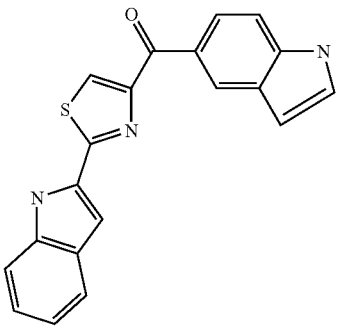 [SMILES: O=C(c1ccc2[nH]ccc2c1)c1csc(-c2cc3ccccc3[nH]2)n1] |

| Compound | Structure |
|---|---|
| 22 | 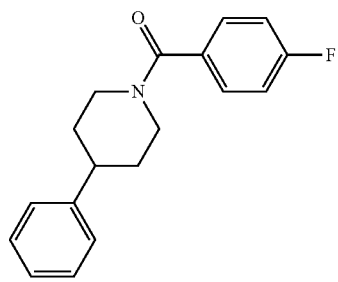 [SMILES: O=C(c1ccc(F)cc1)N1CCC(c2ccccc2)CC1] |
| 23 | 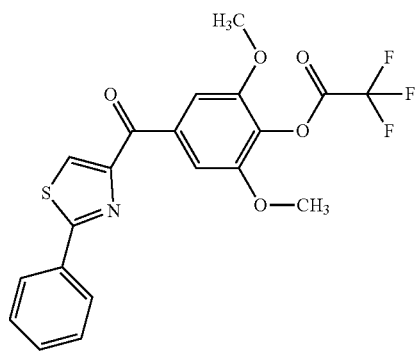 [SMILES: COc1cc(C(=O)c2csc(-c3ccccc3)n2)cc(OC)c1OC(=O)C(F)(F)F] |
| 24 | 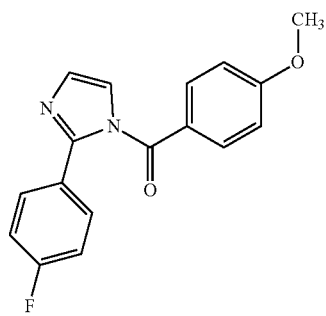 [SMILES: COc1ccc(C(=O)n2ccnc2-c2ccc(F)cc2)cc1] |
| 25 | 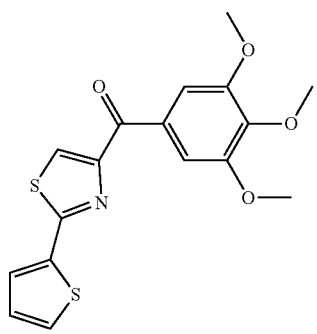 [SMILES: COc1cc(C(=O)c2csc(-c3cccs3)n2)cc(OC)c1OC] |
| 26 | 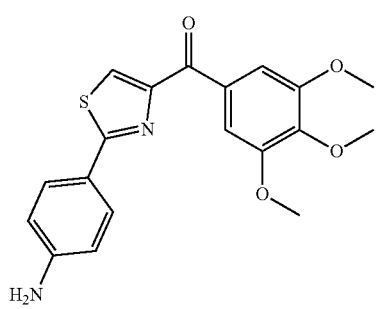 [SMILES: COc1cc(C(=O)c2csc(-c3ccc(N)cc3)n2)cc(OC)c1OC] |
| Compound | Structure |
|---|---|
| 27 | 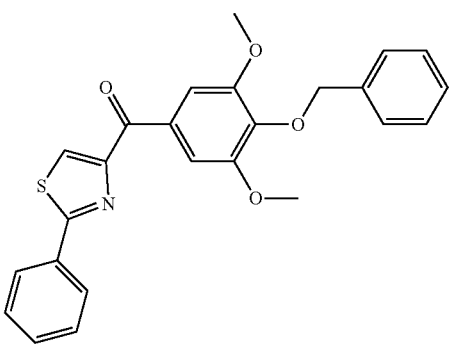 [SMILES: COc1cc(C(=O)c2csc(-c3ccccc3)n2)cc(OC)c1OCc1ccccc1] |
| 28 | 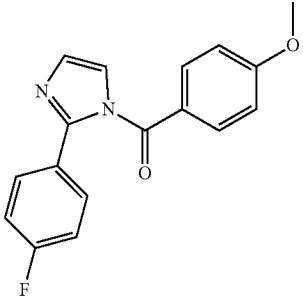 [SMILES: COc1ccc(C(=O)n2ccnc2-c2ccc(F)cc2)cc1] |
| 29 | 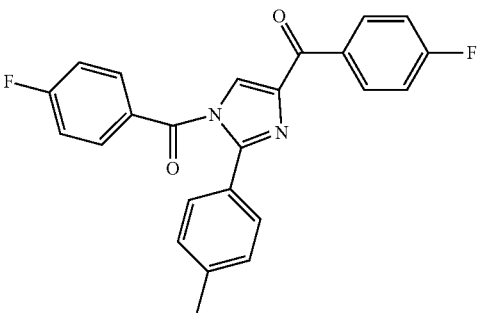 [SMILES: Cc1ccc(-c2nc(C(=O)c3ccc(F)cc3)cn2C(=O)c2ccc(F)cc2)cc1] |
| 30 | 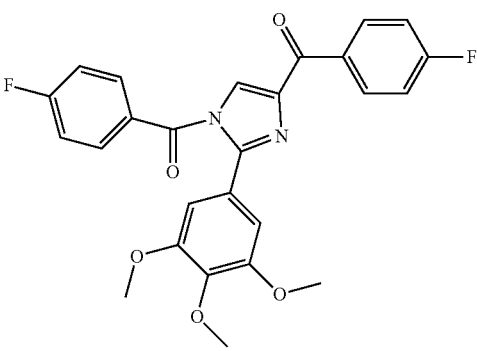 [SMILES: COc1cc(-c2nc(C(=O)c3ccc(F)cc3)cn2C(=O)c2ccc(F)cc2)cc(OC)c1OC] |

| Compound | Structure |
|---|---|
| 32 | 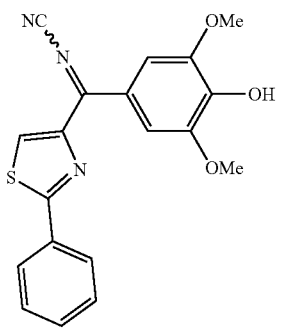 [SMILES: COc1cc(C(=NC#N)c2csc(-c3ccccc3)n2)cc(OC)c1O] |
| 33 | 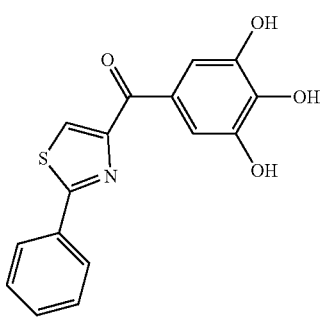 [SMILES: O=C(c1cc(O)c(O)c(O)c1)c1csc(-c2ccccc2)n1] |
| 34 | 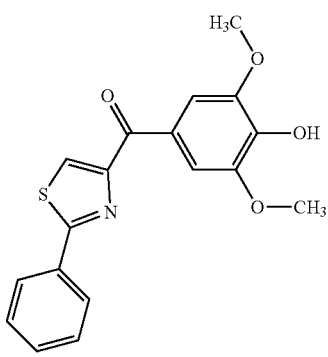 [SMILES: COc1cc(C(=O)c2csc(-c3ccccc3)n2)cc(OC)c1O] |
| 35 | 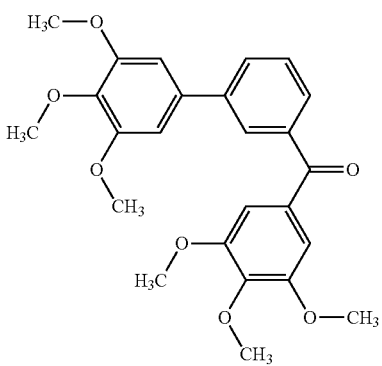 |
| Compound | Structure |
|---|---|
| 40 | 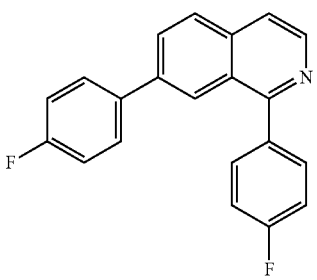 [SMILES: Fc1ccc(-c2ccc3ccnc(-c4ccc(F)cc4)c3c2)cc1] |
| 41 | 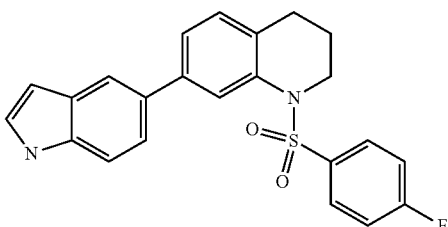 |
| 42 | 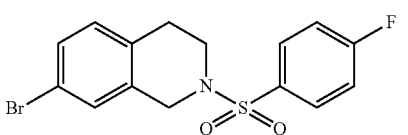 [SMILES: O=S(=O)(c1ccc(F)cc1)N1CCc2ccc(Br)cc2C1] |
| 43 | 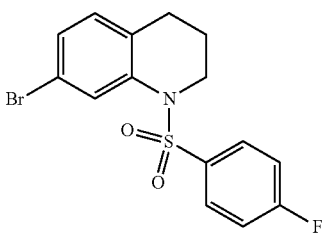 [SMILES: O=S(=O)(c1ccc(F)cc1)N1CCCc2ccc(Br)cc21] |
| 44 | 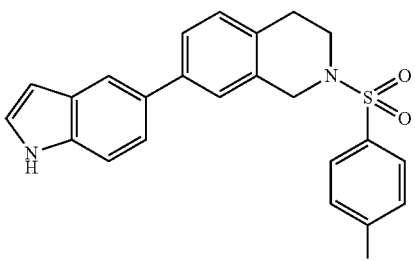 |
| 45 | 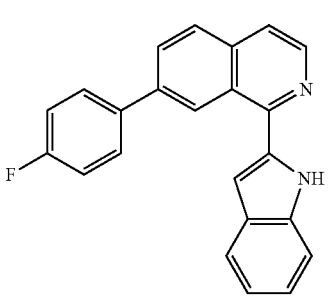 [SMILES: Fc1ccc(-c2ccc3ccnc(-c4cc5ccccc5[nH]4)c3c2)cc1] |

| Compound | Structure |
|---|---|
| 46 | 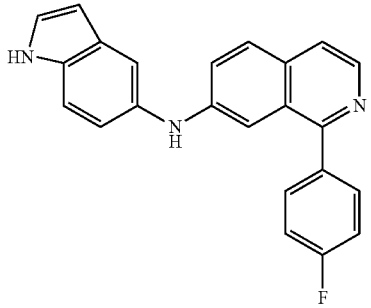 [SMILES: Fc1ccc(-c2nccc3ccc(Nc4ccc5[nH]ccc5c4)cc23)cc1] |
| 47 | 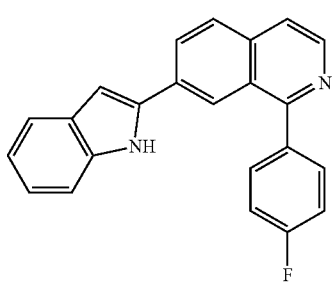 [SMILES: Fc1ccc(-c2nccc3ccc(-c4cc5ccccc5[nH]4)cc23)cc1] |
| 48 | 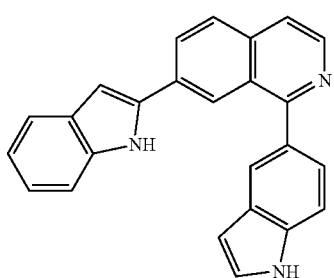 [SMILES: c1ccc2[nH]c(-c3ccc4ccnc(-c5ccc6[nH]ccc6c5)c4c3)cc2c1] |
| 49 | 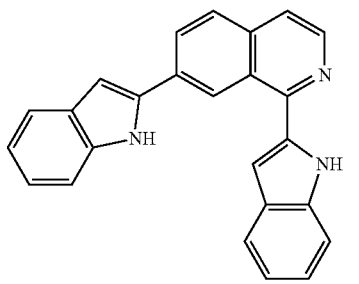 [SMILES: c1ccc2[nH]c(-c3ccc4ccnc(-c5cc6ccccc6[nH]5)c4c3)cc2c1] |
| 50 | 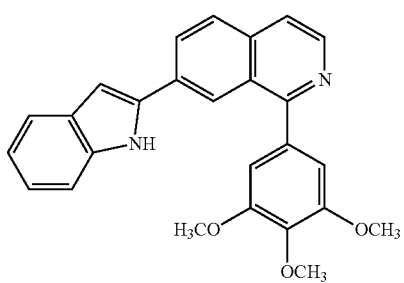 [SMILES: COc1cc(-c2nccc3ccc(-c4cc5ccccc5[nH]4)cc23)cc(OC)c1OC] |
| 51 | 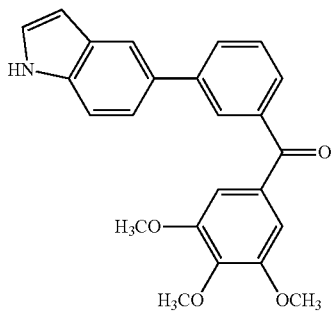 [SMILES: COc1cc(C(=O)c2cccc(-c3ccc4[nH]ccc4c3)c2)cc(OC)c1OC] |
| 52 | 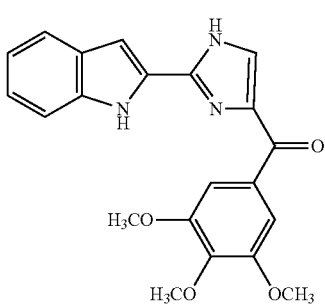 [SMILES: COc1cc(C(=O)c2c[nH]c(-c3cc4ccccc4[nH]3)n2)cc(OC)c1OC] |
| 53 | 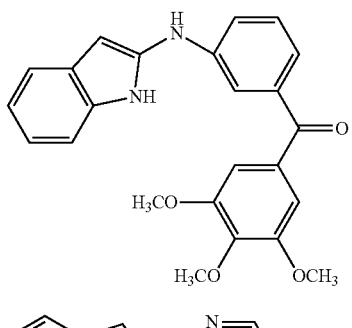 |
| 54 | 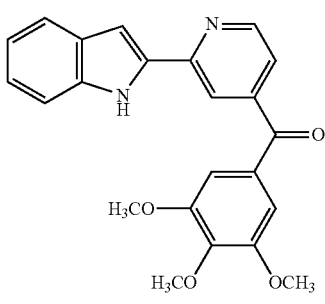 [SMILES: COc1cc(C(=O)c2ccnc(-c3cc4ccccc4[nH]3)c2)cc(OC)c1OC] |

In one embodiment the A, A' and/or C groups of formula I, I(a), IV, IX, IX(a) and XI are independently substituted and unsubstituted furanyl, benzofuranyl, benzothiophenyl, indolyl, pyridinyl, phenyl, biphenyl, triphenyl, diphenylmethane, adamantane-yl, fluorene-yl, and other heterocyclic analogs such as, e.g., pyrrolyl, pyrazolyl, imidazolyl, pyridinyl, pyrimidinyl, pyrazinyl, pyridazinyl, triazinyl, tetrazinyl, pyrrolizinyl, indolyl, isoquinolinyl, quinolinyl, isoquinolinyl, benzimidazolyl, indazolyl, quinolizinyl, cinnolinyl, quinalolinyl, phthalazinyl, naphthyridinyl, quinoxalinyl, oxiranyl, oxetanyl, tetrahydrofuranyl, tetrahydropyranyl, dioxanyl, furanyl, pyrylium, benzodioxolyl, thiranyl, thietanyl, tetrahydrothiophene-yl, dithiolanyl, tetrahydrothiopyranyl, thiophene-yl, thiepinyl, thianaphthenyl, oxathiolanyl, morpholinyl, thioxanyl, thiazolyl, isothiazolyl, thiadiazolyl, oxazolyl, isoxazolyl, oxadiaziolyl).

In one embodiment, the A, A' and/or C groups is substituted and unsubstituted phenyl. In another embodiment, the A, A' and/or C groups is phenyl substituted by Cl, F or methyl. In one embodiment, the A, A' and/or C groups is substituted and unsubstituted isoquinolinyl. In one embodiment, the A, A' and/or C groups include substituted and unsubstituted indolyl groups; most preferably, substituted and unsubstituted 3-indolyl and 5-indolyl.

In one embodiment, the A, A' and/or C groups of formula I, I(a), IV, IX, IX(a) and XI can be substituted or unsubstituted. Thus, although the exemplary groups recited in the preceding paragraph are unsubstituted, it should be appreciated by those of skill in the art that these groups can be substituted by one or more, two or more, three or more, and even up to five substituents (other than hydrogen).

In one embodiment, the most preferred A, A' and/or C groups are substituted by 3,4,5-trimethoxyphenyl. In another embodiment the A, A' and/or C groups are substituted by alkoxy. In another embodiment the A, A' and/or C groups are substituted by methoxy. In another embodiment the A, A' and/or C groups are substituted by alkyl. In another embodiment the A, A' and/or C groups are substituted by methyl. In another embodiment, the A, A' and/or C groups are substituted by halogen. In another embodiment, the A, A' and/or C groups are substituted by F. In another embodiment, the A, A' and/or C groups are substituted by Cl. In another embodiment, the A, A' and/or C rings are substituted by Br.

The substituents of these A, A' and/or C groups of formula I, I(a), IV, IX, IX(a) and XI are independently selected from the group of hydrogen (e.g., no substitution at a particular position), hydroxyl, an aliphatic straight- or branched-chain $C_1$ to $C_{10}$ hydrocarbon, alkoxy, haloalkoxy, aryloxy, nitro, cyano, alkyl-CN, halo, haloalkyl, dihaloalkyl, trihaloalkyl, COOH, C(O)Ph, C(O)-alkyl, C(O)O-alkyl, C(O)H, C(O)NH$_2$, —OC(O)CF$_3$, —OCH$_2$Ph, amino, aminoalkyl, alkylamino, mesylamino, dialkylamino, arylamino, amido, NHC(O)-alkyl, urea, alkyl-urea, alkylamido (e.g., acetamide), haloalkylamido, arylamido, aryl, and $C_5$ to $C_7$ cycloalkyl, arylalkyl, and combinations thereof. Single substituents can be present at the ortho, meta, or para positions. When two or more substituents are present, one of them is preferably, though not necessarily, at the para position.

In one embodiment the B group of formula I, I(a), II, III, IV, IVa and V is selected from substituted or unsubstituted-thiazole, thiazolidine, oxazole, oxazoline, oxazolidine, benzene, pyrimidine, imidazole, pyridine, furan, thiophene, isoxazole, piperidine, pyrazole, indole and isoquinoline, wherein said B ring is linked via any two positions of the ring to X and Y or directly to the A and/or C rings.

In one embodiment the B group of formula I, I(a), II, III, IV, IVa and V is unsubstituted. In another embodiment the B group of formula I, I(a), II, III, IV, IVa and V is:

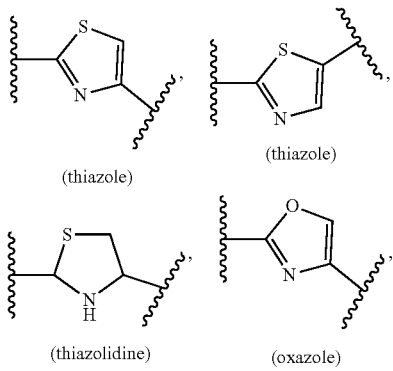

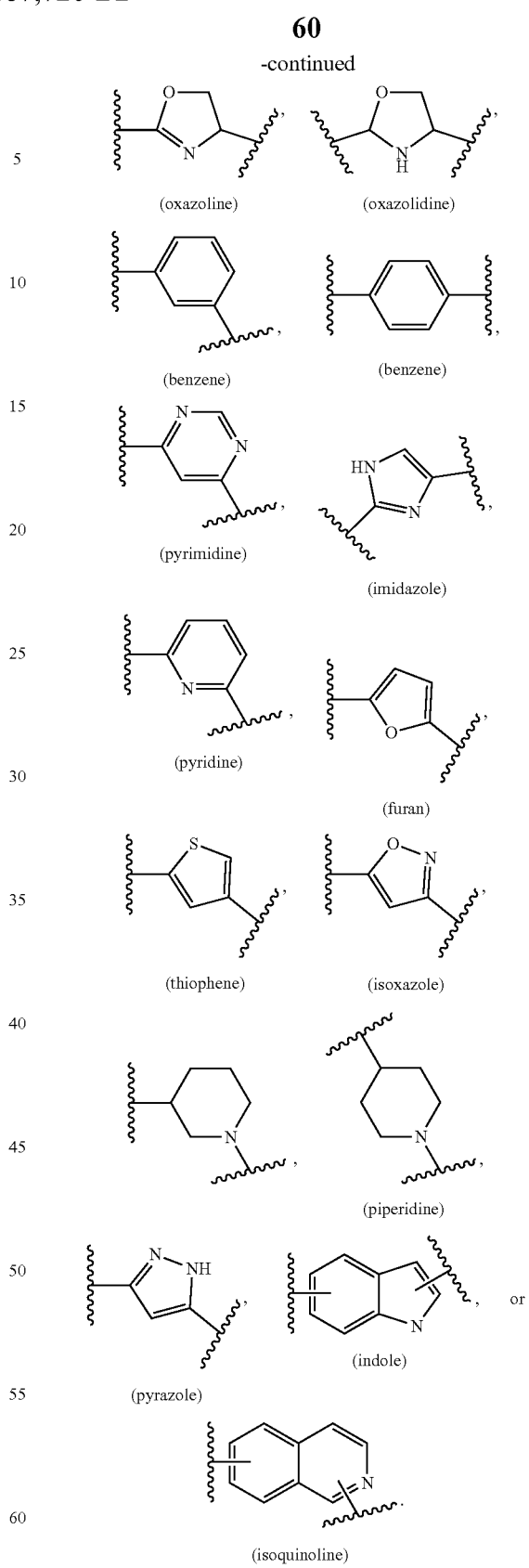

In another embodiment the B group of formula I, I(a), II, III, IV, IVa and V is substituted. In another embodiment the B group of formula I, I(a), II, III, IV, IVa and V is:

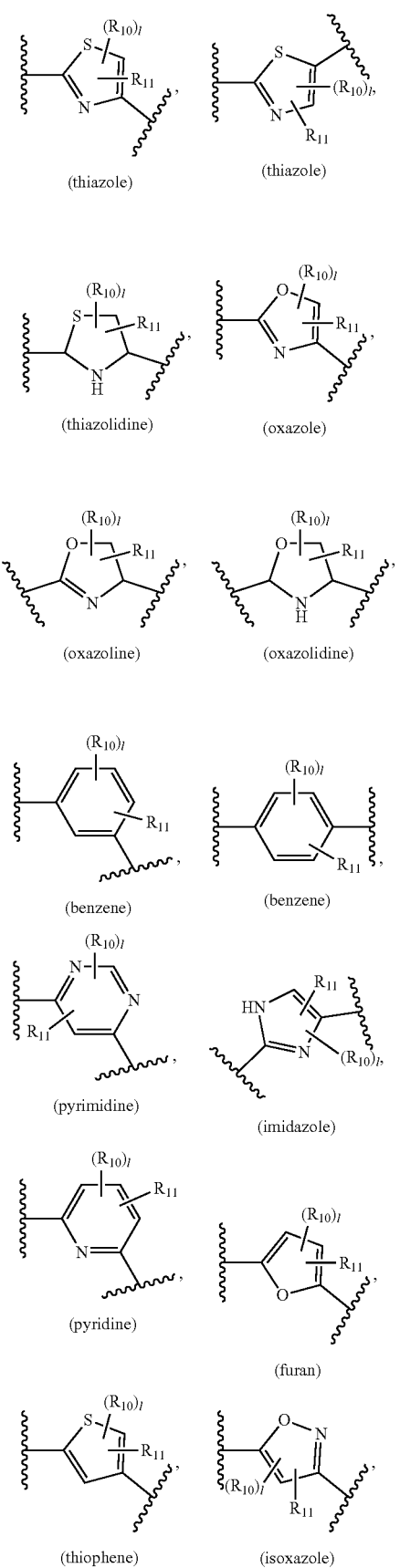
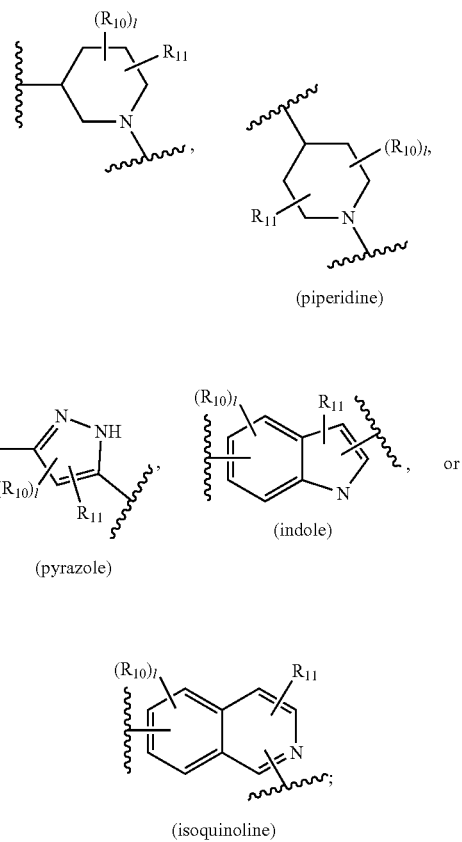

wherein $R_{10}$ and $R_{11}$ are independently hydrogen, O-alkyl, O-haloalkyl, F, Cl, Br, I, haloalkyl, $CF_3$, CN, —$CH_2CN$, $NH_2$, hydroxyl, —$(CH_2)_i NHCH_3$, —$(CH_2)_i NH_2$, —$(CH_2)_i N(CH_3)_2$, —$OC(O)CF_3$, $C_1$-$C_5$ linear or branched alkyl, haloalkyl, alkylamino, aminoalkyl, —$OCH_2Ph$, —NHCO-alkyl, COOH, —C(O)Ph, C(O)O-alkyl, C(O)H, —$C(O)NH_2$ or $NO_2$.

In another embodiment the B group is

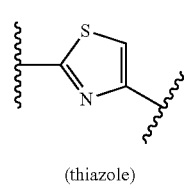

(thiazole)

In another embodiment the B group is

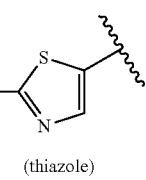

(thiazole)

In another embodiment the B group is

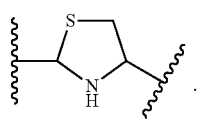

(thiazolidine)

In another embodiment the B group is

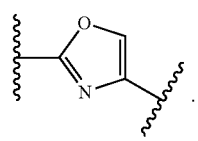

(oxazole)

In another embodiment the B group is

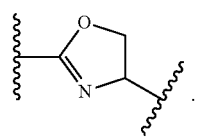

(oxazoline)

In another embodiment the B group is

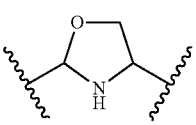

(oxazolidine)

In another embodiment the B group is

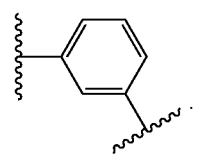

(benzene)

In another embodiment the B group is

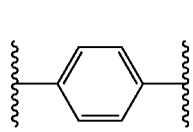

(benzene)

In another embodiment the B group is

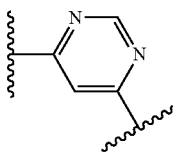

(pyrimidine)

In another embodiment the B group is

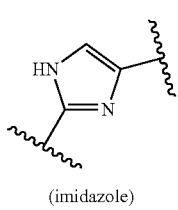

(imidazole)

In another embodiment the B group is

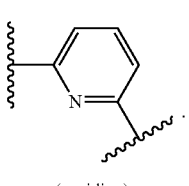

(pyridine)

In another embodiment B group is

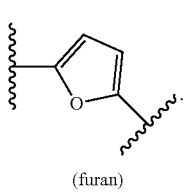 [SMILES: *c1ccc(*)o1]

(furan)

In another embodiment the B group is

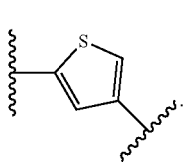

(thiophene)

In another embodiment the B group is

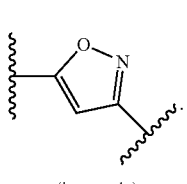

(isoxazole)

In another embodiment the B group is

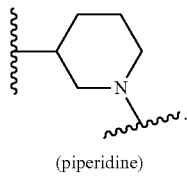 [SMILES: *C1CCCN(*)C1]

(piperidine)

In another embodiment the B group is

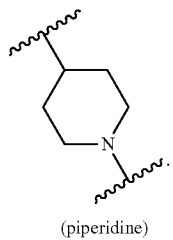 [SMILES: *C1CCN(*)CC1]

(piperidine)

In another embodiment the B group is

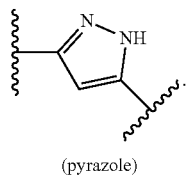 [SMILES: *c1cc(*)[nH]n1]

(pyrazole)

In another embodiment the B group is

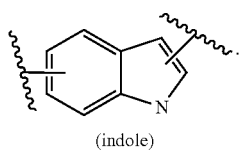

(indole)

In another embodiment the B group is

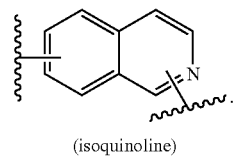

(isoquinoline)

In one embodiment the B group of formula I, I(a), II, III, IV, IVa and V is substituted by $R_{10}$ and $R_{11}$. In another embodiment, $R_{10}$ and $R_{11}$ are both hydrogens. In another embodiment, $R_{10}$ and $R_{11}$ are independently O-alkyl. In another embodiment, $R_{10}$ and $R_{11}$ are independently O-haloalkyl. In another embodiment, $R_{10}$ and $R_{11}$ are independently F. In another embodiment, $R_{10}$ and $R_{11}$ are independently Cl. In another embodiment, $R_{10}$ and $R_{11}$ are independently Br. In another embodiment, $R_{10}$ and $R_{11}$ are independently I. In another embodiment, $R_{10}$ and $R_{11}$ are independently haloalkyl. In another embodiment, $R_{10}$ and $R_{11}$ are independently $CF_3$. In another embodiment, $R_{10}$ and $R_{11}$ are independently CN. In another embodiment, $R_{10}$ and $R_{11}$ are independently —$CH_2CN$. In another embodiment, $R_{10}$ and $R_{11}$ are independently $NH_2$. In another embodiment, $R_{10}$ and $R_{11}$ are independently hydroxyl. In another embodiment, $R_{10}$ and $R_{11}$ are independently —$(CH_2)_iNHCH_3$. In another embodiment, $R_{10}$ and $R_{11}$ are independently —$(CH_2)_iNH_2$. In another embodiment, $R_{10}$ and $R_{11}$ are independently —$(CH_2)_iN(CH_3)_2$. In another embodiment, $R_{10}$ and $R_{11}$ are independently —$OC(O)CF_3$. In another embodiment, $R_{10}$ and $R_{11}$ are independently $C_1$-$C_5$ linear or branched alkyl. In another embodiment, $R_{10}$ and $R_{11}$ are independently $C_1$-$C_5$ linear or branched haloalkyl. In another embodiment, $R_{10}$ and $R_{11}$ are independently $C_1$-$C_5$ linear or branched alkylamino. In another embodiment, $R_{10}$ and $R_{11}$ are independently $C_1$-$C_5$ linear or branched aminoalkyl. In another embodiment, $R_{10}$ and $R_{11}$ are independently —$OCH_2Ph$. In another embodiment, $R_{10}$ and $R_{11}$ are independently —NHCO-alkyl. In another embodiment, $R_{10}$ and $R_{11}$ are independently COOH. In another embodiment, $R_{10}$ and $R_{11}$ are independently —C(O)Ph. In another embodiment, $R_{10}$ and $R_{11}$ are independently C(O)O-alkyl. In another embodiment, $R_{10}$ and $R_{11}$ are independently C(O)H. In another embodiment, $R_{10}$ and $R_{11}$ are independently —$C(O)NH_2$. In another embodiment, $R_{10}$ and $R_{11}$ are independently $NO_2$.

In another embodiment the B group of formula I, I(a), II, III, IV, IVa and V is

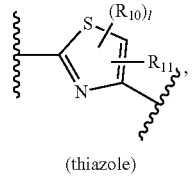

(thiazole)

wherein $R_{10}$ and $R_{11}$ are independently H and l is 1. In another embodiment, $R_{10}$ and $R_{11}$ are independently O-alkyl. In another embodiment, $R_{10}$ and $R_{11}$ are independently O-haloalkyl. In another embodiment, $R_{10}$ and $R_{11}$ are independently F. In another embodiment, $R_{10}$ and $R_{11}$ are independently Cl. In another embodiment, $R_{10}$ and $R_{11}$ are independently Br. In another embodiment, $R_{10}$ and $R_{11}$ are independently I. In another embodiment, $R_{10}$ and $R_{11}$ are independently haloalkyl. In another embodiment, $R_{10}$ and $R_{11}$ are independently $CF_3$. In another embodiment, $R_{10}$ and $R_{11}$ are independently CN. In another embodiment, $R_{10}$ and $R_{11}$ are independently —$CH_2CN$. In another embodiment, $R_{10}$ and $R_{11}$ are independently $NH_2$. In another embodiment, $R_{10}$ and $R_{11}$ are independently hydroxyl. In another embodiment, $R_{10}$ and $R_{11}$ are independently —$(CH_2)_iNHCH_3$. In another embodiment, $R_{10}$ and $R_{11}$ are independently —$(CH_2)_iNH_2$. In another embodiment, $R_{10}$ and $R_{11}$ are independently —$(CH_2)_iN(CH_3)_2$. In another embodiment, $R_{10}$ and $R_{11}$ are independently —$OC(O)CF_3$. In another embodiment, $R_{10}$ and $R_{11}$ are independently $C_1$-$C_5$ linear or branched alkyl. In another embodiment, $R_{10}$ and $R_{11}$ are independently $C_1$-$C_5$ linear or branched haloalkyl. In another embodiment, $R_{10}$ and $R_{11}$ are independently $C_1$-$C_5$ linear or branched alkylamino. In another embodiment, $R_{10}$ and $R_{11}$ are independently $C_1$-$C_5$ linear or branched aminoalkyl. In another embodiment, $R_{10}$ and $R_{11}$ are independently —$OCH_2Ph$. In another embodiment, $R_{10}$ and $R_{11}$ are independently —NHCO-alkyl. In another embodiment, $R_{10}$ and $R_{11}$ are independently COOH. In another embodiment, $R_{10}$ and $R_{11}$ are independently —C(O)Ph. In another embodiment, $R_{10}$ and $R_{11}$ are independently C(O)O-alkyl. In another embodiment, $R_{10}$ and $R_{11}$ are independently C(O)H. In another embodiment, $R_{10}$ and $R_{11}$ are independently —C(O)NH$_2$. In another embodiment, $R_{10}$ and $R_{11}$ are independently NO$_2$.

In another embodiment the B group of formula I, I(a), II, III, IV, IVa and V is

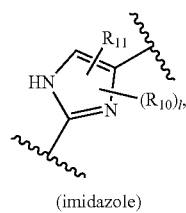

(imidazole)

wherein $R_{10}$ and $R_{11}$ are independently H and 1 is 1. In another embodiment, $R_{10}$ and $R_{11}$ are independently O-alkyl. In another embodiment, $R_{10}$ and $R_{11}$ are independently O-haloalkyl. In another embodiment, $R_{10}$ and $R_{11}$ are independently F. In another embodiment, $R_{10}$ and $R_{11}$ are independently Cl. In another embodiment, $R_{10}$ and $R_{11}$ are independently Br. In another embodiment, $R_{10}$ and Rn are independently I. In another embodiment, $R_{10}$ and $R_{11}$ are independently haloalkyl. In another embodiment, $R_{10}$ and $R_{11}$ are independently CF$_3$. In another embodiment, $R_{10}$ and $R_{11}$ are independently CN. In another embodiment, $R_{10}$ and $R_{11}$ are independently —CH$_2$CN. In another embodiment, $R_{10}$ and $R_{11}$ are independently NH$_2$. In another embodiment, $R_{10}$ and $R_{11}$ are independently hydroxyl. In another embodiment, $R_{10}$ and $R_{11}$ are independently —(CH$_2$)$_i$NHCH$_3$. In another embodiment, $R_{10}$ and $R_{11}$ are independently —(CH$_2$)$_i$NH$_2$. In another embodiment, $R_{10}$ and $R_{11}$ are independently —(CH$_2$)$_i$N(CH$_3$)$_2$. In another embodiment, $R_{10}$ and $R_{11}$ are independently —OC(O)CF$_3$. In another embodiment, $R_{10}$ and $R_{11}$ are independently $C_1$-$C_5$ linear or branched alkyl. In another embodiment, $R_{10}$ and $R_{11}$ are independently $C_1$-$C_5$ linear or branched haloalkyl. In another embodiment, $R_{10}$ and $R_{11}$ are independently $C_1$-$C_5$ linear or branched alkylamino. In another embodiment, $R_{10}$ and $R_{11}$ are independently $C_1$-$C_5$ linear or branched aminoalkyl. In another embodiment, $R_{10}$ and $R_{11}$ are independently —OCH$_2$Ph. In another embodiment, $R_{10}$ and $R_{11}$ are independently —NHCO-alkyl. In another embodiment, $R_{10}$ and $R_{11}$ are independently COOH. In another embodiment, $R_{10}$ and $R_{11}$ are independently —C(O)Ph. In another embodiment, $R_{10}$ and $R_{11}$ are independently C(O)O-alkyl. In another embodiment, $R_{10}$ and $R_{11}$ are independently C(O)H. In another embodiment, $R_{10}$ and $R_{11}$ are independently —C(O)NH$_2$. In another embodiment, $R_{10}$ and $R_{11}$ are independently NO$_2$.

In another embodiment the B group of formula I, I(a), II, III, IV, IVa and V is

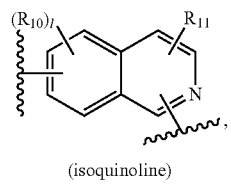

(isoquinoline)

wherein $R_{10}$ and $R_{11}$ are independently H and 1 is 1. In another embodiment, $R_{10}$ and $R_{11}$ are independently O-alkyl. In another embodiment, $R_{10}$ and $R_{11}$ are independently O-haloalkyl. In another embodiment, $R_{10}$ and $R_{11}$ are independently F. In another embodiment, $R_{10}$ and $R_{11}$ are independently Cl. In another embodiment, $R_{10}$ and $R_{11}$ are independently Br. In another embodiment, $R_{10}$ and $R_{11}$ are independently I. In another embodiment, $R_{10}$ and $R_{11}$ are independently haloalkyl. In another embodiment, $R_{10}$ and $R_{11}$ are independently CF$_3$. In another embodiment, $R_{10}$ and $R_{11}$ are independently CN. In another embodiment, $R_{10}$ and $R_{11}$ are independently —CH$_2$CN. In another embodiment, $R_{10}$ and $R_{11}$ are independently NH$_2$. In another embodiment, $R_{10}$ and $R_{11}$ are independently hydroxyl. In another embodiment, $R_{10}$ and $R_{11}$ are independently —(CH$_2$)$_i$NHCH$_3$. In another embodiment, $R_{10}$ and $R_{11}$ are independently —(CH$_2$)$_i$NH$_2$. In another embodiment, $R_{10}$ and $R_{11}$ are independently —(CH$_2$)$_i$N(CH$_3$)$_2$. In another embodiment, $R_{10}$ and $R_{11}$ are independently —OC(O)CF$_3$. In another embodiment, $R_{10}$ and $R_{11}$ are independently $C_1$-$C_5$ linear or branched alkyl. In another embodiment, $R_{10}$ and $R_{11}$ are independently $C_1$-$C_5$ linear or branched haloalkyl. In another embodiment, $R_{10}$ and $R_{11}$ are independently $C_1$-$C_5$ linear or branched alkylamino. In another embodiment, $R_{10}$ and $R_{11}$ are independently $C_1$-$C_5$ linear or branched aminoalkyl. In another embodiment, $R_{10}$ and $R_{11}$ are independently —OCH$_2$Ph. In another embodiment, $R_{10}$ and $R_{11}$ are independently —NHCO-alkyl. In another embodiment, $R_{10}$ and $R_{11}$ are independently COOH. In another embodiment, $R_{10}$ and $R_{11}$ are independently —C(O)Ph. In another embodiment, $R_{10}$ and $R_{11}$ are independently C(O)O-alkyl. In another embodiment, $R_{10}$ and $R_{11}$ are independently C(O)H. In another embodiment, $R_{10}$ and $R_{11}$ are independently —C(O)NH$_2$. In another embodiment, $R_{10}$ and $R_{11}$ are independently NO$_2$.

In one embodiment, the X bridge of formula I, Ia, II, III, IV, IVa and XI is a bond. In another embodiment, the X bridge is NH. In another embodiment, the X bridge is $C_1$ to $C_5$ hydrocarbon. In another embodiment, the X bridge is CH$_2$. In another embodiment, the X bridge is —CH$_2$—CH$_2$—. In another embodiment, the X bridge is O. In another embodiment, the X bridge is S.

In one embodiment, the Y bridge of formula I, Ia, II, III, IV, IVa, VI, and VII is C=O. In another embodiment, the Y bridge is C=S. In another embodiment, the Y bridge is C=N(NH$_2$)—. In another embodiment, the Y bridge is —C=NOH. In another embodiment, the Y bridge is —CH—OH. In another embodiment, the Y bridge is —C=CH—(CN). In another embodiment, the Y bridge is —C=N(CN). In another embodiment, the Y bridge is —C=C(CH$_3$)$_2$. In another embodiment, the Y bridge is —C=N—OMe. In another embodiment, the Y bridge is —(C=O)NH—. In another embodiment, the Y bridge is —NH(C=O)—. In another embodiment, the Y bridge is —(C=O)—O. In another embodiment, the Y bridge is —O—(C=O). In another embodiment, the Y bridge is —(CH$_2$)$_{1-5}$—(C=O). In another embodiment, the Y bridge is —(C=O)—(CH$_2$)$_{1-5}$. In another embodiment, the Y bridge is S. In another embodiment, the Y bridge is SO. In another embodiment, the Y bridge is SO$_2$. In another embodiment, the Y bridge is —CH=CH—. In another embodiment, the Y bridge is —(SO$_2$)—NH—. In another embodiment, the Y bridge is —NH—(SO$_2$)—.

In one embodiment, $R_1$, $R_2$, $R_3$, $R_4$, $R_5$ and $R_6$ of formula Ia, II, III, IV, IV(a), V, VI, VIII, IX, IX(a), XI(a), XI(b), XI(c), XI(d) and XI(e) are independently hydrogen. In another embodiment, $R_1$, $R_2$, $R_3$, $R_4$, $R_5$ and $R_6$ are independently O-alkyl. In another embodiment, $R_1$, $R_2$, $R_3$, $R_4$, $R_5$ and $R_6$ are independently O-haloalkyl. In another embodiment, $R_1$, $R_2$, $R_3$, $R_4$, $R_5$ and $R_6$ are independently F. In another embodiment, $R_1$, $R_2$, $R_3$, $R_4$, $R_5$ and $R_6$ are independently Cl. In another embodiment, $R_1$, $R_2$, $R_3$, $R_4$, $R_5$ and $R_6$ are independently Br. In another embodiment, $R_1$, $R_2$, $R_3$, $R_4$, $R_5$ and $R_6$ are independently I. In another embodiment, $R_1$, $R_2$, $R_3$, $R_4$, $R_5$ and $R_6$ are independently haloalkyl. In another embodiment, $R_1$, $R_2$, $R_3$, $R_4$, $R_5$ and $R_6$ are independently $CF_3$. In another embodiment, $R_1$, $R_2$, $R_3$, $R_4$, $R_5$ and $R_6$ are independently CN. In another embodiment, $R_1$, $R_2$, $R_3$, $R_4$, $R_5$ and $R_6$ are independently —$CH_2CN$. In another embodiment, $R_1$, $R_2$, $R_3$, $R_4$, $R_5$ and $R_6$ are independently $NH_2$. In another embodiment, $R_1$, $R_2$, $R_3$, $R_4$, $R_5$ and $R_6$ are independently hydroxyl. In another embodiment, $R_1$, $R_2$, $R_3$, $R_4$, $R_5$ and $R_6$ are independently —$(CH_2)_iNHCH_3$. In another embodiment, $R_1$, $R_2$, $R_3$, $R_4$, $R_5$ and $R_6$ are independently —$(CH_2)_iNH_2$. In another embodiment, $R_1$, $R_2$, $R_3$, $R_4$, $R_5$ and $R_6$ are independently —$(CH_2)_iN(CH_3)_2$. In another embodiment, $R_1$, $R_2$, $R_3$, $R_4$, $R_5$ and $R_6$ are independently —$OC(O)CF_3$. In another embodiment, $R_1$, $R_2$, $R_3$, $R_4$, $R_5$ and $R_6$ are independently $C_1$-$C_5$ linear or branched alkyl. In another embodiment, $R_1$, $R_2$, $R_3$, $R_4$, $R_5$ and $R_6$ are independently haloalkyl. In another embodiment, $R_1$, $R_2$, $R_3$, $R_4$, $R_5$ and $R_6$ are independently alkylamino. In another embodiment, $R_1$, $R_2$, $R_3$, $R_4$, $R_5$ and $R_6$ are independently aminoalkyl. In another embodiment, $R_1$, $R_2$, $R_3$, $R_4$, $R_5$ and $R_6$ are independently —$OCH_2Ph$. In another embodiment, $R_1$, $R_2$, $R_3$, $R_4$, $R_5$ and $R_6$ are independently —NHCO-alkyl. In another embodiment, $R_1$, $R_2$, $R_3$, $R_4$, $R_5$ and $R_6$ are independently COOH. In another embodiment, $R_1$, $R_2$, $R_3$, $R_4$, $R_5$ and $R_6$ are independently —C(O)Ph. In another embodiment, $R_1$, $R_2$, $R_3$, $R_4$, $R_5$ and $R_6$ are independently C(O)O-alkyl. In another embodiment, $R_1$, $R_2$, $R_3$, $R_4$, $R_5$ and $R_6$ are independently C(O)H. In another embodiment, $R_1$, $R_2$, $R_3$, $R_4$, $R_5$ and $R_6$ are independently —$C(O)NH_2$. In another embodiment, $R_1$, $R_2$, $R_3$, $R_4$, $R_5$ and $R_6$ are independently $NO_2$.

In one embodiment, this invention is directed to a compound of formula XII:

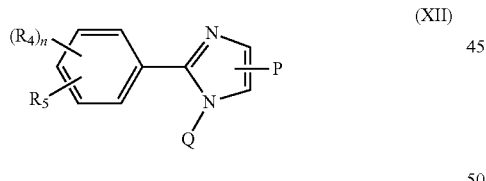

(XII)

wherein,
P and Q are independently H or

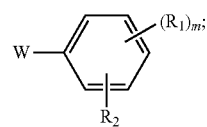

W is C=O, C=S, $SO_2$ or S=O;
wherein at least one of Q or P is not hydrogen;
$R_1$ and $R_4$ are independently H, O-alkyl, I, Br, Cl, F, alkyl, haloalkyl, aminoalkyl, —$OCH_2Ph$, OH, CN, $NO_2$, —NHCO-alkyl, COOH, —$(CH_2)_iNHCH_3$, —$(CH_2)_iNH_2$, —$(CH_2)_iN(CH_3)_2$; C(O)O-alkyl or C(O)H; wherein at least one of $R_1$ and $R_4$ is not hydrogen;
$R_2$ and $R_5$ are independently H, O-alkyl, I, Br, Cl, F, alkyl, haloalkyl, aminoalkyl, —$OCH_2Ph$, OH, CN, $NO_2$, —NHCO-alkyl, COOH, C(O)O-alkyl or C(O)H;
m is an integer between 1-4;
i is an integer between 0-5; and
n is an integer between 1-4;
or its pharmaceutically acceptable salt, hydrate, polymorph, metabolite, tautomer or isomer.

In one embodiment, this invention is directed to a compound of formula XIII:

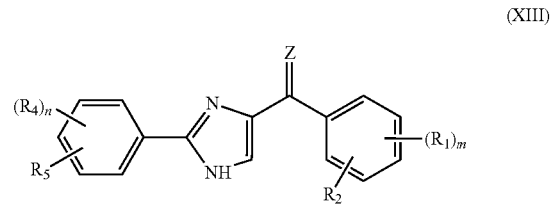

(XIII)

wherein
Z is O or S;
$R_1$ and $R_4$ are independently H, O-alkyl, I, Br, Cl, F, alkyl, haloalkyl, aminoalkyl, —$OCH_2Ph$, OH, CN, $NO_2$, —NHCO-alkyl, haloalkyl, aminoalkyl, —$(CH_2)_iNHCH_3$, —$(CH_2)_iNH_2$, —$(CH_2)_iN(CH_3)_2$; COOH, C(O)O-alkyl or C(O)H; wherein at least one of $R_1$ and $R_4$ is not hydrogen;
$R_2$ and $R_5$ are independently H, O-alkyl, I, Br, Cl, F, alkyl, haloalkyl, aminoalkyl, —$(CH_2)_iNHCH_3$, —$(CH_2)_iNH_2$, —$(CH_2)_iN(CH_3)_2$; $OCH_2Ph$, OH, CN, $NO_2$, —NHCO-alkyl, COOH, C(O)O-alkyl or C(O)H;
m is an integer between 1-4;
i is an integer between 0-5; and
n is an integer between 1-4;
or its pharmaceutically acceptable salt, hydrate, polymorph, metabolite, tautomer or isomer.

In one embodiment, this invention is directed to a compound of formula XIV:

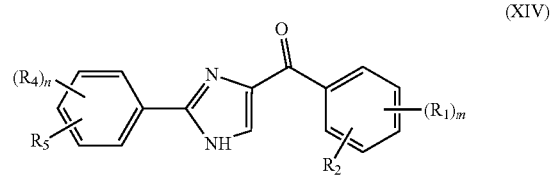

(XIV)

wherein $R_1$ and $R_4$ are independently H, O-alkyl, I, Br, Cl, F, alkyl, haloalkyl, aminoalkyl, —$(CH_2)_iNHCH_3$, —$(CH_2)_iNH_2$, —$(CH_2)_iN(CH_3)_2$, —$OCH_2Ph$, OH, CN, $NO_2$, —NHCO-alkyl, COOH, C(O)O-alkyl or C(O)H; wherein at least one of $R_1$ and $R_4$ is not hydrogen;
$R_2$ and $R_5$ are independently H, O-alkyl, I, Br, Cl, F, alkyl, haloalkyl, aminoalkyl, —$OCH_2Ph$, OH, CN, $NO_2$, —NHCO-alkyl, COOH, C(O)O-alkyl or C(O)H;
m is an integer between 1-4;
i is an integer between 0-5; and
n is an integer between 1-4;
or its pharmaceutically acceptable salt, hydrate, polymorph, metabolite, tautomer or isomer.

In one embodiment, $R_1$ of compound of formula XII, XIII and XIV is $OCH_3$. In another embodiment, $R_1$ of compound of formula XII, XIII and XIV is 4-F. In another embodiment, $R_1$ of compound of formula XII, XIII and XIV is $OCH_3$ and m is 3. In another embodiment, $R_4$ of compound of formula XII, XIII and XIV is 4-F. In another embodiment, $R_4$ of compound of formula XII, XIII and XIV is $OCH_3$. In another embodiment, $R_4$ of compound of formula XIV is $CH_3$. In another embodiment, $R_4$ of compound of formula XII, XIII and XIV is 4-Cl. In another embodiment, $R_4$ of compound of formula XII, XIII and XIV is 4-N(Me)$_2$. In another embodiment, $R_4$ of compound of formula XII, XIII and XIV is OBn. In another embodiment, $R_4$ of compound of formula XII, XIII and XIV is 4-Br. In another embodiment, $R_4$ of compound of formula XII, XIII and XIV is 4-CF$_3$. Non limiting examples of compounds of formula XIV are selected from: (2-phenyl-1H-imidazol-4-yl)(3,4,5-trimethoxyphenyl)methanone (12aa), (4-fluorophenyl)(2-phenyl-1H-imidazol-4-yl)methanone (12af), (2-(4-fluorophenyl)-1H-imidazol-4-yl)(3,4,5-trimethoxyphenyl)methanone (12ba), (2-(4-methoxyphenyl)-1H-imidazol-4-yl)(3,4,5-trimethoxyphenyl)methanone (12ca), (4-fluorophenyl)(2-(4-methoxyphenyl)-1H-imidazol-4-yl)methanone (12cb), (2-(p-tolyl)-1H-imidazol-4-yl)(3,4,5-trimethoxyphenyl)methanone (12da), (4-fluorophenyl)(2-(p-tolyl)-1H-imidazol-4-yl)methanone (12db), (4-hydroxy-3,5-dimethoxyphenyl)(2-(p-tolyl)-1H-imidazol-4-yl)methanone (12dc), (2-(4-chlorophenyl)-1H-imidazol-4-yl)(3,4,5-trimethoxyphenyl)methanone (12fa), (2-(4-chlorophenyl)-1H-imidazol-4-yl)(4-fluorophenyl)methanone (12fb), (2-(4-chlorophenyl)-1H-imidazol-4-yl)(4-hydroxy-3,5-dimethoxyphenyl)methanone (12fc), (2-(4-(dimethylamino)phenyl)-1H-imidazol-4-yl)(3,4,5-trimethoxyphenyl)methanone (12ga); (2-(4-(dimethylamino)phenyl)-1H-imidazol-4-yl)(4-fluorophenyl)methanone (12gb), (2-(3,4-dimethoxyphenyl)-1H-imidazol-4-yl)(3,4,5-trimethoxyphenyl)methanone (12ha), (2-(4-(benzyloxy)phenyl)-1H-imidazol-4-yl)(4-fluorophenyl)methanone (12jb), (2-(4-bromophenyl)-1H-imidazol-4-yl)(3,4,5-trimethoxyphenyl)methanone (12la), (2-(4-(trifluoromethyl)phenyl)-1H-imidazol-4-yl)(3,4,5-trimethoxyphenyl)methanone (12pa).

In one embodiment, this invention is directed to a compound of formula XIVa:

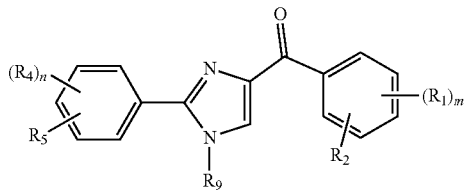

(XIVa)

wherein $R_1$ and $R_4$ are independently H, O-alkyl, I, Br, Cl, F, alkyl, haloalkyl, aminoalkyl, —(CH$_2$)$_i$NHCH$_3$, —(CH$_2$)$_i$NH$_2$, —(CH$_2$)$_i$N(CH$_3$)$_2$, —OCH$_2$Ph, OH, CN, NO$_2$, —NHCO-alkyl, COOH, C(O)O-alkyl or C(O)H; wherein at least one of $R_1$ and $R_4$ is not hydrogen;

$R_2$ and $R_5$ are independently H, O-alkyl, I, Br, Cl, F, alkyl, haloalkyl, aminoalkyl, —(CH$_2$)$_i$NHCH$_3$, —(CH$_2$)$_i$NH$_2$, —(CH$_2$)$_i$N(CH$_3$)$_2$, OCH$_2$Ph, OH, CN, NO$_2$, —NHCO-alkyl, COOH, C(O)O-alkyl or C(O)H;

$R_9$ is H, linear or branched, substituted or unsubstituted alkyl, substituted or unsubstituted aryl, —CH$_2$Ph, substituted benzyl, haloalkyl, aminoalkyl, —OCH$_2$Ph, substituted or unsubstituted SO$_2$-aryl, substituted or unsubstituted —(C=O)-aryl or OH;

wherein substitutions are independently selected from the group of hydrogen (e.g., no substitution at a particular position), hydroxyl, an aliphatic straight- or branched-chain C$_1$ to C$_{10}$ hydrocarbon, alkoxy, haloalkoxy, aryloxy, nitro, cyano, alkyl-CN, halo, haloalkyl, dihaloalkyl, trihaloalkyl, COOH, C(O)Ph, C(O)-alkyl, C(O)O-alkyl, C(O)H, C(O)NH$_2$, —OC(O)CF$_3$, —OCH$_2$Ph, amino, aminoalkyl, alkylamino, mesylamino, dialkylamino, arylamino, amido, NHC(O)-alkyl, urea, alkylurea, alkylamido (e.g., acetamide), haloalkylamido, arylamido, aryl, and C$_5$ to C$_7$ cycloalkyl, arylalkyl, and combinations thereof;

m is an integer between 1-4;
i is an integer between 0-5; and
n is an integer between 1-4;
or its pharmaceutically acceptable salt, hydrate, polymorph, metabolite, tautomer or isomer.

In one embodiment, $R_9$ of compound of formula XIVa is CH$_3$. In another embodiment, $R_9$ of compound of formula XIVa is —CH$_2$Ph. In another embodiment, $R_9$ of compound of formula XIVa is (SO$_2$)Ph. In another embodiment, $R_9$ of compound of formula XIVa is (SO$_2$)—Ph-OCH$_3$. In another embodiment, $R_9$ of compound of formula XIVa is H. In another embodiment, $R_4$ of compound of formula XIVa is H. In another embodiment, $R_4$ of compound of formula XIVa is CH$_3$. In another embodiment, $R_4$ of compound of formula XIVa is OCH$_3$. In another embodiment, $R_4$ of compound of formula XIVa is OH. In another embodiment, $R_4$ of compound of formula XIVa is 4-Cl. In another embodiment, $R_4$ of compound of formula XIVa is 4-N(Me)$_2$. In another embodiment, $R_4$ of compound of formula XIVa is OBn. In another embodiment, $R_1$ of compound of formula XIVa is OCH$_3$; m is 3 and $R_2$ is H. In another embodiment, $R_1$ of compound of formula XIVa is F; m is 1 and $R_2$ is H. Non limiting examples of compounds of formula XIVa are selected from: (4-fluorophenyl)(2-phenyl-1-(phenylsulfonyl)-1H-imidazol-4-yl)methanone (11af), (4-fluorophenyl)(2-(4-methoxyphenyl)-1-(phenylsulfonyl)-1H-imidazol-4-yl)methanone (11cb), (4-fluorophenyl)(1-(phenylsulfonyl)-2-(p-tolyl)-1H-imidazol-4-yl)methanone (11db), (2-(4-chlorophenyl)-1-(phenylsulfonyl)-1H-imidazol-4-yl)(4-fluorophenyl)methanone (11fb), (2-(4-(dimethylamino)phenyl)-1-(phenylsulfonyl)-1H-imidazol-4-yl)(3,4,5-trimethoxyphenyl)methanone (11ga), (2-(4-(dimethylamino)phenyl)-1-(phenylsulfonyl)-1H-imidazol-4-yl)(4-fluorophenyl)methanone (11gb), (2-(3,4-dimethoxyphenyl)-1-(phenylsulfonyl)-1H-imidazol-4-yl)(3,4,5-trimethoxyphenyl)methanone (11ha), (2-(4-(benzyloxy)phenyl)-1-(phenylsulfonyl)-1H-imidazol-4-yl)(4-fluorophenyl)methanone (11jb), (2-(4-(dimethylamino)phenyl)-1-((4-methoxyphenyl)sulfonyl)-1H-imidazol-4-yl)(4-fluorophenyl)methanone (12gba), (1-benzyl-2-(p-tolyl)-1H-imidazol-4-yl)(3,4,5-trimethoxyphenyl)methanone (12daa), (1-methyl-2-(p-tolyl)-1H-imidazol-4-yl)(3,4,5-trimethoxyphenyl)methanone (12dab), (4-fluorophenyl)(2-(4-methoxyphenyl)-1-methyl-1H-imidazol-4-yl)methanone (12cba), (2-(4-ethylphenyl)-1H-imidazol-4-yl)(3,4,5-trimethoxyphenyl)methanone (12q), (2-(4-isopropylphenyl)-1H-imidazol-4-yl)(3,4,5-trimethoxyphenyl)methanone (12v), (2-(4-tert-butylphenyl)-1H-imidazol-4-yl)(3,4,5-trimethoxyphenyl)methanone (12w).

In one embodiment, this invention is directed to a compound of formula XV:

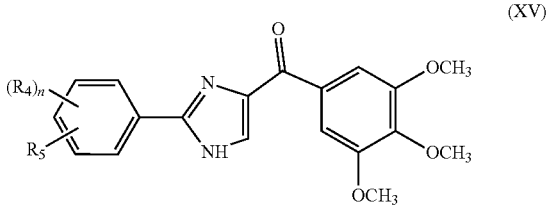

(XV)

wherein $R_4$ and $R_5$ are independently H, O-alkyl, I, Br, Cl, F, alkyl, haloalkyl, aminoalkyl, —$(CH_2)_iNHCH_3$, —$(CH_2)_iNH_2$, —$(CH_2)_iN(CH_3)_2$, —$OCH_2Ph$, OH, CN, $NO_2$, —NHCO-alkyl, COOH, C(O)O-alkyl or C(O)H;

i is an integer between 0-5; and n is an integer between is 1-4;

or its pharmaceutically acceptable salt, hydrate, polymorph, metabolite, tautomer or isomer.

In one embodiment, $R_4$ of compound of formula XV is H. In another embodiment, $R_4$ of compound of formula XV is F. In another embodiment, $R_4$ of compound of formula XV is Cl. In another embodiment, $R_4$ of compound of formula XV is Br. In another embodiment, $R_4$ of compound of formula XV is I. In another embodiment, $R_4$ of compound of formula XV is $N(Me)_2$. In another embodiment, $R_4$ of compound of formula XV is OBn. In another embodiment, $R_4$ of compound of formula XV is $OCH_3$. In another embodiment, $R_4$ of compound of formula XV is $CH_3$. In another embodiment, $R_4$ of compound of formula XV is $CF_3$. Non limiting examples of compounds of formula XV are selected from: (2-phenyl-1H-imidazol-4-yl)(3,4,5-trimethoxyphenyl)methanone (12aa), (2-(4-fluorophenyl)-1H-imidazol-4-yl)(3,4,5-trimethoxyphenyl)methanone (12ba), (2-(4-methoxyphenyl)-1H-imidazol-4-yl)(3,4,5-trimethoxyphenyl)methanone (12ca), (2-(p-tolyl)-1H-imidazol-4-yl)(3,4,5-trimethoxyphenyl)methanone (12da), (3,4,5-trimethoxyphenyl)(2-(3,4,5-trimethoxyphenyl)-1H-imidazol-4-yl)methanone (12ea), (2-(4-chlorophenyl)-1H-imidazol-4-yl)(3,4,5-trimethoxyphenyl)methanone (12fa), (2-(4-(dimethylamino)phenyl)-1H-imidazol-4-yl)(3,4,5-trimethoxyphenyl)methanone (12ga), (2-(3,4-dimethoxyphenyl)-1H-imidazol-4-yl)(3,4,5-trimethoxyphenyl)methanone (12ha), (2-(2-(trifluoromethyl)phenyl)-1H-imidazol-4-yl)(3,4,5-trimethoxyphenyl)methanone (12ia), (2-(4-(benzyloxy)phenyl)-1H-imidazol-4-yl)(3,4,5-trimethoxyphenyl)methanone (12ja), (2-(4-hydroxyphenyl)-1H-imidazol-4-yl)(3,4,5-trimethoxyphenyl)methanone (12ka), (2-(4-bromophenyl)-1H-imidazol-4-yl)(3,4,5-trimethoxyphenyl)methanone (12la), (2-(4-(trifluoromethyl)phenyl)-1H-imidazol-4-yl)(3,4,5-trimethoxyphenyl)methanone (12pa), (2-(4-ethylphenyl)-1H-imidazol-4-yl)(3,4,5-trimethoxyphenyl)methanone (12q), (2-(4-isopropylphenyl)-1H-imidazol-4-yl)(3,4,5-trimethoxyphenyl)methanone (12v), and (2-(4-tert-butylphenyl)-1H-imidazol-4-yl)(3,4,5-trimethoxyphenyl)methanone (12w).

In one embodiment, this invention is directed to a compound of formula XVI:

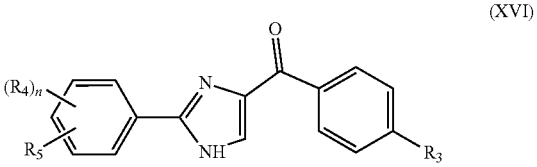

(XVI)

wherein $R_4$ and $R_5$ are independently H, O-alkyl, I, Br, Cl, F, alkyl, haloalkyl, aminoalkyl, —$(CH_2)_iNHCH_3$, —$(CH_2)_iNH_2$, —$(CH_2)_iN(CH_3)_2$, —$OCH_2Ph$, OH, CN, $NO_2$, —NHCO-alkyl, COOH, C(O)O-alkyl or C(O)H;

$R_3$ is I, Br, Cl, or F;

i is an integer between 0-5; and n is an integer between 1-4;

or its pharmaceutically acceptable salt, hydrate, polymorph, metabolite, tautomer or isomer.

In one embodiment, $R_3$ of compound of formula XVI is halogen. In another embodiment, $R_3$ is F. In another embodiment, $R_3$ is Cl. In another embodiment $R_3$ is Br. In another embodiment $R_3$ is I. In another embodiment $R_4$ is H. In another embodiment $R_4$ is $OCH_3$. In another embodiment $R_4$ is $OCH_3$; n is 3 and $R_5$ is H. In another embodiment $R_4$ is $CH_3$. In another embodiment $R_4$ is F. In another embodiment $R_4$ is Cl. In another embodiment $R_4$ is Br. In another embodiment $R_4$ is I. In another embodiment $R_4$ is $N(Me)_2$. In another embodiment $R_4$ is OBn. In another embodiment, $R_3$ is F; $R_5$ is hydrogen; n is 1 and $R_4$ is 4-Cl. In another embodiment, $R_3$ is F;

$R_5$ is hydrogen; n is 1 and $R_4$ is 4-$OCH_3$. In another embodiment, $R_3$ is F; $R_5$ is hydrogen; n is 1 and $R_4$ is 4-$CH_3$. In another embodiment, $R_3$ is F; $R_5$ is hydrogen; n is 1 and $R_4$ is 4-$N(Me)_2$. In another embodiment, $R_3$ is F; $R_5$ is hydrogen; n is I and $R_4$ is 4-OBn. Non limiting examples of compounds of formula XVI are selected from: (4-fluorophenyl)(2-phenyl-1H-imidazol-4-yl)methanone (12af), (4-fluorophenyl)(2-(4-methoxyphenyl)-1H-imidazol-4-yl)methanone (12cb), (4-fluorophenyl)(2-(p-tolyl)-1H-imidazol-4-yl)methanone (12db), 4-fluorophenyl)(2-(3,4,5-trimethoxyphenyl)-1H-imidazol-4-yl)methanone (12eb), (2-(4-chlorophenyl)-1H-imidazol-4-yl)(4-fluorophenyl)methanone (12fb), (2-(4-(dimethylamino)phenyl)-1H-imidazol-4-yl)(4-fluorophenyl)methanone (12gb), (2-(4-(benzyloxy)phenyl)-1H-imidazol-4-yl)(4-fluorophenyl)methanone (12jb).

In one embodiment, this invention is directed to a compound of formula XVII:

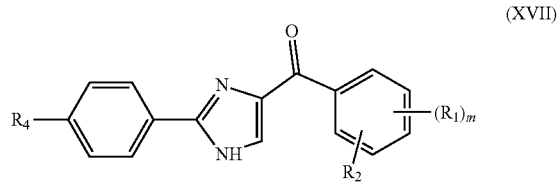

(XVII)

wherein $R_4$ is H, O-alkyl, I, Br, Cl, F, alkyl, haloalkyl, aminoalkyl, —$OCH_2Ph$, OH, CN, $NO_2$, —NHCO-alkyl, COOH, C(O)O-alkyl or C(O)H;

wherein $R_1$ and $R_2$ are independently H, O-alkyl, I, Br, Cl, F, alkyl, haloalkyl, aminoalkyl, —$OCH_2Ph$, OH, CN, $NO_2$, —NHCO-alkyl, COOH, C(O)O-alkyl or C(O)H;

and
m is an integer between 1-4;
or its pharmaceutically acceptable salt, hydrate, polymorph, metabolite, tautomer or isomer.

In one embodiment, $R_4$ of compound of formula XVII is halogen. In another embodiment, $R_4$ is F. In another embodiment, $R_4$ is Cl. In another embodiment $R_4$ is Br. In another embodiment $R_4$ is I. In another embodiment, $R_4$ is $OCH_3$. In another embodiment, $R_4$ is $CH_3$. In another embodiment, $R_4$ is $N(Me)_2$. In another embodiment, $R_4$ is $CF_3$. In another embodiment, $R_4$ is OH. In another embodiment, $R_4$ is OBn. In another embodiment, $R_1$ of compound of formula XVII is halogen. In another embodiment, $R_1$ of compound of formula XVII is F. In another embodiment, $R_1$ of compound of formula XVII is Cl. In another embodiment, $R_1$ of compound of formula XVII is Br. In another embodiment, $R_1$ of compound of formula XVII is I. In another embodiment, $R_1$ of compound of formula XVII is $OCH_3$. In another embodiment, $R_1$ of compound of formula XVII is $OCH_3$, m is 3 and $R_2$ is H. In another embodiment, $R_1$ of compound of formula XVII is F, m is 1 and $R_2$ is H. In another embodiment, $R_4$ is F; $R_2$ is hydrogen; n is 3 and $R_1$ is $OCH_3$. In another embodiment, $R_4$ is $OCH_3$; $R_2$ is hydrogen; n is 3 and $R_1$ is $OCH_3$. In another embodiment, $R_4$ is $CH_3$; $R_2$ is hydrogen; n is 3 and $R_1$ is $OCH_3$. In another embodiment, $R_4$ is Cl; $R_2$ is hydrogen; n is 3 and $R_1$ is $OCH_3$. In another embodiment, $R_4$ is $N(Me)_2$; $R_2$ is hydrogen; n is 3 and $R_1$ is $OCH_3$. In one embodiment, $R_4$ of compound of formula XVII is halogen, $R_1$ is H and $R_2$ is halogen. In one embodiment, $R_4$ of compound of formula XVII is halogen, $R_1$ is halogen and $R_2$ is H. In one embodiment, $R_4$ of compound of formula XVII is alkoxy, $R_1$ is halogen and $R_2$ is H. In one embodiment, $R_4$ of compound of formula XVII is methoxy, $R_1$ is halogen and $R_2$ is H. Non limiting examples of compounds of formula XVII are selected from: (2-(4-fluorophenyl)-1H-imidazol-4-yl)(3,4,5-trimethoxyphenyl)methanone (12ba), (2-(4-methoxyphenyl)-1H-imidazol-4-yl)(3,4,5-trimethoxyphenyl)methanone (12ca), (4-fluorophenyl)(2-(4-methoxyphenyl)-1H-imidazol-4-yl)methanone (12cb), (2-(p-tolyl)-1H-imidazol-4-yl)(3,4,5-trimethoxyphenyl)methanone (12da), (4-fluorophenyl)(2-(p-tolyl)-1H-imidazol-4-yl)methanone (12db), (4-Hydroxy-3,5-dimethoxyphenyl)(2-(p-tolyl)-1H-imidazol-4-yl)methanone (12dc), (2-(4-chlorophenyl)-1H-imidazol-4-yl)(3,4,5-trimethoxyphenyl)methanone (12fa), (2-(4-chlorophenyl)-1H-imidazol-4-yl)(4-fluorophenyl)methanone (12fb), (2-(4-chlorophenyl)-1H-imidazol-4-yl)(3,4,5-trihydroxyphenyl)methanone (13fa), (2-(4-(dimethylamino)phenyl)-1H-imidazol-4-yl)(3,4,5-trimethoxyphenyl)methanone (12ga), (2-(4-(dimethylamino)phenyl)-1H-imidazol-4-yl)(4-fluorophenyl)methanone (12gb), (2-(4-(benzyloxy)phenyl)-1H-imidazol-4-yl)(4-fluorophenyl)methanone (12jb), (2-(4-hydroxyphenyl)-1H-imidazol-4-yl)(3,4,5-trimethoxyphenyl)methanone (12ka), (2-(4-bromophenyl)-1H-imidazol-4-yl)(3,4,5-trimethoxyphenyl)methanone (12la), (2-(4-(trifluoromethyl)phenyl)-1H-imidazol-4-yl)(3,4,5-trimethoxyphenyl)methanone (12pa), (2-(4-ethylphenyl)-1H-imidazol-4-yl)(3,4,5-trimethoxyphenyl)methanone (12q), (2-(4-isopropylphenyl)-1H-imidazol-4-yl)(3,4,5-trimethoxyphenyl)methanone (12v), and (2-(4-tert-butylphenyl)-1H-imidazol-4-yl)(3,4,5-trimethoxyphenyl)methanone (12w).

In another embodiment a compound of formula XVII is represented by the structure of formula 12fb:

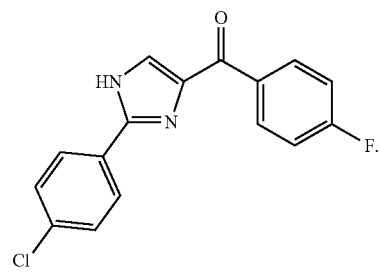

(12fb)

In another embodiment a compound of formula XVII is represented by the structure of formula 12cb:

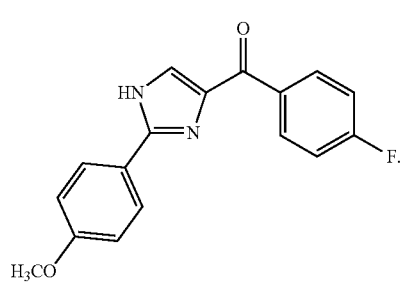

(12cb)

In one embodiment, this invention is directed to a compound of formula XVIII:

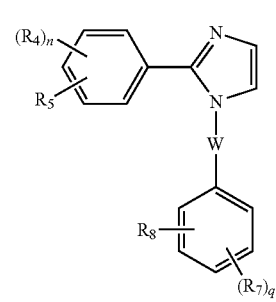

(XVIII)

wherein
W is C=O, C=S, $SO_2$ or S=O;
$R_4$ and $R_7$ are independently H, O-alkyl, I, Br, Cl, F, alkyl, haloalkyl, aminoalkyl, $-(CH_2)_iNHCH_3$, $-(CH_2)_iNH_2$, $-(CH_2)_iN(CH_3)_2$, $-OCH_2Ph$, OH, CN, $NO_2$, $-NHCO$-alkyl, COOH, C(O)O-alkyl or C(O)H;
$R_5$ and $R_8$ are independently H, O-alkyl, I, Br, Cl, F, alkyl, haloalkyl, aminoalkyl, $-(CH_2)_iNHCH_3$, $-(CH_2)_iNH_2$, $-(CH_2)_iN(CH_3)_2$, $-OCH_2Ph$, OH, CN, $NO_2$, $-NHCO$-alkyl, COOH, C(O)O-alkyl or C(O)H;
n is an integer between 1-4;
i is an integer between 0-5; and
q is an integer between 1-4;
or its pharmaceutically acceptable salt, hydrate, polymorph, metabolite, tautomer or isomer.

In one embodiment, W of compound of formula XVIII is C=O. In another embodiment, W of compound of formula XVIII is $SO_2$. In another embodiment, $R_4$ of compound of formula XVIII is H. In another embodiment, $R_4$ of compound of formula XVIII is $NO_2$. In another embodiment, $R_4$ of compound of formula XVIII is OBn. In another embodiment, $R_7$ of compound of formula XVIII is H. In another embodiment, $R_7$ of compound of formula XVIII is $OCH_3$. In another embodiment, $R_7$ of compound of formula XVIII is $OCH_3$ and q is 3. Non limiting examples of compounds of formula XVII are selected from: (4-methoxyphenyl)(2-phenyl-1H-imidazol-1-yl)methanone (12aba), (2-phenyl-1H-imidazol-1-yl)(3,4,5-trimethoxyphenyl)methanone (12aaa), 2-phenyl-1-(phenylsulfonyl)-1H-imidazole (10a), 2-(4-nitrophenyl)-1-(phenylsulfonyl)-1H-imidazole (10x), 2-(4-(benzyloxy)phenyl)-1-(phenylsulfonyl)-1H-imidazole (10j).

In one embodiment, this invention is directed to a compound of formula XIX:

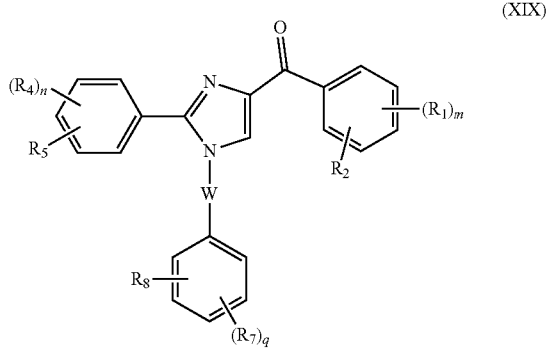

(XIX)

wherein
W is C=O, C=S, $SO_2$, S=O;
$R_1$, $R_4$ and $R_7$ are independently H, O-alkyl, I, Br, Cl, F, alkyl, haloalkyl, aminoalkyl, —$(CH_2)_iNHCH_3$, —$(CH_2)_iNH_2$, —$(CH_2)_iN(CH_3)_2$, —$OCH_2Ph$, OH, CN, $NO_2$, —NHCO-alkyl, COOH, C(O)O-alkyl or C(O)H;
$R_2$, $R_5$ and $R_8$ are independently H, O-alkyl, I, Br, Cl, F, alkyl, haloalkyl, aminoalkyl, —$(CH_2)_iNHCH_3$, —$(CH_2)_iNH_2$, —$(CH_2)_iN(CH_3)_2$, —$OCH_2Ph$, OH, CN, $NO_2$, —NHCO-alkyl, COOH, C(O)O-alkyl or C(O)H;
m is an integer between 1-4;
n is an integer between 1-4;
i is an integer between 0-5; and
q is 1-4;
or its pharmaceutically acceptable salt, hydrate, polymorph, metabolite, tautomer or isomer.

In one embodiment, $R_1$, $R_4$ and $R_7$ of formula XIX are independently H. In another embodiment, $R_1$, $R_4$ and $R_7$ of formula XIX are independently O-alkyl. In another embodiment, $R_1$, $R_4$ and $R_7$ of formula XIX are independently halogen. In another embodiment, $R_1$, $R_4$ and $R_7$ of formula XIX are independently CN. In another embodiment, $R_1$, $R_4$ and $R_7$ of formula XIX are independently OH. In another embodiment, $R_1$, $R_4$ and $R_7$ of formula XIX are independently alkyl. In another embodiment, $R_1$, $R_4$ and $R_7$ of formula XIX are independently —$OCH_2Ph$. In one embodiment $R_2$, $R_5$ and $R_8$ of formula XIX are independently H. In another embodiment, $R_2$, $R_5$ and $R_8$ of formula XIX are independently O-alkyl. In another embodiment, $R_2$, $R_5$ and $R_8$ of formula XIX are independently halogen. In another embodiment, $R_2$, $R_5$ and $R_8$ of formula XIX are independently CN. In another embodiment, $R_2$, $R_5$ and $R_8$ of formula XIX are independently OH. In another embodiment, $R_2$, $R_5$ and $R_8$ of formula XIX are independently alkyl. In another embodiment, $R_2$, $R_5$ and $R_8$ of formula XIX are independently —$OCH_2Ph$. In another embodiment, $R_5$, $R_2$ and $R_8$ of formula XIX are H, $R_4$ is 4-N(Me)$_2$, $R_1$ is $OCH_3$, m is 3 and $R_7$ is $OCH_3$. In another embodiment, $R_5$, $R_2$, $R_7$ and $R_8$ of formula XIX are H, $R_4$ is 4-Br, $R_1$ is $OCH_3$, and m is 3. In another embodiment W is $SO_2$. In another embodiment W is C=O. In another embodiment W is C=S. In another embodiment W is S=O. Non limiting examples of compounds of formula XIX are selected from: (2-(4-(dimethylamino)phenyl)-1-((4-methoxyphenyl)sulfonyl)-1H-imidazol-4-yl)(3,4,5-trimethoxyphenyl)methanone (11gaa); (2-(4-bromophenyl)-1-(phenylsulfonyl)-1H-imidazol-4-yl)(3,4,5-trimethoxyphenyl)methanone (11la), (4-fluorophenyl)(2-(4-methoxyphenyl)-1-(phenylsulfonyl)-1H-imidazol-4-yl)methanone (11oc), (2-(4-chlorophenyl)-1-(phenylsulfonyl)-1H-imidazol-4-yl)(4-fluorophenyl)methanone (11fb), (4-fluorophenyl)(2-phenyl-1-(phenylsulfonyl)-1H-imidazol-4-yl)methanone (11af), (4-fluorophenyl)(1-(phenylsulfonyl)-2-(p-tolyl)-1H-imidazol-4-yl)methanone (11db), (2-(4-(dimethylamino)phenyl)-1-(phenylsulfonyl)-1H-imidazol-4-yl)(3,4,5-trimethoxyphenyl)methanone (11ga), (2-(4-(dimethylamino)phenyl)-1-(phenylsulfonyl)-1H-imidazol-4-yl)(4-fluorophenyl)methanone (11gb), (2-(3,4-dimethoxyphenyl)-1-(phenylsulfonyl)-1H-imidazol-4-yl)(3,4,5-trimethoxyphenyl)methanone (11ha), (2-(4-(benzyloxy)phenyl)-1-(phenylsulfonyl)-1H-imidazol-4-yl)(4-fluorophenyl)methanone (11jb), (2-(4-(dimethylamino)phenyl)-1-((4-methoxyphenyl)sulfonyl)-1H-imidazol-4-yl)(4-fluorophenyl)methanone (12gba).

In another embodiment a compound of formula XIX is represented by the structure of formula 11cb:

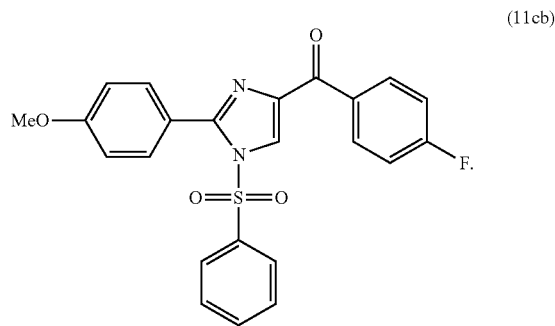 [SMILES: COc1ccc(-c2nc(C(=O)c3ccc(F)cc3)cn2S(=O)(=O)c2ccccc2)cc1]

(11cb)

In another embodiment a compound of formula XIX is represented by the structure of formula 11fb:

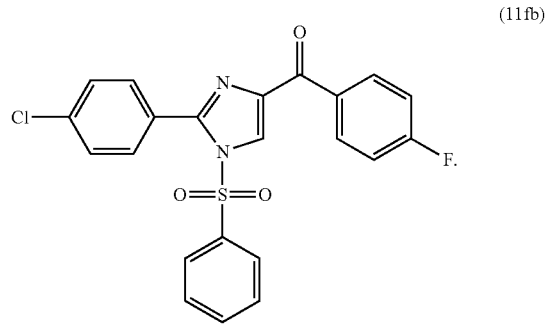 [SMILES: O=C(c1ccc(F)cc1)c1cn(S(=O)(=O)c2ccccc2)c(-c2ccc(Cl)cc2)n1]

(11fb)

In one embodiment, this invention is directed to a compound of formula XX:

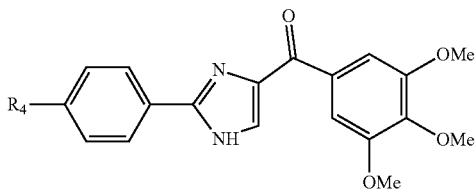

(XX)

wherein

R₄ is H, O-alkyl, I, Br, Cl, F, alkyl, haloalkyl, aminoalkyl, —(CH₂)ᵢNHCH₃, —(CH₂)ᵢNH₂, —(CH₂)ᵢN(CH₃)₂, —OCH₂Ph, OH, CN, NO₂, —NHCO-alkyl, COOH, C(O)O-alkyl or C(O)H; and i is an integer between 0-5;

or its pharmaceutically acceptable salt, hydrate, polymorph, metabolite, tautomer or isomer.

In one embodiment, R₄ of compound of formula XX is H. In another embodiment, R₄ of compound of formula XX is halogen. In another embodiment, R₄ is F. In another embodiment, R₄ is Cl. In another embodiment R₄ is Br. In another embodiment R₄ is I. In another embodiment, R₄ is alkyl. In another embodiment, R₄ is methyl. Non limiting examples of compounds of formula XX are selected from: (2-phenyl-1H-imidazol-4-yl)(3,4,5-trimethoxyphenyl)methanone (12aa), (2-(4-fluorophenyl)-1H-imidazol-4-yl)(3,4,5-trimethoxyphenyl)methanone (12ba), (2-(4-methoxyphenyl)-1H-imidazol-4-yl)(3,4,5-trimethoxyphenyl)methanone (12ca), (2-(p-tolyl)-1H-imidazol-4-yl)(3,4,5-trimethoxyphenyl)methanone (12da), (2-(4-chlorophenyl)-1H-imidazol-4-yl)(3,4,5-trimethoxyphenyl)methanone (12fa), (2-(4-(dimethylamino)phenyl)-1H-imidazol-4-yl)(3,4,5-trimethoxyphenyl)methanone (12ga), (2-(2-(trifluoromethyl)phenyl)-1H-imidazol-4-yl)(3,4,5-trimethoxyphenyl)methanone (12ia), (2-(4-(benzyloxy)phenyl)-1H-imidazol-4-yl)(3,4,5-trimethoxyphenyl)methanone (12ja), (2-(4-hydroxyphenyl)-1H-imidazol-4-yl)(3,4,5-trimethoxyphenyl)methanone (12ka), (2-(4-bromophenyl)-1H-imidazol-4-yl)(3,4,5-trimethoxyphenyl)methanone (12la), (2-(4-(trifluoromethyl)phenyl)-1H-imidazol-4-yl)(3,4,5-trimethoxyphenyl)methanone (12pa), (2-(4-ethylphenyl)-1H-imidazol-4-yl)(3,4,5-trimethoxyphenyl)methanone (12q), (2-(4-isopropylphenyl)-1H-imidazol-4-yl)(3,4,5-trimethoxyphenyl)methanone (12v), and (2-(4-tert-butylphenyl)-1H-imidazol-4-yl)(3,4,5-trimethoxyphenyl)methanone (12w).

In another embodiment a compound of formula XX is represented by the structure of formula 12da:

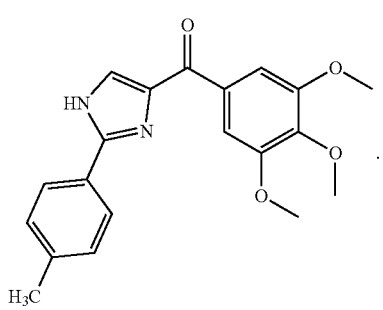

(12da)

In another embodiment a compound of formula XX is represented by the structure of formula 12fa:

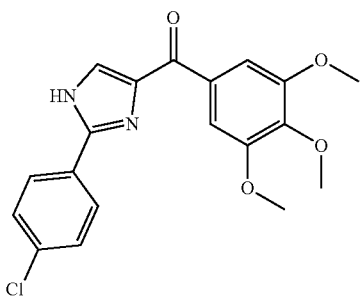

(12fa)

In one embodiment, this invention is directed to a compound of formula XXI:

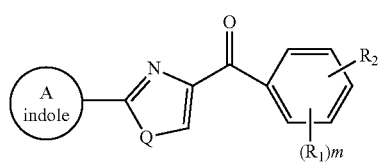

(XXI)

wherein

A is indolyl;

Q is NH, O or S;

R₁ and R₂ are independently H, O-alkyl, I, Br, Cl, F, alkyl, haloalkyl, aminoalkyl, —(CH₂)ᵢNHCH₃, —(CH₂)ᵢNH₂, —(CH₂)ᵢN(CH₃)₂, —OCH₂Ph, OH, CN, NO₂, —NHCO-alkyl, COOH, C(O)O-alkyl or C(O)H; and wherein said A is optionally substituted by substituted or unsubstituted O-alkyl, O-haloalkyl, F, Cl, Br, I, haloalkyl, CF₃, CN, —CH₂CN, NH₂, hydroxyl, —(CH₂)ᵢNHCH₃, —(CH₂)ᵢNH₂, —(CH₂)ᵢN(CH₃)₂, —OC(O)CF₃, substituted or unsubstituted —SO₂-aryl, substituted or unsubstituted C₁-C₅ linear or branched alkyl, substituted or unsubstituted haloalkyl, substituted or unsubstituted alkylamino, substituted or unsubstituted aminoalkyl, —OCH₂Ph, substituted or unsubstituted —NHCO-alkyl, COOH, substituted or unsubstituted —C(O)Ph, substituted or unsubstituted C(O)O— alkyl, C(O)H, —C(O)NH₂, NO₂ or combination thereof;

i is an integer between 0-5; and m is an integer between 1-4;

or its pharmaceutically acceptable salt, hydrate, polymorph, metabolite, tautomer or isomer.

In one embodiment, R₁ of compound of formula XXI is OCH₃; m is 3 and R₂ is hydrogen. In another embodiment, R₁ is F; m is 1 and R₂ is hydrogen. In one embodiment, Q of formula XXI is O. In another embodiment Q of formula XXI is NH. In another embodiment, Q of formula XXI is S.

In one embodiment, A ring of compound of formula XXI is substituted 5-indolyl. In another embodiment the substitution is —(C=O)-aryl. In another embodiment, the aryl is 3,4,5-(OCH₃)₃-Ph.

In another embodiment, A ring of compound of formula XXI is 3-indolyl. In another embodiment, A ring of compound of formula XXI is 5-indolyl. In another embodiment, A ring of compound of formula XXI is 2-indolyl. Non limiting examples of compounds of formula XXI are selected from: (5-(4-(3,4,5-trimethoxybenzoyl)-1H-imidazol-2-yl)-1H-indol-2-yl)(3,4,5-trimethoxyphenyl)methanone (15xaa); (1-(phenylsulfonyl)-2-(1-(phenylsulfonyl)-2-(3,4,5-trimethoxybenzoyl)-1H-indol-5-yl)-1H-imidazol-4-yl)(3,4,5-trimethoxyphenyl)methanone (16xaa); 2-(1H-indol-3-yl)-1H-imidazol-4-yl)(3,4,5-trimethoxyphenyl)methanone (17ya); (2-(1H-indol-2-yl)thiazol-4-yl)(3,4,5-trimethoxyphenyl)methanone (62a); and (2-(1H-indol-5-yl)thiazol-4-yl)(3,4,5-trimethoxyphenyl)methanone (66a).

In one embodiment, this invention is directed to a compound of formula XXIa:

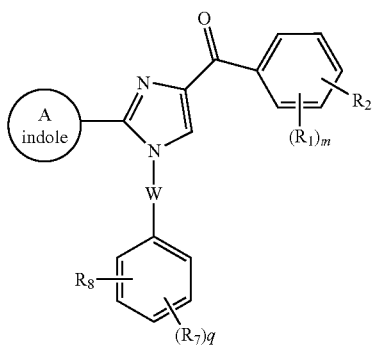

(XXIa)

wherein
W is C=O, C=S, SO$_2$, S=O;
A is indolyl;
R$_1$ and R$_2$ are independently H, O-alkyl, I, Br, Cl, F, alkyl, haloalkyl, aminoalkyl, —(CH$_2$)$_i$NHCH$_3$, —(CH$_2$)$_i$NH$_2$, —(CH$_2$)$_i$N(CH$_3$)$_2$, —OCH$_2$Ph, OH, CN, NO$_2$, —NHCO-alkyl, COOH, C(O)O-alkyl or C(O)H;
R$_7$ and R are independently H, O-alkyl, I, Br, Cl, F, alkyl, haloalkyl, aminoalkyl, —(CH$_2$)$_i$NHCH$_3$, —(CH$_2$)$_i$NH$_2$, —(CH$_2$)$_i$N(CH$_3$)$_2$, —OCH$_2$Ph, OH, CN, NO$_2$, —NHCO-alkyl, COOH, C(O)O-alkyl or C(O)H;
wherein said A is optionally substituted by substituted or unsubstituted O-alkyl, O-haloalkyl, F, Cl, Br, I, haloalkyl, CF$_3$, CN, —CH$_2$CN, NH$_2$, hydroxyl, —(CH$_2$)$_i$NHCH$_3$, —(CH$_2$)$_i$NH$_2$, —(CH$_2$)$_i$N(CH$_3$)$_2$, —OC(O)CF$_3$, substituted or unsubstituted —SO$_2$-aryl, substituted or unsubstituted C$_{1-5}$ linear or branched alkyl, substituted or unsubstituted haloalkyl, substituted or unsubstituted alkylamino, substituted or unsubstituted aminoalkyl, —OCH$_2$Ph, substituted or unsubstituted —NHCO-alkyl, COOH, substituted or unsubstituted —C(O)Ph, substituted or unsubstituted C(O)O— alkyl, C(O)H, —C(O)NH$_2$, NO$_2$ or combination thereof;
i is an integer between 0-5; and
m is an integer between 1-4;
q is an integer between 1-4;
or its pharmaceutically acceptable salt, hydrate, polymorph, metabolite, tautomer or isomer.

In one embodiment, R$_1$ of compound of formula XXIa is OCH$_3$; m is 3 and R$_2$ is hydrogen. In another embodiment, R$_1$ is F; m is 1 and R$_2$ is hydrogen. In another embodiment, A ring of compound of formula XXIa is substituted 5-indolyl. In another embodiment, A ring of compound of formula XXIa is 3-indolyl. Non limiting examples of compounds of formula XXIa are selected from: (1-(phenylsulfonyl)-2-(1-(phenylsulfonyl)-2-(3,4,5-trimethoxybenzoyl)-1H-indol-5-yl)-1H-imidazol-4-yl)(3,4,5-trimethoxyphenyl)methanone (16xaa); (1-(phenylsulfonyl)-2-(1-(phenylsulfonyl)-1H-indol-3-yl)-1H-imidazol-4-yl)(3,4,5-trimethoxyphenyl)methanone (17yaa).

In one embodiment, this invention is directed to a compound of formula XXII:

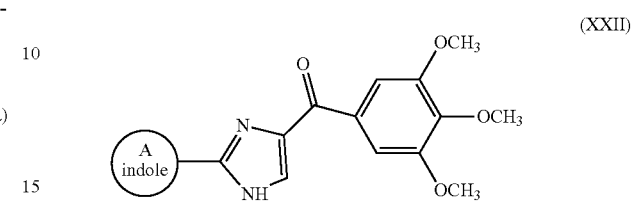

(XXII)

wherein

A is indolyl;

wherein said A is optionally substituted by substituted or unsubstituted O-alkyl, O-haloalkyl, F, Cl, Br, I, haloalkyl, CF$_3$, CN, —CH$_2$CN, NH$_2$, hydroxyl, —(CH$_2$)$_i$NHCH$_3$, —(CH$_2$)$_i$NH$_2$, —(CH$_2$)$_i$N(CH$_3$)$_2$, —OC(O)CF$_3$, substituted or unsubstituted —SO$_2$-aryl, substituted or unsubstituted C$_1$-C$_5$ linear or branched alkyl, substituted or unsubstituted haloalkyl, substituted or unsubstituted alkylamino, substituted or unsubstituted aminoalkyl, —OCH$_2$Ph, substituted or unsubstituted —NHCO-alkyl, COOH, substituted or unsubstituted —C(O)Ph, substituted or unsubstituted C(O)O— alkyl, C(O)H, —C(O)NH$_2$, NO$_2$ or combination thereof;

i is an integer between 0-5;

or its pharmaceutically acceptable salt, hydrate, polymorph, metabolite, tautomer or isomer.

In one embodiment, A ring of compound of formula XXII is substituted 5-indolyl. In another embodiment the substitution is —(C=O)-aryl. In another embodiment, the aryl is 3,4,5-(OCH$_3$)$_3$-Ph.

In another embodiment, A ring of compound of formula XXII is 3-indolyl. Non limiting examples of compounds of formula XXII are selected from: (5-(4-(3,4,5-trimethoxybenzoyl)-1H-imidazol-2-yl)-1H-indol-2-yl)(3,4,5-trimethoxyphenyl)methanone (15xaa); (2-(1H-indol-3-yl)-1H-imidazol-4-yl)(3,4,5-trimethoxyphenyl)methanone (17ya), In another embodiment a compound of formula XXI or XXII is represented by the structure of formula 17ya:

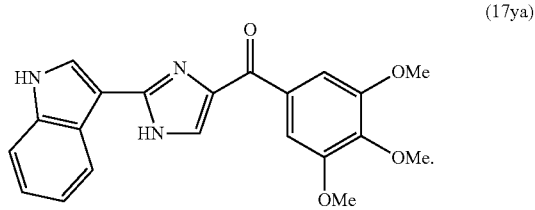 [SMILES: COc1cc(C(=O)c2c[nH]c(-c3c[nH]c4ccccc34)n2)cc(OC)c1OC]

(17ya)

In one embodiment, this invention is directed to a compound of formula XXIII:

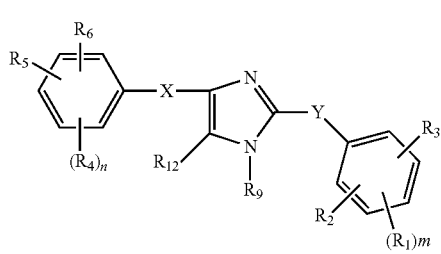

XXIII wherein $R_1$, $R_2$, $R_3$, $R_4$, $R_5$ and $R_6$ are independently hydrogen, O-alkyl, O-haloalkyl, F, Cl, Br, I, haloalkyl, $CF_3$, CN, —$CH_2CN$, $NH_2$, hydroxyl, —$(CH_2)_iNHCH_3$, —$(CH_2)_i NH_2$, —$(CH_2)_iN(CH_3)_2$, —$OC(O)CF_3$, $C_1$-$C_5$ linear or branched alkyl, haloalkyl, alkylamino, aminoalkyl, —$OCH_2Ph$, —NHCO-alkyl, COOH, —C(O)Ph, C(O) O-alkyl, C(O)H, —$C(O)NH_2$ or $NO_2$;

$R_9$ and $R_{11}$ are independently hydrogen, linear or branched, substituted or unsubstituted alkyl, substituted or unsubstituted cycloalkyl, substituted or unsubstituted aryl, —$CH_2Ph$, substituted benzyl, haloalkyl, aminoalkyl, —$OCH_2Ph$, substituted or unsubstituted $SO_2$-aryl, substituted or unsubstituted —(C═O)-aryl or OH;

wherein substitutions are independently selected from the group of hydroxyl, an aliphatic straight- or branched-chain $C_1$ to $C_{10}$ hydrocarbon, alkoxy, haloalkoxy, aryloxy, nitro, cyano, alkyl-CN, halo, haloalkyl, dihaloalkyl, trihaloalkyl, COOH, C(O)Ph, C(O)-alkyl, C(O)O-alkyl, C(O)H, $C(O)NH_2$, —$OC(O)CF_3$, —$OCH_2Ph$, amino, aminoalkyl, alkylamino, mesylamino, dialkylamino, arylamino, amido, NHC(O)-alkyl, urea, alkylurea, alkylamido (e.g., acetamide), haloalkylamido, arylamido, aryl, and $C_5$ to $C_7$ cycloalkyl, arylalkyl, and combinations thereof;

X is a bond, NH, $C_1$ to $C_5$ hydrocarbon, O, or S;

Y is a bond, —C═O, —C═S, —C═N—$NH_2$, —C═N—OH, —CH—OH, —C═CH—CN, —C═N—CN, —CH═CH—, C═$C(CH_3)_2$, —C═N—OMe, —(C═O)—NH, —NH—(C═O), —(C═O)—O, —O—(C═O), —$(CH_2)_{1-5}$—(C═O), (C═O)—$(CH_2)_{1-5}$, —$(SO_2)$—NH—, —NH—$(SO_2)$—, $SO_2$, SO or S;

i is an integer between 0-5;

n is an integer between 1-3; and m is an integer between 1-3;

or its pharmaceutically acceptable salt, hydrate, polymorph, metabolite, tautomer or isomer.

In another embodiment, X of formula XXIII is a bond. In another embodiment, Y of formula XXIII is a C═O. In another embodiment X of formula XXIII is a bond and Y of formula XXIII is C═O. In another embodiment, $R_9$ and $R_{12}$ of formula XXIII are both hydrogens.

In one embodiment, this invention is directed to a compound of formula XXIV:

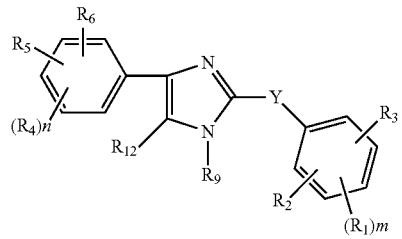

XXIV wherein $R_1$, $R_2$, $R_3$, $R_4$, $R_5$ and $R_6$ are independently hydrogen, O-alkyl, O-haloalkyl, F, Cl, Br, I, haloalkyl, $CF_3$, CN, —$CH_2CN$, $NH_2$, hydroxyl, —$(CH_2)_iNHCH_3$, —$(CH_2)_i NH_2$, —$(CH_2)_iN(CH_3)_2$, —$OC(O)CF_3$, $C_1$-$C_5$ linear or branched alkyl, haloalkyl, alkylamino, aminoalkyl, —$OCH_2Ph$, —NHCO-alkyl, COOH, —C(O)Ph, C(O) O-alkyl, C(O)H, —$C(O)NH_2$ or $NO_2$;

$R_9$ and $R_{12}$ are independently hydrogen, linear or branched, substituted or unsubstituted alkyl, substituted or unsubstituted cycloalkyl, substituted or unsubstituted aryl, —$CH_2Ph$, substituted benzyl, haloalkyl, aminoalkyl, —$OCH_2Ph$, substituted or unsubstituted $SO_2$-aryl, substituted or unsubstituted —(C═O)-aryl or OH;

wherein substitutions are independently selected from the group of hydroxyl, an aliphatic straight- or branched-chain $C_1$ to $C_{10}$ hydrocarbon, alkoxy, haloalkoxy, aryloxy, nitro, cyano, alkyl-CN, halo, haloalkyl, dihaloalkyl, trihaloalkyl, COOH, C(O)Ph, C(O)-alkyl, C(O)O-alkyl, C(O)H, $C(O)NH_2$, —$OC(O)CF_3$, —$OCH_2Ph$, amino, aminoalkyl, alkylamino, mesylamino, dialkylamino, arylamino, amido, NHC(O)-alkyl, urea, alkylurea, alkylamido (e.g., acetamide), haloalkylamido, arylamido, aryl, and $C_5$ to $C_7$ cycloalkyl, arylalkyl, and combinations thereof;

Y is a bond, —C═O, —C═S, —C═N—$NH_2$, —C═N—OH, —CH—OH, —C═CH—CN, —C═N—CN, —CH═CH—, C═$C(CH_3)_2$, —C═N—OMe, —(C═O)—NH, —NH—(C═O), —(C═O)—O, —O—(C═O), —$(CH_2)_{1-5}$—(C═O), (C═O)—$(CH_2)_{1-5}$, —$(SO_2)$—NH—, —NH—$(SO_2)$—, $SO_2$, SO or S;

i is an integer between 0-5;

n is an integer between 1-3; and m is an integer between 1-3;

or its pharmaceutically acceptable salt, hydrate, polymorph, metabolite, tautomer or isomer.

In another embodiment, Y of formula XXIV is C═O.

In another embodiment, $R_9$ and $R_{12}$ of formula XXIV are both hydrogens.

In one embodiment, this invention is directed to a compound of formula XXV:

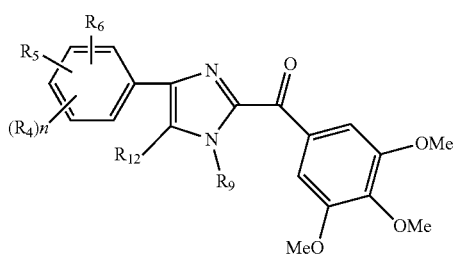

XXV wherein
R$_4$, R$_5$ and R$_6$ are independently hydrogen, O-alkyl, O-haloalkyl, F, Cl, Br, I, haloalkyl, CF$_3$, CN, —CH$_2$CN, NH$_2$, hydroxyl, —(CH$_2$)$_i$NHCH$_3$, —(CH$_2$)$_i$NH$_2$, —(CH$_2$)$_i$N(CH$_3$)$_2$, —OC(O)CF$_3$, C$_1$-C$_5$ linear or branched alkyl, haloalkyl, alkylamino, aminoalkyl, —OCH$_2$Ph, —NHCO-alkyl, COOH, —C(O)Ph, C(O)O-alkyl, C(O)H, —C(O)NH$_2$ or NO$_2$;

R$_9$ and R$_{12}$ are independently hydrogen, linear or branched, substituted or unsubstituted alkyl, substituted or unsubstituted cycloalkyl, substituted or unsubstituted aryl, —CH$_2$Ph, substituted benzyl, haloalkyl, aminoalkyl, —OCH$_2$Ph, substituted or unsubstituted SO$_2$-aryl, substituted or unsubstituted —(C=O)-aryl or OH;

wherein substitutions are independently selected from the group of hydroxyl, an aliphatic straight- or branched-chain C$_1$ to C$_{10}$ hydrocarbon, alkoxy, haloalkoxy, aryloxy, nitro, cyano, alkyl-CN, halo, haloalkyl, dihaloalkyl, trihaloalkyl, COOH, C(O)Ph, C(O)-alkyl, C(O)O-alkyl, C(O)H, C(O)NH$_2$, —OC(O)CF$_3$, —OCH$_2$Ph, amino, aminoalkyl, alkylamino, mesylamino, dialkylamino, amido, NHC(O)-alkyl, urea, alkylurea, alkylamido (e.g., acetamide), haloalkylamido, arylamido, aryl, and C$_5$ to C$_7$ cycloalkyl, arylalkyl, and combinations thereof;

i is an integer between 0-5;
n is an integer between 1-3;
or its pharmaceutically acceptable salt, hydrate, polymorph, metabolite, tautomer or isomer.

It is well understood that in structures presented in this invention wherein the nitrogen atom has less than 3 bonds, H atoms are present to complete the valence of the nitrogen.

In another embodiment, the compound of formula XXIII, XXIV and/or XXV is (4-phenyl-1H-imidazol-2-yl)(3,4,5-trimethoxyphenyl)methanone (70a); (4-(4-fluorophenyl)-1H-imidazol-2-yl)(3,4,5-trimethoxyphenyl)methanone (70b); (4-(4-chlorophenyl)-1H-imidazol-2-yl)(3,4,5-trimethoxyphenyl)methanone (70c); (4-(4-bromophenyl)-1H-imidazol-2-yl)(3,4,5-trimethoxyphenyl)methanone (70d); (4-(4-(trifluoromethyl)phenyl)-1H-imidazol-2-yl)(3,4,5-trimethoxyphenyl)methanone (70e); (4-p-tolyl-1H-imidazol-2-yl)(3,4,5-trimethoxyphenyl)methanone (70f); (4-(4-methoxyphenyl)-1H-imidazol-2-yl)(3,4,5-trimethoxyphenyl)methanone (70g); (4-(4-(dimethylamino)phenyl)-1H-imidazol-2-yl)(3,4,5-trimethoxyphenyl)methanone (70h); (4-(4-hydroxyphenyl)-1H-imidazol-2-yl)(3,4,5-trimethoxyphenyl)methanone (70i); (5-methyl-4-phenyl-1H-imidazol-2-yl)(3,4,5-trimethoxyphenyl)methanone (70j); (5-ethyl-4-phenyl-1H-imidazol-2-yl)(3,4,5-trimethoxyphenyl)methanone (70k); (4-phenyl-5-propyl-1H-imidazol-2-yl)(3,4,5-trimethoxyphenyl)methanone (70l); (1-methyl-4-phenyl-1H-imidazol-2-yl)(3,4,5-trimethoxyphenyl)methanone (70m); (1-ethyl-4-phenyl-1H-imidazol-2-yl)(3,4,5-trimethoxyphenyl)methanone (70n); (1-benzyl-4-phenyl-1H-imidazol-2-yl)(3,4,5-trimethoxyphenyl)methanone (70o); or (1-cyclopentyl-4-phenyl-1H-imidazol-2-yl)(3,4,5-trimethoxyphenyl)methanone (70p).

In one embodiment, Q of compound of formula XII is H and P is

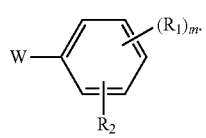

In another embodiment, P of compound of formula XII is H and Q is

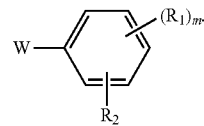

In another embodiment, P of compound of formula XII is

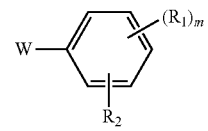

and Q is SO$_2$—Ph. In one embodiment. Q of compound of formula XII is H and P is

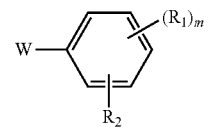

wherein W is C=O.

In another embodiment W of compound of formula XII, XVIII, XIX, or XXIa is C=O. In another embodiment, W of compound of formula XII, XVIII, XIX, or XXIa is SO$_2$. In another embodiment, W of compound of formula XII, XVIII, XIX, or XXIa is C=S. In another embodiment, W of compound of formula XII, XVIII, XIX, or XXIa is S=O.

In one embodiment, Z of compound of formula XIII is oxygen. In another embodiment, Z of compound of formula XIII is sulfur.

In one embodiment, R$_4$ of compound of formula XII-XVI, XVIII, XIX or XXIII-XXV is hydrogen, n is 1 and R$_4$ is in the para position.

In one embodiment, R$_4$ of compound of formula XII-XX or XXIII-XXV is alkyl. In another embodiment, R$_4$ of compound of formula XII-XX or XXIII-XXV is H. In another embodiment, R$_4$ of compound of formula XII-XX or XXIII-XXV is methyl (CH$_3$). In another embodiment, R$_4$ of compound of formula XII-XX or XXIII-XXV is hydroxyl. In another embodiment, R$_4$ of compound of formula XII-XX or XXIII-XXV is ethyl. In another embodiment, R$_4$ of compound of formula XII-XX or XXIII-XXV is propyl. In another embodiment, R$_4$ of compound of formula XII-XX or XXIII-XXV is isopropyl. In another embodiment, R$_4$ of compound of formula XII-XX or XXIII-XXV is tert-butyl. In another embodiment, R$_4$ of compound of formula XII-XX or XXIII-XXV is O-alkyl. In another embodiment, R$_4$ of compound of formula XII-XX is OCH$_3$. In another embodiment, R$_4$ of compound of formula XII-XX or XXIII-XXV is I. In another embodiment, R$_4$ of compound of formula XII-XX or XXIII-XXV is Br. In another embodiment, R$_4$ of compound of formula XII-XX or XXIII-XXV is F. In another embodiment, R$_4$ of compound of formula XII-XX or XXIII-XXV is Cl. In another embodiment, R$_4$ of compound of formula XII-XX or XXIII-XXV is N(Me)$_2$. In another embodiment, R$_4$ of compound of formula XII-XX or XXIII-XXV is OBn. In another embodiment, R$_4$ of compound of formula XII-XX or XXIII-XXV is OH. In another embodiment, $R_4$ of compound of formula XII-XX or XXIII-XXV is $CF_3$.

In one embodiment, $R_2$ of compound of formula XII, XII, XIV, XIVa, XVII, XIX, XXI or XXIa is hydrogen; $R_1$ is $OCH_3$ and m is 3. In another embodiment, $R_2$ of compound of formula XII, XIII, XIV, XIVa, XVII, XIX, XXI or XXIa is hydrogen; m is 1 and $R_1$ is in the para position. In another embodiment, $R_2$ of compound of formula XII, XIII, XIV, XIVa, XVII, XIX, XXI or XXIa is hydrogen; m is 1 and $R_1$ is I. In another embodiment, $R_2$ of compound of formula XII, XIII, XIV, XIVa, XVII, XIX, XXI or XXIa is hydrogen; m is 1 and $R_1$ is Br. In another embodiment, $R_2$ of compound of formula XII, XIII, XIV, XIVa, XVII, XIX, XXI or XXIa is hydrogen; m is 1 and $R_1$ is F. In another embodiment, $R_2$ of compound of formula XII, XIII, XIV, XIVa, XVII, XIX, XXI or XXIa is hydrogen; m is 1 and $R_1$ is Cl. In another embodiment, $R_1$ of compound of formula XII, XIII, XIV, XIVa, XVII, XIX, XXI or XXIa is I. In another embodiment, $R_1$ of compound of formula XII, XIII, XIV, XIVa, XVII, XIX, XXI or XXIa is Br. In another embodiment, $R_1$ of compound of formula XII, XIII, XIV, XIVa, XVII, XIX, XXI or XXIa is Cl. In another embodiment, $R_1$ of compound of formula XII, XIII, XIV, XIVa, XVII, XIX, XXI or XXIa is F.

In one embodiment, $R_1$, $R_2$ and $R_3$ of formula XXIII or XXIV are independently hydrogen. In another embodiment, $R_1$, $R_2$ and $R_3$ are independently O-alkyl. In another embodiment, $R_1$, $R_2$ and $R_3$ are independently methoxy. In another embodiment, $R_1$, $R_2$ and $R_3$ are independently O-haloalkyl. In another embodiment, $R_1$, $R_2$ and $R_3$ are independently F. In another embodiment, $R_1$, $R_2$ and $R_3$ are independently Cl. In another embodiment, $R_1$, $R_2$ and $R_3$ are independently Br. In another embodiment, $R_1$, $R_2$ and $R_3$ are independently I. In another embodiment, $R_1$, $R_2$ and $R_3$ are independently haloalkyl. In another embodiment, $R_1$, $R_2$ and $R_3$ are independently $CF_3$. In another embodiment, $R_1$, $R_2$ and $R_3$ are independently CN. In another embodiment, $R_1$, $R_2$ and $R_3$ are independently —$CH_2CN$. In another embodiment $R_1$, $R_2$ and $R_3$ are independently $NH_2$. In another embodiment, $R_1$, $R_2$ and $R_3$ are independently hydroxyl. In another embodiment, $R_1$, $R_2$ and $R_3$ are independently —$(CH_2)_iNHCH_3$. In another embodiment, $R_1$, $R_2$ and $R_3$ are independently —$(CH_2)_iNH_2$. In another embodiment, $R_1$, $R_2$ and $R_3$ are independently —$(CH_2)_iN(CH_3)_2$. In another embodiment, $R_1$, $R_2$ and $R_3$ are independently —$OC(O)CF_3$. In another embodiment, $R_1$, $R_2$ and $R_3$ are independently $C_1$-$C_5$ linear or branched alkyl. In another embodiment, $R_1$, $R_2$ and $R_3$ are independently haloalkyl. In another embodiment, $R_1$, $R_2$ and $R_3$ are independently alkylamino. In another embodiment, $R_1$, $R_2$ and $R_3$ are independently aminoalkyl. In another embodiment, $R_1$, $R_2$ and $R_3$ are independently —$OCH_2Ph$. In another embodiment, $R_1$, $R_2$ and $R_3$ are independently —NHCO-alkyl. In another embodiment, $R_1$, $R_2$ and $R_3$ are independently COOH. In another embodiment, $R_1$, $R_2$ and $R_3$ are independently —C(O)Ph. In another embodiment, $R_1$, $R_2$ and $R_3$ are independently C(O)O-alkyl. In another embodiment, $R_1$, $R_2$ and $R_3$ are independently C(O)H. In another embodiment, $R_1$, $R_2$ and $R_3$ are independently —$C(O)NH_2$. In another embodiment, $R_1$, $R_2$ and $R_3$ are independently $NO_2$.

In another embodiment, m of formula XXIII and XXIV is 1. In another embodiment, m of formula XXIII and XXIV is 2. In another embodiment, m of formula XXIII and XXIV is 3. In another embodiment, $R_1$ of formula XXIII and XXIV is O-alkyl, $R_2$ and $R_3$ are hydrogens and m is 3.

In one embodiment, $R_4$, $R_5$ and $R_6$ of formula XXIII-XXV are independently hydrogen. In another embodiment, $R_4$, R and $R_6$ of formula XXIII-XXV are independently O-alkyl. In another embodiment, $R_4$, $R_5$ and $R_6$ of formula XXIII-XXV are independently O-haloalkyl. In another embodiment, $R_4$, $R_5$ and $R_6$ of formula XXIII-XXV are independently F. In another embodiment, $R_4$, R and $R_6$ of formula XXIII-XXV are independently Cl. In another embodiment, $R_4$, $R_5$ and $R_6$ of formula XXIII-XXV are independently Br. In another embodiment, $R_4$, $R_5$ and $R_6$ of formula XXIII-XXV are independently I. In another embodiment, $R_4$, $R_5$ and $R_6$ of formula XXIII-XXV are independently haloalkyl. In another embodiment, $R_4$, $R_5$ and $R_6$ of formula XXIII-XXV are independently $CF_3$. In another embodiment, $R_4$, $R_5$ and $R_6$ of formula XXIII-XXV are independently CN. In another embodiment, $R_4$, $R_5$ and $R_6$ of formula XXIII-XXV are independently —$CH_2CN$. In another embodiment, $R_4$, $R_5$ and $R_6$ of formula XXIII-XXV are independently $NH_2$. In another embodiment, $R_4$, $R_5$ and $R_6$ of formula XXIII-XXV are independently hydroxyl. In another embodiment, $R_4$, $R_5$ and $R_6$ of formula XXIII-XXV are independently —$(CH_2)_iNHCH_3$. In another embodiment, $R_4$, $R_5$ and $R_6$ of formula XXIII-XXV are independently —$(CH_2)_iNH_2$. In another embodiment, $R_4$, $R_5$ and $R_6$ of formula XXIII-XXV are independently —$(CH_2)_iN(CH_3)_2$. In another embodiment, $R_4$, $R_5$ and $R_6$ of formula XXIII-XXV are independently —$OC(O)CF_3$. In another embodiment, $R_4$, $R_5$ and $R_6$ of formula XXIII-XXV are independently $C_1$-$C_5$ linear or branched alkyl. In another embodiment, $R_4$, $R_5$ and $R_6$ of formula XXIII-XXV are independently haloalkyl. In another embodiment, $R_4$, $R_5$ and $R_6$ of formula XXIII-XXV are independently alkylamino. In another embodiment, $R_4$, $R_5$ and $R_6$ of formula XXIII-XXV are independently aminoalkyl. In another embodiment, $R_4$, $R_5$ and $R_6$ of formula XXIII-XXV are independently —$OCH_2Ph$. In another embodiment, $R_4$, $R_5$ and $R_6$ of formula XXIII-XXV are independently —NHCO-alkyl. In another embodiment, $R_4$, $R_5$ and $R_6$ of formula XXIII-XXV are independently COOH. In another embodiment, $R_4$, $R_5$ and $R_6$ of formula XXIII-XXV are independently —C(O)Ph. In another embodiment, $R_4$, $R_5$ and $R_6$ of formula XXIII-XXV are independently C(O)O-alkyl. In another embodiment, $R_4$, $R_5$ and $R_6$ of formula XXIII-XXV are independently C(O)H. In another embodiment, $R_4$, $R_5$ and $R_6$ of formula XXIII-XXV are independently —$C(O)NH_2$. In another embodiment, $R_4$, $R_5$ and $R_6$ of formula XXIII-XXV are independently $NO_2$.

In another embodiment, n of formula XXIII-XXV is 1. In another embodiment, n of formula XXIII-XXV is 2. In another embodiment, n of formula XXIII-XXV is 3. In one embodiment, $R_9$ and $R_{12}$ of formula XXIII-XXV is independently hydrogen. In another embodiment, $R_9$ and $R_{12}$ of formula XXIII-XXV is independently a linear or branched alkyl. In another embodiment, $R_9$ and $R_{12}$ of formula XXIII-XXV is independently a methyl. In another embodiment, $R_9$ and $R_{12}$ of formula XXIII-XXV is an ethyl. In another embodiment, $R_9$ and $R_{12}$ of formula XXIII-XXV is a propyl. In another embodiment, $R_9$ and $R_{12}$ of formula XXIII-XXV is isopropyl. In another embodiment, $R_9$ and $R_{12}$ of formula XXIII-XXV is a tert-butyl. In another embodiment, $R_9$ and $R_{12}$ of formula XXIII-XXV is substituted or unsubstituted cycloalkyl. In another embodiment, $R_9$ and $R_{12}$ of formula XXIII-XXV is cyclopentyl. In another embodiment, $R_9$ and $R_{12}$ of formula XXIII-XXV is substituted or unsubstituted aryl. In another embodiment, $R_9$ and $R_{12}$ of formula XXIII-XXV is —$CH_2Ph$. In another embodiment, $R_9$ and $R_{12}$ of formula XXIII-XXV is substituted benzyl. In another embodiment, $R_9$ and $R_{12}$ of formula XXIII-XXV is haloalkyl. In another embodiment, $R_9$ and $R_{12}$ of formula XXIII-XXV is aminoalkyl. In another embodiment, $R_9$ and $R_{12}$ of formula XXII-XXV is —OCH$_2$Ph. In another embodiment, $R_9$ and $R_{12}$ of formula XXIII-XXV is substituted or unsubstituted SO$_2$-aryl. In another embodiment, $R_9$ and $R_{12}$ of formula XXIII-XXV is substituted or unsubstituted —(C=O)-aryl. In another embodiment, $R_9$ and $R_{12}$ of formula XXIII-XXV is OH.

In one embodiment Q of compound of formula XII is H and P is

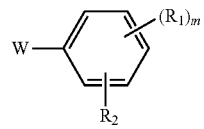

wherein W is C=O. Non-limiting examples of compounds of formula XII-XVII and XX-XXII are selected from (2-phenyl-1H-imidazol-4-yl)(3,4,5-trimethoxyphenyl)methanone (12aa); (4-methoxyphenyl)(2-phenyl-1H-imidazol-4-yl)methanone (12ab); (3-methoxyphenyl)(2-phenyl-1H-imidazol-4-yl)methanone (12ac); (3,5-dimethoxyphenyl)(2-phenyl-1H-imidazol-4-yl)methanone (12ad); (3,4-dimethoxyphenyl)(2-phenyl-1H-imidazol-4-yl)methanone (12ae); (4-fluorophenyl)(2-phenyl-1H-imidazol-4-yl)methanone (12af); (3-fluorophenyl)(2-phenyl-1H-imidazol-4-yl)methanone (12ag); (2-phenyl-1H-imidazol-4-yl)(p-tolyl)methanone (12ah); (2-phenyl-1H-imidazol-4-yl)(m-tolyl)methanone (12ai); (2-(4-fluorophenyl)-1H-imidazol-4-yl)(3,4,5-trimethoxyphenyl)methanone (12ba); (2-(4-methoxyphenyl)-1H-imidazol-4-yl)(3,4,5-trimethoxyphenyl)methanone (12ca); (4-fluorophenyl)(2-(4-methoxyphenyl)-1H-imidazol-4-yl)methanone (12cb); (2-(p-tolyl)-1H-imidazol-4-yl)(3,4,5-trimethoxyphenyl)methanone (12da); (4-fluorophenyl)(2-(p-tolyl)-1H-imidazol-4-yl)methanone (12db); (4-fluorophenyl)(2-(p-tolyl)-1H-imidazol-4-yl)methanone hydrochloride (12db-HCl); (4-hydroxy-3,5-dimethoxyphenyl)(2-(p-tolyl)-1H-imidazol-4-yl)methanone (12dc); (3,4,5-trimethoxyphenyl)(2-(3,4,5-trimethoxyphenyl)-1H-imidazol-4-yl)methanone (12ea); (4-fluorophenyl)(2-(3,4,5-trimethoxyphenyl)-1H-imidazol-4-yl)methanone (12eb); (2-(4-chlorophenyl)-1H-imidazol-4-yl)(3,4,5-trimethoxyphenyl)methanone (12fa); (2-(4-chlorophenyl)-1H-imidazol-4-yl)(4-fluorophenyl)methanone (12fb); (2-(4-chlorophenyl)-1H-imidazol-4-yl)(4-hydroxy-3,5-dimethoxyphenyl)methanone (12fc); (2-(4-(dimethylamino)phenyl)-1H-imidazol-4-yl)(3,4,5-trimethoxyphenyl)methanone (12ga); (2-(4-(dimethylamino)phenyl)-1H-imidazol-4-yl)(4-fluorophenyl)methanone (12gb); (2-(3,4-dimethoxyphenyl)-1H-imidazol-4-yl)(3,4,5-trimethoxyphenyl)methanone (12ha); (2-(3,4-dimethoxyphenyl)-1H-imidazol-4-yl)(4-fluorophenyl)methanone (12hb); (2-(2-(trifluoromethyl)phenyl)-1H-imidazol-4-yl)(3,4,5-trimethoxyphenyl)methanone (12ia); (4-fluorophenyl)(2-(2-(trifluoromethyl)phenyl)-1H-imidazol-4-yl)methanone (12ib); (2-(4-(benzyloxy)phenyl)-1H-imidazol-4-yl)(3,4,5-trimethoxyphenyl)methanone (12ja); (2-(4-(benzyloxy)phenyl)-1H-imidazol-4-yl)(4-fluorophenyl)methanone (12jb); (2-(4-hydroxyphenyl)-1H-imidazol-4-yl)(3,4,5-trimethoxyphenyl)methanone (12ka); (2-(4-(hydroxyphenyl)-1H-imidazol-4-yl)(4-fluorophenyl)methanone (12kb); (2-(4-bromophenyl)-1H-imidazol-4-yl)(3,4,5-trimethoxyphenyl)methanone (12la); (2-(4-(trifluoromethyl)phenyl)-1H-imidazol-4-yl)(3,4,5-trimethoxyphenyl)methanone (12pa); (3,4,5-trihydroxyphenyl)(2-(3,4,5-trihydroxyphenyl)-1H-imidazol-4-yl)methanone (13ea); (2-(4-chlorophenyl)-1H-imidazol-4-yl)(3,4,5-trihydroxyphenyl)methanone (13fa); and 2-(3,4-dihydroxyphenyl)-1H-imidazol-4-yl)(3,4,5-trihydroxyphenyl)methanone (13ha).

In one embodiment, P of compound of formula XII is

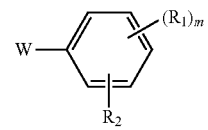

and Q is SO$_2$-Ph. Non-limiting examples of compound of formula XII wherein P of compound of formula XII is

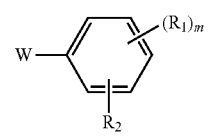

and Q is SO$_2$—Ph are selected from (4-methoxyphenyl)(2-phenyl-1-(phenylsulfonyl)-1H-imidazol-4-yl)methanone (11ab); (3-methoxyphenyl)(2-phenyl-1-(phenylsulfonyl)-1H-imidazol-4-yl)methanone (11ac); (2-phenyl-1-(phenylsulfonyl)-1H-imidazol-4-yl)(p-tolyl)methanone (11ah); (4-fluorophenyl)(2-phenyl-1-(phenylsulfonyl)-1H-imidazol-4-yl)methanone (11af); (3-fluorophenyl)(2-phenyl-1-(phenylsulfonyl)-1H-imidazol-4-yl)methanone (11ag); (4-fluorophenyl)(2-(4-methoxyphenyl)-1-(phenylsulfonyl)-1H-imidazol-4-yl)methanone (11cb); (1-(phenylsulfonyl)-2-(p-tolyl)-1H-imidazol-4-yl)(3,4,5-trimethoxyphenyl)methanone (11da); (4-fluorophenyl)(1-(phenylsulfonyl)-2-(p-tolyl)-1H-imidazol-4-yl)methanone (11db); (1-(phenylsulfonyl)-2-(3,4,5-trimethoxyphenyl)-1H-imidazol-4-yl)(3,4,5-trimethoxyphenyl)methanone (11ea); (4-fluorophenyl)(1-(phenylsulfonyl)-2-(3,4,5-trimethoxyphenyl)-1H-imidazol-4-yl)methanone (11eb); (2-(4-chlorophenyl)-1-(phenylsulfonyl)-1H-imidazol-4-yl)(4-fluorophenyl)methanone (11fb); (2-(4-(dimethylamino)phenyl)-1-(phenylsulfonyl)-1H-imidazol-4-yl)(3,4,5-trimethoxyphenyl)methanone (11ga); (2-(4-(dimethylamino)phenyl)-1-(phenylsulfonyl)-1H-imidazol-4-yl)(4-fluorophenyl)methanone (11gb); (2-(3,4-dimethoxyphenyl)-1-(phenylsulfonyl)-1H-imidazol-4-yl)(3,4,5-trimethoxyphenyl)methanone (11ha); (2-(3,4-dimethoxyphenyl)-1-(phenylsulfonyl)-1H-imidazol-4-yl)(4-fluorophenyl)methanone (11hb); (1-(phenylsulfonyl)-2-(2-(trifluoromethyl)phenyl)-1H-imidazol-4-yl)(3,4,5-trimethoxyphenyl)methanone (11ia); (1-(phenylsulfonyl)-2-(2-(trifluoromethyl)phenyl)-1H-imidazol-4-yl)(4-fluorophenyl)methanone (11ib); and (2-(4-(benzyloxy)phenyl)-1-(phenylsulfonyl)-1H-imidazol-4-yl)(4-fluorophenyl)methanone (11jb); (2-(4-bromophenyl)-1-(phenylsulfonyl)-1H-imidazol-4-yl)(3,4,5-trimethoxyphenyl)methanone (11la); (1-(phenylsulfonyl)-2-(4-(trifluoromethyl)phenyl)-1H-imidazol-4-yl)(3,4,5-trimethoxyphenyl)methanone (11pa).

In one embodiment, $R_4$ and $R_5$ of compounds of formula XIII-XVI are hydrogens. Non-limiting examples of compounds of formula XIII-XVI wherein $R_4$ and $R_5$ are hydrogens are selected from (2-phenyl-1H-imidazol-4-yl)(3,4,5-trimethoxyphenyl)methanone (12aa); (4-methoxyphenyl)(2-phenyl-1H-imidazol-4-yl)methanone (12ab); (3-methoxyphenyl)(2-phenyl-1H-imidazol-4-yl)methanone (12ac); (3,5-dimethoxyphenyl)(2-phenyl-1H-imidazol-4-yl)methanone (12ad); (3,4-dimethoxyphenyl)(2-phenyl-1H-imidazol-4-yl)methanone (12ae); (4-fluorophenyl)(2-phenyl-1H-imidazol-4-yl)methanone (12af); (3-fluorophenyl)(2-phenyl-1H-imidazol-4-yl)methanone (12ag); (2-phenyl-1H-imidazol-4-yl)(p-tolyl)methanone (12ah); and (2-phenyl-1H-imidazol-4-yl)(m-tolyl)methanone (12ai).

In one embodiment, P of compound of formula XII is H and Q is

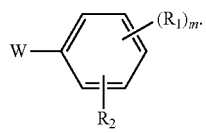

In another embodiment W is C=O. In another embodiment, W of compound of formula XVIII is C=O. Non-limiting examples of compound of formula XVIII wherein W is C=O are selected from (4-methoxyphenyl)(2-phenyl-1H-imidazol-1-yl)methanone (12aba) and (2-phenyl-1H-imidazol-1-yl)(3,4,5-trimethoxyphenyl)methanone (12aaa).

In another embodiment, W of compound of formula XVIII is $SO_2$. Non-limiting examples of compound of formula XVIII wherein W is $SO_2$ are selected from 2-phenyl-1-(phenylsulfonyl)-1H-imidazole (10a); 2-(4-nitrophenyl)-1-(phenylsulfonyl)-1H-imidazole (10x) and 2-(4-(benzyloxy)phenyl)-1-(phenylsulfonyl)-1H-imidazole (10j).

As used herein, "single-, fused- or multiple-ring, aryl or (hetero)cyclic ring systems" can be any such ring, including but not limited to phenyl, biphenyl, triphenyl, naphthyl, cycloalkyl, cycloalkenyl, cyclodienyl, fluorene, adamantane, etc.

"Saturated or unsaturated N-heterocycles" can be any such N-containing heterocycle, including but not limited to aza- and diaza-cycloalkyls such as aziridinyl, azetidinyl, diazatidinyl, pyrrolidinyl, piperidinyl, piperazinyl, and azocanyl, pyrrolyl, pyrazolyl, imidazolyl, pyridinyl, pyrimidinyl, pyrazinyl, pyridazinyl, triazinyl, tetrazinyl, pyrrolizinyl, indolyl, quinolinyl, isoquinolinyl, benzimidazolyl, indazolyl, quinolizinyl, cinnolinyl, quinololinyl, phthalazinyl, naphthyridinyl, quinoxalinyl, etc.

"Saturated or unsaturated 0-Heterocycles" can be any such O-containing heterocycle including but not limited to oxiranyl, oxetanyl, tetrahydrofuranyl, tetrahydropyranyl, dioxanyl, furanyl, pyrylium, benzofuranyl, benzodioxolyl, etc.

"Saturated or unsaturated S-heterocycles" can be any such S-containing heterocycle, including but not limited to thiranyl, thietanyl, tetrahydrothiophene-yl, dithiolanyl, tetrahydrothiopyranyl, thiophene-yl, benzothiophenyl, thiepinyl, thianaphthenyl, etc.

"Saturated or unsaturated mixed heterocycles" can be any heterocycle containing two or more S-, N-, or O-heteroatoms, including but not limited to oxathiolanyl, morpholinyl, thioxanyl, thiazolyl, isothiazolyl, thiadiazolyl, oxazolyl, isoxazolyl, oxadiaziolyl, etc.

As used herein, "aliphatic straight- or branched-chain hydrocarbon" refers to both alkylene groups that contain a single carbon and up to a defined upper limit, as well as alkenyl groups and alkynyl groups that contain two carbons up to the upper limit, whether the carbons are present in a single chain or a branched chain. Unless specifically identified, a hydrocarbon can include up to about 30 carbons, or up to about 20 hydrocarbons, or up to about 10 hydrocarbons. Alkenyl and alkynyl groups can be mono-unsaturated or polyunsaturated. In another embodiment, an alkyl includes $C_1$-$C_6$ carbons. In another embodiment, an alkyl includes $C_1$-$C_5$ carbons. In another embodiment, an alkyl includes $C_1$-$C_{10}$ carbons. In another embodiment, an alkyl is a $C_1$-$C_{12}$ carbons. In another embodiment, an alkyl is a $C_1$-$C_5$ carbons.

As used herein, the term "alkyl" can be any straight- or branched-chain alkyl group containing up to about 30 carbons unless otherwise specified. In another embodiment, an alkyl includes $C_1$-$C_6$ carbons. In another embodiment, an alkyl includes $C_1$-$C_5$ carbons. In another embodiment, an alkyl includes $C_1$-$C_{10}$ carbons. In another embodiment, an alkyl is a $C_1$-$C_{12}$ carbons. In another embodiment, an alkyl is a $C_1$-$C_{20}$ carbons. In another embodiment, cyclic alkyl group has 3-8 carbons. In another embodiment, branched alkyl is an alkyl substituted by alkyl side chains of 1 to 5 carbons.

The alkyl group can be a sole substituent or it can be a component of a larger substituent, such as in an alkoxy, haloalkyl, arylalkyl, alkylamino, dialkylamino, alkylamido, alkylurea, etc. Preferred alkyl groups are methyl, ethyl, and propyl, and thus halomethyl, dihalomethyl, trihalomethyl, haloethyl, dihaloethyl, trihaloethyl, halopropyl, dihalopropyl, trihalopropyl, methoxy, ethoxy, propoxy, arylmethyl, arylethyl, arylpropyl, methylamino, ethylamino, propylamino, dimethylamino, diethylamino, methylamido, acetamido, propylamido, halomethylamido, haloethylamido, halopropylamido, methyl-urea, ethyl-urea, propyl-urea, etc.

As used herein, the term "aryl" refers to any aromatic ring that is directly bonded to another group. The aryl group can be a sole substituent, or the aryl group can be a component of a larger substituent, such as in an arylalkyl, arylamino, arylamido, etc. Exemplary aryl groups include, without limitation, phenyl, tolyl, xylyl, furanyl, naphthyl, pyridinyl, pyrimidinyl, pyridazinyl, pyrazinyl, triazinyl, thiazolyl, oxazolyl, isooxazolyl, pyrazolyl, imidazolyl, thiophene-yl, pyrrolyl, phenylmethyl, phenylethyl, phenylamino, phenylamido, etc.

As used herein, the term "aminoalkyl" refers to an amine group substituted by an alkyl group as defined above. Aminoalkyl refers to monoalkylamine, dialkylamine or trialkylamine. Nonlimiting examples of aminoalkyl groups are $-N(Me)_2$, $-NHMe$, $-NH_3$.

A "haloalkyl" group refers, in another embodiment, to an alkyl group as defined above, which is substituted by one or more halogen atoms, e.g. by F, Cl, Br or I. Nonlimiting examples of haloalkyl groups are $CF_3$, $CF_2CF_3$, $CH_2CF_3$.

In one embodiment, this invention provides a compound of this invention or its isomer, metabolite, pharmaceutically acceptable salt, pharmaceutical product, tautomer, hydrate, N-oxide, polymorph, or crystal or combinations thereof. In one embodiment, this invention provides an isomer of the compound of this invention. In another embodiment, this invention provides a metabolite of the compound of this invention. In another embodiment, this invention provides a pharmaceutically acceptable salt of the compound of this invention. In another embodiment, this invention provides a pharmaceutical product of the compound of this invention. In another embodiment, this invention provides a tautomer of the compound of this invention. In another embodiment, this invention provides a hydrate of the compound of this invention. In another embodiment, this invention provides an N-oxide of the compound of this invention. In another embodiment, this invention provides a polymorph of the compound of this invention. In another embodiment, this invention provides a crystal of the compound of this invention. In another embodiment, this invention provides composition comprising a compound of this invention, as described herein, or, in another embodiment, a combination of an isomer, metabolite, pharmaceutically acceptable salt, pharmaceutical product, tautomer, hydrate, N-oxide, polymorph, or crystal of the compound of this invention.

In one embodiment, the term "isomer" includes, but is not limited to, optical isomers and analogs, structural isomers and analogs, conformational isomers and analogs, and the like.

In one embodiment, the compounds of this invention are the pure (E)-isomers. In another embodiment, the compounds of this invention are the pure (Z)-isomers. In another embodiment, the compounds of this invention are a mixture of the (E) and the (Z) isomers. In one embodiment, the compounds of this invention are the pure (R)-isomers. In another embodiment, the compounds of this invention are the pure (S)-isomers. In another embodiment, the compounds of this invention are a mixture of the (R) and the (S) isomers.

The compounds of the present invention can also be present in the form of a racemic mixture, containing substantially equivalent amounts of stereoisomers. In another embodiment, the compounds of the present invention can be prepared or otherwise isolated, using known procedures, to obtain a stereoisomer substantially free of its corresponding stereoisomer (i.e., substantially pure). By substantially pure, it is intended that a stereoisomer is at least about 95% pure, more preferably at least about 98% pure, most preferably at least about 99% pure.

Compounds of the present invention can also be in the form of a hydrate, which means that the compound further includes a stoichiometric or non-stoichiometric amount of water bound by non-covalent intermolecular forces.

Compounds of the present invention may exist in the form of one or more of the possible tautomers and depending on the particular conditions it may be possible to separate some or all of the tautomers into individual and distinct entities. It is to be understood that all of the possible tautomers, including all additional enol and keto tautomers and/or isomers are hereby covered. For example, the following tautomers, but not limited to these, are included.

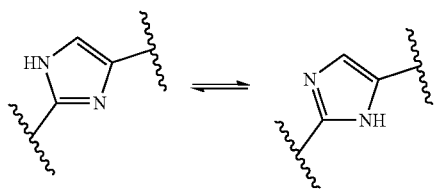

Tautomerization of the imidazole ring

The tautomers of this invention are freely interconverting tautomers, not unresolved mixtures. The imidazoles and other ring systems of this invention are tautomerizable. All tautomers are considered as part of the invention. Non limiting examples of tautomers of this invention are (5-methyl-4-phenyl-1H-imidazol-2-yl)(3,4,5-trimethoxyphenyl)methanone and (4-methyl-5-phenyl-1H-imidazol-2-yl)(3,4,5-trimethoxyphenyl)methanone (70j); (5-ethyl-4-phenyl-1H-imidazol-2-yl)(3,4,5-trimethoxyphenyl) methanone and (4-ethyl-5-phenyl-1H-imidazol-2-yl)(3,4,5-trimethoxyphenyl)methanone (70k); (4-phenyl-5-propyl-1H-imidazol-2-yl)(3,4,5-trimethoxyphenyl)methanone and (5-phenyl-4-propyl-1H-imidazol-2-yl)(3,4,5-trimethoxyphenyl)methanone (70l); phenyl-(4-phenyl-1H-imidazol-2-yl)methanone and phenyl-(5-phenyl-1H-imidazol-2-yl)methanone (70aa); (4-fluorophenyl)(4-(4-fluorophenyl)-1H-imidazol-2-yl)methanone and (4-fluorophenyl)(5-(4-fluorophenyl)-1H-imidazol-2-yl)methanone (70r); (4-chlorophenyl)(4-(4-chlorophenyl)-1H-imidazol-2-yl) methanone and (4-chlorophenyl)(5-(4-chlorophenyl)-1H-imidazol-2-yl)methanone (70s); 4-bromophenyl-(4-(4-bromophenyl)-1H-imidazol-2-yl)ketone and 4-bromophenyl-(5-(4-bromophenyl)-1H-imidazol-2-yl)methanone (70t); p-tolyl(4-p-tolyl-1H-imidazol-2-yl)methanone and p-tolyl (5-p-tolyl-1H-imidazol-2-yl)methanone (70v); (4-(trifluoromethyl)phenyl)(4-(4-(trifluoromethyl)phenyl)-1H-imidazol-2-yl)methanone and (4-(trifluoromethyl)phenyl)(5-(4-(trifluoromethyl)phenyl)-1H-imidazol-2-yl)methanone (70u); (4-methoxyphenyl)(4-(4-methoxyphenyl)-1H-imidazol-2-yl)methanone and (4-methoxyphenyl)(5-(4-methoxyphenyl)-1H-imidazol-2-yl)methanone (70w); (4-(dimethylamino)phenyl)(4-(4-(dimethylamino)phenyl)-1H-imidazol-2-yl)methanone and (4-(dimethylamino)phenyl)(5-(4-(dimethylamino)phenyl)-1H-imidazol-2-yl)methanone (70hh); 5-methyl-4-phenyl-2-(3,4,5-trimethoxybenzyl)-1H-imidazole and 4-methyl-5-phenyl-2-(3,4,5-trimethoxybenzyl)-1H-imidazole (102b); 5-ethyl-4-phenyl-2-(3,4,5-trimethoxybenzyl)-1H-imidazole and 4-ethyl-5-phenyl-2-(3,4,5-trimethoxybenzyl)-1H-imidazole (102c); 4-phenyl-5-propyl-2-(3,4,5-trimethoxybenzyl)-1H-imidazole and 5-phenyl-4-propyl-2-(3,4,5-trimethoxybenzyl)-1H-imidazole (102d); 3,4,5-trimethoxyphenyl-(4-(3,4,5-trimethoxyphenyl)-1H-imidazol-2-yl)methanone and 3,4,5-trimethoxyphenyl-(5-(3,4,5-trimethoxyphenyl)-1H-imidazol-2-yl) methanone (70q); (4-phenyl-1H-imidazol-2-yl)(3,4,5-trimethoxyphenyl)methanone and (5-phenyl-1H-imidazol-2-yl)(3,4,5-trimethoxyphenyl)methanone (70a); (4-(4-fluorophenyl)-1H-imidazol-2-yl)(3,4,5-trimethoxyphenyl) methanone and (5-(4-fluorophenyl)-1H-imidazol-2-yl)(3,4,5-trimethoxyphenyl)methanone (70b); (4-(4-bromophenyl)-1H-imidazol-2-yl)(3,4,5-trimethoxyphenyl)methanone and (5-(4-bromophenyl)-1H-imidazol-2-yl)(3,4,5-trimethoxyphenyl)methanone (70d); 4-bromophenyl(4-(3,4,5-trimethoxyphenyl)-1H-imidazol-2-yl)methanone and 4-bromophenyl(5-(3,4,5-trimethoxyphenyl)-1H-imidazol-2-yl) methanone (70z).

The invention includes "pharmaceutically acceptable salts" of the compounds of this invention, which may be produced, by reaction of a compound of this invention with an acid or base. Certain compounds, particularly those possessing acid or basic groups, can also be in the form of a salt, preferably a pharmaceutically acceptable salt. The term "pharmaceutically acceptable salt" refers to those salts that retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcysteine and the like. Other salts are known to those of skill in the art and can readily be adapted for use in accordance with the present invention.

Suitable pharmaceutically-acceptable salts of amines of compounds the compounds of this invention may be prepared from an inorganic acid or from an organic acid. In one embodiment, examples of inorganic salts of amines are bisulfates, borates, bromides, chlorides, hemisulfates, hydrobromates, hydrochlorates, 2-hydroxyethylsulfonates (hydroxyethanesulfonates), iodates, iodides, isothionates, nitrates, persulfates, phosphate, sulfates, sulfamates, sulfanilates, sulfonic acids (alkylsulfonates, arylsulfonates, halogen substituted alkylsulfonates, halogen substituted arylsulfonates), sulfonates and thiocyanates.

In one embodiment, examples of organic salts of amines may be selected from aliphatic, cycloaliphatic, aromatic, araliphatic, heterocyclic, carboxylic and sulfonic classes of organic acids, examples of which are acetates, arginines, aspartates, ascorbates, adipates, anthranilates, algenates, alkane carboxylates, substituted alkane carboxylates, alginates, benzenesulfonates, benzoates, bisulfates, butyrates, bicarbonates, bitartrates, citrates, camphorates, camphorsulfonates, cyclohexylsulfamates, cyclopentanepropionates, calcium edetates, camsylates, carbonates, clavulanates, cinnamates, dicarboxylates, digluconates, dodecylsulfonates, dihydrochlorides, decanoates, enanthuates, ethanesulfonates, edetates, edisylates, estolates, esylates, fumarates, formates, fluorides, galacturonates gluconates, glutamates, glycolates, glucorate, glucoheptanoates, glycerophosphates, gluceptates, glycollylarsanilates, glutarates, glutamate, heptanoates, hexanoates, hydroxymaleates, hydroxycarboxlic acids, hexylresorcinates, hydroxybenzoates, hydroxynaphthoates, hydrofluorates, lactates, lactobionates, laurates, malates, maleates, methylenebis(beta-oxynaphthoate), malonates, mandelates, mesylates, methane sulfonates, methylbromides, methylnitrates, methylsulfonates, monopotassium maleates, mucates, monocarboxylates, naphthalenesulfonates, 2-naphthalenesulfonates, nicotinates, nitrates, napsylates, N-methylglucamines, oxalates, octanoates, oleates, pamoates, phenylacetates, picrates, phenylbenzoates, pivalates, propionates, phthalates, phenylacetate, pectinates, phenylpropionates, palmitates, pantothenates, polygalacturates, pyruvates, quinates, salicylates, succinates, stearates, sulfanilate, subacetates, tartrates, theophyllineacetates, p-toluenesulfonates (tosylates), trifluoroacetates, terephthalates, tannates, teoclates, trihaloacetates, triethiodide, tricarboxylates, undecanoates and valerates.

In one embodiment, examples of inorganic salts of carboxylic acids or hydroxyls may be selected from ammonium, alkali metals to include lithium, sodium, potassium, cesium; alkaline earth metals to include calcium, magnesium, aluminium; zinc, barium, cholines, quaternary ammoniums.

In another embodiment, examples of organic salts of carboxylic acids or hydroxyl may be selected from arginine, organic amines to include aliphatic organic amines, alicyclic organic amines, aromatic organic amines, benzathines, t-butylamines, benethamines (N-benzylphenethylamine), dicyclohexylamines, dimethylamines, diethanolamines, ethanolamines, ethylenediamines, hydrabamines, imidazoles, lysines, methylamines, meglamines, N-methyl-D-glucamines, N,N'-dibenzylethylenediamines, nicotinamides, organic amines, ornithines, pyridines, picolies, piperazines, procain, tris(hydroxymethyl)methylamines, triethylamines, triethanolamines, trimethylamines, tromethamines and ureas.

In one embodiment, the salts may be formed by conventional means, such as by reacting the free base or free acid form of the product with one or more equivalents of the appropriate acid or base in a solvent or medium in which the salt is insoluble or in a solvent such as water, which is removed in vacuo or by freeze drying or by exchanging the ions of a existing salt for another ion or suitable ion-exchange resin.

In some embodiments, this invention provides a process for the preparation of the compounds of this invention. In one embodiment, the aryl-imidazole is prepared by reacting an appropriately substituted benzaldehyde with ethylenediamine to construct the imidazoline ring, followed by oxidation of the imidazoline by an oxidizing agent to the corresponding imidazole. In another embodiment the oxidizing agent is diacetoxyiodobenzene, bromotrichloromethane and 1,8-diazabicyclo[5.4.0]undec-7-ene (DBU), carbon-02 system or palladium-carbon system. In another embodiment, the aryl-imidazole is prepared by reacting an appropriately substituted benzaldehyde with ethylene diamine in the presence of iodine and potassium carbonate in order to construct the imidazoline ring, followed by oxidation of the imidazoline ring catalyzed by diacetoxyiodobenzene, bromotrichloromethane and 1,8-diazabicyclo[5.4.0]undec-7-ene (DBU), carbon-$O_2$ system or palladium-carbon system to the corresponding imidazole. In another embodiment, the aryl-imidazole is prepared by reacting an appropriately substituted benzaldehyde with ethylene diamine in the presence of iodine and potassium carbonate in order to construct the imidazoline ring, followed by oxidation of the imidazoline ring catalyzed by diacetoxyiodobenzene to the corresponding imidazole. In another embodiment, the aryl-imidazole is prepared by reacting an appropriately substituted benzaldehyde with ethylene diamine in the presence of iodine and potassium carbonate in order to construct the imidazoline ring, followed by oxidation of the imidazoline ring catalyzed by bromotrichloromethane and 1,8-diazabicyclo[5.4.0]undec-7-ene (DBU) to the corresponding imidazole. In one embodiment, the aryl-imidazole is prepared by reacting the appropriate benzaldehyde in ethanol with oxalaldehyde and ammonia hydroxide to construct the imidazole ring system.

In one embodiment an aryl-benzoyl-imidazole compound of this invention is prepared by protecting the aryl-imidazole followed by coupling with an appropriately substituted benzoyl chloride, followed by removing the protecting group. In another embodiment, the protecting group is a phenyl sulfonyl group, phthalimide, di-tert-butyl dicarbonate (Boc), fluorenylmethyloxycarbonyl (Fmoc), benzyloxycarbonyl (Cbz), or monomethoxytrityl (MMT). In another embodiment, the aryl-imidazole is protected with phenyl sulfonyl to yield the N-sulfonyl protected aryl-imidazole. In another embodiment, the protected aryl-imidazole compound is prepared by reacting the aryl-imidazole with phenylsulfonyl chloride and sodium hydride in THF. In another embodiment, the protected aryl-imidazole is prepared according to FIGS. 7 and 8.

In one embodiment, the protected aryl-imidazole is coupled with an appropriately substituted benzoyl chloride to obtain a protected aryl-benzoyl imidazole. In another embodiment, aryl-imidazole is coupled with an appropriately substituted benzoyl chloride in the presence of tert-butyl lithium to obtain aryl-phenylsulfonyl (2-aryl-1-(phenylsulfonyl)-1H-imidazol-4-yl)methanone. In another embodiment, the (2-aryl-1-(phenylsulfonyl)-1H-imidazol-4-yl)methanone is prepared according to FIGS. 7 and 8 steps e and c, respectively.

In one embodiment, an aryl-benzoyl-imidazole is prepared by removing the protecting group of the aryl-benzoyl-imidazole. In another embodiment, the removal of the protecting group depends on the protecting group used and can be removed by known conditions which are known in the art. In another embodiment, the phenyl sulfonyl protecting group is removed by tetrabutylammonium fluoride in THF. In another embodiment, phenylsulfonyl is removed according to FIGS. 7 and 8.

In one embodiment, compounds of formula I, Ia, II, III, V and XI are prepared according to FIG. 1. In another embodiment, compounds of formula I, Ia, II, III, V, VI, VII and XI are prepared according to FIG. 2. In another embodiment, compounds of formula I, Ia, II, III, V and VI are prepared according to FIG. 3. In another embodiment, compounds of formula I, Ia, II, III, V and VI are prepared according to FIG. 4. In another embodiment, compounds of formula I, Ia, II, III, IV, IVa, V, VI and XI are prepared according to FIG. 5. In another embodiment, compounds of formula I, Ia, II, III, VIII and XI are prepared according to FIG. 6.

Figure 9:
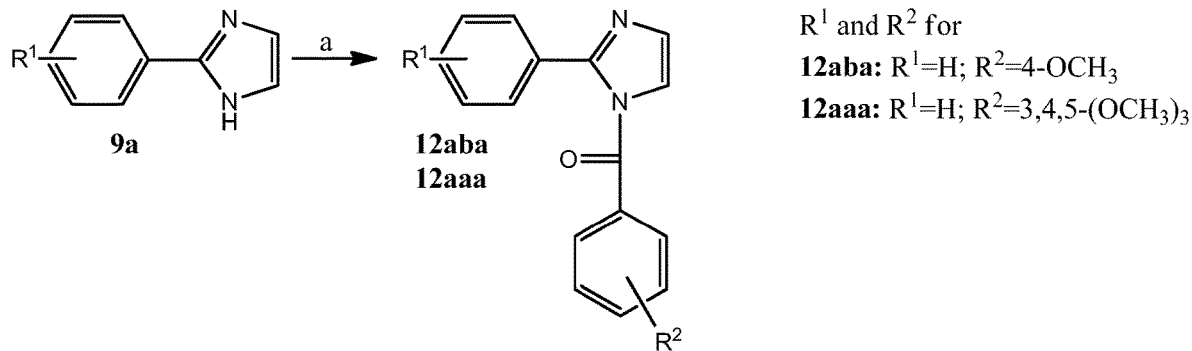
FIG. 9 depicts a synthetic scheme for the preparation of Aryl-Benzoyl-Imidazole (ABI) compounds of this invention. Reagents and conditions: (a) NaH, substituted benzoyl chloride, THF

In one embodiment, compounds of formula XII and XVIII are prepared according to FIG. 9. In another embodiment, compounds of formula XII, XIII, XIV, XIVa, XV, XVI, XVII, XIX and XX are prepared according to FIG. 10. In another embodiment, compounds of formula XIVa and XIX are prepared according to FIG. 11. In another embodiment, compounds of formula I, Ia, IV, IVa, XI, XXI, XXIa and XXII are prepared according to FIG. 12. In another embodiment, compounds of formula I, Ia, IV, IVa, XI, XIb, XXI, XXIa and XXII are prepared according to FIG. 13. In another embodiment, compounds of formula I, Ia, II, III, V, XI, XII, XIII, XIV, XV, XVII, XIX and XX are prepared according to FIG. 14. In another embodiment, compounds of formula I, Ia, II, IV, IVa, XI and XIc, are prepared according to FIG. 15.

In one embodiment, compounds of formula IX and IXa are prepared according to FIG. 16.

Pharmaceutical Composition

Another aspect of the present invention relates to a pharmaceutical composition including a pharmaceutically acceptable carrier and a compound according to the aspects of the present invention. The pharmaceutical composition can contain one or more of the above-identified compounds of the present invention. Typically, the pharmaceutical composition of the present invention will include a compound of the present invention or its pharmaceutically acceptable salt, as well as a pharmaceutically acceptable carrier. The term "pharmaceutically acceptable carrier" refers to any suitable adjuvants, carriers, excipients, or stabilizers, and can be in solid or liquid form such as, tablets, capsules, powders, solutions, suspensions, or emulsions.

Typically, the composition will contain from about 0.01 to 99 percent, preferably from about 20 to 75 percent of active compound(s), together with the adjuvants, carriers and/or excipients. While individual needs may vary, determination of optimal ranges of effective amounts of each component is within the skill of the art. Typical dosages comprise about 0.01 to about 100 mg/kg body wt. The preferred dosages comprise about 0.1 to about 100 mg/kg body wt. The most preferred dosages comprise about 1 to about 100 mg/kg body wt. Treatment regimen for the administration of the compounds of the present invention can also be determined readily by those with ordinary skill in art. That is, the frequency of administration and size of the dose can be established by routine optimization, preferably while minimizing any side effects.

The solid unit dosage forms can be of the conventional type. The solid form can be a capsule and the like, such as an ordinary gelatin type containing the compounds of the present invention and a carrier, for example, lubricants and inert fillers such as, lactose, sucrose, or cornstarch. In another embodiment, these compounds are tabulated with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate.

The tablets, capsules, and the like can also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it can contain, in addition to materials of the above type, a liquid carrier such as a fatty oil.

Various other materials may be present as coatings or to modify the physical form of the dosage unit. For instance, tablets can be coated with shellac, sugar, or both. A syrup can contain, in addition to active ingredient, sucrose as a sweetening agent, methyl and propylparabens as preservatives, a dye, and flavoring such as cherry or orange flavor.

For oral therapeutic administration, these active compounds can be incorporated with excipients and used in the form of tablets, capsules, elixirs, suspensions, syrups, and the like. Such compositions and preparations should contain at least 0.1% of active compound. The percentage of the compound in these compositions can, of course, be varied and can conveniently be between about 2% to about 60% of the weight of the unit. The amount of active compound in such therapeutically useful compositions is such that a suitable dosage will be obtained. Preferred compositions according to the present invention are prepared so that an oral dosage unit contains between about 1 mg and 800 mg of active compound.

The active compounds of the present invention may be orally administered, for example, with an inert diluent, or with an assimilable edible carrier, or they can be enclosed in hard or soft shell capsules, or they can be compressed into tablets, or they can be incorporated directly with the food of the diet.

The pharmaceutical forms suitable for injectable use include sterile aqueous solutions or dispersions and sterile powders for the extemporaneous preparation of sterile injectable solutions or dispersions. In all cases, the form should be sterile and should be fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The compounds or pharmaceutical compositions of the present invention may also be administered in injectable dosages by solution or suspension of these materials in a physiologically acceptable diluent with a pharmaceutical adjuvant, carrier or excipient. Such adjuvants, carriers and/or excipients include, but are not limited to, sterile liquids, such as water and oils, with or without the addition of a surfactant and other pharmaceutically and physiologically acceptable components. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

These active compounds may also be administered parenterally. Solutions or suspensions of these active compounds can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

In one embodiment, the compounds of this invention are administered in combination with an anti-cancer agent. In one embodiment, the anti-cancer agent is a monoclonal antibody. In some embodiments, the monoclonal antibodies are used for diagnosis, monitoring, or treatment of cancer. In one embodiment, monoclonal antibodies react against specific antigens on cancer cells. In one embodiment, the monoclonal antibody acts as a cancer cell receptor antagonist. In one embodiment, monoclonal antibodies enhance the patient's immune response. In one embodiment, monoclonal antibodies act against cell growth factors, thus blocking cancer cell growth. In one embodiment, anti-cancer monoclonal antibodies are conjugated or linked to anti-cancer drugs, radioisotopes, other biologic response modifiers, other toxins, or a combination thereof. In one embodiment, anti-cancer monoclonal antibodies are conjugated or linked to a compound of this invention as described hereinabove.

Yet another aspect of the present invention relates to a method of treating cancer that includes selecting a subject in need of treatment for cancer, and administering to the subject a pharmaceutical composition comprising a compound according to the first aspect of the present invention and a pharmaceutically acceptable carrier under conditions effective to treat cancer.

When administering the compounds of the present invention, they can be administered systemically or, alternatively, they can be administered directly to a specific site where cancer cells or precancerous cells are present. Thus, administering can be accomplished in any manner effective for delivering the compounds or the pharmaceutical compositions to the cancer cells or precancerous cells. Exemplary modes of administration include, without limitation, administering the compounds or compositions orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes.

Biological Activity

In one embodiment, the invention provides compounds and compositions, including any embodiment described herein, for use in any of the methods of this invention. In one embodiment, use of a compound of this invention or a composition comprising the same, will have utility in inhibiting, suppressing, enhancing or stimulating a desired response in a subject, as will be understood by one skilled in the art. In another embodiment, the compositions may further comprise additional active ingredients, whose activity is useful for the particular application for which the compound of this invention is being administered.

In one embodiment, this invention is directed to a method of treating, suppressing, reducing the severity, reducing the risk of developing or inhibiting cancer comprising administering a compound of this invention to a subject suffering from cancer under conditions effective to treat the cancer.

Drug resistance is the major cause of cancer chemotherapy failure. One major contributor to multidrug resistance is overexpression of P-glycoprotein (P-gp). This protein is a clinically important transporter protein belonging to the ATP-binding cassette family of cell membrane transporters. It can pump substrates including anticancer drugs out of tumor cells through an ATP-dependent mechanism.

In one embodiment, this invention provides methods for: a) treating, suppressing, reducing the severity, reducing the risk, or inhibiting drug resistant tumors; b) treating, suppressing, reducing the severity, reducing the risk, or inhibiting metastatic cancer; c) treating, suppressing, reducing the severity, reducing the risk, or inhibiting drug resistant cancer; d) treating, suppressing, reducing the severity, reducing the risk, or inhibiting a drug resistant cancer wherein the cancer is melanoma; e) a method of treating, suppressing, reducing the severity, reducing the risk, or inhibiting a drug resistant cancer wherein the cancer is prostate cancer; f) a method of treating, suppressing, reducing the severity, reducing the risk, or inhibiting metastatic melanoma; g) a method of treating, suppressing, reducing the severity, reducing the risk, or inhibiting prostate cancer; h) treating, suppressing, reducing the severity, reducing the risk, or inhibiting cancer in a subject, wherein the subject has been previously treated with chemotherapy, radiotherapy, or biological therapy; comprising the step of administering to said subject a compound of this invention and/or an isomer, metabolite, pharmaceutically acceptable salt, pharmaceutical product, tautomer, hydrate, N-oxide, polymorph, or crystal of said compound, or any combination thereof.

The compounds of the present invention are useful in the treatment, reducing the severity, reducing the risk, or inhibition of cancer, metastatic cancer, drug resistant tumors, drug resistant cancer and various forms of cancer. In a preferred embodiment the cancer is prostate cancer, breast cancer, ovarian cancer, skin cancer (e.g., melanoma), lung cancer, colon cancer, leukemia, lymphoma, head and neck, pancreatic, esophageal, renal cancer or CNS cancer (e.g., glioma, glioblastoma). Treatment of these different cancers is supported by the Examples herein. Moreover, based upon their believed mode of action as tubulin inhibitors, it is believed that other forms of cancer will likewise be treatable or preventable upon administration of the compounds or compositions of the present invention to a patient. Preferred compounds of the present invention are selectively disruptive to cancer cells, causing ablation of cancer cells but preferably not normal cells. Significantly, harm to normal cells is minimized because the cancer cells are susceptible to disruption at much lower concentrations of the compounds of the present invention.

In some embodiments, this invention provides for the use of a compound as herein described, or its isomer, metabolite, pharmaceutically acceptable salt, pharmaceutical product, tautomer, polymorph, crystal, N-oxide, hydrate or any combination thereof, for treating, suppressing, reducing the severity, reducing the risk, or inhibiting cancer in a subject. In another embodiment, the cancer is adrenocortical carcinoma, anal cancer, bladder cancer, brain tumor, brain stem tumor, breast cancer, glioma, cerebellar astrocytoma, cerebral astrocytoma, ependymoma, medulloblastoma, supratentorial primitive neuroectodermal, pineal tumors, hypothalamic glioma, breast cancer, carcinoid tumor, carcinoma, cervical cancer, colon cancer, central nervous system (CNS) cancer, endometrial cancer, esophageal cancer, extrahepatic bile duct cancer, Ewing's family of tumors (Pnet), extracranial germ cell tumor, eye cancer, intraocular melanoma, gallbladder cancer, gastric cancer, germ cell tumor, extragonadal, gestational trophoblastic tumor, head and neck cancer, hypopharyngeal cancer, islet cell carcinoma, laryngeal cancer, leukemia, acute lymphoblastic, leukemia, oral cavity cancer, liver cancer, lung cancer, non-small cell lung cancer, small cell, lymphoma, AIDS-related lymphoma, central nervous system (primary), lymphoma, cutaneous T-cell, lymphoma, Hodgkin's disease, non-Hodgkin's disease, malignant mesothelioma, melanoma, Merkel cell carcinoma, metasatic squamous carcinoma, multiple myeloma, plasma cell neoplasms, mycosis fungoides, myelodysplastic syndrome, myeloproliferative disorders, nasopharyngeal cancer, neuroblastoma, oropharyngeal cancer, osteosarcoma, ovarian cancer, ovarian epithelial cancer, ovarian germ cell tumor, ovarian low malignant potential tumor, pancreatic cancer, exocrine, pancreatic cancer, islet cell carcinoma, paranasal sinus and nasal cavity cancer, parathyroid cancer, penile cancer, pheochromocytoma cancer, pituitary cancer, plasma cell neoplasm, prostate cancer, rhabdomyosarcoma, rectal cancer, renal cancer, renal cell cancer, salivary gland cancer, Sezary syndrome, skin cancer, cutaneous T-cell lymphoma, skin cancer, Kaposi's sarcoma, skin cancer, melanoma, small intestine cancer, soft tissue sarcoma, soft tissue sarcoma, testicular cancer, thymoma, malignant, thyroid cancer, urethral cancer, uterine cancer, sarcoma, unusual cancer of childhood, vaginal cancer, vulvar cancer, Wilms' tumor, or any combination thereof. In another embodiment the subject has been previously treated with chemotherapy, radiotherapy or biological therapy.

In some embodiments, this invention provides for the use of a compound as herein described, or its isomer, metabolite, pharmaceutically acceptable salt, pharmaceutical product, tautomer, polymorph, crystal, N-oxide, hydrate or any combination thereof, for treating, suppressing, reducing the severity, reducing the risk, or inhibiting a metastatic cancer in a subject. In another embodiment, the cancer is adrenocortical carcinoma, anal cancer, bladder cancer, brain tumor, brain stem tumor, breast cancer, glioma, cerebellar astrocytoma, cerebral astrocytoma, ependymoma, medulloblastoma, supratentorial primitive neuroectodermal, pineal tumors, hypothalamic glioma, breast cancer, carcinoid tumor, carcinoma, cervical cancer, colon cancer, central nervous system (CNS) cancer, endometrial cancer, esophageal cancer, extrahepatic bile duct cancer, Ewing's family of tumors (Pnet), extracranial germ cell tumor, eye cancer, intraocular melanoma, gallbladder cancer, gastric cancer, germ cell tumor, extragonadal, gestational trophoblastic tumor, head and neck cancer, hypopharyngeal cancer, islet cell carcinoma, laryngeal cancer, leukemia, acute lymphoblastic, leukemia, oral cavity cancer, liver cancer, lung cancer, non-small cell lung cancer, small cell, lymphoma, AIDS-related lymphoma, central nervous system (primary), lymphoma, cutaneous T-cell, lymphoma, Hodgkin's disease, non-Hodgkin's disease, malignant mesothelioma, melanoma, Merkel cell carcinoma, metasatic squamous carcinoma, multiple myeloma, plasma cell neoplasms, mycosis fungoides, myelodysplastic syndrome, myeloproliferative disorders, nasopharyngeal cancer, neuroblastoma, oropharyngeal cancer, osteosarcoma, ovarian cancer, ovarian epithelial cancer, ovarian germ cell tumor, ovarian low malignant potential tumor, pancreatic cancer, exocrine, pancreatic cancer, islet cell carcinoma, paranasal sinus and nasal cavity cancer, parathyroid cancer, penile cancer, pheochromocytoma cancer, pituitary cancer, plasma cell neoplasm, prostate cancer, rhabdomyosarcoma, rectal cancer, renal cancer, renal cell cancer, salivary gland cancer, Sezary syndrome, skin cancer, cutaneous T-cell lymphoma, skin cancer, Kaposi's sarcoma, skin cancer, melanoma, small intestine cancer, soft tissue sarcoma, soft tissue sarcoma, testicular cancer, thymoma, malignant, thyroid cancer, urethral cancer, uterine cancer, sarcoma, unusual cancer of childhood, vaginal cancer, vulvar cancer, Wilms' tumor, or any combination thereof.

In some embodiments, this invention provides for the use of a compound as herein described, or its isomer, metabolite, pharmaceutically acceptable salt, pharmaceutical product, tautomer, polymorph, crystal, N-oxide, hydrate or any combination thereof, for treating, suppressing, reducing the severity, reducing the risk, or inhibiting a drug-resistant cancer or resistant cancer in a subject. In another embodiment, the cancer is adrenocortical carcinoma, anal cancer, bladder cancer, brain tumor, brain stem tumor, breast cancer, glioma, cerebellar astrocytoma, cerebral astrocytoma, ependymoma, medulloblastoma, supratentorial primitive neuroectodermal, pineal tumors, hypothalamic glioma, breast cancer, carcinoid tumor, carcinoma, cervical cancer, colon cancer, central nervous system (CNS) cancer, endometrial cancer, esophageal cancer, extrahepatic bile duct cancer, Ewing's family of tumors (Pnet), extracranial germ cell tumor, eye cancer, intraocular melanoma, gallbladder cancer, gastric cancer, germ cell tumor, extragonadal, gestational trophoblastic tumor, head and neck cancer, hypopharyngeal cancer, islet cell carcinoma, laryngeal cancer, leukemia, acute lymphoblastic, leukemia, oral cavity cancer, liver cancer, lung cancer, non-small cell lung cancer, small cell, lymphoma, AIDS-related lymphoma, central nervous system (primary), lymphoma, cutaneous T-cell, lymphoma, Hodgkin's disease, non-Hodgkin's disease, malignant mesothelioma, melanoma, Merkel cell carcinoma, metasatic squamous carcinoma, multiple myeloma, plasma cell neoplasms, mycosis fungoides, myelodysplastic syndrome, myeloproliferative disorders, nasopharyngeal cancer, neuroblastoma, oropharyngeal cancer, osteosarcoma, ovarian cancer, ovarian epithelial cancer, ovarian germ cell tumor, ovarian low malignant potential tumor, pancreatic cancer, exocrine, pancreatic cancer, islet cell carcinoma, paranasal sinus and nasal cavity cancer, parathyroid cancer, penile cancer, pheochromocytoma cancer, pituitary cancer, plasma cell neoplasm, prostate cancer, rhabdomyosarcoma, rectal cancer, renal cancer, renal cell cancer, salivary gland cancer, Sezary syndrome, skin cancer, cutaneous T-cell lymphoma, skin cancer, Kaposi's sarcoma, skin cancer, melanoma, small intestine cancer, soft tissue sarcoma, soft tissue sarcoma, testicular cancer, thymoma, malignant, thyroid cancer, urethral cancer, uterine cancer, sarcoma, unusual cancer of childhood, vaginal cancer, vulvar cancer, Wilms' tumor, or any combination thereof.

The invention also encompasses the treatment of cervical cancer by the administration of compounds of the invention. In particular, compound 17ya is used in the treatment of cervical cancer.

In one embodiment "metastatic cancer" refers to a cancer that spread (metastasized) from its original site to another area of the body. Virtually all cancers have the potential to spread. Whether metastases develop depends on the complex interaction of many tumor cell factors, including the type of cancer, the degree of maturity (differentiation) of the tumor cells, the location and how long the cancer has been present, as well as other incompletely understood factors. Metastases spread in three ways—by local extension from the tumor to the surrounding tissues, through the bloodstream to distant sites or through the lymphatic system to neighboring or distant lymph nodes. Each kind of cancer may have a typical route of spread. The tumor is called by the primary site (ex. breast cancer that has spread to the brain is called metastatic breast cancer to the brain).

In one embodiment "drug-resistant cancer" refers to cancer cells that acquire resistance to chemotherapy. Cancer cells can acquire resistance to chemotherapy by a range of mechanisms, including the mutation or overexpression of the drug target, inactivation of the drug, or elimination of the drug from the cell. Tumors that recur after an initial response to chemotherapy may be resistant to multiple drugs (they are multidrug resistant). In the conventional view of drug resistance, one or several cells in the tumor population acquire genetic changes that confer drug resistance. Accordingly, the reasons for drug resistance, inter alia, are: a) some of the cells that are not killed by the chemotherapy mutate (change) and become resistant to the drug. Once they multiply, there may be more resistant cells than cells that are sensitive to the chemotherapy; b) Gene amplification. A cancer cell may produce hundreds of copies of a particular gene. This gene triggers an overproduction of protein that renders the anticancer drug ineffective; c) cancer cells may pump the drug out of the cell as fast as it is going in using a molecule called p-glycoprotein; d) cancer cells may stop taking in the drugs because the protein that transports the drug across the cell wall stops working; e) the cancer cells may learn how to repair the DNA breaks caused by some anti-cancer drugs; f) cancer cells may develop a mechanism that inactivates the drug. One major contributor to multidrug resistance is overexpression of P-glycoprotein (P-gp). This protein is a clinically important transporter protein belonging to the ATP-binding cassette family of cell membrane transporters. It can pump substrates including anticancer drugs out of tumor cells through an ATP-dependent mechanism. Thus, the resistance to anticancer agents used in chemotherapy is the main cause of treatment failure in malignant disorders, provoking tumors to become resistant. Drug resistance is the major cause of cancer chemotherapy failure.

In one embodiment "resistant cancer" refers to drug-resistant cancer as described herein above. In another embodiment "resistant cancer" refers to cancer cells that acquire resistance to any treatment such as chemotherapy, radiotherapy or biological therapy.

In one embodiment, this invention is directed to treating, suppressing, reducing the severity, reducing the risk, or inhibiting cancer in a subject, wherein the subject has been previously treated with chemotherapy, radiotherapy or biological therapy.

In one embodiment "Chemotherapy" refers to chemical treatment for cancer such as drugs that kill cancer cells directly. Such drugs are referred as "anti-cancer" drugs or "antineoplastics." Today's therapy uses more than 100 drugs to treat cancer. To cure a specific cancer. Chemotherapy is used to control tumor growth when cure is not possible; to shrink tumors before surgery or radiation therapy; to relieve symptoms (such as pain); and to destroy microscopic cancer cells that may be present after the known tumor is removed by surgery (called adjuvant therapy). Adjuvant therapy is given to prevent a possible cancer reoccurrence.

In one embodiment, "Radiotherapy" refers to high energy x-rays and similar rays (such as electrons) to treat disease. Many people with cancer will have radiotherapy as part of their treatment. This can be given either as external radiotherapy from outside the body using x-rays or from within the body as internal radiotherapy. Radiotherapy works by destroying the cancer cells in the treated area. Although normal cells can also be damaged by the radiotherapy, they can usually repair themselves. Radiotherapy treatment can cure some cancers and can also reduce the chance of a cancer coming back after surgery. It may be used to reduce cancer symptoms.

In one embodiment "Biological therapy" refers to substances that occur naturally in the body to destroy cancer cells. There are several types of treatment including: monoclonal antibodies, cancer growth inhibitors, vaccines and gene therapy. Biological therapy is also known as immunotherapy.

In one embodiment, this invention provides a method of treating a subject suffering from prostate cancer, metastatic prostate cancer, resistant prostate cancer or drug-resistant prostate cancer comprising the step of administering to said subject a compound of this invention, or its isomer, metabolite, pharmaceutically acceptable salt, pharmaceutical product, tautomer, hydrate, N-oxide, polymorph, crystal or any combination thereof, or a composition comprising the same in an amount effective to treat prostate cancer in the subject. In another embodiment, the compound is compound 12db. In another embodiment, the compound is compound 116c. In another embodiment, the compound is compound 11fb. In another embodiment, the compound is compound 12da. In another embodiment, the compound is compound 12fa. In another embodiment, the compound is compound 12fb. In another embodiment, the compound is compound 12cb. In another embodiment, the compound is compound 55. In another embodiment, the compound is compound 6b. In another embodiment, the compound is compound 17ya. In another embodiment, the compound is compound 12q. In another embodiment, the compound is compound 70a. In another embodiment, the compound is compound 70d. In another embodiment, the compound is compound 70f. In another embodiment, the compound is compound 70m.

In one embodiment, this invention provides a method for suppressing, reducing the severity, reducing the risk, delaying the progression, or inhibiting prostate cancer, metastatic prostate cancer, resistant prostate cancer or drug-resistant prostate cancer in a subject, comprising administering to the subject a compound of this invention and/or its isomer, metabolite, pharmaceutically acceptable salt, pharmaceutical product, tautomer, hydrate, N-oxide, polymorph, crystal or any combination thereof or a composition comprising the same. In another embodiment, the compound is compound 12db. In another embodiment, the compound is compound 11cb. In another embodiment, the compound is compound 11fb. In another embodiment, the compound is compound 12da. In another embodiment, the compound is compound 12fa. In another embodiment, the compound is compound 12fb. In another embodiment, the compound is compound 12cb. In another embodiment, the compound is compound 55. In another embodiment, the compound is compound 6b. In another embodiment, the compound is compound 17ya. In another embodiment, the compound is compound 12q. In another embodiment, the compound is compound 70a. In another embodiment, the compound is compound 70d. In another embodiment, the compound is compound 70f. In another embodiment, the compound is compound 70m.

In one embodiment, this invention provides a method of treating a subject suffering from breast cancer, metastatic breast cancer, resistant breast cancer or drug-resistant breast cancer comprising the step of administering to said subject a compound of this invention, or its isomer, metabolite, pharmaceutically acceptable salt, pharmaceutical product, tautomer, hydrate, N-oxide, polymorph, crystal or any combination thereof, or a composition comprising the same. In another embodiment, the subject is a male or female. In another embodiment, the compound is compound 12db. In another embodiment, the compound is compound 11cb. In another embodiment, the compound is compound 11fb. In another embodiment, the compound is compound 12da. In another embodiment, the compound is compound 12fa. In another embodiment, the compound is compound 12fb. In another embodiment, the compound is compound 12cb. In another embodiment, the compound is compound 55. In another embodiment, the compound is compound 6b. In another embodiment, the compound is compound 17ya. In another embodiment, the compound is compound 12q. In another embodiment, the compound is compound 70a. In another embodiment, the compound is compound 70d. In another embodiment, the compound is compound 70f. In another embodiment, the compound is compound 70m.

In one embodiment, this invention provides a method of suppressing, reducing the severity, reducing the risk, delaying the progression, or inhibiting breast cancer, metastatic breast cancer, resistant breast cancer or drug-resistant breast cancer in a subject comprising the step of administering to said subject a compound of this invention or its isomer, metabolite, pharmaceutically acceptable salt, pharmaceutical product, tautomer, hydrate, N-oxide, polymorph, crystal or any combination thereof, or a composition comprising the same. In another embodiment, the subject is a male or female. In another embodiment, the compound is compound 12db. In another embodiment, the compound is compound 11cb. In another embodiment, the compound is compound 11Mf. In another embodiment, the compound is compound 12da. In another embodiment, the compound is compound 12fa. In another embodiment, the compound is compound 12fb. In another embodiment, the compound is compound 12cb. In another embodiment, the compound is compound 55. In another embodiment, the compound is compound 6b. In another embodiment, the compound is compound 17ya.

In another embodiment, this invention provides for the use of a compound as herein described, or its isomer, metabolite, pharmaceutically acceptable salt, pharmaceutical product, tautomer, hydrate, N-oxide, polymorph, crystal or any combination thereof, for treating, suppressing, reducing the severity, reducing the risk, delaying the progression, or inhibiting ovarian cancer, metastatic ovarian cancer, resistant ovarian cancer or drug-resistant ovarian cancer in a subject. In another embodiment, the compound is compound 12db. In another embodiment, the compound is compound 11cb. In another embodiment, the compound is compound 11Tb. In another embodiment, the compound is compound 12da. In another embodiment, the compound is compound 12fa. In another embodiment, the compound is compound 12fb. In another embodiment, the compound is compound 12cb. In another embodiment, the compound is compound 55. In another embodiment, the compound is compound 6b. In another embodiment, the compound is compound 17ya. In another embodiment, the compound is compound 12q. In another embodiment, the compound is compound 70a. In another embodiment, the compound is compound 70d. In another embodiment, the compound is compound 70f. In another embodiment, the compound is compound 70m.

In one embodiment, this invention provides a method for treating, suppressing, reducing the severity, reducing the risk or inhibiting melanoma, metastatic melanoma, resistant melanoma or drug-resistant melanoma in a subject, comprising administering to the subject a compound of this invention and/or its isomer, metabolite, pharmaceutically acceptable salt, pharmaceutical product, tautomer, hydrate, N-oxide, polymorph, crystal or any combination thereof. In another embodiment, the compound is compound 12db. In another embodiment, the compound is compound 11cb. In another embodiment, the compound is compound 11fb. In another embodiment, the compound is compound 12da. In another embodiment, the compound is compound 12fa. In another embodiment, the compound is compound 12fb. In another embodiment, the compound is compound 12cb. In another embodiment, the compound is compound 55. In another embodiment, the compound is compound 6b. In another embodiment, the compound is compound 17ya. In another embodiment, the compound is compound 12q. In another embodiment, the compound is compound 70a. In another embodiment, the compound is compound 70d. In another embodiment, the compound is compound 70f. In another embodiment, the compound is compound 70m.

In another embodiment, this invention provides for the use of a compound as herein described, or isomer, metabolite, pharmaceutically acceptable salt, pharmaceutical product, tautomer, hydrate, N-oxide, polymorph, crystal or any combination thereof, for treating, suppressing, reducing the severity, reducing the risk, delaying the progression, or inhibiting lung cancer, metastatic lung cancer, resistant lung cancer or drug-resistant lung cancer. In another embodiment, the compound is compound 12db. In another embodiment, the compound is compound 11eb. In another embodiment, the compound is compound 11fb. In another embodiment, the compound is compound 12da. In another embodiment, the compound is compound 12fa. In another embodiment, the compound is compound 12fb. In another embodiment, the compound is compound 12cb. In another embodiment, the compound is compound 55. In another embodiment, the compound is compound 6b. In another embodiment, the compound is compound 17ya. In another embodiment, the compound is compound 12q. In another embodiment, the compound is compound 70a. In another embodiment, the compound is compound 70d. In another embodiment, the compound is compound 70f. In another embodiment, the compound is compound 70m.

In another embodiment, this invention provides for the use of a compound as herein described, or isomer, metabolite, pharmaceutically acceptable salt, pharmaceutical product, tautomer, hydrate, N-oxide, polymorph, crystal any combination thereof, for treating, suppressing, reducing the severity, reducing the risk, delaying the progression, or inhibiting non-small cell lung cancer, metastatic small cell lung cancer, resistant small cell lung cancer or drug-resistant small cell lung cancer. In another embodiment, the compound is compound 12db. In another embodiment, the compound is compound 11cb. In another embodiment, the compound is compound 11fb. In another embodiment, the compound is compound 12da. In another embodiment, the compound is compound 12fa. In another embodiment, the compound is compound 12fb. In another embodiment, the compound is compound 12cb. In another embodiment, the compound is compound 55. In another embodiment, the compound is compound 6b. In another embodiment, the compound is compound 17ya. In another embodiment, the compound is compound 12q. In another embodiment, the compound is compound 70a. In another embodiment, the compound is compound 70d. In another embodiment, the compound is compound 70f. In another embodiment, the compound is compound 70m.

In another embodiment, this invention provides for the use of a compound as herein described, or isomer, metabolite, pharmaceutically acceptable salt, pharmaceutical product, tautomer, hydrate, N-oxide, polymorph, crystal any combination thereof, for treating, suppressing, reducing the severity, reducing the risk, delaying the progression, or inhibiting colon cancer, metastatic colon cancer, resistant colon cancer or drug-resistant colon cancer. In another embodiment, the compound is compound 12db. In another embodiment, the compound is compound 11cb. In another embodiment, the compound is compound 11fb. In another embodiment, the compound is compound 12da. In another embodiment, the compound is compound 12fa. In another embodiment, the compound is compound 12fb. In another embodiment, the compound is compound 12cb. In another embodiment, the compound is compound 55. In another embodiment, the compound is compound 6b. In another embodiment, the compound is compound 17ya. In another embodiment, the compound is compound 12q. In another embodiment, the compound is compound 70a. In another embodiment, the compound is compound 70d. In another embodiment, the compound is compound 70f. In another embodiment, the compound is compound 70m.

In another embodiment, this invention provides for the use of a compound as herein described, or isomer, metabolite, pharmaceutically acceptable salt, pharmaceutical product, tautomer, hydrate, N-oxide, polymorph, crystal any combination thereof, for treating, suppressing, reducing the severity, reducing the risk, delaying the progression, or inhibiting of leukemia, metastatic leukemia, resistant leukemia or drug-resistant leukemia. In another embodiment, the compound is compound 12db. In another embodiment, the compound is compound 11cb. In another embodiment, the compound is compound 11fb. In another embodiment, the compound is compound 12da. In another embodiment, the compound is compound 12fa. In another embodiment, the compound is compound 12fb. In another embodiment, the compound is compound 12cb. In another embodiment, the compound is compound 55. In another embodiment, the compound is compound 6b. In another embodiment, the compound is compound 17ya. In another embodiment, the compound is compound 12q. In another embodiment, the compound is compound 70a. In another embodiment, the compound is compound 70d. In another embodiment, the compound is compound 70f. In another embodiment, the compound is compound 70m.

In another embodiment, this invention provides for the use of a compound as herein described, or isomer, metabolite, pharmaceutically acceptable salt, pharmaceutical product, tautomer, hydrate, N-oxide, polymorph, crystal any combination thereof, for treating, suppressing, reducing the severity, reducing the risk, delaying the progression, or inhibiting lymphoma, metastatic lymphoma, lymphoma or drug-resistant lymphoma. In another embodiment, the compound is compound 12db. In another embodiment, the compound is compound 11cb. In another embodiment, the compound is compound 11fb. In another embodiment, the compound is compound 12da. In another embodiment, the compound is compound 12fa. In another embodiment, the compound is compound 12fb. In another embodiment, the compound is compound 12cb. In another embodiment, the compound is compound 55. In another embodiment, the compound is compound 6b. In another embodiment, the compound is compound 17ya. In another embodiment, the compound is compound 12q. In another embodiment, the compound is compound 70a. In another embodiment, the compound is compound 70d. In another embodiment, the compound is compound 70f. In another embodiment, the compound is compound 70m.

In another embodiment, this invention provides for the use of a compound as herein described, or isomer, metabolite, pharmaceutically acceptable salt, pharmaceutical product, tautomer, hydrate, N-oxide, polymorph, crystal any combination thereof, for treating, suppressing, reducing the severity, reducing the risk, delaying the progression, or inhibiting head and neck cancer, metastatic head and neck cancer, resistant head and neck cancer or drug-resistant head and neck cancer. In another embodiment, the compound is compound 12db. In another embodiment, the compound is compound 11cb. In another embodiment, the compound is compound 11fb. In another embodiment, the compound is compound 12da. In another embodiment, the compound is compound 12fa. In another embodiment, the compound is compound 12fb. In another embodiment, the compound is compound 12cb. In another embodiment, the compound is compound 55. In another embodiment, the compound is compound 6b. In another embodiment, the compound is compound 17ya. In another embodiment, the compound is compound 12q. In another embodiment, the compound is compound 70a. In another embodiment, the compound is compound 70d. In another embodiment, the compound is compound 70f. In another embodiment, the compound is compound 70m.

In another embodiment, this invention provides for the use of a compound as herein described, or isomer, metabolite, pharmaceutically acceptable salt, pharmaceutical product, tautomer, hydrate, N-oxide, polymorph, crystal any combination thereof, for treating, suppressing, reducing the severity, reducing the risk, delaying the progression, or inhibiting of pancreatic cancer, metastatic pancreatic cancer, resistant pancreatic cancer or drug-resistant pancreatic cancer. In another embodiment, the compound is compound 12db. In another embodiment, the compound is compound 11cb. In another embodiment, the compound is compound 11fb. In another embodiment, the compound is compound 12da. In another embodiment, the compound is compound 12fa. In another embodiment, the compound is compound 12fb. In another embodiment, the compound is compound 12cb. In another embodiment, the compound is compound 55. In another embodiment, the compound is compound 6b. In another embodiment, the compound is compound 17ya. In another embodiment, the compound is compound 12q. In another embodiment, the compound is compound 70a. In another embodiment, the compound is compound 70d. In another embodiment, the compound is compound 70f. In another embodiment, the compound is compound 70m.

In another embodiment, this invention provides for the use of a compound as herein described, or isomer, metabolite, pharmaceutically acceptable salt, pharmaceutical product, tautomer, hydrate, N-oxide, polymorph, crystal any combination thereof, for treating, suppressing, reducing the severity, reducing the risk, delaying the progression, or inhibiting esophageal cancer, metastatic esophageal cancer, resistant esophageal cancer or drug-resistant esophageal cancer. In another embodiment, the compound is compound 12db. In another embodiment, the compound is compound 11cb. In another embodiment, the compound is compound 11fb. In another embodiment, the compound is compound 12da. In another embodiment, the compound is compound 12fa. In another embodiment, the compound is compound 12fb. In another embodiment, the compound is compound 12cb. In another embodiment, the compound is compound 55. In another embodiment, the compound is compound 6b. In another embodiment, the compound is compound 17ya. In another embodiment, the compound is compound 12q. In another embodiment, the compound is compound 70a. In another embodiment, the compound is compound 70d. In another embodiment, the compound is compound 70f. In another embodiment, the compound is compound 70m.

In another embodiment, this invention provides for the use of a compound as herein described, or isomer, metabolite, pharmaceutically acceptable salt, pharmaceutical product, tautomer, hydrate, N-oxide, polymorph, crystal any combination thereof, for treating, suppressing, reducing the severity, reducing the risk, delaying the progression, or inhibiting renal cancer, metastatic renal cancer, resistant renal cancer or drug-resistant renal cancer. In another embodiment, the compound is compound 12db. In another embodiment, the compound is compound 11cb. In another embodiment, the compound is compound 11fb. In another embodiment, the compound is compound 12da. In another embodiment, the compound is compound 12fa. In another embodiment, the compound is compound 12fb. In another embodiment, the compound is compound 12cb. In another embodiment, the compound is compound 55. In another embodiment, the compound is compound 6b. In another embodiment, the compound is compound 17ya. In another embodiment, the compound is compound 12q. In another embodiment, the compound is compound 70a. In another embodiment, the compound is compound 70d. In another embodiment, the compound is compound 70f. In another embodiment, the compound is compound 70m.

In another embodiment, this invention provides for the use of a compound as herein described, or isomer, metabolite, pharmaceutically acceptable salt, pharmaceutical product, tautomer, hydrate, N-oxide, polymorph, crystal any combination thereof, for treating, suppressing, reducing the severity, reducing the risk, delaying the progression, or inhibiting CNS cancer, metastatic CNS cancer, resistant CNS cancer or drug-resistant CNS cancer. In another embodiment, the compound is compound 12db. In another embodiment, the compound is compound 11cb. In another embodiment, the compound is compound 11fb. In another embodiment, the compound is compound 12da. In another embodiment, the compound is compound 12fa. In another embodiment, the compound is compound 12fb. In another embodiment, the compound is compound 12cb. In another embodiment, the compound is compound 55. In another embodiment, the compound is compound 6b. In another embodiment, the compound is compound 17ya. In another embodiment, the compound is compound 12q. In another embodiment, the compound is compound 70a. In another embodiment, the compound is compound 70d. In another embodiment, the compound is compound 70f. In another embodiment, the compound is compound 70m.

In some embodiments, this invention provides for the use of a compound as herein described, or its isomer, metabolite, pharmaceutically acceptable salt, pharmaceutical product, tautomer, polymorph, crystal, N-oxide, hydrate or any combination thereof, for treating, suppressing, reducing the severity, reducing the risk, or inhibiting a drug resistant cancerous tumor or tumors in a subject. In another embodiment, the cancer is adrenocortical carcinoma, anal cancer, bladder cancer, brain tumor, brain stem tumor, breast cancer, glioma, cerebellar astrocytoma, cerebral astrocytoma, ependymoma, medulloblastoma, supratentorial primitive neuroectodermal, pineal tumors, hypothalamic glioma, breast cancer, carcinoid tumor, carcinoma, cervical cancer, colon cancer, central nervous system (CNS) cancer, endometrial cancer, esophageal cancer, extrahepatic bile duct cancer, Ewing's family of tumors (Pnet), extracranial germ cell tumor, eye cancer, intraocular melanoma, gallbladder cancer, gastric cancer, germ cell tumor, extragonadal, gestational trophoblastic tumor, head and neck cancer, hypopharyngeal cancer, islet cell carcinoma, laryngeal cancer, leukemia, acute lymphoblastic, leukemia, oral cavity cancer, liver cancer, lung cancer, non-small cell lung cancer, small cell, lymphoma, AIDS-related lymphoma, central nervous system (primary), lymphoma, cutaneous T-cell, lymphoma, Hodgkin's disease, non-Hodgkin's disease, malignant mesothelioma, melanoma, Merkel cell carcinoma, metasatic squamous carcinoma, multiple myeloma, plasma cell neoplasms, mycosis fungoides, myelodysplastic syndrome, myeloproliferative disorders, nasopharyngeal cancer, neuroblastoma, oropharyngeal cancer, osteosarcoma, ovarian cancer, ovarian epithelial cancer, ovarian germ cell tumor, ovarian low malignant potential tumor, pancreatic cancer, exocrine, pancreatic cancer, islet cell carcinoma, paranasal sinus and nasal cavity cancer, parathyroid cancer, penile cancer, pheochromocytoma cancer, pituitary cancer, plasma cell neoplasm, prostate cancer, rhabdomyosarcoma, rectal cancer, renal cancer, renal cell cancer, salivary gland cancer, Sezary syndrome, skin cancer, cutaneous T-cell lymphoma, skin cancer, Kaposi's sarcoma, skin cancer, melanoma, small intestine cancer, soft tissue sarcoma, soft tissue sarcoma, testicular cancer, thymoma, malignant, thyroid cancer, urethral cancer, uterine cancer, sarcoma, unusual cancer of childhood, vaginal cancer, vulvar cancer, Wilms' tumor, or any combination thereof. In another embodiment, the compound is compound 12db. In another embodiment, the compound is compound 11cb. In another embodiment, the compound is compound 11fb. In another embodiment, the compound is compound 12da. In another embodiment, the compound is compound 12fa. In another embodiment, the compound is compound 12fb. In another embodiment, the compound is compound 12cb. In another embodiment, the compound is compound 55. In another embodiment, the compound is compound 6b. In another embodiment, the compound is compound 17ya. In another embodiment, the compound is compound 12q. In another embodiment, the compound is compound 70a. In another embodiment, the compound is compound 70d. In another embodiment, the compound is compound 70f. In another embodiment, the compound is compound 70m.

In another embodiment, the tumor is prostate cancer tumor. In another embodiment, the tumor is ovarian cancer tumor. In another embodiment, the tumor is a melanoma tumor. In another embodiment, the tumor is a multidrug resistant (MDR) melanoma tumor.

In one embodiment, this invention is directed to a method of destroying a cancerous cell comprising: providing a compound of this invention and contacting the cancerous cell with the compound under conditions effective to destroy the contacted cancerous cell. According to various embodiments of destroying the cancerous cells, the cells to be destroyed can be located either in vivo or ex vivo (i.e., in culture). In another embodiment, the compound is compound 12db. In another embodiment, the compound is compound 11cb. In another embodiment, the compound is compound 11Th. In another embodiment, the compound is compound 12da. In another embodiment, the compound is compound 12fa. In another embodiment, the compound is compound 12fb. In another embodiment, the compound is compound 12cb. In another embodiment, the compound is compound 55. In another embodiment, the compound is compound 6b. In another embodiment, the compound is compound 17ya. In another embodiment, the compound is compound 12q. In another embodiment, the compound is compound 70a. In another embodiment, the compound is compound 70d. In another embodiment, the compound is compound 70f. In another embodiment, the compound is compound 70m.

In another embodiment, the cancer is selected from the group consisting of prostate cancer, breast cancer, ovarian cancer, skin cancer, melanoma, lung cancer, colon cancer, leukemia, renal cancer, CNS cancer, and combinations thereof.

A still further aspect of the present invention relates to a method of treating or preventing a cancerous condition that includes: providing a compound of the present invention and then administering an effective amount of the compound to a patient in a manner effective to treat or prevent a cancerous condition.

According to one embodiment, the patient to be treated is characterized by the presence of a precancerous condition, and the administering of the compound is effective to prevent development of the precancerous condition into the cancerous condition. This can occur by destroying the precancerous cell prior to or concurrent with its further development into a cancerous state.

According to another embodiment, the patient to be treated is characterized by the presence of a cancerous condition, and the administering of the compound is effective either to cause regression of the cancerous condition or to inhibit growth of the cancerous condition, i.e., stopping its growth altogether or reducing its rate of growth. This preferably occurs by destroying cancer cells, regardless of their location in the patient body. That is, whether the cancer cells are located at a primary tumor site or whether the cancer cells have metastasized and created secondary tumors within the patient body.

As used herein, subject or patient refers to any mammalian patient, including without limitation, humans and other primates, dogs, cats, horses, cows, sheep, pigs, rats, mice, and other rodents. In one embodiment, the subject is male. In another embodiment, the subject is female. In some embodiments, while the methods as described herein may be useful for treating either males or females.

When administering the compounds of the present invention, they can be administered systemically or, alternatively, they can be administered directly to a specific site where cancer cells or precancerous cells are present. Thus, administering can be accomplished in any manner effective for delivering the compounds or the pharmaceutical compositions to the cancer cells or precancerous cells. Exemplary modes of administration include, without limitation, administering the compounds or compositions orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes.

The compounds of the present invention are useful in the treatment or prevention of various forms of cancer, particularly prostate cancer, breast cancer, ovarian, skin cancer (e.g., melanoma), lung cancer, colon cancer, leukemia, renal cancer, and CNS cancer (e.g., glioma, glioblastoma). Treatment of these different cancers is supported by the Examples herein. Moreover, based upon their believed mode of action as tubulin inhibitors, it is believed that other forms of cancer will likewise be treatable or preventable upon administration of the compounds or compositions of the present invention to a patient. Preferred compounds of the present invention are selectively disruptive to cancer cells, causing ablation of cancer cells but preferably not normal cells. Significantly, harm to normal cells is minimized because the cancer cells are susceptible to disruption at much lower concentrations of the compounds of the present invention.

The compounds of the present invention are useful in the treatment, reducing the severity, reducing the risk, or inhibition of cancer, metastatic cancer, resistant cancer or drug-resistant cancer. In another embodiment, the cancer is prostate cancer, breast cancer, ovarian, skin cancer (e.g., melanoma), lung cancer, colon cancer, leukemia, lymphoma, head and neck, pancreatic, esophageal, renal cancer or CNS cancer. Treatment of these different cancers is supported by the Examples herein. Moreover, based upon their believed mode of action as tubulin inhibitors, it is believed that other forms of cancer will likewise be treatable or preventable upon administration of the compounds or compositions of the present invention to a patient. Preferred compounds of the present invention are selectively disruptive to cancer cells, causing ablation of cancer cells but preferably not normal cells. Significantly, harm to normal cells is minimized because the cancer cells are susceptible to disruption at much lower concentrations of the compounds of the present invention. In another embodiment, the compound is compound 12db. In another embodiment, the compound is compound 11cb. In another embodiment, the compound is compound 11fb. In another embodiment, the compound is compound 12da. In another embodiment, the compound is compound 12fa. In another embodiment, the compound is compound 12fb. In another embodiment, the compound is compound 12cb. In another embodiment, the compound is compound 55. In another embodiment, the compound is compound 6b. In another embodiment, the compound is compound 17ya. In another embodiment, the compound is compound 12q. In another embodiment, the compound is compound 70a. In another embodiment, the compound is compound 70d. In another embodiment, the compound is compound 70f. In another embodiment, the compound is compound 70m.

As used herein, subject or patient refers to any mammalian patient, including without limitation, humans and other primates, dogs, cats, horses, cows, sheep, pigs, rats, mice, and other rodents. In some embodiments, while the methods as described herein may be useful for treating either males or females.

In one embodiment, the compound is administered in combination with an anti-cancer agent by administering the compounds as herein described, alone or in combination with other agents.

When the compounds or pharmaceutical compositions of the present invention are administered to treat, suppress, reduce the severity, reduce the risk, or inhibit a cancerous condition, the pharmaceutical composition can also contain, or can be administered in conjunction with, other therapeutic agents or treatment regimen presently known or hereafter developed for the treatment of various types of cancer. Examples of other therapeutic agents or treatment regimen include, without limitation, radiation therapy, immunotherapy, chemotherapy, surgical intervention, and combinations thereof.

The following examples are presented in order to more fully illustrate the preferred embodiments of the invention.

They should in no way, however, be construed as limiting the broad scope of the invention.

EXAMPLES

The Examples set forth below are for illustrative purposes only and are not intended to limit, in any way, the scope of the present invention.

Materials and Methods:

General. All reagents were purchased from Sigma-Aldrich Chemical Co., Fisher Scientific (Pittsburgh, PA), AK Scientific (Mountain View, CA), Oakwood Products (West Columbia, SC), etc. and were used without further purification. Moisture-sensitive reactions were carried under an argon atmosphere. ABT-751 was prepared according methods reported by Yoshino et al.[26] Routine thin layer chromatography (TLC) was performed on aluminum backed Uniplates (Analtech, Newark, DE). Melting points were measured with Fisher-Johns melting point apparatus (uncorrected). NMR spectra were obtained on a Bruker AX 300 (Billerica, MA) spectrometer or Varian Inova-500 (Vernon Hills, Illinois) spectrometer. Chemical shifts are reported as parts per million (ppm) relative to TMS in $CDCl_3$. Mass spectral data was collected on a Bruker ESQUIRE electrospray/ion trap instrument in positive and negative ion modes. Elemental analyses were performed by Atlantic Microlab Inc.

Cell Culture and Cytotoxicity Assay of Prostate Cancer and Melanoma. All cell lines were obtained from ATCC (American Type Culture Collection, Manassas, VA, USA), while cell culture supplies were purchased from Cellgro Mediatech (Herndon, VA, USA). We examined the antiproliferative activity of our anti-tubulin compounds in four human prostate cancer cell lines (LNCaP, DU 145, PC-3, and PPC-1) and two human melanoma cell lines (A375 and WM-164). Human ovarian cell line OVCAR-8 and its resistant cell line that over-expresses P-gp (NCI/ADR-RES) were used as MDR models. Both ovarian cell lines were obtained from National Cancer Institutes (NCI). All cell lines were tested and authenticated by either ATCC or NCI. All prostate cancer and ovarian cancer cell lines were cultured in RPMI 1640, supplemented with 10% fetal bovine serum (FBS). Melanoma cells were cultured in DMEM, supplemented with 5% FBS, 1% antibiotic/antimycotic mixture (Sigma-Aldrich, Inc., St. Louis, MO, USA) and bovine insulin (5 μg/mL; Sigma-Aldrich). The cytotoxic potential of the anti-tubulin compounds was evaluated using the sulforhodamine B (SRB) assay after 96 h of treatment.

Aqueous Solubility. The solubility of drugs was determined by Multiscreen Solubility Filter Plate (Millipore Corporate, Billerica, MA) coupled with LC-MS/MS. Briefly, 198 μL of phosphate buffered saline (PBS) buffer (pH 7.4) was loaded into 96-well plate, and 2 μL of 10 mM test compounds (in DMSO) was dispensed and mixed with gentle shaking (200-300 rpm) for 1.5 h at RT (N=3). The plate was centrifuged at 800g for 5 min, and the filtrate was used to determine its concentration and solubility of test compound by LC-MS/MS as described below.

Pharmacokinetic Study. Female Sprague-Dawley rats (n=3 or 4; 254±4 g) were purchased from Harlan Inc. (Indianapolis, IN). Rat thoracic jugular vein catheters were purchased from Braintree Scientific Inc. (Braintree, MA). On arrival at the animal facility, the animals were acclimated for 3 days in a temperature-controlled room (20-22° C.) with a 12 h light/dark cycle before any treatment. Compound 1h was administered intravenously (i.v.) into the jugular vein catheters at a dose of 2.5 mg/kg (in DMSO/PEG300, 2/8), whereas 5Ha and 5Hc were dosed at 5 mg/kg (in DMSO/PEG300, 1/9). An equal volume of heparinized saline was injected to replace the removed blood, and blood samples (250 μL) were collected via the jugular vein catheters at 10, 20, 30 min, and 1, 2, 4, 8, 12, 24 h. Compounds 1 h, 5Ha and 5Hc were given (p.o.) by oral gavage at 10 mg/kg (in Tween80/DMSO/$H_2O$, 2/1/7). All blood samples (250 μL) after oral administration were collected via the jugular vein catheters at 30, 60, 90 min, 120 min, 150 min, 180 min, 210 min, 240 min, and 8, 12, 24 h. Heparinized syringes and vials were prepared prior to blood collection. Plasma samples were prepared by centrifuging the blood samples at 8,000 g for 5 min. All plasma samples were stored immediately at −80° C. until analyzed.

Analytes were extracted from 100 μL of plasma with 200 μL of acetonitrile containing 200 nM the internal standard ((3,5-dimethoxyphenyl)(2-phenyl-1H-imidazol-4-yl)methanone). The samples were thoroughly mixed, centrifuged, and the organic extract was transferred to autosampler for LC-MS/MS analysis. Multiple reaction monitoring (MRM) mode, scanning m/z 356→188 (compound 1h), m/z 371→203 (compound 5Ha), m/z 389→221 (compound 5Hc), and m/z 309→171 (the internal standard), was used to obtain the most sensitive signals. The pharmacokinetic parameters were determined using non-compartmental analysis (WinNonlin, Pharsight Corporation, Mountain View, CA)

Analytical Method. Sample solution (10 μL) was injected into an Agilent series HPLC system (Agilent 1100 Series Agilent 1100 Chemstation, Agilent Technology Co, Ltd). All analytes were separated on a narrow-bore C18 column (Alltech Alltima HP, 2.1×100 mm, 3 μm, Fisher, Fair Lawn, NJ). Two gradient modes were used. Gradient mode was used to achieve the separation of analytes using mixtures of mobile phase A [ACN/$H_2O$ (5%/95%, v/v) containing 0.1% formic acid] and mobile phase B [ACN/$H_2O$ (95%/5%, v/v) containing 0.1% formic acid] at a flow rate of 300 μL/min. Mobile phase A was used at 15% from 0 to 1 min followed by a linearly programmed gradient to 100% of mobile phase B within 6 min, 100% of mobile phase B was maintained for 0.5 min before a quick ramp to 15% mobile phase A. Mobile phase A was continued for another 12 min towards the end of analysis.

In Vitro Tubulin Polymerization Assay. Bovine brain tubulin (0.4 mg, >97% pure) (Cytoskeleton, Denver, CO) was mixed with 10 μM of the test compounds and incubated in 100 μL of general tubulin buffer (80 mM PIPES, 2.0 mM $MgCl_2$, 0.5 mM EGTA, and 1 mM GTP) at pH 6.9. The absorbance of wavelength at 340 nm was monitored every 1 min for 20 min by the SYNERGY 4 Microplate Reader (Bio-Tek Instruments, Winooski, VT). The spectrophotometer was set at 37° C. for tubulin polymerization.

A triple-quadruple mass spectrometer, API Qtrap 4000™ (Applied Biosystems/MDS SCIEX, Concord, Ontario, Canada), operating with a TurboIonSpray source was used. The spraying needle voltage was set at 5 kV for positive mode. Curtain gas was set at 10; Gas 1 and gas 2 were set 50. Collision-Assisted-Dissociation (CAD) gas at medium and the source heater probe temperature at 500° C. Data acquisition and quantitative processing were accomplished using Analyst™ software, Ver. 1.4.1 (Applied Biosystems).

The purity of the final compounds was tested via RP-HPLC on a Waters 2695 HPLC system installed with a Photodiode Array Detector. Two RP-HPLC methods were conducted using a Supelco Ascentis™ 5 μM C-18 column (250×4.6 mm) at ambient temperature, and a flow rate of 0.7 mL/min. HPLC1: Gradient: Solvent A (water) and Solvent B (methanol): 0-20 min 40-100% B (linear gradient), 20-27 min 100% B. HPLC2: Gradient: Solvent A (water) and Solvent B (methanol): 0-15 min 40-100% B (linear gradient), 15-25 min 100% B. UV detection at 254 nm.

The compounds of this invention were prepared according to FIGS. 1-17.

Example 1

Synthesis of B Ring Variant Compounds

Figure 2:
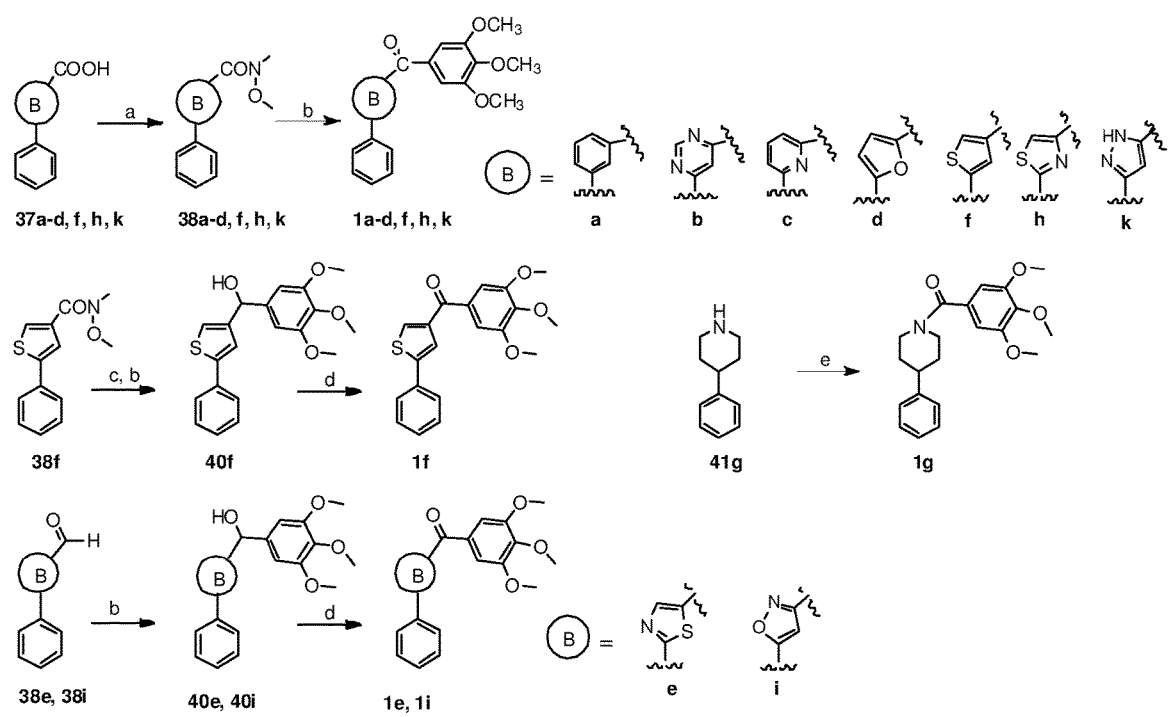
FIG. 2 depicts the synthesis of the diverse B-ring templates. Reagents and conditions: (a) EDCI, HOBt, NMM, CH$_3$OCH$_3$NH·HCl, CH$_2$Cl$_2$, 51-95%; (b) 3,4,5-trimethoxyphenyl-magnesium bromide, THF, 48-78%; (c) LAH, −78° C., THF, 85%; (d) Dess-Martin reagent, CH$_2$Cl$_2$, 81%; (e) EDCI, HOBt, NMM, 3,4,5-trimethoxybenzoic acid, CH$_2$Cl$_2$, 58%.

B ring variant compounds were synthesized according to FIGS. 1 and 2.

Oxazole B Ring

Synthesis of (2-Phenyl-oxazol-4-yl)-(3,4,5-trimethoxy-phenyl)-methanone (36a) (FIG. 1)

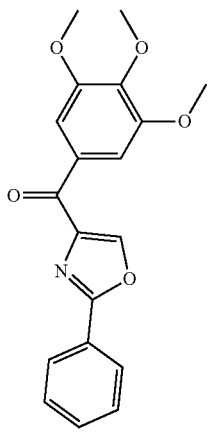

(36a)

(2R)-2-Phenyl-4,5-dihydro-oxazole-4-carboxylic acid methyl ester (32a). Acetyl chloride (6.8 mL) was added dropwise to ice-cold methanol (30 mL). After the addition of L-serine (0.48 mmol), the reaction mixture was warmed to room temperature (RT) and stirred overnight. Evaporation of the solvent gave white solid (2R)-3-hydroxy-2-methyl-propionic acid methyl ester HCl salt, which was used without purification in the next step. Triethylamine (11 mL, 72.3 mmol) was added slowly to a solution of ethyl benzimidate hydrochloride (11.6 g, 62.8 mmol) in $CH_2Cl_2$ (150 mL). The reaction mixture was stirred at RT for 30 min and (2R)-3-hydroxy-2-methyl-propionic acid methyl ester HCl salt (13.5 g, 79.6 mmol) was added by portion. The resulting mixture was stirred for 48 h and concentrated under reduced pressure. The compound 32a was separated from flash column as a yellow oil (12.3 g, 95.9%). $^1$H NMR ($CDCl_3$) δ 7.99-7.38 (m, 5H), 4.97 (dd, 1H, J=7.8 Hz, J=10.5 Hz), 4.70 (t, 1H, J=8.7 Hz), 4.62 (dd, 1H, J=8.7 Hz, J=10.5 Hz), 3.82 (s, 3H); MS (ESI) m/z 206.1 $(M+H)^+$.

(2R)-2-Phenyl-4,5-dihydro-oxazole-4-carboxylic acid (33a). To an ice-cooled solution of 32a in $MeOH/H_2O$ was added LiOH (2.5 equiv) with stirring. The mixture was allowed to warm to RT in 1 h, concentrated in vacuo, and the white solid was dissolved in $H_2O$ and acidified with 1 N HCl to pH 2.0 and extracted with $MgSO_4$, filtered and concentrated in vacuo to provide the acid 33a as a white solid (95.8%). $^1$H NMR ($CDCl_3$) δ 7.98 (d, 2H), 7.57-7.42 (m, 3H), 5.04 (dd, 1H, J=7.8 Hz, J=10.8 Hz), 4.80 (t, 1H, J=8.7 Hz), 4.70 (dd, 1H, J=9.0 Hz, J=10.8 Hz); MS (ESI) m/z 191.9 $(M+H)^+$, 189.7 (M−H)—, 145.8 $(M-COOH)^-$.

(2R)-2-Phenyl-4,5-dihydro-oxazole-4-carboxylic acid methoxy-methyl-amide (34a). To a mixture of 33a (5 mmol), EDCI (6 mmol), HOBt (5 mmol) and $Et_3N$ (5 mmol) in $CH_2Cl_2$ (50 mL) was added $HNCH_3OCH_3$ (5 mmol) and stirring continued at RT for 6-8 h. The reaction mixture was diluted with $CH_2Cl_2$ (100 mL) and sequentially washed with water, satd. $NaHCO_3$, brine and dried over $MgSO_4$. The solvent was removed under reduced pressure to yield a crude product 34a, which was purified by column chromatography as a white solid (61.0%). $^1$H NMR ($CDCl_3$) δ 7.98-7.36 (m, 5H), 7.57-7.42 (m, 3H), 5.35 (br, t, 1H), 4.81 (br, t, 1H), 4.52 (dd, 1H, J=8.7 Hz, J=10.2 Hz), 3.90 (s, 3H), 3.27 (s, 3H); MS (ESI) m/z 257.0 $(M+H)^+$.

(2R)-(2-Phenyl-4,5-dihydro-oxazol-4-yl)-(3,4,5-trimethoxy-phenyl)-methanone (35a). To a solution of n-BuLi (1.6 M, 0.713 mL) in 8 mL THF was added a solution of 3,4,5-trimethoxybromobenzene (1.09 mmol) in 3 mL THF under −78° C. The mixture was allowed to stir for 2 h and a solution of Weinreb amide 34a (1.14 mmol) in 3 mL THF was charged. The temperature was allowed to increase at RT and stirred overnight. The reaction mixture was quenched with satd. $NH_4Cl$, extracted with ethyl ether, dried with $MgSO_4$. The solvent was removed under reduced pressure to yield a crude product, which was purified by column chromatography to obtain pure compound 35a as a white solid (47.9%). $^1$H NMR ($CDCl_3$) δ 7.97-7.94 (m, 2H), 7.62 (s, 2H), 7.54-7.37 (m, 3H), 5.61 (q, 1H, J=7.5 Hz, 9.9 Hz), 5.12 (t, 1H, J=7.5 Hz), 4.57 (q, 1H, J=7.8 Hz, 9.9 Hz), 3.96 (s, 6H), 3.95 (s, 3H); MS (ESI) m/z 364.1$(M+Na)^+$, 340.1 (M−H)—.

(2-Phenyl-oxazol-4-yl)-(3,4,5-trimethoxy-phenyl)-methanone (36a). A mixture of 35a (1.48 mmol), $CBrCl_3$ (2.59 mmol) and DBU (2.97 mmol) in $CH_2Cl_2$ (20 mL) was stirred overnight. The reaction mixture was absorbed on silica gel and purified by column chromatography to yield pure 36a as desired (61.6%). $^1$H NMR ($CDCl_3$) δ 8.37 (s, 1H), 8.14-8.12 (m, 2H), 7.74 (s, 2H), 7.52-7.49 (m, 3H), 3.97 (s, 9H); MS (ESI) m/z 362.1$(M+Na)^+$.

Benzene, pyrimidine, pyridine, furan, thiophene, thiazole, pyrazole and piperidine B ring variants (FIG. 2): B ring variants (1a-1d, 1k) were obtained from their corresponding acids (37a-37d, 37k). Compound 1f with thiophene in B ring position can not be separated from the mixture of 1f and a Grignard reagent coupling by-product 3,4,5,3',4',5'-hexamethoxybiphenyl using flash column. So, an alternative method was used to prepare 1f: Weinreb amide 38f was converted into its corresponding aldehyde which was further reacted with 3,4,5-trimethoxyphenylmagnesium bromide to afford the alcohol 40f, which can be easily separated from 3,4,5,3',4',5'-hexamethoxybiphenyl using flash column chromatography. Oxidation with pyridinium dichromate (PDC) or DMSO did not afford 1f from secondary alcohol 40f with good yields. But using Dess-Martin periodinane reagent as oxidant successfully formed the desired ketone compound 1f. 1e and 1i were prepared from alcohols 40e and 40i using a similar method. Compound 1g was obtained via a coupling reaction from piperidine 41g and 3,4,5-trimethoxybenzoic acid.

Benzene B Ring

Synthesis of Biphenyl-3-yl(3,4,5-trimethoxyphenyl)methanone (1a) (FIG. 2)

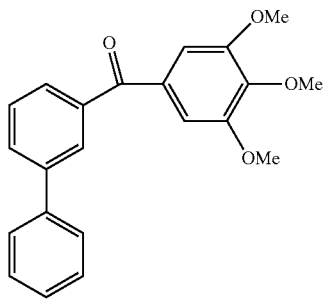

N-Methoxy-N-methylbiphenyl-3-carboxamide (38a). To a mixture of 37a (5 mmol), EDCI (6 mmol), HOBt (5 mmol) and NMM (11 mmol) in CH$_2$Cl$_2$ (50 mL) was added HNCH$_3$OCH$_3$HCl salt (5 mmol) and stirring continued at RT for 2 h. The reaction mixture was diluted with CH$_2$Cl$_2$ (100 mL) and sequentially washed with water, satd. NaHCO$_3$, brine and dried over MgSO$_4$. The solvent was removed under reduced pressure to yield a colorless oil, which was used for next step (58.4%). MS (ESI) m/z 264.0 (M+Na)$^+$.

Biphenyl-3-yl(3,4,5-trimethoxyphenyl)methanone (1a). To a solution of 38a (FIG. 2) (0.174 g, 0.72 mmoL) in 5 mL THF was added a THF solution of 3,4,5-trimethoxyphenyl-magnesiumbromide (0.5 N, 1.08 mmol) at 0° C. The mixture was allowed to stir for 30 min and quenched with satd. NH$_4$Cl, extracted with ethyl ether, dried with MgSO$_4$. The solvent was removed under reduced pressure to yield a crude product, which was purified by column chromatography to obtain pure compound 1a as a white solid (43.8%). $^1$H NMR (CDCl$_3$) δ 8.02 (t, 1H), 7.84-7.74 (m, 2H), 7.64-7.38 (m, 6H), 7.11 (s, 2H), 3.95 (s, 3H), 3.88 (s, 6H); MS (ESI) m/z 371.1(M+Na)$^+$.

Pyrimidine B Ring

Synthesis of (6-Phenylpyrimidin-4-yl)(3,4,5-trimethoxyphenyl)methanone (1b) (FIG. 2)

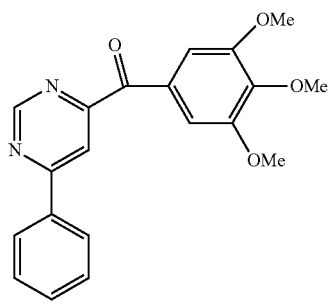

N-Methoxy-N-methyl-6-phenylpyrimidine-4-carboxamide (38b). To a mixture of 37b (5 mmol), EDCI (6 mmol), HOBt (5 mmol) and NMM (11 mmol) in CH$_2$Cl$_2$ (50 mL) was added HNCH$_3$OCH$_3$HCl salt (5 mmol) and stirring continued at RT for overnight. The reaction mixture was diluted with CH$_2$Cl$_2$ (100 mL) and sequentially washed with water, satd. NaHCO$_3$, brine and dried over MgSO$_4$. The solvent was removed under reduced pressure to yield a crude product, which was purified by column chromatography to obtain pure compound 38b as a yellow solid (62.3%). $^1$H NMR (CDCl$_3$) δ 9.28 (s, 1H), 8.14-8.06 (m, 2H), 7.96 (br, s, 1H), 7.54-7.50 (m, 3H), 5.35 (br, t, 1H), 4.81 (br, t, 1H), 4.52 (dd, 1H, J=8.7 Hz, J=10.2 Hz), 3.79 (s, 3H), 3.42 (s, 3H); MS (ESI) m/z 266.0 (M+Na)$^+$.

(6-Phenylpyrimidin-4-yl)(3,4,5-trimethoxyphenyl)methanone (1b). To a solution of 38b (0.243 g, 1 mmoL) in 5 mL THF was added a THF solution of 3,4,5-trimethoxyphenylmagnesiumbromide (0.5 N, 5.6 mL, 1.4 mmol) at 0° C. The mixture was allowed to stir for 30 min and quenched with satd. NH$_4$Cl, extracted with ethyl ether, dried with MgSO$_4$. The solvent was removed under reduced pressure to yield a crude product, which was purified by column chromatography to obtain pure compound 1b (52.3%). $^1$H NMR (CDCl$_3$) δ 9.40 (d, 1H, J=1.5 Hz), 8.29 (d, 1H, J=1.5 Hz), 8.22-8.18, 7.57-7.54 (m, 5H), 7.46 (s, 2H), 3.96 (s, 3H), 3.91 (s, 6H); MS (ESI) m/z 351.1(M+H)$^+$.

Pyridine B Ring

Synthesis of (6-Phenylpyridin-2-yl)(3,4,5-trimethoxyphenyl)methanone (1c) (FIG. 2)

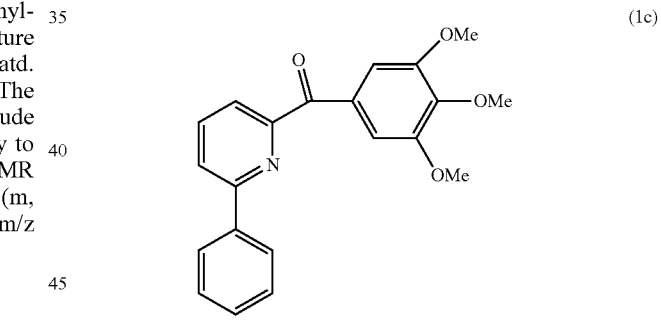

N-Methoxy-N-methyl-6-phenylpicolinamide (38c). To a mixture of 37c (1.77 mmol), EDCI (2.12 mmol), HOBt (1.86 mmol) and NMM (3.54 mmol) in CH$_2$Cl$_2$ (20 mL) was added HNCH$_3$OCH$_3$HCl salt (1.86 mmol) and stirring continued at RT for overnight. The reaction mixture was diluted with CH$_2$Cl$_2$ (40 mL) and sequentially washed with water, satd. NaHCO$_3$, brine and dried over MgSO$_4$. The solvent was removed under reduced pressure to yield a crude product, which was purified by column chromatography to obtain pure compound 38c as a colorless oil (51.2%). $^1$H NMR (CDCl$_3$) δ 8.02 (d, 1H, J=7.0 Hz), 7.86-7.81 (m, 2H), 7.55 (br, 1H), 7.48 (t, 2H), 7.44-7.41 (m, 1H), 3.82 (s, 3H), 3.44 (s, br, 3H); MS (ESI) m/z 265.0 (M+Na)$^+$.

(6-Phenylpyridin-2-yl)(3,4,5-trimethoxyphenyl)methanone (1c). To a solution of 38c (0.210 g, 0.86 mmoL) in 5 mL THF was added a THF solution of 3,4,5-trimethoxyphenylmagnesiumbromide (0.5 N, 3.5 mL, 1.73 mmol) at 0° C. The mixture was allowed to stir for 30 min and quenched with water, extracted with ethyl acetate and dried with MgSO$_4$. The solvent was removed under reduced pressure to yield a crude product, which was purified by column chromatography to obtain pure 1c as white needle crystals (78%). $^1$H NMR (CDCl$_3$) δ 8.10 (d, br, 2H), 8.02-8.00 (m, 1H), 7.97-7.96 (m, 2H), 7.66 (s, 2H), 7.49-7.43 (m, 3H), 3.97 (s, 3H), 3.89 (s, 6H); MS (ESI) m/z 372.6 (M+Na)$^+$.

Furan B Ring

Synthesis of (5-Phenylfuran-2-yl)(3,4,5-trimethoxyphenyl)methanone (1d) (FIG. 2)

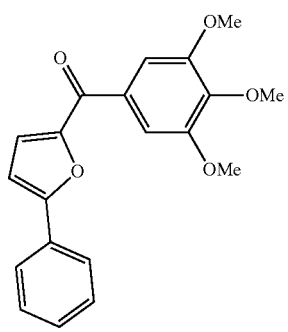

(1d)

N-Methoxy-N-methyl-5-phenylfuran-2-carboxamide (38d). To a mixture of 37d (10 mmol), EDCI (12 mmol), HOBt (11 mmol) and NMM (21 mmol) in CH$_2$Cl$_2$ (200 mL) was added HNCH$_3$OCH$_3$HCl salt (10.5 mmol) and stirring continued at RT for overnight. The reaction mixture was diluted with CH$_2$Cl$_2$ (200 mL) and sequentially washed with water, satd. NaHCO$_3$, brine and dried over MgSO$_4$. The solvent was removed under reduced pressure to yield a crude product, which was purified by column chromatography to obtain pure compound 38d. (95.2%). $^1$H NMR (CDCl$_3$) δ 7.82 (d, 1H, J=7.0 Hz), 7.46-7.43 (t, 2H), 7.37-7.34 (m, 1H), 7.25 (d, 1H, J=4.0 Hz), 6.78 (d, 1H, J=4.0 Hz), 3.86 (s, 3H), 3.41 (s, 3H); MS (ESI) m/z 254.1 (M+Na)$^+$.

(5-Phenylfuran-2-yl)(3,4,5-trimethoxyphenyl)methanone (1d). To a solution of 38d (0.231 g, 1 mmoL) in 5 mL THF was added a THF solution of 3,4,5-trimethoxyphenylmagnesiumbromide (0.5 N, 4.0 mL, 2 mmol) at 0° C. The mixture was allowed to stir for 30 min and quenched with water, extracted with ethyl acetate and dried with MgSO$_4$. The solvent was removed under reduced pressure to yield a crude product, which was purified by column chromatography to obtain pure compound 1d as white crystals (35.5%). $^1$H NMR (CDCl$_3$) δ 7.85-7.82 (m, 1H), 7.48-7.36 (m, 4H), 7.35 (s, 2H), 7.25 (d, 1H, J=4.0 Hz), 6.86 (d, 1H, J=4.2 Hz), 3.96 (s, 3H), 3.95 (s, 6H); MS (ESI) m/z 339.1 (M+H)$^+$.

Thiazole B Ring

Synthesis of (2-Phenylthiazol-5-yl)(3,4,5-trimethoxyphenyl)methanone (1e) (FIG. 2)

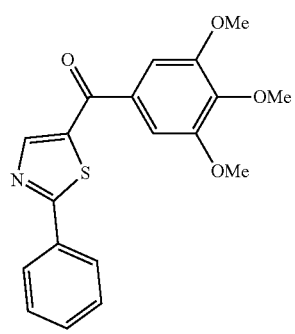

(1e)

(2-Phenylthiazol-5-yl)(3,4,5-trimethoxyphenyl)methanol (40e). To a solution of 2-phenylthiazole-5-carbaldehyde 38e (0.567 g, 3 mmoL) in 15 mL THF was added a THF solution of 3,4,5-trimethoxyphenylmagnesiumbromide (0.5 N, 6.5 mL, 3.25 mmol) at 0° C. The mixture was allowed to stir for 30 min and quenched with satd. NH$_4$Cl, extracted with ethyl ether, dried with MgSO$_4$. The solvent was removed under reduced pressure to yield a crude product, which was purified by column chromatography to obtain pure compound 40e (72.9%). $^1$H NMR (CDCl$_3$) δ 7.90 (m, 2H), 7.64 (s, 1H), 7.41 (m, 3H), 6.69 (s, br, 2H), 6.04 (s, 1H), 3.86 (s, 6H), 3.85 (s, 3H), 1.57 (d, 1H, J=5.5 Hz); MS (ESI) m/z 358.1 (M+Na)$^+$.

(2-Phenylthiazol-5-yl)(3,4,5-trimethoxyphenyl)methanone (1e). To a solution of 40e (0.357 g, 1 mmoL) in 40 mL anhydrous CH$_2$Cl$_2$ was added Dess-Martin reagent (0.848 g, 2 mmol). The mixture was allowed to stir for 30 min and quenched with sat. Na$_2$S$_2$O$_3$ solution, extracted with ethyl acetate and dried with MgSO$_4$. The solvent was removed under reduced pressure to yield a crude product, which was purified by column chromatography to give pure compound 1e (80.1%). $^1$H NMR (CDCl$_3$) δ 8.33 (s, 1H), 8.04 (m, 2H), 7.51 (m, 3H), 7.18 (s, 2H), 3.96 (s, 3H), 3.93 (s, 6H); MS (ESI) m/z 378.1 (M+H)$^+$.

Thiophene B Ring

Synthesis of (5-Phenylthiophen-3-yl)(3,4,5-trimethoxyphenyl)methanone (1f) (FIG. 2)

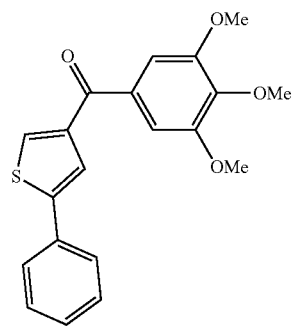

(1f)

N-Methoxy-N-methyl-5-phenylthiophene-3-carboxamide (38f). To a mixture of 37f (2.5 mmol), EDCI (2.9 mmol), HOBt (2.6 mmol) and NMM (5.3 mmol) in CH$_2$Cl$_2$ (30 mL) was added HNCH$_3$OCH$_3$HCl salt (2.6 mmol) and stirring continued at RT for overnight. The reaction mixture was diluted with CH$_2$Cl$_2$ (20 mL) and sequentially washed with water, satd. NaHCO$_3$, brine and dried over MgSO$_4$. The solvent was removed under reduced pressure to yield a crude product, which was purified by column chromatography to obtain pure compound 38f. (90.8%). $^1$H NMR (CDCl$_3$) δ 8.28 (d, 1H, J=1.5 Hz), 7.69 (d, 1H, J=1.5 Hz), 7.64 (d, 2H, J=7.0 Hz), 7.44 (t, 2H, J=7.0 Hz), 7.35-7.32 (m, 1H), 6.78 (d, 1H, J=4.0 Hz), 3.86 (s, 3H), 3.41 (s, 3H); MS (ESI) m/z 270.0 (M+Na)$^+$.

(5-Phenylthiophen-3-yl)(3,4,5-trimethoxyphenyl)methanol (40f). At −78° C., to a solution of 38f (2.5 mmol) in 5 mL THF under argon protection was added a solution of LiAlH$_4$ in THF (1 N, 1.42 mL) and stirring continued at 1 h at −20° C. The reaction mixture was placed on an ice bath and quenched by 20% H$_2$SO$_4$ solution, extracted with ethyl acetate and dried over MgSO$_4$. The solvent was removed under reduced pressure and purified by column chromatography to yield 5-phenylthiophene-3-carbaldehyde (not shown) (84.8%). $^1$H NMR (CDCl$_3$) δ 9.98 (s, 1H), 8.04 (d, 1H, J=1.5 Hz), 7.86 (br, 1H), 7.61-7.58 (br, 2H), 7.47-7.33 (m, 3H), 7.35-7.32 (m, 1H), 6.78 (d, 1H, J=4.0 Hz); MS (ESI) m/z 210.9 (M+Na)$^+$. To a solution of 5-phenylthiophene-3-carbaldehyde (0.195 g, 1.04 mmoL) in 5 mL THF was added a THF solution of 3,4,5-trimethoxyphenylmagnesiumbromide (0.5 N, 2.3 mL, 1.14 mmol) at 0° C. The mixture was allowed to stir for 30 min and quenched with satd. NH$_4$Cl, extracted with ethyl ether, dried with MgSO$_4$. The solvent was removed under reduced pressure to yield a crude product, which was purified by column chromatography to obtain pure compound 40f. (70.5%). $^1$H NMR (CDCl$_3$) δ 7.55-7.52 (m, 2H), 7.40-7.35 (m, 3H), 7.30 (br, 1H), 7.20 (br, 1 H), 6.72 (s, 2H), 6.01 (d, 1H, J=3.9 Hz), 3.86 (s, 6H), 3.85 (s, 3H), 2.42 (d, 1H, J=3.9 Hz); MS (ESI) m/z 339.1 (M−OH)$^−$.

(5-Phenylthiophen-3-yl)(3,4,5-trimethoxyphenyl)methanone (1f). To a solution of 40f (0.260 g, 0.73 mmoL) in 20 mL anhydrous CH$_2$Cl$_2$ was added Dess-Martin reagent (0.465 g, 1.36 mmol). The mixture was allowed to stir for 30 min and quenched with sat. Na$_2$S$_2$O$_3$ solution, extracted with ethyl acetate and dried with MgSO$_4$. The solvent was removed under reduced pressure to yield a crude product, which was purified by column chromatography to give pure compound if as light yellow crystals (60.9%). $^1$H NMR (CDCl$_3$) δ 7.97 (d, 1H, J=1.5 Hz), 7.82 (d, 1H, J=1.5 Hz), 7.59-7.57 (m, 2H), 7.45-7.34 (m, 3H), 7.19 (s, 2H), 3.95 (s, 3H), 3.93 (s, 6H); MS (ESI) m/z 355.1 (M+H)$^+$.

Piperidine B Ring

Synthesis of (4-Phenylpiperidin-1-yl)(3,4,5-trimethoxyphenyl)methanone (1g) (FIG. 2)

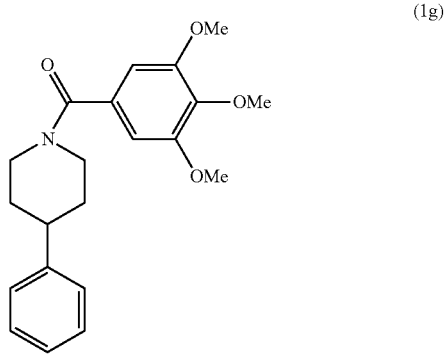 [SMILES: COc1cc(C(=O)N2CCC(c3ccccc3)CC2)cc(OC)c1OC]

(1g)

(4-Phenylpiperidin-1-yl)(3,4,5-trimethoxyphenyl)methanone (1g). To a mixture of 4-phenylpiperidine 41g (5 mmol), EDCI (6 mmol), HOBt (5.5 mmol) and NMM (6 mmol) in CH$_2$Cl$_2$ (50 mL) was added 3,4,5-trimethoxybenzoic acid (5.3 mmol) and stirring continued at RT for overnight. The reaction mixture was diluted with CH$_2$Cl$_2$ (100 mL) and sequentially washed with water, satd. NaHCO$_3$, brine and dried over MgSO$_4$. The solvent was removed under reduced pressure to yield a crude product, which was purified by column chromatography to obtain pure compound 1g. (57.9%). $^1$H NMR (CDCl$_3$) δ 7.35-7.21 (m, 5H), 6.66 (s, 2H), 4.84 (br, 1H), 3.95 (br, 1H), 3.88 (s, 6H), 3.86 (s, 3H), 3.20-2.87 (br, 2H), 2.85-2.74 (tt, 1H, J=3.6 Hz, J=15.6 Hz) 1.92 (br, 2H), 1.70 (br, 2H); MS (ESI) m/z 378.1 (M+Na)$^+$.

Isoxazole B Ring

Synthesis of (5-Phenylisoxazol-3-yl)(3,4,5-trimethoxyphenyl)methanone (1i) (FIG. 2)

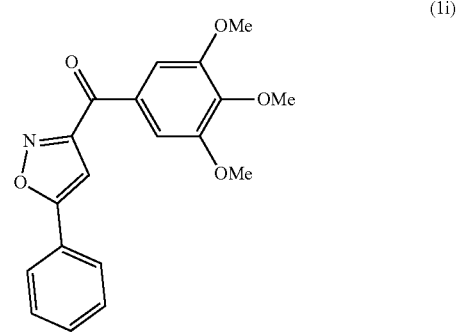 [SMILES: COc1cc(C(=O)c2cc(-c3ccccc3)on2)cc(OC)c1OC]

(1i)

(5-Phenylisoxazol-3-yl)(3,4,5-trimethoxyphenyl)methanol (40i). To a solution of 5-phenylisoxazole-3-carbaldehyde 38i (0.365 g, 2.1 mmol) in 15 mL THF was added a THF solution of 3,4,5-trimethoxyphenylmagnesiumbromide (0.5 N, 5.5 mL, 2.74 mmol) at 0° C. The mixture was allowed to stir for 30 min and quenched with satd. NH$_4$Cl, extracted with ethyl ether, dried with MgSO$_4$. The solvent was removed under reduced pressure to yield a crude product, which was purified by column chromatography to obtain pure compound 40i as a white solid. (48.8%). $^1$H NMR (CDCl$_3$) δ 7.78-7.77 (m, 2H), 7.48-7.46 (m, 3H), 6.74 (s, 2H), 6.45 (s, 1H), 5.98 (d, 1H, J=3.5 Hz) 3.89 (s, 6H), 3.86 (s, 3H), 2.77 (d, 1H, J=3.5 Hz); MS (ESI) m/z 364.1 (M+Na)$^+$.

(5-Phenylisoxazol-3-yl)(3,4,5-trimethoxyphenyl)methanone (1i). To a solution of 40i (0.110 g, 0.73 mmoL) in 8 mL anhydrous CH$_2$Cl$_2$ was added Dess-Martin reagent (0.274 g, 0.645 mmol). The mixture was allowed to stir for 30 min and quenched with sat. Na$_2$S$_2$O$_3$ solution, extracted with ethyl acetate and dried with MgSO$_4$. The solvent was removed under reduced pressure to yield a crude product, which was purified by column chromatography to give pure compound 1i (70.1%). $^1$H NMR (CDCl$_3$) δ 7.87-7.85 (m, 2H), 7.72 (s, 2H), 7.53-7.49 (m, 3H), 7.05 (s, 1H), 7.82 (d, 1H, J=1.5 Hz), 3.97 (s, 3H), 3.96 (s, 6H); MS (ESI) m/z 362.1 (M+H)$^+$.

Pyrazole B Ring

Synthesis of (3-Phenyl-1H-pyrazol-5-yl)(3,4,5-trimethoxyphenyl)methanone (1k) (FIG. 2)

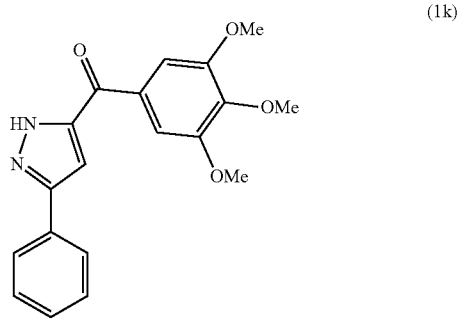 [SMILES: COc1cc(C(=O)c2cc(-c3ccccc3)n[nH]2)cc(OC)c1OC]

(1k)

(3-Phenyl-1H-pyrazol-5-yl)(3,4,5-trimethoxyphenyl) methanone (1k) was prepared using the same method as used of compound 1c from 3-phenyl-1H-pyrazole-5-carboxylic acid. $^1$H NMR (500 MHz, CDCl$_3$□□δ 10.97 (br, 1H), 7.77 (s, br, 2H), 7.48-7.38 (m, 5H), 7.14 (s, br, 1H), 3.96 (s, 3H), 3.94 (s, 6H); MS (ESI) m/z 361.1(M+Na)$^+$, 337.0 (M−H)$^−$.

Example 2

Synthesis of Compounds of this Invention Having Different Y Linkers

The compounds of this invention possess different Y linkers. Such compounds, with different Y linkers, were synthesized according to FIGS. 3 and 4.

Compound 1h was synthesized from 2-phenyl-4,5-dihydro-thiazole-4-carboxylic acid 42a through three steps described before (Lu, Y.; Wang, Z.; Li, C. M.; Chen, J.; Dalton, J. T.; Li, W.; Miller, D. D., Synthesis, in vitro structure-activity relationship, and in vivo studies of 2-arylthiazolidine-4-carboxylic acid amides as anticancer agents. *Bioorg Med Chem* 2010, 18, (2), 477-95 which is incorporated herein by reference in its entirely). 1h was converted to oxime isomers 2e-cis,trans and 2f-cis,trans upon reaction with hydroxylamines, NH$_2$OH or NH$_2$OCH$_3$. Assignments were made on the basis of chemical and spectral data as described infra. An improved Beckmann rearrangement readily produced the rearranged amides 2g and 2h from the two geometric stereoisomers 2e-cis and 2e-trans via their reaction with tosyl chloride and subsequent basic aluminum oxide column. Hydrazide derivatives 2d-cis and 2d-trans were prepared by mixing 1 h with hydrazine hydrate in ethanol and refluxing for 24 h. Acrylonitriles 2c-trans,cis were obtained from Wittig reaction of 1 h with diethyl cyanomethylphosphonate. Cyanoimine 2j was prepared using the procedure as by described by Cuccia (Cuccia, S. J.; Fleming, L. B.; France, D. J., A novel and efficient synthesis of 4-phenyl-2-chloropyrimidines from acetophenone cyanoimines. Synthetic Communications 2002, 32, (19), 3011-3018., incorporated herein by reference in its entirely). The carbonyl group in compound 1h was also reduced to a secondary alcohol 2b or converted to an alkene (2a) as illustrated in FIG. 3.

Figure 4:
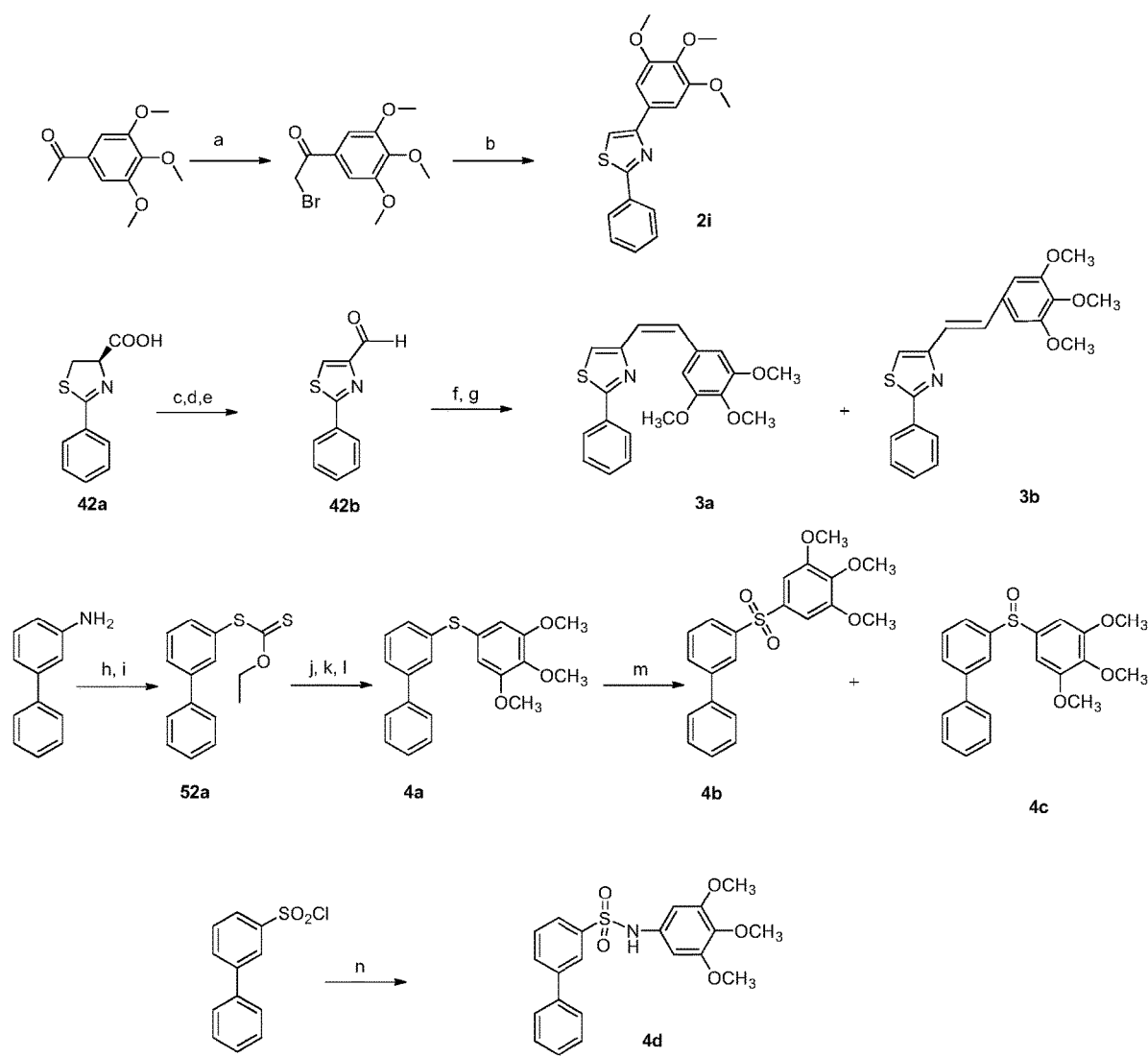
FIG. 4 depicts the synthetic scheme of compounds of this invention. Reagents and conditions: (a) bromine, EtOH; (b) benzothioamide, EtOH, reflux; (c) EDCI, HOBt, NMM, HNCH$_3$OCH$_3$, CH$_2$Cl$_2$; (d) CBrCl$_3$, DBU, CH$_2$Cl$_2$; (e) LAH, THF; (f) 5-(bromomethyl)-1,2,3-trimethoxybenzene, Ph$_3$P, THF; (g) n-BuLi, THF; (h) (1) HCl, H$_2$O; (2) NaNO$_2$, H$_2$O, 0° C.; (i) ethyl potassium xanthate; (j) KOH/EtOH; (k) H$_2$O, HCl; (l) 5-iodo-1,2,3-trimethoxybenzene, CuI, t-BuONa; (m) 2 equiv or 1 equiv m-CPBA, CH$_2$Cl$_2$; (n) 3,4,5-trimethoxyaniline, NEt$_3$, DMF.

Attempts to remove the carbonyl group between B and C rings in 1h, resulted in the formation of compound 2i as shown in FIG. 4. Introducing cis- and trans-double bonds into the carbonyl position formed compounds (3a and 3b), which were synthesized from a Wittig reaction with 2-phenylthiazole-4-carbaldehyde. The sulfide compound 4a, sulfone 4b and sulfoxide 4c were prepared using 3-aminobiphenyl as starting material through an initial Sandmeyer reaction to yield carbonodithioate 52a, followed by CuI catalyzed coupling reaction and m-CPBA oxidation. Sulfonamide linked compound 4d was prepared from reaction of 3-biphenylsulfonyl chloride with 3,4,5-trimethoxyaniline in the presence of NEt$_3$ in DMF.

Figure 3:
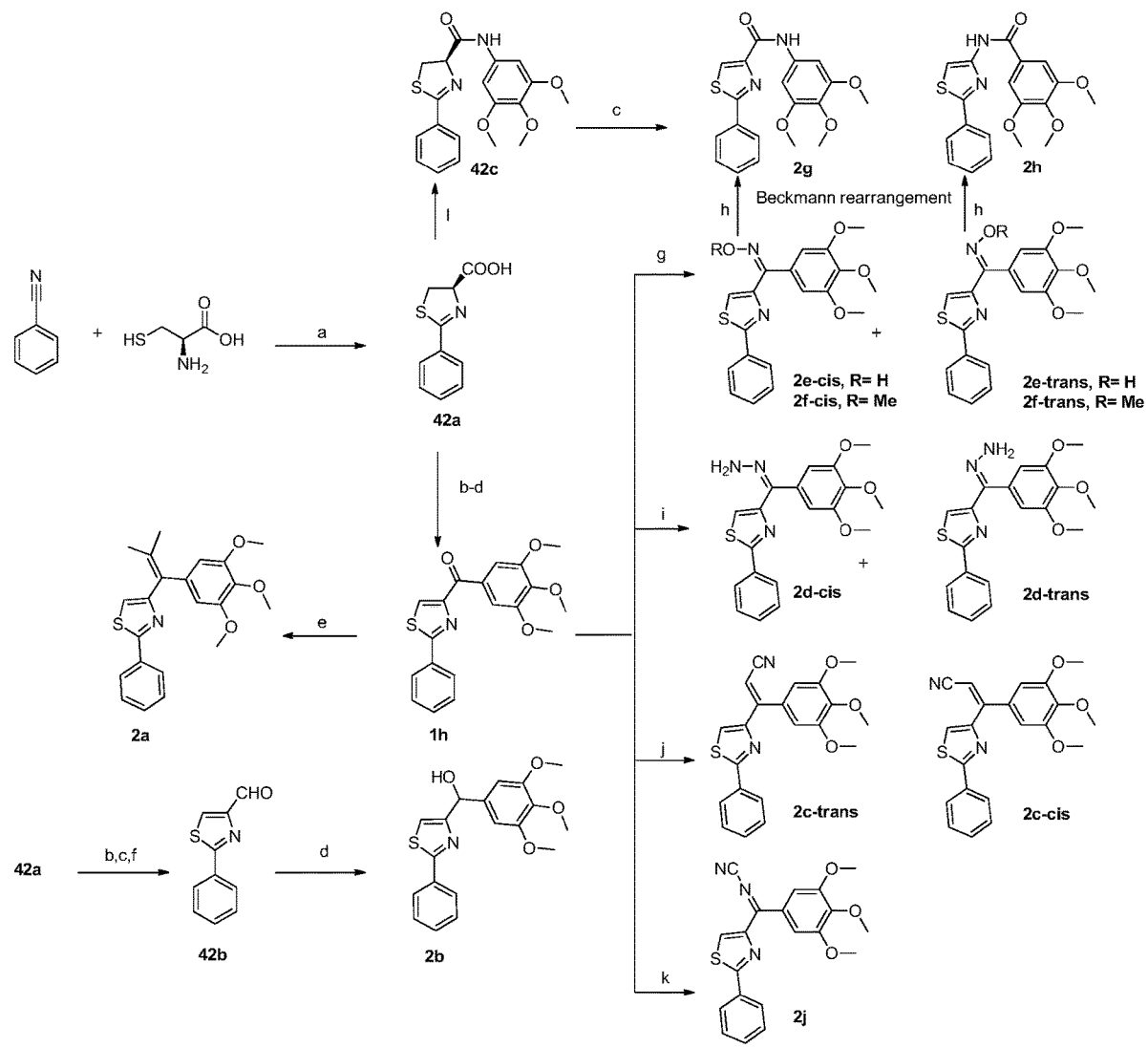
FIG. 3 depicts the synthetic scheme of compounds of this invention. Reagents and conditions: (a) MeOH/pH=6.4 phosphate buffer, RT; (b) EDCI, HOBt, NMM, HNCH$_3$OCH$_3$; (c) CBrCl$_3$, DBU, CH$_2$Cl$_2$; (d) 3,4,5-trimethoxyphenylmagnesium bromide, THF; (e) isopropyl triphenylphosphonium iodide, n-BuLi, THF; (f) LAH, THF; (g) For 2e-cis and 2e-trans, NH$_2$OH·HCl, C$_2$H$_5$OH, H$_2$O, NaOH; For 2g and 2h, NH$_2$OMe·HCl, pyridine; (h) TsCl, NaH, basic Al$_2$O$_3$; (i) NH$_2$NH$_2$·xH$_2$O, CH$_2$Cl$_2$, t-BuOH; (j) diethyl cyanomethylphosphonate, n-BuLi, THF; (k) bis-trimethylsilylcarbodiimide, TiCl$_4$, CH$_2$Cl$_2$; (l) EDCI, HOBt, Et$_3$N, 3,4,5-trimethoxyaniline, CH$_2$Cl$_2$.

Synthesis of (2-Phenyl-thiazol-4-yl)-(3,4,5-trimethoxy-phenyl)-methanone (1h) [FIG. 3]

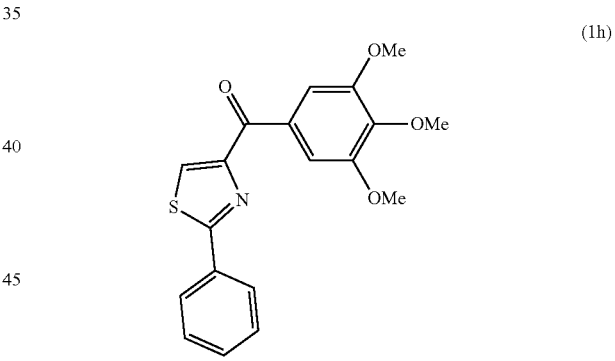

(1h)

(2-Phenyl-thiazol-4-yl)-(3,4,5-trimethoxy-phenyl)-methanone (1h). A mixture of 2-phenyl-4,5-dihydrothiazole-4-carboxylic acid (5 mmol), EDCI (6 mmol) and HOBt (5 mmol) in CH$_2$Cl$_2$ (50 mL) was stirred for 10 min. To this solution, NMM (5 mmol) and HNCH$_3$OCH$_3$ (5 mmol) were added and stirring continued at RT for 6-8 h. The reaction mixture was diluted with CH$_2$Cl$_2$ (100 mL) and sequentially washed with water, satd. NaHCO$_3$, brine and dried over MgSO$_4$. The solvent was removed under reduced pressure to yield a crude product, which was purified by column chromatography to get 2-phenyl-4,5-dihydrothiazole-4-carboxylic acid methoxymethylamide. A solution of 2-phenyl-4,5-dihydrothiazole-4-carboxylic acid methoxymethylamide (1 equiv) in CH$_2$Cl$_2$ was cooled to 0° C., and distilled DBU (2 equiv) was added. Bromotrichloromethane (1.7 equiv) was then introduced dropwise via syringe over 10 min. The reaction mixtures were allowed to warm to RT and stirred overnight. Upon washing with satd. aqueous NH$_4$Cl (2×50 mL), the aqueous phase was extracted with EtOAc (3×50 mL). The combined organic layers were dried on MgSO$_4$, filtered and concentrated in vacuo. The residue was purified by flash chromatography as needed providing 2-phenyl-thiazole-4-carboxylic acid methoxymethylamide (73.6%). $^1$H NMR (300 MHz, CDCl$_3$) δ 8.01 (s, 1H), 7.99-7.96 (m, 2H), 7.47-7.44 (m, 3H), 3.88 (s, 3H), 3.49 (s, 3H). MS (ESI) m/z 271.0 (M+Na)$^+$. To a solution of 3,4,5-trimethoxyphenylmagnesium bromide (0.5 N, 3 mL) in 2 mL THF was charged a solution of 2-phenyl-thiazole-4-carboxylic acid methoxymethylamide (1 mmol) in 3 mL THF at 0° C. The mixtures were stirred for 30 min until amides disappeared on TLC plates. The reaction mixture was quenched with satd. NH$_4$Cl, extracted with ethyl ether, dried with MgSO$_4$. The solvent was removed under reduced pressure to yield a crude product, which was purified by column chromatography to obtain pure compound 1h. Yield: 27.3%. $^1$H NMR (300 MHz, CDCl$_3$) δ 8.29 (s, 1H), 8.03 (q, 2H), 7.80 (s, 2H), 7.49-7.47 (m, 3H), 3.96 (s, 6H), 3.97 (s, 3H). MS (ESI) m/z 378.1 (M+Na)$^+$.

Synthesis of 4-(2-Methyl-1-(3,4,5-trimethoxyphenyl)prop-1-enyl)-2-phenylthiazole (2a) [FIG. 3]

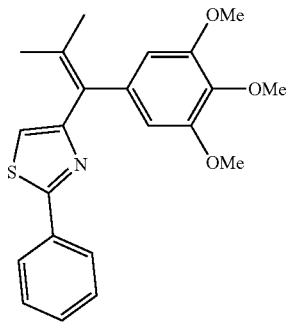

(2a)

4-(2-Methyl-1-(3,4,5-trimethoxyphenyl)prop-1-enyl)-2-phenylthiazole (2a) [FIG. 3]. At −78° C., to a solution of 223 mg isopropyl triphenylphosphonium iodide (0.52 mmol) in 5 mL of THF was added dropwise 0.4 mL of 1.6 N n-BuLi in hexane under Ar$_2$ protection. And the mixture was stirred at 0° C. for 40 min. A solution of 140 mg (0.39 mmol) of 1h in 5 mL of THF was added dropwise at 0° C., and the mixture was stirred for 1 h at RT. The reaction mixture was treated with saturated NH$_4$Cl solution. After a conventional workup, column chromatography (silica gel, petroleum ether/ethyl acetate) gave compound 2a (86 mg, 57.3%). $^1$H NMR (300 MHz, CDCl$_3$) δ 7.98-7.97 (m, 2H), 7.45-7.40 (m, 3H), 6.77 (s, 1H), 6.48 (s, 2H), 3.86 (s, 3H), 3.82 (s, 6H), 2.15 (s, 3H), 1.81 (s, 3H). MS (ESI) m/z 404.1 (M+Na)$^+$.

Synthesis of (2-Phenylthiazol-4-yl)(3,4,5-trimethoxyphenyl)methanol (2b)[FIG. 3]

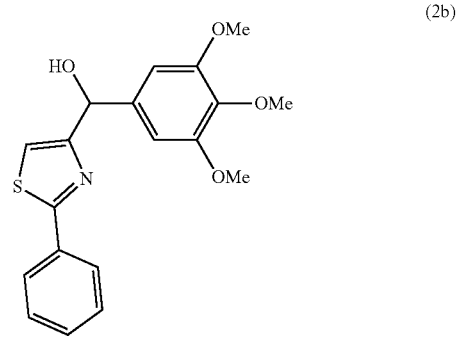 [SMILES: COc1cc(C(O)c2csc(-c3ccccc3)n2)cc(OC)c1OC]

(2b)

2-Phenyl-4,5-dihydrothiazole-4-carboxylic acid (42a). Benzonitrile (40 mmol) was combined with L-cysteine (45 mmol) in 100 mL of 1:1 MeOH/pH 6.4 phosphate buffer solution. The reaction was stirred at 40° C. for 3 days. The precipitate was removed by filtration, and MeOH was removed using rotary evaporation. To the remaining solution was added 1M HCl to adjust to pH=2 under 0° C. The resulting precipitate was filtered to yield a white solid 2-phenyl-4,5-dihydrothiazole-4-carboxylic acid 42a, which was used directly to next step without purification.

2-Phenylthiazole-4-carbaldehyde (42b). At −78° C., to a solution of 2-phenyl-thiazole-4-carboxylic acid methoxymethylamide (1equiv) in THF was added LiAlH$_4$ (1 equiv, 1 N in THF) and stirring for 1 h at −20° C. The reaction mixture was placed on an ice bath and quenched by 20% H$_2$SO$_4$ solution, extracted with ethyl acetate and dried over MgSO$_4$. The solvent was removed under reduced pressure and purified by column chromatography to yield 42b (45.8%). $^1$H NMR (300 MHz, CDCl$_3$) δ 10.1 (s, 1H), 8.17 (s, 1H), 8.02-8.00 (m, 2H), 7.50-7.48 (m, 3H). MS (ESI) n/z 244.1 (M+Na+MeOH)$^+$.

(2-Phenylthiazol-4-yl)(3,4,5-trimethoxyphenyl)methanol (2b) [FIG. 3]. At 0° C., to a solution of 104 mg of 42b (0.55 mmol, 1 eq.) in 6 mL THF was added 3,4,5-trimethoxyphenylmagnesium bromide (0.5 N in THF, 2.9 mL). The mixtures were stirred for 30 min until aldehyde disappeared on TLC plates. The reaction mixture was quenched with satd. NH$_4$Cl, extracted with ethyl ether, dried with MgSO$_4$. The solvent was removed under reduced pressure to yield a crude product, which was purified by column chromatography to obtain pure compound (2b). $^1$H NMR (300 MHz, CDCl$_3$) δ 7.95-7.92 (m, 2H), 7.44-7.43 (m, 4H), 6.97 (s, 1H), 6.76 (s, 2H), 5.93 (d, 1H, J=3.6 Hz), 3.86 (s, 9H). MS (ESI) m/z 402.1 (M+Na)$^+$.

Synthesis of (Z)-3-(2-phenylthiazol-4-yl)-3-(3,4,5-trimethoxyphenyl)acrylonitrile (2c-trans) and (E)-3-(2-phenylthiazol-4-yl)-3-(3,4,5-trimethoxyphenyl)acrylonitrile (2c-cis) [FIG. 3]

Synthesis of (Z)-4-(hydrazono(3,4,5-trimethoxyphenyl)methyl)-2-phenylthiazole (2d-cis) and (E)-4-(hydrazono(3,4,5-trimethoxyphenyl)methyl)-2-phenylthiazole (2d-trans) [FIG. 3]

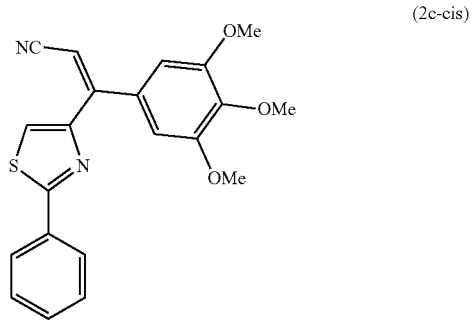
(2c-cis)

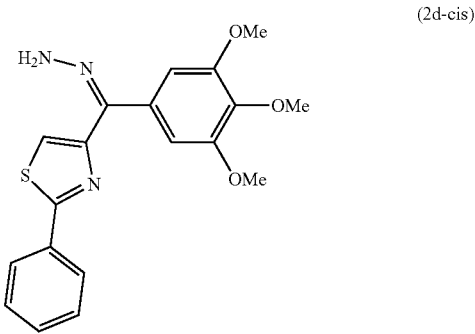
(2d-cis)

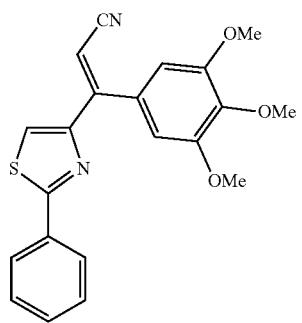
(2c-trans)

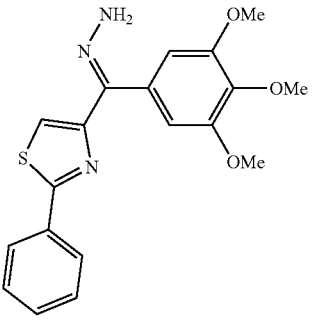
(2d-trans)

(Z)-3-(2-phenylthiazol-4-yl)-3-(3,4,5-trimethoxyphenyl)acrylonitrile (2c-trans). To a solution of 0.4 mL of 2.5 N n-BuLi in hexane and 10 mL of THF was added dropwise a solution of 177 mg (1 mmol) of diethyl cyanomethylphosphonate in 5 mL of THF at 0° C. under $Ar_2$. The ice bath was removed, and the mixture was stirred at 25° C. for 40 min. A solution of 200 mg (0.56 mmol) of 1h in 10 mL of THF was added dropwise at 0° C., and the mixture was stirred for 1 h at RT. The reaction mixture was treated with saturated $NH_4Cl$ solution. After a conventional workup, column chromatography (silica gel, petroleum ether/ethyl acetate) gave compounds 2c-trans (83 mg) and 2c-cis (76 mg). $^1$H NMR (300 MHz, $CDCl_3$) δ 8.01-7.99 (m, 2H), 7.44-7.40 (m, 3H), 7.21 (s, 1H), 6.74 (s, 2H), 6.67 (s, 1H), 3.93 (s, 3H), 3.89 (s, 6H). MS (ESI) m/z 401.1 (M+Na)$^+$.

(E)-3-(2-phenylthiazol-4-yl)-3-(3,4,5-trimethoxyphenyl)acrylonitrile (2c-cis). $^1$H NMR (300 MHz, $CDCl_3$) δ 8.07-8.05 (m, 2H), 7.49-7.46 (m, 4H), 6.66 (s, 2H), 5.64 (s, 1H), 3.91 (s, 3H), 3.86 (s, 6H). MS (ESI) m/z 401.1 (M+Na)$^+$.

(Z)-4-(hydrazono(3,4,5-trimethoxyphenyl)methyl)-2-phenylthiazole (2d-cis). To a mixture of 1h (230 mg, 0.65 mmol) in 3 mL $CH_2Cl_2$ and 3 mL ethanol was added hydrazine hydrate (2 mL). Then the mixture was refluxed for overnight. After completion of the reaction, the residue was absorbed on silica gel and purified by column chromatography to give compounds 2d-cis (80 mg) and 2d-trans (56 mg). $^1$H NMR (300 MHz, $CDCl_3$) δ 8.01-7.98 (m, 2H), 7.49-7.46 (m, 5H), 7.33 (s, 1H), 6.82 (s, 2H), 3.87 (s, 3H), 3.85 (s, 6H). MS (ESI) m/z 370.1 (M+H)$^+$.

(E)-4-(hydrazono(3,4,5-trimethoxyphenyl)methyl)-2-phenylthiazole (2d-trans). $^1$H NMR (300 MHz, $CDCl_3$) δ 8.04-8.01 (m, 2H), 7.44-7.40 (m, 3H), 6.95 (s, 1H), 6.65 (s, 2H), 5.62 (s, 2H), 3.93 (s, 3H), 3.87 (s, 6H). MS (ESI) m/z 370.1 (M+H)$^+$.

Synthesis of (Z)-(2-Phenylthiazol-4-yl)(3,4,5-trimethoxyphenyl)methanone oxime (2e-cis) and (E)-(2-Phenylthiazol-4-yl)(3,4,5-trimethoxyphenyl)methanone oxime (2e-trans) [FIG. 3]

Synthesis of (Z)-(2-Phenylthiazol-4-yl)(3,4,5-trimethoxyphenyl)methanone O-methyl oxime (2f-cis) and (E)-(2-Phenylthiazol-4-yl)(3,4,5-trimethoxyphenyl)methanone O-methyl oxime (2f-trans) [FIG. 3]

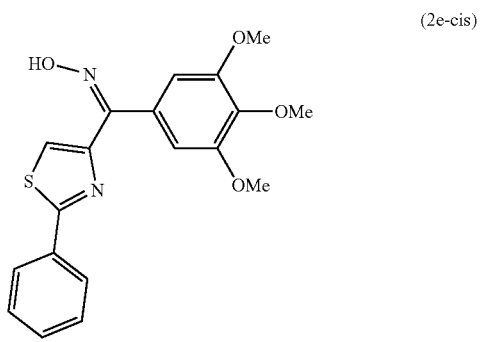
(2e-cis)

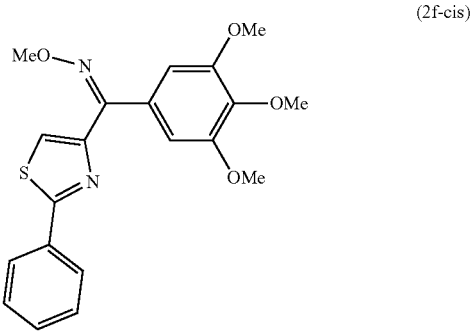
(2f-cis)

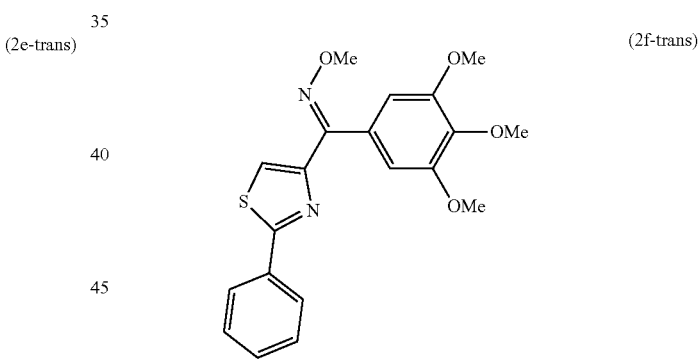
(2e-trans)

(2f-trans)

(Z)-(2-Phenylthiazol-4-yl)(3,4,5-trimethoxyphenyl)methanone oxime (2e-cis) To a suspension of 1h (210 mg, 0.59 mmol) in 10 mL ethanol was added an aqueous solution (2 mL) of hydroxylamine hydrochloride (127 mg, 1.83 mmol). Then 2 mL 1 N NaOH was added dropwise to the reaction mixture and the mixture was stirred at 55° C. for 3 h. After completion of the reaction, the residue was absorbed on silica gel and purified by column chromatography to give compounds 2e-cis (85 mg) and 2e-trans (50 mg). $^1$H NMR (300 MHz, DMSO-$d_6$) δ 11.95 (s, 1H), 8.35 (s, 1H), 7.91-7.89 (m, 2H), 7.50-7.44 (br, 3H), 6.85 (s, 2H), 3.73 (s, 6H), 3.70 (s, 3H). MS (ESI) m/z 393.1 (M+Na)$^+$; 368.9 (M–H)$^-$.

(E)-(2-Phenylthiazol-4-yl)(3,4,5-trimethoxyphenyl) methanone oxime 2e-trans). $^1$H NMR (300 MHz, DMSO-$d_6$) δ 11.49 (s, 1H), 7.92-7.89 (m, 2H), 7.64 (s, 1H), 7.51-7.49 (m, 3H), 7.34 (s, 1H), 6.75 (s, 2H), 3.75 (s, 6H), 3.72 (s, 3H). MS (ESI) m/z 393.1 (M+Na)$^+$; 368.9 (M–H)—.

(Z)-(2-Phenylthiazol-4-yl)(3,4,5-trimethoxyphenyl) methanone O-methyl oxime (2f-cis). To a suspension of 1h (110 mg, 0.59 mmol) in 10 mL pyridine was added O—methylhydroxylamine hydrochloride (52 mg, 0.63 mmol) and the mixture was stirred at 60° C. for overnight. The reaction was quenched with 1 N HCl solution, extracted with ethyl acetate and dried with MgSO$_4$. The solvent was removed under reduced pressure to yield a crude product, which was purified by column chromatography to give pure compounds 2f-cis (41 mg) and 2f-trans (33 mg). $^1$H NMR (500 MHz, CDCl$_3$) δ 8.13 (s, 1H), 7.96-7.94 (m, 2H), 7.45-7.44 (m, 3H), 6.94 (s, 2H), 4.13 (s, 3H), 3.91 (s, 6H), 3.88 (s, 3H). MS (ESI) m/z 407.2 (M+Na)$^+$.

(E)-(2-Phenylthiazol-4-yl)(3,4,5-trimethoxyphenyl) methanone O-methyl oxime (2f-trans). $^1$H NMR (500 MHz, CDCl$_3$) δ 8.00-7.98 (m, 2H), 7.44-7.43 (m, 3H), 7.28 (s, 1H), 6.70 (s, 2H), 4.08 (s, 3H), 3.91 (s, 6H), 3.85 (s, 3H). MS (ESI) m/z 407.0 (M+Na)$^+$.

Synthesis of 2-Phenyl-N-(3,4,5-trimethoxyphenyl)thiazole-4-carboxamide (2g) [FIG. 3]

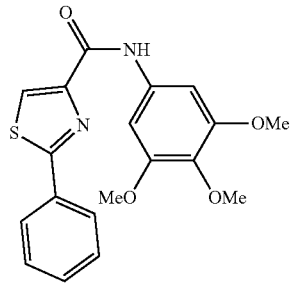

(2g)

2-Phenyl-N-(3,4,5-trimethoxyphenyl)thiazole-4-carboxamide (2g). To a solution of 2e-cis (21 mg, 0.06 mmol) in 5 mL CH$_2$Cl$_2$ was added p-toluenesulfonyl chloride (23 mg, 0.12 mmol) and NaH (5 mg, 60% in light mineral oil). Then the reaction mixture was stirred for 20 min. After completion of the reaction, the residue was absorbed on silica gel and purified by Al$_2$O$_3$ column chromatography to give compound 2g (15 mg). $^1$H NMR (300 MHz, CDCl$_3$) δ 9.22 (s, 1H), 8.19 (s, 1H), 8.02-7.99 (m, 2H), 7.52-7.50 (m, 3H), 7.07 (s, 2H), 3.92 (s, 6H), 3.85 (s, 3H). MS (ESI) m/z 371.1 (M+H)$^+$.

Synthesis of 3,4,5-Trimethoxy-N-(2-phenylthiazol-4-yl)benzamide (2h) [FIG. 3]

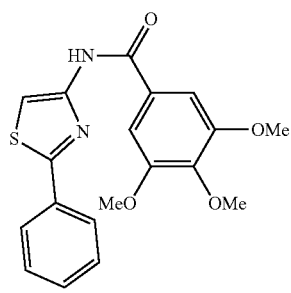

(2h)

3,4,5-Trimethoxy-N-(2-phenylthiazol-4-yl)benzamide (2h). To a solution of 2e-trans (26 mg, 0.07 mmol) in 5 mL CH$_2$Cl$_2$ was added p-toluenesulfonyl chloride (27 mg, 0.14 mmol) and NaH (5 mg, 60% in light mineral oil). Then the reaction mixture was stirred for 20 min. After completion of the reaction, the residue was absorbed on silica gel and purified by Al$_2$O$_3$ column chromatography to give compound 2h (15 mg). $^1$H NMR (300 MHz, CDCl$_3$) δ 8.88 (s, 1H), 7.94-7.91 (m, 2H), 7.83 (s, 1H), 7.48-7.46 (m, 3H), 7.18 (s, 2H), 3.97 (s, 6H), 3.94 (s, 3H). MS (ESI) m/z 393.1 (M+Na)$^+$.

Synthesis of N-((2-phenylthiazol-4-yl)(3,4,5-trimethoxyphenyl)methylene)cyanamide (2j) [FIG. 3]

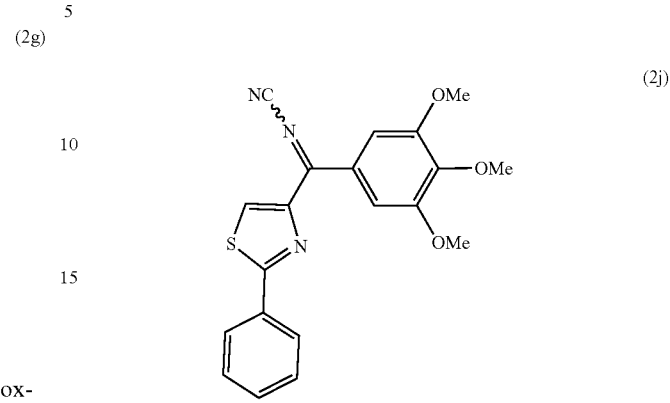

(2j)

N-((2-phenylthiazol-4-yl)(3,4,5-trimethoxyphenyl)methylene)cyanamide (2j). 100 mg of 1h (0.28 mmol, 1 eq.) was dissolved in 10 mL methylene chloride. Titanium tetrachloride in methylene chloride (1.0 N, 0.7 mL, 2.5 eq.) was added dropwise at 0° C. and stirred for 30 min. Bis-trimethylsilylcarbodiimide (2.4 eq.) in 2 mL methylene chloride was added and the reaction stirred overnight protected from air and moisture. The reaction was treated with ice-water mixture followed by extraction with methylene chloride. The organic phase was dried over magnesium sulfate, filtered through celite and concentrated to give the crude acetophenone cyanoimines which were purified by flash column as isomers with a ratio of 3:7. $^1$H NMR (300 MHz, CDCl$_3$) δ 8.72 (br, 0.3H), 8.63 (s, 0.7H), 8.09-8.07 (m, 1.4H), 7.99 (br, 0.6H), 7.58-7.56 (br, 3H), 7.26 (s, 1.4H), 7.18 (s, 0.6H), 3.84, 3.83 (s, s, 6H), 3.82 (s, 3H). MS (ESI) m/z 402.1 (M+Na)$^+$.

Synthesis of N-((4-hydroxy-3,5-dimethoxyphenyl)(2-phenylthiazol-4-yl)methylene)cyanamide (32)

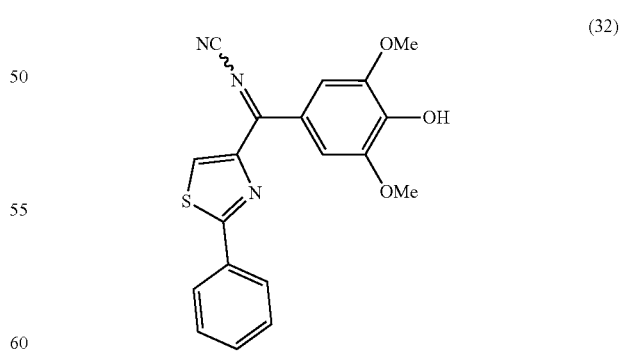

(32)

N-((4-hydroxy-3,5-dimethoxyphenyl)(2-phenylthiazol-4-yl)methylene)cyanamide (32) was obtained as a by-product from synthesis of 2j. $^1$H NMR (500 MHz, CDCl$_3$) δ 8.23 (s, 1H), 8.02 (m, 2H), 7.92 (s, 2H), 7.55 (m, 3H), 6.02 (s, 1H), 3.99 (s, 6H). MS (ESI) m/z 364.1(M+H)$^+$.

Synthesis of (Z)-2-Phenyl-4-(3,4,5-trimethoxystyryl)thiazole (3a) and (E)-2-Phenyl-4-(3,4,5-trimethoxystyryl)thiazole (3b) [FIG. 4]

Synthesis of Biphenyl-3-yl(3,4,5-trimethoxyphenyl)sulfane (4a), 3-(3,4,5-Trimethoxyphenylsulfonyl)biphenyl (4b) and 3-(3,4,5-Trimethoxyphenylsulfinyl)biphenyl (4c) [FIG. 4]

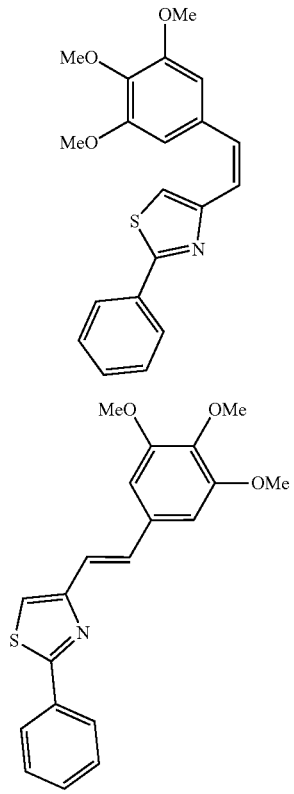

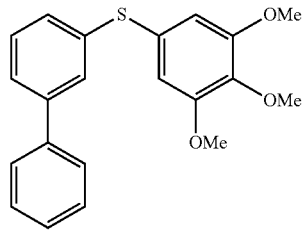

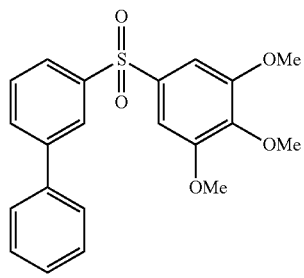

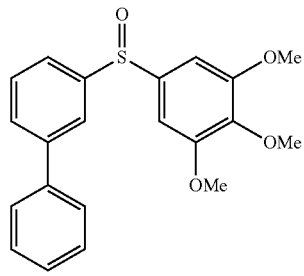

(Z)-2-Phenyl-4-(3,4,5-trimethoxystyryl)thiazole (3a). Triphenylphosphine (3.41 g, 13 mmol) was added to a solution of 5-(bromomethyl)-1,2,3-trimethoxybenzene (2.61 g, 10 mmol) in dry THF (30 mL). The mixture was refluxed with stirring for 6 h. The resulting white solid was filtered and washed with ether/hexane to afford the product 3,4,5-trimethoxybenzyltriphenylphosphonium bromide in 96.4% yield. $^1$H NMR (500 MHz, CDCl$_3$) δ 7.77-7.73, 7.65-7.61 (m, 15H), 6.44 (d, 2H, J=1.5 Hz), 5.37 (d, 2H, J=14 Hz), 3.76 (s, 3H), 3.51 (d, 6H); MS (ESI) m/z 443.1 (M−Br)$^+$. At −78° C., n-BuLi (0.42 mL, 2.5 N in hexane) was added to a solution of 3,4,5-trimethoxybenzyltriphenylphosphonium bromide (500 mg, 0.96 mmol) in 10 mL THF. After stirring at RT for 2 h, aldehyde 42b (109 mg, 0.58 mmol) in 3 mL THF was charged and stirred for 30 min. The reaction mixture was treated with saturated NH$_4$Cl solution. After a conventional workup, column chromatography (silica gel, petroleum ether/ethyl acetate) gave compounds 3a (57 mg) and 3b (99 mg). $^1$H NMR (500 MHz, CDCl$_3$) δ 7.90-7.89 (m, 2H), 7.42-7.40 (m, 3H), 7.07 (s, 1H), 6.71 (s, 2H), 6.66 (s, 1H), 3.87 (s, 6H), 3.75 (s, 3H); MS (ESI) m/z 376.1 (M+Na)$^+$.

(E)-2-Phenyl-4-(3,4,5-trimethoxystyryl)thiazole (3b). $^1$H NMR (500 MHz, CDCl$_3$) δ 8.03-8.01 (m, 2H), 7.52 (d, 1H, J=16 Hz), 7.47-7.44 (m, 3H), 7.16 (s, 1H), 7.05 (d, 1H, J=16 Hz), 6.79 (s, 2H), 3.92 (s, 6H), 3.88 (s, 3H). MS (ESI) m/z 354.1 (M+H)$^+$.

S-Biphenyl-3-yl O-ethyl carbonodithioate (52a). To a solution of 1 equiv. of biphenyl-3-amine (1 g, 5.92 mmol) in water (7.3 mL) at 0° C. was added concentrated hydrochloric acid (1 mL). A cold solution of 1.1 equiv. of sodium nitrite (450 mg, 6.5 mmol) in water (3 mL) was added slowly and stirred for 15 min. The cold diazonium solution was added slowly to a solution of 1.3 equiv. of potassium ethyl xanthate (1.16 g, 1.3 mmol) in water (1.3 mL) at 45° C. The reaction mixture was stirred for an additional 30 min at 45° C. and then cooled to RT. The reaction mixture was extracted with diethyl ether (3×50 mL). The combined organic extracts were washed with 1 N NaOH solution (100 mL), water (3×50 mL), brine (50 mL), dried over MgSO4, filtered and evaporated under reduced pressure. The resulting crude xanthate 52a was used directly in the next step without further purification. MS (ESI) m/z 275.0 (M+H)$^+$.

Biphenyl-3-yl(3,4,5-trimethoxyphenyl)sulfane (4a). To a solution of 52a (1.1 g, crude compound) in ethanol (8 mL) was added potassium hydroxide (2.1 g, 12 mL) and heated to reflux for overnight. The solution was cooled to RT and the ethanol was evaporated under reduced pressure. The residue was dissolved in water and washed with diethyl ether (10 mL). The aqueous layer was acidified with 2 N HCl and extracted with diethyl ether (3×50 mL). The organic extracts were washed with water (50 mL), brine (50 mL), dried over MgSO4, filtered and evaporated under reduced pressure to afford 0.85 g (77.3%) of crude biphenyl-3-thiol product (overall, 3 steps). Into a round-bottomed flask, stirred magnetically, were placed 0.1 g (1.04 mmol) of sodium tert-butoxide and 83 mg of copper iodide (0.43 mmol). After the reaction vessel was sealed, 0.13 g (0.71 mmol) of 4-methoxybenzenethiol and 0.19 g (0.65 mmol) of 5-iodo-1,2,3-trimethoxybenzene in 3.0 mL of toluene were injected through the septum. The reaction mixture was heated for overnight at 110° C. Purification was performed by flash chromatography, and an amorphous solid was obtained (40% yield). $^1$H NMR (500 MHz, CDCl$_3$) δ 7.54-7.52 (m, 3H), 7.44-7.41 (m, 3H), 7.37-7.33 (m, 2H), 7.23 (s, br, 1H), 6.69 (s, 2H), 3.86 (s, 3H), 3.80 (s, 6H). MS (ESI) m/z 353.2 (M+H)$^+$.

3-(3,4,5-Trimethoxyphenylsulfonyl)biphenyl (4b). To a solution of 60 mg (0.17 mmol) of compound 4a and 5 mL of dichloromethane was added very slowly 2 equiv. of m-CPBA over 3 h. Sulfoxide formation was monitored by thin-layer chromatography. Purification was performed with a flash chromatographic column, and an amorphous powder of (4b) was obtained (73% yield). 1H NMR (500 MHz, CDCl$_3$) δ 8.14 (br, 1H), 7.89 (d, 1H), 7.78 (d, 1H), 7.59-7.56 (m, 3H), 7.49-7.39 (m, 3H), 7.19 (s, 2H), 3.89 (s, 6H), 3.87 (s, 3H). MS (ESI) m/z 385.0 (M+Na)$^+$.

3-(3,4,5-Trimethoxyphenylsulfinyl)biphenyl (4c). At 0° C., to a solution of 500 mg (1.42 mmol) of compound (4a) and 5 mL of dichloromethane was added very slowly 1 equiv. of m-CPBA over 3 h. Sulfoxide formation was monitored by thin-layer chromatography. Purification was performed with a flash chromatographic column, and an amorphous powder of (4c) was obtained (87% yield). $^1$H NMR (500 MHz, CDCl$_3$) δ 7.92 (br, 1H), 7.71 (d, 2H), 7.62-7.60 (m, 3H), 7.58-7.40 (m, 4H), 6.94 (s, 2H), 3.79 (s, 3H), 3.74 (s, 6H). MS (ESI) m/z 369.1 (M+H)$^+$.

Synthesis of
N-(3,4,5-trimethoxyphenyl)biphenyl-3-sulfonamide
(4d) [FIG. 4]

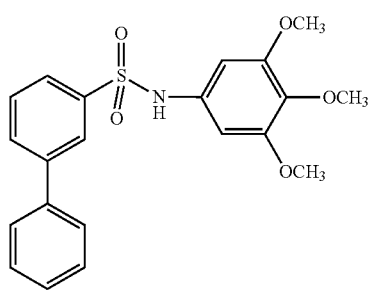 [SMILES: COc1cc(NS(=O)(=O)c2cccc(-c3ccccc3)c2)cc(OC)c1OC]

N-(3,4,5-Trimethoxyphenyl)biphenyl-3-sulfonamide (4d). A mixture of 65 mg of biphenyl-3-sulfonyl chloride (0.25 mmol), 44 mg of 3,4,5-trimethoxyaniline (0.24 mmol), and 0.3 mmol of triethylamine in 5 mL DMF was stirred overnight. The reaction mixture was treated with water and extracted with ethyl acetate. After a conventional workup, column chromatography (silica gel, petroleum ether/ethyl acetate) gave 88 mg compounds (4d) (91.7%). $^1$H NMR (500 MHz, CDCl$_3$) δ 7.96 (t, 1H, J=1.8 Hz), 7.81-7.74 (m, 2H), 7.57-7.40 (m, 6H), 6.33 (s, 2H), 3.86 (s, 3H), 3.80 (s, 6H). MS (ESI) m/z 422.1 (M+Na)$^+$.

2-Phenyl-4-(3,4,5-trimethoxyphenyl)thiazole (2i)
[FIG. 4]

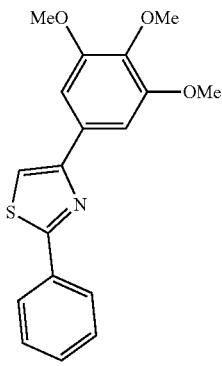 [SMILES: COc1cc(-c2csc(-c3ccccc3)n2)cc(OC)c1OC]

2-Phenyl-4-(3,4,5-trimethoxyphenyl)thiazole (2i). Bromine (160 mg, 1 mmol) was added dropwise to a stirred solution of an 1-(3,4,5-trimethoxyphenyl)ethanone (210 mg, 1 mmol) in ethanol (30 mL) and the solution was stirred at 0° C. for 1 h and then poured into water to form a precipitate. This was recrystallized from ethanol to give bromoacetophenone (70%) and used directly for next step. A mixture of bromoacetophenone (288 mg, 1 mmol) and benzothioamide (137 mg, 1 mmol) in ethanol was refluxed for 1 h. The reaction mixture was concentrated in vacuo and purified with flash column to give 2i (167 mg, 51.1%). $^1$H NMR (500 MHz, CDCl$_3$) δ 8.05-8.03 (m, 2H), 7.48-7.44 (m, 3H), 7.41 (s, 1H), 7.22 (s, 2H), 3.97 (s, 6H), 3.89 (s, 3H). MS (ESI) m/z 350.1 (M+Na)$^+$.

Example 3

Synthesis of Methoxy Benzoyl Thiazole
Compounds Having Different "A" Rings and/or
Substituted "A" Ring The compounds of this invention possess different substituted or unsubstituted A rings such as phenyl or indolyl. Such compounds were synthesized according to FIGS. 5 and 6.

Hydroxyl and aminomethyl were introduced at the para-position of the phenyl A-ring, as well as the phenyl was replaced with 5-indolyl and 2-indolyl rings. Weinreb amides 57a, 61a, 65a, and 67a were prepared by the procedure presented in FIG. 5 using aryl nitriles as starting materials. 2-Cyano-indole 60a was prepared according to a standard procedure (Pletnev, A. A.; Tian, Q.; Larock, R. C., Carbopalladation of nitriles: synthesis of 2,3-diarylindenones and polycyclic aromatic ketones by the Pd-catalyzed annulation of alkynes and bicyclic alkenes by 2-iodoarenenitriles. *J Org Chem* 2002, 67(26), 9276-87; incorporated herein by reference in its entirely). Protections of hydroxyl (TBDMSCl), indolyl (PhSO$_2$Cl) and amino (Boc$_2$O) groups were used in preparations. Deprotection of TBDMS and oxidation from thiazoline (58a) to thiazole (21) took place in one-step using TBAF/THF solution. This thiazoline-thiazole oxidation takes place spontaneously in the reaction of thiazoline Weinreb amide and Grignard reagent. The same phenomena is observed during preparation of the indole compounds 62a and 66a.

Compound 62a was separated as a pure thiazole compound after reaction with 3,4,5-trimethoxphenyllithium without the need for further oxidation. Compound 66a was obtained by removing the phenylsulfonyl protecting groups in hot NaOH ethanol solution. para-OH and NH$_2$ on the A ring of 21 and 2r were obtained by similar Grignard reactions from the Weinreb amides 58a and 68a. Compound 2r was further converted to the HCl salt (2r-HCl) and the HCl salt of monomethyl amine 2s-HCl using NaH/MeI conditions and dimethylamine 2u under HCHO/NaBH$_3$CN conditions.

Substituted a Ring

Figure 5:
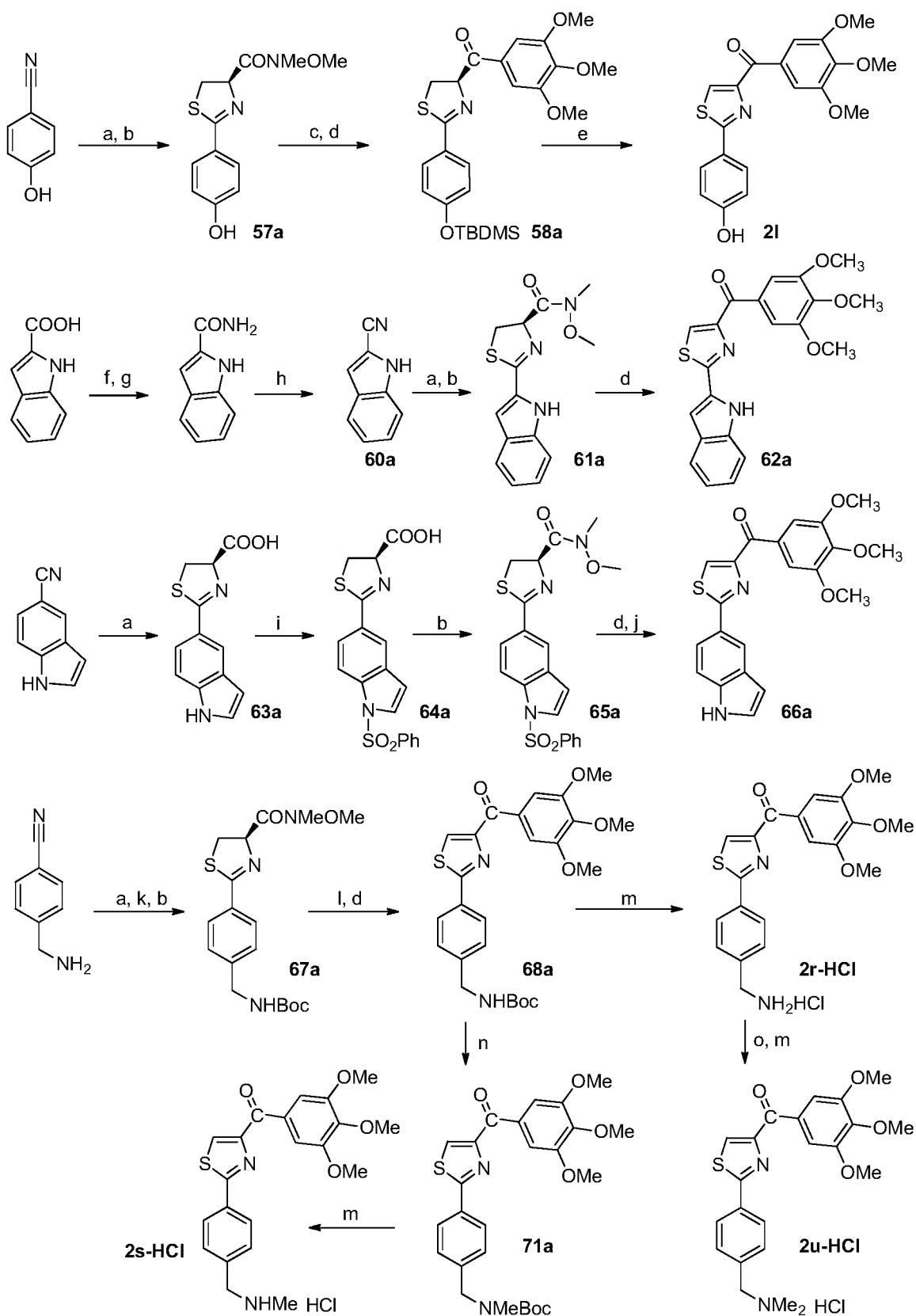
FIG. 5 depicts the synthetic scheme of compounds of this invention. Reagents and conditions: (a) L-cysteine, EtOH, 65° C.; (b) EDCI, HOBt, NMM, HNCH$_3$OCH$_3$, CH$_2$Cl$_2$; (c) TBDMSCl, imidazole, THF; (d) 3,4,5-trimethoxyphenyl-bromide, BuLi, THF; (e) TBAF, THF; (f) SOCl$_2$, Et$_2$O; (g) NH$_3$, MeOH; (h) POCl$_3$; (i) PhSO$_2$Cl, Bu$_4$NHSO$_4$, toluene, 50% NaOH; (j) 1 N NaOH, EtOH, reflux; (k) Boc$_2$O, 1 N NaOH, 1,4-dioxane; (l) CBrCl$_3$, DBU, CH$_2$Cl$_2$; (m) 4 N HCl in 1,4-dioxane; (n) NaH, DMF, MeI; (o) HCHO, NaBH$_3$CN, Et$_3$N.

Synthesis of (2-(4-Hydroxyphenyl)thiazol-4-yl)(3,4,5-trimethoxyphenyl)methanone (21) [FIG. 5]

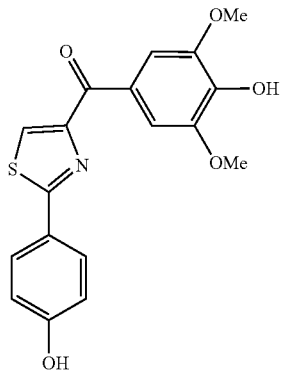

(21)

(R)-2-(4-Hydroxyphenyl)-N-methoxy-N-methyl-4,5-dihydrothiazole-4-carboxamide (57a) was synthesized using the same method as used for 38d. Quantitative yield. $^1$H NMR (500 MHz, CDCl$_3$) δ 7.56 (d, 2H, J=8.5 Hz), 6.84 (br, 1H), 6.73 (d, 2H, J=8.5 Hz), 5.64 (t, br, 1H), 3.87 (s, 3H), 3.30 (s, 3H). MS (ESI) m/z 289.0 (M+Na)$^+$, 264.9 (M−H)$^−$.

(R)-(2-(4-(tert-Butyldimethylsilyloxy)phenyl)-4,5-dihydrothiazol-4-yl)(3,4,5-trimethoxyphenyl)methanone (58a) was synthesized using the same method as used for (35a)-see Example 1. 67.0% yield. 1H NMR (300 MHz, CDCl$_3$) δ 7.73 (d, 2H, J=8.7 Hz), 7.61 (s, 2H), 6.83 (d, 2H, J=8.7 Hz), 5.95 (dd, 1H, J=8.1 Hz, 9.0 Hz), 4.09, (dd, 1H, J=7.8 Hz, 11.1 Hz), 3.95 (s, 3H), 3.94 (s, 6H), 3.55 (dd, 1H, J=9.3 Hz, 11.1 Hz), 0.97 (s, 9H), 0.19 (s, 6H). MS (ESI) m/z 510.4 (M+Na)$^+$, 486.0 (M−H)$^−$.

(2-(4-Hydroxyphenyl)thiazol-4-yl)(3,4,5-trimethoxyphenyl)methanone (21). At 0° C., to a solution of 58a (0.2 mmol) in 5 mL CH$_2$Cl$_2$ was added a solution of tetrabutylammonium fluoride in THF (1 N, 0.6 mmol) and stirred at RT for around 14 h until reaction was finished by TLC monitor. 67.0% yield. $^1$H NMR (500 MHz, DMSO-d$_6$) δ 10.1 (s, 1H), 8.51 (s, 1H), 7.85 (d, 2H, J=8.50 Hz), 7.62 (s, 2H), 6.91 (d, 2H, J=8.5 Hz), 3.86 (s, 6H), 3.79 (s, 3H). MS (ESI) m/z 394.1 (M+Na)$^+$, 369.9 (M−H)$^−$.

(2-(4-(Aminomethyl)phenyl)thiazol-4-yl)(3,4,5-trimethoxyphenyl)methanone hydrochloride (2r or 2r-HCl) [FIG. 5]

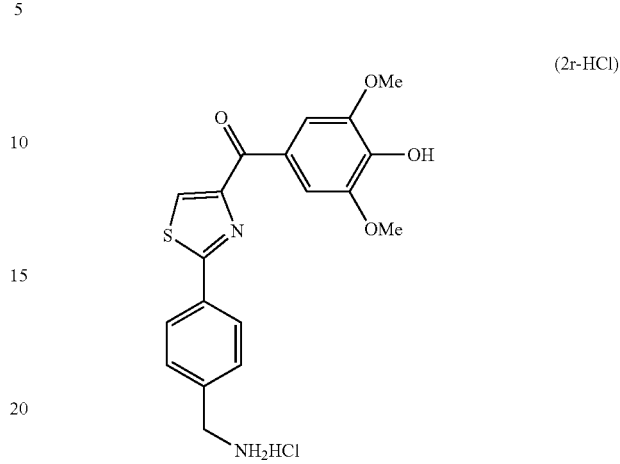

(R)-tert-Butyl 4-(4-(methoxy(methyl)carbamoyl)-4,5-dihydrothiazol-2-yl)benzyl carbamate (67a). 4-(Aminomethyl)benzonitrile (25.09 g, 0.149 mol) and L-cysteine (18.1 g, 0.149 mol) were suspended in 500 mL MeOH and pH 6.4 buffer solutions (1:1) and stirred for 3 days at RT. Triethylamine (30 mL) was added to the mixture and Boc$_2$O (68 g, 0.31 mol) was added to this mixture and stirred for 2 h. The solvents were removed and filtered to yield white solid (R)-2-(4-((tert-butoxycarbonylamino)methyl)phenyl)-4,5-dihydrothiazole-4-carboxylic acid (38.4 g, 76.8%). Compound 67a was obtained from this acid following the same method as used for 38d. Yield: 84.4%. $^1$H NMR (500 MHz, CDCl$_3$) δ 7.75-7.77 (d, 2H, J=7.5 Hz), 7.27-7.26 (d, 2H, J=7.5 Hz), 7.23 (s, 1H), 5.62 (br, 1H), 4.87 (br, 1H), 4.30 (br, 2H), 3.86 (s, 3H), 3.78 (t, J=10.0 Hz, 1H), 3.48-3.4 (m, 1H), 3.25 (s, 3H), 1.42 (s, 9H). MS (ESI) m/z 402.1(M+Na)$^+$, 378.0 (M−H)$^−$.

tert-Butyl 4-(4-(3,4,5-trimethoxybenzoyl)thiazol-2-yl) benzylcarbamate (68a). A mixture of 67a (2.5 mmol), CBrCl$_3$ (3.2 mmol) and DBU (5.0 mmol) in CH$_2$Cl$_2$ (20 mL) was stirred overnight. The reaction mixture was absorbed on silica gel and purified by column chromatography to yield an intermediate thiazole Weinreb amide. To a solution of (3,4,5-trimethoxyphenyl)magnesium bromide (0.5 M, 5.5 mL) in THF was added a solution of the intermediate thiazole Weinreb amide (1.83 mmol) in 10 mL THF under 0° C. and stirred for 30 min. The reaction mixture was quenched with satd. NH$_4$Cl, extracted with ethyl ether, dried with MgSO4. The solvent was removed under reduced pressure to yield a crude product, which was purified by column chromatography to obtain pure compound as a light yellow solid (32.3%). $^1$H NMR (300M, CDCl$_3$) δ 8.27 (s, 1H), 7.98 (d, 2H, J=8.1 Hz), 7.78 (s, 2H), 7.39 (d, 2H, J=8.1 Hz), 7.27-7.26 (d, 2H, J=7.5 Hz), 7.23 (s, 1H), 4.93 (br, 1H), 4.37 (br, d, 1H), 3.96 (s, 3H), 3.95 (s, 6H), 1.47 (s, 9H); MS (ESI) m/z 507.1(M+Na)$^+$.

(2-(4-(Aminomethyl)phenyl)thiazol-4-yl)(3,4,5-trimethoxyphenyl)methanone hydrochloride (2r or 2r-HCl). At 0° C., to a solution of 68a (200 mg) in 10 mL CH$_2$Cl$_2$ was added a solution of HCl in 1,4-dioxane (4 N, 2 mL) and stirred at RT for 4 h. The precipitate (2r) was filtered and washed with diethyl ether. Yield: 81.3%. $^1$H NMR (500 MHz, DMSO-d$_6$) δ 8.68 (s, 1H), 8.38 (br, 3H), 8.10 (d, 2H, J=8.4 Hz), 7.66 (d, 2H, J=8.4 Hz), 7.62 (s, 2H), 4.11 (s, 2H), 3.87 (s, 6H), 3.80 (s, 3H). MS (ESI) m/z 385.1 (M+H)⁺.

(2-(4-((Dimethylamino)methyl)phenyl)thiazol-4-yl)(3,4,5-trimethoxyphenyl)methanone hydrochloride (2u or 2u-HCl) [FIG. 5]

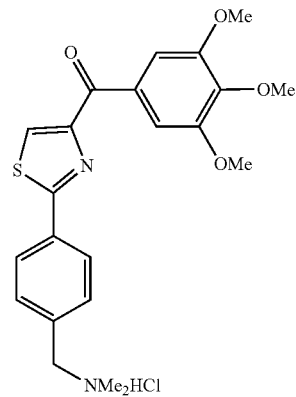
(2u-HCl)

tert-Butyl methyl(4-(4-(3,4,5-trimethoxybenzoyl)thiazol-2-yl)benzyl)carbamate (71a). At 0° C., to a solution of compound 68a (100 mg, 0.2 mmol) in 5 mL DMF was added sodium hydride (10 mg, 0.2 mmol), then iodomethane (77 mg, 0.4 mmol) was added to the reaction mixture and stirred at RT overnight. The mixture was quenched with a sat. NaHCO₃ solution, extracted with ethyl acetate and dried with MgSO4. The solvent was removed under reduced pressure to yield a crude product, which was purified by column chromatography to obtain pure compound 71a. Yield: 61.3%. 1H NMR (500 MHz, DMSO-d₆) δ 8.30 (s, 1H), 8.02 (d, 2H, J=8.0 Hz), 7.82 (s, 2H), 7.36 (br, 2H), 4.50 (s, 2H), 4.00 (s, 3H), 3.98 (s, 6H), 2.90 (d, br, 3H), 1.50 (s, 9H). MS (ESI) m/z 521.2 (M+Na)⁺, 496.9 (M−H)⁻.

(2-(4-((Methylamino)methyl)phenyl)thiazol-4-yl)(3,4,5-trimethoxyphenyl)methanone hydrochloride (2s or 2s-HCl). At 0° C., to a solution of 71a (60 mg) in 5 mL CH₂Cl₂ was added a solution of HCl in 1,4-dioxane (4 N, 2 mL) and stirred at RT for overnight. The precipitate (2s-HCl) was filtered and washed with diethyl ether. Yield: 81.3%. ¹H NMR (500 MHz, CDCl₃) δ 10.0 (s, 1H), 8.29 (s, 1H), 8.05 (d, 2H, J=6.0 Hz), 7.74 (s, 2H), 7.72 (d, 2H, J=6.0 Hz), 4.15 (s, 2H), 3.99 (s, 3H), 3.96 (s, 6H), 2.61 (s, 3H). MS (ESI) m/z 399.1 (M+H)⁺.

(2-(4-((Dimethylamino)methyl)phenyl)thiazol-4-yl)(3,4,5-trimethoxyphenyl)methanone hydrochloride (2u or 2u-HCl). To a solution of 2r (53 mg, 0.14 mmol) in 5 mL CH₂Cl₂ was added formaldehyde solution (37% in H₂O, 340 mg, 4.2 mmol), and sodium cyanoborohydride (34 mg, 0.55 mmol), the reaction mixture was absorbed on silica gel and free base was purified after flash column (41 mg, 70.9%). At 0° C., to a solution of free base (41 mg) in 5 mL CH₂Cl₂ was added a solution of HCl in 1, 4-dioxane (4 N, 2 mL) and stirred at RT for overnight. The precipitate (2u) was filtered and washed with diethyl ether. Yield: 71.3%. ¹H NMR (500 MHz, CDCl₃) δ 13.0 (s, 1H), 8.34 (s, 1H), 8.13 (d, 2H, J=7.0 Hz), 7.82 (d, 2H, J=7.5 Hz), 7.75 (s, 2H), 4.24 (s, 2H), 3.99 (s, 3H), 3.97 (s, 6H), 2.83 (s, 6H). MS (ESI) m/z 413.1 (M+H)⁺.

2-(4-(4-(3,4,5-Trimethoxybenzoyl)thiazol-2-yl)phenyl)acetonitrile (2n)

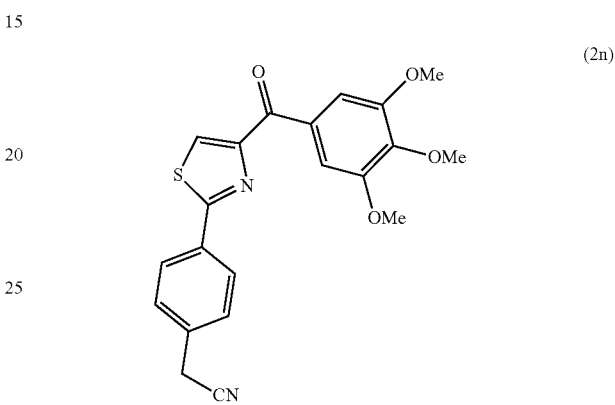
(2n)

2-(4-(4-(3,4,5-Trimethoxybenzoyl)thiazol-2-yl)phenyl)acetonitrile (2n) was prepared using the same method as used of compound 1h from terephthalonitrile and cysteine. ¹H NMR (500 MHz, CDCl₃) δ 8.30 (s, 1H), 8.04 (d, 2H), 7.76 (s, 2H), 7.46 (d, 2H), 3.97 (s, 3H), 3.95 (s, 6H), 3.83 (s, 2H).

Synthesis of (2-(4-(Dimethylamino)phenyl)thiazol-4-yl)(3,4,5-trimethoxyphenyl)methanone (2o)

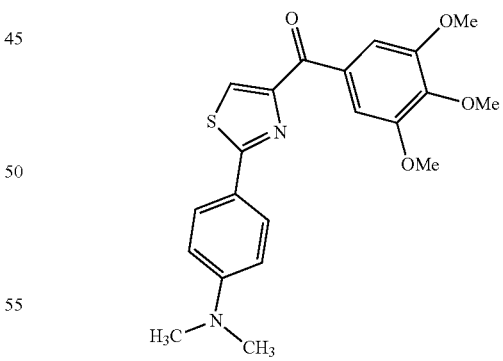

(2-(4-(Dimethylamino)phenyl)thiazol-4-yl)(3,4,5-trimethoxyphenyl)methanone (2o) was prepared using the same method as used of compound 1h from 4-(dimethylamino)benzonitrile and cysteine. ¹H NMR (300 MHz, CDCl₃) δ 8.12 (s, 1H), 7.88 (d, 2H), 7.80 (s, 2H), 6.73 (d, 2H), 3.96 (s, 3H), 3.95 (s, 6H), 3.05 (s, 6H); MS (ESI) m/z 421.1(M+Na)⁺.

141

Indolyl a Ring

Synthesis of (2-(1H-indol-2-yl)thiazol-4-yl)(3,4,5-trimethoxyphenyl)methanone (62a) [FIG. 5]

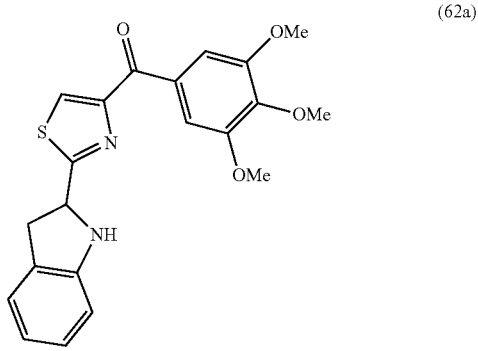 [SMILES: COc1cc(C(=O)c2csc(C3Cc4ccccc4N3)n2)cc(OC)c1OC]

(62a)

1H-Indole-2-carbonitrile (60a). To a cooled solution of indole-2-carboxylic acid (2.0 g, 12.4 mmol) in 60 mL of anhydrous Et$_2$O was added 1.9 mL of SOCl$_2$ (26 mmol). After stirring for 40 min at RT, the ether was removed under reduced pressure at a temperature not exceeding 35° C. The obtained acyl chloride was dissolved in 40 mL of anhydrous Et$_2$O and the resulting solution was added immediately to a stirred solution of liquid ammonia in 80 ml of Et$_2$O. The reaction mixture was stirred at RT for 24 h. The solvent was then evaporated under reduced pressure, and the white indole-2-carboxamide was crystallized from 50% aq EtOH and dried in air, after which it was dissolved in POCl$_3$ and heated under reflux for 5 min. The cooled solution was poured onto crushed ice and aq NH$_4$OH was added to maintain a basic pH. The aqueous mixture was extracted with Et$_2$O, the extracts were dried over Na$_2$SO$_4$ and evaporated. The brown indole-2-carbonitrile 60a (63.3% overall yield from indole-2-carboxylic acid) was obtained. $^1$H NMR (500 MHz, CDCl$_3$) δ 8.56 (br, s, 1H), 7.68 (d, 1H, J=8.0 Hz), 7.43-7.34 (m, 2H), 7.24-7.21 (m, 2H). MS (ESI) m/z 144.0 (M+H)$^+$, 140.8 (M−H)$^−$.

(R)-2-(1H-indol-2-yl)-N-methoxy-N-methyl-4,5-dihydrothiazole-4-carboxamide (61a) was synthesized using the same method as used of 38d. 67.1% yield. $^1$H NMR (300 MHz, CDCl$_3$) δ 9.06 (s, br, 1H), 7.64 (d, 2H, J=8.1 Hz), 7.36-7.24 (m, 2H), 7.12 (dt, 1H, J=8.1 Hz, 1.2 Hz), 6.95 (d, 1H, J=1.8 Hz), 5.60 (t, br, 1H, J=8.7 Hz), 3.86 (s, 3H), 3.78 (t, 1H, J=10.2 Hz), 3.58 (dd, 1H, J=9.0 Hz, 10.2 Hz), 3.30 (s, 3H). MS (ESI) m/z 312.1 (M+Na)$^+$, 287.9 (M−H)$^−$.

(2-(1H-indol-2-yl)thiazol-4-yl)(3,4,5-trimethoxyphenyl)methanone (62a) was synthesized from 61a using the same method as used for 35a. 45.8% yield. $^1$H NMR (500 MHz, DMSO-d$_6$) δ 9.26 (s, 1H), 8.11 (s, 1H), 7.66 (d, 1H, J=8.0 Hz), 7.46 (s, 2H), 7.42 (d, 1H, J=8.0 Hz), 7.29 (t, 1H, J=7.5 Hz), 7.16 (t, 1H, J=7.5 Hz), 7.10 (s, 1H), 3.97 (s, 3H), 3.93 (s, 6H). MS (ESI) m/z 417.1 (M+Na)$^+$, 392.9 (M−H)$^−$.

142

Synthesis of (2-(1H-indol-5-yl)thiazol-4-yl)(3,4,5-trimethoxyphenyl)methanone (66a) [FIG. 5]

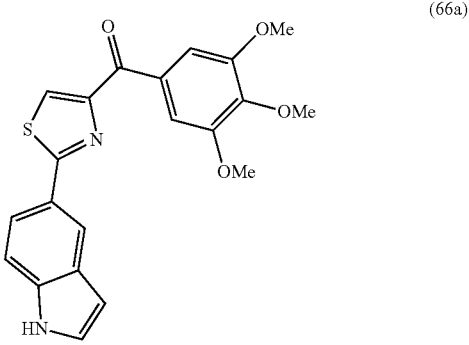 [SMILES: COc1cc(C(=O)c2csc(-c3ccc4[nH]ccc4c3)n2)cc(OC)c1OC]

(66a)

(R)-2-(1-(Phenylsulfonyl)-1H-indol-5-yl)-4,5-dihydrothiazole-4-carboxylic acid (64a). (R)-2-(1H-indol-5-yl)-4,5-dihydrothiazole-4-carboxylic acid 63a was synthesized using the same method as used for 42a from 1H-indole-5-carbonitrile and used without further purification. To a vigorously stirring solution of 63a (1 mmol) and tetrabutylammonium hydrogen sulfate (0.15 mmol) in toluene (10 mL) at 0° C. was added 50% aqueous sodium hydroxide (10 mL) and sulfonyl chloride (2 mmol). The resultant solution was stirred at RT for 6 h. Then 1 N HCl was added to acidify the mixture to pH=2 and extracted with CH$_2$Cl$_2$, the organic layer was separated and dried (MgSO$_4$); then evaporated to dryness to yield 64a, which were used in subsequent steps without further purification.

(R)—N-methoxy-N-methyl-2-(1-(phenylsulfonyl)-1H-indol-5-yl)-4,5-dihydrothiazole-4-carboxamide (65a) was prepared from 64a with the same method as used for 38d. 57.1% yield. $^1$H NMR (500 MHz, CDCl$_3$) δ 7.92 (m, 2H), 7.77 (m, 3H), 7.51 (d, 1H, J=3.0 Hz), 7.46 (t, 1H), 7.35 (t, 1H), 6.61 (d, 1H), 5.58 (br, t, 1H) 3.82 (s, 3H), 3.73 (t, 1H), 3.43 (m, 1H), 3.21 (s, 3H). MS (ESI) m/z 452.1 (M+Na)$^+$.

(2-(1H-indol-5-yl)thiazol-4-yl)(3,4,5-trimethoxyphenyl)methanone (66a). To a solution of n-BuLi (1.6 M, 1.7 mL) in 8 mL THF was added a solution of 3,4,5-trimethoxybromobenzene (2.47 mmol) in 3 mL THF under −78° C. The mixture was allowed to stir for 2 h and a solution of Weinreb amide 65a (1.24 mmol) in 3 mL THF was charged. The temperature was allowed to increase at RT and stirred overnight. The reaction mixture was quenched with satd. NH$_4$Cl, extracted with ethyl ether, dried with MgSO$_4$. The solvent was removed under reduced pressure to yield a crude product, which was refluxed in 1 N NaOH in 5 mL ethanol solution to obtain the deprotected compound 66a and purified by column chromatography to obtain pure compound as a light yellow solid (36.3%). $^1$H NMR (300M, CDCl$_3$) δ 8.36 (br, s, 1H), 8.31 (s, 1H), 8.21 (s, 1H), 7.92, 7.89 (dd, 1H, J=1.8, 2.7 Hz), 7.46 (d, 1H,) 7.62 (s, 2H, J=8.7 Hz), 7.29 (t, 1H, J=2.7 Hz), 6.64 (br, 1H), 3.97 (s, 6H), 3.97 (s, 3H); MS (ESI) m/z 417.1(M+Na)$^+$, 392.9 (M−H)$^−$.

Synthesis of (2-(1H-Indol-2-yl)thiazol-4-yl)(1H-indol-2-yl)methanone (8)

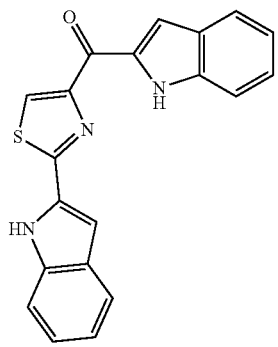

(8)

(2-(1H-Indol-2-yl)thiazol-4-yl)(1H-indol-2-yl)methanone (8) was prepared using the similar method as used of compound 1h from 2-(1H-indol-2-yl)-4,5-dihydrothiazole-4-carboxylic acid and cysteine. $^1$H NMR (500 MHz, CDCl$_3$) δ 9.39 (s, 1H), 8.54 (s, 1H), 8.46 (s, 1H), 8.06 (s, 1H), 8.03 (dd, 1H), 7.66 (d, 1H), 7.51 (d, 1H), 7.41 (d, 1H), 7.33 (t, 1H), 7.29 (d, 1H), 7.15 (t, 1H), 7.09 (d, 1H), 6.72 (s, 1H). MS (ESI) m/z 366.1(M+Na)$^+$, 341.9 (M−H)$^−$.

Synthesis of (2-(1H-indol-2-yl)thiazol-4-yl)(1H-indol-5-yl)methanone (21)

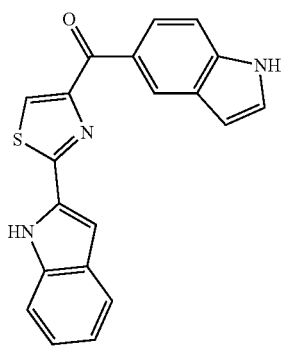

(21)

(2-(1H-indol-2-yl)thiazol-4-yl)(1H-indol-5-yl)methanone (21) was prepared using the similar method as used of compound 1h from 2-(1H-indol-2-yl)-4,5-dihydrothiazole-4-carboxylic acid and cysteine. $^1$H NMR (500 MHz, CDCl$_3$) δ 9.60 (s, 1H), 9.26 (s, 1H), 8.31 (s, 1H), 8.03 (s, 1H), 7.83 (dd, 1H), 7.69 (d, 1H), 7.53-7.49 (m, 2H), 7.41 (t, 1H), 7.33 (t, 1H), 7.21-7.18 (m, 2H), 7.13 (s, 1H). MS (ESI) m/z 366.1(M+Na)$^+$, 341.9 (M−H)$^−$.

Example 4

Synthesis of Compounds of this Invention Having a Nitrogen Linker (X=NH)

Figure 6:
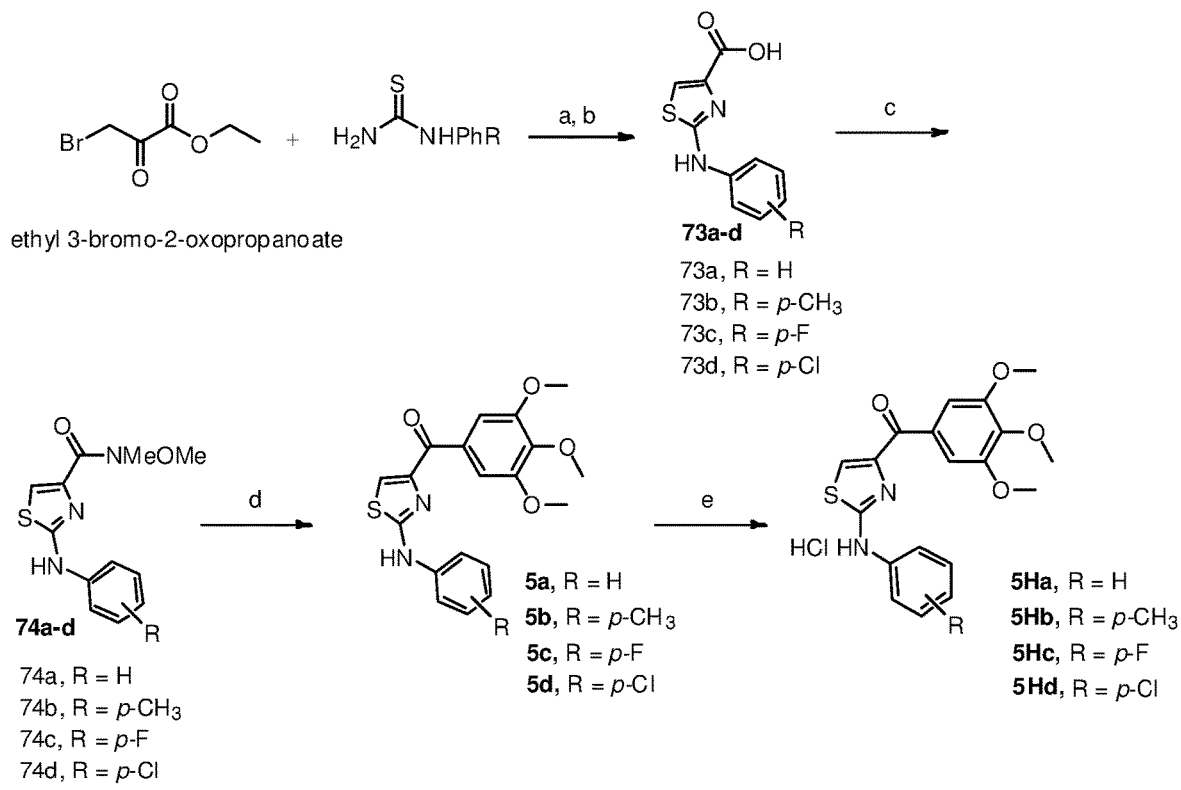
FIG. 6 depicts the synthetic scheme of compounds of this invention. Reagents and conditions: (a) EtOH, 65° C.; (b) NaOH, C$_2$H$_5$OH, refluxing; (c) EDCI, HOBt, NMM, HNCH$_3$OCH$_3$, CH$_2$Cl$_2$; (d) 3,4,5-trimethoxyphenylbromide, BuLi, THF; (e) 2 N HCl in 1,4-dioxane.

To improve bioavailability, an NH linker was introduced between A phenyl and B thiazole rings. This new series of compounds was synthesized as shown in FIG. 6. Reaction of 3-bromo-2-oxopropanoic acid ethyl ester and acylthiourea in ethanol under 65° C. produced 2-(arylamino)-thiazole-4-carboxylic acids 73a-d with high yields. These acids were converted to Weinreb amides 74a-d, followed by reactions with 3,4,5-trimethoxphenyllithium that yielded aniline linked free bases 5a-d, which can be converted into HCl salts 5Ha-d.

Synthesis of (2-(Phenylamino)thiazol-4-yl)(3,4,5-trimethoxyphenyl)methanone derivatives (5a-d) and their HCl salt [FIG. 6]

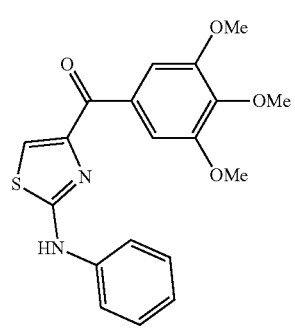

(5a)

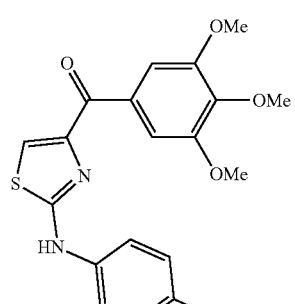

(5b)

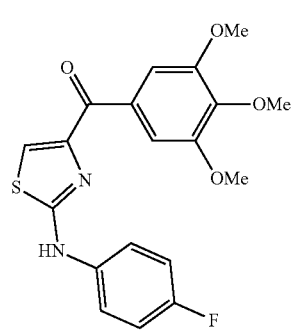

(5c)

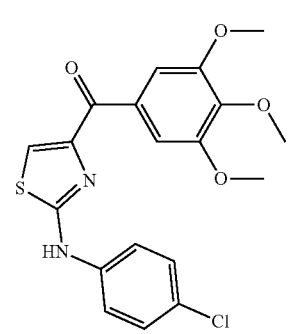

(5d)

-continued

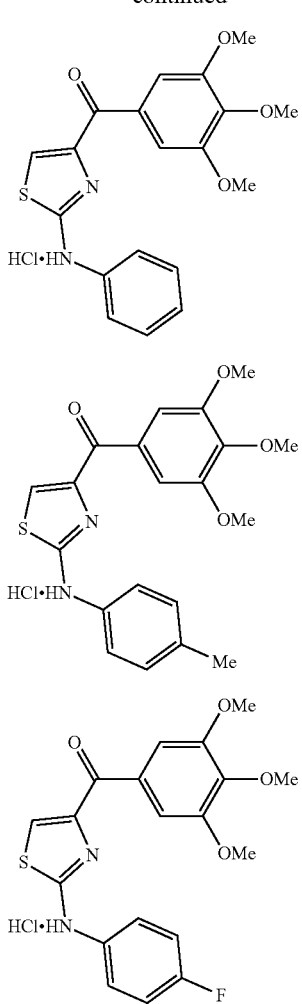

(5Ha)

(5Hb)

(5Hc)

General procedure for the synthesis of 2-(arylamino) thiazole-4-carboxylic acids (37a-d). N-Aryl thiourea (0.01 mol) and ethyl bromopyruvate (0.011 mol) were dissolved in 3 mL ethanol and held at reflux for 2 h. The reaction was cooled, the crystalline ethyl 2-(substituted phenylamino) thiazole-4-carboxylate were collected by filtration and washed with ethanol. Refluxing the mixture of ethyl esters with the NaOH-ethanol solution gave final compounds 73a-d which were used directly in the next steps.

N-Methoxy-N-methyl-2-(arylamino)thiazole-4-carboxamides (74a-d) were synthesized using the same method as used for 38d (see Example 1, FIG. 2).

N-Methoxy-N-methyl-2-(phenylamino)thiazole-4-carboxamide (74a). 90.2% yield. $^1$H NMR (500 MHz, CDCl$_3$) δ 7.39 (s, 2H), 7.38 (br, 1H), 7.36-7.33 (m, br, 4H), 7.09 (t, br, 1H), 3.77 (s, 3H), 3.43 (s, 3H), 2.33 (s, 3H). MS (ESI) m/z 286.0 (M+Na)$^+$.

N-Methoxy-N-methyl-2-(p-tolylamino)thiazole-4-carboxamide (74b). 93.3% yield. $^1$H NMR (500 MHz, CDCl$_3$) δ 7.35 (s, 1H), 7.31 (br, 1H), 7.22 (d, 2H), 7.16 (d, 2H), 3.76 (s, 3H), 3.42 (s, 3H), 2.33 (s, 3H). MS (ESI) m/z 278.0 (M+H)$^+$.

2-(4-Fluorophenylamino)-N-methoxy-N-methylthiazole-4-carboxamide (74c). 89.7% yield. $^1$H NMR (500 MHz, CDCl$_3$) δ 7.36 (s, 1H), 7.36-7.31 (m, 2H), 7.07-7.04 (m, 6H), 3.76 (s, 3H), 3.42 (s, 3H). MS (ESI) m/z 282.0 (M+Na)$^+$, 280.8 (M−H)$^−$.

2-(4-Chlorophenylamino)-N-methoxy-N-methylthiazole-4-carboxamide (74d). 15 $^1$H NMR (500 MHz, CDCl$_3$) δ 7.66 (s, br, 1H), 7.41 (s, 1H), 7.34 (d, 2H), 7.29 (d, 2H), 3.76 (s, 3H), 3.42 (s, 3H). MS: 295.8 (M−1)-; 320.0 (M+Na)$^+$.

General procedure for the synthesis of (2-(arylamino) thiazol-4-yl)(3,4,5-trimethoxyphenyl)methanones (5a-d). At −78° C., to a solution of 5-bromo-1,2,3-trimethoxybenzene (1.235 g, 5.0 mmol) in 30 mL THF was charged n-BuLi in hexane (2.5 N, 2.4 mL, 6 mmol) under Ar$_2$ protection and stirred for 10 min. Weinreb amide 74a-d (1 mmol) in 10 mL THF was added to the lithium reagent and allowed to stir at RT for 2 hs. The reaction mixture was quenched with satd. NH$_4$Cl, extracted with ethyl ether, dried with MgSO$_4$. The solvent was removed under reduced pressure to yield a crude product, which was purified by column chromatography to obtain pure compound (5a-d).

(2-(Phenylamino)thiazol-4-yl)(3,4,5-trimethoxyphenyl) methanone (5a). 33.3% yield. 1H NMR (500 MHz, DMSO-d$_6$) δ 10.4 (s, 1H), 7.85 (s, 1H), 7.68 (d, 2H, J=8.0 Hz), 7.31 (t, 2H, J=8.0 Hz), 6.98 (t, 1H, J=8.0 Hz), 3.83 (s, 6H), 3.78 (s, 3H). MS (ESI) m/z 393.1 (M+H)$^+$, 368.9 (M−H)$^−$.

(2-(p-Tolylamino)thiazol-4-yl)(3,4,5-trimethoxyphenyl) methanone (5b). 40.6% yield. $^1$H NMR (500 MHz, CDCl$_3$) δ 7.48 (s, 1H), 7.47 (s, 2H), 7.30 (br, 1H), 7.27 (d, 2H, J=8.5 Hz), 7.17 (d, 2H, J=8.5 Hz), 3.93 (s, 3H). 3.90 (s, 6H), 2.34 (s, 3H). MS (ESI) m/z 385.1 (M+H)$^+$, 382.9 (M−H)$^−$.

(2-(p-Fluorophenylamino)thiazol-4-yl)(3,4,5-trimethoxyphenyl)methanone (Sc). 39.6% yield. $^1$H NMR (500 MHz, CDCl$_3$) δ 7.52 (br, 1H), 7.49 (s, 1H), 7.45 (s, 2H), 7.40-7.37 (q, 2H, J=4.5 Hz), 7.08-7.04 (t, 2H, J=8.0 Hz), 3.93 (s, 3H), 3.89 (s, 6H). MS (ESI) m/z 389.3 (M+H)$^+$, 386.9 (M−H)$^−$.

(2-((4-Chlorophenyl)amino)thiazol-4-yl)(3,4,5-trimethoxyphenyl)methanone (5d) was prepared using the same method as used for 5a from 1-(4-chlorophenyl)thiourea and ethyl bromopyruvate. Melting point: 165-166° C. $^1$H NMR (500 MHz, CDCl$_3$) δ 7.60 (s, br, 1H), 7.56 (s, 1H), 7.47 (s, 2H), 7.38 (d, 2H), 7.31 (d, 2H), 3.94 (s, 3H), 3.89 (s, 6H). MS: 402.9 (M−1)-; 427.0 (M+Na)$^+$.

General procedure for the synthesis of hydrochloride salts (5Ha-c). At 0° C., to a solution of compound 5a-c (0.1 mmol) in 5 mL CH$_2$Cl$_2$ was added a solution of HCl in 1,4-dioxane (4 N, 2 mL) and stirred at RT for overnight. The precipitates 5Ha-c were collected and washed with diethyl ether.

(2-(Phenylamino)thiazol-4-yl)(3,4,5-trimethoxyphenyl) methanone hydrochloride salt (5Ha). 91.6% yield. $^1$H NMR (500 MHz, DMSO-d$_6$) δ 12.9 (br, 1H), 7.49-7.46 (m, 2H), 7.42-7.40 (m, 2H), 7.37-7.34 (m, br, 2H), 7.11 (s, 2H), 3.94 (s, 3H), 3.92 (s, 6H). MS (ESI) m/z 389.1 (M+H)$^+$.

(2-(p-Tolylamino)thiazol-4-yl)(3,4,5-trimethoxyphenyl) methanone hydrochloride salt (5Hb). 39.6% yield. 1H NMR (500 MHz, CDCl$_3$) δ 7.30-7.25 (m, br, 5H), 7.12 (s, 2H), 3.94 (s, 3H), 3.92 (s, 6H), 2.38 (s, 3H). MS (ESI) m/z 389.1 (M+H)$^+$.

(2-(p-Fluorophenylamino)thiazol-4-yl)(3,4,5-trimethoxyphenyl)methanone hydrochloride salt (5Hc). 89.3% yield. $^1$H NMR (500 MHz, CDCl$_3$) δ 10.55 (s, 1H), 7.85 (s, 1H), 7.72-7.69 (q, 2H, J=4.5 Hz), 7.50 (s, 1H), 7.18-7.15 (t, 2H, J=8.5 Hz), 4.30 (br, 1H), 3.82 (s, 6H), 3.78 (s, 3H). MS (ESI) m/z 389.3 (M+H)$^+$.

Synthesis of (2-(Phenylamino)-1H-imidazol-4-yl)(3,4,5-trimethoxyphenyl)methanone (5e)

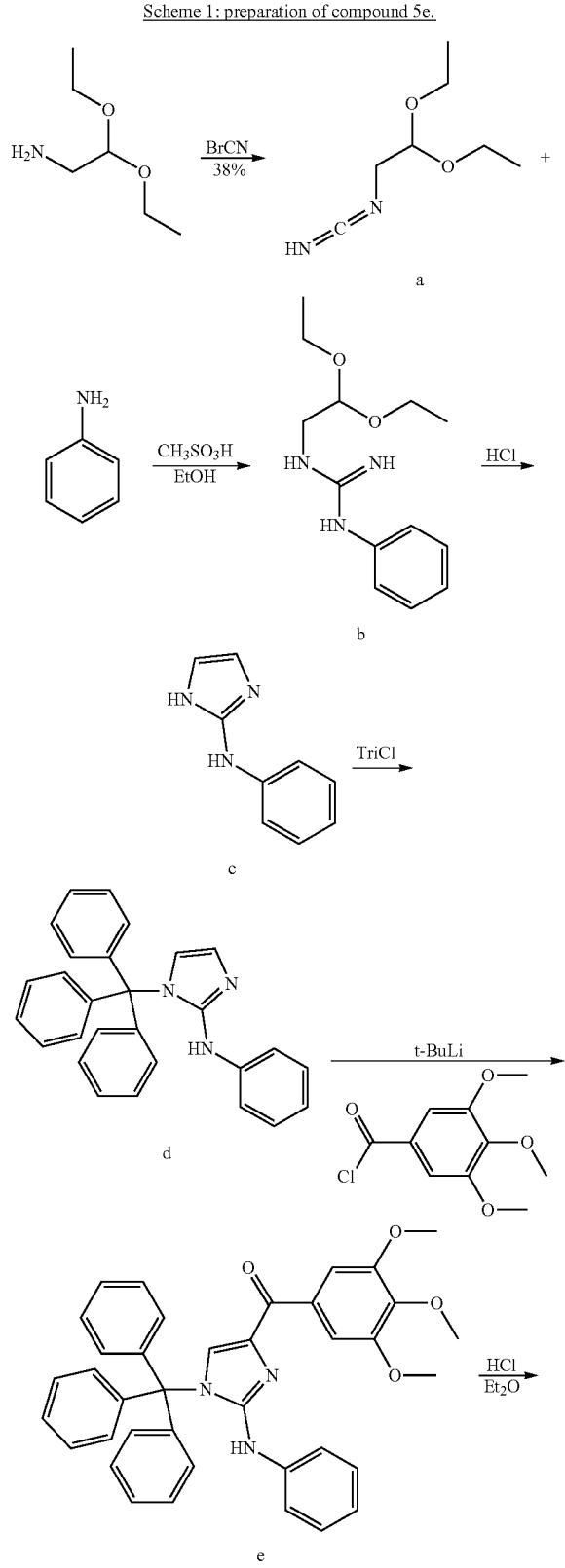

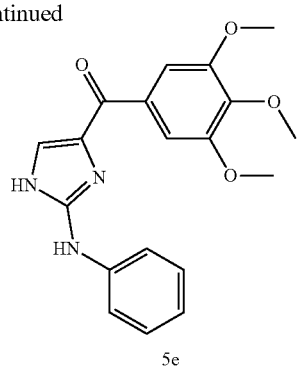

2,2-Diethoxy-N-(iminomethylene)ethanamine (a). A solution of the aminoacetaldehyde diethyl acetal (5.32 g, 40 mmol) in ether (20 mL) was added to a suspension of CNBr (4.22 g, 40 mmol) in hexane (20 mL) at RT. The reaction mixture was stirred at RT overnight. The solid was removed by filtration and washed with ether. The combined filtrate was concentrated. Flash chromatography of the concentrated residue afforded 2.82 g (45%) of the N-(2,2-diethoxyethyl) carbodiimide (a). $^1$H NMR (500 MHz, CDCl$_3$): 4.58 (t, J=5.5 Hz, 1H), 3.85 (br s, 1H), 3.73 (m, 2H), 3.56 (m, 2H), 3.16 (J=5.5 Hz, 2H), 1.23 (t, J=7.0 Hz, 3H), MS: 156.8 (M−H)$^-$; 180.9 (M+Na)$^+$.

1-(2,2-Diethoxyethyl)-3-phenylguanidine (b). Aniline (1.66 g, 17.8 mmol) was dissolved in ethanol (25 mL), and N-(2,2-diethoxyethyl)carbodiimide (a), (2.82 g, 17.8 mmol), was added dropwise. Then methanesulfonic acid (1.71 g, 17.8 mmol) was added, and the mixture was warmed at reflux for 24 h. The reaction mixture was poured into NaOH (0.5 M) and extracted with CH$_2$Cl$_2$. Drying and concentration afforded a product that was subjected to flash chromatography to give the intermediate guanidine (b) (3.3 g, 73.8%). $^1$H NMR (500 MHz, DMSO-d$_6$) δ 7.27-6.90 (m, 5H), 4.55 (t, 1H), 3.76-3.70 (m, 2H), 3.60-3.54 (m, 2H), 3.35-3.34 (d, 2H), 1.22 (pent, 6H). MS: 249.8 (M−H)$^-$; 252.1(M+H)$^+$.

N-Phenyl-1H-imidazol-2-amine (c). The guanidine (b) was dissolved in HCl (5 mL, 6 µM) at 0° C. and then stirred for 2 h. After the starting material was consumed, NaOH (25%) was added until a precipitate formed. This mixture was stirred for 30 min. The reaction was then poured into NaOH (0.5 µM), extracted with CH$_2$Cl$_2$, dried and concentrated. Flash chromatography afforded (c) (0.95 g, 50%). $^1$H NMR (500 MHz, DMSO-d$_6$) δ 8.58 (s, br, 1H), 7.34-6.74 (m, 5H), 6.68 (s, 2H), 6.62 (br, 2H), 3.82 (s, 6H), 3.73 (s, 3H). MS: 157.6 (M−H)$^-$; 160.0 (M+H)$^+$.

N-Phenyl-1-trityl-1H-imidazol-2-amine (d). Trityl chloride (2.79 g, 10 mmol) was added to an ice-cooled solution of phenyl amino imidazole (c) (1.59 g, 10 mmol) and triethylamine (1.01 g, 10 mmol) in methylene dichloride (50 mL). The reaction mixture was allowed to warm to RT and stirred overnight. The mixture was diluted with methylene dichloride, washed successively with H$_2$O, saturated NaHCO$_3$, brine and dried with MgSO$_4$. Filtration and evaporation of the solvent followed by chromatography separation gave the product (d). $^1$H NMR (500 MHz, CDCl$_3$) δ 7.52-7.35 (m, 5H), 7.28-7.43 (m, 15H), 6.85 (s, 2H), 6.41 (s, 1H), 6.08 (s, 1H). MS: 1399.8 (M−H)$^-$; 402.8 (M+H)$^+$.

(2-(Phenylamino)-1-trityl-1H-imidazol-4-yl)(3,4,5 trimethoxyphenyl)methanone (e). At −78° C., t-BuLi in THF (1.7 M, 0.34 mL, 0.58 mmol) was added to a solution of trityl protected compound (d) (116 mg, 0.289 mmol) in THF. Then 3,4,5-trimethoxybenzoyl chloride (66.5 mg, 0.289 mmol) was added and stirred overnight. The reaction mixture was quenched with saturated NH$_4$Cl, and dried with MgSO$_4$. Filtration and evaporation of the solvent followed by chromatography afforded compound (e) (75 mg, 43.7%). $^1$H NMR (500 MHz, CDCl$_3$) δ 7.55-7.41 (m, 5H), 7.32 (s, 1H), 7.28-7.18 (m, 15H), 6.94 (s, 2H), 3.78 (s, 6H), 3.70 (s, 3H). MS: 594.2 (M−H)$^−$; 596.3 (M+H)$^+$.

(2-(Phenylamino)-1H-imidazol-4-yl)(3,4,5-trimethoxyphenyl)methanone (5e). To a solution of trityl protected compound (e) (50 mg, 0.084 mmol) in ethyl ether was added 2 M HCl in ether (1 mL, 1 mmol). The reaction mixture was stirred overnight and washed with saturated NaHCO$_3$ and dried with MgSO$_4$. Filtration and evaporation of the solvent followed by flash chromatography to yield de-protection compound 5e (18 mg, 63%). $^1$H NMR (500 MHz, DMSO-d$_6$) δ 7.54 (s, br, 1H), 7.51-7.43 (m, 3H), 7.33 (d, 2H), 7.04 (s, 2H), 6.62 (br, 2H) 3.82 (s, 6H), 3.73 (s, 3H). MS: 352.1 (M−H)$^−$; 354.3 (M+H)$^+$.

Example 5

Synthesis of Selected Aryl-Benzoyl-Imidazole Compounds

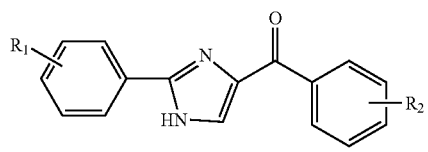

Figure 7:
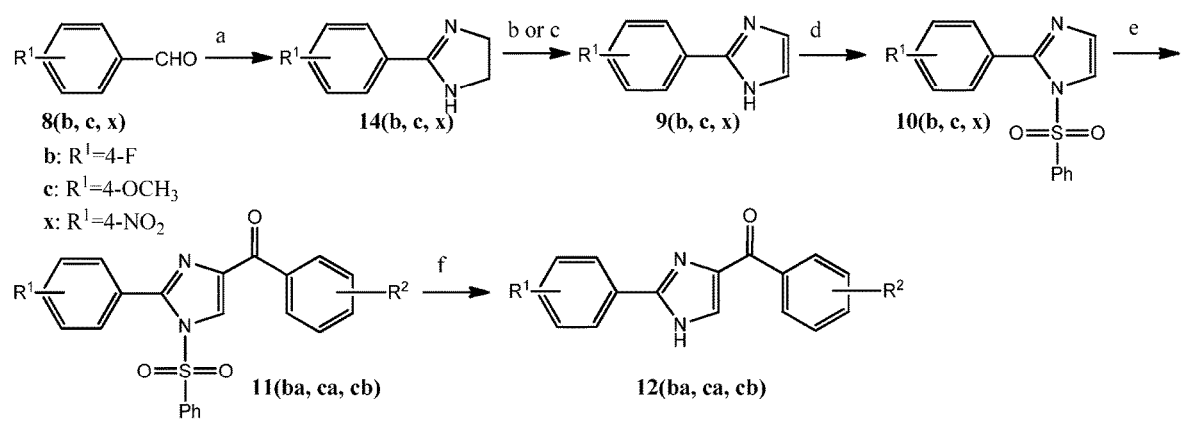
FIG. 7 depicts a synthetic scheme for the preparation of Aryl-Benzoyl-Imidazole (ABI) compounds of this invention. Reagents and conditions: (a) t-BuOH, I$_2$, ethylenediamine, K$_2$CO$_3$, reflux; (b) PhI (OAc)$_2$, K$_2$CO$_3$, DMSO; (c) DBU, CBrCl$_3$, DMF; (d) NaH, PhSO$_2$Cl, THF, 0° C.-RT; (e) t-BuLi, substituted benzoyl chloride, THF, −78° C.; (f) Bu$_4$NF, THF, RT.

Preparation of 2-aryl-4,5-dihydro-1H-imidazoles 14b, 14c, 14x (FIG. 7)

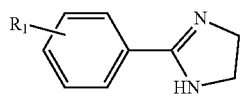

To a solution of appropriate benzaldehyde 8(b, c, x) (60 mmol) in t-BuOH (300 mL) was added ethylenediamine (66 mmol) and stirred for 30 min at RT. Potassium carbonate (75 mmol) and iodine (180 mmol) were added to the reaction mixture sequentially followed by stirring at 70° C. for 3 h. Sodium sulfite (Na$_2$SO$_3$) was added and the mixture was extracted by chloroform. The organic layer was dried over magnesium sulfate and concentrated. The residue was purified by flash column chromatography (chloroform:methanol 20:1) to give a white solid. Yield: 50-60%.

Figure 8:
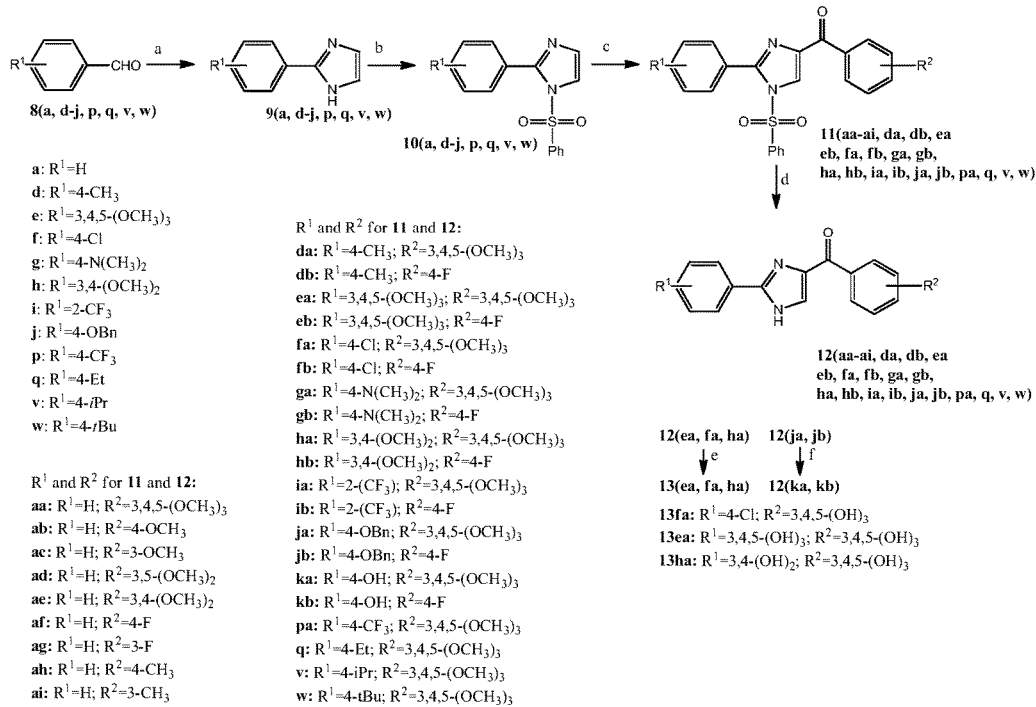
FIG. 8 depicts a synthetic scheme for the preparation of Aryl-Benzoyl-Imidazole (ABI) compounds of this invention. Reagents and conditions: (a) NH$_4$OH, oxalaldehyde, ethanol, RT; (b) NaH, PhSO$_2$Cl, THF, 0° C.-RT; (c) t-BuLi, substituted benzoyl chloride, THF, −78° C.; (d) Bu$_4$NF, THF, RT; (e) BBr$_3$, CH$_2$Cl$_2$; (f) c-HCl, AcOH, reflux.

Preparation of 2-aryl-1H-imidazoles (9a-j, p, x; FIGS. 7 and 8)

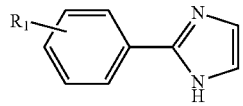

Method A (essential for only 9b, 9x FIG. 7): To a solution of 2-aryl-4,5-dihydro-1H-imidazole 14b, x (35 mmol) in DMSO (100 mL) was added potassium carbonate (38.5 mmol) and diacetoxyiodobenzene (38.5 mmol). The reaction mixture was stirred overnight in darkness. Water was added followed by extraction with dichloromethane. The organic layer was dried over magnesium sulfate and concentrated. The residue was subjected to flash column chromatography (hexane:ethyl acetate 3:2) to give a white solid. Yield: 30%-50%.

Method B (essential for only 9c; FIG. 7): To a solution of 2-aryl-4,5-dihydro-1H-imidazole 14c (50 mmol) in DMF (70 mL) was added DBU (55 mmol) and CBrCl$_3$ (55 mmol). The reaction mixture was stirred overnight and a saturated NaHCO$_3$ (aqueous) solution was added followed by extraction with dichloromethane. The organic layer was dried over magnesium sulfate and concentrated. The residue was subjected to flash column chromatography (chloroform:methanol 50:1) to yield a white solid. Yield: 7%.

Method C (essential for 9a, 9d-j, 9p; FIG. 8): To a solution of appropriate benzaldehyde (8a, 8d-j, 8p) (100 mmol) in ethanol (350 mL) at 0° C. was added a solution of 40% oxalaldehyde in water (12.8 mL, 110 mmol) and a solution of 29% ammonium hydroxide in water (1000 mmol, 140 mL). After stirring for 2-3 days at RT, the reaction mixture was concentrated and the residue was subjected to flash column chromatography with dichloromethane as eluent to yield the titled compound as a yellow powder. Yield: 20%-40%.

Preparation of 2-aryl-1-(phenylsulfonyl)-1H-imidazoles (Oa-j, p, x; FIGS. 7 and 8)

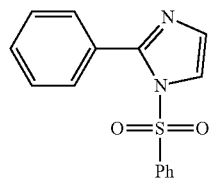

To a solution of 2-aryl-1H-imidazole 9a-j, p, x (20 mmol) in anhydrous THF (200 mL) at 0° C. was added sodium hydride (60% dispersion in mineral oil, 1.2 g, 30 mmol) and stirred for 30 min. Benzenesulfonyl chloride (2.82 mL, 22 mmol) was added and the reaction mixture was stirred overnight. After dilution by 100 mL of saturated NaHCO$_3$ solution (aqueous), the reaction mixture was extracted by ethyl acetate (500 mL). The organic layer was dried over magnesium sulfate and concentrated. The residue was purified by flash column chromatography (hexane:ethyl acetate 2:1) to give a pale solid. Yield: 50%-70%.

Preparation of aryl (2-aryl-1-(phenylsulfonyl)-1H-imidazol-4-yl)methanones (11aa-ai, ba, ca, cb, da, db, ea, eb, fa, fb, ga, gb, ha, hb, ia, ib, ja, jb, pa; FIGS. 7 and 8)

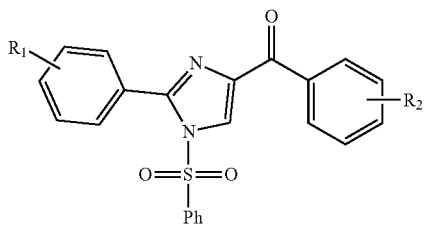

To a solution of 2-aryl-1-(phenylsulfonyl)-1H-imidazole (6.0 mmol) 10a-j, p, x in anhydrous THF (30 mL) at −78° C. was added 1.7M tert-butyllithium in pentane (5.3 mL, 9.0 mmol) and stirred for 10 min. Appropriate substituted benzoyl chloride (7.2 mmol) was added at −78° C. and stirred for overnight. The reaction mixture was diluted with 100 mL of saturated NaHCO$_3$ solution (aqueous) and extracted by ethyl acetate (200 mL). The organic layer was dried over magnesium sulfate and concentrated. The residue was purified by flash column chromatography (hexane:ethyl acetate 4:1) to give a white solid. Yield: 15%-40%. General procedure for the preparation of aryl (2-aryl-1H-imidazol-4-yl)methanones (12aa-ai, ba, ca, cb, da, db, ea, eb, fa, fb, ga, gb, ha, hb, ia, ib, ja, jb, pa; FIGS. 7 and 8).

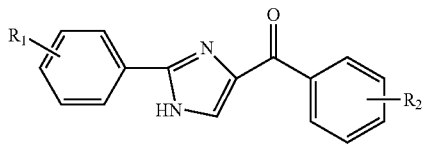

To a solution of aryl (2-aryl-1-(phenylsulfonyl)-1H-imidazol-4-yl)methanones (2.0 mmol) 11aa-ai, ba, ca, cb, da, db, ea, eb, fa, fb, ga, gb, ha, hb, ia, ib, ja, jb, pa in THF (20.0 ml) was added 1.0M tetrabutyl ammonium fluoride (4.0 mmol) and stirred overnight. The reaction mixture was diluted by 50 mL of saturated NaHCO$_3$ solution (aqueous) and extracted by ethyl acetate (100 mL). The organic layer was dried over magnesium sulfate and concentrated. The residue was purified by flash column chromatography (hexane:ethyl acetate 3:1) or recrystallized from water and methanol to give a white solid. Yield: 80-95%.

Preparation of (2-(4-hydroxyphenyl)-1H-imidazol-4-yl) (aryl)methanones (12ka, 12kb; FIG. 8)

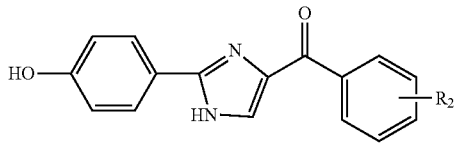

To a solution of (2-(4-(benzyloxy)phenyl)-1H-imidazol-4-yl)(aryl)methanone 12ja or 12jb, (1 mmol) in AcOH (20 mL) was added concentrated HCl (2 mL) and refluxed overnight. After removing the solvent, the residue was recrystallized from dichloromethane to give the titled compound as a yellow solid. Yield: 70-85%.

Preparation of (2-aryl-H-imidazol-4-yl) (3,4,5-trihydroxyphenyl)methanones 13ea, 13fa, 13ha (FIG. 8)

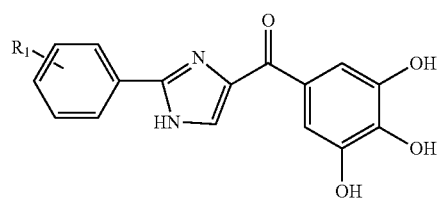

To a solution of aryl (2-aryl-1H-imidazol-4-yl)methanone 12ea, 12fa or 12ha (0.5 mmol) in CH$_2$Cl$_2$ (6.0 mL) was added 1.0 M of BBr$_3$ (2 mmol) in CH$_2$Cl$_2$ and stirred for 1 h at RT. Water was added to destroy excess BBr$_3$. The precipitated solid was filtered and recrystallized from MeOH to afford a yellow solid. Yield: 60-80%.

Preparation of aryl (2-aryl-1H-imidazol-4-yl)methanone-HCl salt (12db-HCl)

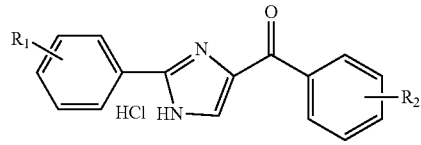

To a solution of 12db (0.5 mmol) in methanol (20 mL) was added 2 M solution of hydrogen chloride (5 mmol) in ethyl ether and stirred overnight at RT. The reaction mixture was concentrated and the residue was washed by CH$_2$Cl$_2$ to yield the titled compound. Yield: 95%.

Preparation of aryl (2-phenyl-1H-imidazol-1-yl)methanone (12aba, 12aaa; FIG. 9)

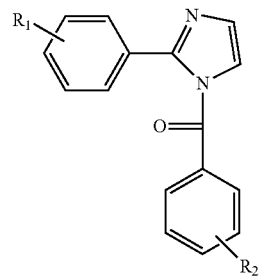

To a solution of 2-phenyl-1H-imidazole 9a (10 mmol) in THF (20 mL) was added NaH (15 mmol) and substituted benzoyl chloride (12 mmol) at 0° C. The reaction mixture was stirred overnight and diluted by saturated NaHCO$_3$ solution followed by extraction with ethyl acetate. The organic layer was dried over magnesium sulfate and concentrated. The residue was purified by flash column chromatography (chloroform) to give a white solid. Yield: 12-16%.

Figure 10:
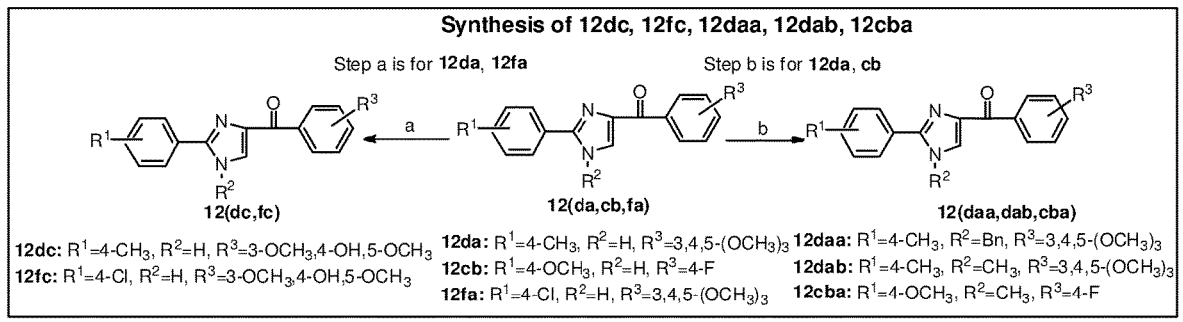
FIG. 10 depicts the synthetic scheme of compounds 12dc, 12fc, 12daa, 12dab, 12cba. (a) AlCl$_3$, THF, reflux; (b) NaH, CH$_3$I for 12dab and 12cba and BnBr for 12daa, THF, reflux.
Figure 11:
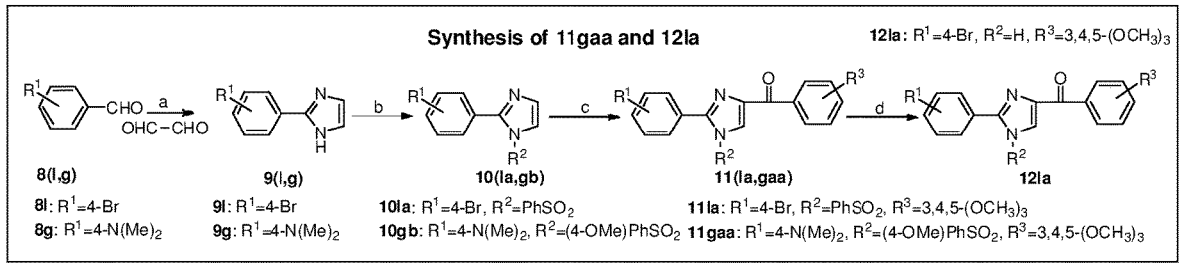
FIG. 11 depicts the synthetic scheme of compounds 11gaa, 121a. (a) NH$_4$OH, ethanol, glyoxal, RT; (b) NaH, substituted PhSO$_2$Cl, THF, 0° C.-RT; (c) t-BuLi (1.7 M in pentane), substituted benzoyl chloride, THF, −78° C.; (d) Bu$_4$NF, RT.

Preparation of 1-substituted-(2-phenyl-1H-imidazol-1-yl)-aryl-methanone (12dc, 12fc, 12daa, 12 dab, 12 cba, 11gaa, 12la; FIGS. 10-11)

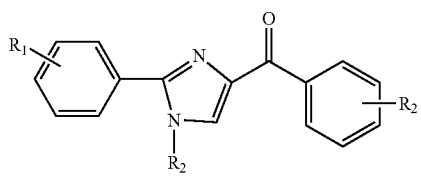

The synthesis of 12dc, 12fc and 12daa, 12dab and 12cba is summarized in FIG. 10. Compounds 12da, 12cb and 12fa were synthesized according to the synthesis described above and in FIGS. 7 and 8. Treatment of 12da and 12fa with aluminum chloride provided the para-demethylated 12dc, 12fc with the 3,5-dimethoxy being intact. Compound 12daa was prepared by benzylation of the N-1 position of 12da. While methylation of the N-1 position of 12da and 12cb afforded compounds 12dab and 12cba, respectively.

Synthesis of 12dc, 12fc, 12daa, 12dab, 12cba:
Method D. (for 12dc and 12fc) [FIG. 10]

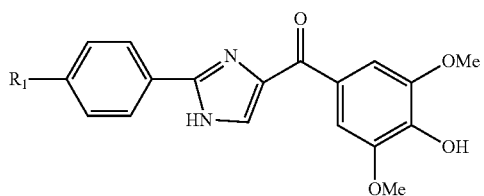

$R_1$=CH$_3$ (12dc)
$R_1$=Cl (12fc)

To a solution of 12da and 12fa (200 mg) in THF (20 mL) was added aluminum chloride (10 equiv). The reaction mixture was stirred overnight. Water was added followed by extraction with ethyl acetate. The organic layer was dried over magnesium sulfate and concentrated. The residue was subjected to flash column chromatography (hexane:ethyl acetate 1:1) to give a white-yellowish solid. Yield: 60%-80%.

Synthesis of 12daa, 12dab, 12cba, Method E: [FIG. 10]

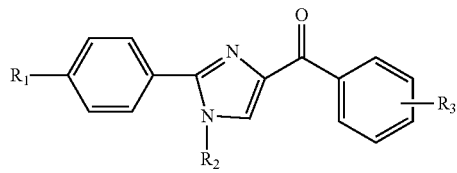

$R_1$=Me; $R_2$=Bn; $R_3$=3,4,5-(OMe)$_3$ (12daa)
$R_1$=Me; $R_2$=CH$_3$; $R_3$=3,4,5-(OMe)$_3$ (12dab)
$R_1$=OMe; $R_2$=CH$_3$; $R_3$=F (12cba)

To a solution of 12da and 12cb (100 mg) in THF (10 mL) in an ice-bath was added sodium hydride (1.2 equiv) followed by the addition of methyl iodide (for 12dab, 12cba) or benzyl bromide (for 12daa) (2 equiv). The resulted reaction mixture was stirred for 5 h under reflux condition. After dilution by 50 mL of saturated NaHCO$_3$ solution (aqueous), the reaction mixture was extracted by ethyl acetate (100 mL). The organic layer was dried over magnesium sulfate and concentrated. The residue was purified by flash column chromatography (hexane:ethyl acetate 2:1) to give a white solid. Yield: 50%-98%.12daa: Yield: 92.8%; mp 135-137° C. $^1$H NMR (CDCl$_3$, 500 MHz) δ 7.81 (s, 1H), 7.80 (d, J=6.5 Hz, 2H), 7.58 (d, J=8.0 Hz, 2H), 7.41-7.45 (m, 3H), 7.31-7.33 (m, 2H), 7.20 (d, J=7.0 Hz, 2H), 5.33 (s, 2H), 3.99 (s, 3H), 3.98 (s, 6H), 2.47 (s, 3H). MS (ESI) calcd for C$_{27}$H$_{26}$N$_2$O$_4$ 442.2, found 443.1 [M+H]$^+$. HPLCl: t$_R$ 4.28 min, purity>99%.

Synthesis of 11gaa and 12la (FIG. 11)

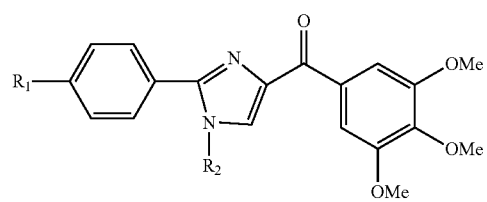

$R_1$=N(Me)$_2$; $R_2$=(4-OMe)PhSO$_2$ (11gaa)
$R_1$=Br; $R_2$=H (12la)

The substituted benzaldehyde compounds 8(1, g) were converted to compounds 9(1, g) in the presence of ammonium hydroxide and glyoxal to construct the imidazole scaffold. The imidazole rings of compounds 9(1, g) were protected by an appropriate phenylsulfonyl group followed by coupling with 3,4,5-trimethoxybenzoyl chloride to achieve compound 11(la,gaa). Treatment of 11la with tert-butylammoniumfluoride to remove the protecting group afforded 12la.

Structural Characterization of (1-Benzyl-2-(p-tolyl)-1H-imidazol-4-yl)(3,4,5-trimethoxyphenyl)methanone (12daa) (FIG. 11)

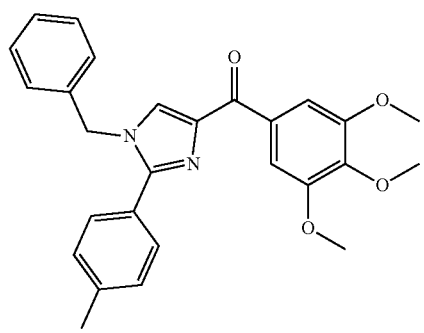

(12daa)

Yield: 92.8%; mp 135-137° C. $^1$H NMR (CDCl$_3$, 500 MHz) δ 7.81 (s, 1H), 7.80 (d, J=6.5 Hz, 2H), 7.58 (d, J=8.0 Hz, 2H), 7.41-7.45 (m, 3H), 7.31-7.33 (m, 2H), 7.20 (d, J=7.0 Hz, 2H), 5.33 (s, 2H), 3.99 (s, 3H), 3.98 (s, 6H), 2.47 (s, 3H). MS (ESI) calcd for $C_{27}H_{26}N_2O_4$ 442.2, found 443.1 [M+Na]+. HPLC1: $t_R$ 4.28 min, purity>99%.

Structural Characterization of (2-(4-(dimethylamino)phenyl)-1-((4-methoxyphenyl)sulfonyl)-1H-imidazol-4-yl)(4-fluorophenyl)methanone (12gba)

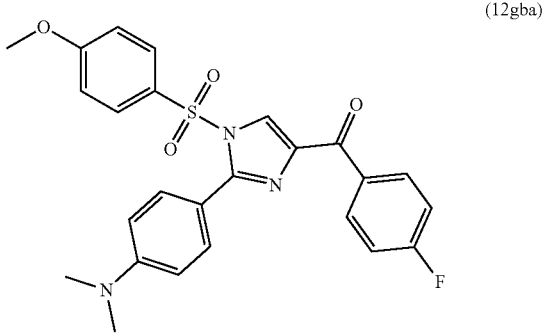 [SMILES: COc1ccc(S(=O)(=O)n2cc(C(=O)c3ccc(F)cc3)nc2-c2ccc(N(C)C)cc2)cc1]

(12gba)

Yield: 34.1%; mp 147-149° C. $^1$H NMR (CDCl$_3$, 500 MHz) δ 8.07 (q, J=8.5 Hz, 5.5 Hz, 2H), 7.78 (d, J=9.0 Hz, 2H), 7.41 (d, J=8.5 Hz, 2H), 7.39 (s, 1H), 7.23 (t, J=8.5 Hz, 2H), 6.91 (d, J=9.0 Hz, 2H), 6.68 (d, J=9.0 Hz, 2H), 3.89 (s, 3H), 3.08 (s, 3H). MS (ESI) calcd for $C_{25}H_{22}FN_3O_4S$ 479.1, found 502.1 [M+Na]+. HPLC2: $t_R$ 18.6 min, purity 96.9%.

Synthesis of (2-(4-bromophenyl)-1H-imidazol-4-yl)(3,4,5-trimethoxyphenyl)methanone (12la) (FIG. 11)

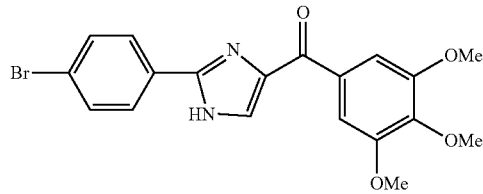

Synthesis of 9l, 9g: To a solution of appropriate benzaldehyde (8l, and 8g, 100 mmol) in ethanol (400 mL) at 0° C. was added a solution of 40% oxalaldehyde (glyoxal) in water (1.1 equiv) and a solution of 29% ammonium hydroxide in water (10 equiv). After stirring for 2-3 days at RT, the reaction mixture was concentrated and the residue was subjected to flash column chromatography with dichloromethane as eluent to yield the titled compound as a yellow powder. Yield: 10%-30%.

Synthesis of 101a, 10gb: To a solution of imidazoles (9l, 9g) (10 mmol) in anhydrous THF (200 mL) at 0° C. was added sodium hydride (60% dispersion in mineral oil, 1.2 equiv) and stirred for 20 min. 4-Methoxybenzenesulfonyl chloride (for 10gb) or benzenesulfonyl chloride (for others) (1.2 equiv) was added and the reaction mixture was stirred overnight. After dilution by 200 mL of saturated NaHCO$_3$ solution (aqueous), the reaction mixture was extracted by ethyl acetate (600 mL). The organic layer was dried over magnesium sulfate and concentrated. The residue was purified by flash column chromatography (hexane:ethyl acetate 2:1) to give a pale solid. Yield: 40%-95%.

Synthesis of 11la, 11gaa: To a solution of 2-aryl-1-(phenylsulfonyl)-1H-imidazole (101a, 10gb) (5.0 mmol) in anhydrous THF (30 mL) at −78° C. was added 1.7 M tert-butyllithium in pentane (1.2 equiv) and stirred for 10 min. 3,4,5-Trimethoxybenzoyl chloride (1.2 equiv) was added at −78° C. and stirred overnight. The reaction mixture was diluted with 100 mL of saturated NaHCO$_3$ solution (aqueous) and extracted by ethyl acetate (300 mL). The organic layer was dried over magnesium sulfate and concentrated. The residue was purified by flash column chromatography (hexane:ethyl acetate 3:1) to give a white solid. Yield: 5%-45%.

Synthesis of 12la: To a solution of aryl (2-aryl-1-(phenylsulfonyl)-1H-imidazol-4-yl)methanone (11la), 2.0 mmol) in THF (25.0 mL) was added 1.0 M tetrabutyl ammonium fluoride (2 equiv) and stirred overnight. The reaction mixture was diluted by 60 mL of saturated NaHCO$_3$ solution (aqueous) and extracted by ethyl acetate (150 mL). The organic layer was dried over magnesium sulfate and concentrated. The residue was purified by flash column chromatography (hexane:ethyl acetate 4:1) or recrystallized from water and methanol to give a white solid. Yield: 80-98%.

Synthesis of (4-Fluorophenyl)(2-(4-methoxyphenyl)-1H-imidazol-4-yl)methanone (12cb) (FIG. 7)

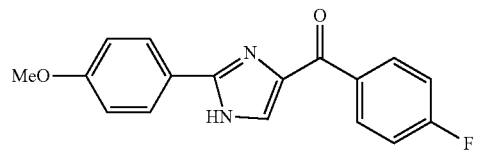 [SMILES: COc1ccc(-c2nc(C(=O)c3ccc(F)cc3)c[nH]2)cc1]

To a solution of (4-fluorophenyl)(2-(4-methoxyphenyl)-1-(phenylsulfonyl)-1H-imidazol-4-yl)methanone (11cb, 872 mg, 2.0 mmol) in THF (20.0 mL) was added 1.0 M tetrabutyl ammonium fluoride (4.0 mL, 4.0 mmol) and stirred overnight. The reaction mixture was diluted by 50 mL of saturated NaHCO$_3$ solution (aqueous) and extracted by ethyl acetate (100 mL). The organic layer was dried over magnesium sulfate and concentrated. The residue was recrystallized from water and methanol to give a white solid. Yield: 90%; mp 245-247° C.

Synthesis of (2-(p-Tolyl)-1H-imidazol-4-yl)(3,4,5-trimethoxyphenyl)methanone (12da) (FIG. 8)

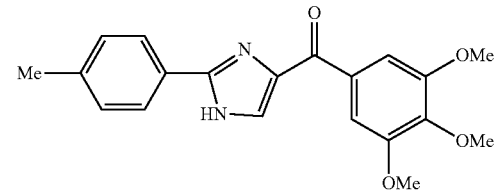 [SMILES: COc1cc(C(=O)c2c[nH]c(-c3ccc(C)cc3)n2)cc(OC)c1OC]

To a solution of (1-(phenylsulfonyl)-2-(p-tolyl)-1H-imidazol-4-yl)(3,4,5-trimethoxyphenyl)methanone (11da, 492 mg, 1.0 mmol) in THF (15.0 mL) was added 1.0 M tetrabutyl ammonium fluoride (2.0 mL, 2.0 mmol) and stirred overnight. The reaction mixture was diluted by 30 mL of saturated NaHCO$_3$ solution (aqueous) and extracted by ethyl acetate (80 mL). The organic layer was dried over magnesium sulfate and concentrated. The residue was recrystallized from water and methanol to give a white solid. Yield: 88.5%.

Figure 14:
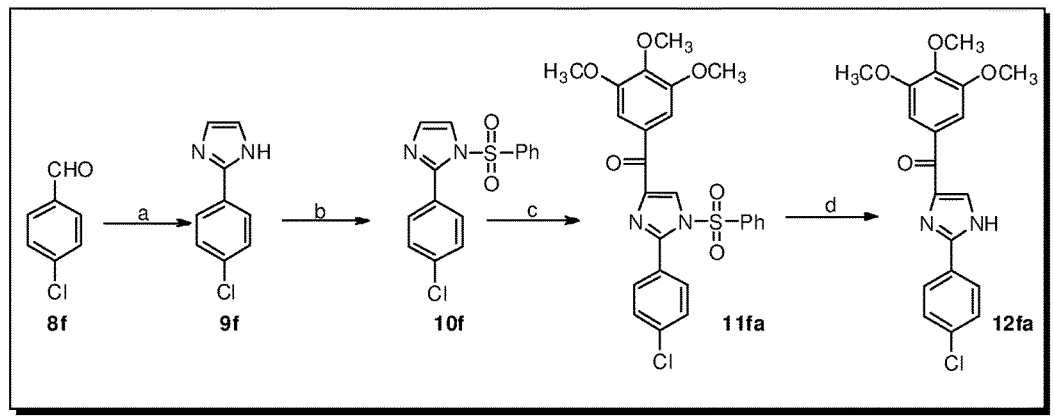
FIG. 14 depicts synthetic scheme of 12fa. (a) NH$_4$OH, oxalaldehyde, ethanol, RT; (b) NaH, PhSO$_2$Cl, THF, 0° C.-RT; (c) t-BuLi, 3,4,5-trimethoxybenzoyl chloride, THF, −78° C.; (d) Bu$_4$NF, THF, RT.

Synthesis of (2-(4-Chlorophenyl)-1H-imidazol-4-yl) (3,4,5-trimethoxyphenyl)methanone (12fa) (FIGS. 8 and 14)

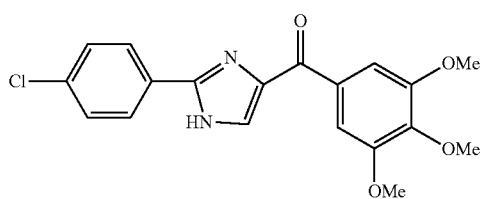 [SMILES: COc1cc(C(=O)c2c[nH]c(-c3ccc(Cl)cc3)n2)cc(OC)c1OC]

2-(4-Chlorophenyl)-1H-imidazole (9f): To a solution of 4-chlorobenzaldehyde (8f) (100 mmol) in ethanol (350 mL) at 0° C. was added a solution of 40% oxalaldehyde in water (12.8 mL, 110 mmol) and a solution of 29% ammonium hydroxide in water (1000 mmol, 140 mL). After stirring for 2-3 days at RT, the reaction mixture was concentrated and the residue was subjected to flash column chromatography with dichloromethane as eluent to yield the titled compound as a yellow powder. Yield: 19.8%. $^1$H NMR (500 MHz, DMSO-$d_6$) δ 13.60 (br, 1H), 7.94 (d, J=8.5 Hz, 2H), 7.51 (d, J=8.0 Hz, 2H), 7.27 (s, 1H), 7.03 (s, 1H). MS (ESI): calculated for $C_9H_7ClN_2$, 178.0, found 178.9 [M+H]$^+$.

2-(4-Chlorophenyl)-1-(phenylsulfonyl)-1H-imidazole (10f): To a solution of 2-(4-chlorophenyl)-1H-imidazole (9f) (20 mmol) in anhydrous THF (200 mL) at 0° C. was added sodium hydride (60% dispersion in mineral oil, 1.2 g, 30 mmol) and stirred for 30 min. Benzenesulfonyl chloride (2.82 mL, 22 mmol) was added and the reaction mixture was stirred overnight. After dilution by 100 mL of saturated NaHCO$_3$ solution (aqueous), the reaction mixture was extracted by ethyl acetate (500 mL). The organic layer was dried over magnesium sulfate and concentrated. The residue was purified by flash column chromatography (hexane:ethyl acetate 2:1) to give a pale solid. Yield: 54.9%. $^1$H NMR (500 MHz, CDCl$_3$) δ 7.65 (d, J=2.0 Hz, 1H), 7.58 (t, J=7.5 Hz, 1H), 7.43 (d, J=8.5 Hz, 2H), 7.38 (t, J=8.0 Hz, 2H), 7.34-7.36 (m, 4H), 7.12 (d, J=1.5 Hz, 1H). MS (ESI): calculated for $C_{15}H_{11}ClN_2O_2S$, 318.0, found 341.0 [M+Na]$^+$.

(2-(4-Chlorophenyl)-1-(phenylsulfonyl)-1H-imidazol-4-yl)(3,4,5-trimethoxyphenyl)methanone (11fa): To a solution of 2-(4-chlorophenyl)-1-(phenylsulfonyl)-1H-imidazole (10f) (6.0 mmol) in anhydrous THF (30 mL) at −78° C. was added 1.7 M tert-butyllithium in pentane (5.3 mL, 9.0 mmol) and stirred for 10 min. 3,4,5-Trimethoxybenzoyl chloride (7.2 mmol) was added at −78° C. and stirred for overnight. The reaction mixture was diluted with 100 mL of saturated NaHCO$_3$ solution (aqueous) and extracted by ethyl acetate (200 mL). The organic layer was dried over magnesium sulfate and concentrated. The residue was purified by flash column chromatography (hexane:ethyl acetate 4:1) to give a white solid. Yield: 36.8%; $^1$H NMR (500 MHz, CDCl$_3$) δ 8.05 (d, J=7.5 Hz, 2H), 7.77 (t, J=7.5 Hz, 1H), 7.62 (t, J=8.0 Hz, 2H), 7.48 (s, 1H), 7.44 (d, J=9.0 Hz, 2H), 7.39 (d, J=8.5 Hz, 2H), 7.37 (s, 2H). MS (ESI): calculated for $C_{25}H_{21}ClN_2O_6S$, 512.1, found 513.1 [M+H]$^+$.

(2-(4-Chlorophenyl)-1H-imidazol-4-yl)(3,4,5-trimethoxyphenyl)methanone (12fa): To a solution of (2-(4-chlorophenyl)-1-(phenylsulfonyl)-1H-imidazol-4-yl)(3,4,5-trimethoxyphenyl)methanone (11fa) (2.0 mmol) in THF (20.0 mL) was added 1.0 M tetrabutyl ammonium fluoride (4.0 mmol) and stirred overnight. The reaction mixture was diluted by 50 mL of saturated NaHCO$_3$ solution (aqueous) and extracted by ethyl acetate (100 mL). The organic layer was dried over magnesium sulfate and concentrated. The residue was purified by flash column chromatography (hexane:ethyl acetate 3:1) or recrystallized from water and methanol to give a white solid. Yield: 80-95%. Yield: 36.9%; mp 193-195° C. $^1$H NMR (500 MHz, CDCl$_3$) δ 10.75 (br, 1H), 7.96 (d, J=8.5 Hz, 2H), 7.83 (s, 1H), 7.47 (d, J=9.0 Hz, 2H), 7.23 (s, 2H), 3.97 (s, 3H), 3.94 (s, 6H), 2.43 (s, 3H). MS (ESI): calculated for $C_{19}H_{17}ClN_2O_4$, 372.1, found 395.1 [M+Na]$^+$, 370.9 [M−H]$^−$. HPLC Gradient: Solvent A (water) and Solvent B (methanol): 0-15 min 40-100% B (linear gradient), 15-25 min 100% B: $t_R$ 16.36 min, purity>99%.

Synthesis of (2-(4-Chlorophenyl)-1H-imidazol-4-yl) (4-fluorophenyl)methanone (12fb) (FIG. 8)

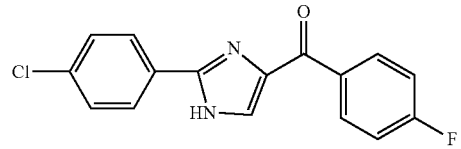 [SMILES: O=C(c1ccc(F)cc1)c1c[nH]c(-c2ccc(Cl)cc2)n1]

To a solution of (2-(4-chlorophenyl)-1-(phenylsulfonyl)-1H-imidazol-4-yl)(4-fluorophenyl)methanone (11fb, 440 mg, 1.0 mmol) in THF (12.0 mL) was added 1.0 M tetrabutyl ammonium fluoride (2.0 mL, 2.0 mmol) and stirred overnight. The reaction mixture was diluted by 20 mL of saturated NaHCO$_3$ solution (aqueous) and extracted by ethyl acetate (60 mQ). The organic layer was dried over magnesium sulfate and concentrated. The residue was recrystallized from water and methanol to give a white solid. Yield: 83.7%.

Physicochemical Characterization of Aryl-Benzoyl-Imidazole Compounds and Intermediates

| Compound | Physicochemical Cheracterization |
|---|---|
| 2-phenyl-1H-imidazole (9a) | Yield: 36.8 %. $^1$H NMR (500 MHz, DMSO-$d_6$) δ 12.52 (br, 1 H), 7.95 (d, J = 7.0 Hz, 2 H), 7.44 (t, J = 7.5 Hz, 2 H), 7.34 (t, J = 7.0 Hz, 1H), 7.25-7.27 ☐m, 1 H), 7.04-7.07 ☐m, 1 H). MS (ESI): calculated for $C_9H_8N_2$, 144.1, found 167.1 [M + Na]$^+$. |
| 2-(4-fluorophenyl)-1H-imidazole (9b) | Yield: 56.5 %. $^1$H NMR (300 MHz, DMSO-$d_6$) δ 12.46 (br, 1 H), 7.94-7.99 (m, 2 H), 7.24- |

| Compound | Physicochemical Cherecterization |
|---|---|
| | 7.30 (m, 2 H), 7.00-7.03 (m, 2 H). MS (ESI): calculated for $C_9H_7FN_2$, 162.1, found 163 [M + H]$^+$, 160.6 [M − H]$^-$. |
| 2-(4-methoxyphenyl)-1H-imidazole (9c) | Yield: 22.2 %. $^1$H NMR (500 MHz, CDCl$_3$) δ 7.80 (d, J = 10.0 Hz, 2 H), 7.15 (s, 2 H), 3.86 (s, 3 H). MS (ESI): calculated for $C_{10}H_{10}N_2O$, 174.1, found 175 [M + H]$^+$, 172.8 [M − H]$^-$. |
| 2-(p-tolyl)-1H-imidazole (9d) | Yield: 36.1%. $^1$H NMR (500 MHz, CDCl$_3$) δ 7.64 (d, J = 7.5 Hz, 2 H), 7.16 (d, J = 7.5 Hz, 2 H), 7.12 (s, 1 H), 7.02 (s, 1 H). MS (ESI): calculated for $C_{10}H_{10}N_2$, 158.1, found 159.0 [M + H]$^+$, 156.8 [M − H]$^-$. |
| 2-(3,4,5-trimethoxyphenyl)-1H-imidazole (9e) | Yield: 26.0%. $^1$H NMR (500 MHz, CDCl$_3$) δ 7.26 (s, 2 H), 7.08 (d, J = 1.5 Hz, 2 H), 3.86 (s, 3 H), 3.82 (s, 6 H). MS (ESI): calculated for $C_{12}H_{14}N_2O_3$, 234.1, found 234.9 [M + H]$^+$. |
| 2-(4-chlorophenyl)-1H-imidazole (9f) | Yield: 19.8 %. $^1$H NMR (500 MHz, DMSO-d6) δ 13.60 (br, 1 H), 7.94 (d, J = 8.5 Hz, 2 H), 7.51 (d, J = 8.0 Hz, 2 H), 7.27 (s, 1 H), 7.03 (s, 1 H). MS (ESI): calculated for $C_9H_7ClN_2$, 178.0, found 178.9 [M + H]$^+$. |
| 4-(1H-imidazol-2-yl)-N,N-dimethylaniline (9g) | Yield: 16.5%. $^1$H NMR (300 MHz, CDCl$_3$) δ 7.70 (dd, J = 7.0 Hz, 2.0 Hz, 2 H), 7.10 (s, 2 H), 6.75 (dd, J = 9.0 Hz, 2.0 Hz, 2 H), 3.02 (s, 6 H). MS (ESI): calculated for $C_{11}H_{13}N_3$, 187.1, found 187.9 [M + H]$^+$, 185.8 [M − H]$^-$. |
| 2-(3,4-dimethoxyphenyl)-1H-imidazole (9h) | Yield: 22.0 %. $^1$H NMR (500 MHz, CDCl$_3$) δ 7.52 (d, J = 1.5 Hz, 1 H), 7.27-7.28 (m, 1 H), 7.14 (s, 2 H), 6.88 (d, J = 8.0 Hz, 1 H), 3.91 (s, 3 H), 3.87 (s, 3 H). MS (ESI): calculated for $C_{11}H_{12}N_2O_2$, 204.1, found 205.1 [M + H]$^+$, 202.8 [M − H]$^-$. |
| 2-(2-(trifluoromethyl)phenyl)-1H-imidazole (9i) | Yield: 25.5%. $^1$H NMR (500 MHz, DMSO-d$_6$) δ 12.31 (br, 1 H), 7.84 (d, J = 8.0 Hz, 1 H), 7.76 (t, J = 8.0 Hz, 1 H), 7.65 (t, J = 7.5 Hz, 1 H), 7.16 (br, 2 H). MS (ESI): calculated for $C_{10}H_7F_3N_2$, 212.1, found 212.9 [M + H]$^+$, 210.7 [M − H]$^-$. |
| 2-(4-(benzyloxy)phenyl)-1H-imidazole (9j) | Yield: 12.1 %. $^1$H NMR (500 MHz, CDCl$_3$) δ 7.77 (d, J = 8.5 Hz, 2 H), 7.36-7.47 (m, 5 H), 7.10-7.18 (m, 2 H), 7.06 (d, J = 9.0 Hz, 2 H), 5.13 (s, 2 H). MS (ESI): calculated for $C16H_{14}N_2O$, 250.1, found 251.1 [M + H]$^+$, 248.8 [M − H]$^-$. |
| 2-(4-Bromophenyl)-1H-imidazole (9l) | Yield: 19.5%. $^1$H NMR (300 MHz, CDCl$_3$) δ 12.59 (s, 1 H), 7.87 (d, J = 8.1 Hz, 2 H), 7.64 (d, J = 8.1 Hz, 1 H), 7.27 (s, 1 H), 7.04 (s, 1 H). MS (ESI) calcd for $C_9H_7BrN_2$ 222.0, found 222.8 [M + H]$^+$. |
| 2-(4-(Trifluoromethyl)phenyl)-1H-imidazole (9p) | Yield: 26.2 %; $^1$H NMR (500 MHz, CDCl$_3$) δ 8.03 (d, J = 8.0 Hz, 2 H), 7.66 (d, J = 8.0 Hz, 2 H), 7.25 (s, 2 H). MS (ESI) calcd for $C_{10}H_7F_3N_2$ 212.1, found 213.1 [M + H]$^+$. |
| 2-(4-nitrophenyl)-1H-imidazole (9x) | Yield: 53.7%. $^1$H NMR (500 MHz, DMSO-d$_6$) δ 12.97 (br, 1 H), 8.32 (d, J = 9.0 Hz, 2 H), 8.17 (d, J = 9.0 Hz, 2 H), 7.42 (s, 1 H), 7.17 (s, 1H). MS (ESI): calculated for $C_9H_7N_3O_2$, 189.1, found 189.9 [M + H]$^+$, 187.8 [M − H]$^-$. |
| 2-phenyl-1-(phenylsulfonyl)-1H-imidazole (10a) | Yield: 50.3%. $^1$H NMR (500 MHz, CDCl$_3$) δ 7.64-7.67 (m, 1 H), 7.56 (t, J = 9.0 Hz, 1 H), 7.32-7.48 (m, 9 H), 7.12-7.16 (m, 1 H). MS (ESI): calculated for $C_{15}H_{12}N_2O_2S$, 284.1, found 307.1 [M + Na]$^+$. |
| 2-(4-fluorophenyl)-1-(phenylsulfonyl)-1H-imidazole (10b) | Yield: 56.9%. $^1$H NMR (500 MHz, CDCl$_3$) δ 7.66 (d, J = 2.0 Hz, 1 H), 7.58 (t, J = 10.0 Hz, 1 H), 7.36-7.42 (m, 6 H), 7.12 (d, J = 2.0 Hz, 1 H), 7.06 (t, J = 10.0 Hz, 2 H). MS (ESI): calculated for $C_{15}H_{11}FN_2O_2S$, 302.1, found 300.8 [M − H]$^-$. |
| 2-(4-methoxyphenyl)-1-(phenylsulfonyl)-1H-imidazole (10c) | Yield: 40.9 %. $^1$H NMR (500 MHz, CDCl3) δ 7.62 (d, J = 5.0 Hz, 1 H), 7.56 (tt, J = 15.0 Hz, 5.0 Hz, 1 H), 7.32-7.43 (m, 6 H), 7.10 (d, J = 5.0 Hz, 1 H), 6.88 (dt, J = 16.0 Hz, 6.0 Hz, 2 H), 3.87 (s, 3 H). MS (ESI): calculated for $C_{16}H_{14}N_2O_3S$, 314.1, found 337.1 [M + Na]$^+$, 312.9 [M − H]$^-$. |

-continued

| Compound | Physicochemical Cheracterization |
|---|---|
| 1-(phenylsulfonyl)-2-(p-tolyl)-1H-imidazole (10d) | Yield: 46.6%. $^1$H NMR (500 MHz, CDCl$_3$) δ 7.63 (d, J = 1.0 Hz, 1 H), 7.55 (t, J = 8.0 Hz, 1 H), 7.42 (d, J = 8.0 Hz, 2 H), 7.35 (t, J = 7.5 Hz, 2 H), 7.27-7.29 (m, 2 H), 7.16 (d, J = 7.5 Hz, 2 H), 7.10 (s, 1 H), 2.41 (s, 3 H). MS (ESI): calculated for C$_{16}$H$_{14}$N$_2$O$_2$S, 298.1, found 321.1 [M + Na]$^+$. |
| 1-(phenylsulfonyl)-2-(3,4,5-trimethoxyphenyl)-1H-imidazole (10e) | Yield: 55.7%. $^1$H NMR (500 MHz, CDCl$_3$) δ 7.68 (d, J = 1.5 Hz, 1 H), 7.55 (t, J = 7.0 Hz, 1 H), 7.42 (d, J = 7.5 Hz, 2 H), 7.35 (t, J = 8.5 Hz, 2 H), 7.11 (d, J = 1.5 Hz, 2 H), 6.60 (s, 1 H), 3.90 (s, 3 H), 3.79 (s, 6 H). MS (ESI): calculated for C$_{18}$H$_{18}$N$_2$O$_5$S, 374.1, found 397.1 [M + Na]$^+$. |
| 2-(4-chlorophenyl)-1-(phenylsulfonyl)-1H-imidazole (10f) | Yield: 54.9%. $^1$H NMR (500 MHz, CDCl$_3$) δ 7.65 (d, J = 2.0 Hz, 1 H), 7.58 (t, J = 7.5 Hz, 1 H), 7.43 (d, J = 8.5 Hz, 2 H), 7.38 (t, J = 8.0 Hz, 2 H), 7.34-7.36 (m, 4 H), 7.12 (d, J = 1.5 Hz, 1 H). MS (ESI): calculated for C$_{15}$H$_{11}$ClN$_2$O$_2$S, 318.0, found 341.0 [M + Na]$^+$. |
| N,N-dimethyl-4-(1-(phenylsulfonyl)-1H-imidazol-2-yl) aniline (10g) | Yield: 48.3%. $^1$H NMR (300 MHz, CDCl$_3$) δ 7.59 (d, J = 2.0 Hz, 1 H), 7.55 (t, J = 8.0 Hz, 1 H), 7.45 (d, J = 7.5 Hz, 2 H), 7.28-7.38 (m, 4 H), 7.07 (d, J = 2.0 Hz, 1 H), 6.68 (d, J = 8.5 Hz, 2 H), 3.04 (s, 3 H). MS (ESI): calculated for C$_{17}$H$_{17}$N$_3$O$_2$S, 327.10, found 350.0 [M + Na]$^+$, 325.9 [M − H]$^-$. |
| 4-(1-((4-Methoxyphenyl)sulfonyl)-1H-imidazol-2-yl)-N,N-dimethylaniline (10gb) | Yield: 61.5%. $^1$H NMR (500 MHz, CDCl$_3$) δ 7.58 (d, J = 1.5 Hz, 1 H), 7.36 (t, J = 8.43 Hz, 4 H), 7.03-7.09 (m, 1 H), 6.80 (d, J = 9.0 Hz, 2 H), 6.69 (d, J = 8.8 Hz, 2 H), 3.84 (s, 3 H), 3.05 (s, 6 H). MS (ESI): calculated for C$_{17}$H$_{17}$N$_3$O$_2$S, 327.1, found 358.2 [M + Na]$^+$. |
| 2-(3,4-dimethoxyphenyl)-1-(phenylsulfonyl)-1H-imidazole (10h) | Yield: 60.3%. $^1$H NMR (500 MHz, CDCl$_3$) δ 7.64 (d, J = 7.0 Hz, 1 H), 7.55 (t, J = 7.5 Hz, 1 H), 7.40 (dd, J = 8.5 Hz, 1.5 Hz, 2 H), 7.35 (t, J = 8.0 Hz, 2H), 7.09 (d, J = 2.0 Hz, 1 H), 7.02 (dd, J = 8.0 Hz, 2.0 Hz, 1 H), 6.89 (d, J = 1.5 Hz, 1 H), 6.86 (d, J = 8.0 Hz, 1 H), 3.95 (s, 3 H), 3.81 (s, 3 H). MS (ESI): calculated for C$_{17}$H$_{16}$N$_2$O$_4$S, 344.10, found 367.0 [M + Na]$^+$. |
| 1-(phenylsulfonyl)-2-(2-(trifluoromethyl)phenyl)-1H-imidazole (10i) | Yield: 58.6%. $^1$H NMR (500 MHz, CDCl$_3$) δ 7.64-7.67 (m, 2 H), 7.61-7.63 (m, 3 H), 7.40-7.46 (m, 5 H), 7.16 (d, J = 1.5 Hz, 1 H). MS (ESI): calculated for C$_{16}$H$_{11}$F$_3$N$_2$O$_2$S, 352.10, found 353.1 [M + H]$^+$. |
| 2-(4-(benzyloxy)phenyl)-1-(phenylsulfonyl)-1H-imidazole (10j) | Yield: 62.0%; mp 102-104° C. $^1$H NMR (500 MHz, CDCl$_3$) δ 7.56 (d, J = 1.0 Hz, 1 H), 7.46 (t, J = 8.0 Hz, 1 H), 7.20-7.40 (m, 11 H), 7.03 (d, J = 1.0 Hz, 1H), 6.89 (t, J = 8.0 Hz, 2 H), 5.08 (s, 2 H). MS (ESI): calculated for C$_{22}$H$_{18}$N$_2$O$_3$S, 390.10, found 413.1 [M + Na]$^+$. HPLC2: t$_R$ 18.22 min, purity 95.9%. |
| 2-(4-Bromophenyl)-1-(phenylsulfonyl)-1H-imidazole (10la) | Yield: 61.2%. $^1$H NMR (500 MHz, CDCl$_3$) δ 7.71 (d, J = 2.0 Hz, 1 H), 7.64 (t, J = 7.0 Hz, 1 H), 7.57 (d, J = 9.0 Hz, 2 H), 7.49 (d, J = 7.0 Hz, 2 H), 7.45 (t, J = 9.0 Hz, 2 H), 7.34 (d, J = 8.5 Hz, 2 H), 7.18 (d, J = 1.5 Hz, 1 H). MS (ESI) calcd for C$_{15}$H$_{11}$BrN$_2$O$_2$S 362.0, found 363.0 [M + H]$^+$. |
| 1-(Phenylsulfonyl)-2-(4-(trifluoromethyl)phenyl)-1H-imidazole (10p) | Yield: 36.7 %; $^1$H NMR (500 MHz, CDCl$_3$) δ 7.75 (d, J = 2.0 Hz, 1 H), 7.69 (d, J = 8.0 Hz, 2 H), 7.65 (t, J = 8.0 Hz, 1 H), 7.60 (d, J = 8.0 Hz, 2 H), 7.48 (d, J = 7.5 Hz, 2 H), 7.43 (t, J = 8.0 Hz, 2 H), 7.22 (d, J = 2.0 Hz, 1 H). MS (ESI) calcd for C$_{16}$H$_{11}$F$_3$N$_2$O$_2$S 352.1, found 553.1 [M + H]$^+$. |
| 2-(4-nitrophenyl)-1-(phenylsulfonyl)-1H-imidazole (10x) | Yield: 50%; mp 145 - 147° C. $^1$H NMR (500 MHz, DMSO-d$_6$) δ 8.28 (d, J = 8.5 Hz, 2 H), 8.03 (d, J = 1.5 Hz, 1 H), 7.78 (t, J = 7.5 Hz, 1 H), 7.64-7.68 (m, 4H), 7.60 (t, J = 8.0 Hz, 2 H), 7.30 (d, J = 1.5 Hz, 1 H). MS (ESI): calculated for C$_{15}$H$_{11}$N$_3$O$_4$S, 329.10, found 352.0 [M + Na]$^+$, 327.9 [M − H]$^-$. HPLC2: t$_R$ 14.87 min, purity 98.8%. |
| (4-methoxyphenyl)(2-phenyl-1-(phenylsulfonyl)-1H-imidazol-4-yl)methanone (11ab) | Yield: 26.3%; mp 118-120° C. $^1$H NMR (500 MHz, DMSO-d$_6$) δ 8.37 (d, J = 1.0 Hz, 1 H), 8.15-8.18 (m, 2 H), 8.12 (d, J = 9.0 Hz, 2 H), |

| Compound | Physicochemical Cheracterization |
|---|---|
| | 7.56-7.64 (m, 5 H), 7.46-7.50 (m, 3 H), 7.16 (d, J = 8.0 Hz, 2 H), 3.90 (s, 3 H). MS (ESI): calculated for $C_{23}H_{18}N_2O_4S$, 418.10, found 419.1 $[M + H]^+$. HPLC2: $t_R$ 17.72 min, purity 95.7%. |
| (3-methoxyphenyl)(2-phenyl-1-(phenylsulfonyl)-1H-imidazol-4-yl)methanone (11ac) | Yield: 31.2%; mp 136-138° C. $^1$H NMR (500 MHz, CDCl$_3$) δ 8.35 (s, 1 H), 7.86 (d, J = 8.0 Hz, 1 H),7.72 (s, 1 H), 7.60 (t, J = 7.5 Hz, 1 H), 7.51 (t, J = 7.5 Hz, 1 H), 7.35-7.42 (m, 9H), 7.14 (dd, J = 8.0 Hz, 2.0 Hz, 1 H), 3.88 (s, 3 H). MS (ESI): calculated for $C_{23}H_{18}N_2O_4S$, 418.10, found 419.1 $[M + H]^+$. HPLC2: $t_R$ 17.72 min, purity 95.7%. |
| (2-phenyl-1-(phenylsulfonyl)-1H-imidazol-4-yl)(p-tolyl)methanone (11ah) | Yield: 28.9%; mp 108-110° C. $^1$H NMR (500 MHz, CDCl$_3$) δ 8.00 (d, J = 7.5 Hz, 2 H), 7.98 (q, J = 8.0 Hz, 1.5 Hz, 2 H), 7.91 (d, J = 8.0 Hz, 1 H), 7.81 (s, 1 H), 7.44-7.48 (m, 3 H), 7.35-7.40 (m, 2 H), 7.30 (t, J = 8.0 Hz, 2 H), 7.20 (s, 2 H), 2.42 (s, 3 H). MS (ESI): calculated for $C_{23}H_{18}N_2O_3S$, 402.10, found 403.1 $[M + H]^+$. HPLC2: $t_R$ 16.06 min, purity 96.2%. |
| (4-fluorophenyl)(2-phenyl-1-(phenylsulfonyl)-1H-imidazol-4-yl)methanone (11af) | Yield: 25.4%; mp 114-116° C. $^1$H NMR (500 MHz, CDCl$_3$) δ 8.10 (q, J = 3.5 Hz, 5.5 Hz, 2 H), 7.88 (d, J = 7.5 Hz, 2 H), 7.67 (t, J = 7.5 Hz, 1 H), 7.48-7.54 (m, 3 H), 7.38-7.41 (m, 5 H), 7.24 (t, J = 8.5 Hz, 2 H). MS (ESI): calculated for $C_{22}H_{15}FN_2O_3S$, 406.10, found 429.1 $[M + Na]^+$. HPLCC2: $t_R$ 15.43 min, purity 96.1%. |
| (3-fluorophenyl)(2-phenyl-1-(phenylsulfonyl)-1H-imidazol-4-yl)methanone (11ag) | Yield: 18.3%; mp 102-104° C. $^1$H NMR (500 MHz, CDCl$_3$) δ 8.14 (d, J = 7.5 Hz, 1 H), 7.76-7.87 (m, 3 H), 7.74 (d, J = 9.0 Hz, 1 H), 7.37-7.57 (m, 10 H), 7.38-7.41 (m, 5 H), 7.24 (t, J = 8.5 Hz, 2 H). MS (ESI): calculated for $C22H_{15}FN_2O_3S$, 406.10, found 429.1 $[M + Na]^+$. HPLC2: $t_R$ 15.75 min, purity 96.5%. |
| (4-fluorophenyl)(2-(4-methoxyphenyl)-1-(phenylsulfonyl)-1H-imidazol-4-yl)methanone (11cb) | Yield: 23.5%; mp 135-137° C. $^1$H NMR (500 MHz, CDCl$_3$) δ 8.00 (d, J = 5.5 Hz, 2 H), 7.74-7.76 (m, 2 H), 7.54-7.58 (m, 1 H), 7.40 (d, J = 7.0 Hz, 2 H), 7.28-7.30 (m, 3 H), 7.14-7.16 (m, 2 H), 6.80-6.82 (m, 2 H), 3.80 (s, 3 H). MS (ESI): calculated for $C_{23}H_{17}FN_2O_4S$, 436.10, found 459.0 $[M + Na]^+$, 434.9 $[M − H]^−$. HPLC2: $t_R$ 16.53 min, Purity 96.1%. |
| (1-(phenylsulfonyl)-2-(p-tolyl)-1H-imidazol-4-yl)(3,4,5-trimethoxyphenyl)methanone (11da) | Yield: 33.8%; $^1$H NMR (500 MHz, CDCl$_3$) δ 8.00 (d, J = 8.0 Hz, 2 H), 7.70 (t, J = 7.5 Hz, 1 H), 7.55 (t, J = 8.0 Hz, 2 H), 7.44 (s, 2 H), 7.34 (s, 2H), 7.31 (d, J = 8.0 Hz, 2 H), 7.21 (d, J = 8.0 Hz, 2 H), 4.00 (s, 3 H), 3.98 (s, 6 H). MS (ESI): calculated for $C_{26}H_{24}N_2O_6S$, 492.14, found 515.2 $[M + Na]^+$ |
| (4-fluorophenyl)(1-(phenylsulfonyl)-2-(p-tolyl)-1H-imidazol-4-yl)methanone (11db) | Yield: 18.6%; mp 142-144° C. $^1$H NMR (500 MHz, CDCl$_3$) δ 8.07 (q, J = 8.5 Hz, 5.5 Hz, 2 H), 7.88 (d, J = 7.5 Hz, 2 H), 7.64 (t, J = 8.0 Hz, 1 H), 7.49 (d, J = 8.0 Hz, 2 H), 7.38 (s, 1H), 7.30 (d, J = 8.0 Hz, 2 H), 7.18-7.24 (m, 4 H), 2.43 (s, 3 H). MS (ESI): calculated for $C_{23}H_{17}FN_2O_3S$, 420.10, found 443.0 $[M + Na]^+$, 418.9 $[M − H]^−$. HPLC2: $t_R$ 17.28 min, purity 97.3%. |
| (1-(phenylsulfonyl)-2-(3,4,5-trimethoxyphenyl)-1H-imidazol-4-yl)(3,4,5-trimethoxyphenyl)methanone (11ea) | Yield: 21.1%; mp 135-137° C. $^1$H NMR (500 MHz, CDCl$_3$) δ 7.91 (d, J = 8 .0 Hz, 2 H), 7.65 (t, J = 7.5 Hz, 1 H), 7.51 (t, J = 8.0 Hz, 2 H), 7.44 (s, 1 H), 7.34 (s, 2 H), 6.60 (s, 2 H), 3.98 (s, 3 H), 3.96 (s, 6 H), 3.91 (s, 3 H), 3.73 (s, 6 H). MS (ESI): calculated for $C_{28}H_{28}N_2O_9S$, 568.2, found 569.2 $[M + H]^+$. HPLC1: $t_R$ 17.86 min, purity 98.9%. |
| (4-fluorophenyl)(1-(phenylsulfonyl)-2-(3,4,5-trimethoxyphenyl)-1H-imidazol-4-yl)methanone (11eb) | Yield: 18.8%; mp 135 - 137° C. $^1$H NMR (500 MHz, CDCl$_3$) δ 8.11 (q, J = 5.5 Hz, 3.0 Hz, 1 H), 8.00 -8.03 (m, 1 H), 7.82 (d, J = 7.5 Hz, 1 H), 7.78 (s, 1 H), 7.64 (t, J = 7.0 Hz, 1 H), 7.48 (t, J = 8 .0 Hz, 1 H), 7.42 (s, 1 H), 7.21 - 7.26 (m, 4 H), 6.62 (s, 1 H), 3.98 (s, 3 H), 3.96 (s, 6 H), 3.93 (s, 3 H). MS (ESI): calculated for $C_{25}H_{21}FN_2O_6S$, 496.10, found 497.1 $[M + H]^+$. HPLC2: $t_R$ 15.26 min, purity 98%. |

| Compound | Physicochemical Cherecterization |
|---|---|
| (2-(4-chlorophenyl)-1-(phenylsulfonyl)-1H-imidazol-4-yl)(4-fluorophenyl)methanone (11fb) | Yield: 36.8%; mp 153-155° C. $^1$H NMR (500 MHz, CDCl$_3$) δ 8.06 (q, J = 5.5 Hz, 3.0Hz, 2 H), 7.89 (d, J = 7.5 Hz, 2 H), 7.68 (t, J = 8.0 Hz, 1 H), 7.52 (t, J = 8.0 Hz, 2 H), 7.34-7.38 (m, 5H), 7.23 (t, J = 8.5 Hz, 2 H). MS (ESI): calculated for C$_{22}$H$_{14}$ClFN$_2$O$_3$S, 440.0, found 463.0 [M + Na]$^+$. HPLC2: $t_R$ 17.72 min, purity 97.38%. |
| (2-(4-(dimethylamino)phenyl)-1-(phenylsulfonyl)-1H-imidazol-4-yl)(3,4,5-trimethoxyphenyl)methanone (11ga) | Yield: 32.2%; mp 157 - 159° C. $^1$H NMR (500 MHz, CDCl3) δ 7.89 (d, J = 8 .0 Hz, 2 H), 7.62 (t, J = 7.5 Hz, 1 H), 7.48 (t, J = 8.0 Hz, 2 H), 7.43 (s, 1 H), 7.32 (d, J = 8.5 Hz, 2 H), 7.30 (s, 2H), 6.62 (d, J = 9.0 Hz, 2 H), 3.97 (s, 3 H), 3.95 (s, 6 H), 3.05 (s, 6 H). MS (ESI): calculated for C$_{27}$H$_{27}$N$_3$O$_6$S, 521.2, found 544.1 [M + Na]$^+$, 519.8 [M − H]$^-$. HPLC2: $t_R$ 16.00 min, purity 97.9%. |
| (2-(4-(dimethylamino)phenyl)-1-(phenylsulfonyl)-1H-imidazol-4-yl)(4-fluorophenyl)methanone (11gb) | Yield: 38.5%; mp 125-127° C. $^1$H NMR (500 MHz, CDCl$_3$) δ 8.04 (q, J = 5.5 Hz, 3.5Hz, 2 H), 7.80 (d, J = 7.5 Hz, 2 H), 7.61 (t, J = 8.0 Hz, 1 H), 7.45 (t, J = 8.0 Hz, 2 H), 7.39 (s, 1 H), 7.35 (d, J = 9.0 Hz, 2 H), 7.21 (t, J = 8.5 Hz, 2 H), 6.62 (d, J = 9.0 Hz, 2 H), 3.05 (s, 6 H). MS (ESI): calculated for C$_{24}$H$_2$OFN$_3$O$_3$S , 449.10, found 472.1 [M + Na]$^+$, 447.9 [M − H]$^-$. HPLC2: $t_R$ 16.85 min, purity 96.5%. |
| (2-(3,4-dimethoxyphenyl)-1-(phenylsulfonyl)-1H-imidazol-4-yl)(3,4,5-trimethoxyphenyl)methanone (11ha) | Yield: 28.6%; mp 136-138° C. $^1$H NMR (300 MHz, CDCl$_3$) δ 7.92 (dd, J = 8.5 Hz, 1.5 Hz, 2 H), 7.66 (t, J = 7 .5 Hz, 2 H), 7.51 (t, J = 7 .5 Hz, 2 H), 7.43 (s, 1 H), 7.33 (s, 2 H), 7.02 (dd, J = 8.0 Hz, 2.0 Hz, 1 H), 6.91 (d, J = 2.0 Hz, 1 H), 6.86 (d, J = 8.5 Hz, 1 H), 3.98 (s, 3 H), 3.96 (s, 9 H), 3.77 (s, 3 H). MS (ESI): calculated for C$_{27}$H$_{26}$N$_2$O$_8$S, 538.10, found 561.1 [M + Na]$^+$, 536.8 [M − H]$^-$. HPLC2: $t_R$ 14.67 min, purity 98.2%. |
| (2-(3,4-dimethoxyphenyl)-1-(phenylsulfonyl)-1H-imidazol-4-yl)(4-fluorophenyl)methanone (11hb) | Yield: 31.9%; mp 144-145° C. $^1$H NMR (300 MHz, CDCl$_3$) δ 8.09 (q, J = 5.5 Hz, 3.5 Hz, 2 H), 7.81 (d, J = 8.0 Hz, 2 H), 7.62 (t, J = 7.5 Hz, 2 H), 7.48 (t, J = 7.5 Hz, 2 H), 7.40 (s, 1 H), 7.21-7.25 (m, 2 H), 7.04 (dd, J = 8.0 Hz, 2.0 Hz, 1 H), 6.92 (d, J = 2.0 Hz, 1 H), 6.86 (d, J = 8.5 Hz, 1 H),3.96 (s, 3 H), 3.79 (s, 6 H). MS (ESI): calculated for C24H$_{19}$FN$_2$O$_5$S, 466.10, found 489.1 [M + Na]$^+$, 464.8 [M − H]$^-$. HPLC2: $t_R$ 15.52 min, purity 97.4%. |
| (1-(phenylsulfonyl)-2-(2-(trifluoromethyl)phenyl)-1H-imidazol-4-yl)(3,4,5-trimethoxyphenyl)methanone (11ia) | Yield: 25.0%; mp 155-157° C. $^1$H NMR (500 MHz, DMSO-d$_6$) δ 7.91 (d, J = 8.0 Hz, 1 H), 7.84 (q, J = 7 .5 Hz, 5.0 Hz, 2 H), 7.77-7.80 (m, 2 H), 7.75 (s, 2 H), 7.66 (t, J = 8.0 Hz, 2 H), 7.56 (d, J = 7 .5 Hz, 1 H), 7.18 (s, 1 H), 3.87 (s, 6 H), 3.81 (s, 3 H). MS (ESI): calculated for C$_{26}$H$_{21}$F$_3$N$_2$O$_6$S, 546.10, found 569.0 [M + Na]$^+$ HPLC2: $t_R$ 16.16 min, purity 98.9%. |
| (1-(phenylsulfonyl)-2-(2-(trifluoromethyl)phenyl)-1H-imidazol-4-yl)(4-fluorophenyl)methanone (11ib) | Yield: 25.0%; mp 151-153° C. $^1$H NMR (500 MHz, CDCl$_3$) δ 8.03 (q, J = 5.5 Hz, 3.0 Hz, 2 H), 7.90 (d, J = 8.0 Hz, 2 H), 7.80 (d, J = 8.0 Hz, 1 H), 7.69 (q, J = 7 .0 Hz, 6.5 Hz, 2 H), 7.61 (t, J = 8.0 Hz, 1 H), 7.52 (t, J = 8.0 Hz, 2 H), 7.34 - 7.36 (m, 2 H), 7.23 (t, J = 8.5 Hz, 2 H). MS (ESI): calculated for C$_{23}$H$_{14}$F$_4$N$_2$O$_3$S, 474.10, found 497.0 [M + Na]$^+$. HPLC2: $t_R$ 16.80 min, purity 98.2%. |
| (2-(4-(benzyloxy)phenyl)-1-(phenylsulfonyl)-1H-imidazol-4-yl)(4-fluorophenyl)methanone (11jb) | Yield: 22.3.0%; mp 149-151° C. $^1$H NMR (500 MHz, CDCl$_3$) δ 8.09 (q, J = 5.5 Hz, 3.5 Hz, 2 H), 7.82 (d, J = 7 .5 Hz, 2 H), 7.63 (t, 7.5 Hz, 1 H), 7.36-7.50(m, 10 H), 7.25 (t, J = 8.5 Hz, 2 H), 6.98 (d, J = 8.0 Hz, 2 H), 5.17 (s, 2 H). MS (ESI): calculated for C$_{29}$H$_{21}$FN$_2$O$_4$S, 512.10, found 535.0 [M + Na]$^+$. HPLC2: $t_R$ 18.35 min, purity 95.1%. |
| (2-(4-bromophenyl)-1-(phenylsulfonyl)-1H-imidazol-4-yl)(3,4,5-trimethoxyphenyl)methanone (11la) | Yield: 32.6% $^1$H NMR (500 MHz, CDCl$_3$) δ 8.06 (d, J = 8.0 Hz, 2 H), 7.88 (d, J = 8.5 Hz, 1 H), 7.77 (t, J = 7.0 Hz, 1 H), 7.54-7.63 (m, 4 H), 7.31-7.36 (m, 4 H), 4.04 (s, 3 H), 4.01 (s, 6 H). MS (ESI) calcd for C$_{25}$H$_{21}$BrN2O$_6$S 556.0, found 557.0 [M + H]$^+$. |

-continued

| Compound | Physicochemical Cheracterization |
|---|---|
| (1-(phenylsulfonyl)-2-(4-(trifluoromethyl)phenyl)-1H-imidazol-4-yl)(3,4,5-trimethoxyphenyl)methanone (11pa) | Yield: 36.7 %; $^1$H NMR (500 MHz, CDCl$_3$) δ 8.06 (d, J = 7.5 Hz, 2 H), 7.78 (t, J = 8.0 Hz, 1 H), 7.72 (d, J = 8.0 Hz, 2 H), 7.62 (d, J = 8.0 Hz, 2 H), 7.59 (d, J = 8.0 Hz, 2 H), 7.50 (s, 1 H), 7.37 (s, 2 H), 4.04 (s, 3 H), 4.02 (s, 6 H). MS (ESI) calcd for C$_{26}$H$_{21}$F$_3$N$_2$O$_6$S 546.1, found 547.1 [M + H]$^+$. |
| (2-(4-(dimethylamino)phenyl)-1-((4-methoxyphenyl)sulfonyl)-1H-imidazol-4-yl)(3,4,5-trimethoxyphenyl)methanone (11gaa) | Yield: 34.1%; mp 147-149° C. $^1$H NMR (500 MHz, CDCl$_3$) δ 8.07 (q, J = 8.5 Hz, 5.5 Hz, 2 H), 7.78 (d, J = 9.0 Hz, 2 H), 7.41 (d, J = 8.5 Hz, 2 H), 7.39 (s, 1 H), 7.23 (t, J = 8.5 Hz, 2 H), 6.91 (d, J = 9.0 Hz, 2 H), 6.68 (d, J = 9.0 Hz, 2 H), 3.89 (s, 3 H), 3.08 (s, 3 H). MS (ESI) calcd for C$_{28}$H$_{29}$N$_3$O$_7$S 551.2, found 573.1 [M + Na]$^+$. HPLC2: t$_R$ 18.6 min, purity 96.9%. |
| (2-phenyl-1H-imidazol-4-yl)(3,4,5-trimethoxyphenyl)methanone (12aa) | Yield: 10.1 %; mp 227-229° C. $^1$H NMR (500 MHz, CDCl$_3$) δ 8.0-8.03 (m, 2 H), 7.83 (s, 1 H), 7.34-7.38 (m, 3 H), 7.21 (s, 2 H), 3.90 (s, 3 H), 3.84 (s, 6 H). MS (ESI): calculated for C$_{19}$H$_{18}$N$_2$O, 338.1, found 337.1 [M − H]$^-$. HPLC2: t$_R$ 14.19 min, purity 96.3%. |
| (4-methoxyphenyl)(2-phenyl-1H-imidazol-4-yl)methanone (12ab) | Yield: 16.6%; mp 179-181° C. $^1$H NMR (500 MHz, CDCl$_3$) δ 11.1 (br, 1 H), 8.07-8.10 (m, 2 H), 8.04 (d, J = 8.5 Hz, 2 H), 7.84 (d, J = 1.0 Hz, 1 H), 7.49-7.51 (m, 3 H), 7.07 (d, J = 9.0 Hz, 2 H), 3.95 (s, 3 H). MS (ESI): calculated for C$_{17}$H$_{14}$N$_2$O$_2$, 278.10, found 279.0 [M + H]$^+$. HPLC1: t$_R$ 15.14 min, purity >99%. |
| (3-methoxyphenyl)(2-phenyl-1H-imidazol-4-yl)methanone (12ac) | Yield: 22.5 %; mp 160-162° C. 41 NMR (500 MHz, CDCl$_3$) δ 11.2 (br, 1 H), 8.10-8.12 (m, 2 H), 7.87 (d, J = 1.0 Hz, 1 H), 7.61 (d, J = 7.5 Hz, 1 H), 7.48 - 7.52 (m, 5 H), 7.21 (dd, J = 2.5 Hz, 8.5Hz, 1 H), 3.91 (s, 3 H). MS (ESI): calculated for C$_{17}$H$_{14}$N$_2$O$_2$, 278.10, found 279.0 [M + H]$^+$. HPLC2: t$_R$ 15.07 min, purity >99%. |
| (3,5-dimethoxyphenyl)(2-phenyl-1H-imidazol-4-yl)methanone (12ad) | Yield: 26.2%; mp 168-170° C. 41 NMR (500 MHz, CDCl$_3$) δ 8.04-8.06 (m, 2 H), 7.88 (s, 1 H), 7.50-7.52 (m, 3 H), 7.15 (d, J = 2.0 Hz, 2 H), 6.75 (t, J = 1.0 Hz, 1 H), 3.89 (s, 6 H). MS (ESI): calculated for C$_{18}$H$_{16}$N$_2$O$_3$, 308.10, found 331.1 [M + Na]$^+$, 306.9 [M − H]$^-$. HPLC2: t$_R$ 15.59 min, purity >99%. |
| (3,4-dimethoxyphenyl)(2-phenyl-1H-imidazol-4-yl)methanone (12ae) | Yield: 18.6%; mp 162-164° C. $^1$H NMR (500 MHz, CDCl$_3$) δ 10.9 (br, 1 H), 8.05 (dd, J = 1.5 Hz, 8.0 Hz, 2 H), 7.86 (d, J = 1.5 Hz, 1 H), 7.74 (dd, J = 2.0 Hz, 8.5 Hz, 1 H), 7.56 (d, J = 2.0 Hz, 1 H), 7.50-7.52 (m, 3 H), 7.04 (d, J = 8.5 Hz, 1 H), 4.03 (s, 3 H), 3.99 (s, 3 H). MS (ESI): calculated for C$_{18}$H$_{16}$N$_2$O$_3$, 308.10, found 331.1 [M + Na]$^+$, 306.9 [M − H]$^-$. HPLC2: t$_R$ 13.54 min, purity >99%. |
| (4-fluorophenyl)(2-phenyl-1H-imidazol-4-yl)methanone (12af) | Yield: 30.2%; mp 231-233° C. $^1$H NMR (500 MHz, CDCl$_3$) δ 10.6 (br, 1 H), 8.02-8.05 (m, 4 H), 7.81 (d, J = 1.0 Hz, 1 H), 7.51-7.54 (m, 3 H), 7.27 (t, J = 8.5 Hz, 2 H). MS (ESI): calculated for C$_{16}$H$_{11}$FN$_2$O, 266.10, found 267.0 [M + H]$^+$, 264.8 [M − H]$^-$. HPLC1: t$_R$ 15.37 min, purity 98.9%. |
| (3-fluorophenyl)(2-phenyl-1H-imidazol-4-yl)methanone (12ag) | Yield: 23.4%; mp 212-214° C. $^1$H NMR (500 MHz, CDCl$_3$) δ 8.05 (dd, J = 1.5 Hz, 7.5 Hz, 2 H), 7.86 (s, 1 H), 7.84 (d, J = 7.0 Hz, 1 H), 7.74 (d, J = 8.5 Hz, 1 H), 7.52-7.58 (m, 4 H), 7.37 (dt, J = 2.0 Hz, 6.0 Hz, 1 H). MS (ESI): calculated for C$_{16}$H$_{11}$FN$_2$O, 266.10, found 267.0 [M + H]$^+$, 264.8 [M − H]$^-$. HPLC1: t$_R$ 15.29 min, purity >99%. |
| (2-phenyl-1H-imidazol-4-yl)(p-tolyl)methanone (12ah) | Yield: 15.6%; mp 225-227° C. $^1$H NMR (500 MHz, CDCl$_3$) δ 11.1 (br, 1 H), 8.08 (d, J = 7.5 Hz, 2 H), 7.93 (d, J = 9.0 Hz, 2 H), 7.84 (s, 1 H), 7.48-7.52 (m, 3 H), 7.38 (d, J = 10.0 Hz, 2 H), 2.50 (s, 3 H). MS (ESI): calculated for C$_{17}$H$_{14}$N$_2$O, 262.10, found 263.0 [M + H]$^+$, 260.8 [M − H]$^-$. HPLC2: t$_R$ 15.86 min, purity 98.7%. |
| (2-phenyl-1H-imidazol-4-yl)(m-tolyl)methanone (12ai) | Yield: 20.5%; mp 168-169° C. $^1$H NMR (500 MHz, CDCl$_3$) δ 11.0 (br, 1 H), 8.09-8.11 (m, 2 |

| Compound | Physicochemical Cheracterization |
|---|---|
| | H), 7.84 (d, J = 1.5 Hz, 1 H), 7.81-7.82 (m, 2 H), 7.47-7.52 (m, 5 H), 2.50 (s, 3 H). MS (ESI): calculated for $C_{17}H_{14}N_2O$, 262.10, found 285.0 $[M + Na]^+$, 260.8 $[M - H]^-$. HPLC2: $t_R$ 15.89 min, purity >99%. |
| (2-(4-fluorophenyl)-1H-imidazol-4-yl)(3,4,5-trimethoxyphenyl)methanone (12ba) | Yield: 12.2%. mp 176-178° C. $^1$H NMR (500 MHz, CDCl$_3$) δ 10.72 (br, 1 H), 8.02 (q, J = 5.0 Hz, 2 H), 7.84 (s, 1 H), 7.19 (t, J = 10.0 Hz, 2 H), 4.00 (s, 6 H), 3.97 (s, 3 H). MS (ESI): calculated for $C_{19}H_{17}FN_2O_4$, 356.10, found 379.1 $[M + Na]^+$, 354.9 $[M - H]^-$. HPLC1: $t_R$ 17.23 min, purity >99% |
| (2-(4-methoxyphenyl)-1H-imidazol-4-yl)(3,4,5-trimethoxyphenyl)methanone (12ca) | Yield: 10.2%; mp 220-222° C. $^1$H NMR (300 MHz, CDCl$_3$) δ 10.24 (br, 1 H), 7.93 (d, J = 14.5 Hz, 2 H), 7.81 (s, 1 H), 7.24 (s, 2 H), 7.03 (d, J = 14.5 Hz, 2 H), 3.97 (s, 3 H), 3.95 (s, 6 H), 3.90 (s, 3 H). MS (ESI): calculated for $C_{20}H_{20}N_2O_5$, 368.10, found 391.0 $[M + Na]^+$, 367.0 $[M - H]^-$. HPLC2: $t_R$ 14.46 min, purity 98.4%. |
| (4-fluorophenyl)(2-(4-methoxyphenyl)-1H-imidazol-4-yl)methanone (12cb) | Yield: 15.2%; mp 245 - 247° C. $^1$H NMR (500 MHz, CDCl$_3$) δ 10.20 (br, 1 H), 7.93-7.96 (m, 2 H), 7.85 (d, J = 5.0 Hz, 2 H), 7.68 (s, 1 H), 7.15-7.17 (m, 2 H), 6.95 (d, J = 6.0 Hz, 2 H), 3.82 (s, 3 H). MS (ESI): calculated for $C_{17}H_{13}FN_2O_2$, 296.10, found 319.1 $[M + Na]^+$, 294.9 $[M - H]^-$. HPLC2: $t_R$ 15.40 min, purity 98.8%. |
| (2-(p-tolyl)-1H-imidazol-4-yl)(3,4,5-trimethoxyphenyl)methanone (12da) | Yield: 48.5%; mp 201-203° C. $^1$H NMR (500 MHz, CDCl$_3$) δ 10.40 (br, 1 H), 7.88 (d, J = 8.0 Hz, 2 H), 7.82 (s, 1 H), 7.31 (d, J = 8.0 Hz, 2 H), 7.24 (s, 2 H), 3.96 (s, 3 H), 3.94 (s, 6 H), 2.43 (s, 3 H). MS (ESI): calculated for $C_{20}H_{20}N_2O_4$, 352.10, found 375.2 $[M + Na]^+$ HPLC2: $t_R$ 15.45 min, purity 97.4%. |
| (4-fluorophenyl)(2-(p-tolyl)-1H-imidazol-4-yl)methanone (12db) | Yield: 56.3%; mp 229-231° C. $^1$H NMR (500 MHz, CDCl$_3$) δ 10.50 (br, 1 H), 7.99-8.02 (m, 2 H), 7.88 (d, J = 8.0 Hz, 2 H), 7.60 (d, J = 1.0 Hz, 1 H), 7.30 (d, J = 8.0 Hz, 2 H), 7.23 (t, J = 9.0 Hz, 2 H), 2.43 (s, 3 H). MS (ESI): calculated for $C_{17}H_{13}FN_2O$, 280.10, found 281.0 $[M + H]^+$, 278.9 $[M - H]^-$. HPLC2: $t_R$ 16.31 min, purity >99%. |
| (4-hydroxy-3,5-dimethoxyphenyl)(2-(p-tolyl)-1H-imidazol-4-yl)methanone (12dc) | Yield: 56.8%; mp 220-222° C. $^1$H NMR (500 MHz, CDCl$_3$) δ 8.02 (d, J = 8.0 Hz, 2H), 7.91(s, 1H), 7.39 (s, 2H), 7.28 (d, J = 7.5 Hz, 2H), 4.00 (s, 6H), 2.44 (s, 3H). MS (ESI) calcd for $C_{19}H_{18}FN_2O_4$ 338.1, found 339.1 $[M + H]^+$. HPLC1: $t_R$ 3.91 min, purity >99%. |
| (3,4,5-trimethoxyphenyl)(2-(3,4,5-trimethoxyphenyl)-1H-imidazol-4-yl)methanone (12ea) | Yield: 86.8%; mp 196 - 198° C. $^1$H NMR (500 MHz, DMSO-d$_6$) δ 13.3 (br, 0.47 H), 13.50 (br, 0.52 H), 8.19 (s, 0.49 H), 7.90 (s, 1 H), 7.83 (s, 0.5 H), 7.59 (s, 1 H), 7.40 (s, 1 H), 7.18 (s, 1 H), 3.89 (s, 6 H), 3.86 (s, 6 H), 3.77 (s, 3 H), 3.72 (s, 3 H). MS (ESI): calculated for $C_{22}H_{24}N_2O_7$, 428.2, found 451.1$[M + Na]^+$, 426.9 $[M - H]^-$. HPLC2: $t_R$ 14.49 min, purity >99%. |
| (4-fluorophenyl)(2-(3,4,5-trimethoxyphenyl)-1H-imidazol-4-yl)methanone (12eb) | Yield: 90.2%; mp 153-155° C. $^1$H NMR (500 MHz, CDCl$_3$) δ 10.42 (br, 1 H), 8.00 (q, J = 5.5 Hz, 3.0Hz, 2 H), 7.76 (s, 1 H), 7.23 (t, J = 8.5 Hz, 2 H), 7.19 (s, 2 H), 3.94 (s, 3 H), 3.92 (s, 3 H). MS (ESI): calculated for $C_{19}H_{17}FN_2O_4$, 356.1, found 379.0 $[M + Na]^+$, 354.9 $[M - H]^-$. HPLC2: $t_R$ 15.31 min, purity >99%. |
| (2-(4-chlorophenyl)-1H-imidazol-4-yl)(3,4,5-trimethoxyphenyl)methanone (12fa) | Yield: 36.9%; mp 193 - 195° C. $^1$H NMR (500 MHz, CDCl$_3$) δ 10.75 (br, 1 H), 7.96 (d, J = 8.5 Hz, 2 H), 7.83 (s, 1 H), 7.47 (d, J = 9.0 Hz, 2 H), 7.23 (s, 2 H), 3.97 (s, 3 H), 3.94 (s, 6 H), 2.43 (s, 3 H). MS (ESI): calculated for $C_{19}H_{17}ClN_2O_4$, 372.1, found 395.1 $[M + Na]^+$, 370.9 $[M - H]^-$. HPLC2: $t_R$ 16.36 min, purity > 99%. |
| (2-(4-chlorophenyl)-1H-imidazol-4-yl)(4-fluorophenyl)methanone (12fb) | Yield: 83.7%; mp 232 - 234° C. $^1$H NMR (500 MHz, CDCl$_3$) δ 10.78 (br, 1 H), 8.00 (q, J = 5.5 Hz, 3.0Hz, 2 H), 7.96 (d, J = 9.0 Hz, 2 H), 7.78 (s, 1 H), 7.47 (d, J = 8.0 Hz, 2 H), 7.24 (t, J = 8.5 Hz, 2 H). MS (ESI): calculated for $C_{16}H_{10}ClFN_2O$, 300.1, found 323.0 $[M + Na]^+$, |

| Compound | Physicochemical Cheracterization |
|---|---|
| | 298.8 [M − H]⁻. HPLC2: $t_R$ 17.08 min, purity >99%. |
| (2-(4-chlorophenyl)-1H-imidazol-4-yl)(4-hydroxy-3,5-dimethoxyphenyl)methanone (12fc) | Yield: 80.2%; mp 216-218° C. ¹H NMR (500 MHz, CD₃OD) δ 8.06 (d, J = 8.5 Hz, 2 H), 7.99 (s, 1 H), 7.61 (d, J = 8.0 Hz, 2 H), 7.52 (s, 2 H), 4.01 (s, 6 H). MS (ESI) calcd for $C_{18}H_{15}ClN_2O_4$ 358.1, found 359.1 [M + H]⁺. HPLC2: $t_R$ 4.12 min, purity >99%. |
| (2-(4-(dimethylamino)phenyl)-1H-imidazol-4-yl)(3,4,5-trimethoxyphenyl)methanone (12ga) | Yield: 91.2%; mp 195-197° C. ¹H NMR (500 MHz, CDCl₃) δ 10.39 (br, 1 H), 7.87 (d, J = 8.5 Hz, 2 H), 7.80 (s, 1 H), 7.23 (s, 2 H), 6.75(d, J = 9.0 Hz, 2 H), 3.95 (s, 3 H), 3.94 (s, 6 H), 3.05 (s, 6 H). MS (ESI): calculated for $C_{21}H_{23}N_3O_4$, 381.2, found 404.2 [M + Na]⁺, 380.0 [M − H]⁻. HPLC2: $t_R$ 15.20 min, purity 95.8%. |
| (2-(4-(dimethylamino)phenyl)-1H-imidazol-4-yl)(4-fluorophenyl)methanone (12gb) | Yield: 86.7%; mp 278-280° C. ¹H NMR (500 MHz, CDCl₃) δ 10.21 (br, 1 H), 7.98 (q, J = 5.0 Hz, 3.5Hz, 2 H), 7.84 (d, J = 8.5 Hz, 2 H), 7.72 (s, 1 H), 7.20 (t, J = 8.5 Hz, 2 H), 6.76 (t, J = 9.0 Hz, 2 H), 3.06 (s, 6 H). MS (ESI): calculated for $C_{18}H_{16}FN_3O$, 309.1, found 332.1 [M + Na]⁺, 307.9 [M − H]⁻. HPLC2: $t_R$ 16.06 min, purity 95.6%. |
| (2-(3,4-dimethoxyphenyl)-1H-imidazol-4-yl)(3,4,5-trimethoxyphenyl)methanone (12ha) | Yield: 85.0 %; mp 100-102° C. ¹H NMR (500 MHz, CDCl₃) δ 10.19 (br, 1 H), 7.81 (s, 1 H), 7.58 (d, J = 1.5 Hz, 1 H), 7.48 (d, J = 8.0 Hz, 1 H), 7.25 (s, 2 H), 6.97 (d, J = 8.5 Hz, 1 H), 4.00 (s, 3 H), 3.96 (s, 6 H), 3.95 (s, 6 H). MS (ESI): calculated for $C_{21}H_{22}N_2O_6$, 398.2, found 399.1 [M + H]⁺ 397.0 [M − H]⁻. HPLC2: $t_R$ 13.73 min, purity >99%. |
| (2-(3,4-dimethoxyphenyl)-1H-imidazol-4-yl)(4-fluorophenyl)methanone (12hb) | Yield: 78.3%; mp 174-176° C. ¹H NMR (500 MHz, CDCl₃) δ 8.02 (t, J = 9.0 Hz, 2 H), 7.75 (s, 1 H), 7.57 (s, 1 H), 7.48 (d, J = 8.5 Hz, 1 H), 7.23 (t, J = 8.5 Hz, 2 H), 6.95 (d, J = 8.5 Hz, 1 H), 3.99 (s, 3 H), 3.96 (s, 3 H). MS (ESI): calculated for $C_{18}H_{15}FN_2O_3$, 326.1, found 349.0 [M + Na]⁺, 324.9 [M − H]⁻. HPLC2: $t_R$ 14.65 min, purity >99%. |
| (2-(2-(trifluoromethyl)phenyl)-1H-imidazol-4-yl)(3,4,5-trimethoxyphenyl)methanone (12ia) | Yield: 83.8%; mp 75-77° C. ¹H NMR (500 MHz, CDCl₃) δ 10.37 (br, 1 H), 8.00-8.02 (m, 1 H), 7.87 (s, 1 H), 7.82-7.85 (m, 1 H), 7.69-7.74 (m, 1 H), 7.62-7.66 (m, 1 H), 7.25 (s, 2 H), 3.99 (s, 3 H), 3.98 (s, 6 H). MS (ESI): calculated for $C_{20}H_{17}F_3N_2O_4$, 406.1, found 429.1 [M + Na]⁺, 405.0 [M − H]⁻. HPLC2: $t_R$ 13.98 min, purity >99%. |
| (4-fluorophenyl)(2-(2-(trifluoromethyl)phenyl)-1H-imidazol-4-yl)methanone (12ib) | Yield: 91.1%; mp 152-154° C. ¹H NMR (500 MHz, CDCl₃) δ 8.12-8.14 (m, 2 H), 7.97 (d, J = 7.5 Hz, 1 H), 7.82-7.85 (m, 2 H), 7.69 (t, J = 7.5 Hz, 1 H), 7.61 (t, J = 8.0 Hz, 1 H), 7.22 (t, J = 9.0 Hz, 2 H). MS (ESI): calculated for $C_{17}H_{10}R_4N_2O$, 334.1, found 357.1 [M + Na]⁺, 332.9 [M − H]⁻. HPLC2: $t_R$ 15.10 min, purity > 99%. |
| (2-(4-(benzyloxy)phenyl)-1H-imidazol-4-yl)(3,4,5-trimethoxyphenyl)methanone (12ja) | Yield: 16.5%; mp 191-193° C. ¹H NMR (500 MHz, CDCl₃) δ 10.22 (br, 1 H), 7.93 (d, J = 9.0 Hz, 2 H), 7.81 (s, 1 H), 7.37-7.47 (m, 5 H), 7.24 (s, 2 H), 7.11 (d, J = 8.5 Hz, 2 H), 5.16 (s, 2 H), 3.97 (s, 3 H), 3.95 (s, 6 H). MS (ESI): calculated for $C_{26}H_{24}N_2O_5$, 444.2, found 467.1 [M + Na]⁺, 442.9 [M − H]⁻. HPLC2: $t_R$ 17.36 min, purity 95.5%. |
| (2-(4-(benzyloxy)phenyl)-1H-imidazol-4-yl)(4-fluorophenyl)methanone (12jb) | Yield: 84.7%; mp 212-214° C. ¹H NMR (300 MHz, CDCl₃) δ 10.28 (br, 1 H), 799-8.04 (m, 2 H), 7.92-7.95 (m, 2 H), 7.76 (d, J = 1.5 Hz, 1 H), 7.38-7.48 (m, 5 H), 7.20-7.25 (m, 2 H), 7.09-7.12 (m, 2 H), 5.16 (s, 2 H). MS (ESI): calculated for $C_{23}H_{17}FN_2O_2$, 372.1, found 395.1 [M + Na]⁺. HPLC2: $t_R$ 17.97 min, purity 97.8%. |
| (2-(4-hydroxyphenyl)-1H-imidazol-4-yl)(3,4,5-trimethoxyphenyl)methanone (12ka) | Yield: 72.3%. mp 191-193° C. ¹H NMR (500 MHz, CD₃OD) δ 8.31 (s, 1 H), 7.90 (d, J = 8.5 Hz, 2 H), 7.31 (s, 2 H), 7.05 (s, 2 H), 3.95 (s, 6 H), 3.88 (s, 3 H). MS (ESI): calculated for $C_{19}H_{18}N_2O_5$, 354.1, found 355.1 [M + H]⁺, 352.9 [M − H]⁻. HPLC2: $t_R$ 12.25 min, purity 98.7%. |

-continued

| Compound | Physicochemical Cherecterization |
|---|---|
| (2-(4-(hydroxyphenyl)-1H-imidazol-4-yl)(4-fluorophenyl)methanone (12kb) | Yield: 89.0%; mp 276-278° C. $^1$H NMR (500 MHz, CDCl$_3$) δ 8.31 (s, 1 H), 8.13 (q, J = 5.5 Hz, 3.0 Hz, 2 H), 7.93 (d, J = 8.5 Hz, 2 H), 7.38 (t, J = 8.5 Hz, 2 H), 7.07 (d, J = 8.5 Hz, 2 H). MS (ESI): calculated for C$_{16}$H$_{11}$FN$_2$O$_2$, 282.1, found 283.0 [M + H]$^+$, 280.9 [M − H]$^-$. HPLC2: t$_R$ 13.46 min, purity 97.65%. |
| (2-(4-bromophenyl)-1H-imidazol-4-yl)(3,4,5-trimethoxyphenyl)methanone (12la) | Yield: 25.6%; mp 190-192° C. $^1$H NMR (500 MHz, CDCl$_3$) δ 7.99 (d, J = 8.5 Hz, 2 H), 7.92 (s, 1 H), 7.70 (d, J = 8.5 Hz, 2 H), 7.32 (s, 2 H), 4.03 (s, 3 H), 4.00 (s, 6 H). MS (ESI) calcd for C$_{19}$H$_{17}$BrN$_2$O$_4$ 416.0, found 417.0 [M + H]$^+$. HPLC2: t$_R$ 4.24 min, purity 98.8%. |
| (2-(4-(trifluoromethyl)phenyl)-1H-imidazol-4-yl)(3,4,5-trimethoxyphenyl)methanone (12pa) | Yield: 85.3%; mp 195-196° C. $^1$H NMR (500 MHz, CDCl$_3$) δ 8.22 (d, J = 8.5 Hz, 2 H), 7.96 (s, 1 H), 7.83 (d, J = 8.5 Hz, 2 H), 7.34 (s, 2 H), 4.04 (s, 3 H), 4.00 (s, 6 H). MS (ESI) calcd for C$_{20}$H$_{17}$F$_3$N$_2$O$_4$. 406.1, found 407.1 [M + H]$^+$, HPLC2: t$_R$ 18.00 min, purity >99%. |
| (2-phenyl-1H-imidazol-1-yl)(3,4,5-trimethoxyphenyl)methanone (12aaa) | Yield: 39.8%; mp 113-115° C. $^1$H NMR (500 MHz, CDCl$_3$) δ 7.53 (q, J = 5.0 Hz, 3.0 Hz, 2 H), 7.41 (d, J = 1.0 Hz, 1 H), 7.33-7.35 (m, 3 H), 7.23 (d, J = 1.0 Hz, 1 H), 7.03 (s, 2 H), 3.93 (s, 3 H), 3.85 (s, 6 H). MS (ESI): calculated for C$_{19}$H$_{18}$N$_2$O$_4$, 338.1, found 339.1 [M + H]$^+$. HPLC2: t$_R$ 13.8 min, purity 95.6%. |
| (4-methoxyphenyl)(2-phenyl-1H-imidazol-1-yl)methanone (12aba) | Yield: 56.3%; mp 68-70° C. $^1$H NMR (500 MHz, CDCl$_3$) δ 7.78 (d, J = 9.0 Hz, 2 H), 7.54-7.56 (m, 2 H), 7.32-7.34 (m, 4 H), 7.21 (d, J = 1.0 Hz, 1 H), 6.93 (d, J = 8.5 Hz, 2 H), 3.90 (s, 3 H). MS (ESI): calculated for C$_{17}$H$_{14}$N$_2$O$_2$, 278.1, found 301.0 [M + Na]$^+$, 276.8 [M − H]$^-$. HPLC2: t$_R$ 14.72 min, purity 95.7%. |
| (4-fluorophenyl)(2-(p-tolyl)-1H-imidazol-4-yl)methanone HCl salt (12db-HCl) | Yield: 95%; mp 115-117° C. $^1$H NMR (500 MHz, DMSO-d$_6$) δ 8.20-8.23 (m, 2 H), 8.18 (s, 1 H), 8.04 (d, J = 6.5 Hz, 2 H), 7.42 (t, J = 8.0 Hz, 2 H), 7.37 (d, J = 7.0 Hz, 2 H), 2.38 (s, 3 H). MS (ESI): calculated for C$_{17}$H$_{14}$FClN$_2$O, 316.1, found 281.0 [M − HCl + H]$^+$. HPLC2: t$_R$ 17.16 min, purity >99%. |
| (4-fluorophenyl)(2-(4-methoxyphenyl)-1-methyl-1H-imidazol-4-yl)methanone (12cba) | Yield: 90.2%; mp 148-150° C. $^1$H NMR (500 MHz, CDCl$_3$) δ 8.45 (q, J = 8.5 Hz, 5.5 Hz, 2 H), 7.79 (s, 1 H), 7.63 (d, J = 8.5 Hz, 2 H), 7.16 (t, J = 8.5 Hz, 2 H), 7.03 (d, J = 9.0 Hz, 2 H), 3.89 (s, 3 H), 3.82 (s, 3 H). MS (ESI) calcd for C$_{18}$H$_{15}$FN$_2$O$_2$ 310.1, found 311.0 [M + H]$^+$. HPLC2: t$_R$ 4.01 min, purity 97.6%. |
| (1-benzyl-2-(p-tolyl)-1H-imidazol-4-yl)(3,4,5-trimethoxyphenyl)methanone (12daa) | Yield: 92.8%; mp 135-137° C. $^1$H NMR (500 MHz, CDCl$_3$) δ 7.81 (s, 1 H), 7.80 (d, J = 6.5 Hz, 2 H), 7.58 (d, J = 8.0 Hz, 2 H), 7.41-7.45 (m, 3 H), 7.31-7.33 (m, 2 H), 7.20 (d, J = 7.0 Hz, 2 H), 5.33 (s, 2 H), 3.99 (s, 3 H), 3.98 (s, 6 H), 2.47 (s, 3 H). MS (ESI) calcd for C$_{27}$H$_{26}$N$_2$O$_4$ 442.2, found 443.1 [M + Na]$^+$ HPLC1: t$_R$ 4.28 min, purity >99%. |
| (1-methyl-2-(p-tolyl)-1H-imidazol-4-yl)(3,4,5-trimethoxyphenyl)methanone (12dab) | Yield: 87.4%; mp 110-112° C. $^1$H NMR (500 MHz, CDCl$_3$) δ 7.87 (s, 2 H), 7.86 (d, J = 8.0 Hz, 1 H), 7.65 (d, J = 10 Hz, 2 H), 7.37 (d, J = 10 Hz, 2 H), 4.01 (s, 6 H), 4.00 (s, 3 H), 3.90 (s, 3 H). MS (ESI) calcd for C$_{21}$H$_{22}$N$_2$O$_4$ 366.2, found 367.2 [M + H]$^+$. HPLC1: tR 4.23 min, purity >99%. |
| (2-(4-(dimethylamino)phenyl)-1-((4-methoxyphenyl)sulfonyl)-1H-imidazol-4-yl)(4-fluorophenyl)methanone (12gba) | Yield: 34.1%; mp 147-149° C. $^1$H NMR (CDCl$_3$, 500 MHz) δ 8.07 (q, J = 8.5 Hz, 5.5 Hz, 2 H), 7.78 (d, J = 9.0 Hz, 2 H), 7.41 (d, J = 8.5 Hz, 2 H), 7.39 (s, 1 H), 7.23 (t, J = 8.5 Hz, 2 H), 6.91 (d, J = 9.0 Hz, 2 H), 6.68 (d, J = 9.0 Hz, 2 H), 3.89 (s, 3 H), 3.08 (s, 3 H). MS (ESI) calcd for C$_{25}$H$_{22}$FN$_3$O$_4$S 479.1, found 502.1 [M + Na]$^+$. HPLC2: t$_R$ 18.6 min, purity 96.9%. |
| (3,4,5-trihydroxyphenyl)(2-(3,4,5-trihydroxyphenyl)-1H-imidazol-4-yl)methanone (13ea) | Yield: 66.1 %. mp 294 - 296° C. $^1$H NMR (500 MHz, CD$_3$OD) δ 8.07 (s, 1 H), 7.07 (s, 2 H), 7.02 (s, 2 H). MS (ESI): calculated for C$_{16}$H$_{12}$N$_2$O$_7$, 344.1, found 345.0[M + H]$^+$, 342.9 [M − H]$^-$. HPLC2: t$_R$ 3.62 min, purity 97.9%. |
| (2-(4-chlorophenyl)-1H-imidazol-4-yl)(3,4,5-trihydroxyphenyl)methanone (13fa) | Yield: 79.3%; mp >300° C. $^1$H NMR (500 MHz, CD$_3$OD) δ 8.02 (d, J = 8.5 Hz, 2 H), 7.77 |

| Compound | Physicochemical Cheracterization |
| --- | --- |
| (2-(3,4-dihydroxyphenyl)-1H-imidazol-4-yl)(3,4,5-trihydroxyphenyl)methanone (13ha) | (s, 1 H), 7.54 (d, J = 8.5 Hz, 2 H), 7.14 (s, 2 H). MS (ESI): calculated for $C_{16}H_{11}ClN_2O_4$, 330.0, found 331.1 [M + Na]$^+$, 328.9 [M − H]$^-$. HPLC2: $t_R$ 11.9 min, purity 95.6%. Yield: 62.2 %; mp >300° C. $^1$H NMR (500 MHz, $CD_3OD$) δ 8.11 (s, 1 H), 7.46 (d, J = 2.0 Hz, 1 H), 7.42 (dd, J = 8.5 Hz, 2.0 Hz, 1 H), 7.10 (s, 2 H), 7.02 (d, J = 8.5 Hz, 1 H). MS (ESI): calculated for $C_{16}H_{12}N_2O_6$, 328.1, found 329.0 [M + H]$^+$ 326.9 [M − H]$^-$. HPLC2: $t_R$ 3.64 min, purity 97.9%. |
| 2-(4-nitrophenyl)-4,5-dihydro-1H-imidazole (14x) | Yield: 70.3%. $^1$H NMR (500 MHz, CDCl$_3$) δ 8.30 (d, J = 9.0 Hz, 2 H), 7.98 (d, J = 8.5 Hz, 2 H), 3.88-3.95 (m, 4 H). MS (ESI): calculated for $C_9H_9N_3O_2$, 191.10, found 191.9 [M + H]$^+$, 189.7 [M − H]$^-$. |
| 2-(4-fluorophenyl)-4,5-dihydro-1H-imidazole (14b) | Yield: 60.2%. $^1$H NMR (500 MHz, CDCl$_3$) δ 7.80 (q, J = 7.0 Hz, 2 H), 7.11 (d, J = 10.0 Hz, 2 H), 3.82 (br, 4 H). MS (ESI): calculated for $C_9H_9FN_2$, 164.10, found 165 [M + H]$^+$. |
| 2-(4-methoxyphenyl)-4,5-dihydro-1H-imidazole (14c) | Yield: 56.9%. $^1$H NMR (500 MHz, CDCl$_3$) δ 7.84 (d, J = 8.5 Hz, 2 H), 6.94 (d, J = 9.0 Hz, 2 H), 3.87 (s, 3 H), 3.85 (br, 4 H). MS (ESI): calculated for $C_{10}H_{12}N_2O$, 176.10, found 177.0 [M + H]$^+$. |

Example 6

Synthesis of Selected Indolyl-Benzoyl-Imidazole Compounds

Figure 12:
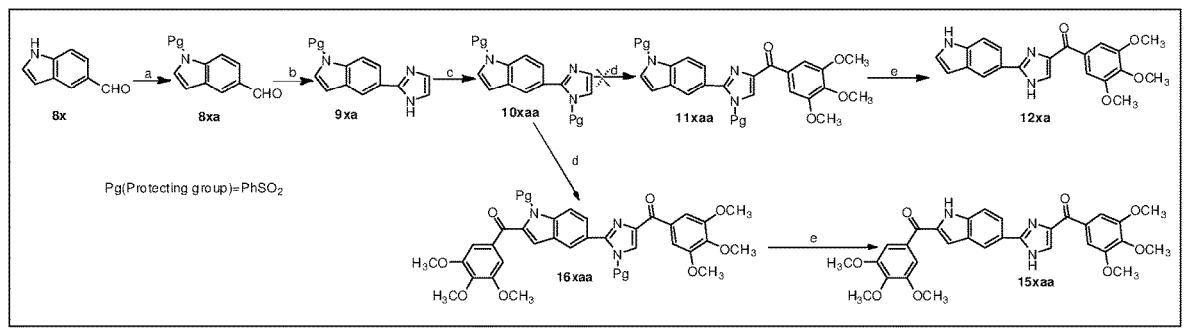
FIG. 12 depicts the synthetic scheme of compound 15xaa and 12xa. (a) 1. KOH, ethanol; 2. PhSO$_2$Cl, acetone, RT; (b) NH$_4$OH, glyoxal, ethanol, RT; (c) NaH, PhSO$_2$Cl, THF, 0° C.-RT; (d) t-BuLi (1.7 M in pentane), 3,4,5-trimethoxybenzoyl chloride, THF, −78° C.; (e) NaOH, ethanol, H$_2$O, reflux.

The synthesis of 15xaa is outlined in FIG. 12. This route was originally designed for the synthesis of 12xa, but the nonselectively of the benzoylation at the indole-2 and imidazole-4 positions resulted in the formation of 15xaa, which is a closely related but bulkier analog of 11xaa. The indole-5-carboxaldehyde 8x was protected by a phenylsulfonyl group on the indole NH to afford intermediate 8xa. 8xa was reacted with glyoxal and ammonium hydroxide to generate the 2-aryl-imidazole 9xa. Protection of the imidazole NH with phenylsulfonyl gave the intermediate 10xaa which was coupled with 3,4,5-trimethoxybenzoyl chloride to produce 16xaa. Removal of the protecting group from 16xaa provided 15xaa.

Synthesis of 1-(Phenylsulfonyl)-1H-indole-5-carbaldehyde (8xa). To a solution of indole-3-carboxaldehyde (100 mmol) in ethanol (500 mL) at room temperature was added potassium hydroxide (110 equiv), the mixture was stirred until total solubilization. The ethanol was completely removed in vacuum and acetone (250 mL) added followed by benzenesulfonyl chloride (110 equiv). The precipitate was filtered off and the filtrate was concentrated and recrystallized from methanol to give a white solid. Yield: 32.6% $^1$H NMR (500 MHz, CDCl$_3$) δ 10.17 (s, 1H), 8.25-8.39 (m, 2H), 7.97-8.09 (m, 3H), 7.69 (t, J=7.33 Hz, 1H), 7.59 (t, J=7.5 Hz, 2H), 7.39-7.54 (m, 2H). MS (ESI) calcd for $C_{15}H_{11}NO_3S$ 285.1, found 286.0 [M+H]$^+$.

Synthesis of (5-(4-(3,4,5-Trimethoxybenzoyl)-1H-imidazol-2-yl)-1H-indol-2-yl)(3,4,5-trimethoxyphenyl)methanone (15xaa): To a solution of (1-(phenylsulfonyl)-2-(1-(phenylsulfonyl)-2-(3,4,5-trimethoxybenzoyl)-1H-indol-5-yl)-1H-imidazol-4-yl)(3,4,5-trimethoxyphenyl)methanone (16xaa) (1 mmol) in ethanol (20 mL) was added sodium hydroxide (10 equiv) and stirred overnight in darkness. The reaction mixture was diluted by 50 mL of water and extracted by ethyl acetate (250 mL). The organic layer was dried over magnesium sulfate and concentrated. The residue was purified by flash column chromatography (hexane:ethyl acetate 3:1) or recrystallized from water and methanol to give a white solid. Yield: 30-95%.

5-(1H-Imidazol-2-yl)-1-(phenylsulfonyl)-1H-indole (9xa). Yield: 12.0%. $^1$H NMR (500 MHz, DMSO-d$_6$) δ 8.33 (d, J=2.9 Hz, 2H), 8.13 (d, J=7.8 Hz, 2H), 7.98-8.04 (m, 1H), 7.62-7.67 (m, 1H), 7.55 (d, J=7.82 Hz, 2H), 7.22-7.34 (m, 4H). MS (ESI) calcd for $C_{17}H_{13}N_3O_2S$ 323.1, found 324.0 [M+H]$^+$.

1-(Phenylsulfonyl)-5-(1-(phenylsulfonyl)-1H-imidazol-2-yl)-1H-indole (10xaa). Yield: 23.6%. $^1$H NMR (500 MHz, CDCl$_3$) δ 8.01 (d, J=8.5 Hz, 1H), 7.95 (d, J=7.5 Hz, 2H), 7.73 (d, J=1.0 Hz, 1H), 7.70 (d, J=4.0 Hz, 1H), 7.63-7.66 (m, 2H), 7.52-7.56 (m, 3H), 7.31-7.34 (m, 3H), 7.22 (t, J=8.5 Hz, 2H), 7.17 (s, 1H), 6.14 (d, J=3.5 Hz, 1H). MS (ESI) calcd for $C_{23}H_{17}N_3O_4S_2$ 463.1, found 464.0 [M+H]$^+$.

(1-(Phenylsulfonyl)-2-(1-(phenylsulfonyl)-2-(3,4,5-trimethoxybenzoyl)-1H-indol-5-yl)-1H-imidazol-4-yl)(3,4,5-trimethoxyphenyl)methanone (16xaa). Yield: 15.9%. $^1$H NMR (500 MHz, CDCl$_3$) δ 8.18-8.25 (m, 3H), 8.04 (d, J=8.1 Hz, 2H), 7.70-7.78 (m, 2H), 7.61-7.69 (m, 3H), 7.55 (t, J=7.7 Hz, 3H), 7.50 (s, 1H), 7.38 (s, 2H), 7.34 (s, 2H), 6.94 (s, 1H), 3.99-4.06 (m, 12H), 3.94-3.99 (m, 6H). MS (ESI) calcd for $C_{43}H_{37}N_3O_{12}S_2$ 851.2, found 852.1 [M+H]$^+$.

(5-(4-(3,4,5-Trimethoxybenzoyl)-1H-imidazol-2-yl)-1H-indol-2-yl)(3,4,5-trimethoxyphenyl)methanone (15xaa). Yield: 45.9%; mp 239-241° C. $^1$H NMR (500 MHz, CDCl$_3$) δ 10.45 (s, 1H), 9.44 (s, 1H), 8.41 (s, 1H), 8.04 (d, J=8.5 Hz, 1H), 7.86 (s, 1H), 7.61 (d, J=8.5 Hz, 1H), 7.29 (s, 2H), 7.26 (s, 2H), 3.99 (s, 3H), 3.95-3.97 (m, 15H). MS (ESI) calcd for $C_{31}H_{29}N_3O_8$ 571.2, found 572.2 [M+H]$^+$. HPLC2: $t_R$ 4.09 min, purity 96.3%.

Example 7

Figure 13:
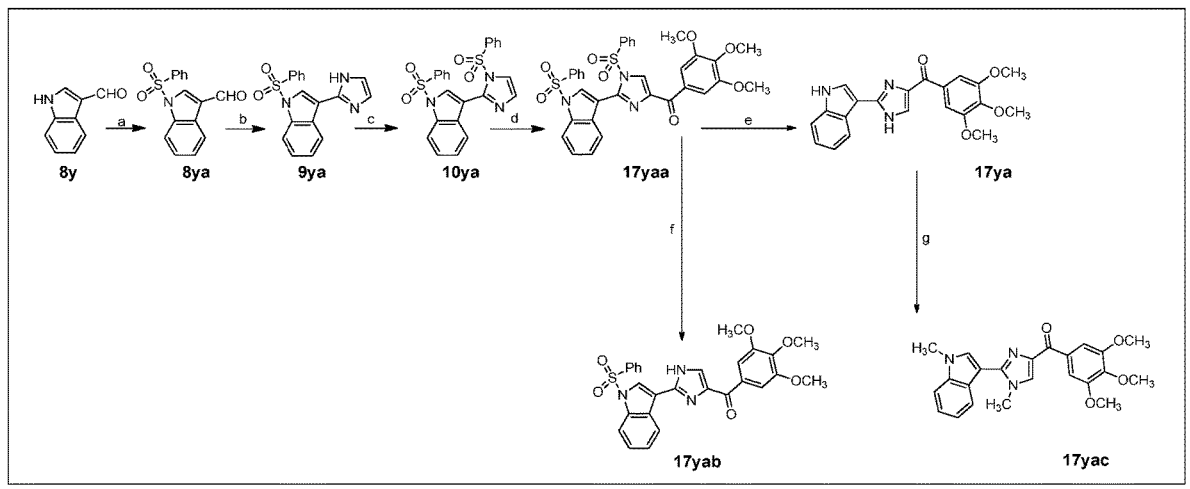
FIG. 13 depicts synthetic scheme of 17ya, 17yab and 17yac. (a) 1. KOH, ethanol, 2. PhSO$_2$Cl, acetone, RT; (b) NH$_4$OH, glyoxal, ethanol, RT; (c) NaH, PhSO$_2$Cl, THF, 0° C.-RT; (d) t-BuLi (1.7 M in pentane), 3,4,5-trimethoxybenzoyl chloride, THF, −78° C.; (e) NaOH, ethanol, H$_2$O, reflux; (f) TBAF, THF, RT; (g) NaH, CH$_3$I, THF.

SYNTHESIS OF (INDOLYL)-1H-IMIDAZOL-4-YL)(3,4,5-TRIMETHOXYPHENYL)METHA-NONES (17ya), (17yab) and (17yac) (FIG. 13)

Synthesis of (2-(1H-indol-3-yl)-1H-imidazol-4-yl)(3,4,5-trimethoxyphenyl)methanone (17ya)

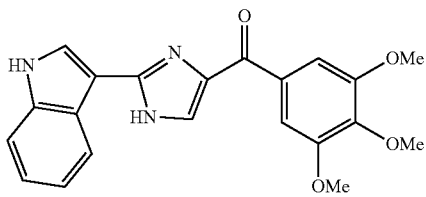

(17ya)

Synthesis of 1-(phenylsulfonyl)-1H-indole-3-carboxaldehyde (8ya): To a solution of indole 3-carboxaldehyde (8y) (100 mmol) in ethanol (500 mL) at RT was added potassium hydroxide (1.1 equiv). The mixture was stirred until total solubilization. The ethanol was completely removed in vacuum and the residual was dissolved in acetone (250 mL) followed by adding benzenesulfonyl chloride (1.1 equiv, 110 mmol). The reaction mixture was stirred for half hour. The precipitate was filtered off and the filtrate was concentrated and recrystallized from methanol to give a white solid. Yield: 33%. $^1$H NMR (500 MHz, CDCl$_3$) δ 10.17 (s, 1H), 8.25-8.39 (m, 2H), 7.97-8.09 (m, 3H), 7.69 (t, J=7.33 Hz, 1H), 7.59 (t, J=7.5 Hz, 2H), 7.39-7.54 (m, 2H). MS (ESI) calcd for C$_{15}$H$_{11}$NO$_3$S 285.1, found 286.0 [M+H]$^+$.

Synthesis of 3-(1H-imidazol-2-yl)-1-(phenylsulfonyl)-1H-indole (9ya): To a solution of 1-(phenylsulfonyl)-1H-indole-3-carboxaldehyde (8ya) (100 mmol) in ethanol (400 mL) at 0° C. was added a solution of 40% oxalaldehyde (glyoxal) in water (1.1 equiv, 110 mmol) and a solution of 29% ammonium hydroxide in water (10 equiv, 1000 mmol). After stirring for 2-3 days at RT, the reaction mixture was quenched by water and extracted by dichloromethane. The organic layer was removed by vacuum and the residue was subjected to flash column chromatography with hexane/ethyl acetate (4:1-2:1) as eluent to yield the titled compound as a yellow powder. Yield: 12%. $^1$H NMR (500 MHz, DMSO-d$_6$) δ 8.33 (d, J=2.9 Hz, 2H), 8.13 (d, J=7.8 Hz, 2H), 7.98-8.04 (m, 1H), 7.62-7.67 (m, 1H), 7.55 (d, J=7.82 Hz, 2H), 7.22-7.34 (m, 4H). MS (ESI) calcd for C$_{17}$H$_{13}$N$_3$O$_2$S 323.1, found 324.0 [M+H]$^+$.

Synthesis of 1-(phenylsulfonyl)-3-(1-(phenylsulfonyl)-1H-imidazol-2-yl)-1H-indole (10ya): To a solution of 3-(1H-imidazol-2-yl)-1-(phenylsulfonyl)-1H-indole (9ya) (20 mmol) in anhydrous THF (300 mL) at 0° C. was added sodium hydride (60% dispersion in mineral oil, 1.2 equiv, 24 mmol) and stirred for 20 min. Benzenesulfonyl chloride (1.2 equiv, 24 mmol) was added and the reaction mixture was stirred overnight. After dilution by 200 mL of saturated NaHCO$_3$ solution (aqueous), the reaction mixture was extracted by ethyl acetate (600 mL). The organic layer was dried over magnesium sulfate and concentrated. The residue was purified by flash column chromatography (hexane:ethyl acetate 5:1) to give a white solid. Yield: 40%. $^1$H NMR (CDCl$_3$, 300 MHz) δ 8.02-8.08 (m, 4H), 7.72 (d, J=1.5 Hz, 1H), 7.35-7.60 (m, 8H), 7.23 (d, J=1.5 Hz, 1H), 7.10-7.16 (m, 3H). MS (ESI) calcd for C$_{23}$H$_{17}$N$_3$O$_4$S$_2$ 463.1, found 486.0 [M+Na]$^+$.

Synthesis of (1-(phenylsulfonyl)-2-(1-(phenylsulfonyl)-1H-indol-3-yl)-1H-imidazol-4-yl)(3,4,5-trimethoxyphenyl)methanone (17yaa): To a solution of 1-(phenylsulfonyl)-3-(1-(phenylsulfonyl)-1H-imidazol-2-yl)-1H-indole (10ya) (5.0 mol) in anhydrous THF (100 mL) at −78° C. was added 1.7 M tert-butyllithium in pentane (1.2 equiv, 6.0 mmol) and stirred for 10 min. A solution of 3,4,5-trimethoxybenzoyl chloride (1.2 equiv, 6.0 mmol) in THF was added at −78° C. and stirred overnight. The reaction mixture was quenched with 100 mL of saturated NaHCO$_3$ solution (aqueous) and extracted by ethyl acetate (300 mL). The organic layer was dried over magnesium sulfate and concentrated. The residue was purified by flash column chromatography (hexane:ethyl acetate 3:1) to give a white solid. Yield: 30%. $^1$H NMR (500 MHz, CDCl$_3$) δ 8.09 (d, J=10 Hz, 1H), 8.04 (d, J=10 Hz, 2H), 7.91 (s, 1H), 7.76 (d, J=5 Hz, 2H), 7.65 (t, J=10 Hz, 1H), 7.55-7.58 (m, 5H), 7.40 (s, 2H), 7.33-7.36 (m, 3H), 7.25 (t, J=10 Hz, 1H), 4.05 (s, 3H), 4.03 (s, 6H). MS (ESI) calcd for C$_{33}$H$_{27}$N$_3$O$_8$ 657.0, found 680.1 [M+Na]$^+$.

Synthesis of (2-(1H-indol-3-yl)-1H-imidazol-4-yl)(3,4,5-trimethoxyphenyl)methanone (17ya): To a solution of (1-(phenylsulfonyl)-2-(1-(phenylsulfonyl)-1H-indol-3-yl)-1H-imidazol-4-yl)(3,4,5-trimethoxyphenyl)methanone (17yaa) (1 mmol) in ethanol (40 mL) and water (4 mL) was added sodium hydroxide (10 equiv, 10 mmol) and stirred overnight under refluxing condition in darkness. The reaction mixture was diluted by 50 mL of water and extracted by ethyl acetate (200 mL). The organic layer was dried over magnesium sulfate and concentrated. The residue was purified by flash column chromatography (hexane:ethyl acetate 1:1) to give a yellow solid. Yield: 60%. $^1$H NMR (500 MHz, CD$_3$OD) δ 8.31 (d, J=6.5 Hz, 1H), 7.99 (s, 1H), 7.90 (s, 1H), 7.48-7.52 (m, 3H), 7.24-7.28 (m, 2H), 4.00 (s, 6H), 3.93 (s, 3H). MS (ESI) calcd for C$_{21}$H$_{19}$N$_3$O$_4$ 377.1, found 400.1 [M+Na]$^+$. Mp 208-210° C.

Synthesis of (2-(1-(Phenylsulfonyl)-1H-indol-3-yl)-1H-imidazol-4-yl)(3,4,5-trimethoxyphenyl)methanone (17yab)

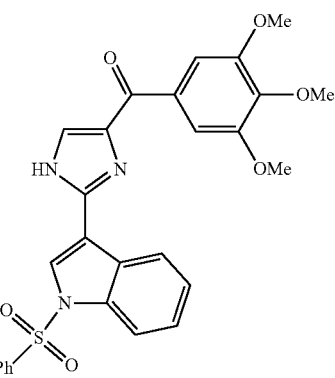

(17yab)

To a solution of compound 17yaa (66 mg) in THF (1.0 ml) was added 1.0 M tetrabutyl ammonium fluoride (0.4 mL, 0.4 mmol) and stirred overnight. The reaction mixture was diluted by 20 ml of saturated NaHCO$_3$ solution (aqueous) and extracted by ethyl acetate (20 ml). The organic layer was dried over magnesium sulfate and concentrated. The residue was purified by flash column chromatography (hexane:ethyl acetate, 2:1) to give a pale white solid. Yield: 45%. Mp 110-112° C. $^1$H NMR (CDCl$_3$, 500 MHz) δ 8.40-8.42 (m, 2H), 8.09 (d, J=8.0 Hz, 1H), 7.93-7.98 (m, 4H), 7.59 (t, J=7.5 Hz, 1H), 7.41-7.49 (m, 5H), 4.01 (s, 3H), 3.97 (s, 6H). MS (ESI) calcd for C$_{27}$H$_{23}$N$_3$O$_6$S 517.1, found 540.0 [M+Na]$^+$. HPLC: t$_R$ 6.81 min, purity 96.3%.

Synthesis of (1-methyl-2-(1-(methyl)-1H-indol-3-yl)-1H-imidazol-4-yl)(3,4,5-trimethoxyphenyl)methanone (17yac)

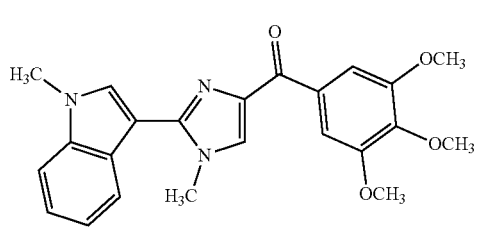

(17yac)

To a solution of 17ya (75 mg, 0.2 mmol) in anhydrous THF (20 ml) at 0° C. was added sodium hydride (60% dispersion in mineral oil, 20 mg, 0.5 mmol) and stirred for 20 min. Methyl iodide (70 mg, 0.5 mmol) was added, and the reaction mixture was stirred 1 h. After dilution by 20 ml of saturated NaHCO$_3$ solution (aqueous), the reaction mixture was extracted by ethyl acetate (60 ml). The organic layer was dried over magnesium sulfate and concentrated. The residue was recrystallized from water and methanol to give a white solid. 75% yield. Mp 164-166° C. $^1$H NMR (CDCl$_3$, 500 MHz) δ 8.30 (d, J=7.5 Hz, 1H), 8.01 (s, 1H), 7.87 (s, 1H), 7.41 (t, J=8.5 Hz, 1H), 7.39 (s, 1H), 7.35 (t, J=7.0 Hz, 1H), 7.23 (t, J=7.0 Hz, 1H), 3.98 (s, 6H), 3.95 (s, 3H), 3.91 (s, 3H), 3.89 (s, 3H). MS (ESI) calcd for C$_{23}$H$_{23}$N$_3$O$_4$ 405.2, found 406.4 [M−+H]$^+$. HPLC: t$_R$ 4.80 min, purity>99%.

Example 8

Figure 15:
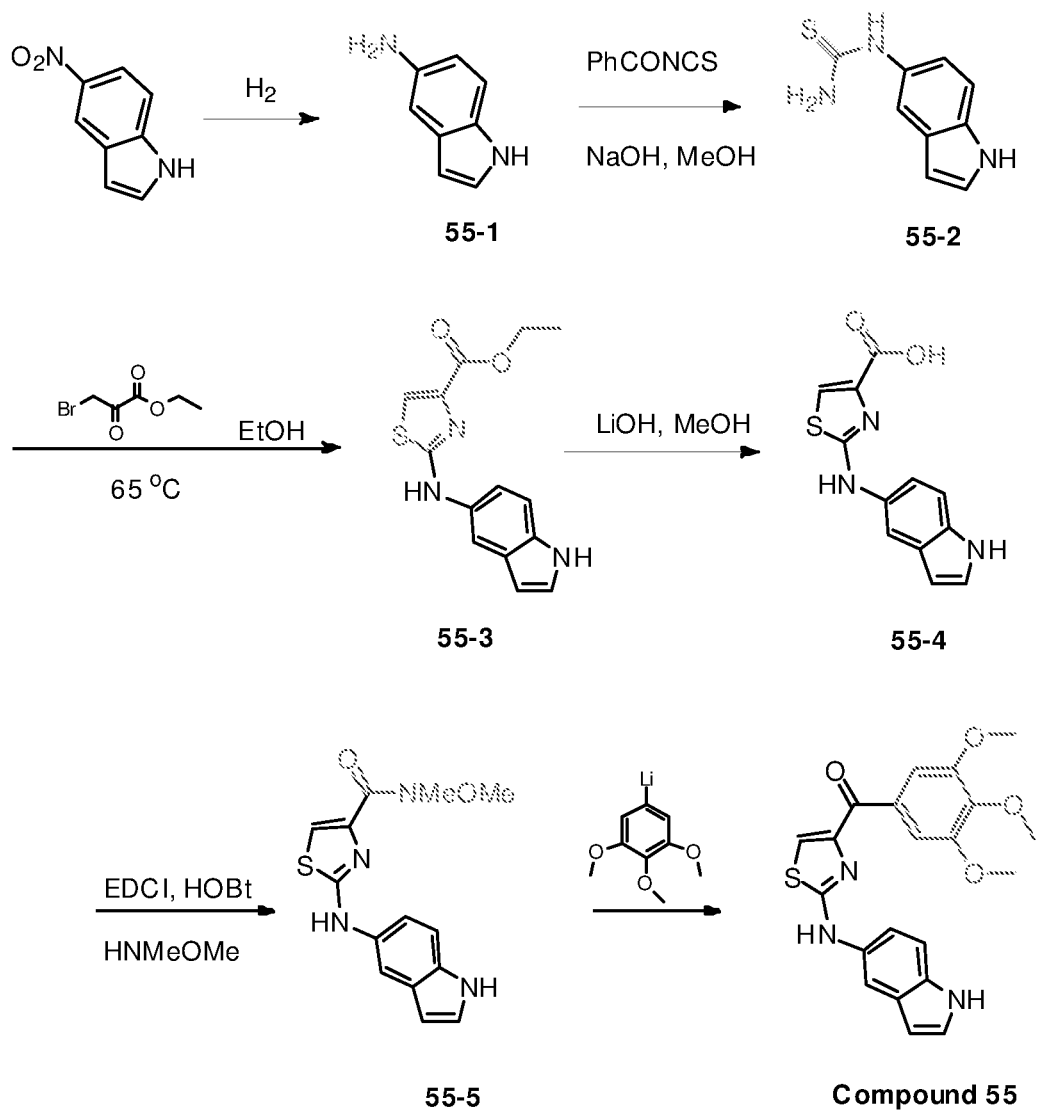
FIG. 15 depicts a synthetic scheme of compound 55.

SYNTHESIS OF (2-(1H-INDOL-5-YLAMINO)THIAZOL-4-YL)(3,4,5-TRIMETHOXYPHENYL)METHANONE (COMPOUND 55) (FIG. 15)

A mixture of 5-nitro-1H-indole (11 g, 67.9 mmol) and Pd/C (5%; 1 g), dissolved in ethanol (50 mL), was hydrogenated for 3 h at 40 psi. The reaction mixture was filtered and the excess of ethanol was evaporated under reduced pressure. Solid product was recrystallized from hexane to obtain the pure compound 5-aminoindole (55-1). Yield: 92.5%. $^1$H NMR (500 MHz, CDCl$_3$): δ 7.96 (br, 1H), 7.20 (d, 1H), 7.13 (s, 1H), 6.95 (s, 1H), 6.67 (dd, 1H), 6.37 (s, 1H), 3.50 (s, 2H). MS (ESI) m/z 133.0 (M+H)$^+$.

A solution of 5-aminoindole (8 g, 60.6 mmol) in acetone (150 mL) was reacted with benzoylisothiocyanate (9.88 g, 60. mmol) at RT for about 4 h. The resulting solid was filtered and treated with 2 N NaOH in THF (120 mL). The mixture was refluxed for about 6 h and allowed to warm to RT. The solvent was evaporated off under vacuum. The residue was diluted with water (20 mL) and neutralized to pH 7 with 1 N HCl. The resulting solid was filtered and dried under vacuum to afford 5-indolylthiourea (55-2). 5-Indolyl thiourea (0.01 mol) and ethyl bromopyruvate (0.011 mol) were dissolved in 3 mL ethanol and held at reflux for 2 h.

The reaction was cooled, the crystalline ethyl 2-(1H-indol-5-ylamino)thiazole-4-carboxylate (55-3) was collected by filtration and washed with ethanol. Refluxing the mixture of ethyl esters with the NaOH-ethanol solution gave 2-(1H-indol-5-ylamino)thiazole-4-carboxylic acid (55-4) which was used directly in next steps. To a mixture of the crude acid (2.5 mmol), EDCl (2.9 mmol), HOBt (2.6 mmol) and NMM (5.3 mmol) in CH$_2$Cl$_2$ (30 mL) was added HNCH$_3$OCH$_3$HCl salt (2.6 mmol) and stirring continued at RT for overnight. The reaction mixture was diluted with CH$_2$Cl$_2$ (20 mL) and sequentially washed with water, satd. NaHCO$_3$, brine and dried over MgSO4. The solvent was removed under reduced pressure to yield a crude product, which was purified by column chromatography to obtain pure compound 2-(1H-indol-5-ylamino)-N-methoxy-N-methylthiazole-4-carboxamide (55-5) (45.6% yield for overall 5 steps). At −78° C., to a solution of 5-bromo-1,2,3-trimethoxybenzene (1.235 g, 5.0 mmol) in 30 mL THF was charged n-BuLi in hexane (2.5 N, 2.4 mL, 6 mmol) under Ar$_2$ protection and stirred for 10 min Weinreb amide (1 mmol) in 10 mL THF was added to lithium reagent and allowed to stir at RT for 2 h. The reaction mixture was quenched with satd. NH$_4$Cl, extracted with ethyl ether, dried with MgSO4. The solvent was removed under reduced pressure to yield a crude product, which was purified by column chromatography to obtain pure compound 55 (51.7% yield). $^1$H NMR (300 MHz, CDCl$_3$) δ 8.29 (br, 1H), 7.68 (d, 1H), 7.46 (s, 2H), 7.39 (s, 1H), 7.36 (s, 1H), 7.28-7.26 (m, 1H), 7.15-7.12 (m, 1H), 6.55 (m, 1H), 3.93 (s, 3H), 3.89 (s, 6H). MS (ESI) m/z 432.1 (M+Na)$^+$, 408.0 (M−H)$^-$.

Example 9

Synthesis of Quinoline- and Isoquinoline-Aryl Compounds (FIG. 16)

A series of compounds were prepared by Suzuki coupling of 7-bromo-1-chloroisoquinoline with various arylboronic acids.

Synthesis of 1-Chloro-7-(1H-indol-5-yl)-isoquinoline (6d) (FIG. 16C)

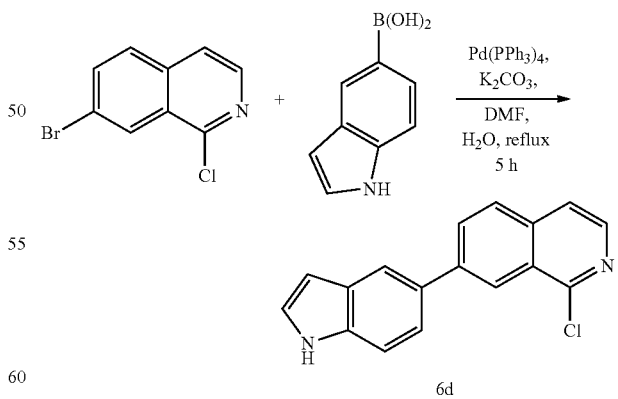

A mixture of 7-bromo-1-chloroisoquinoline (0.50 g, 2.1 mmol), 5-indoleboronic acid (0.40 g, 2.5 mmol), tetrakis(triphenylphosphine)palladium (0.035 g, 0.08 mmol), potassium carbonate (2.1 mL, 2 M, 4.1 mmol), N,N-dimethylformamide (11 mL) was stirred while purging the headspace with argon for 30 min. The mixture was then brought to reflux for 16 h before being allowed to cool to RT. The mixture was filtered through a bed of silica gel, diluted with water (50 mL), and extracted with ethyl acetate (50 mL). The organic layer was separated and washed with NaOH (2×20 mL, 10% aq.), water (5×30 mL, until refractive changes were no longer seen at the organic-aqueous interface), and ammonium chloride (20 mL, sat.). The organic layer was then adsorbed onto silica gel and flash-chromatographed (ethyl acetate/hexanes) to afford 0.14 g (25%) of a yellow solid. MS (ESI): calculated for $C_{17}H_{11}ClN_2$, 278.1, found 301.0 [M+Na]$^+$. $^1$H NMR (300 MHz, DMSO-d$_6$) δ 6.56-6.58 (m, 1H), 7.44 (t, J=2.77 Hz, 1H), 7.57-7.59 (m, 2H), 7.93 (m, 1H), 8.04 (s, 1H), 8.13-8.20 (m, 1H), 8.27-8.31 (m, 2H), 8.43 (m, 1H), 11.25 (brs, 1H).

Figure 16D:
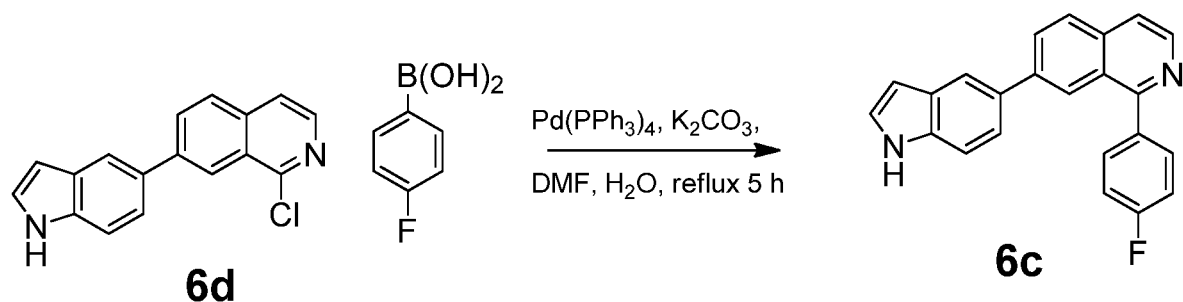
Figure 16E:
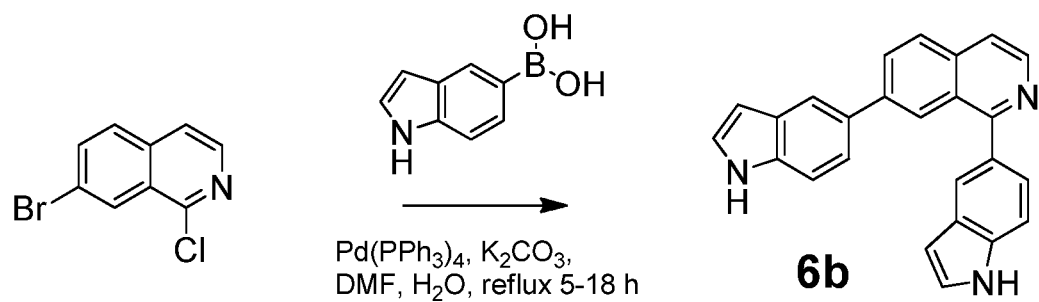

1,7-Bis-(1H-indol-5-yl)-isoquinoline (6b) (FIG. 16E)

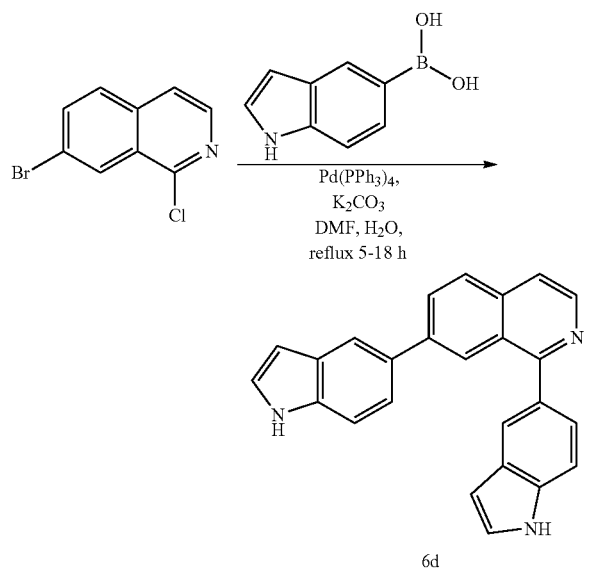

6d

A mixture of 7-bromo-1-chloroisoquinoline (0.20 g, 2.1 mmol), 5-indoleboronic acid (0.80 g, 5.0 mmol), tetrakis(triphenylphosphene)palladium (0.19 g, 0.16 mmol), potassium carbonate (2.1 mL, 2 M, 4.1 mmol), N,N-dimethylformamide (11 mL) was stirred while purging the headspace with argon for 30 min. The mixture was then brought to reflux for 16 h before being allowed to cool to RT. The mixture was filtered through a bed of silica gel, diluted with water (50 mL), and extracted with ethyl acetate (50 mL). The organic layer was separated and washed with NaOH (2×20 mL, 10% aq.), water (5×30 mL, until refractive changes were no longer seen at the organic-aqueous interface), and ammonium chloride (20 mL, sat.). The organic layer was then adsorbed onto silica gel and flash-chromatographed (ethyl acetate/hexanes) to afford 0.29 g (39%) of a yellow solid. MS (ESI): calculated for $C_{25}H_{17}N_3$, 359.1, found 360.2 [M+H]$^+$ 382.1 [M+Na]$^+$, and 358.0 [M−H]$^−$. $^1$H NMR (500 MHz, DMSO-d$_6$) δ 6.46-6.50 (m, 1H) 6.52-6.59 (m, 1H) 7.34-7.36 (m, 1H) 7.36-7.41 (m, 2H) 7.42-7.52 (m, 3H) 7.58 (d, J=8.30 Hz, 1H) 7.81 (dd, J=5.49, 5.00 Hz, 2H) 7.92 (s, 1H) 8.08-8.17 (m, 2H) 8.33 (s, 1H) 8.54 (d, J=5.61 Hz, 1H) 11.18 (br. s., 1H) 11.30 (br. s., 1H) ppm.

1-(4-Fluoro-phenyl)-7-(1H-indol-5-yl)-isoquinoline (6c) (FIG. 16D)

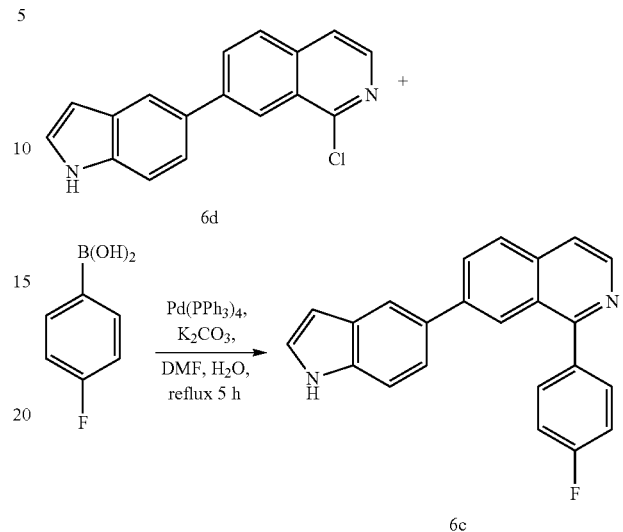

A mixture of 6d (0.20 g, 0.72 mmol), 4-fluorophenylboronic acid (0.12 g, 0.86 mmol), tetrakis(triphenylphosphene) palladium (0.033 g, 0.03 mmol), potassium carbonate (0.72 mL, 2 M, 1.4 mmol), N,N-dimethylformamide (22 mL) was stirred while purging the headspace with argon for 30 min. The mixture was then brought to reflux for 16 h before being allowed to cool to RT. The mixture was filtered through a bed of silica gel, diluted with water (50 mL), and extracted with ethyl acetate (50 mL). The organic layer was separated and washed with NaOH (2×20 mL, 10% aq.), water (5×30 mL, until refractive changes were no longer seen at the organic-aqueous interface), and ammonium chloride (20 mL, sat.). The organic layer was then adsorbed onto silica gel and flash-chromatographed (ethyl acetate/hexanes) to afford 0.038 g (16%) of a yellow solid. MS (ESI): calculated for $C_{23}H_{15}FN_2$, 338.12, found 339.2 [M+H]$^+$ and 361.2 [M+Na]$^+$. $^1$H NMR (300 MHz, DMSO-d$_6$) δ 6.47-6.55 (m, 1H), 6.80 (d, J=9.16 Hz, 2H), 7.38-7.45 (m, 2H), 7.47-7.62 (m, 3H), 7.72 (d, J=8.85 Hz, 2H), 7.79-7.96 (m, 3H), 11.18 (br. s., 1H).

1,7-Bis-(4-fluoro-phenyl)-isoquinoline (40) (FIG. 16A)

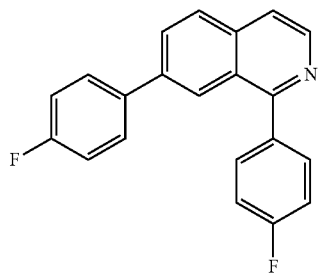

(40)

MS (ESI): calculated for $C_{21}H_{13}F_2N$, 317.10, found 318.1 [M+H]$^+$, 340.1 [M+Na]$^+$, and 315.9 [M−H]$^−$. $^1$H NMR (500 MHz, DMSO-d$_6$) δ 7.31 (br. s., 1H) 7.31-7.37 (m, 2H) 7.39

(br. s., 1H) 7.41 (t, J=8.54 Hz, 2H) 7.72-7.77 (m, 2H) 7.78-7.84 (m, 2H) 7.89 (br. s., 1H) 7.90-7.99 (m, 1H) 8.09-8.19 (m, 3H) 8.59 (br. s., 1H) 8.60-8.65 (m, 1H).

Synthesis of 7-Bromo-1-(4-fluoro-benzenesulfonyl)-1,2,3,4-tetrahydro-quinoline (43) and 1-(4-Fluoro-benzenesulfonyl)-7-(1H-indol-5-yl)-1,2,3,4-tetrahydroquinoline (41). (FIG. 16B)

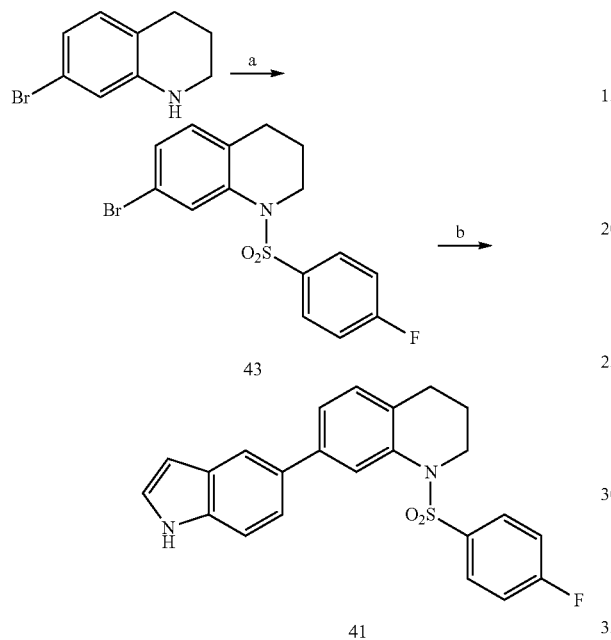

7-Bromo-1,2,3,4-tetrahydroquinoline (0.60 g, 2.8 mmol) was stirred with 4-fluorophenylsulphonyl chloride (1.65 g, 8.49 mmol) in pyridine (5 mL) at 80° C. for 3 h. The mixture was cooled, concentrated, and the residue was chromatographed (EtOAc/Hexanes on SiO$_2$) to give 845 mg of a brown solid (81%) of compound 43. C$_{15}$H$_{13}$BrFNO$_2$S 368.98, found 394.0 [M+Na]$^+$ and 367.8 [M–H]$^-$. $^1$H NMR (500 MHz, CDCl$_3$) δ 1.58-1.67 (m, 2H) 2.41 (t, J=6.71 Hz, 2H) 3.72-3.82 (m, 2H) 6.89 (d, J=8.30 Hz, 1H) 7.08-7.17 (m, 2H) 7.18-7.24 (m, 1H) 7.59-7.68 (m, 2H) 7.92-8.01 (m, 1H).

43 (0.46 g, 1.3 mmol), 5-indoleboronic acid (0.26 g, 1.6 mmol), tetrakis(triphenylphosphene)palladium (0.031 g, 0.03 mmol), potassium carbonate (1.35 mL, 2-M, 2.7 mmol), and N,N-dimethylformamide (135 mL) were stirred while purging the headspace with argon for 30 min. The mixture was then brought to reflux for 16 h before being allowed to cool to RT. The mixture was filtered through a bed of silica gel, diluted with water (50 mL), and extracted with ethyl acetate (50 mL). The organic layer was separated and washed with NaOH (2×20 mL, 10% aq.), water (5×30 mL, until refractive changes were no longer seen at the organic-aqueous interface), and ammonium chloride (20 mL, sat.). The organic layer was then adsorbed onto silica gel and flash-chromatographed (ethyl acetate/hexanes) to afford 0.38 g (77%) of a white crystalline solid of compound 41. MS (ESI): calculated for C$_{23}$H$_{19}$FN$_2$O$_2$S, 406.12, found 404.9 [M–H]$^-$ and 429.1 [M+Na]$^+$. $^1$H NMR (500 MHz, DMSO-d$_6$) δ 1.56-1.66 (m, 2H) 2.48 (t, J=6.59 Hz, 2H) 3.76-3.86 (m, 2H) 6.46-6.56 (m, 1H) 7.14 (m, J=7.81 Hz, 1H) 7.33-7.37 (m, 1H) 7.38-7.45 (m, 4H) 7.49 (m, J=8.54 Hz, 1H) 7.66-7.74 (m, 2H) 7.74-7.81 (m, 1H) 7.85-7.94 (m, 1H) 11.17 (br. s., 1H).

7-Bromo-2-(4-fluoro-benzenesulfonyl)-1,2,3,4-tetrahydro-isoquinoline (42) (FIG. 16B)

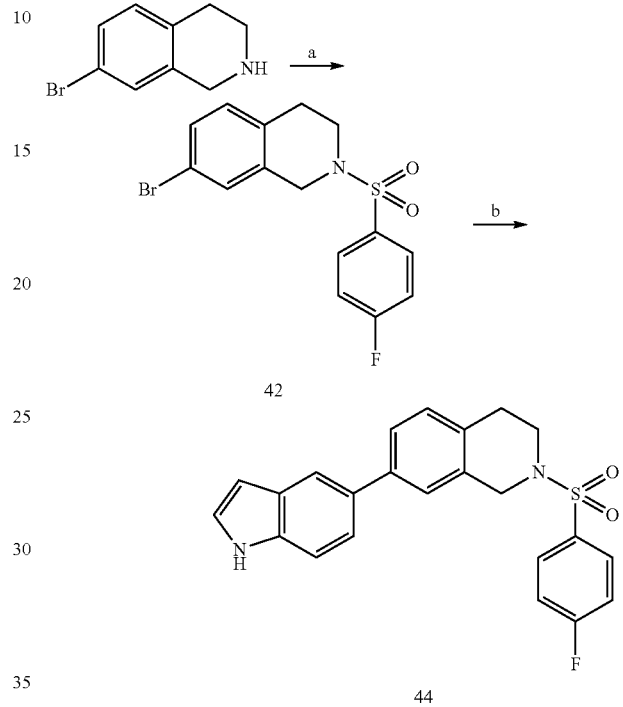

Yield 23%. C$_{15}$H$_{13}$BrFNO$_2$S, 369.0, found 392.0 [M+Na]$^+$ and 367.7 [M–H]$^-$. $^1$H NMR (500 MHz, DMSO-d$_6$) δ 2.75-2.82 (m, 2H) 3.32 (t, J=6.10 Hz, 2H) 4.24 (s, 2H) 7.07 (d, J=8.30 Hz, 1H) 7.29-7.37 (m, 1H) 7.37-7.43 (m, 1H) 7.47 (t, J=8.79 Hz, 2H) 7.87-7.93 (m, 2H).

2-(4-Fluoro-benzenesulfonyl)-7-(1H-indol-5-yl)-1,2,3,4-tetrahydro-isoquinoline (44)

Yield 77%. $^1$H NMR (500 MHz, DMSO-d$_6$) δ 2.84-2.91 (m, 2H) 3.35 (t, J=5.98 Hz, 2H) 4.30 (s, 2H) 6.44-6.48 (m, 1H) 7.17 (d, J=7.81 Hz, 1H) 7.32-7.40 (m, 2H) 7.41-7.51 (m, 3H) 7.75-7.79 (m, 1H) 7.89-7.96 (m, 1H) 11.13 (br. s., 1H).

Example 10

Figure 17:
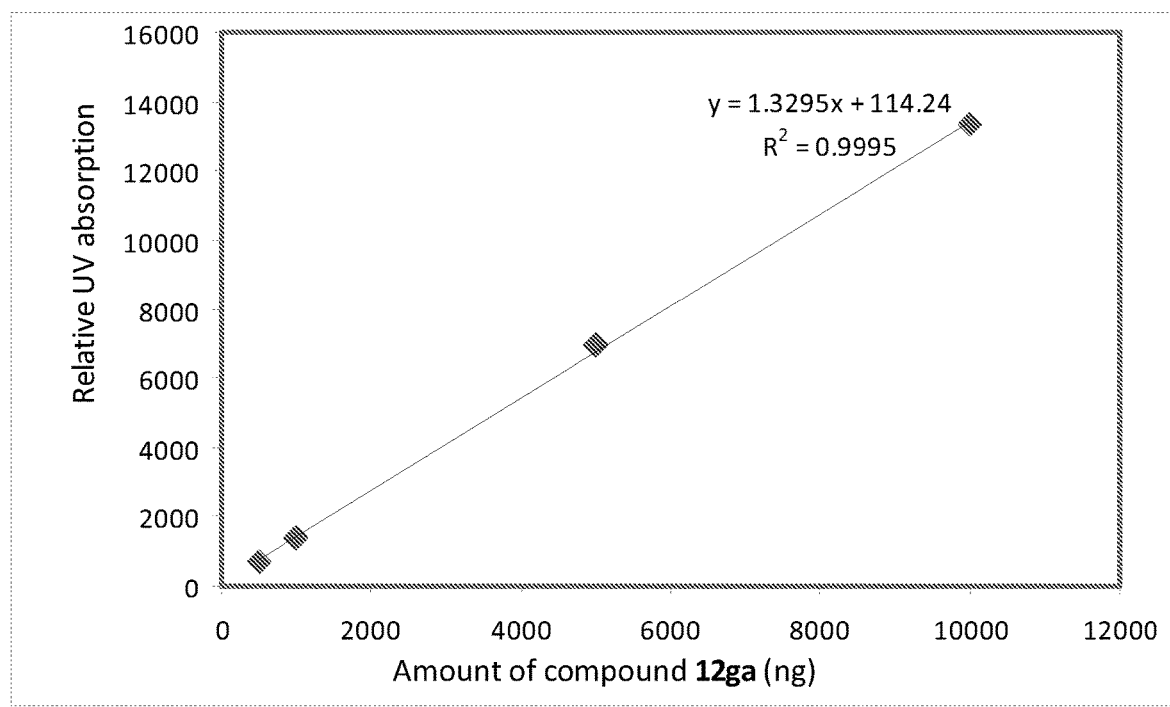
FIG. 17 depicts a standard solubility curve for ABI compound 12ga (dissolved in acetonitrile). X-axis is the amount of compound and y-axis is the m/z peak area.

Water Solubility of Aryl-Benzoyl-Imidazole (ABI) Compounds (FIG. 17)

Figure 19:
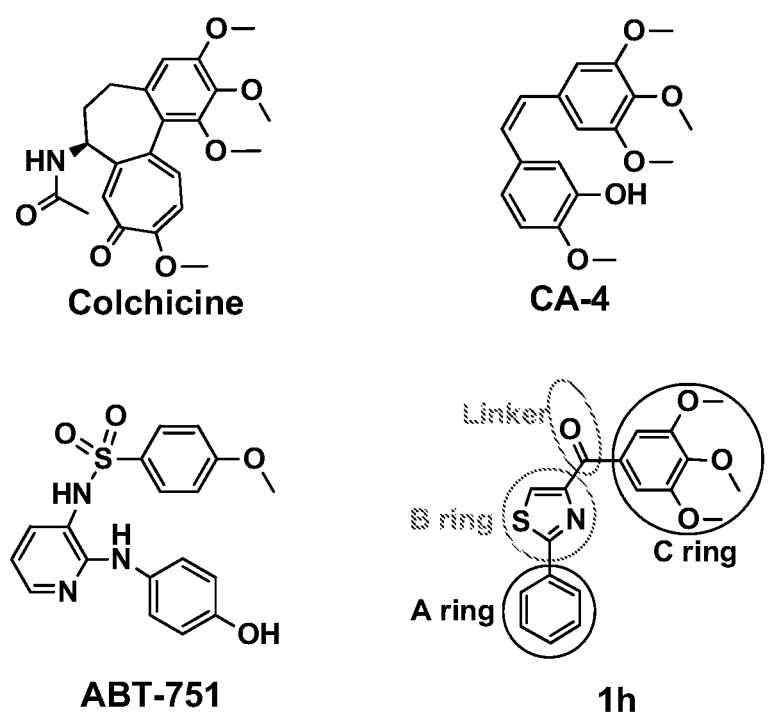
FIG. 19 depicts the structures of colchicine-binding site tubulin inhibitors.

Determination of water solubility. To determine water solubility, 1 mg of each compound was suspended in 1 mL water and shaken for 48 h at room temperature (RT). The suspension was centrifuged at 10,000 rpm for 10 min and filtered on 0.22 μm filter. Concentrations of each compound were measured by LC-MS, consisting of an HP S1100 HPLC instrument (Agilent, Foster ceity, CA) and a Bruker ESQUIRE MS detector with electrospray/ion trap instrument in positive ion mode (Bruker, Fremont, CA). For HPLC, a reverse phase Nova-pak C$_{18}$ column (150 mm×3.9 mm, Waters, Milford, MA) was used. The mobile phase was composed of 20:80 v/v water/acetonitrile. For MASS, the peak was extracted at 382 m/z (for imidazole compounds) and 399 m/z (for thiazole compounds) respectively. The concentration of each compound was calculated by MS peak area according to the following calibration equation: $y=1.3295x+114.24$ ($R^2=1.00$). To make the standard curve (FIG. 17) from which the equation was derived, 50, 100 μL of each 100 μg/mL, 10 μg/mL of ABI compound 12ga, and its corresponding thiazole analog, as well as CA-4 (see FIG. 19 for structure) in acetonitrile, were injected into HPLC and monitored by mass spectroscopy. The amount (ng) in each injection was plotted again its relative mass peak area to generate the standard curve in FIG. 17.

The HPLC retention times of ABI compound 12ga (1.5 min) was compared to its corresponding thiazole analog (2.2 min) using 80/20 methanol/water mobile phase at 1 mL/min flow rate and a reversed phase column, indicating that the imidazole derivative was more hydrophilic than its corresponding thiazole analog. The calculated logP values for ABI compound 12ga and the corresponding thiazole analog were approximately 2.9 and 4.4, respectively. The water solubility of compound 12ga was 13 μg/mL, or about 200 times greater than its thiazole counterpart (72 ng/mL).

Example 11

Biological Evaluation of Compounds of this Invention

Example 11A: In Vitro Cell Growth Inhibitions

Cell Culture and Cytotoxicity Assay of Prostate Cancer and Melanoma. All cell lines were obtained from ATCC (American Type Culture Collection, Manassas, VA, USA), while cell culture supplies were purchased from Cellgro Mediatech (Herndon, VA, USA). We examined the antiproliferative activity of our anti-tubulin compounds in four human prostate cancer cell lines (LNCaP, DU 145, PC-3, and PPC-1) and two human melanoma cell lines (A375 and WM-164). Human ovarian cell line OVCAR-8 and its resistant cell line that over-expresses P-gp (NCI/ADR-RES) were used as MDR models. Both ovarian cell lines were obtained from National Cancer Institutes (NCI). All cell lines were tested and authenticated by either ATCC or NCI. All prostate cancer and ovarian cancer cell lines were cultured in RPMI 1640, supplemented with 10% fetal bovine serum (FBS).

Melanoma cells were cultured in DMEM, supplemented with 5% FBS, 1% antibiotic/antimycotic mixture (Sigma-Aldrich, Inc., St. Louis, MO, USA) and bovine insulin (5 μg/mL; Sigma-Aldrich). The cytotoxic potential of the anti-tubulin compounds was evaluated using the sulforhodamine B (SRB) assay after 96 h of treatment.

All of the reported compounds were first evaluated for cytotoxicity in the mouse melanoma cell line B16-F1, human melanoma cell lines (A375 and WM-164) and prostate cancer cell lines (DU145, PC-3, LNCaP, PPC-1). Compound 1 h and ABT-751 (E7010, Abbott Laboratories/Eisai Co Ltd), which has entered phase II clinical studies in treating patients with different cancers, were included in the assays as examples of colchicine-site binding agents. $IC_{50}$ values for cell growth inhibition are shown in Tables 1, 2 and 3.

Results

TABLE 1

SAR of B ring Optimizing Compounds

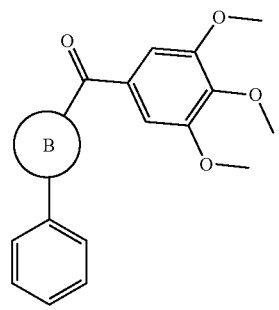

| | | $IC_{50}$ ± SEM (nM) | | | | | |
|---|---|---|---|---|---|---|---|
| | B ring | B16-F1 | A375 | DU 145 | PC-3 | LNCaP | PPC-1 |
| 1a | 1,3-phenyl | 500 ± 200 | 87 ± 15 | 178 | 81 | 234 | 85 |
| 1b | 4,6-pyrimidine | >30000 | >30000 | 6900 | 8300 | 7000 | 3700 |
| 1c | 2,6-pyridine | 39 ± 12 | 30 ± 14 | 33 ± 3 | 32 ± 2 | 27 ± 2 | 25 ± 1 |
| 1d | 2,5-furan | 151 ± 24 | 27 ± 8 | 35 | 21 | 23 | 20 |
| 1e | 2,5-thiazole | 12500 ± 5200 | 13600 ± 3800 | >10000 | >10000 | >10000 | >10000 |
| 1f | 2,4-thiophene | 72 ± 15 | 15 ± 6 | 26 | 12 | 17 | 15 |
| 1g | 1,4-piperidine | >30000 | >30000 | >20000 | >20000 | >20000 | >20000 |
| 1h | 2,4-thiazole | 55 ± 5 | 28 ± 5 | 71 ± 4 | 21 ± 1 | 28 ± 4 | 43 ± 5 |
| 1i | 3,5-isoxazole | >30000 | >30000 | >10000 | >10000 | >10000 | >10000 |
| 36a | 2,4-oxazole | 600 ± 200 | 300 ± 100 | 292 | 294 | 310 | 324 |
| 35a | 2,4-oxazoline | 6500 ± 800 | 500 ± 100 | 1200 ± 100 | 1200 ± 100 | 1200 ± 100 | 1100 ± 100 |

TABLE 2

SAR of Carbonyl Linker Optimizing Compounds

IC$_{50}$ ± SEM (nM)

| | X linker | B16-F1 | A375 | WM-164 | DU 145 | PC-3 | LNCaP | PPC-1 |
|---|---|---|---|---|---|---|---|---|
| 1h | C=O | 55 ± 5 | 28 ± 5 | 64 ± 4 | 71 ± 4 | 21 ± 1 | 28 ± 4 | 43 ± 5 |
| 2a | C=CMe$_2$ | 3800 ± 1300 | 1900 ± 800 | 3700 ± 1200 | 2650 | 2470 | 1390 | 2040 |
| 2b | CHOH | >30000 | >30000 | ND | >10000 | >10000 | >10000 | >10000 |
| 2c-trans | syn-C=C—CN | 5400 ± 2100 | 4600 ± 1500 | 4900 ± 1300 | 2280 | 890 | 580 | 900 |
| 2c-cis | anti-C=C—CN | 1200 ± 300 | 1200 ± 400 | 1000 ± 200 | ~10000 | ~10000 | 1990 | ~10000 |
| 2d-cis | syn-C=N—NH$_2$ | 2000 ± 800 | 900 ± 300 | ND | 1210 | 1120 | 1800 | 872 |
| 2d-trans | Anti-C=N—NH$_2$ | 1800 ± 700 | 600 ± 200 | ND | 1210 | 1040 | 1300 | 966 |
| 2e-cis | syn-C=N—OH | 300 ± 100 | 200 ± 100 | ND* | 102 | 120 | 189 | 160 |
| 2e-trans | anti-C=N—OH | 11400 ± 2100 | 7800 ± 1200 | ND | >10000 | >10000 | >10000 | >10000 |
| 2f-cis | syn-C=N—OMe | 3800 ± 1600 | 2900 ± 1200 | 3400 ± 1800 | >10000 | >10000 | >10000 | >10000 |
| 2f-trans | Anti-C=N—OMe | >10000 | >10000 | >10000 | >10000 | >10000 | >10000 | >10000 |
| 2g | CONH | >30000 | >30000 | ND | >10000 | >10000 | >10000 | >10000 |
| 2h | NHCO | >30000 | >30000 | ND | >10000 | >10000 | >10000 | >10000 |
| 2i | Bond (none) | >10000 | >10000 | >10000 | >10000 | >10000 | >10000 | >10000 |
| 2j | C=N—CN | 60 ± 21 | 28 ± 12 | 27 ± 13 | 42 ± 2 | 27 ± 1 | 23 ± 2 | 20 ± 1 |
| 3a | cis-C=C | 11000 ± 2800 | 46500 ± 23300 | 10600 ± 5800 | >10000 | >10000 | >10000 | >10000 |
| 3b | trans-C=C | 32800 ± 13000 | >10000 | 30800 ± 12000 | >10000 | >10000 | >10000 | >10000 |
| 4a | S | 2400 ± 900 | 1600 ± 400 | 2000 ± 1200 | >10000 | >10000 | 2300 ± 200 | 2300 ± 100 |
| 4b | SO$_2$ | >10000 | >10000 | >10000 | >10000 | >10000 | >10000 | >10000 |
| 4c | SO | >10000 | >10000 | >10000 | >10000 | >10000 | >10000 | >10000 |
| 4d | SO$_2$NH$_2$ | >10000 | >10000 | >10000 | >10000 | >10000 | >10000 | >10000 |

*ND = Not determined

TABLE 3

Antiproliferative Activity of Modified Compounds with Improved Aqueous Solubility IC$_{50}$ ± SEM (nM)

| | A part | B16-F1 | A375 | DU 145 | PC-3 | LNCaP | PPC-1 |
|---|---|---|---|---|---|---|---|
| 58a | 4-OTBDMSPh | 500 ± 200 | 700 ± 300 | 434 ± 30 | 183 ± 24 | 549 | 246 ± 8 |
| 21 | 4-OHPh | 110 | 100 | 116 | 87 | 103 | 76 |
| 62a | 2-indolyl | 43 ± 21 | 19 ± 9 | 32 | 24 | 28 | 28 |
| 66a | 5-indolyl | 25 ± 13 | 8 ± 1 | 13 | 7 | 10 | 8 |
| 68a | 4-BocNHCH$_2$Ph | 2900 ± 400 | 7900 ± 500 | 4400 | 3100 | 2600 | 2700 |
| 2r | 4-NH$_2$CH$_2$Ph | 38 ± 11 | 41 ± 13 | 25 | 80 | 13 | 34 |
| 2s | 4-NHMeCH$_2$Ph | >10000 | >10000 | ~10000 | >10000 | 114 ± 80 | ~1000 |
| 2u | 4-NMe$_2$CH$_2$Ph | >10000 | >10000 | >10000 | >10000 | 1025 ± 200 | >10000 |
| 5a | PhNH | 65 ± 12 | 45 ± 8 | 70 ± 4 | 57 ± 3 | 51 ± 1 | 54 ± 1 |
| 5Hb | 4-CH$_3$PhNH | ND* | ND | 35 ± 1 | 38 ± 2 | 35 ± 1 | 36 ± 1 |
| 5c | 4-FPhNH | ND | ND | 63 ± 1 | 43 ± 1 | 41 ± 1 | 37 ± 1 |
| 1h | Ph | 55 ± 5 | 28 ± 5 | 71 ± 4 | 21 ± 1 | 28 ± 4 | 43 ± 5 |
| ABT-751 | | 2127 ± 351 | 1111 ± 108 | 839 ± 719 | 786 ± 89 | 658 ± 117 | 701 ± 307 |

*ND = Not determined

SAR of alternative "B" ring molecules. The first series was targeted to alternatives to the thiazole "B" ring. Accordingly, a series of heterocyclic "B" rings were examined. As shown in Table 1, the successful replacements of the thiazole were pyridine 1c, furan 1d and thiophene 1f. The $IC_{50}S$ (12 nM—35 nM against prostate cancer cells) are close to the thiazole compound 1b. Introducing phenyl (1a), oxazoline (35a), and oxazole (36a) maintained activity in the hundreds of nanomolar range. But introducing of pyrimidine (1b, $IC_{50}$: 3.7-8.3 µM), a reversed 2,5-thiazole and 3,5-isoxazole (1e and 1i, $IC_{50}$: >10 µM) caused obvious losses of potency. Modification of "B" ring to the saturated ring of piperidine (1g) also totally abolished activity ($IC_{50}$>20 µM).

SAR of Alternative Linkers. In vitro hepatic metabolic stability studies revealed that the carbonyl linker between "B" and "C" rings in SMART compounds caused short half lives (5-17 min) primarily due to carbonyl reduction. For the sake of blocking this ketone reduction to the inactive hydroxyl linker compound 2b, the carbonyl linker in the second series of compounds was modified (Table 2). The carbonyl linker was replaced with double bonds (2a, 3a and 3b), amides (2 g, 2h), oximes (2e-cis,trans and 2f-cis,trans), hydrazide (2d-cis, 2d-trans), acrylonitriles (2c-trans, 2c-cis), cyanoimine (2j), sulfonyl amide (4d), sulfur ether (4a), sulfonyl and sulfinyl compounds (4b, 4c). A direct link compound 2i without any linker between "B" and "C" rings was also prepared. Among these linker modifications, only cyanoimine linkage (2j) showed promising potential (20-60 nM) compared with carbonyl compound 1h, but an in vitro metabolism study showed that the half life of 2j in human liver microsome was less than 5 min. This suggested that although the ketone reduction is blocked, it might introduce a new metabolic liability in compound 2j. The isomer pairs of compounds containing double bonds, oximes and hydrazides were separated. Compound 3a was designed to mimic the structure of CA-4, (FIG. 19) which contain a cis-C=C between two aryl rings, unfortunately 3a and other isomer pairs lost activity after replacing the C=O linker. One interesting phenomenon is syn-isomer of 2e-cis (0.1~0.3 µM) showed 10 fold more activity than its anti-isomer 2e-trans (>10 µM). The half life of 2e-cis in human liver microsome is extended to 35 min, while half lives of compounds 2d can be prolonged to 55 min. But decreased activity (~1 µM) of 2d also reduced their potency.

Example 11B: Aqueous Solubility of Compounds of the Invention

The solubility of drugs was determined by Multiscreen Solubility Filter Plate (Millipore Corporate, Billerica, MA) coupled with LC-MS/MS. Briefly, 198 µL of phosphate buffered saline (PBS) buffer (pH 7.4) was loaded into 96-well plate, and 2 µL of 10 mM test compounds (in DMSO) was dispensed and mixed with gentle shaking (200-300 rpm) for 1.5 h at RT (N=3). The plate was centrifuged at 800g for 5 min, and the filtrate was used to determine its concentration and solubility of test compound by LC-MS/MS as described below.

Figure 18:
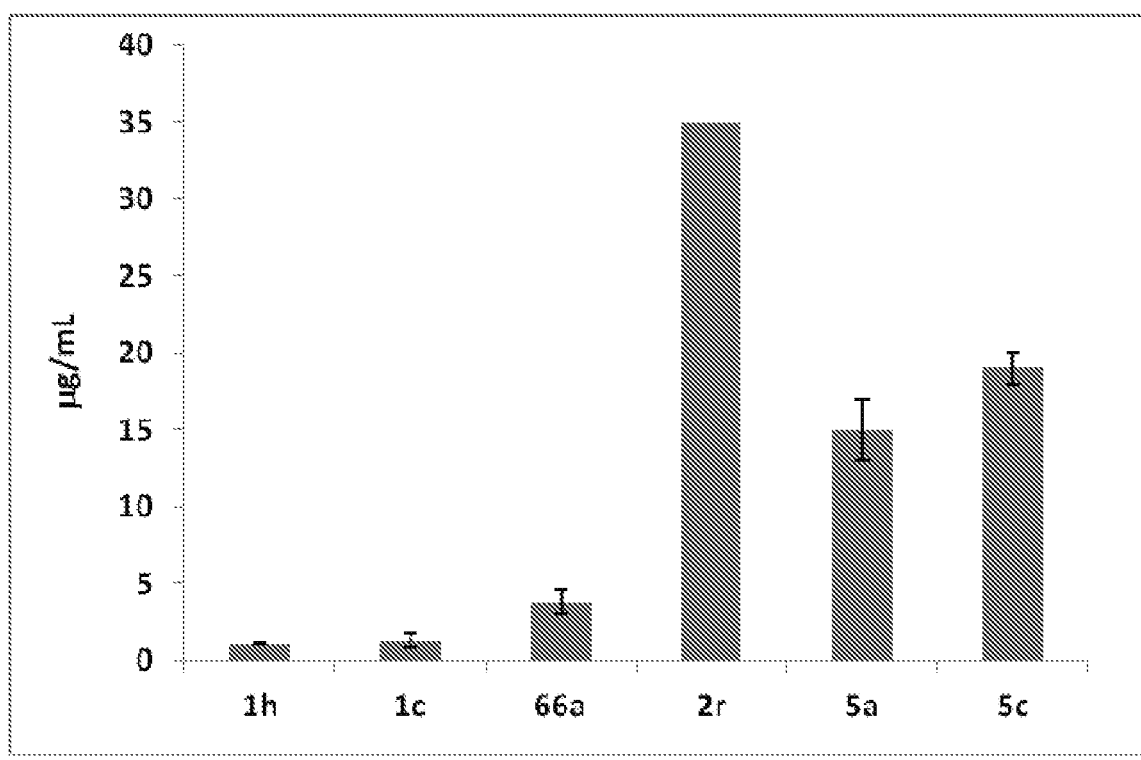
FIG. 18 depicts the measured aqueous solubility for anti-tubulin compounds 1h, 1c, 66a, 2r-HCl, 5a, and 5c.

Introducing polar and ionizable groups into the antitubulin agents. One major limitation of the SMART agents is low aqueous solubility. Surfactants such as Tween 80, were used to study in vivo SMART behavior, accordingly favorable results were obtained. But these surfactants are biologically active and are responsible for many side effects. In addition, it was thought that low aqueous solubility of 1h resulted in low oral bioavailability (3.3%, Table 4). In the third series of compounds, the aqueous solubility was successfully increased without impacting the potency by introducing polar groups like hydroxyl and indolyls. In addition, ionizable groups like amino and alkylamino groups were also introduced into "A" ring para-position. As shown in FIG. 5 and Table 3, introducing indolyl groups to the "A" ring especially 5-indolyl (66a, 7-25 nM) increased the potency compared with the 4-OH compound 21 (76-116 nM). Aminomethyl—$CH_2NH_2$ at the "A" ring para position also maintained potency (2r, 13-80 nM), but p-NHMe (2s) or p-$NMe_2$ (2u) abrogated activity. As shown in FIG. 18, analytical measurement to estimate aqueous solubility showed that indolyl compound 66a increased solubility in PBS from 1.1 µg/mL (compound 1h) to 3.8 µg/mL. Aminomethyl compound 2r was converted to the HCl salt, which increased solubility over 35-fold (>35 µg/mL). Although compound 2r showed satisfactory aqueous solubility, the pharmacokinetic studies showed this compound still had very poor bioavailability (F %=0.2%). It was thought that compound 2r was ionized in the stomach, and therefore not absorbed into the circulation system.

Example 11C: Pharmacokinetic Studies

Pharmacokinetic Study. Female Sprague-Dawley rats (n=3 or 4; 254±4 g) were purchased from Harlan Inc. (Indianapolis, IN). Rat thoracic jugular vein catheters were purchased from Braintree Scientific Inc. (Braintree, MA). On arrival at the animal facility, the animals were acclimated for 3 days in a temperature-controlled room (20-22° C.) with a 12 h light/dark cycle before any treatment. Compound 1h was administered intravenously (i.v.) into the jugular vein catheters at a dose of 2.5 mg/kg (in DMSO/PEG300, 2/8), whereas 5Ha and 5Hc were dosed at 5 mg/kg (in DMSO/PEG300, 1/9). An equal volume of heparinized saline was injected to replace the removed blood, and blood samples (250 µL) were collected via the jugular vein catheters at 10, 20, 30 min, and 1, 2, 4, 8, 12, 24 h. Compounds 1 h, 5Ha and 5Hc were given (p.o.) by oral gavage at 10 mg/kg (in Tween80/DMSO/$H_2O$, 2/1/7). All blood samples (250 µL) after oral administration were collected via the jugular vein catheters at 30, 60, 90 min, 120 min, 150 min, 180 min, 210 min, 240 min, and 8, 12, 24 h. Heparinized syringes and vials were prepared prior to blood collection. Plasma samples were prepared by centrifuging the blood samples at 8,000 g for 5 min. All plasma samples were stored immediately at −80° C. until analyzed.

Analytes were extracted from 100 µL of plasma with 200 µL of acetonitrile containing 200 nM the internal standard ((3,5-dimethoxyphenyl)(2-phenyl-1H-imidazol-4-yl)methanone). The samples were thoroughly mixed, centrifuged, and the organic extract was transferred to autosampler for LC-MS/MS analysis. Multiple reaction monitoring (MRM) mode, scanning m/z 356→188 (compound 1h), m/z 371→203 (compound 5Ha), m/z 389→221 (compound 5Hc), and m/z 309→171 (the internal standard), was used to obtain the most sensitive signals. The pharmacokinetic parameters were determined using non-compartmental analysis (WinNonlin, Pharsight Corporation, Mountain View, CA) Results:

TABLE 4

Pharmacokinetic Parameters for Compounds Tested in vivo.

| | 1h | | 2r | | 5Ha | | 5Hc | |
|---|---|---|---|---|---|---|---|---|
| Route | IV | PO | IV | PO | IV | PO | IV | PO |
| $N^a$ | 4 | 3 | 3 | 3 | 3 | 3 | 3 | 3 |
| Dose(mg/kg) | 2.5 | 10 | 2.5 | 4 | 5 | 10 | 5 | 10 |
| $CL^b$(mL/min/kg) | 7.7 ± 1.0 | — | 22 ± 13 | — | 17 ± 3 | — | 13 ± 2 | — |
| $Vss^c$(L/kg) | 4.9 ± 1.9 | — | 0.33 ± 0.25 | — | 1.4 ± 0.2 | — | 1.4 ± 0.2 | — |
| $AUC^d$(min*mg/mL) | 279 ± 53 | 37 ± 20 | 139 ± 77 | 0.4 | 296 ± 46 | 65 ± 20 | 381 ± 65 | 160 ± 13 |
| $C_{max}{}^e$(ng/mL) | 3816 ± 509 | 212 | 3.2 ± 1.6 | 3794 ± 1580 | 4198 ± 438 | 814 ± 255 | 3349 ± 686 | 1262 ± 362 |
| $F^f$ (%) | | 3.3 | | 0.2 | | 11 | | 21 |

[a] Numbers of rats.
[b] Systemic clearance.
[c] Volume of distribution following intravenous dosing.
[d] Area under the curve following intravenous dosing, integrated drug concentration with respect to time and integrated drug concentration with respect to time following oral dosing.
[e] Maximum plasma concentration following intravenous dosing.
[f] Percent oral bioavailability.

Modifying Substituted Methoxybenzoyl Aryl Thiazole (SMART) Molecules to Improve Oral Bioavailability. Many established tubulin targeting anticancer drugs like taxanes and vinblastine require intravenous administration because of low oral bioavailability. Oral bioavailability is a complex parameter involving many chemical and physiological processes, such as solubility, permeability, and metabolic stability. The solubility of these tubulin inhibitors was improved by inserting an amino linker between the "A" and "B" rings as in 5a-d (FIG. 6), Table 3 demonstrates that the NH bridged compounds (5a-c) had similar potency (35-65 nM) as 1h with increased solubility (15 and 19 μg/mL for 5a and 5c, respectively (FIG. 18), but they are over 20 fold more active than ABT-751 (Table 3 and FIG. 19 for the structure of ABT-751).

Rat pharmacokinetic studies were performed to study whether these new compounds exhibited improved bioavailability compared to compound 1h (Table 4). The data clearly showed that 5Hc (HCl salt of 5c) exhibited more than 4.3-fold increased exposure (AUC) by the oral route as compared to 1h, suggesting that improved aqueous solubility by the amino linker successfully improved oral bioavailability. In addition, the maximal concentration (Cmax) of 5Ha and 5Hc by oral administration was 814 and 1262 ng/mL, respectively. While Cmax of 1h was only 212 ng/mL. Overall, the bioavailability of 5Ha and 5Hc was increased from 3.3% of 1h to 11% and 21%, respectively (Table 4). Compound 5Hc exhibited moderate clearance, moderate volume of distribution, and acceptable oral bioavailability. This data suggested that these new synthesized amino linked compounds have the potency and PK profile to be developed as a new class of orally bioavailable antitubulin agents.

Example 11D: In Vitro Tubulin Polymerization Inhibition by Compounds of the Invention In Vitro Tubulin Polymerization Assay. Bovine brain tubulin (0.4 mg, >97% pure) (Cytoskeleton, Denver, CO) was mixed with 10 μM of the test compounds and incubated in 100 μl of general tubulin buffer (80 mM PIPES, 2.0 mM $MgCl_2$, 0.5 mM EGTA, and 1 mM GTP) at pH 6.9. The absorbance of wavelength at 340 nm was monitored every 1 min for 20 min by the SYNERGY 4 Microplate Reader (Bio-Tek Instruments, Winooski, VT). The spectrophotometer was set at 37° C. for tubulin polymerization.

Results

Figure 20A:
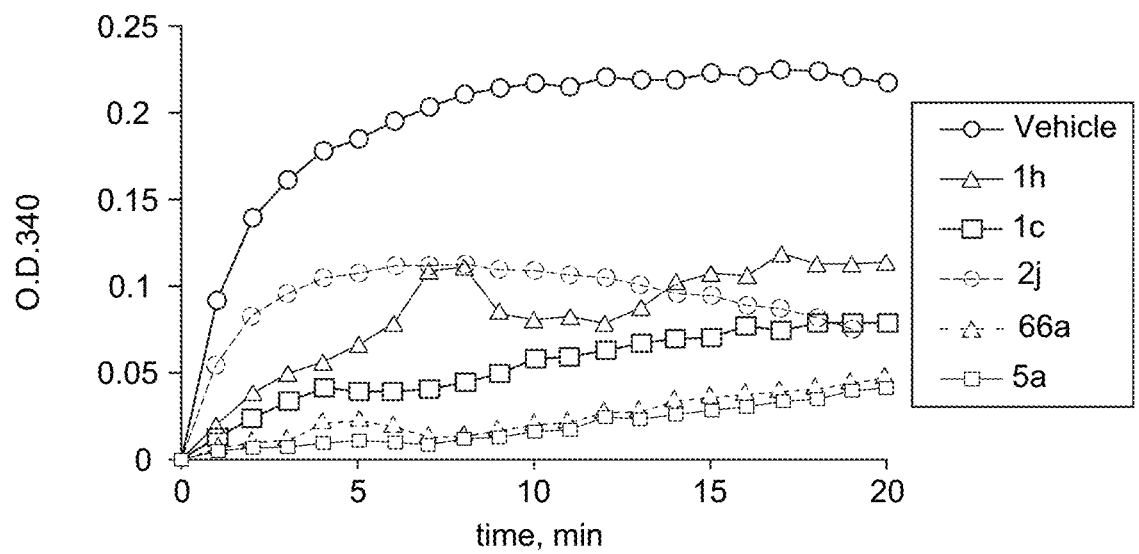
FIGS. 20A-C depict the ability of anti-tubulin compounds 1h, 1c, 2j, 66a and 5a to inhibit tubulin polymerization in vitro (FIG. 20A) and 5c (FIG. 20B), and the 5Hc binding to colchicine site (FIG. 20C).

The inhibition of tubulin polymerization by selected potent compounds 1c, 2j, 66a, and 5a was investigated by all three design strategies (alternative B-rings, novel linkers, and solubilizing moieties) and compared with 1h. Bovine brain tubulin (>97% pure) was incubated with the individual compounds (10 μM) to test their effect on tubulin polymerization (FIG. 20A). After 20 min incubation, tubulin polymerization was inhibited 47% by 1h, as compared to vehicle. Both 1c and 2j inhibited 64% of polymerization at 20 min with different inhibition patterns. Compounds 5a and 66a provided greater inhibitions as 78% and 81%, respectively. These data suggest that these compounds exhibit strong antitubulin polymerization activity that corresponds well with their cytotoxicity.

Figure 20B:
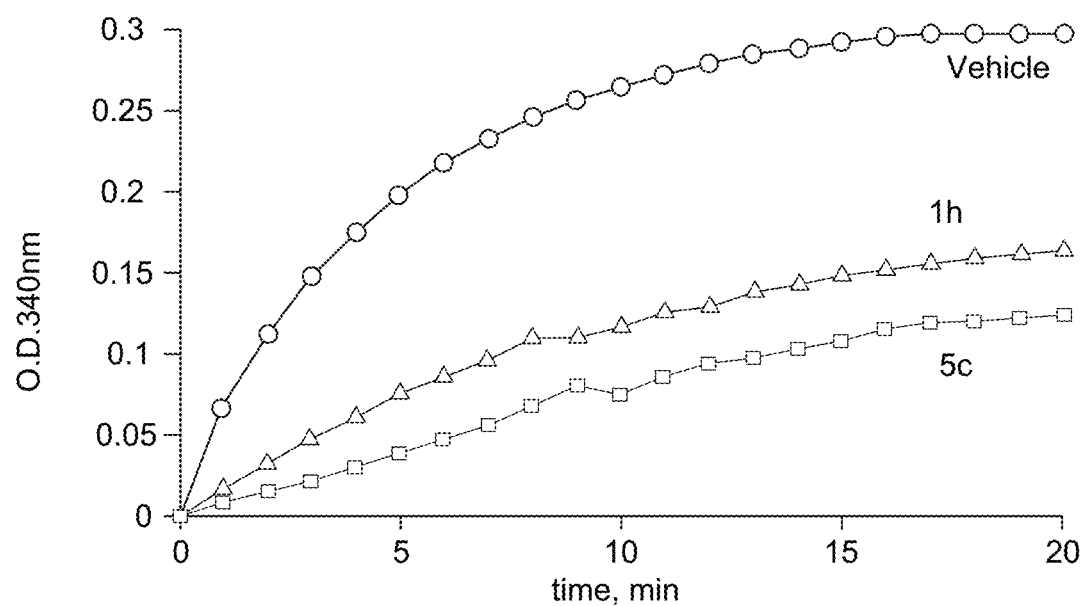
Figure 20C:
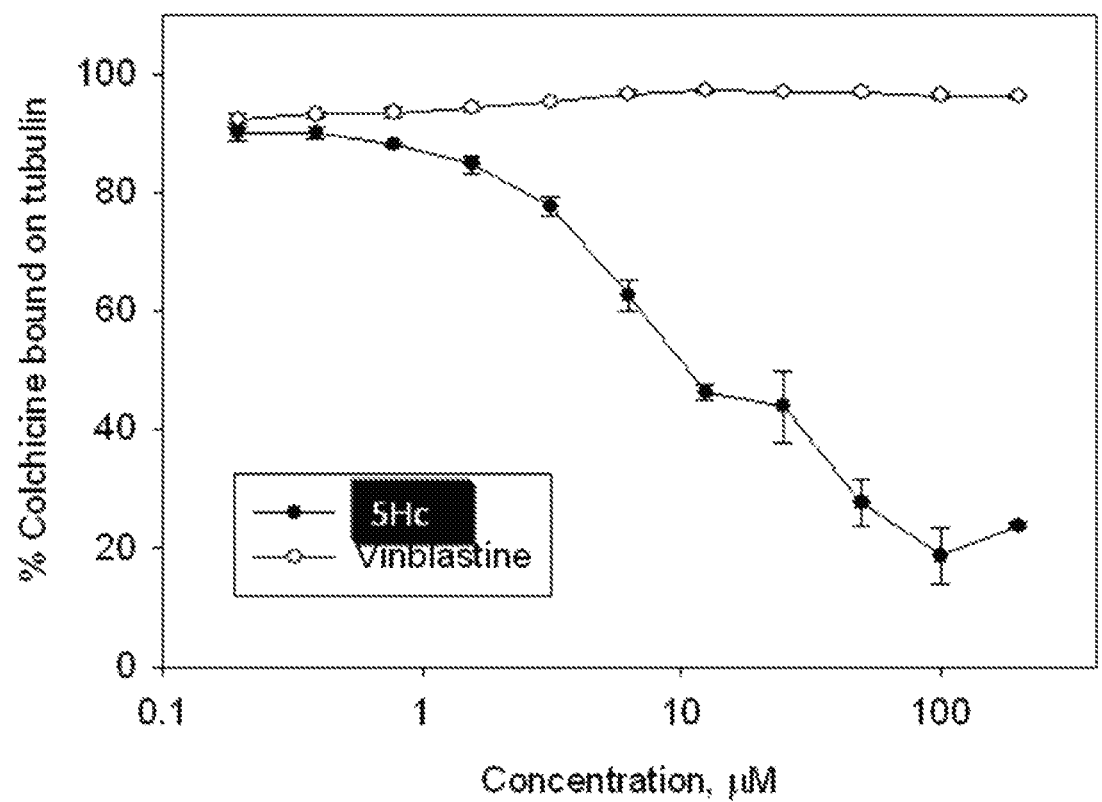
Figure 21A:
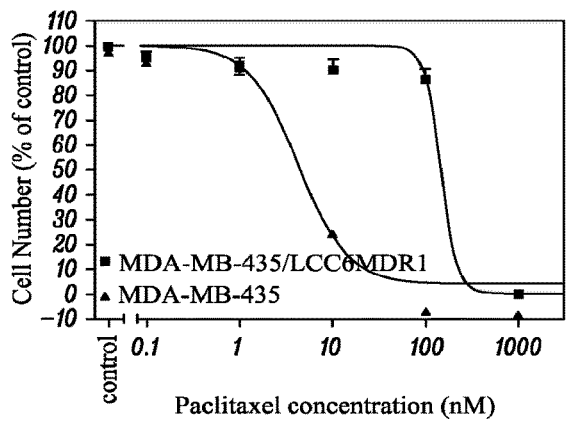
FIGS. 21A-F depict dose-response curves of 2-aryl-4-benzoyl-imidazole compounds (ABIs) compared with other anticancer drugs and compounds on multidrug resistant melanoma cell line (MDR cell) and the matched sensitive parent cell line (Normal Melanoma cell). The large distance between the two curves for paclitaxel (FIG. 21A), vinblastine (FIG. 21B), and colchicine (FIG. 21C) indicates that they were substrates for P-glycoprotein (P-gp). The overlapping two curves of each ABI compound (FIG. 21D-12fb.
Figure 21B:
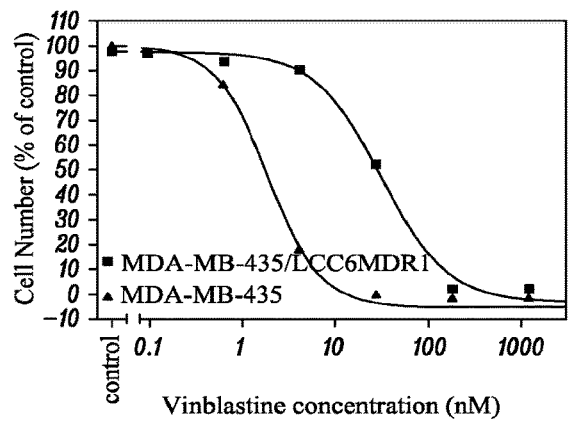
Figure 21C:
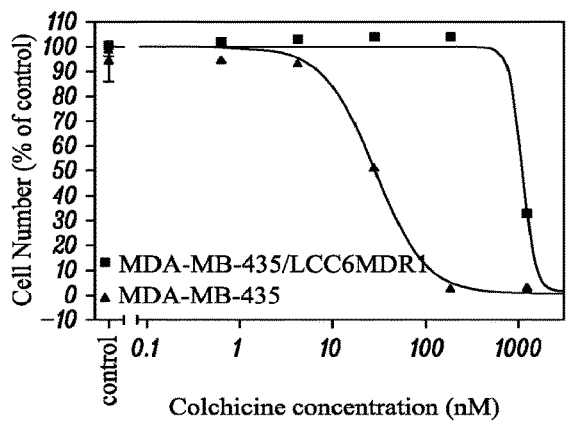
Figure 21D:
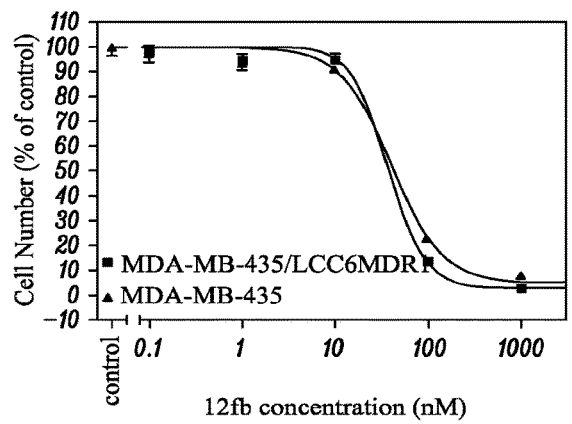
Figure 21E:
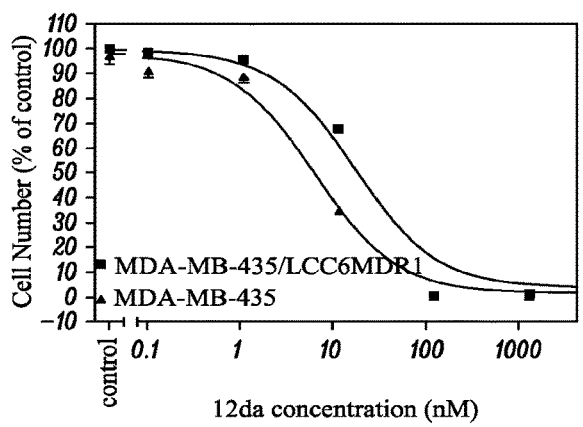
Figure 21F:
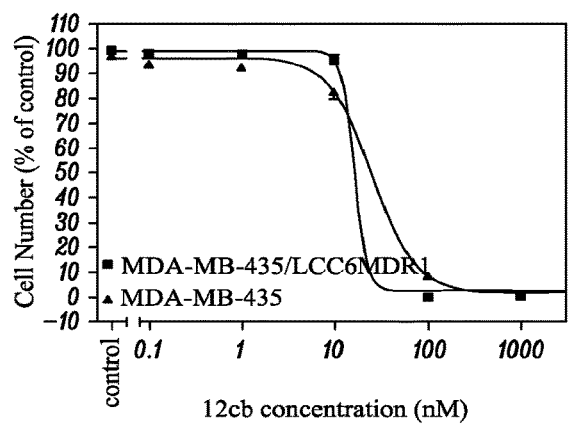

The inhibition of tubulin polymerization by compound 5c by binding with colchicines binding site and compared with compound 1h is demonstrated in FIGS. 20B and 20c.

Example 11E: Novel Anti-tubulin Compounds Overcome P-Glycoprotein Mediated Multidrug Resistance The P-glycoprotein (P-gp) system appears to be a primary physiological mechanism of multidrug resistance (MDR) which acts as an ATP-dependent drug efflux pump, actively removing a variety of structurally diverse cytotoxic compounds. Enhanced efflux of these compounds reduces their intracellular accumulation and so reduces their cytotoxicity. Therefore, novel compounds which are not susceptible to drug resistance could be of high therapeutic and economic value. In addition to P-gp, clinically used antitubulin agents have other resistance mechanisms such as changes in microtubule dynamics and mutations in P-tubulin which are known to limit sensitivity to the taxanes. The anti-tubulin compounds of the invention were tested against an ovarian cancer cell line OVCAR-8 (parent) and P-gp over-expressing NCI/ADR-RES cell line (Tables 5A, 5B).

Results

TABLE 5A

Antiproliferative Activity of Selected Compounds against P-gp over-expressed MDR cell lines.

| Compound | IC$_{50}$ (nM) | | Resistance factor |
| --- | --- | --- | --- |
| | OVCAR-8 | NCI/ADR-RES | |
| 1c | 33 ± 3 | 13 ± 0.8 | 0.4 |
| 2j | 34 ± 2 | 14 ± 1 | 0.4 |
| 66a | 10 ± 3 | 4 ± 2 | 0.4 |
| 2r | 26 ± 2 | 11 ± 2 | 0.4 |
| 5a | 46 ± 6 | 27 | 0.6 |
| 5b | 28 | 21 | 0.8 |
| 5c | 44 ± 3 | 25 ± 6 | 0.6 |
| 1h | 35 ± 2 | 13 ± 1 | 0.4 |
| paclitaxel* | 4.7 ± 0.1 | 6263 ± 634 | 1333 |
| vinblastine | 3.9 ± 0.1 | 582 ± 57 | 149 |
| colchicine | 17 ± 1 | 1113 ± 79 | 65 |

Notably, the anti-tubulin compounds of the invention demonstrated equipotent antiproliferative effects against OVCAR-8 and NCI/ADR-RES cell lines, suggesting that they are not P-gp substrates and that they function in a P-gp-independent manner. This feature is distinct from that of paclitaxel, vinblastine, and colchicine in NCI/ADR-RES cells.

TABLE 5B

Antiproliferative activity of selected phenyl-amino thiazole compounds

| | R | IC$_{50}$ ± SEM (nM) | | | | | |
| --- | --- | --- | --- | --- | --- | --- | --- |
| | | B16-F1 | A375 | DU 145 | PC-3 | LNCaP | PPC-1 |
| 5a | H | 65 ± 12 | 45 ± 8 | 70 ± 4 | 57 ± 3 | 51 ± 1 | 54 ± 1 |
| 5Hb | 4-CH$_3$ | ND* | ND | 35 ± 1 | 38 ± 2 | 35 ± 1 | 36 ± 1 |
| 5c | 4-F | ND | ND | 63 ± 1 | 43 ± 1 | 41 ± 1 | 37 ± 1 |
| 5d | 4-Cl | ND | 25 ± 7 | 73 ± 1 | 33 ± 1 | 45 ± 1 | 36 ± 1 |
| 1h | — | 55 ± 5 | 28 ± 5 | 71 ± 4 | 21 ± 1 | 28 ± 4 | 43 ± 5 |
| ABT-751 | — | 2127 ± 351 | 1111 ± 108 | 839 ± 719 | 786 ± 89 | 658 ± 117 | 701 ± 307 |

The phenyl amino thiazole compounds 5a, 5Hb, 5c and 5d demonstrated potent activity in a number of prostate cancer cell lines. Unexpectedly, the phenyl amino imidazole compound 5e demonstrated no activity (IC$_{50}$>1000 nM in LNCaP, PC-3, DU-145, and PPC-1) in these prostate cancer cell lines. The positive controls for this experiment were 55 and 17ya which demonstrated IC$_{50}$ values between 7.5 nM and 24.1 nM in the same cell lines (Table SC).

TABLE 5C

| | IC$_{50}$ ± SEM (nM) | | | | | |
| --- | --- | --- | --- | --- | --- | --- |
| | B16-F1 | A375 | DU 145 | PC-3 | LNCaP | PPC-1 |
| 5a | 65 ± 12 | 45 ± 8 | 70 ± 4 | 57 ± 3 | 51 ± 1 | 54 ± 1 |
| 5Hb | ND | ND | 35 ± 1 | 38 ± 2 | 35 ± 1 | 36 ± 1 |
| 5c | ND | ND | 63 ± 1 | 43 ± 1 | 41 ± 1 | 37 ± 1 |
| 5d | ND | 25 ± 7 | 73 ± 1 | 33 ± 1 | 45 ± 1 | 36 ± 1 |
| 1h | 55 ± 5 | 28 ± 5 | 71 ± 4 | 21 ± 1 | 28 ± 4 | 43 ± 5 |
| ABT-751 | 2127 ± 351 | 1111 ± 108 | 839 ± 719 | 786 ± 89 | 658 ± 117 | 701 ± 307 |
| d | ND | ND | >1000 | >1000 | >1000 | >1000 |
| e | ND | ND | >1000 | >1000 | >1000 | >1000 |
| 5e | ND | ND | >1000 | >1000 | >1000 | >1000 |
| 55 | ND | ND | 24 ± 6 | 12 ± 1 | 13 ± 1 | 15 ± 1 |
| 17ya | ND | ND | 11 ± 1 | 5 ± 2 | 8 ± 2 | 8 ± 1 |

A new series of tubulin polymerization inhibitors with acceptable oral bioavailability and equi-potent activity in multidrug resistant tumor cell lines has been discovered. Medicinal chemistry efforts starting from optimizing SMART compound 1h. Chemical modifications of different substituted aryl in "B" ring and linkages between "B" and "C" rings were investigated based on biological evaluation against cancer cells in vitro. SAR studies revealed that optimal "B" rings include pyridine (1c), thiophene (1f), and furan (1d) which maintain excellent in vitro potency. Replacing carbonyl linker with cyanoimine (2j) between "B" and "C" ring will increase the activity. Structure modifications to increase aqueous solubility and bioavailability were performed. Introducing an amino between "A" and "B" rings gave us compounds 5a-c, which showed similar in vitro antiproliferative potency against tested cancer cells as well as MDR(+) and MDR(−) cell lines, furthermore, the solubility and in vivo bioavailability were improved greatly over those of the 1h. Therefore, these new anti-tubulin compounds represent a new family of compounds that may be very useful in the treatment of cancer.

Example 12

Antiproliferative Activity of Compounds of this Invention

The antiproliferative activity of analogs prepared by the methods of the invention are shown in Tables 6 and 6A.

TABLE 6

| | $IC_{50}$ ± SEM (nM) | | | | | | | | | | |
|---|---|---|---|---|---|---|---|---|---|---|---|
| ID | LNCaP | PC-3 | DU 145 | PPC-1 | A375 | B16-F1 | WM164 | MES-SA | MES-SA/Dx5 | OVCAR-8 | NCI/ADR-RES |
| Paclitaxel | 1.7 | 4.8 | 5.1 | 2.3 | 12 | 17 | | 2.7 | 6.6 | 4.7 | 6263 |
| Vinblastine | 1.1 | 2.1 | 1.8 | 1.1 | 1 | 4.7 | | 1.4 | 16 | 3.9 | 582 |
| Colchicine | 16 | 11 | 10 | 20 | 20 | 29 | | 8.4 | 22 | 17 | 1113 |
| 1k | 101 | 101 | 140 | 84 | 100 | 245 | 220 | | | | |
| 2k | 6 | 13 | 12 | 8 | 33 | 43 | | 11 | 19 | 34 | 12 |
| 2m | 19 | 8.7 | 6.9 | 6.2 | 11 | 21 | | | | | |
| 2n | 101 | 131 | 143 | 99 | 210 | 290 | | | | | |
| 2o | 65 | 73 | 121 | 73 | 38 | 42 | | | | | |
| 2p | >10000 | 2385 | 1899 | 1079 | 2200 | 16560 | | | | | |
| 2q | >10000 | >10000 | >10000 | >10000 | >20000 | >20000 | | | | | |
| 5c-HCl | 53 | 53 | 70 | 43 | | | | | | | |
| 6d | 703 | 908 | 1637 | 929 | | | | | | | |

*ND: not determined

TABLE 6A

| | | $IC_{50}$ (nM) | | | | | | | | | |
|---|---|---|---|---|---|---|---|---|---|---|---|
| Structure | ID | LNCaP | PC-3 | DU 145 | PPC-1 | A375 | B16-F1 | WM164 | MES-SA | MES-SA/Dx5 | OVCAR-8 | NCI/ADR-RES |
| 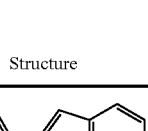 | 8 | 346 | 704 | 580 | 230 | 318 | 570 | 404 | | | | |
| 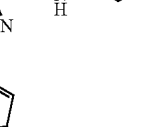 | 9 | ~10000 | ~10000 | ~10000 | ~10000 | | | | | | | |

TABLE 6A-continued
| Structure | ID | LNCaP | PC-3 | DU 145 | PPC-1 | A375 | B16-F1 | WM164 | MES-SA | MES-SA/Dx5 | OVCAR-8 | NCI/ADR-RES |
|---|---|---|---|---|---|---|---|---|---|---|---|---|
| 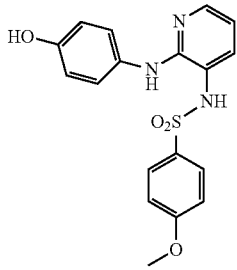 [SMILES: COc1ccc(S(=O)(=O)Nc2cccnc2Nc2ccc(O)cc2)cc1] | 10 | 658 | 786 | 839 | 701 | 1111 | 2127 | 661 | | | | |
| 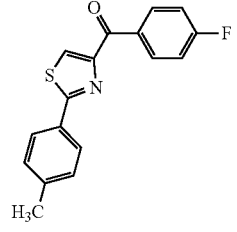 [SMILES: Cc1ccc(-c2nc(C(=O)c3ccc(F)cc3)cs2)cc1] | 11 | >10000 | >10000 | ~10000 | ~10000 | 3470 | 4900 | 4700 | | | | |
| 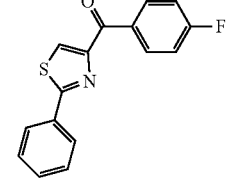 | 12 | >10000 | >10000 | >10000 | >10000 | >10000 | >10000 | | | | | |
| 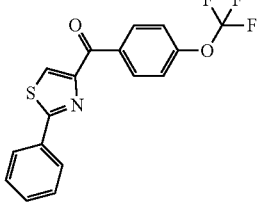 | 13 | >10000 | >10000 | >10000 | >10000 | >10000 | >10000 | >10000 | | | | |
| 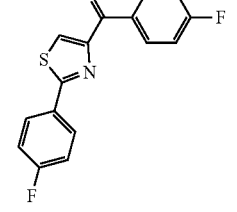 | 14 | >10000 | >10000 | >10000 | >10000 | >10000 | >10000 | | | | | |
| 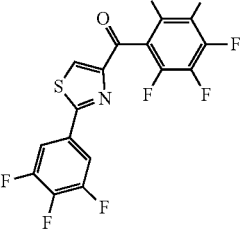 | 16 | >10000 | >10000 | >10000 | >10000 | 15200 | 6900 | | | | | |

TABLE 6A-continued
| | | IC$_{50}$ (nM) | | | | | | | | | |
|---|---|---|---|---|---|---|---|---|---|---|---|
| Structure | ID | LNCaP | PC-3 | DU 145 | PPC-1 | A375 | B16-F1 | WM164 | MES-SA | MES-SA/Dx5 | OVCAR-8 | NCI/ADR-RES |
| 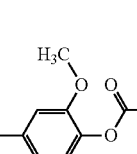 | 17 | 2100 | 1900 | 2600 | 1300 | 4300 | 9800 | | | | | |
| 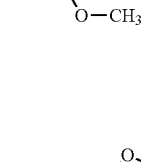 | 18 | ~10000 | ~10000 | ~10000 | ~10000 | | | | | | | |
| 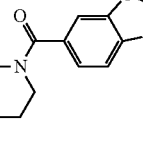 | 19 | >20000 | >20000 | >20000 | >20000 | >20000 | >20000 | | | | | |
| 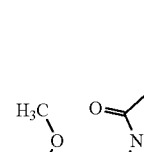 | 20 | 1452 | >10000 | 642 | 633 | 2300 | 3100 | 1300 | | | | |
| 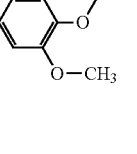 | 21 | 314 | 403 | 435 | 216 | 383 | 924 | 408 | | | | |
| 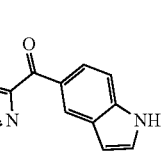 | 22 | >20000 | >20000 | >20000 | >20000 | >20000 | >20000 | | | | | |

TABLE 6A-continued
| | | IC$_{50}$ (nM) | | | | | | | | | |
|---|---|---|---|---|---|---|---|---|---|---|---|
| Structure | ID | LNCaP | PC-3 | DU 145 | PPC-1 | A375 | B16-F1 | WM164 | MES-SA | MES-SA/Dx5 | OVCAR-8 | NCI/ADR-RES |
| 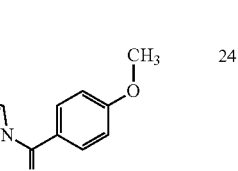 | 23 | ~10000 | ~10000 | ~10000 | ~10000 | | | | | | | |
| 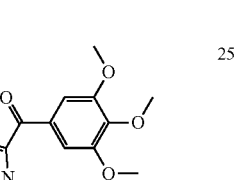 | 24 | >10000 | >10000 | >10000 | >10000 | >10000 | >10000 | >10000 | | | | |
| 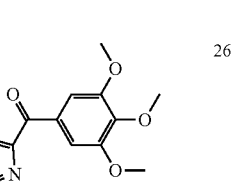 | 25 | 48 | 44 | 24 | 13 | 20 | 38 | | | | | |
| 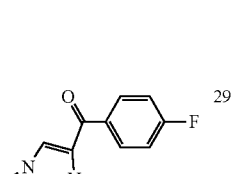 | 26 | 23 | 16 | 16 | 15 | 11 | 14 | | | | | |
| 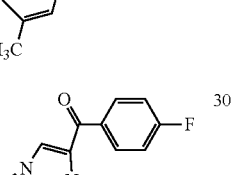 | 29 | 1788 | >10000 | >10000 | >10000 | >10000 | >10000 | | | | | |
| 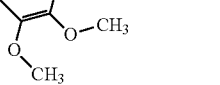 | 30 | >10000 | >10000 | >10000 | >10000 | >10000 | >10000 | | | | | |

TABLE 6A-continued
| | | IC$_{50}$ (nM) | | | | | | | | | |
|---|---|---|---|---|---|---|---|---|---|---|---|
| Structure | ID | LNCaP | PC-3 | DU 145 | PPC-1 | A375 | B16-F1 | WM164 | MES-SA | MES-SA/Dx5 | OVCAR-8 | NCI/ADR-RES |
| 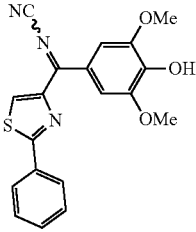 [SMILES: COc1cc(C(=NC#N)c2csc(-c3ccccc3)n2)cc(OC)c1O] | 32 | 1664 | 2291 | 4601 | 1170 | 2700 | >10000 | 2600 | | | | |
| 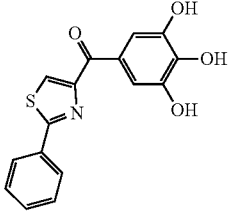 [SMILES: O=C(c1cc(O)c(O)c(O)c1)c1csc(-c2ccccc2)n1] | 33 | >2000 | >2000 | >2000 | >2000 | 9800 | >20000 | | | | | |
| 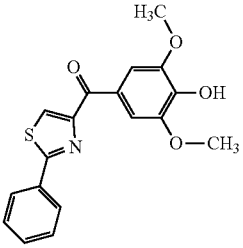 [SMILES: COc1cc(C(=O)c2csc(-c3ccccc3)n2)cc(OC)c1O] | 34 | >10000 | >10000 | >10000 | >10000 | >10000 | >10000 | >10000 | | | | |
| 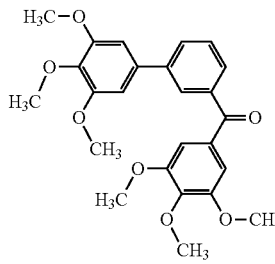 | 35 | 1500 | 40100 | 21900 | 15000 | | | | | | | |
| 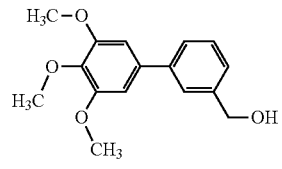 | 39 | 4300 | 32500 | 16800 | 21400 | | | | | | | |
| 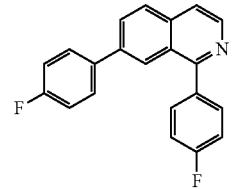 [SMILES: Fc1ccc(-c2ccc3ccnc(-c4ccc(F)cc4)c3c2)cc1] | 40 | 13400 | 19600 | 18400 | 6200 | | | | | | | |

TABLE 6A-continued
| | | | | | | | | | MES- | | NCI/ |
| | | | | DU | | | B16- | | MES- | SA/ | OVCAR- | ADR- |
| Structure | ID | LNCaP | PC-3 | 145 | PPC-1 | A375 | F1 | WM164 | SA | Dx5 | 8 | RES |
|---|---|---|---|---|---|---|---|---|---|---|---|---|
| 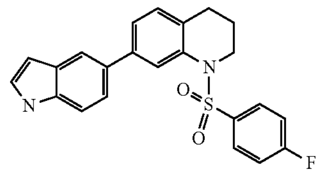 [SMILES: O=S(=O)(c1ccc(F)cc1)N1CCCc2ccc(-c3ccc4[nH]ccc4c3)cc21] | 41 | 15750 | 18170 | 17040 | >20000 | | | | | | | |
| 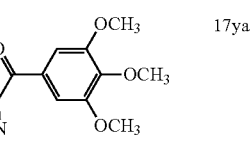 | 42 | 43590 | 23790 | 24880 | >20000 | | | | | | | |
| | 43 | 12690 | 14720 | 17210 | >20000 | | | | | | | |
| 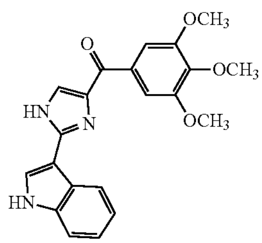 [SMILES: COc1cc(C(=O)c2c[nH]c(-c3c[nH]c4ccccc34)n2)cc(OC)c1OC] | 17ya | 12 | 10 | 17 | 21 | 17.35 | 32.94 | 12.08 | | | | |
| 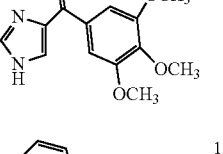 | 17yac | 233.7 | 148.3 | 592.1 | 208.9 | 481.2 | 538.7 | 467.6 | | | | |
| 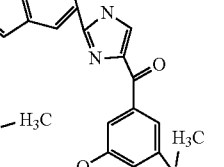 | 15xaa | 1068 | 2628 | 5917 | 4575 | 1800 | 1390 | 1700 | | | | |
| 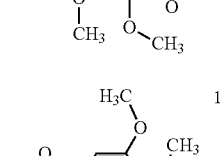 | 16xaa | >10000 | >10000 | >10000 | >10000 | >10000 | >10000 | >10000 | | | | |

Example 13

Biological Evaluation of Isoquinoline Derivatives of this Invention

Cell Culture.

LNCaP, PC-3, DU-145, PPC-1, MES-SA, and MES-SA/DX5 were originally obtained from ATCC (Rockville, MD). All cells obtained from ATCC were immediately expanded and frozen down such that all cell lines could be restarted every 2-3 months from a frozen vial of the same batch of cells. For the in vivo xenograft studies, PC-3 was authenticated at Research Animal Diagnostic Laboratory (Columbia, MO) within four months before studies. Inter-species contamination was tested by PCR and the identity of the cell lines was verified by generating a genetic profile. MES-SA and MES-SA/DX5 were maintained in McCoy's 5A Medium containing 2 mM L-glutamine supplemented with 10% fetal bovine serum (FBS). All other cells were maintained in RPMI-1640 medium with 2 mM L-glutamine and 10% FBS.

Growth Inhibition Assay.

The cytotoxic or antiproliferative activity of test compounds was investigated in several cell lines using the sulforhodamine B (SRB) assay. Cultured cells were plated into 96-well plates and incubated with medium containing different concentrations of the test compounds for 96 h. Cells were stained with SRB solution. The optical density was determined at 540 nm on a microplate reader (Dynex Technologies, Chantilly, VA). Plots of percent inhibition of cell growth versus drug concentration were constructed, and the concentration that inhibited cell growth by 50% relative to the untreated control ($IC_{50}$) was determined by nonlinear least squares regression using WinNonlin software (Pharsight Corporation, Cary, NC).

Cell Cycle Analysis.

Cell cycle distribution was determined by propidium iodide (PI) staining. Treated cells were washed with PBS and fixed with 70% ice-cold ethanol overnight. Fixed cells were then stained with 20 μg/mL of PI in the presence of RNase A (300 μg/mL) at 37° C. for 30 min. Cell cycle distribution was analyzed by fluorescence-activated cell sorting (FACS) analysis core services at the University of Tennessee Health Science Center, TN.

In Vitro Metabolism Studies.

For both phase I, the incubation mixture, in 65 mM potassium phosphate buffer (pH 7.4), consisted of 1 mg/mL liver microsomal proteins, 3 mM NADPH, and 0.5 μM test compound. The concentration of methanol (used for dissolving the substrate) was 1% (v/v). Total volume of the incubation was 200 μL and the reaction mixtures were incubated at 37° C. To generate the stability curves for test compounds different incubations were stopped at 10, 20, 30, 60, and 90 minutes for analysis of compounds remaining. All reactions were stopped by the addition of 200 μL ice-cold acetonitrile. Subsequently, the samples were then centrifuged at 3000 g for 5 min and supernatant was analyzed by LC-MS/MS.

Pharmacokinetic Studies in Mice.

Male ICR mice (5-6 weeks, 20-25 g) were used. For 6a, 6b, and 6c a dose of 5 mg/kg was administered via the i.v., i.p., and p.o. route. I.v. doses were administered via the tail vein. Oral doses were administered by gavage. At each time point, three to four mice were euthanized by isoflurane (Baxter Healthcare, Deerfield, IL) and blood samples (up to 600 μL each) were taken from the posterior vena cava. Plasma samples were stored at –20° C. prior to analysis. Plasma proteins were precipitated by the addition of acetonitrile (150 μL, containing the internal standard) to 100 μL of mouse plasma. Samples were vortexed and then centrifuged at 8000g for 10 min. The supernatant was transferred to a clean vial for injection into the mass spectrometer for analysis.

In Vivo Antitumor Efficacy Study.

PC-3 cells ($2.5 \times 10^6$ cells/site) plus Matrigel (BD biosciences, San Jose, CA) were injected subcutaneously into flanks of male nu/nu mice. Tumor size was measured using calipers every 2-4 days and calculated as $V = \pi/6 \times (\text{length}) \times (\text{width})^2$. When tumors reached a volume of approximately 100-150 mm³, drug treatment was initiated. The control group was treated with vehicle (20% Captex200 in Tween80). During the treatment, tumor size and body weights were measured every 2-4 days.

White Blood Cell Counting.

Whole blood was obtained from nude mice at the end of efficacy study. To count white blood cells (WBC) using a hemacytometer, 10 μL of whole blood sample was diluted with the 190 μL of 2% acetic acid. With proper light adjustment, the leukocytes appeared as dark dots on the hemacytometer. WBC in each sample was counted twice within one hours following dilution and average was calculated.

Results

TABLE 7

Anticancer efficacy of isoquinoline compounds in different cancer cell lines and MDR cell lines mediated by P-glycoprotein

| | $IC_{50}$ (nM) | | | | |
|---|---|---|---|---|---|
| | 6a | 6b | 6c | Vinblastine | Docetaxel |
| LNCaP | 80.6 ± 17.1 | 98.1 ± 17.9 | 38.3 ± 9.7 | 3.4 ± 0.9 | 4.7 ± 1.3 |
| PC-3 | 64.4 ± 12.2 | 71.8 ± 9.1 | 25.6 ± 8.3 | 1.4 ± 0.3 | 6.3 ± 0.4 |
| DU-145 | 91.7 ± 10.2 | 113.4 ± 21.4 | 46.6 ± 13.8 | 2.6 ± 1.0 | 5.2 ± 1.0 |
| PPC-1 | 60.6 ± 3.4 | 47.9 ± 10.0 | 27.7 ± 4.5 | 1.1 ± 0.4 | 2.7 ± 1.0 |
| P-gp | | | | | |
| MES-SA | 78.2 ± 1.8 | 129.8 ± 38.0 | 35.6 ± 2.8 | 2.3 ± 0.8 | 5.9 ± 1.1 |
| MES-SA/DX5 | 119.4 ± 0.4 | 177.8 ± 32.8 | 59.2 ± 0.1 | 45.7 ± 5.3 | 76.4 ± 8.7 |
| Resistance factor | 1.5 | 1.4 | 1.7 | 20 | 13 |

NOTE:
P-gp is over-expressed in MES-SA/DX5. The resistance factor (RF) was calculated as the ratio of $IC_{50}$ values for the resistant cell subline to that of the parental cell line. All experiments were performed at least in three replicates.

TABLE 8

Compound 6a, 6b, and 6c arrested PC-3 cells in $G_2M$ phase.

| | $G_2M$ phase arrest $EC_{50}$ (nM) |
|---|---|
| 6a | 53.4 |
| 6b | 91.9 |
| 6c | 23.3 |

TABLE 9

Summary of half lives (phase I pathway) of 6a, 6b, and 6c in mouse, rat, hamster, rabbit, guinea pig, dog, monkey, and human liver microsomes.

| | T ½ (min) | | |
|---|---|---|---|
| | 6a | 6b | 6c |
| Mouse | 3.4 | 10 | 13 |
| Rat | 12 | 9 | 14 |
| Hamster | 6 | 11 | 20 |
| Rabbit | 17 | 16 | 16 |
| Guinea pig | 15 | 15 | 8 |
| Dog | 13 | 30 | 29 |
| Monkey | 16 | 13 | 9 |
| Human | 32 | 40 | 47 |

TABLE 10

Summary of pharmacokinetic properties of compound 6a, 6b, and 6c in mice.

| | | 6a | 6b | 6c |
|---|---|---|---|---|
| MW | | 410.5 | 359.4 | 338.4 |
| IV CL (mL * min$^{-1}$kg$^{-1}$) | 5 mg/kg | 51 | 14 | 30 |
| IV $V_d$ (L * kg$^{-1}$) | 5 mg/kg | 2.3 | 1.1 | 1.8 |
| IP $C_{max}$ (ng/mL) | 5 mg/kg | 678.4 | 1500 | 1100 |
| IP AUC (min * μg/mL) | 5 mg/kg | 59 | 218 | 55 |
| IP Bioavailability | $F_{ip}$ % | 60 | 60 | 33 |
| PO $C_{max}$ (ng/mL) | 5 mg/kg | 6.7 | 50 | 50 |
| AUC (min * μg/mL) | 5 mg/kg | 5 | 7 | 4 |
| PO Bioavailability | $F_{po}$ % | 5 | 2.1 | 2.7 |

Efficacy and tolerability of 6b and 6c was measured in xenograft models after i.p. injection (FIG. 34). PC-3 xenografts were treated with vehicle (qd), 6b (40 mg/kg, qd), or 6c (40 mg/kg, qd) for 3 weeks. Dosing vehicles were composed of 20% Captex200 in Tween80. The tumor volumes (mm$^3$) were plotted against time and are the means±SD from eight animals. The tumor volumes and survival rates or body weights are shown in FIGS. 34A and 34B. The liver size (g) of each nude mouse was measured after 3 weeks treatment and is shown in FIG. 34C. The number of white blood cells was counted in whole blood collected from animal after 3 weeks treatment and is shown in FIG. 34D.

Example 14

Antiproliferative Activity of Selected Abi Compounds of this Invention
Cell Culture Cytotoxicity Assay Materials and Methods The antiproliferative activity of the ABI compounds in three melanoma cell lines (A375 and WM-164, human melanoma cell line; B16-F1, mouse melanoma cell line) and four human prostate cancer cell lines (LNCaP, DU 145, PC-3, and PPC-1) were studied. All these cell lines were purchased from ATCC (American Type Culture Collection, Manassas, VA) except the PPC-1 cell line. MDA-MB-435 and MDA-MB-435/LCCMDR1 cells were kindly provided by Dr. Robert Clarke at Georgetown University School of Medicine, Washington, DC. Melanoma cells were cultured in DMEM (Cellgro Mediatech, Inc., Herndon, VA) and prostate cancer cells were cultured in RPMI 1640 (Cellgro Mediatech, Inc., Herndon, VA) supplemented with 10% FBS (Cellgro Mediatech). Cultures were maintained at 37° C. in a humidified atmosphere containing 5% $CO_2$. 1000 to 5000 cells were plated into each well of 96-well plates depending on growth rate and exposed to different concentrations of a test compound for 48 h (fast growing melanoma cells) or 96 h (slow growing prostate cancer cells) in three to five replicates. Cell numbers at the end of the drug treatment were measured by the sulforhodamine B (SRB) assay. Briefly, the cells were fixed with 10% trichloroacetic acid and stained with 0.4% SRB, and the absorbances at 540 nm were measured using a plate reader (DYNEX Technologies, Chantilly, VA). Percentages of cell survival versus drug concentrations were plotted, and the $IC_{50}$ (concentration that inhibited cell growth by 50% of untreated control) values were obtained by nonlinear regression analysis using GraphPad Prism (GraphPad Software, San Diego, CA).

Results

The results of the in vitro antiproliferative activities of the compounds of this invention using three melanoma cell lines (one murine melanoma cell line, B16-F1, and two human metastatic melanoma cell lines, A375 and WM-164) and four human prostate cancer cell lines (LNCaP, PC-3, Du 145, and PPC-1) are summarized in Tables 11-13.

μM for 12ad). Compound with 4-fluoro on the C ring (12af) also showed relatively good activity ($IC_{50}$=0.91 μM), a finding that has an important implication, because replacing the trimethoxy moiety with a 4-fluoro group may provide good activity and improved metabolic stability. The position of the fluorine on the C ring was critical for activity because a shift from 4-fluoro to 3-fluoro resulted in a total loss of activity ($IC_{50}$>10 μM for 12ag compared with 0.91 μM for

TABLE 11

In vitro growth inhibitory effects of compounds without A ring substitutions.

| Structure | ID | R | $IC_{50}$ (nM) | | | | | | |
|---|---|---|---|---|---|---|---|---|---|
| | | | A375 | B16-F1 | WM164 | LNCaP | PC-3 | Du 145 | PPC-1 |
| 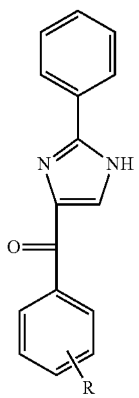 | 12aa | 3,4,5-(OMe)$_3$ | 160 | 120 | 10 | 152 | 288 | 196 | 133 |
| | 12ab | 4-OMe | >10000 | >10000 | >10000 | >10000 | >10000 | >10000 | >10000 |
| | 12ac | 3-OMe | >10000 | >10000 | >10000 | >10000 | >10000 | >10000 | >10000 |
| | 12ad | 3,5-(OMe)$_2$ | 2800 | 5400 | 2100 | 3611 | 3274 | 2590 | 2129 |
| | 12ae | 3,4-(OMe)$_2$ | >10000 | >10000 | >10000 | >10000 | >10000 | >10000 | >10000 |
| | 12af | 4-F | 580 | 930 | 630 | 613 | 2197 | 846 | 575 |
| | 12ag | 3-F | >10000 | >10000 | >10000 | >10000 | >10000 | >10000 | >10000 |
| | 12ah | 4-Me | >10000 | >10000 | >10000 | >10000 | >10000 | >10000 | >10000 |
| | 12ai | 3-Me | >10000 | >10000 | >10000 | >10000 | >10000 | >10000 | >10000 |
| 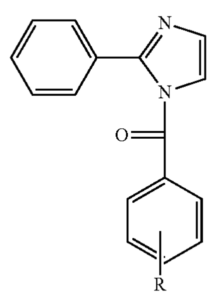 | 12aba | 4-OMe | >10000 | >10000 | >10000 | >10000 | >10000 | >10000 | >10000 |
| | 12aaa | 3,4,5-(OMe)$_3$ | >10000 | >10000 | >10000 | >10000 | >10000 | >10000 | >10000 |
| 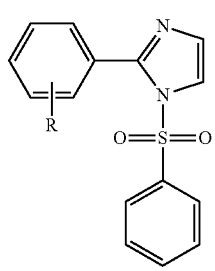 | 10a | H | >10000 | >10000 | >10000 | >10000 | >10000 | >10000 | >10000 |
| | 10x | 4-NO$_2$ | >10000 | >10000 | >10000 | >10000 | >10000 | >10000 | >10000 |
| | 10j | 4-OBn | >10000 | >10000 | >10000 | >10000 | >10000 | >10000 | >10000 |

From Table 11, compounds 12aa-12ai showed moderate activity with $IC_{50}$ values in the μM range (average of all seven cell lines). The most potent compound of this series was 12aa with an average $IC_{50}$ value of 160 nM. The removal of one of the methoxy groups from the 3,4,5-trimethoxy on the C ring (12ad, 12ae) led to a significant loss of activity ($IC_{50}$>10 μM for 12ae and an average $IC_{50}$ of 3.1 μM for 12ad). This result suggested that a potential hydrogen bond donor is present close to the 4-position of this ring.

As clearly indicated in Table 11, the positions of the A and C rings were critical. A simple shift of the C-ring moiety from position 4 to position 1 in the imidazole ring (B ring) resulted in total loss of activity ($IC_{50}$>10 μM for 12aba, 12aaa, 10a, 10x, 10j).

TABLE 12

In vitro growth inhibitory effects of compounds with substitutions on A ring.

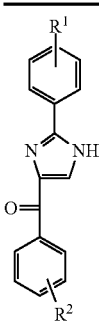

| | | | IC$_{50}$ ± SEM (nM) | | | |
|---|---|---|---|---|---|---|
| ID | R$^1$ | R$^2$ | A375 | B16-F1 | WM164 | LNCaP |
| 12ba | 4-F | 3,4,5-(OMe)$_3$ | 205 ± 19 | 320 ± 41 | 73 ± 8 | 98 ± 2 |
| 12ca | 4-OMe | 3,4,5-(OMe)$_3$ | 30 ± 5 | 108 ± 12 | 31 ± 4 | 31 ± 1 |
| 12cb | 4-OMe | 4-F | 31 ± 5 | 63 ± 7 | 28 ± 3 | 28 ± 2 |
| 12da | 4-Me | 3,4,5-(OMe)$_3$ | 9 ± 2 | 46 ± 5 | 8 ± 2 | 12 ± 1 |
| 12db | 4-Me | 4-F | 143 ± 13 | 222 ± 10 | 156 ± 19 | 45 ± 2 |
| 12db-HCl | | | 108 ± 11 | 297 ± 23 | 112 ± 9 | ND |
| 12dc | 4-Me | 3,5-(OMe)$_2$-4-OH | 105 | 387 | 123 | 134 |
| 12ea | 3,4,5-(OMe)$_3$ | 3,4,5-(OMe)$_3$ | 4800 | >10000 | >10000 | >10000 |
| 12eb | 3,4,5-(OMe)$_3$ | 4-F | >10000 | >10000 | >10000 | >10000 |
| 12fa | 4-Cl | 3,4,5-(OMe)$_3$ | 43 ± 5 | 168 ± 14 | 26 ± 3 | 24 ± 1 |
| 12fb | 4-Cl | 4-F | 52 ± 4 | 73 ± 6 | 74 ± 9 | 49 ± 2 |
| 13fa | 4-Cl | 3,4,5-(OH)$_3$ | 3900 | 1810 | 2100 | 10000 |
| 12ga | 4-N(Me)$_2$ | 3,4,5-(OMe)$_3$ | 82 ± 9 | 361 ± 29 | 80 ± 11 | 58 ± 2 |
| 12gb | 4-N(Me)$_2$ | 4-F | 56 ± 7 | 129 ± 11 | 62 ± 8 | 57 ± 6 |
| 12ha | 3,4-(OMe)$_2$ | 3,4,5-(OMe)$_3$ | 113 ± 14 | 1400 ± 200 | 191 ± 18 | 121 ± 10 |
| 12hb | 3,4-(OMe)$_2$ | 4-F | 10000 | 4210 | 1400 | 2533 |
| 12ia | 2-CF$_3$ | 3,4,5-(OMe)$_3$ | >10000 | >10000 | >10000 | >10000 |
| 12ib | 2-CF$_3$ | 4-F | >10000 | >10000 | >10000 | >10000 |
| 13ea | 3,4,5-(OH)$_3$ | 3,4,5-(OH)$_3$ | >10000 | >10000 | >10000 | >10000 |
| 12ja | 4-OBn | 3,4,5-(OMe)$_3$ | 5200 | 10000 | 5500 | 2786 |
| 12jb | 4-OBn | 4-F | 93 ± 8 | 117 ± 16 | 90 ± 12 | 44 ± 7 |
| 12ka | 4-OH | 3,4,5-(OMe)$_3$ | 1600 | 2400 | 1800 | ND |
| 12kb | 4-OH | 4-F | 10000 | >10000 | >10000 | 10000 |
| 12kc | 4-OH | 3-OH, 4,5-(OMe)$_2$ | 10000 | 5600 | 6400 | |
| 12la | 4-Br | 3,4,5-(OMe)$_3$ | 32 | 74 | 36 | 34 |
| 12pa | 4-CF3 | 3,4,5-(OMe)$_3$ | 163.1 | 468.7 | 175 | 134 |
| 13ha | 3,4-(OH)$_2$ | 3,4,5-(OH)$_3$ | >10000 | >10000 | >10000 | ND |
| 12q | 4-Et | 3,4,5-(OMe)$_3$ | ND | ND | ND | 9 |
| 12v | 4-CH(CH$_3$)$_2$ | 3,4,5-(OMe)$_3$ | ND | ND | ND | 171 |
| 12w | 4-C(CH$_3$)$_3$ | 3,4,5-(OMe)$_3$ | ND | ND | ND | 423 |
| Colchicine | | | 20 ± 3 | 29 ± 5 | ND | 16 ± 4 |

| | IC$_{50}$ ± SEM (nM) | | | | |
|---|---|---|---|---|---|
| ID | PC-3 | Du 145 | PPC-1 | OVCAR-8 | NCI/ADR-RES |
| 12ba | 169 ± 12 | 132 ± 24 | 81 ± 1 | | |
| 12ca | 45 ± 1 | 48 ± 0.5 | 34 ± 0.3 | | |
| 12cb | 31 ± 2 | 41 ± 38 | 29 ± 1 | | |
| 12da | 9 ± 0.4 | 15 ± 0.5 | 11 ± 0.1 | | |
| 12db | 66 ± 3 | 78 ± 5 | 54 ± 1 | | |
| 12db-HCl | ND | ND | ND | | |
| 12dc | 127 | 174 | 110 | | |
| 12ea | >10000 | >10000 | >10000 | | |
| 12eb | >10000 | >10000 | >10000 | | |
| 12fa | 35 ± 1 | 36 ± 0.4 | 26 ± 0.2 | 47 | 19 |
| 12fb | 81 ± 2 | 65 ± 1 | 52 ± 1 | | |
| 13fa | 10000 | 10000 | >10000 | | |
| 12ga | 92 ± 4 | 95 ± 1 | 67 ± 0.7 | | |
| 12gb | 81 ± 3 | 72 ± 0.4 | 45 ± 0.3 | | |
| 12ha | 203 ± 7 | 168 ± 15 | 117 ± 1 | | |
| 12hb | 10000 | 10000 | 2172 ± 48 | | |
| 12ia | >10000 | >10000 | >10000 | | |
| 12ib | >10000 | >10000 | >10000 | | |
| 13ea | >10000 | >10000 | >10000 | | |
| 12ja | 10000 | 10000 | 2844 | | |
| 12jb | 79 ± 0.4 | 60 ± 3 | 43 ± 0.2 | | |
| 12ka | ND | ND | ND | | |
| 12kb | >10000 | >10000 | >10000 | | |
| 12kc | | | | | |
| 12la | 36 | 49 | 33 | | |
| 12pa | 127 | 174 | 110 | | |
| 13ha | ND | ND | ND | | |
| 12q | 13 (PC3/TXR = 8) | 25 (DU145/TXR = 20) | 15 | | |

TABLE 12-continued

In vitro growth inhibitory effects of compounds with substitutions on A ring.

| | | | |
|---|---|---|---|
| 12v | 136 | 482 | 173 |
| 12w | 436 | 1698 | 294 |
| Colchicine | 11 ± 1 | 10 ± 2 | 20 ± 1 |

ND—not determined

From Table 12 compounds with 3,4,5-trimethoxy and 4-fluoro substitutions on the C ring showed good activity with different substitutions on the A ring. These compounds demonstrated excellent antiproliferative activity with $IC_{50}$ values as low as 8.0 nM on WM164 cell line (12da). In general, compounds incorporating a single substituent on the para-position of the A ring were more potent as can be seen from the activities of 12ca, 12cb, 12da, 12db, 12fa, 12fb, 12ga, and 12gb ($IC_{50}$=7.9-110 nM). 12db-HCl salt ($IC_{50}$=172 nM) showed slightly diminished activity compared with the corresponding free base 12db ($IC_{50}$=109 nM). Compound 12fb ($IC_{50}$=63.7 nM), with a single halogen substituent in the para-position of the A and C rings, demonstrated potent and was devoid of a methoxy moiety. Compounds with 3,4,5-trimethoxy substituents on the A ring lost activity completely ($IC_{50}$>10 μM for 12ea, 12eb), suggesting very different binding environments near the A ring and C ring. Removal of the 5-methoxy substituent from the A-ring improved activity significantly ($IC_{50}$=330 nM and >10 μM for 12ha, 12ea respectively). Demethylation of the 3,4,5-trimethoxy decreased activity sharply from 43 nM (12fa) to 3.89 μM (13fa). Similar results were observed for 13ea, 12ka, 12kb, and 13ha due to the demethylation of substituents on either the A or C ring. Electron-donating groups (4-methoxy, 4-dimethylamino, 4-methyl) and electron-withdrawing groups (4-chloro, 2-trifluoromethyl) on the A ring did not show substantial differences in activity. The introduction of a trifluoromethyl group at the ortho position of the A ring caused complete loss of activity ($IC_{50}$>10 μM for 12ia, 12ib). The presence of a benzyloxy group at the para position of A ring ($IC_{50}$=75 nM for 12jb) resulted in a 440-fold increase in activity when compared with the para-hydroxy compound 12kb ($IC_{50}$=33 μM). It is worthwhile to note that compound 12jb, with the 4-fluoro in the C ring, has better activity than does its counterpart 12ja, which has a 3,4,5-trimethoxy group in the C ring ($IC_{50}$ is 75 nM for 12jb, and 7.3 μM for 12ja).

TABLE 13

In vitro growth inhibitory effects of compounds with protection on B ring.

| Structure | ID | R$^1$ | R$^2$ | R$^3$ | $IC_{50}$ ± SEM (nM) | |
|---|---|---|---|---|---|---|
| | | | | | A375 | B16-F1 |
| 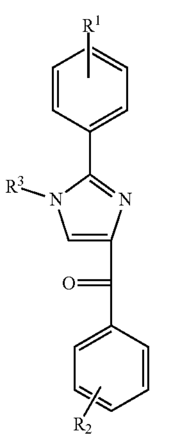 | 11ab | H | 4-OMe | SO$_2$Ph | >10000 | >10000 |
| | 11ac | H | 3-OMe | SO$_2$Ph | >10000 | >10000 |
| | 11ah | H | 4-Me | SO$_2$Ph | >10000 | >10000 |
| | 11af | H | 4-F | SO$_2$Ph | 630 ± 72 | 946 ± 86 |
| | 11ag | H | 3-F | SO$_2$Ph | >10000 | >10000 |
| | 11cb | 4-OMe | 4-F | SO$_2$Ph | 36 ± 5 | 71 ± 8 |
| | 11db | 4-Me | 4-F | SO$_2$Ph | 113 ± 14 | 287 ± 31 |
| | 11ea | 3,4,5-(OMe)$_3$ | 3,4,5-(OMe)$_3$ | SO$_2$Ph | >10000 | >10000 |
| | 11eb | 3,4,5-(OMe)$_3$ | 4-F | SO$_2$Ph | 3840 | >10000 |
| | 11fb | 4-Cl | 4-F | SO$_2$Ph | 88 ± 9 | 107 ± 12 |
| | 11ga | 4-N(Me)$_2$ | 3,4,5-(OMe)$_3$ | SO$_2$Ph | 162 ± 13 | 1200 ± 90 |
| | 11gb | 4-N(Me)$_2$ | 4-F | SO$_2$Ph | 55 ± 7 | 242 ± 26 |
| | 11ha | 3,4-(OMe)$_2$ | 3,4,5-(OMe)$_3$ | SO$_2$Ph | 192 ± 15 | 970 ± 68 |
| | 11hb | 3,4-(OMe)$_2$ | 4-F | SO$_2$Ph | 960 ± 59 | 2000 ± 400 |
| | 11ia | 2-CF$_3$ | 3,4,5-(OMe)$_3$ | SO$_2$Ph | >10000 | >10000 |
| | 11ib | 2-CF$_3$ | 4-F | SO$_2$Ph | >10000 | >10000 |
| | 11jb | 4-OBn | 4-F | SO$_2$Ph | 64 ± 7 | 110 ± 15 |
| | 12dab | 4-Me | 3,4,5-(OMe)$_3$ | Me | 32 | 134 |
| | 12cba | 4-OMe | 4-F | Me | >10000 | >10000 |
| | 12daa | 4-Me | 3,4,5-(OMe)$_3$ | CH$_2$Ph | | |
| | 12gba | 4-N(Me)$_2$ | 4-F | SO$_2$PhOMe | ~100 | ~100 |

TABLE 13-continued

In vitro growth inhibitory effects of compounds with protection on B ring.

| Structure | ID | IC$_{50}$ ± SEM (nM) | | | | |
|---|---|---|---|---|---|---|
| | | WM164 | LNCaP | PC-3 | Du 145 | PPC-1 |
| 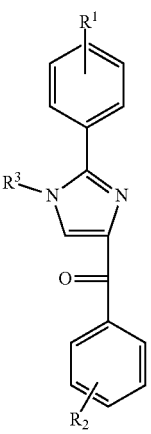 | 11ab | >10000 | >10000 | >10000 | >10000 | >10000 |
| | 11ac | >10000 | >10000 | >10000 | >10000 | >10000 |
| | 11ah | >10000 | >10000 | >10000 | >10000 | >10000 |
| | 11af | 596 ± 61 | 573 | 2233 | 846 | 575 |
| | 11ag | >10000 | >10000 | >10000 | >10000 | >10000 |
| | 11cb | 43 ± 6 | 31 ± 2 | 33 ± 2 | 52 ± 3 | 32 ± 0.7 |
| | 11db | 107 ± 14 | 55 ± 3 | 80 ± 1 | 80 ± 1 | 57 ± 1 |
| | 11ea | >10000 | >10000 | >10000 | >10000 | >10000 |
| | 11eb | >10000 | >10000 | >10000 | >10000 | >10000 |
| | 11fb | 70 ± 6 | 48 ± 1 | 76 ± 2 | 64 ± 1 | 54 ± 1 |
| | 11ga | 308 ± 32 | 62 ± 2 | 93 ± 6 | 99 ± 2 | 72 ± 0.4 |
| | 11gb | 56 ± 4 | 56 ± 6 | 83 ± 3 | 74 ± 0.5 | 48 ± 0.3 |
| | 11ha | 139 ± 15 | 114 ± 6 | 197 ± 9 | 144 ± 29 | 117 ± 2 |
| | 11hb | 1400 ± 30 | 1915 ± 77 | 10000 | 3312 | 1441 ± 49 |
| | 11ia | >10000 | >10000 | >10000 | >10000 | >10000 |
| | 11ib | >10000 | >10000 | >10000 | >10000 | >10000 |
| | 11jb | 48 ± 5 | 35 ± 1 | 75 ± 0.5 | 58 ± 1 | 38 ± 0.2 |
| | 12dab | 40 | 32 | 46 | 36 | 28 |
| | 12cba | >10000 | >10000 | >10000 | >10000 | >10000 |
| | 12daa | | 683.2 | 465.8 | 1501 | 777.9 |
| | 12gba | ~100 | 73.2 | 44.14 | 129.4 | 63.4 |

TABLE 13A

Reversed aryl benzoyl imidazole (RABI)-inhibitory effects

| Structure | ID | R$_4$ | R$_9$ | R$_{12}$ | LNCaP (nM) | PC3 (nM) | PC3/ TXR (nM) | PPC1 (nM) | DU145 (nM) | DU145/ TXR (nM) |
|---|---|---|---|---|---|---|---|---|---|---|
| 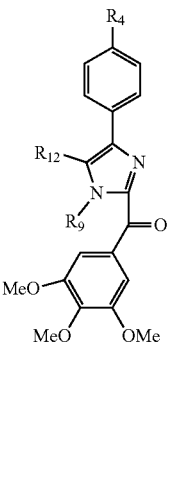 | 70a | —H | —H | —H | 6 | 14 | 4 | 13 | 21.5 | 22.9 |
| | 70b | —F | —H | —H | 114 | 196 | — | 13 | 353 | — |
| | 70c | —Cl | —H | —H | 22 | 64 | 25 | 51 | 125 | 121 |
| | 70d | —Br | —H | —H | 15 | 33 | 17 | 30 | 66 | 63 |
| | 70e | —CF$_3$ | —H | —H | 47 | 93 | 46 | 75 | 210 | 202 |
| | 70f | —CH$_3$ | —H | —H | 13 | 19 | 10 | 18 | 30 | 21 |
| | 70g | —OCH$_3$ | —H | —H | 30 | 61 | 25 | 54 | 210 | 111 |
| | 70h | —N(CH$_3$)$_2$ | —H | —H | 96 | 117 | — | 120 | 263 | — |
| | 70i | —OH | —H | —H | 219 | 155 | — | 122 | 518 | — |
| | 70j | —H | —H | —Me | 938 | 1617 | — | 860 | 2001 | — |
| | 70k | —H | —H | —Et | 2029 | 3654 | — | 2078 | 5079 | — |
| | 70l | —H | —H | -n-Pr | 3094 | 12360 | — | 11410 | 16350 | — |
| | 70m | —H | —Me | —H | 10 | 16 | 7.5 | 13 | 26 | 27 |
| | 70n | —H | —Et | —H | 29 | 25 | 20 | 30 | 66 | 66 |
| | 70o | —H | —Bn | —H | 67 | 72 | — | 77 | 160 | — |
| | 70p | —H | —cyclopentyl | —H | 51 | 56 | — | 63 | 167 | — |
| | 70ab | —H | n-Pr | —H | 49.4 | 25.6 | — | 9.8 | 71.6 | — |
| | 70ac | —H | —CH(CH$_3$)$_2$ | —H | 62.2 | 52.5 | — | 15.0 | 114.1 | — |
| | 70ad | —H | 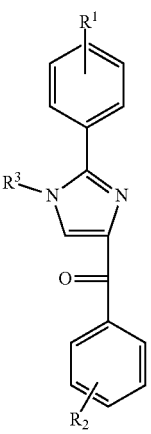 | —H | 19.5 | 11.1 | — | 7.8 | 36.3 | — |

TABLE 13B

Reversed aryl benzoyl imidazole (RABI)-inhibitory effects

| Structure | ID | R₁ | R₂ | R₃ | R₄ | R₅ | R₆ | LNCaP (nM) | PC3 (nM) | PPC1 (nM) | DU145 (nM) |
|---|---|---|---|---|---|---|---|---|---|---|---|
| (see structure) | 70q | OMe | OMe | OMe | OMe | OMe | OMe | >50000 | >50000 | >50000 | >50000 |
| | 70r | F | H | H | F | H | H | >50000 | >50000 | >50000 | >50000 |
| | 70s | Cl | H | H | Cl | H | H | >50000 | >50000 | >50000 | >50000 |
| | 70t | Br | H | H | Br | H | H | 16930 | 18940 | 13210 | 25490 |
| | 70u | CF₃ | H | H | CF₃ | H | H | >50000 | >50000 | >50000 | >50000 |
| | 70v | CH₃ | H | H | CH₃ | H | H | 3762 | 5159 | 2405 | 6541 |
| | 70w | OMe | H | H | OMe | H | H | 6410 | 23370 | 38150 | 9389 |
| | 70x | H | H | H | OMe | OMe | OMe | 195.4 | 631.5 | 408.5 | 1301 |
| | 70y | OMe | H | H | OMe | OMe | OMe | 708.5 | 10390 | 5685 | >50000 |
| | 70z | Br | H | H | OMe | OMe | OMe | 131 | 371 | 107 | 430 |
| | 70aa | H | H | H | H | H | H | >50000 | >50000 | >50000 | >50000 |

From Table 13, compounds with a phenylsulfonyl protection group attached to the nitrogen of the imidazole ring (11cb, 11db, 11fb, 11ga, 11gb, 11ha, 11jb) were also very active with $IC_{50}$ in the nM range (Table 13). Generally the activities of these compounds are comparable to their corresponding unprotected counterparts as exemplified by comparing the activities of 11cb (43 nM), 11db (111 nM), 11fb (72 nM), 11ga (285 nM), 11gb (87 nM), 11ha (268 nM), and 11jb (61 nM) with their corresponding unprotected counterparts 12cb (36 nM), 12db (109 nM), 12fb (64 nM), 12ga (131 nM), 12gb (72 nM), 12ha (330 nM), and 12jb (75 nM). Other compounds (11ab-11ag, 11ea, 11eb, 11hb, 11ia, and 11ib, 1-50 μM) were generally much less active, also in line with their counterparts (12ab-12ag, 12ea, 12eb, 12hb, 12ia, and 12ib, 1-50 μM).

The PC3 cell cycle distributions of compounds of this invention are presented in FIG. 39.

Method

Cell Cycle Analysis.

Cell cycle distribution was determined by propidium iodide (PI) staining. Treated cells were washed with PBS and fixed with 70% ice-cold ethanol overnight. Fixed cells were then stained with 20 μg/mL of PI in the presence of RNase A (300 μg/mL) at 37° C. for 30 min. Cell cycle distribution was analyzed by fluorescence-activated cell sorting (FACS) analysis core services at the University of Tennessee Health Science Center, TN.

Result

Reversed ABIs (RABIs) demonstrated by cell cycle analysis that they arrest cells in the G2/M phase. Compounds 12q, 70a, 70f, and 70m were treated on PC3 cells for 24 h (FIG. 39) and the distribution of PI stained cells was investigated by FACS analysis. Four different concentrations—1, 10, 50, and 100 nM—of each compound were chosen to examine the dose effect. In the vehicle treated group, about 18% of PC3 cells were distributed in the G2/M phase. RABIs increased the proportion of cells in G2/M phase up to 70% approximately in a concentration-dependent manner. The potency of the different concentrations in arresting cells in the G2/M phase positively correlated with in vitro cell growth inhibitory activity.

Example 15

Activity of Aryl-Benzoyl-Imidazole (Abi) Compounds in Drug-Resistant Melanoma Cells P-glycoprotein (Pgp)-mediated drug efflux represents a major mechanism for cancer cells to prevent the build up of effective anticancer intracellular drug concentrations. The activity of the ABI compounds were compared against multidrug-resistant (MDR) melanoma cells (MDA-MB-435/LCCMDR1) and their parental nonresistant cancer cells (MDA-MB-435). Although MDA-MB-435 was originally designated as a breast cancer cell line, it has been shown definitively to originate from the M14 melanoma cell line. Compounds 12da, 12fb, 12cb, 11cb, and 11fb together with other tubulin-targeting agents including colchicine, paclitaxel, and vinblastine were tested on both the MDR melanoma cell line and its parental melanoma cell line (Table 14A). Paclitaxel and vinblastine are clinically used anticancer drugs known to target cell tubulin. Although colchicine is not an FDA-approved drug for cancer treatment, its prodrug, ZD6126, is in clinical trial for solid tumors. Bortezomib is the first therapeutic proteasome inhibitor and was approved in 2003 by the FDA for use in multiple myeloma. ABT-751 is known to target the tubulin colchicine binding site. It is a promising drug candidate in clinical trial for children with relapsed or refractory neuroblastoma. Compounds 12da, 12fb, 12cb, 11cb, 11fb had much better resistance indices (3.0 for 12da, 0.9 for 12fb, 1.3 for 12cb, 0.8 for 11cb, 0.7 for 11fb) than colchicine (65.8), paclitaxel (69.3), and vinblastine (27.5). Although colchicine, paclitaxel, and vinblastine showed excellent activity in nonresistant melanoma cell lines (0.5-10 nM), these compounds were significantly less potent in the MDR melanoma cell line (277-658 nM). In contrast, 12cb, 11cb, 11fb had essentially equivalent potency on both MDR (15 nM, 38 nM, 30 nM, 30 nM, 35 nM for 12da, 12fb, 12cb, 11cb and 11fb respectively) and nonresistant melanoma cell lines (5 nM, 41 nM, 24 nM, 38 nM, 50 nM for 12da, 12fb, 12cb, 11cb and 11fb respectively). Compound 12da was more active than paclitaxel and colchicine on A375 and WM-164 cells.

TABLE 14A

In vitro growth inhibitory effects of the ABI compounds in comparison to other anticancer drugs on multidrug-resistant melanoma cell line (MDR cell) and the matching sensitive parent cell line (Normal Melanoma cell).

| Compound ID | IC$_{50}$ ± SEM (nM) (n = 3) | | | | | | |
|---|---|---|---|---|---|---|---|
| | A375 | B16-F1 | WM-164 | Tubulin binding (µM) | MDA-MB-435 | MDA-MB-435/ LCC6MDR1 | Resistance index* |
| 12da | 9 ± 2 | 46 ± 5 | 8 ± 2 | 0.2 ± 0.1 | 5 ± 1 | 15 ± 2 | 3.0 |
| 12fb | 52 ± 4 | 73 ± 6 | 74 ± 9 | 3.9 ± 2.1 | 41 ± 2 | 38 ± 2 | 0.9 |
| 12cb | 31 ± 5 | 63 ± 7 | 28 ± 3 | 3.4 ± 1.5 | 24 ± 2 | 30 ± 4 | 1.3 |
| 11cb | 36 ± 5 | 71 ± 8 | 43 ± 6 | ND | 38 ± 3 | 30 ± 2 | 0.8 |
| 11fb | 88 ± 9 | 107 ± 12 | 74 ± 8 | ND | 50 ± 6 | 35 ± 3 | 0.7 |
| Paclitaxel | 12 ± 3 | 17 ± 2 | 18 ± 3 | N/A | 4 ± 1 | 277 ± 41 | 69.3 |
| Vinblastine | 1.1 ± 0.2 | 4.7 ± 0.7 | 0.6 ± 0.1 | ND | 0.4 ± 0.1 | 11 ± 1 | 27.5 |
| Colchicine | 20 ± 3 | 29 ± 5 | 10 ± 2 | 1.8 ± 0.5 | 10 ± 1 | 658 ± 50 | 65.8 |
| Bortezomib | 8 ± 1 | 24 ± 2 | 8 ± 1 | ND | ND | ND | ND |
| ABT-751 | 1111 ± 108 | 2127 ± 351 | 661 ± 56 | ND | ND | ND | ND |

*Resistance indexes were calculated by dividing IC$_{50}$ values on multidrug-resistant cell line MDA-MB-435/LCC6MDR1 by IC$_{50}$ values on the matching sensitive parental cell line MDA-MB-435.
Abbreviations: N/A, value not available;
ND, not determined.

TABLE 14B

Anticancer efficacy and colchicine site binding affinity of ABIs in different cancer and MDR cell lines with different resistance mechanisms. ABIs showed excellent potency against all tested melanoma cell lines including highly metastatic and multidrug resistant cell lines. High binding affinity of ABIs to the colchicine binding site in tubulin confirmed their target inside cells.

| | IC$_{50}$ ± SEM (nmol/L) (n = 3) | | | | | | | |
|---|---|---|---|---|---|---|---|---|
| | 12cb | 12da | 12fb | Paclitaxel | Vinblastine | Colchicine | ABT-751 | SN-38 |
| A375 | 31 ± 5 | 9 ± 2 | 52 ± 4 | 12 ± 3 | 1 ± 0.1 | 20 ± 3 | 685 ± 108 | ND |
| A375MA2 | 44 ± 5 | 8 ± 1 | 55 ± 4 | 8 ± 1 | 1 ± 0.2 | 18 ± 2 | 265 ± 36 | ND |
| B16-F1 | 63 ± 7 | 46 ± 5 | 73 ± 6 | 17 ± 2 | 5 ± 1 | 29 ± 5 | 2127 ± 351 | ND |
| WM-164 | 28 ± 3 | 8 ± 2 | 74 ± 9 | 18 ± 3 | 0.6 ± 0.1 | 10 ± 2 | 661 ± 56 | ND |
| MDR1 | | | | | | | | |
| MDA-MB-435* | 24 ± 2 | 5 ± 1 | 41 ± 2 | 4 ± 1 | 0.4 ± 0.1 | 10 ± 1 | 417 ± 23 | ND |
| MDA-MB-435/ LCC6MDR1 | 30 ± 4 (1) | 11 ± 2 (2) | 38 ± 2 (1) | 277 ± 4 (69) | 11 ± 1 (28) | 658 ± 50 (66) | 577 ± 31 (1) | ND |
| OVCAR-8* | 25 ± 2 | 11 ± 1 | 45 ± 2 | 10 ± 0.2 | 2 ± 0.1 | 12 ± 1 | 785 ± 17 | 2 ± 0.2 |
| NCI/ADR-RES | 13 ± 1 (0.5) | 5 ± 0.1 (0.5) | 20 ± 6 (0.4) | 5109 ± 170 (511) | 570 ± 84 (285) | 737 ± 51 (61) | 864 ± 42 (1) | 10 ± 1 (5) |
| MRP | | | | | | | | |
| HEK293-pcDNA3.1* | 12 ± 2 | 9 ± 1 | 54 ± 0.3 | 9 ± 0.3 | 5 ± 0.1 | 3 ± 0.4 | 645 ± 153 | 3 ± 0.4 |
| HEK293-MRP1 | 16 ± 2 (1) | 8 ± 1 (0.9) | 33 ± 7 (0.6) | 30 ± 3 (3) | 24 ± 1 (5) | 5 ± 0.1 (2) | 717 ± 28 (1) | 9 ± 0.04 (3) |
| HEK293-MRP2 | 14 ± 4 (1) | 8 ± 0.3 (0.9) | 39 ± 12 (0.7) | 37 ± 2 (4) | 28 ± 2 (6) | 3 ± 0.3 (1) | 747 ± 7 (1) | 7 ± 0.1 (2) |
| BCRP | | | | | | | | |
| HEK293-482R2 | 17 ± 1 (1) | 8 ± 1 (0.9) | 23 ± 3 (0.4) | 50 ± 1 (6) | 25 ± 1 (5) | 5 ± 0.1 (2) | 653 ± 72 (1) | 123 ± 28 (41) |
| Tubulin binding (µM)[+] | 3 ± 1 | 0.2 ± 0.1 | 4 ± 1 | N/A | ND | 2 ± 1 | 3.1[++] | ND |

Notes:
*parental cell line to drug resistant cell subline;
MDR1 were overexpressed in MDA-MB-435/LCC6MDR1 and NCI/ADR-RES;
MRP1, MRP2 and BCRP were overexpressed in HEK293-MRP1, HEK293-MRP2, and HEK293-482R2.
The resistance indexes (numbers in the parenthesis) were calculated by dividing IC$_{50}$ values on the resistant cell subline by that of the matching parental cell line.
[+]IC$_{50}$ for tubulin binding was calculated from [$^3$H]colchicine competition-binding scintillation proximity assay.
[++]binding affinity reported in the literature for ABT-751.
Abbreviations: N/A, not applicable since they bind to tubulin at different sites.

TABLE 14C

Anti-proliferative activity of methylene linked compounds (aryl-benzyl-imidazoles) in melanoma cells.

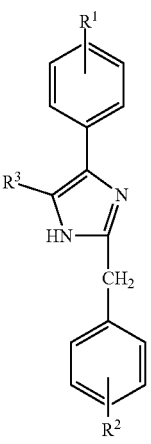

| Structure | ID | $R_1$ | $R_2$ | $R_3$ | $IC_{50} \pm SEM$ (μm) | | |
|---|---|---|---|---|---|---|---|
| | | | | | A375 | MDA-MB-435 | MDA-MB-435/ LCC6MDR1 |
| 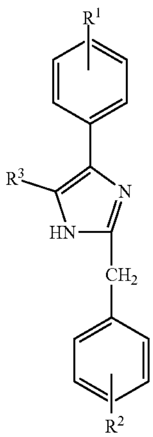 | 102a | H | 3,4,5-OMe)$_3$ | H | 10.204 ± 0.392 | ND | ND |
| | 102b | F | 3,4,5-OMe)$_3$ | Me | >50 | ND | ND |
| | 102c | H | 3,4,5-OMe)$_3$ | Et | ND | >50 | >50 |
| | 102d | H | 3,4,5-OMe)$_3$ | n-Pr | ND | 10.951 ± 0.037 | 15.949 ± 0.012 |
| | 102e | H | 3,4,5-OMe)$_3$ | Ph | ND | >50 | >50 |
| | Colchicine | N/A | N/A | N/A | 0.024 ± 0.003 | 0.011 ± 0.002 | 0.643 ± 0.009 |

*N/A = not applicable
ND = not determined

TABLE 14D

Anti-proliferative activity of aryl-benzoyl-imidazoles in melanoma cells.

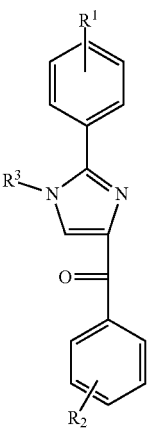

| Structure | ID | $R_1$ | $R_2$ | $R_3$ | $IC_{50} \pm SEM$ (pm) | | |
|---|---|---|---|---|---|---|---|
| | | | | | A375 | MDA-MB-435 | MDA-MB-435/ LCC6MDR1 |
| 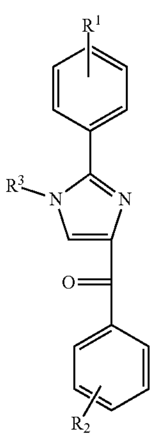 | 12q | 4-Et | 3,4,5-(OMe)$_3$ | H | 0.0014 ± 0.005 | 0.107 ± 0.005 | 0.027 ± 0.003 |
| | 12v | 4-iPr | 3,4,5-(OMe)$_3$ | H | ND | 0.312 ± 0004 | 0.250 ± 0.004 |
| | 12w | 4-tBu | 3,4,5-(OMe)$_3$ | H | ND | 3.691 ± 0.006 | 3.074 ± 0.005 |

TABLE 14D-continued

Anti-proliferative activity of aryl-benzoyl-imidazoles in melanoma cells.

| | | | | | | $IC_{50} \pm$ SEM (pm) | |
| --- | --- | --- | --- | --- | --- | --- | --- |
| Structure | ID | $R_1$ | $R_2$ | $R_3$ | A375 | MDA-MB-435 | MDA-MB-435/ LCC6MDR1 |
| 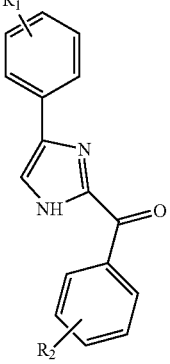 | 70aa | H | H | N/A | ND | >50 | >50 |
| | 70a | H | 3,4,5-(OMe)$_3$ | N/A | ND | 0.079 ± 0.003 | 0.043 ± 0.002 |
| | 70x | 3,4,5-(OMe)$_3$ | H | N/A | ND | 4.605 ± 0.007 | 5.770 ± 0.006 |
| | 70q | 3,4,5-(OMe)$_3$ | 3,4,5-(OMe)$_3$ | N/A | ND | 0.149 ± 0.003 | 0.211 ± 0.005 |

*N/A = not applicable
ND = not determined

The results of Table 14A showed that cell line MDA-MB-435/LCCMDR1 was very resistant to colchicine, paclitaxel, and vinblastine. But the ABIs of this invention showed equal potency to the drug-resistant cell line and the sensitive parent cell line. This result strongly suggests that ABIs are not substrates for P-gp. Thus, they overcame the multidrug resistance found in MDA-MB-435/LCCMDR1 cells. The dose response curves are shown in FIG. 21 for 12fb, 12da, and 12cb. Table 14B explores further the resistance mechanisms for paclitaxel, SN-38, vinblastine, and colchicine as compared to the ABIs 12cb, 12da, and 12fb. MRP and BCRP conferred moderate resistance to pacleitaxel (resistance indexes of 4 and 6, respectively), vinblastine (resistance indexes of 6 and 5, respectively), and BCRP conferred significant resistance to SN-38 (resistance index of 41). However, none of the ABIs were susceptible to MRP- or BCRP-mediated resistance (resistance indexes ranged from 0.4 to 1.0). ABT-751, like the ABIs, was not susceptible to MDR1, MRP, or BCRP.

Example 16

In Vitro Microtubule Polymerization Assay

Materials and Methods

Bovine brain tubulin (0.4 mg) (Cytoskeleton, Denver, CO) was mixed with 10 μM of the test compound and incubated in 110 μl of general tubulin buffer (80 mM PIPES, 2.0 mM MgCl$_2$, 0.5 mM EGTA, and 1 mM GTP) at pH 6.9. The absorbance at 340 nm was monitored every 1 min for 15 min by the SYNERGY 4 Microplate Reader (Bio-Tek Instruments, Winooski, VT). The spectrophotometer was set at 37° C. for tubulin polymerization.

Results

Figure 22:
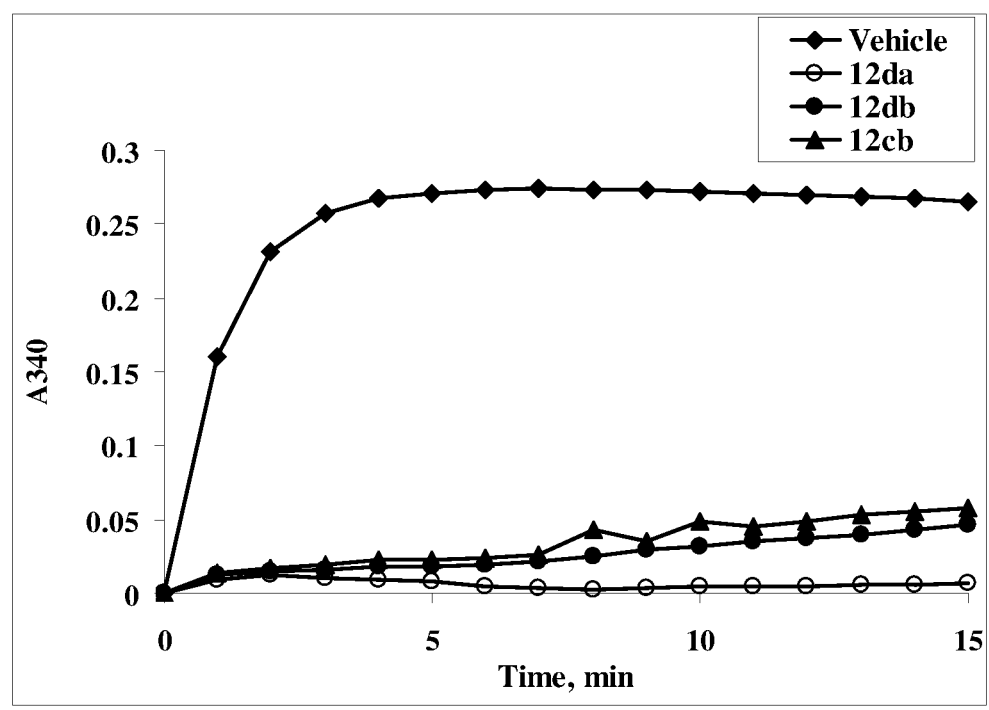
FIG. 22 presents the effect of ABI compounds on tubulin polymerization in vitro. Tubulin (0.4 mg/assay) was exposed to 10 μM ABI compounds (vehicle control, 5% DMSO). Absorbance at 340 nm was monitored at 37° C. every minute for 15 min and demonstrated that ABI compounds 12da, 12db, and 12cb inhibited tubulin polymerization in vitro.

The inhibition of tublin polymerization by Aryl-Benzoyl-Imidazole (ABI) compounds was examined. Bovine brain tubulin (>97% pure) was incubated with three potent ABI compounds, 12cb, 12da, and 12db at a concentration of 10 μM, to determine the effect of these ABI compounds on tubulin polymerization (FIG. 22). Tubulin polymerization was completely inhibited by compound 12da, while ~80% inhibition was observed during incubation with compounds 12cb and 12db.

This microtubule destabilization effect was similar to that of colchicine and vinblastine but was opposite to that of paclitaxel. The results not only confirmed that ABIs can directly interact with tubulin but also suggested that they may share the same binding site with colchicine (or vinblastine).

Example 17

Melanoma Inhibition In Vitro

Materials and Methods

B16-F1 melanoma cells were plated at a colony-forming density (2000 cells per well on six-well plates) on top of 0.8% base agar. Cells were grown in 0.4% agar together with DMEM medium supplemented with fetal bovine serum and an antibiotic-antimycotic solution at 37° C. in an atmosphere of 95% air and 5% CO$_2$. Cells were treated with compounds 12da, 12cb and 12fb at different concentrations (20, 100, and 500 nM). Compounds were added to the media from 1 mM DMSO stock solutions, and a corresponding dilution of DMSO was used as control. Cells were grown for 14 days. Plates were photographed, and the number of colonies was measured by Artek 880 Automated Colony Counter (Artek Systems Corporation, Farmingdale, NY).

Results

Figure 23A:
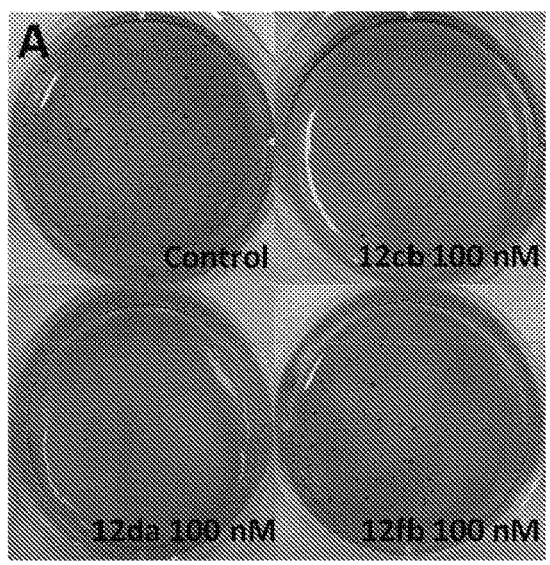
FIGS. 23A-B depict B16-F1 melanoma colony formation assay in soft agar which showed that ABI compounds inhibited colony formation in a concentration-dependent manner.
Figure 23B:
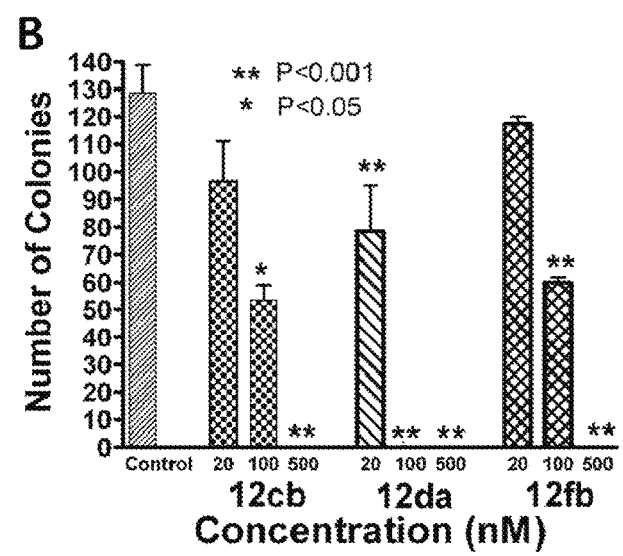

Four representative photos are shown in FIG. 23. After 14 days of incubation, about 130 detectable colonies (diameter larger than 100 μm) were formed in controls (no treatment). Compounds 12cb and 12da effectively inhibited B16-F1 melanoma colony formation even at the lowest tested concentration, 20 nM (p<0.05 compared with control). 12fb showed effective inhibition at 100 nM. All three tested compounds showed complete inhibition of colony formation at 0.5 μM, further proving ABIs' antimelanoma efficacy.

Example 18

In Vivo Anti-Tumor Activity

Materials and Methods

Animals: Female C57/BL mice, age 4-6 weeks, were purchased from Harlan Laboratories (Harlan Laboratories Inc., Indianapolis, IN). The animal housing met the Association for Assessment and Accreditation and Laboratory Animal Care specifications. All of the procedures were conducted in accordance with guidelines of our Institutional Animal Care and Use Committee.

In vivo evaluation of efficacy. Mouse melanoma B16-F1 cells were prepared in FBS-free DMEM medium (Cellgro Mediatech) at a concentration of $5 \times 10^6$ viable cells/mL. The cell suspension (100 μL) was injected subcutaneously in the right dorsal flank of each mouse. When tumor size reached about 100-150 mm$^3$, about 7 days after cell inoculation, all mice bearing tumors were divided into control and treatment groups based on tumor size (n=5 per group). Each group had similar average tumor size. Mice in control groups (negative control) were injected intraperitoneally with 50 μL vehicle solution only or DTIC at 60 mg/kg (positive control) once daily. Tumor volume was measured every 2 days with a traceable electronic digital caliper (Fisher Scientific, Inc., Pittsburgh, PA) and calculated using the formula $a \times b^2 \times 0.5$, where a and b represented the larger and smaller diameters, respectively. Tumor volume was expressed in cubic millimeters. Data were expressed as mean±SE for each group and plotted as a function of time. Percentage tumor reduction at the conclusion of the experiment (14 days after starting treatment) was calculated with the formula $100-100 \times [(T-T_0)/(C-C_0)]$, where T represents mean tumor volume of a treated group on a specific day, To represents mean tumor volume of the same group on the first day of treatment, C represents mean tumor volume of a control on a specific day, and Co represents mean tumor volume of the same group on the first day of treatment. Animal activity and average body weight of each group were monitored during the entire experiment period to assess compound toxicity. At the end of treatment, all mice were euthanized by $CO_2$ followed by cervical dislocation, and tumors were harvested for further studies.

Results

Figure 24A:
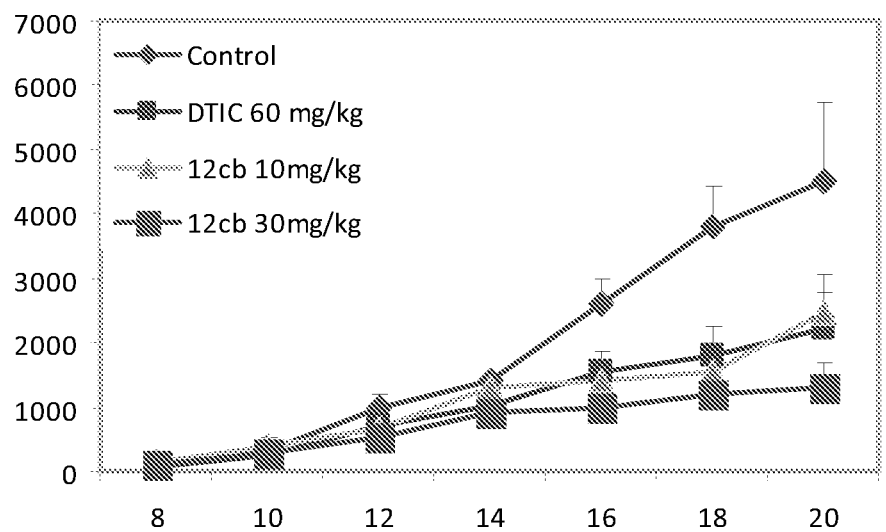
FIGS. 24A-C depict in vivo study of ABI compounds.
Figure 24B:
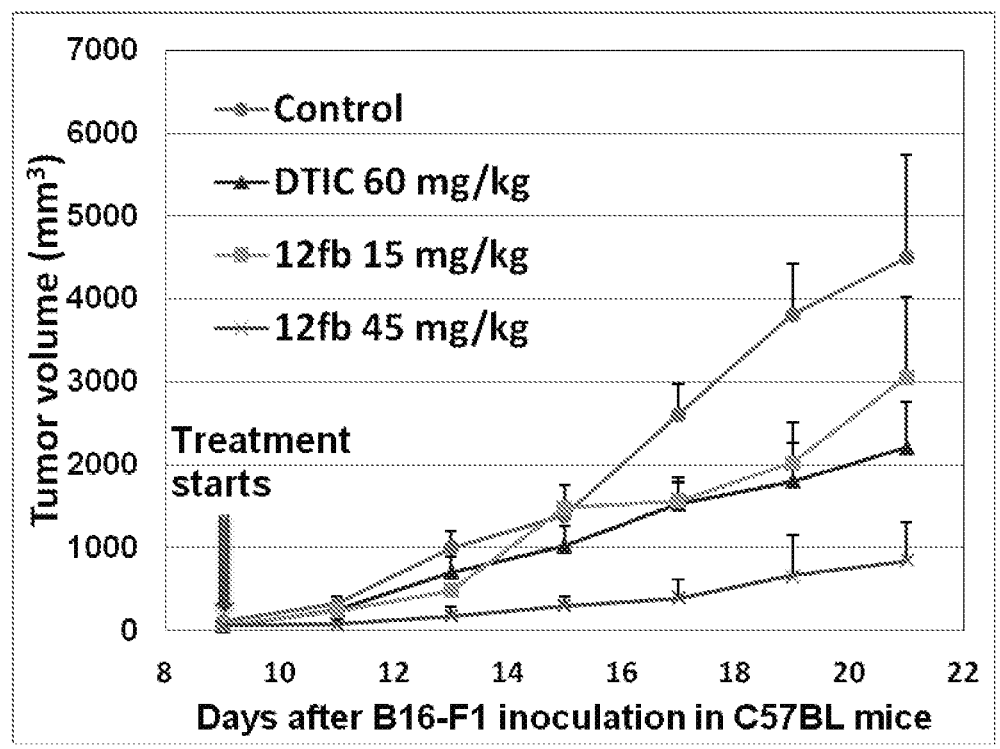
Figure 24C:
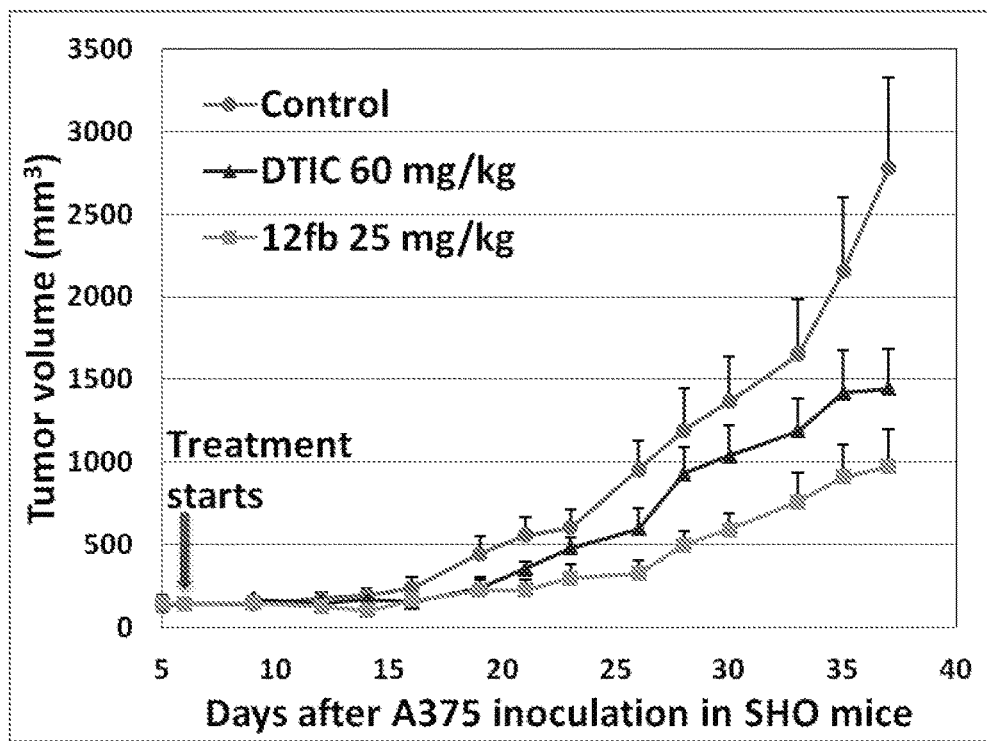

To evaluate efficacy of ABI analogs in vivo, we tested the antitumor activity of compound 12cb on mice melanoma B16-F1 xenograft. against DTIC, the gold standard in malignant melanoma treatment, was used as a positive control (FIG. 24A). Twenty female C57/BL mice were divided into four groups: a vehicle control group, a DTIC (60 mg/kg) treatment group, a 12cb (10 mg/kg) treatment group, and a 12cb (30 mg/kg) treatment group. Each mouse was injected with 0.5 million B16-F1 melanoma cells subcutaneously. Seven days after tumor inoculation, treatment started with each compound injected intraperitoneally daily (FIG. 24). Tumor volume was significantly (p<0.05) reduced 47%, 51%, and 73% for 12cb (10 mg/kg), DTIC (60 mg/kg), and 12cb (30 mg/kg), respectively, after 14 days of treatment. No significant weight loss was observed in any of the treatment groups during the experiment.

Two dose levels of 12fb, 15 and 45 mg/kg, were chosen. DTIC at 60 mg/kg was used as a positive control. B16-F1 melanoma allograft model on $C_{57}BL/6$ mice was first chosen for study. After 13 days of treatment (FIG. 24B), compound 12fb inhibited melanoma tumor growth (TGI value) by 32% at 15 mg/kg and 82% at 45 mg/kg. Student's t test p value of 12fb at 45 mg/kg compared with control was less than 0.001, indicating a significant difference. The t test p value of 12fb at 15 mg/kg compared with control was 0.08, suggesting that this dose was not effective. Comparing 12fb at 45 mg/kg with DTIC at 60 mg/kg, which had a TGI of 51%, the t test p value was about 0.001, suggesting that 12fb had substantially better activity than did DTIC. For the control and 12fb 15 mg/kg treatment groups, average body weight increased slightly throughout the experiment period.

To further confirm ABIs' in vivo activity, A375 human melanoma xenograft model on SHO mice was used, and 12fb at 25 mg/kg was tested. DTIC at 60 mg/kg was used as a positive control again. After 31 days of treatment (FIG. 24C), 12fb inhibited melanoma tumor growth (TGI value) by 69%, whereas DTIC inhibited growth by 52%. The t test p value of 12fb treatment versus control was less than 0.001, suggesting that 12fb significantly inhibited melanoma tumor growth at 25 mg/kg. The t test p value of 12fb treatment versus DTIC was less than 0.05, suggesting again that 12fb had better activity than did DTIC. Average body weight of all groups increased slightly throughout the experiment period. Physical activities for the mice also looked normal, suggesting that 25 mg/kg was a well tolerated dose for SHO mice.

Example 19

Binding to Colchicine Site

Materials and Methods

Each test compound was prepared at 20×concentration in G-PEM buffer (Cytoskeleton Inc., Denver, CO) followed by pipetting 10 μL of test compound into the 96-well plates. Ten microliters of tritiated labeled colchicine (Perkin-Elmer, Waltham, MA) was added to each testing well. Subsequently, 180 μL bead/tubulin (GE Healthcare Bio-Sciences Corp., Piscataway, NJ) suspension was added into each well. The plate was incubated for 45 min at 37° C. before it was read by a Topcount NXT plate reader (Perkin-Elmer, Waltham, MA). Nonradiolabeled "cold" colchicine was included as a positive control and paclitaxel as a negative control because paclitaxel binds to a different site in tubulin and does not compete for the colchicine site binding. Data were processed using GraphPad Prism software.

Cell Cycle Analysis

Flow cytometry analysis was performed to study cell cycle phase distribution. A375 cells were cultured in 10-cm tissue culture dishes until the confluence was about 80%, and then cells were treated with 0, 10, 50, 200, and 1000 nM of colchicine, 12da, 12fb and 12cb, for 24 h in growth media. Cellular DNA was stained with PBS containing 50 μg/mL propidium iodide and 100 μg/mL RNase A. The cell cycle was determined using a BD LSR-II cytometer (BD Biosciences, San Jose, CA) with 10,000 cells scored. Data were analyzed and graphs were prepared using the Modfit 2.0 program (Verity Software House, Topsham, ME).

Results

Figure 25A:
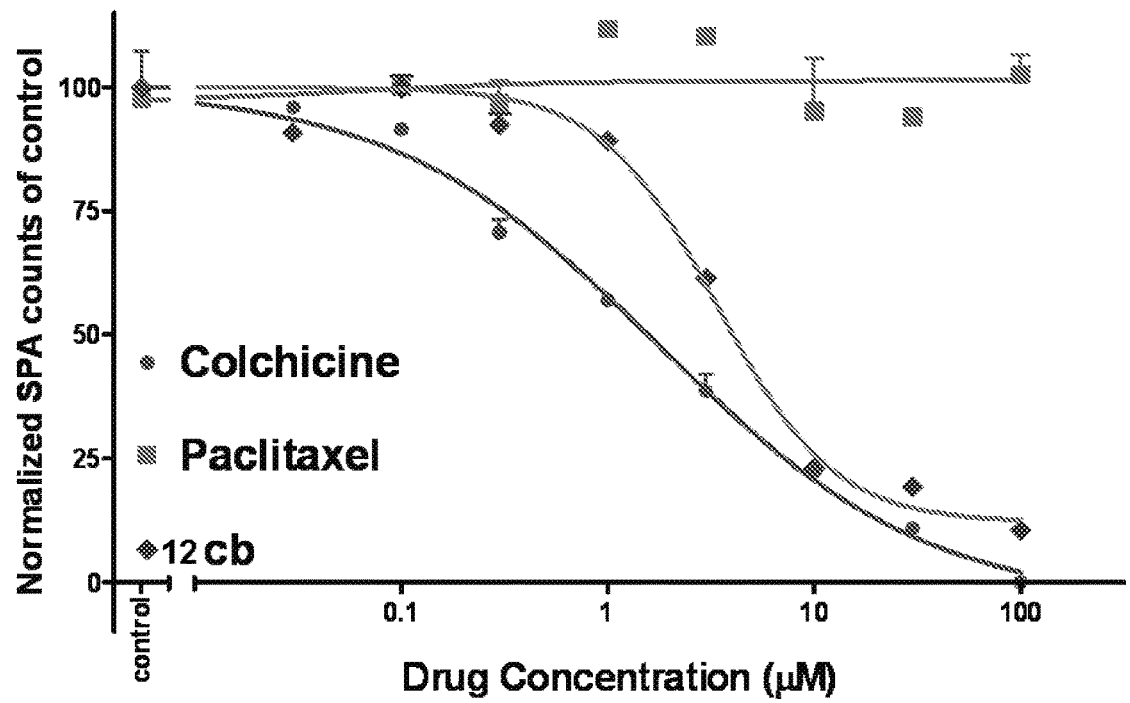
FIGS. 25A-D depict a competitive colchicine binding assay.

Three ligand binding sites in tubulin α/β-heterodimer have been reported: paclitaxel binding site, vinblastine binding site, and colchicine binding site. The binding affinity of compound 12cb using $^3$H-labeled colchicine and a competitive binding scintillation proximity assay (SPA) was measured. The results confirmed the strong binding of 12cb with a binding affinity of 3.4±1.5 µM (FIG. 25A). Colchicine bound tubulin with an IC$_{50}$ value of 1.8±0.5 µM under these conditions. These results clearly indicated that ABI compounds effectively inhibit tubulin polymerization.

The binding graph (FIG. 25A) clearly shows that ABIs can competitively bind to the tubulin colchicine binding site. As the concentration of the three tested compounds increased from 0.03 µM to 100 µM, increased tritiated colchicine was competitively stripped away from tubulin and emitted lower SPA counts. The negative control, paclitaxel, gave only a flat line, because theoretically it should not bind to the colchicine binding site on tubulin. Second, ABIs have relatively high binding affinity to the tubulin colchicine binding site. GraphPad Prism calculated IC$_{50}$ values for binding showed that 12da has the highest binding affinity. The binding affinity was positively correlated to in vitro antimelanoma activity; the higher the binding affinity, the higher the antimelanoma activity.

Figure 25B:
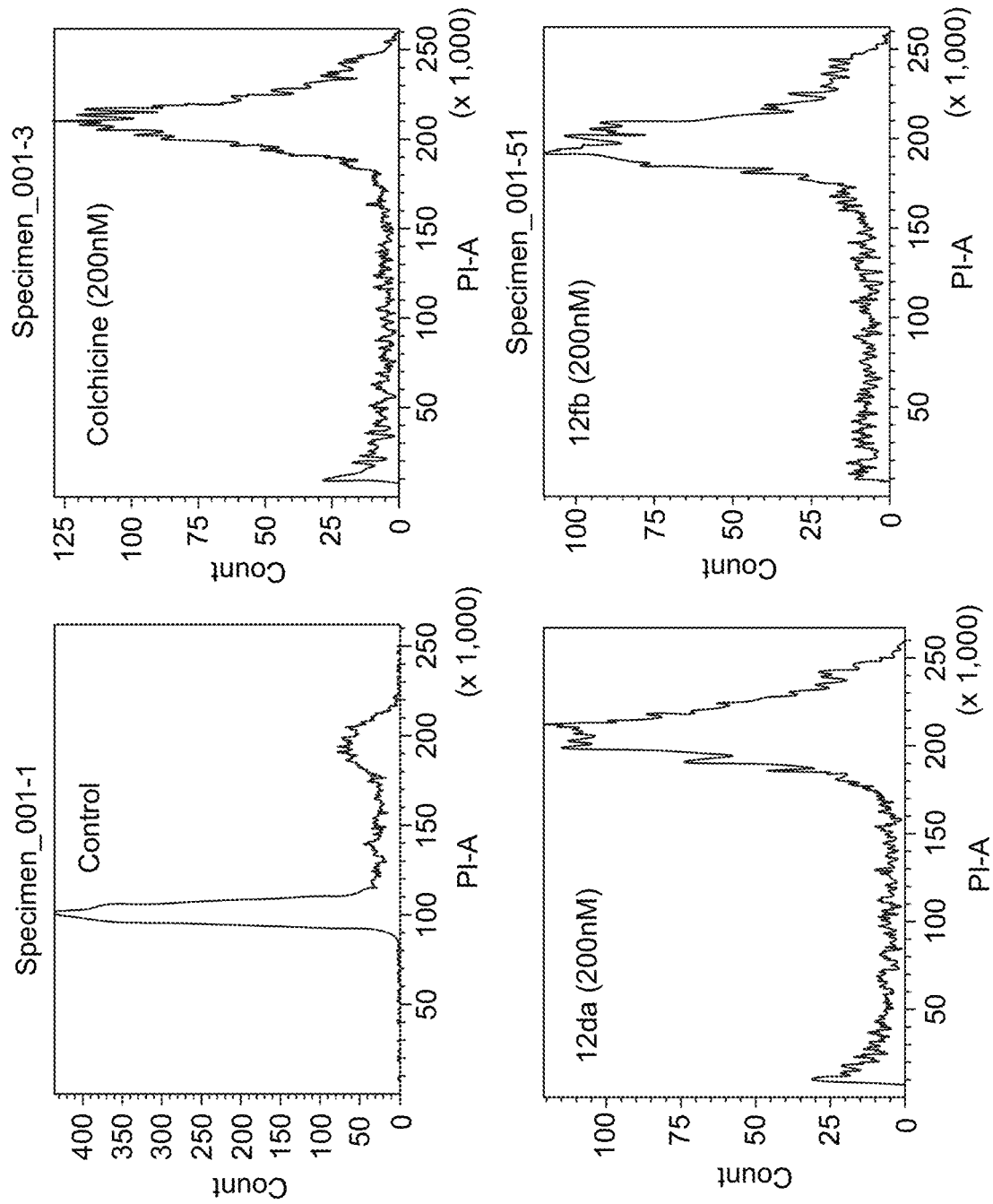
Figure 25C:
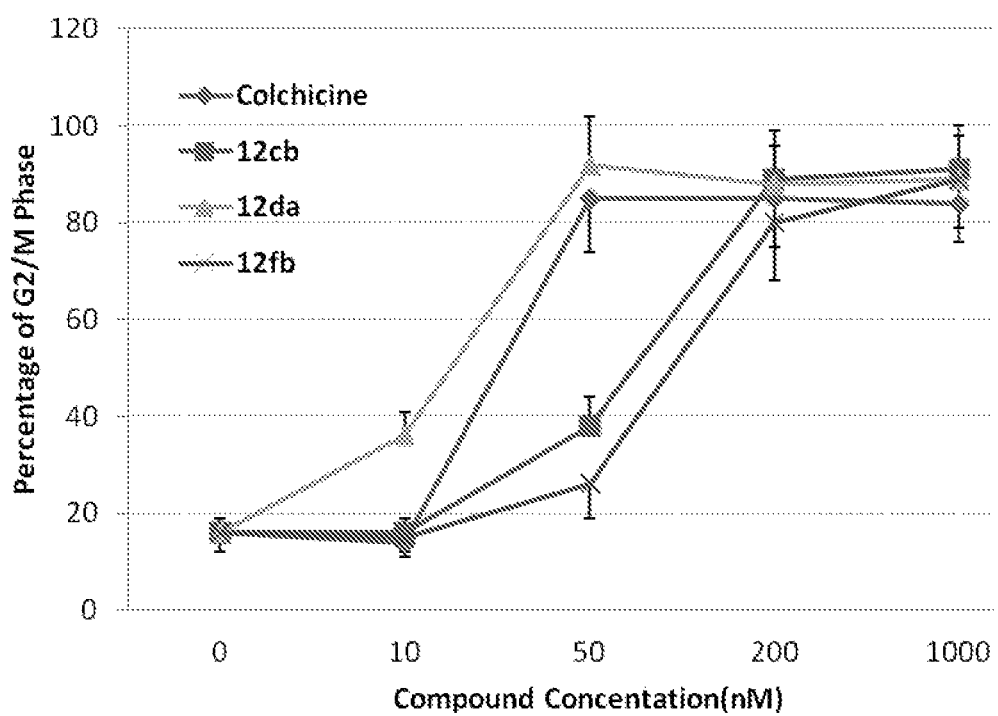
Figure 25D:
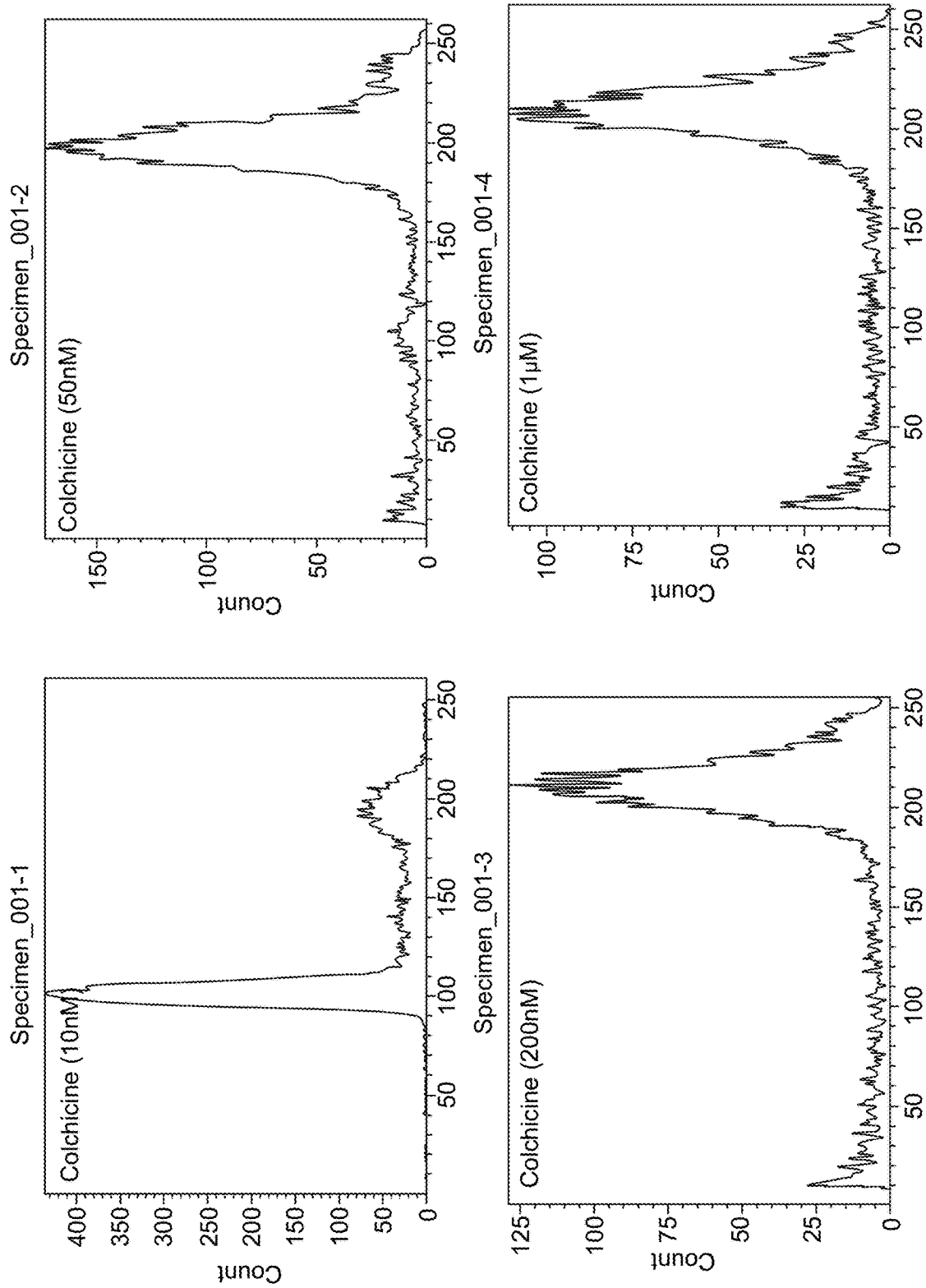
Figure 25D:
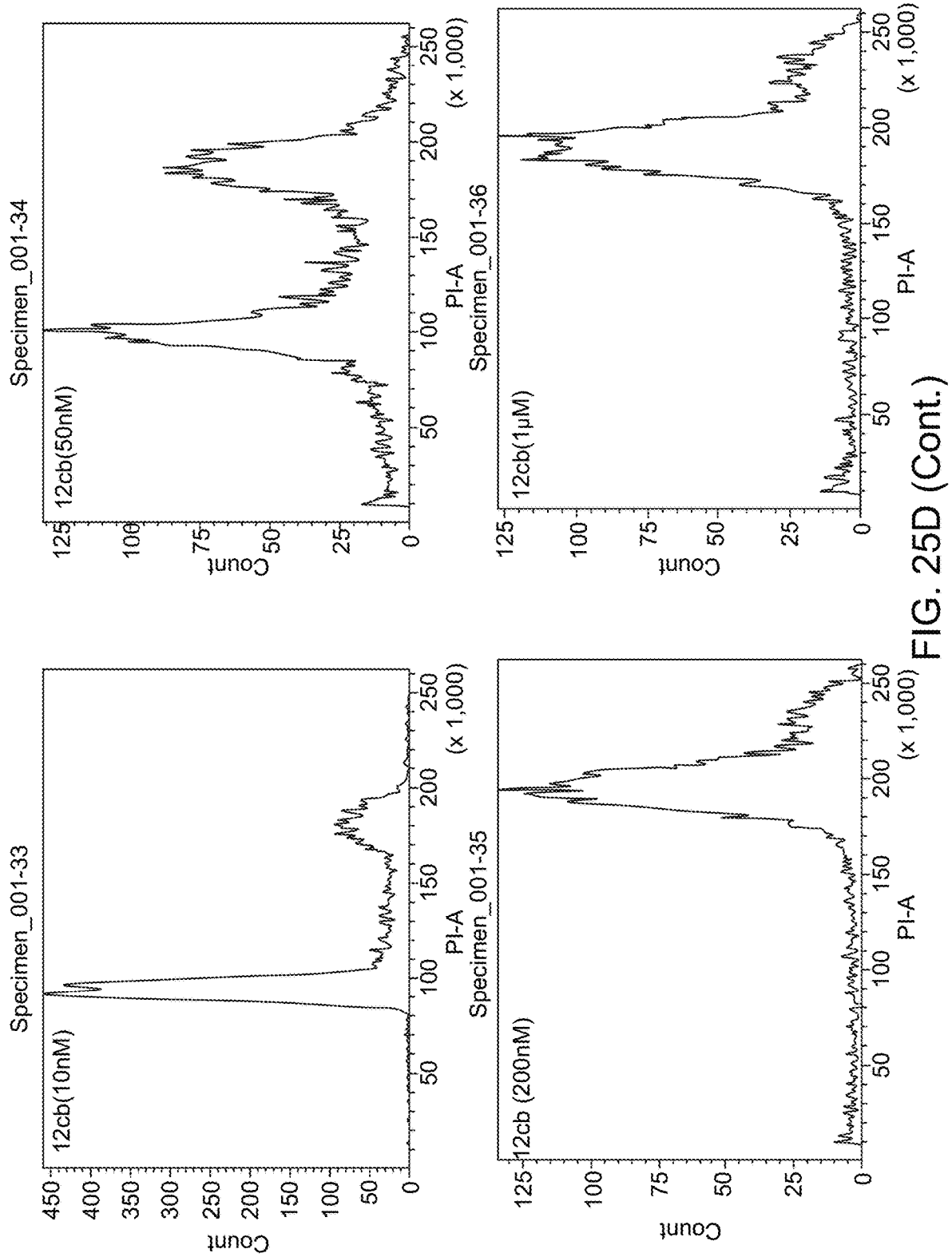
Figure 25D:
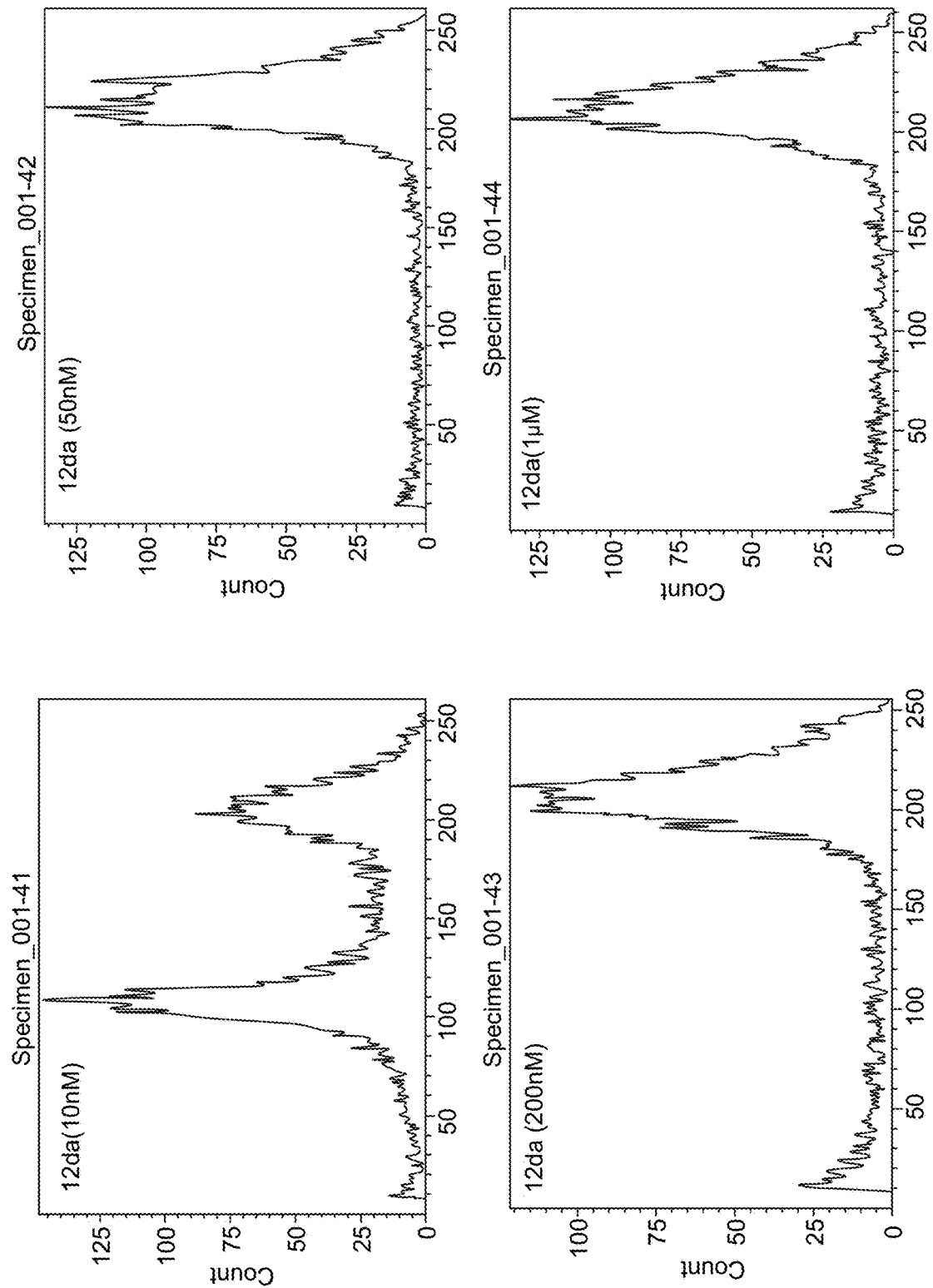
Figure 25D:
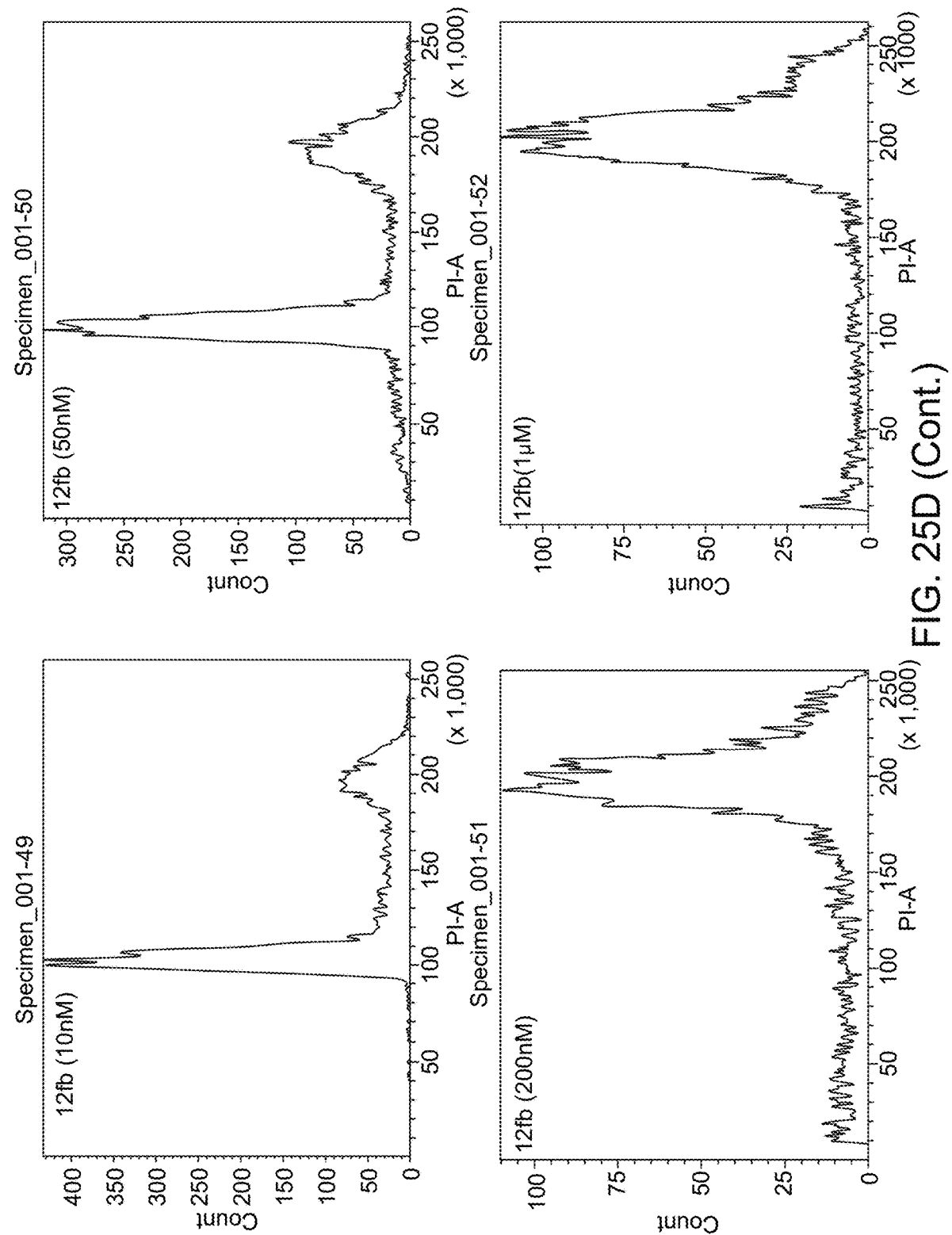
Figure 26A:
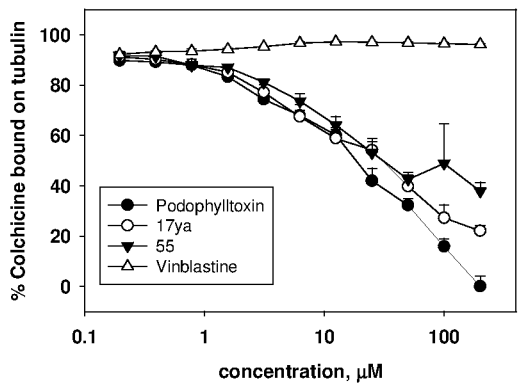
FIGS. 26A-D depict the effect of 17ya and 55 on tubulin polymerization. Compounds 17ya and 55 bind to colchicine-binding site on tubulin, and inhibit tubulin polymerization.
Figure 26B:
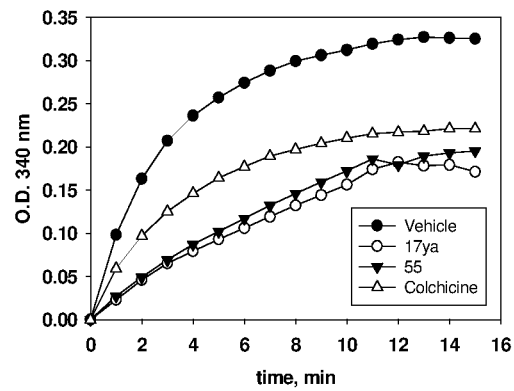
Figure 26C:
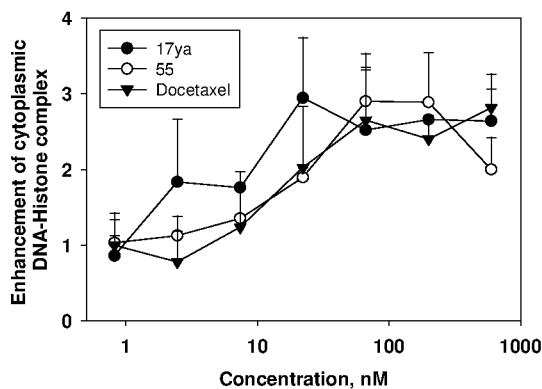
Figure 26D:
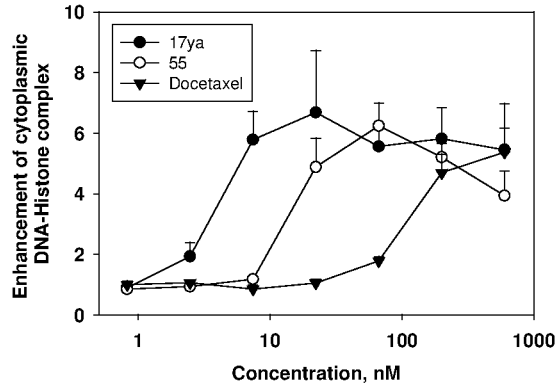

ABIs demonstrated that they arrest cells by cell cycle analysis in the G2/M phase as indication that they target tubulin. Compounds 12da, 12fb and 12cb were tested together with colchicine as a positive control on A375 cells (FIG. 25B). Four different concentrations—10, 50, 200, and 1000 nM—of each compound were chosen to show the dose effect (FIGS. 25C and 25D). For controls (no treatment) without interference, about 16% of A375 cells were distributed in the G2/M phase. For the colchicine treatment group, as concentration increased from 10 nM to 50 nM, the percentage of cells distributed in the G2/M phase increased from 14% to 85%. ABIs had similar results for A375 cells, in arresting them in the G2/M phase in a dose-dependent manner. The potency of the different concentrations in arresting cells in the G2/M phase positively correlated with in vitro activity.

Example 20

In Vitro and In Vivo Pharmacology of Compounds 17ya, 12fa, AND 55

Materials and Methods

Cell culture and cytotoxicity assay of prostate cancer. All prostate cancer cell lines (LNCaP, PC-3, and DU145, PPC-1) were obtained from ATCC (American Type Culture Collection, Manassas, VA, USA). Human PC-3_TxR, was resistant to paclitaxel and used a MDR model compared with PC-3. Cell culture supplies were purchased from Cellgro Mediatech (Herndon, VA, USA). All cell lines were used to test the antiproliferative activity of compounds 17ya, 12fa, and 55 by sulforhodamine B (SRB) assay. All cancer cell lines were maintained in RPMI 1640 media with 2 mM glutamine and 10% fetal bovine serum (FBS).

In vitro microtubule polymerization assay. Porcine brain tubulin (0.4 mg) (Cytoskeleton, Denver, CO) was mixed with 1 and 5 µM of the test compound or vehicle (DMSO) and incubated in 100 µL of buffer (80 mM PIPES, 2.0 mM MgCl$_2$, 0.5 mM EGTA, pH 6.9 and 1 mM GTP). The absorbance at 340 nm wavelength was monitored every min for 15 min (SYNERGY 4 Microplate Reader, Bio-Tek Instruments, Winooski, VT). The spectrophotometer was maintained at 37° C. for tubulin polymerization.

Metabolic incubations. Metabolic stability studies were conducted by incubating 0.5 µM of test compounds in a total reaction volume of 1 mL containing 1 mg/mL microsomal protein in reaction buffer [0.2 M of phosphate buffer solution (pH 7.4), 1.3 mM NADP$^+$, 3.3 mM glucose-6-phosphate, and 0.4 U/mL glucose-6-phosphate dehydrogenase] at 37° C. in a shaking water bath. The NADPH regenerating system (solution A and B) was obtained from BD Biosciences (Bedford, MA). For glucuronidation studies, 2 mM UDP-glucuronic acid (Sigma, St. Louis, MO) cofactor in deionized water was incubated with 8 mM MgCl$_2$, 25 µg of alamethicin (Sigma, St. Louis, MO) in deionized water, and NADPH regenerating solutions (BD Biosciences, Bedford, MA) as described previously. The total DMSO concentration in the reaction solution was approximately 0.5% (v/v). Aliquots (100 µL) from the reaction mixtures used to determine metabolic stability were sampled at 5, 10, 20, 30, 60, and 90 min. Acetonitrile (150 µL) containing 200 nM of the internal standard was added to quench the reaction and to precipitate the proteins. Samples were then centrifuged at 4,000g for 30 min at RT, and the supernatant was analyzed directly by LC-MS/MS.

Analytical method. Sample solution (10 µL) was injected into an Agilent series HPLC system (Agilent 1100 Series Agilent 1100 Chemstation, Agilent Technology Co, Ltd). All analytes were separated on a narrow-bore C$_{18}$ column (Alltech Alltima HP, 2.1×100 mm, 3 µm, Fisher, Fair Lawn, NJ). Two gradient modes were used. For metabolic stability studies, gradient mode was used to achieve the separation of analytes using mixtures of mobile phase A [ACN/H$_2$O (5%/95%, v/v) containing 0.1% formic acid] and mobile phase B [ACN/H$_2$O (95%/5%, v/v) containing 0.1% formic acid] at a flow rate of 300 µL/min. Mobile phase A was used at 10% from 0 to 1 min followed by a linearly programmed gradient to 100% of mobile phase B within 4 min, 100% of mobile phase B was maintained for 0.5 min before a quick ramp to 10% mobile phase A. Mobile phase A was continued for another 10 min towards the end of analysis.

A triple-quadruple mass spectrometer, API Qtrap 4000™ (Applied Biosystems/MDS SCIEX, Concord, Ontario, Canada), operating with a TurbolonSpray source was used. The spraying needle voltage was set at 5 kV for positive mode. Curtain gas was set at 10; Gas 1 and gas 2 were set 50. Collision-Assisted-Dissociation (CAD) gas at medium and the source heater probe temperature at 500° C. Multiple reaction monitoring (MRM) mode, scanning m/z 378→210 (17ya), m/z 373→205 (12fa), m/z 410→242 (55) and m/z 309→171 (internal standard), was used to obtain the most sensitive signals. Data acquisition and quantitative processing were accomplished using Analyst™ software, Ver. 1.4.1 (Applied Biosystems).

Aqueous solubility. The solubility of drugs was determined by Multiscreen Solubility Filter Plate (Millipore Corporate, Billerica, MA) coupled with LC-MS/MS. Briefly, 198 µL of phosphate buffered saline (PBS) buffer (pH 7.4) was loaded into 96-well plate, and 2 µL of 10 mM test compounds (in DMSO) was dispensed and mixed with gentle shaking (200-300 rpm) for 1.5 hours at RT (N=3). The plate was centrifuged at 800g for 10 min, and the filtrate was used to determine its concentration and solubility of test compound by LC-MS/MS as described previously.

Pharmacokinetic study. Male ICR mice (n=3 per group) 6 to 8 weeks of age were purchased from Harlan Inc., and used to examine the pharmacokinetics (PK) of 17ya, 12fa, and 55. All compounds (10 mg/kg) were dissolved in DMSO/PEG300 (1/9) and administered by a single intravenously (i.v.) injection (50 µL) into the tail vein. Blood samples were collected at 5, 15, and 30 min, 1, 1.5, 2, 3, 4, 8, 12, and 24 h after i.v. administration. Mice were given (p.o.) by oral gavage at 20 mg/kg (in Tween80/DMSO/$H_2O$, 2/2/6) of each test compound to evaluate their oral bioavailability. Blood samples were collected at 0.5, 1, 1.5, 2, 3, 4, 8, 12, and 24 h after p.o. administration.

Female Sprague-Dawley rats (n=3; 254±4 g) were purchased from Harlan Inc. (Indianapolis, IN). Rat thoracic jugular vein catheters were purchased from Braintree Scientific Inc. (Braintree, MA). On arrival at the animal facility, the animals were acclimated for 3 days in a temperature-controlled room (20-22° C.) with a 12 h light/dark cycle before any treatment. Compounds 17ya, 12fa, and 55 were administered i.v. into the thoracic jugular vein at a dose of 5 mg/kg (in DMSO/PEG300, 1/9). An equal volume of heparinized saline was injected to replace the removed blood, and blood samples (250 μL) were collected via the jugular vein catheter at 10, 20, 30 min, and 1, 2, 4, 8, 12, 24 h. Rats were given (p.o.) by oral gavage at 10 mg/kg (in Tween80/DMSO/$H_2O$, 2/2/6) of each test compound to evaluate their oral bioavailability. All blood samples (250 μL) after oral administration were collected via the jugular vein catheter at 30, 60, 90 min, 120 min, 150 min, 180 min, 210 min, 240 min, and 8, 12, 24 h. Heparinized syringes and vials were prepared prior to blood collection. Plasma samples were prepared by centrifuging the blood samples at 8,000g for 5 min. All plasma samples were stored immediately at −80° C. until analyzed.

Analytes were extracted from 100 μL of plasma with 200 μL of acetonitrile containing 200 nM the internal standard. The samples were thoroughly mixed, centrifuged, and the organic extract was transferred to autosampler for LC-MS/MS analysis.

PC-3_TxR xenograft studies. PC-3_TxR cells (10×10⁷ per mL) were prepared in RPMI1640 growth media containing 10% FBS, and mixed with Matrigel (BD Biosciences, San Jose, CA) at 1:1 ratio. Tumors were established by injecting 100 μL of the mixture (5×10⁶ cells per animal) subcutaneously (s.c.) into the flank of 6-8-week-old male athymic nude mice. Length and width of tumors were measured and the tumor volume (mm³) was calculated by the formula, n/6×L×$W^2$, where length (L) and width (W) were determined in mm. When the tumor volumes reached 300 mm³, the animals bearing PC-3_TxR tumors were treated with vehicle [Tween80/DMSO/$H_2O$ (2/2/6)], or 17ya (10 mg/kg) orally. The dosing schedule was 3 times a week for four weeks.

Results 17a and 55 exhibit broad cytotoxicity in cells, including multidrug-resistant cells. The ability of 17ya and 55 to inhibit the growth of cancer cell lines was evaluated using SRB assay (Table 15). Both compounds inhibited the growth of several human cancer cell lines, including five prostate and one glioma cancer cell lines, with $IC_{50}$ values in the low nanomolar range. 17ya exhibited 1.7-4.3 fold higher potency than 55 in these cell lines. Paclitaxel-resistant PC-3 (PC-3/TxR) cell line that over-expresses P-glycoprotein (P-gp), was used to study the effect of drug resistance on 17ya and 55 and to compare against its parent, PC-3 cell line. The $IC_{50}$ values of docetaxel were 1.2±0.1 nM and 17.7±0.7 nM in PC-3 and PC-3/TxR cells, respectively. 17ya and 55 were both equipotent against parent PC-3 and PC-3/TxR, whereas paclitaxel and docetaxel exhibited relative resistance of 85- and 15-fold, respectively. These data indicate that both 17ya and 55 circumvent P-gp-mediated drug resistance.

TABLE 15

Cytotoxicity data of 17ya and 55.

Cytotoxicity [$IC_{50}$ values, mean ± SD nM]

| Cell line | Type | 17ya | 55 | Paclitaxel |
|---|---|---|---|---|
| PC-3 | Prostate | 5.2 ± 0.2 | 16 ± 1.5 | 0.6 ± 0.05 |
| PC-3/TxR | Prostate | 2.1 ± 0.1 (0.4) | 6.7 ± 0.5 (0.4) | 51 ± 2.3 (85) |
| LNCaP | Prostate | 12 ± 0.1 | 27 ± 0.6 | 1.7 ± 0.2 |
| Du-145 | Prostate | 17 ± 0.2 | 38 ± 0.6 | 5.1 ± 0.1 |
| PPC-1 | Prostate | 21 ± 0.1 | 36 ± 0.4 | 2.3 ± 0.8 |
| U87MG | Glioma | 10 ± 1.6 | 22 ± 3.0 | NR |

$IC_{50}$ values (mean ± SD) were determined after 96 h treatment (N = 3). Paclitaxel was used as a positive control. Data in parentheses indicated resistance factor when compared $IC_{50}$ values in PC-3 and PC-3/TxR. NR, Not Reported.

17ya and 55 bind to colchicine-binding site on tubulin, inhibit tubulin polymerization, and induce cell apoptosis (FIG. 26). A competitive mass binding assay was developed to study the interaction of small molecule inhibitors with tubulin. In this study, varying concentrations of 17ya or 55 were used to compete with colchicine-tubulin binding. Both compounds competed effectively with colchicine for tubulin binding (FIG. 26A); however, their competitive binding curves deviated substantially from zero at higher concentrations when compared to podophylltoxin, a known potent colchicine-site binding ligand. This suggests that both 17ya and 55 exhibited less affinity than podophylltoxin or they partially bind to the colchicine-binding site. Vinblastine, the negative control, did not inhibit the colchicine-tubulin binding, successfully demonstrating the specificity of this competitive mass binding assay Porcine brain tubulin (>97% pure) was incubated with 17ya or 55 (5 μM) to test their effect on tubulin polymerization (FIG. 26B). 17ya and 55 inhibited tubulin polymerization by 47% and 40% at 15 min, respectively. Colchicine at 5 μM was used as a positive control and inhibited tubulin polymerization by 32%. These data suggest that both 17ya and 55 have slightly greater inhibition of tubulin polymerization than colchicine. Therefore, the molecular mechanism of these compounds is binding to the colchicine-binding site, inhibiting tubulin polymerization, and inducing cytotoxicity.

PC-3 and PC-3/TxR cells were exposed to 0.8 to 600 nmol/L of 17ya, 55, or docetaxel for 24 h. The levels of DNA-histone complexes were used to represent cell apoptosis. Both 17ya and 55 were equally potent to induce cell apoptosis in PC-3 (FIG. 26C) and PC-3/TxR (FIG. 26D) in 24 h. Though, docetaxel was highly potent to induce apoptosis of PC-3 cells, it was weaker in PC-3/TxR cells due to over-expression of P-gp.

17ya and 55 exhibited favorable drug-like properties. Drug-like properties, such as metabolic stability, permeability, aqueous solubility, and drug-drug interactions, were examined for 17ya and 55 (Table 16A). 17ya exhibited greater metabolic stability, and aqueous solubility than 55. Both chemicals exhibited more than adequate permeability values, suggesting their potential to be orally used. In addition, both 17ya and 55 showed high $IC_{50}$ values in micromolar range on CYP enzyme inhibition assays, indicating that both compounds may avoid drug-drug interactions through main CYP liver enzymes. Overall, both compounds exhibited favorable drug-like properties.

TABLE 16A

Drug-like properties of compound 17a and 55. Metabolic stability, permeability, solubility, and potential drug-drug interactions were evaluated. Each value represents the mean from duplicate studies.

| Measurment | Units | 17ya | 55 | positive controls (mean) |
|---|---|---|---|---|
| Metabolic stability | | | | |
| half-life in human liver microsomes | min | >60 | 28 | Verapamil (12) |
| Permeability | | | | |
| $P_{app(A \to B)}$ in CaCO-2 assay | $10^{-6}$ cm/s | 36 | 99 | Propranolol (19) |
| Aqueous solubility | μg/mL | >75 | 19 | 1 h (1.1) |
| Drug-drug interactions | | | | |
| $IC_{50}$ value in Cyp3A4 (substrate: Testosterone) | μM | 20 | 5.5 | Ketoconazole (0.02) |
| $IC_{50}$ value in Cyp2D6 (substrate: Dextromethorphan) | μM | >50 | 34 | Quinindine (0.1) |
| $IC_{50}$ value in Cyp2C19 (substrate: (S)-mephenytoin) | μM | 6.6 | 5.3 | Ticlopidine (0.37) |
| $IC_{50}$ value in Cyp2C9 (substrate: Diclofenac) | μM | 17 | 4.9 | Sulfaphenazole (0.5) |
| $IC_{50}$ value in Cyp1A2 (substrate: Phenacetin) | μM | 9.2 | 8.1 | Furafylline (2.2) |

TABLE 16B

Summary of drug-like and pharmacokinetic properties of 17ya, 12fa, 55, and 1h.

| | 17ya | 12fa |
|---|---|---|
| | 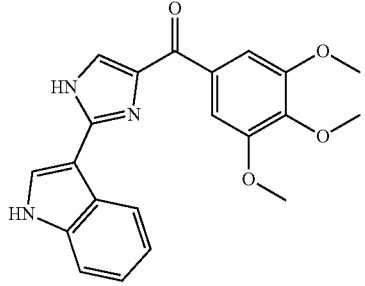 [SMILES: COc1cc(C(=O)c2c[nH]c(-c3c[nH]c4ccccc34)n2)cc(OC)c1OC] | 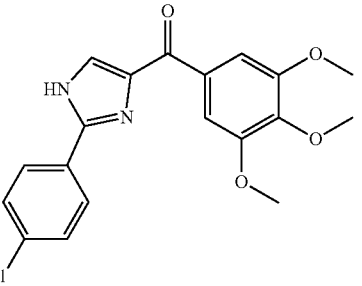 |
| Molecular weight | 377 | 372 |
| $IC_{50}$ in PC3 (nM)   nM | 10 | 35 |

TABLE 16B-continued

Summary of drug-like and pharmacokinetic properties of 17ya, 12fa, 55, and 1h.

| | | | |
|---|---|---|---|
| Half-life in HLM (Phase I) | min | ~80 | 44 |
| Half-life in HLM (Phase I + II) | min | ~90 | NA |
| Solubility | µg/mL | >75 | 12 |
| RatPK_IV5mgk_Cl | mL/min/kg | | 16 |
| RatPK_IV5mgk_V | L/kg | | 1.9 |
| RatPK_PO10mgk_Cmax | ng/mL | | 1109 |
| RatPK_PO10mgk_AUC | min * µg/mL | | 218 |
| RatPK_Bioavailability | % F | | 35 |
| MousePK_IV10mgk_Cl | mL/min/kg | | 61 |
| MousePK_IV10mgk_V | L/kg | | 4 |
| MousePK_PO20mgk_Cmax | ng/mL | | 2592 |
| MousePK_PO20mgk_AUC | min * µg/mL | | 201 |
| MousePK_Bioavailability | % F | | 62 |

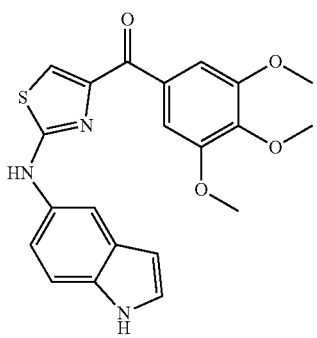 [SMILES: COc1cc(C(=O)c2csc(Nc3ccc4[nH]ccc4c3)n2)cc(OC)c1OC]

| | | 55 | 1h |
|---|---|---|---|
| Molecular weight | | 409 | 355 |
| $IC_{50}$ in PC3 (nM) | nM | 28 | 21 |
| Half-life in HLM (Phase I) | min | 30 | 17 |
| Half-life in HLM (Phase I + II) | min | 43 | 17 |
| Solubility | µg/mL | 19 | 1 |
| RatPK_IV5mgk_Cl | mL/min/kg | | 7.7 (2.5 mpk) |
| RatPK_IV5mgk_V | L/kg | | 4.9 (2.5 mpk) |
| RatPK_PO10mgk_Cmax | ng/mL | | 212 |
| RatPK_PO10mgk_AUC | min * µg/mL | | 37 |
| RatPK_Bioavailability | % F | | 3.3 |
| MousePK_IV10mgk_Cl | mL/min/kg | | 130 |
| MousePK_IV10mgk_V | L/kg | | 4.9 |
| MousePK_PO20mgk_Cmax | ng/mL | | NA |
| MousePK_PO20mgk_AUC | min * µg/mL | | NA |
| MousePK_Bioavailability | % F | | NA |

As shown in Table 16B, 17ya had a half-life of 80 min by phase I reaction, suggesting that 17ya was stable in phase I metabolic processes. The half-life (90 min) in the presence of UDP-glucuronic acid was similar to that observed in its absence. These data suggested that 17ya is stable in human liver microsomes, and it was hoped that low clearance and long half-life will be obtained in human. On the other hand, 55 exhibited 30 and 43 min as half lives when it was in the presence and absence of UDP-glucuronic acid, respectively. Compound 12fa shows the half-life with 44 in phase I. These data suggested that all three compounds showed acceptable stability in human liver microsomes, and 17ya is more stable than 12fa and 55. When investigating their metabolism, it was found that 12fa and 55 exhibited higher levels of ketone-reduction (data not shown), suggesting that 12fa and 55 are more labile than 17ya.

Compound 17ya exhibited great aqueous solubility, 12fa and 55 showed acceptable solubility.

Compound 17ya contained an imidazole ring, and this ring improved aqueous solubility, resulting in >75 µg/mL aqueous solubility (Table 16A). Compounds 12fa and 55 exhibited less aqueous solubility, and exhibited 12 and 19 µg/mL, respectively. Overall, 17ya demonstrated a great aqueous solubility, and 12fa and 55 showed acceptable aqueous solubility, and much improved over 1 h. The greater solubility of 12fa translated into much improved oral bioavailability compared to 1h (35% vs. 3.3% in rat). Similarly, for 17ya and 55, aqueous solubility correlated with much improved oral bioavailability as discussed infra (Table 17).

Pharmacokinetic studies of 17ya and 55 in mice, rats and dogs. The pharmacokinetic parameters of 17ya and 55 given in a single (i.v. or p.o.) dose in ICR mice, Sprague-Dawley rats, and beagle dogs are summarized in Table 17. 17ya exhibited low clearance in mice and rats, suggesting that 17ya exhibited metabolic stability, and minimal first-pass metabolism in these species. In addition, 17ya had moderate volume of distribution in mice and rats, indicating that it may properly distribute into tissues, including tumors. Unlike in mice and rats, surprisingly, the total clearance of 17ya in dogs was high. Two abundant metabolites in dog plasma, a hydroxylated metabolite and an unknown metabolite with+34 m/z of the parent (data not shown), were consistent with those found in dog liver microsomes. In summary, higher clearance and lower oral exposure was obtained for 17ya compared to 55 in dogs, but not in mice and rats. In addition, 17ya exhibited abundant metabolites only in dog liver microsomes, but not in mouse, rat or human liver microsomes (data not shown). 17ya showed acceptable 21%, 36%, and 50% oral bioavailability in rats, mice, and dogs, respectively. Meanwhile, 55 had low clearance in rats, and moderate clearance in mice and dogs. Similar to 17ya, 55 exhibited moderate volume of distribution in these species. 55 had constant oral bioavailability rates among three species (24%-36%). These properties indicate that both 17ya and 55 are potential orally available tubulin inhibitors.

TABLE 17

Pharmacokinetic studies of compounds 17ya and 55 in mice, rats, and dogs.

|  | 17ya | | 55 | |
| --- | --- | --- | --- | --- |
|  | IV | PO | IV | PO |
| Mouse PK (N = 3) | | | | |
| Dose, mg/kg | 10 | 20 | 10 | 20 |
| Clearance, mL/min/kg | 19 | NR | 40 | NR |
| Vss, L/kg | 2.9 | NR | 1.3 | NR |
| $t_{1/2}$, min | 101 | 339 | 46 | 126 |
| AUC, min * µg/mL | 540 | 384 | 249 | 171 |
| $C_{max}$, ng/mL | 4800 | 1560 | 7739 | 1253 |
| F, % |  | 36% |  | 34% |
| Rat PK (N = 3) | | | | |
| Dose, mg/kg | 5 | 10 | 5 | 10 |
| Clearance, mL/min/kg | 9.5 ± 2.3 | NR | 10 ± 1.4 | NR |
| Vss, L/kg | 1.8 ± 0.2 | NR | 1.0 ± 0.1 | NR |
| $t_{1/2}$, min | 139 ± 24 | 206 ± 12 | 73 ± 5.0 | 350 ± 214 |
| AUC, min * µg/mL | 553 ± 143 | 233 ± 134 | 509 ± 73 | 246 ± 163 |
| $C_{max}$, ng/mL | 3672 ± 519 | 999 ± 445 | 4609 ± 55 | 757 ± 520 |
| F, % |  | 21% |  | 24% |
| Dog PK (N = 4) | | | | |
| Dose, mg/kg | 2 | 5 | 2 | 5 |
| Clearance, mL/min/kg | 109 ± 29 | NR | 15 ± 3.2 | NR |
| Vss, L/kg | 94 ± 95 | NR | 0.9 ± 0.2 | NR |
| $t_{1/2}$, min | 2757 ± 1573 | 1695 ± 439 | 82 ± 15 | 191 ± 9.0 |
| AUC, min* µg/mL | 18.5 ± 4.7 | 231 ± 11.3 | 141 ± 30 | 128 ± 154 |
| $C_{max}$, ng/mL | 400 ± 118 | 210 ± 133 | 2552 ± 576 | 862 ± 1010 |
| F, % |  | 50% |  | 36% |

Figure 27A:
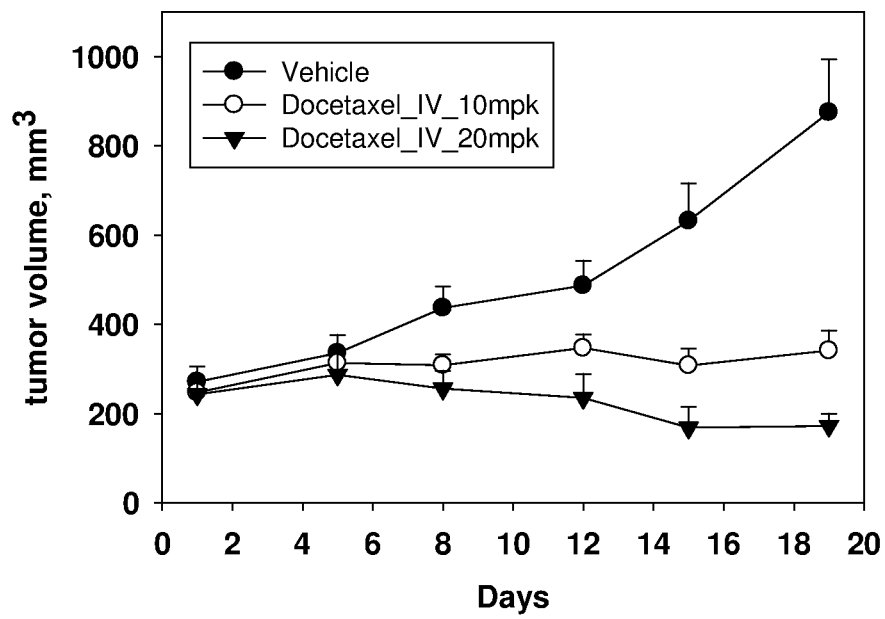
FIGS. 27A-D depict in vivo anticancer efficacy.
Figure 27B:
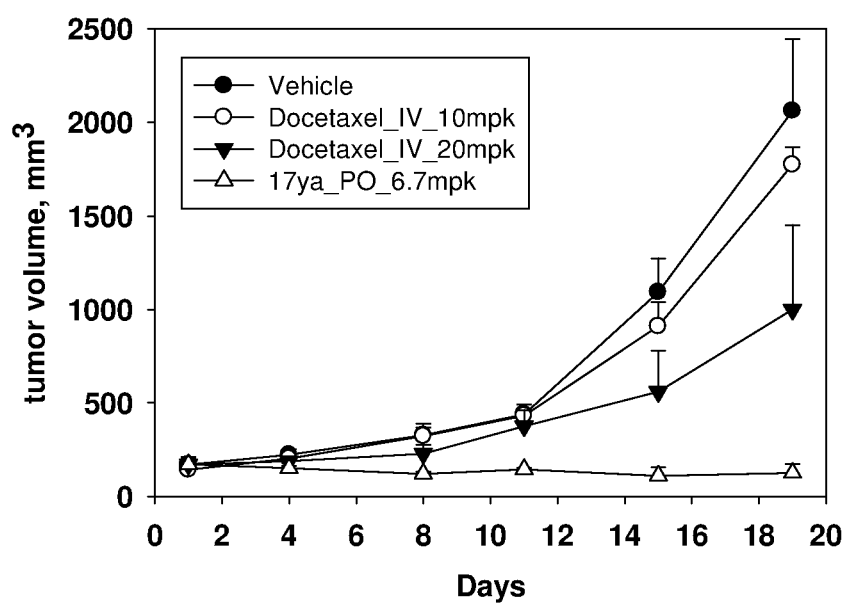
Figure 27C:
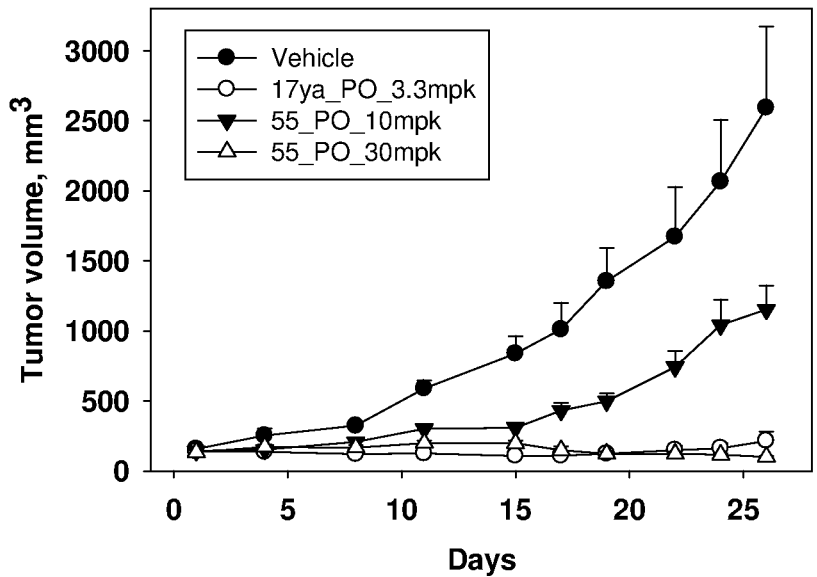
Figure 27D:
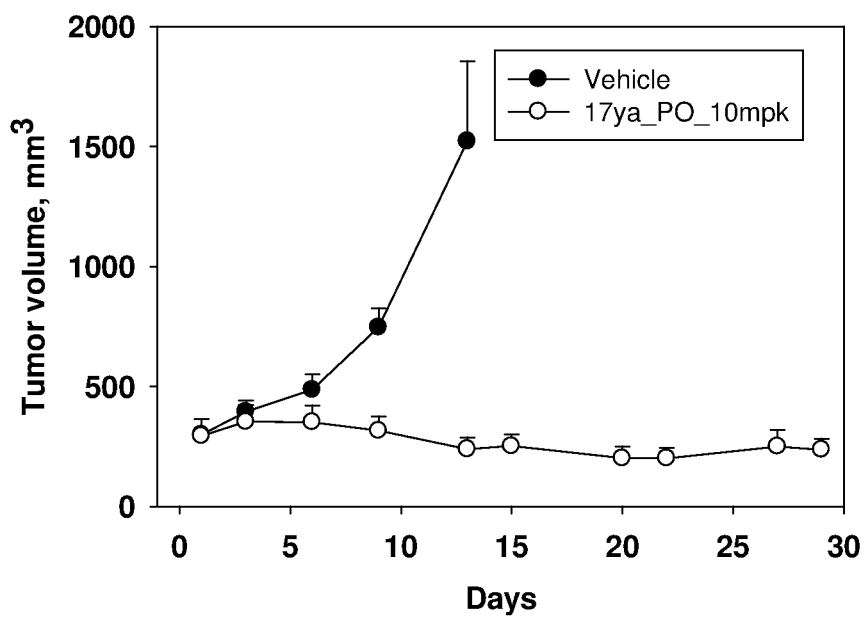

17ya and 55 inhibit paclitaxel resistant prostate (PC-3/TxR) xenografts growth. PC-3 (FIG. 27A) and paclitaxel-resistant prostate cancer (PC-3/TxR) (FIG. 27B) cells were inoculated in nude mice and the tumor volumes were allowed to reach about 150-300 mm³. Docetaxel (10 or 20 mg/kg), which is in clinic for prostate cancer, was used to evaluate its effectiveness in models of P-gp-mediated drug resistance in vivo. PC-3/TxR tumor was found to be fast-growing and the volume reached 1500-2500 mm³ at the termination of the study. Though and 20 mg/kg intravenously administered docetaxel exhibited a dose response in both models (FIGS. 27A and 27B), the tumor growth inhibition (TGI) effect decreased from 84% TGI in PC-3 tumors to 14% TGI in PC-3/TxR tumors when intravenously dosed at 10 mg/kg (Table 18). In addition, at the higher dose (20 mg/kg), docetaxel elicited partial regression (>100% TGI) of PC-3 tumors, but barely 56% TGI in PC-3/TxR tumors. The effectiveness of docetaxel in PC-3/TxR tumors was dramatically decreased when compared to that in PC-3 tumors, suggesting that the efficacy was impaired by P-gp-mediated drug resistance, and these results are in very good agreement with our in vitro cytotoxicity or apoptosis data. In contrast to the lack of efficacy of docetaxel in PC-3/TxR tumors, orally administered 17ya (6.7 mg/kg) demonstrated more than 100% TGI without an effect on their body weights (FIG. 27B and Table 18). In addition, 2 out of 4 nude mice bearing PC-3/TxR tumors were tumor free on day 19 (data not shown). The PC-3/TxR xenograft model was further utilized to evaluate efficacies of 17ya (in other dosing schedules) and 55. The maximal tolerated dose (body weight loss>20%) of 17ya was found to be 10 mg/kg, when orally dosed once daily for four days; or at 3.3 mg/kg twice a day (b.i.d.) for five days (data not shown). As shown in FIG. 27C, 3.3 mg/kg of 17ya was dosed b.i.d. for first consecutive four days in the first week, and the schedule was then changed to once daily between weeks 2 and 4. The result shows that partial regression was obtained during day 4-19, and the TGI was 97%, and one of the seven mice was tumor free on day 26. Higher dose (10 mg/kg) with lower dosing frequency (q2d) of 17ya (FIG. 27D) elicited partial regression during days 13 to 29. These data suggest that regimens with optimized doses and dosing schedules will facilitate 17ya to successfully inhibit PC-3/TxR tumors. 55, was orally administered to nude mice with 10 or 30 mg/kg b.i.d., and five times a week between weeks 1 and 4. As shown in FIG. 27C, the inhibition profiles exhibit a dose-response in PC-3/TxR tumor. The TGI value was 59% for the treatment group with a lower dose (10 mg/kg). Moreover, the higher dose (30 mg/kg) started to show partial regression (>100% TGI) from day 19 to the termination of the study (day 26). Some mice in the vehicle group lost body weight at the endpoint, in part, due to cancer cachexia. On the contrary, mice treated with 17ya (3.3 mg/kg) or 55 (30 mg/kg) were gaining weight (Table 18), suggesting that these optimized doses of 17ya or 55 may be well-tolerated and were preventive of cancer cachexia.

TABLE 18

Antitumor activity of compounds 17ya and 55 versus concomitantly evaluated docetaxel in vivo.

|  | Dosing Schedule | End point | Number End/Start | Body weight (g) | | Tumor size (mm³) | | TGI (%) |
| --- | --- | --- | --- | --- | --- | --- | --- | --- |
|  |  |  |  | Start | End | Start | End |  |
| PC-3 xenograft | | | | | | | | |
| Vehicle_IV | day 1 and 9 | day 19 | 6/6 | 30 ± 2 | 32 ± 4 | 271 ± 83 | 875 ± 292 | — |
| Docetaxel_IV_10 mpk | day 1 and 9 | day 19 | 5/5 | 29 ± 2 | 24 ± 2 | 247 ± 49 | 341 ± 101 | 84 |

TABLE 18-continued

Antitumor activity of compounds 17ya and 55 versus concomitantly evaluated docetaxel in vivo.

| | Dosing Schedule | End point | Number End/Start | Body weight (g) Start | Body weight (g) End | Tumor size (mm³) Start | Tumor size (mm³) End | TGI (%) |
|---|---|---|---|---|---|---|---|---|
| Docetaxel_IV_20 mpk PC-3/TxR xenograft | day 1 and 9 | day 19 | 5/5 | 28 ± 3 | 24 ± 3 | 243 ± 68 | 172 ± 62 | >100 |
| Vehicle_IV | day 1 and 9 | day 19 | 5/5 | 33 ± 1 | 26 ± 5 | 171 ± 57 | 2061 ± 858 | — |
| Docetaxel_IV_10 mpk | day 1 and 9 | day 19 | 4/4 | 31 ± 2 | 25 ± 2 | 143 ± 20 | 1774 ± 183 | 14 |
| Docetaxel_IV_20 mpk | day 1 and 9 | day 19 | 4/4 | 30 ± 1 | 25 ± 4 | 170 ± 86 | 999 ± 905 | 56 |
| 17ya_PO_6.7 mpk | qd × 5/w | day 19 | 4/4 | 33 ± 3 | 34 ± 3 | 172 ± 69 | 126 ± 100 | >100 |
| Vehicle_PO | b.i.d × 5/w | day 26 | 6/7 | 30 ± 2 | 25 ± 2 | 156 ± 30 | 2591 ± 1423 | — |
| 55_PO_10 mpk | b.i.d × 5/w | day 26 | 7/7 | 29 ± 2 | 26 ± 3 | 143 ± 44 | 1152 ± 433 | 59 |
| 55_PO_30 mpk | b.i.d × 5/w | day 26 | 7/7 | 29 ± 3 | 30 ± 2 | 134 ± 34 | 101 ± 19 | >100 |
| 17ya_PO_3.3 mpk[a] | qd × 5/w | day 26 | 7/7 | 29 ± 2 | 30 ± 2 | 139 ± 44 | 214 ± 172 | 97 |
| Vehicle_PO | q2d × 3/w | day 29 | 5/5 | 24 ± 2 | 21 ± 1 | 299 ± 40 | 1521 ± 580 | — |
| 17ya_PO_10 mpk | q2d × 3/w | day 29 | 5/5 | 24 ± 2 | 28 ± 2 | 294 ± 156 | 237 ± 103 | >100 |

Dosing schedule: qd × 5/w = one administration given on five consecutive days per week;
b.i.d. × 5/w = two administrations given on five consecutive days per week; or
q2d × 3/w = every other day administration or three times a week.
[a]Dose schedule was two administrations given on four consecutive days of the first week, and dose schedule was changed (because of toxicity) to one administration given on five consecutive days per week for the second to fourth week.

Brain penetration of 17ya and 55 in nude mice. Whole brain concentrations in nude mice at 1 h and 4 h after oral administration of 20 mg/kg 17ya or 55 were determined (Table 19). The ratios of brain to plasma concentrations were determined and compared to docetaxel in the nude mice. 55 exhibited greater brain penetration than 17ya and docetaxel. 17ya only exhibited slightly greater brain/plasma concentration ratios than docetaxel at both 1 and 4 h. The brain concentrations of 55 reached 14 to 19% of plasma concentrations at 1 h and 4 h, respectively, showing a 3.2-fold higher brain/plasma ratio at both 1 h and 4 h compared to docetaxel. These data suggest that 55 exhibited potentially favorable properties to treat glioma, since it has greater brain penetration and high potency (22 nM, Table 15) in glioma cells.

TABLE 19

Brain-Blood Barrier (BBB) studies of compounds 17ya and 55. Brain and plasma concentrations were determined in nude mice at 1 and 4 h after administration of docetaxel (IP, 10 mpk), 17ya (PO, 20 mpk), and 55 (PO, 20 mpk). Each value represents the mean ± SD from 3 nude mice.

| | Docetaxel | | 17ya | | 55 | |
|---|---|---|---|---|---|---|
| Measurement | 1 hr | 4 hr | 1 hr | 4 hr | 1 hr | 4 hr |
| Brain (ng/mL) | 33 ± 14 | 20 ± 9 | 124 ± 108 | 49 ± 32 | 180 ± 44 | 73 ± 18 |
| Plasma (ng/mL) | 768 ± 92 | 345 ± 94 | 2058 ± 1252 | 570 ± 438 | 1669 ± 867 | 380 ± 32 |
| Brain/plasma (%) | 4.4 ± 2.0 | 6.0 ± 2.9 | 5.4 ± 1.9 | 8.9 ± 1.7 | 14 ± 7.9 | 19 ± 3.1 |

Example 21

Pharmacokinetics of Compounds of this Invention

TABLE 20

| Compound ID | Half life in Human liver microsome (min) | Half life in Mouse liver microsome (min) | Half life in Rat liver microsome (min) | Half life in Dog liver microsome (min) | Half life in Monkey liver microsome (min) |
|---|---|---|---|---|---|
| 1h | 17 | <5 | 31 | 19 | <5 |
| 2e-cis | 35 | | | | |
| 2i | 32 | | | | |
| 2k | 10 | 9 | 32 | 16 | <5 |
| 2l | 20 | 11 | 49 | 30 | 8 |
| 6a | 32 | 3.43 | 12 | 13 | 16 |
| 6b | 40 | 10 | 9 | 30 | 13 |
| 6c | 47 | 13 | 14 | 29 | 9 |
| 7d | 24 | 37 | 42 | 29 | 15 |
| 12da | 23 | 8 | 28 | 17 | |
| 12fa | 56 | 23 | 46 | 26 | |
| 12fb | 37 | | | | |
| 12dab | 21 | <5 | 12 | 46 | |

Example 22

Biological Activity of 4-Substituted Methoxybenzoyl-Aryl Thiazole (Smart) Compounds 1 h, 2k, and 2l: Active Microtubule Inhibitors

Materials and Methods

In vitro microtubule polymerization assay. Bovine brain tubulin (0.4 mg) (Cytoskeleton, Denver, CO) was mixed with 10 µM of the test compound or vehicle (DMSO) and incubated in 100 µl of buffer (80 mM PIPES, 2.0 mM $MgCl_2$, 0.5 mM EGTA, pH 6.9 and 1 mM GTP). The absorbance at 340 nm wavelength was monitored every min for 15 min (SYNERGY 4 Microplate Reader, Bio-Tek Instruments, Winooski, VT). The spectrophotometer was maintained at 37° C. for tubulin polymerization.

MS competition binding assay. Colchicine, vinblastine, and paclitaxel (1.2 µM for each) were incubated with tubulin (1.2 mg/mL) in the incubation buffer (80 mM PIPES, 2.0 mM $MgCl_2$, 0.5 mM EGTA, pH 6.9) at 37° C. for 1 hr. 1h (0.5-125 µM) was examined to individually compete with colchicine-, vinblastine-, and paclitaxel-tubulin binding. The free-form ligands were separated from tubulin or microtubule using an ultrafiltration method (microconcentrator) (Microcon, Bedford, MA) with a molecular cutoff size of 30k Da. Colchicine, vinblastine and paclitaxel were determined by LCMS/MS method. The ability of 1h to inhibit the binding of ligands was expressed as a percentage of control binding in the absence of any competitor. Each reaction was run in triplicate.

Cell culture and cytotoxicity assay of prostate and melanoma cancer. All prostate and melanoma cell lines were obtained from ATCC (American Type Culture Collection, Manassas, VA, USA), while cell culture supplies were purchased from Cellgro Mediatech (Herndon, VA, USA). The antiproliferative activity of the compounds was examined in four human prostate cancer cell lines (LNCaP, DU 145, PC-3, and PPC-1) and two human melanoma cell lines (A375 and WM-164). Human ovarian cell line OVCAR-8 and its resistant cell line that over-expresses P-gp, NCI/ADR-RES, were used as MDR models. Both ovarian cell lines were obtained from National Cancer Institutes (NCI). All prostate cancer cell lines were cultured with 10% fetal bovine serum (FBS).

Cell cycle analysis. Flow cytometry was performed to study the effects of the compounds on cell cycle distribution. PC-3 and A375 cells were treated in growth media with the indicated concentrations of compounds 1 h, 2k, 2l for 24 h. Cellular DNA was stained with 100 µg/mL propidium iodide and 100 µg/mL RNase A in PBS and flow cytometry was performed to determine the cell cycle distribution of the cells.

Apoptosis detection by ELISA. Quantification of the enrichment of mono- and oligonucleosomes in the cytoplasm was used to determine the ability of the compounds to induce apoptosis (cell death detection ELISA PLUS, Roche, Germany) following the manufacturer's instructions.

Pharmacokinetic study. Male ICR mice (n=3 or 4 per group) 6 to 8 weeks of age were purchased from Harlan Inc., and used to examine the pharmacokinetics (PK) of the compounds. 1 h, 2k, 2l (15 mg/kg) were dissolved in PEG300/DMSO (¼) and administered by a single i.v. injection into the tail vein. Blood samples were collected at 2, 5, 15, and 30 min, 1, 2, 4, 8, 16, and 24 hr after administration. Male Sprague-Dawley rats (n=4; 254 □±4 g) were purchased from Harlan Inc. (Indianapolis, IN). 1 h, 2k, were administered intravenously into the jugular venous catheters at 2.5 mg/kg (in DMSO/PEG300, ¼). Blood samples (250 µL) were collected at 10, 20, 30 min, and 1, 2, 4, 8, 12, 24, 48 h. A protein precipitation method was used for sample preparation. An aliquot (200 µL) of acetonitrile (ACN) was added to 100 µL of plasma and then was thoroughly vortexed for 15 s. After centrifugation, the supernatant was analyzed by liquid chromatography tandem mass spectrometry (LC-MS/MS). The PK parameters were determined using Non compartment analysis (WinNonlin, Pharsight Corporation, Mountain View, CA).

PC-3 and A375 tumor xenograft studies. PC-3 and A375 cells ($5 \times 10^7$ per mL) were prepared in phenol red-free growth media containing 10% FBS, and mixed with Matrigel (BD Biosciences, San Jose, CA) at 1:1 ratio. Tumors were established by injecting 100 µL of the mixture ($2.5 \times 10^6$ cells per animal) subcutaneously (s.c.) into the flank of 6-8-week-old male athymic nude mice. Length and width of tumors were measured and the tumor volume ($mm^3$) was calculated by the formula, $7r/6 \times \Box L \times \Box W^2$, where length (L) and width (W) were determined in mm. When the tumor volumes reached 150 $mm^3$, the animals bearing PC-3 tumors were treated with vehicle [Captex200/Tween80 (¼)], 1h (5 and 15 mg/kg), 2k (5 and 15 mg/kg) and 2l (50 mg/kg) intraperitorally for 21 days. Vinblastine (0.5 mg/kg) was used as the positive control and dosed q2d with vehicle [DMSO/PEG300 (1/9)]. On the other hand, A375 tumor bearing mice were treated for 34 days with vehicle [Captex200/Tween80 (¼)], 1h (20 mg/kg) or 2k (15 mg/kg). Doses were selected based on acute toxicity studies of 1 h and 2k in ICR mice (n=2/group) showing that doses up to 30 mg/kg and 15 mg/kg, respectively, did not cause greater than 10% loss of body weight after 4 consecutive days of intraperitoneal dosing.

In vivo antitumor activity [tumor growth inhibition (% T/C), tumor growth delay (T-C value), and tumor cell kill (total log cell kill)]. Evidence of drug effect is described by the following parameters: % T/C=[Δ□tumor volume of treated group]/[Δ tumor volume of control group]×□100%. The T-C values (tumor growth delay) were based on the median time (in days), required for the treatment (T) and the control group (C) tumors, to reach a predetermined size (600 $mm^3$ in this study). These values were then used for the quantitation of the tumor cell kill following the equation: log cell kill=(T-C)/(3.32×□Td). Td is the tumor volume-doubling time in days. In this study, we defined the doubling time required for the tumor to increase from 300 to 600 $mm^3$.

Rotarod test. ICR mice received training three times a day for two days to enable them to stay on the rotating rod for >120 seconds at 12 rpm. Mice were then randomized by the length of time that they could stay on the rotating rod and divided into 7-8 mice per group. 1h at a dose of 5 or 15 mg/kg in Captex200/Tween80 (¼) was administered by intraperitoneal injection. Vinblastine at a dose of 0.5 mg/kg/day was used as a positive control under the same conditions. The rotarod test was performed twice a week. Treatment was stopped on day 31, and post observation was examined on weeks 1, 2, and 4 after termination of the treatment. The rod speed was increased from 59 rpm to 40 rpm over a period of 5 min. Performance was measured as the length of time that a mouse could stay on the rotating rod.

In vivo drug resistance studies. At the end of the PC-3 xenograft studies, solid tumors from control and 1h treated (15 mg/kg) groups were removed and digested with 0.1% collagenase (Type I) and 50 mg/mL DNAse (Worthington Biochemical Corp., Freehold, NJ). Dispersed cells were plated in RPMI medium+10% FBS and incubated at 37° C. and 5% $CO_2$ for 24 hr to allow attachment. The antiproliferative effects of 1h were compared to determine whether tumor cells remaining in PC-3 xenografts retained sensitivity to drug. The PC-3 cells obtained from ATCC were used as in vitro control. Statistical analyses were performed using simple t-Test.

Results

Figure 28A:
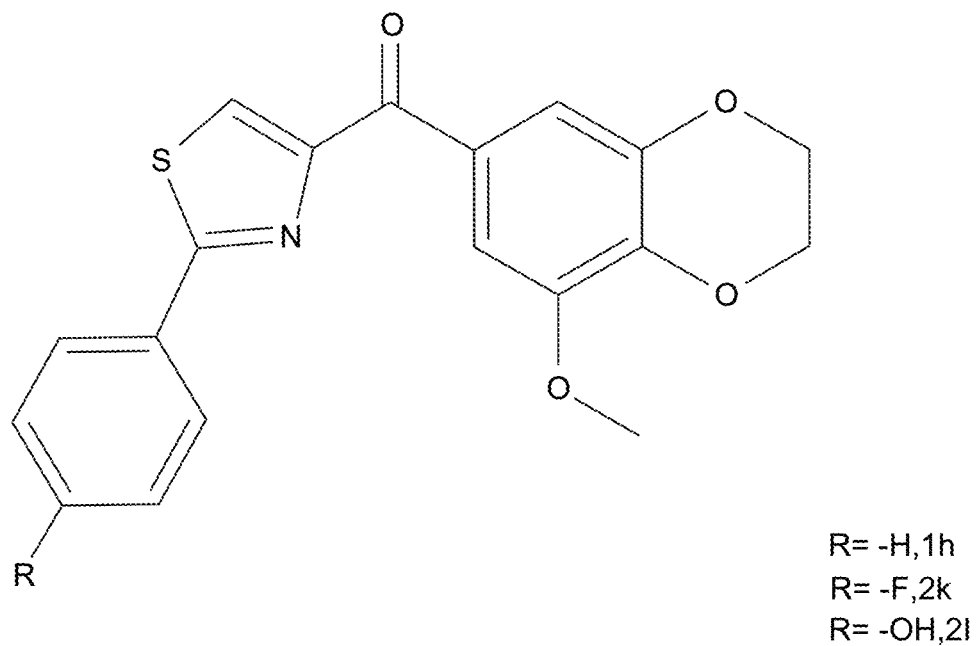
FIGS. 28A-C depict that compounds 1h, 2k, and 21 inhibit tubulin polymerization via binding to the colchicine binding site on tubulin.

Based on structure-activity relationship studies, three compounds (FIG. 28A) were selected for biological characterization. While 1 h and 2k are highly potent molecules with low nanomolar cytotoxic properties, 21, which was rationally designed as a potential metabolite with improved solubility, had the least potent antiproliferative effects (Table 21).

several human cancer cell lines, including four prostate cancer cell lines, and two melanoma cell lines, with $IC_{50}$ values in the low nanomolar range. Out of the three compounds, 21 was the least potent ($IC_{50}$ 76-116 nM). 2k exhibited the best antiproliferative effect with $IC_{50}$ values between 6 and 43 nM in prostate cancer and melanoma cell lines. In addition, the effect of the compounds in the OVCAR-8 and NCI/ADR-RES cell lines was also evaluated (Table 21). The compounds were equally potent against MDR cell (NCI-ADR-RES) and the parent cell line (OVCAR-8). Paclitaxel, vinblastine, and colchicine exhibited relative resistance values of 1333, 149, and 65 times, respectively (Table 21). These data indicate that the compounds circumvent P-gp-mediated drug resistance.

SMART compounds arrest PC-3 (prostate) and A375 (melanoma) cells in G2/M phase of cell cycle and induce cell apoptosis. PC-3 and A375 cells were exposed to 10, 50, 200, and 1000 nM of the compounds for 24 h. Treatment

TABLE 21

In vitro efficacy of compounds on prostate, melanoma and drug resistant cell lines (n = 3, mean ± SE). Paciltaxel, vinblastine, and colchicine were used as positive controls as previously reported.

| | | $IC_{50}$ ± SEM (nM) | | | | | |
|---|---|---|---|---|---|---|---|
| Cell Line | Cell type | SMART-H | SMART-F | SMART-OH | Paclitaxel | Vinblastine | Colchicine |
| LNCaP | Prostate | 28 ± 4[a] | 6 ± 1[a] | 103 ± 9 | 1.7 ± 0.2 | 1.1 ± 0.1 | 16 ± 4 |
| PC-3 | Prostate | 21 ± 1[a] | 13 ± 1[a] | 87 ± 5 | 4.8 ± 0.3 | 2.1 ± 0.2 | 11 ± 1 |
| Du-145 | Prostate | 71 ± 4[a] | 12 ± 1[a] | 116 ± 14 | 5.1 ± 0.1 | 1.8 ± 1.1 | 10 ± 2 |
| PPC-1 | Prostate | 43 ± 5[a] | 8 ± 1[a] | 76 ± 2 | 2.3 ± 0.8 | 1.1 ± 0.4 | 20 ± 1 |
| B16-F1 | Melanoma | 55 ± 5[a] | 43 ± 21[a] | 113 ± 6 | 17 ± 2 | 4.7 ± 0.7 | 29 ± 5 |
| A375 | Melanoma | 28 ± 5[a] | 33 ± 14[a] | 93 ± 11 | 12 ± 3 | 1.1 ± 0.2 | 20 ± 3 |
| OVCAR-8 | Ovarian | 35 ± 2 | 34 ± 3 | 110 ± 8 | 4.7 ± 0.1 | 3.9 ± 0.1 | 17 ± 1 |
| NCT/ADR-RES | Ovarian | 13 ± 1 | 12 ± 1 | 45 ± 5 | 6263 ± 634 | 582 ± 57 | 1113 ± 79 |
| Resistance Factor | | 0.4 | 0.4 | 0.4 | 1333 | 149 | 65 |

SMART-H in Table 21 is 1h;
SMART-F in Table 21 is 2k; and
SMART-OH in Table 21 is 2l.

SMARTs Inhibit Microtubule Polymerization by Binding to the Colchicine Binding Site on Tubulin.

Figure 28B:
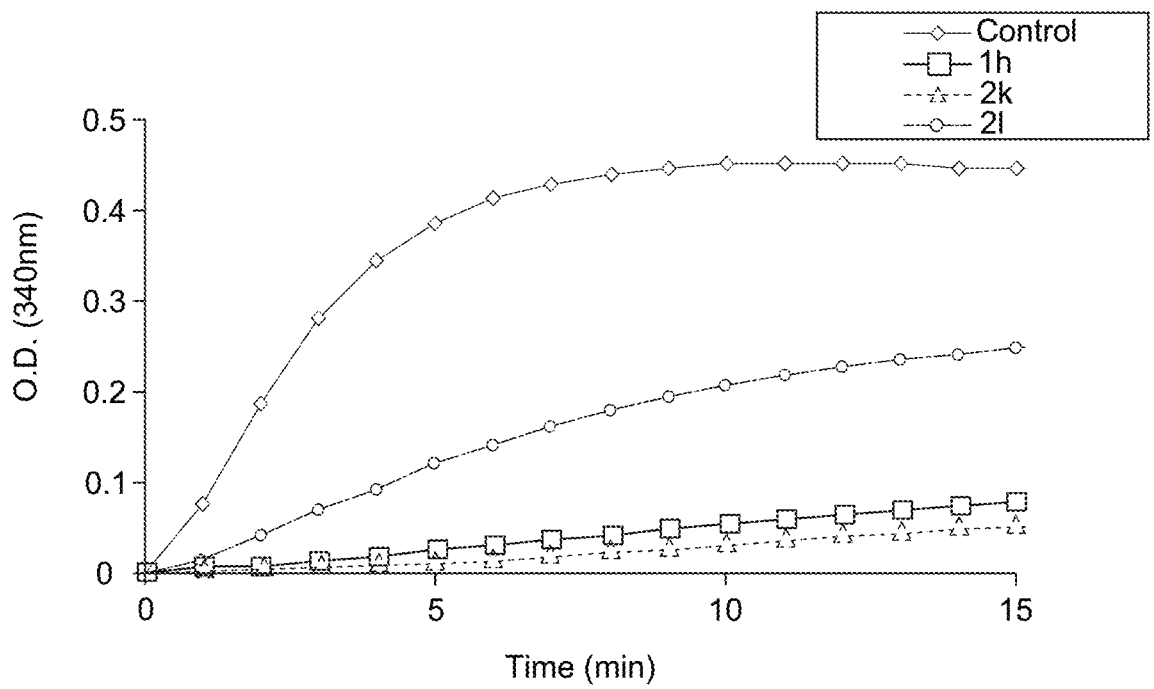
Figure 28C:
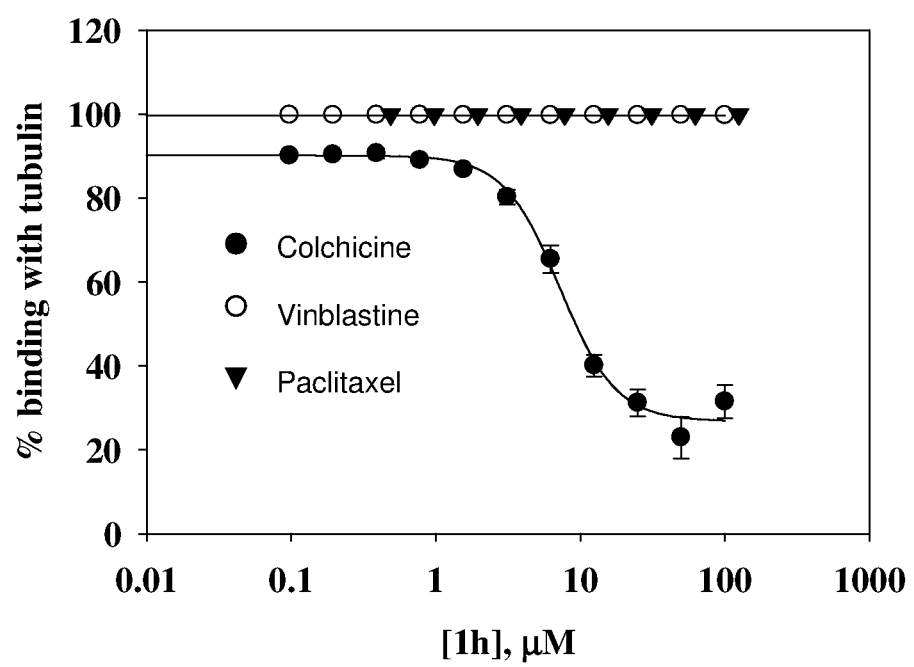

Bovine brain tubulin (>97% pure) was incubated with the individual compounds (10 µM) to test their effect on tubulin polymerization (FIG. 28B). While 1 h and 2k inhibited tubulin polymerization by 90%, 21 inhibited the polymerization by only 55%. Previous studies demonstrated a concentration-dependent inhibition of tubulin polymerization by 1h. In addition, under the same experimental conditions, the $IC_{50}$ for 1h (4.23 µM) is similar to that of colchicine (4.91 µM). These data suggest that the compounds exhibit strong antitubulin polymerization activity that corresponds well with their cytotoxicity (Table 21). The ability of the compounds to compete for known binding sites on tubulin was determined using a novel MS competitive binding assay, which was developed in our laboratory. Three tubulin ligands, corresponding to the three binding sites on tubulin, colchicine, vinblastine, and paclitaxel were used for these competitive binding studies. It was found that, over a concentration range of 0.1-125 µM, 1h specifically competed with colchicine binding to tubulin, but it did not compete with either vinblastine or paclitaxel binding to tubulin (FIG. 28C).

SMART Compounds Inhibit the Growth of Multidrug-Resistant Cancer Cell Lines.

Figure 29B:
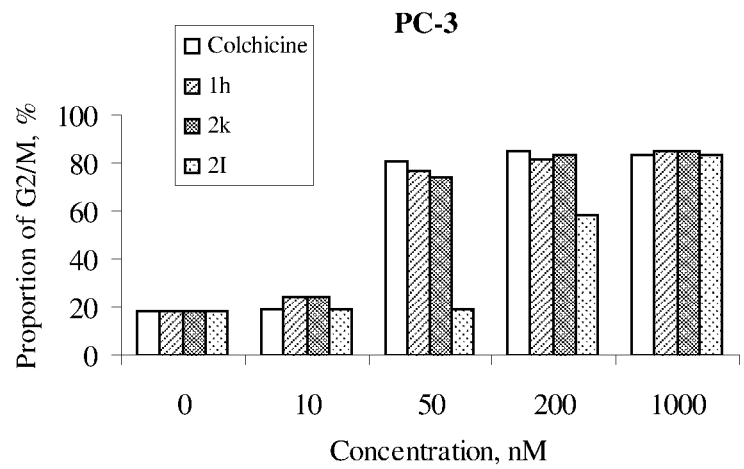
Figure 29C:
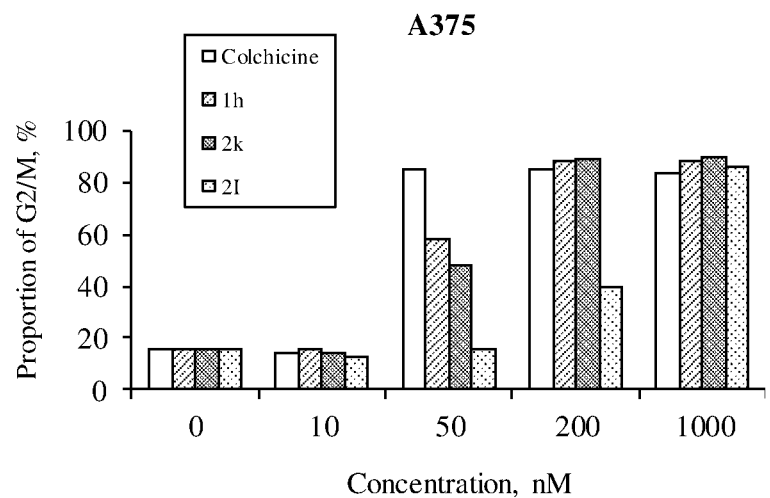
Figure 29D:
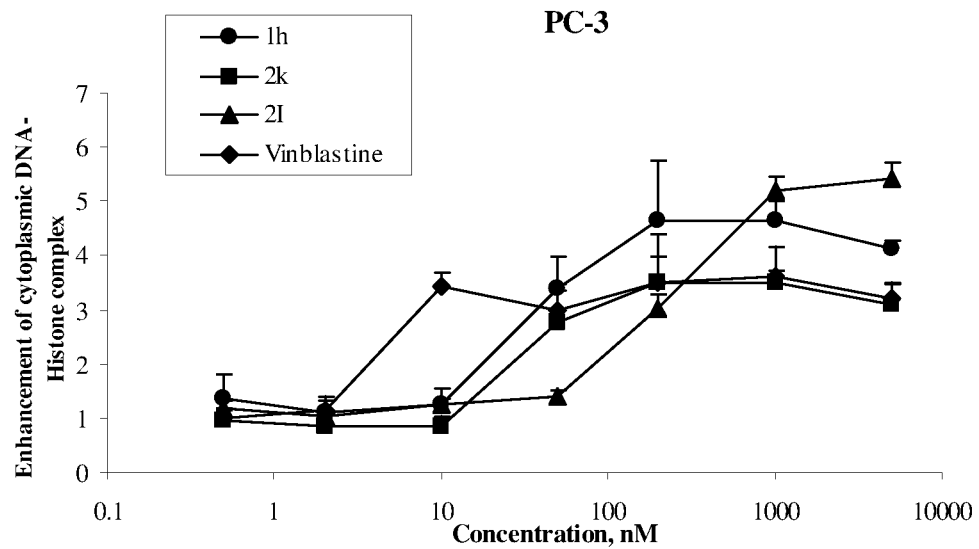
Figure 29E:
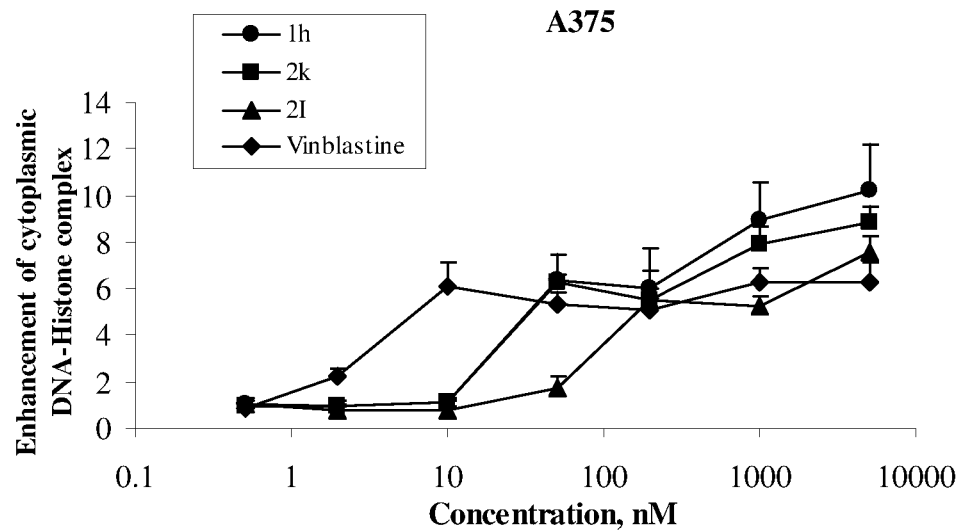

The ability of the compounds to inhibit the growth of cancer cell lines was evaluated using the SRB assay. As shown in Table 21, the compounds inhibited the growth of with the SMART compounds resulted in concentration-dependent accumulation of both PC-3 and A375 cells in the G2/M phase with concomitant decreases in the percentage of cells in G0/G1 phase (FIGS. 29A(i)-29A(iv), 29B and 29C). The proportion of cells in G2/M phase significantly increased when treated with 50 to 200 nM of 1 h, 2k, 21. Apoptosis was then examined by measuring the level of cytoplasmic DNA-histone complexes in PC-3 and A375 cells after 24 h treatment. Increasing concentration of the SMART compounds increased the level of cytoplasmic DNA-histone complexes in PC-3 and A375 cells (FIG. 29D). The effect was more pronounced in A375 cells than PC-3 cells, but apoptosis was evident in both cell types. 1h and 2k induced moderate apoptosis at a concentration of 50 nM, while 21 induced apoptosis only at concentrations greater than or equal to 200 nM.

Figure 30A:
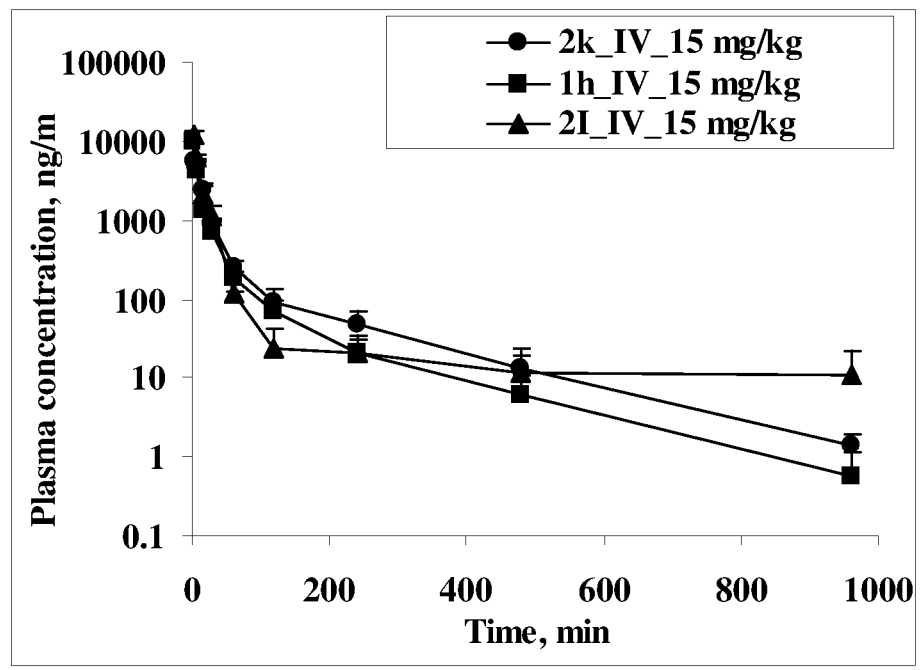
FIGS. 30A-B depict pharmacokinetic studies of 1h, 2k and 21 administered i.p. in mice and rats.
Figure 30B:
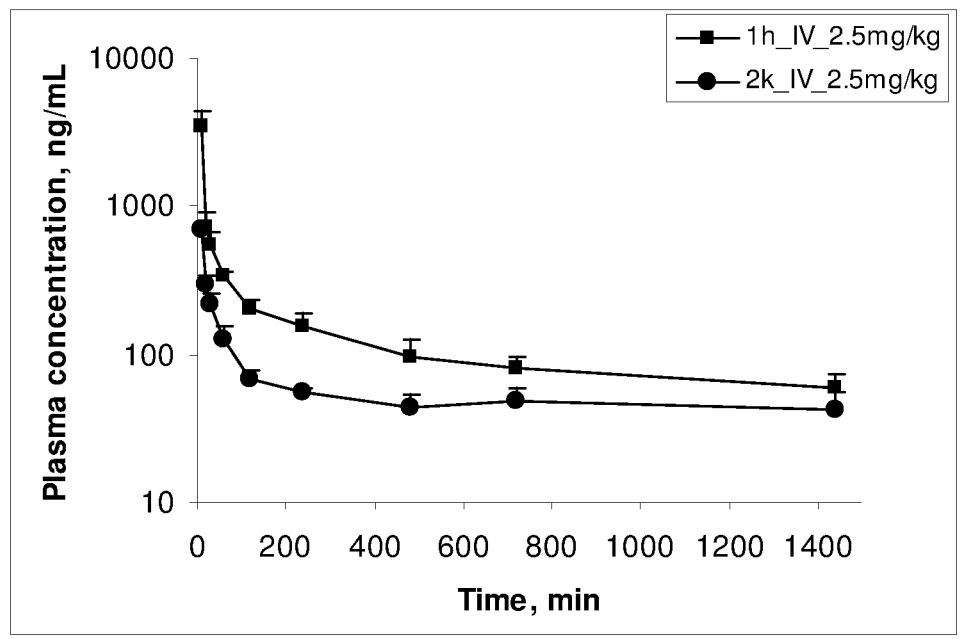

In vivo PK profile of SMART compounds. A single dose bolus of each compound (15 mg/kg) was administered by tail vein injection to ICR mice to characterize their pharmacokinetics (FIG. 30A). 1h and 2k exhibited similar PK properties, but 21 exhibited slightly greater AUC than 1 h and 2k indicative of a lower clearance for 21 (Table 22). 21 also had 2-3 times higher $V_{ss}$ than that of 1h and 2k. The clearance values for all three compounds were equal to or higher than 90 mL/min/kg, the hepatic blood flow rate in mice, suggesting that in addition to hepatic removal, other degradation routes may be involved in the elimination of the compounds. The pharmacokinetics of 1h and 2k (2.5 mg/kg)

were also examined in rats (FIG. 30B). Interestingly, low clearance values and hepatic extraction rates were obtained by both compounds, suggesting that these compounds exhibit species differences in clearance. In rats, 1h exhibited favorable pharmacokinetic properties, which are low clearance (6 mL/min/kg), moderate volume of distribution (7.6 L/kg), long half-life (24 hr), and high exposure (AUC, 5.8 hr*μg/mL) (Table 22) when administered iv.

TABLE 22

Pharmacokinetic parameters of SMART compounds. SMARTs were administered 15 mg/kg and 2.5 mg/kg i.v. in mice and rats, respectively.
In vivo, pharmacokinetic parameters of SMART compounds

| Species | Parameter | Unit | SMART-H | SMART-F | SMART-OH |
|---|---|---|---|---|---|
| Mice | AUC | hr * μg/mL | 1.9 | 22 | 26 |
|  | $t_{1/2}$ | min | 140 | 141 | 740 |
|  | $V_{ss}$ | L/kg | 4.9 | 6.6 | 16.5 |
|  | CL | mL/min/kg | 130 | 112 | 90 |
| Rats | AUC | hr * μg/mL | 5.8 | 1.6 | NA |
|  | $t_{1/2}$ | min | 1431 | 2410 | NA |
|  | $V_{ss}$ | L/kg | 7.6 | 34 | NA |
|  | CL | mL/min/kg | 6 | 11 | NA |

NA, not available

SMART-H in Table 22 is 1h; SMART-F in Table 22 is 2k; and SMART-OH in Table 22 is 21.

Figure 31A:
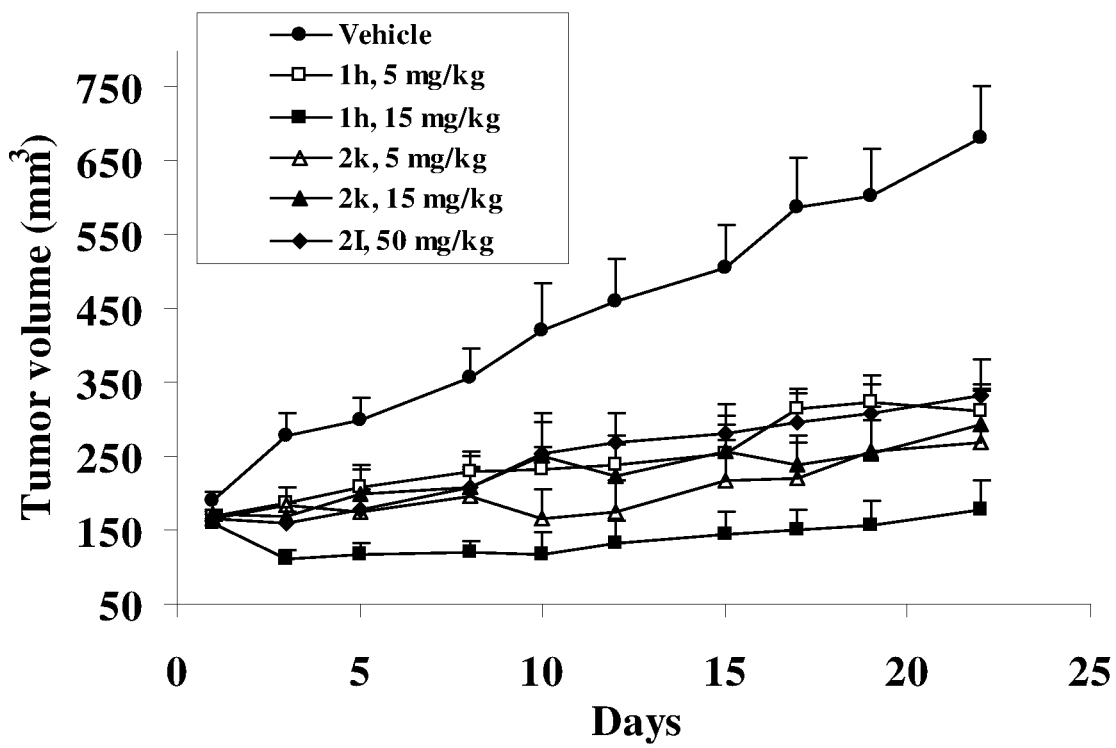
FIGS. 31A-D present in vivo anti-cancer efficacy (administered i.p.) and neurotoxicity of SMART compounds in mice.

SMART compounds inhibit prostate and melanoma xenografts growth without neurotoxicity. Prostate cancer PC-3 and melanoma A375 tumors in mice were allowed to reach a volume of 150 mm³ and then tumor-bearing mice were treated with the SMART compounds. As shown in FIG. 31A, tumor volumes in the control group increased to 680 mm³ over the 21 day duration of the study. Tumor volumes in the 1h treated group increased to 370 mm³ (5 mg/kg treatment) and 176 mm³ (15 mg/kg treatment) by day 21, indicating strong anti-tumor activity for this compound. Tumors in the 2k-treated animals increased to 269 mm³ (5 mg/kg treatment) and 292 mm³ (15 mg/kg treatment), while animals in the 21 (50 mg/kg) treated group had tumors of 331 mm³ at day 21. This reduction in tumor volume reversed upon withdrawal of SMART compounds (data not shown). Table 23 summarized the in vivo efficacy (% T/C, T-C values, and log cell kill) of SMART compounds.

TABLE 23

In vivo efficacy of SMART compounds (administered i.p.) on prostate (PC-3), melanoma (A375). % T/C, T-C value, and log cell kill are summarized. The doubling time of melanoma xenograft was 4.6 d. Vinblastine was used as the positive control. % T/C ≤42% is considered to be moderately active by National Cancer Institute criteria. NA, not available.

| Compound | Dosage (mg/kg) | Xenograft model | % T/C | Median time to reach 600 mm³ (days) | T-C | Total log cell kill |
|---|---|---|---|---|---|---|
| Vehicle | NA | Prostate | 100 | 19 days | NA | NA |
| Vinblastine | 0.5 | Prostate | 29 | NA | NA | NA |
| SMART-H | 5 | Prostate | 29 | NA | NA | NA |
| SMART-H | 15 | Prostate | 4 | NA | NA | NA |
| SMART-F | 5 | Prostate | 21 | NA | NA | NA |
| SMART-F | 15 | Prostate | 24 | NA | NA | NA |
| SMART-OH | 50 | Prostate | 34 | NA | NA | NA |
| Vehicle | NA | Melanoma | 100 | 18 days | NA | NA |
| SMART-H | 20 | Melanoma | 30 | 28 days | 10 | 0.7 |
| SMART-F | 15 | Melanoma | 28 | 29 days | 11 | 0.7 |

SMART-H in Table 23 is 1h;
SMART-F in Table 23 is 2k; and
SMART-OH in Table 23 is 2l.

Figure 31B:
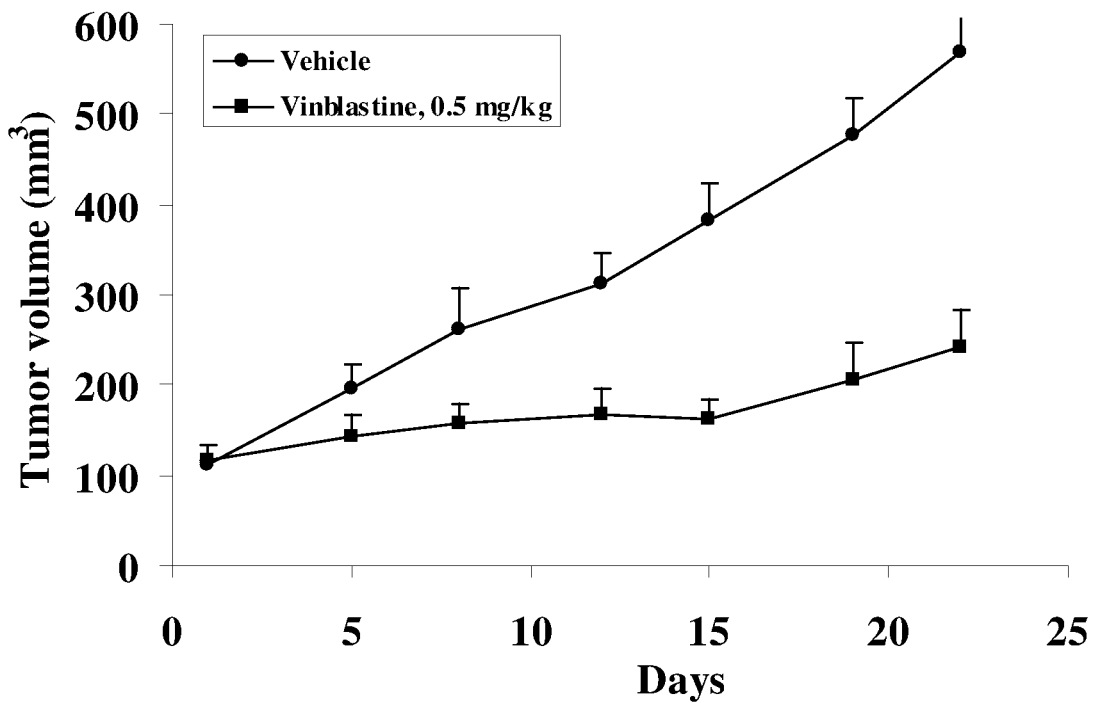
Figure 31C:
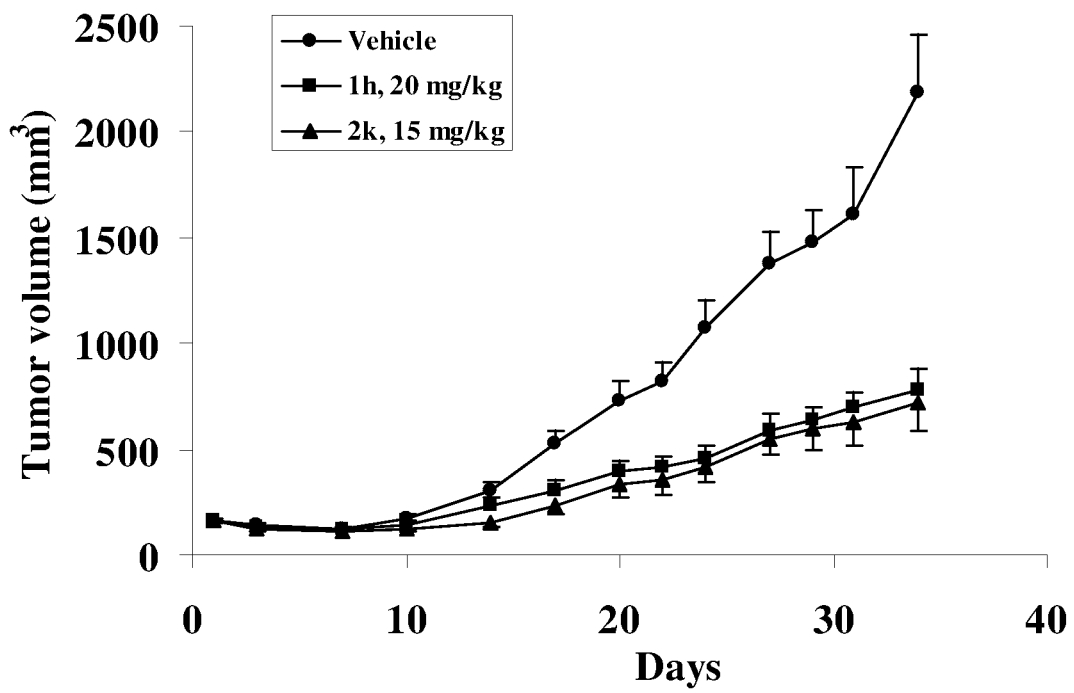
Figure 31D:
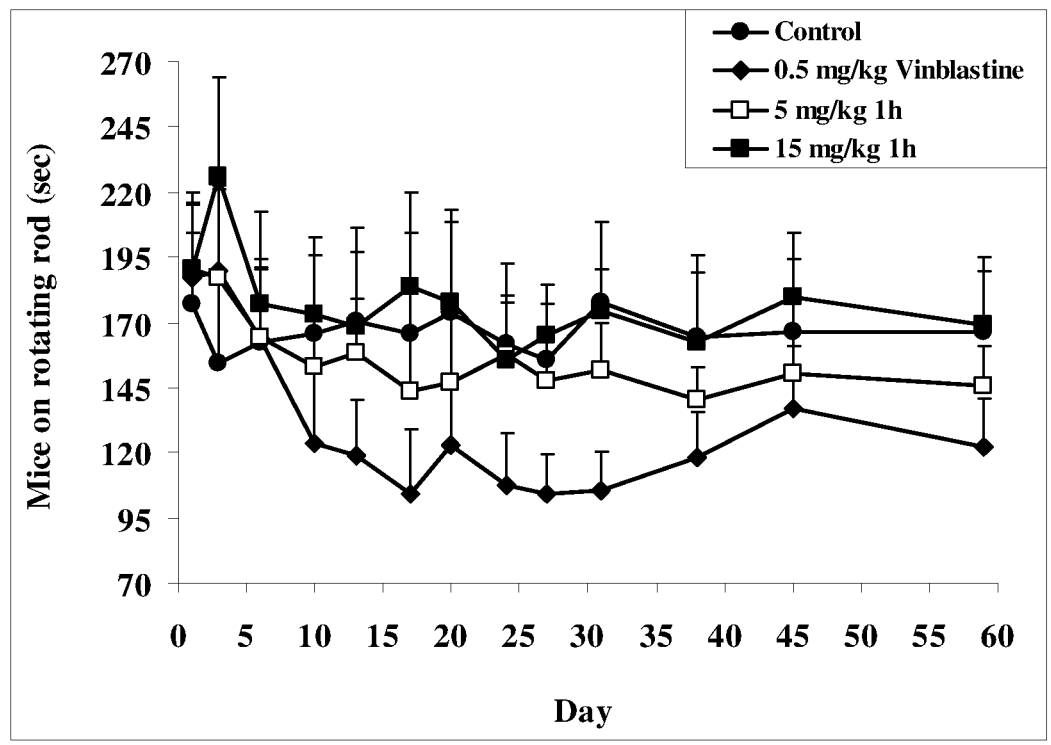

1h tumor elicited % T/C=29% and 4% at 5 and 15 mg/kg treatment (all doses were intraperitoneal (i.p.)), respectively, whereas, 2k elicited % T/C of 21% and 24% at 5 and 15 mg/kg treatment, respectively. The high dose of 21 (50 mg/kg) exhibited the % T/C of 34%. Vinblastine, the positive control, showed % T/C of 29% at day 22 in PC-3 xenografts (FIG. 31B). Body weight measurements, to monitor toxicity, indicated that only 1 of 8 mice treated with 1h (15 mg/kg), and 2 out of 7 mice treated with 2k (15 mg/kg) lost more than 15% body weight. In addition to the antitumor effects of the compounds on PC-3 prostate tumors, 1h (20 mg/kg) and 2k (15 mg/kg) demonstrated a significant reduction of A375 tumors. As shown in FIG. 31C, the tumor volumes of control group increased to 2183 mm³, whereas the 14 volumes in 1 h and 2k treatment groups increased to 775 mm³ and 722 mm³, respectively. 1 h and 2k treatment evoked % T/C of 28% and 29%, respectively. Rotarod tests were performed to examine the in vivo neurotoxic effects of 1h. Based on the result of in vivo efficacy experiments, 5 or 15 mg/kg [i.p. administration, Captex200/Tween80 (¼)] of 1h was chosen to study the effect on motor coordination. A 0.5 mg/kg treatment with vinblastine was used as the positive control under the same conditions. As shown in FIG. 31D, vinblastine gradually reduced the time (in seconds) that the mice could stay on the rotating rod, and attained significance by days 27 and 31 (p<0.05) compared to the vehicle group. However, no significant difference was observed in the 1h treatment groups, suggesting that 1h did not cause neurotoxicity in ICR mice at doses that are associated with antitumor effects.

1h did not develop drug-resistance in PC-3 tumor bearing mice. We excised the PC-3 tumors from nude mice after 21 days of treatment with vehicle (n=3) or 15 mg/kg 1h (n=3). Solid tumors were digested and dispersed into cells as described in the methods section. PC-3 cell line from ATCC (American Type Culture Collection, Manassas, VA, USA) was used as a control. $IC_{50}$ values were 29.1 1.1, 29.1±0.8, and 30.4±0.5 nM in PC-3 cells from ATCC, and dissociated cells from vehicle and 1h treated tumors, respectively. These data demonstrate that 1h did not induce drug-resistance in PC-3 tumors after 21 days of continuous 1h treatment.

Example 23

Molecular Modeling

Methods

All molecular modeling studies were performed with Schrödinger Molecular Modeling Suite 2008 (Schrödinger LLC, New York, NY), running on a Dell Linux workstation. Because the size of ABI compounds are much closer to that of ABT-751, rather than DAMA-colchichine, we selected tubulin complex with ABT-751 (PDB code: 3KHC) as our modeling system. ABIs were built and prepared using the Ligprep module, and they were docked into the ABT-751 site using the Glide module in Schrödinger Suite. The best docking complexes were subject to restricted molecular dynamics to release any strains using Macromodel module with OPLS-2005 forcefield. The ligand and its surrounding residues within 15 Å were allowed to move freely, while residues outside the 15 Å radius were kept rigid.

Results

Molecular modeling for binding ABI compounds in tubulin was studied. Several crystal structures of the ligand-tubulin complex are available in the PDB databank, with the most recent one from Dorleans et al. In general, the colchicine binding pocket tolerates a variety of molecular structures, which may indicate substantial conformation changes upon ligand binding. In fact, Dorleans et al. solved the crystal structures of both the empty tubulin dimer and the ligand-tubulin complex. They found that, without the presence of ligand, loop 7 (T7, residues 244-251, FIG. 32) in the beta-monomer folds in to occupy the binding pocket, while it flips out upon ligand binding. The associated helix 7 (H7, residues 224-243) and helix 8 (H8, residues 252-260) were displaced upon ligand binding. It is conceivable that the extent to which T7 is displaced depends on the size of individual ligand. This flexibility presents a significant challenge to understand the precise binding modes for individual ligands without solving actual crystal structures. Nevertheless, careful analysis of the possible binding modes could provide some insights into the binding of different ligands.

Figure 32A:
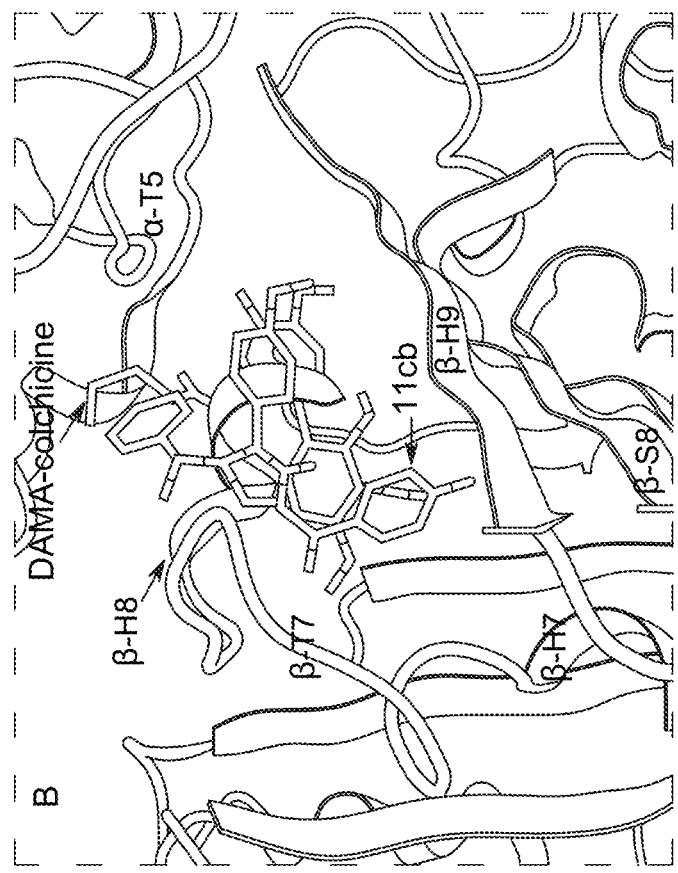
FIGS. 32A-B depict molecular modeling of ABI compounds that target tubulin in the colchicine binding site.
Figure 32B:
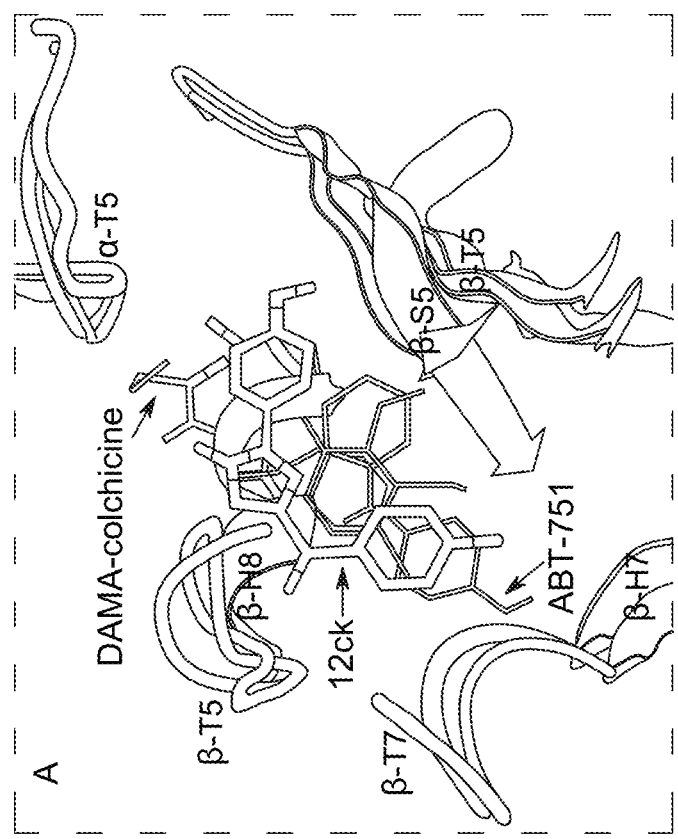
Figure 34A:
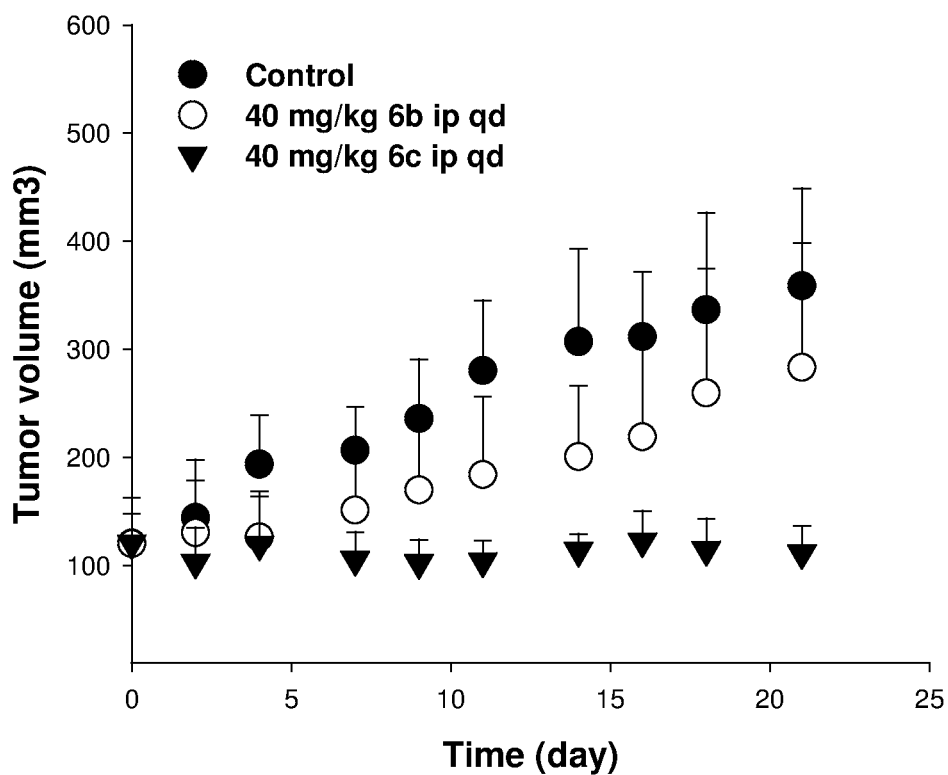
FIGS. 34A-D depict the efficacy and tolerability of 6b and 6c in xenograft models after i.p. injection. PC-3 xenografts were treated with vehicle (qd), 6b (40 mg/kg, qd), or 6c (40 mg/kg, qd) for 3 weeks. Dosing vehicles were composed of 20% Captex200 in Tween80. The tumor volumes (mm$^3$) were plotted against time and are the means±SD from eight animals. The tumor volumes were shown in FIG. 34A and body weights were shown in FIG. 34B.
Figure 34B:
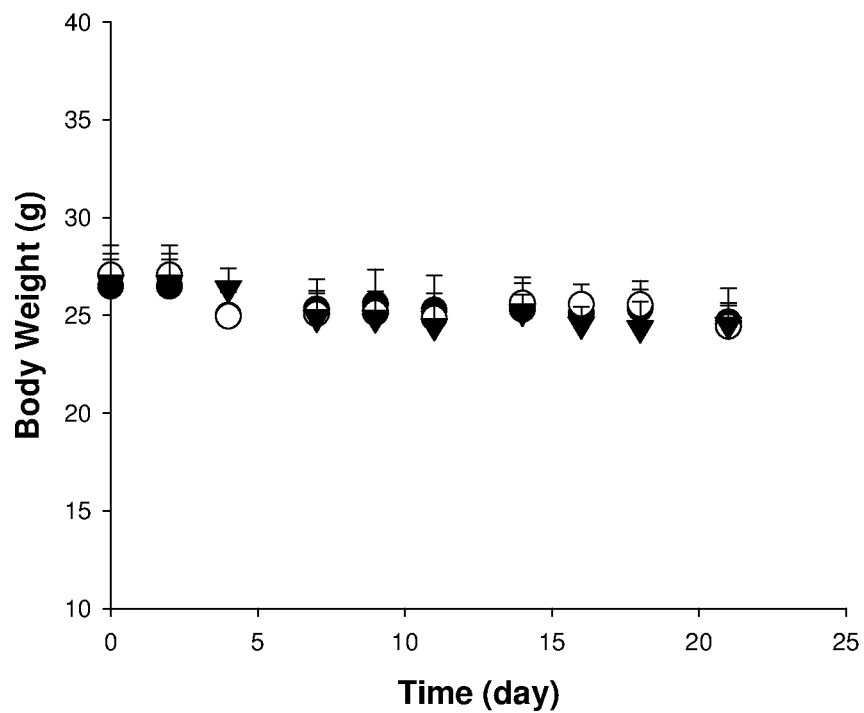
Figure 34C:
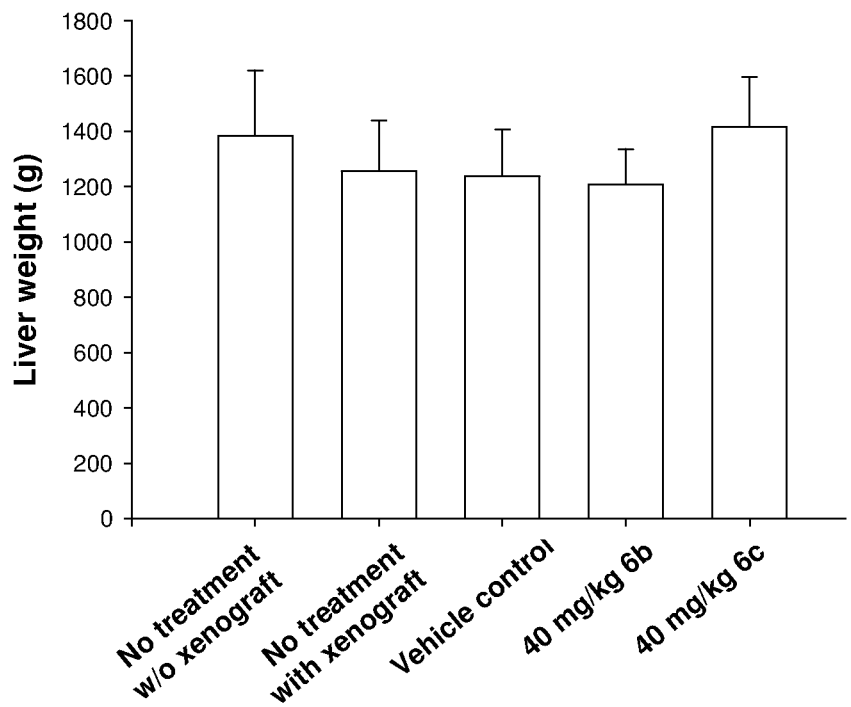
Figure 34D:
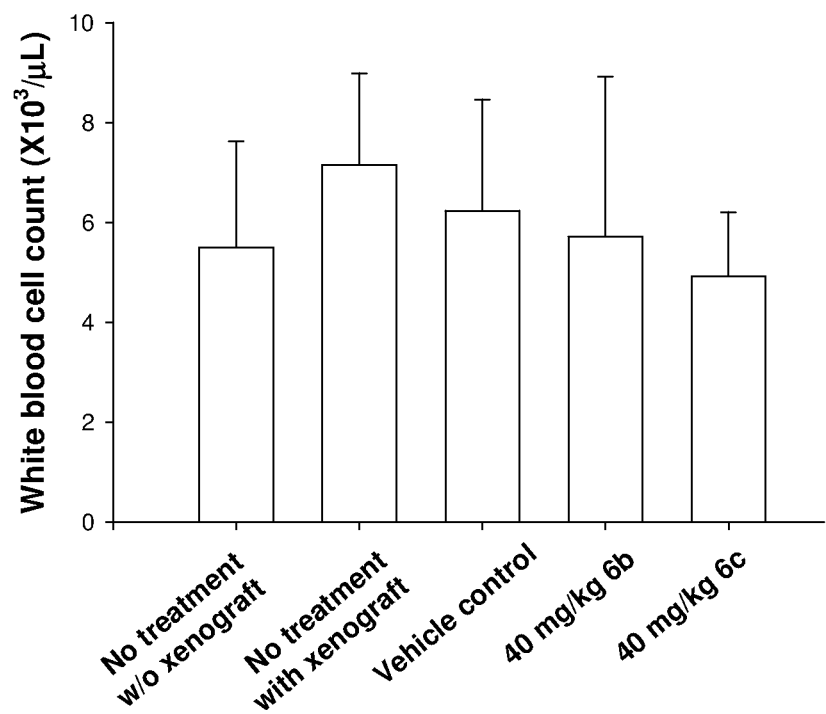

The binding modes of 12cb and 11cb (stick model) are shown in FIGS. 32A and 32B. For comparison, the crystal structure complexes of ABT-751 and DAMA-colchicine (wire models) along with ABI-12cb/tubulin complex in FIG. 32A is displayed. For clarity, only the related secondary structures forming the binding pocket in β-tubulin are shown in FIG. 32A. The overall structures of 12cb, ABT-751 and DAMA-colchicine overlapped very well in the binding pocket. Several potential hydrogen bonding interactions between compound 12cb and tubulin were identified. The carbonyl group in 12cb was in sufficient proximity to form two hydrogen bond interactions with the backbone NH of Leu-252 in H8 and the sidechain of Asp-251 in T7 of the tubulin β-monomer. The para-fluorine substituent in the C-ring was close to the sidechain of Cys241 in T7 and Tyr202 in S6, possibly forming one or two hydrogen bonds. The imidazole proton is very close and likely to form a hydrogen bond to Thr179 in T5 loop (residues 173-182) of the tubulin α-monomer (FIG. 32A). Together with the hydrophobic interactions provided by the aromatic rings, the likely formation of these hydrogen bonds would contribute to the high binding affinity to the tubulin dimer, resulting in high antiproliferative potency.

The binding mode of 11cb will be conceivably less defined since two of the three aromatic rings may occupy the binding pocket in the β-monomer while the third ring may extend toward the interface of the α/β-monomers, similar to how the sidechain of DAMA-colchicine binds. Our modeling indicates that the protecting group likely extends to the tubulin dimer interface, while the A, C rings of 11cb occupy similar binding pocket and orientation as 12cb (FIG. 32B). This may explain the similar activity between the two compounds, even though 11cb has an extra ring system. From the molecular modeling studies presented in FIGS. 32A and 32B, the hydrogen bond donor is likely to be the thiol group in Cys-241 in loop 7 of the β-subuint in α/β-tubulin dimer.

The binding mode of ABI 12fb was modeled (not shown) and compared to DAMA-colchicine (see FIG. 19 for structure of colchicine) in the α/β-tubulin heterodimer. The overall structure of 12fb and DAMA-cochicine overlapped very well. The p-fluoro phenyl moiety overlaps with the trimethoxypheny moiety which is interacting with the T7 loop in the β-subunit. Similarly, the p-chloro phenyl moiety occupies the other side of the pocket where the seven-member ring of the DAMA-cochicine is, with the chlorine atom occupying the pocket where the methoxy moiety interacts.

Example 24

Microtubule Imaging

Materials and Methods

Cellomics Cytoskeleton rearrangement kit (Thermo Scientific, Rockford, IL) was used to get a visually appreciable proof of ABIs interacting with tubulin inside the cells. WM-164 melanoma cells were treated with each compound for 18 h in duplicate using a collagen-coated 96-well plate (Becton Dickinson Labware, Bedford, MA). Then cells were fixed with 4% paraformaldehyde (Thermo Scientific, Rockford, IL) and permeabilized using permeabilization buffer supply from the kit. Primary antibody for tubulin and fluorescence-labeled secondary antibody were subsequently added to the cells. Cell nuclei were stained by DAPI. Whole Cell Stain Green was also applied to all cells. All images were acquired with an Olympus IX71 inverted fluorescence microscope (Olympus Corp., Tokyo, Japan) with overlays from separate images of tubulin (red), nuclei (blue), and whole cells (green). For comparison, paclitaxel, colchicine and ABT-751, along with ABIs are included.

Results

Visual proof of ABIs interacting with tubulin inside the cells was examined. The mictotubule arrangement in human melanoma WM-164 cells upon treatment with different compounds is presented in FIG. 33. The microtubule images clearly showed that all five tested compounds resulted in cytoskeleton rearrangement. There was a significant difference between paclitaxel and the other four compounds (colchicine, ABT-751, 12cb, and 12da). Treatment with paclitaxel resulted in a condensation of microtubules orderly lying around the nuclei compared with controls, consistent with its mechanisms of action for stabilizing microtubules. On the contrary, treatment with colchicine, ABT-751, 12cb, and 12da had similar effects on microtubules and resulted in some degree of microtubule fragmentation, consistent with their common mechanism of action for destabilizing microtubules. These results also confirmed that ABIs shared the same cellular target with colchicine and induced the same cellular effect.

Example 25

Vascular Disrupting Activity of Compounds 17Ya and 55

Method

Cells. HUVECs (Human Umbilical Vein Endothelial Cells) were cultured and grown in EGM-2 BulletKit (Lonza, Cat No. CC-3162), which contains growth supplements including hydrocortisone, human fibroblast growth factor-basic with heparin (hFGF-B), vascular endothelial growth factor (VEGF), $R_3$-insulin-like growth factor 1 (IGF-1), ascorbic acid, heparin, fetal bovine serum, human epidermal growth factor (hEGF), and GA-1000 (gentamicin and amphotericin B) in Endothelial Cell Basal Medium-2. Cells between the third and fifth passages were used for experiments. PC-3 human prostate cancer cells and T47D human breast cancer cells were cultured in RPMI-1640 medium with 5% fetal bovine serum.

Cell growth inhibition studies. Cytotoxic or antiproliferative activity of test compounds was investigated in several cell lines using the sulforhodamine B (SRB) assay. Cultured cells were plated into 96-well plates and incubated in medium containing different concentrations of the test compounds for 24 h or 48 h. Cells were stained with sulphorhodamine B (SRB) solution. The optical density was determined at 540 nm on a microplate reader (Dynex Technologies, Chantilly, VA). Plots of percent inhibition of cell growth versus drug concentration were constructed, and the concentration that inhibited cell growth by 50% relative to the vehicle control ($IC_{50}$) was determined by nonlinear least squares regression using WinNonlin software (Pharsight Corporation, Cary, NC).

Capillary formation and disruption assays. Capillary formation assays were performed in 96-well plates by plating 12,000 cells/well of HUVECs on a Matrigel layer (BD Biosciences). In order to evaluate the anti-capillary action, capillaries were allowed to form over a 16 h period before the addition of test compound or vehicle-control. In addition, capillary formation inhibitory effect of test compound was investigated by treating HUVEC cells with test compounds before capillary formation. Images were acquired immediately following compound addition, 5, 10, 15, and 25 h after exposure to test compound. Capillary formation was quantified by counting the number of tubes and nodes having at least three edges.

Endothelial monolayer permeability assay. The permeability of an endothelial cell monolayer was assessed in the transwell system. HUVECs were plated at $2 \times 10^6$ cells per insert of 24 well plate in EGM-2 medium and incubated for 72 h to reach 100% confluency. Test compounds were diluted in EGM-2 medium and added to the upper chamber of the apparatus. Following 1, 2, and 4 h of incubation, the compounds were removed and 75 μg/mL FITC-conjugated dextran (MW 40,000) was added for 5 minutes. Fluorescent measurements of the lower chamber were taken after excitation at 485 nm and emission was measured at 520 nm using a BioTek Synergy 4 Microplate Reader.

Result

Figure 35A:
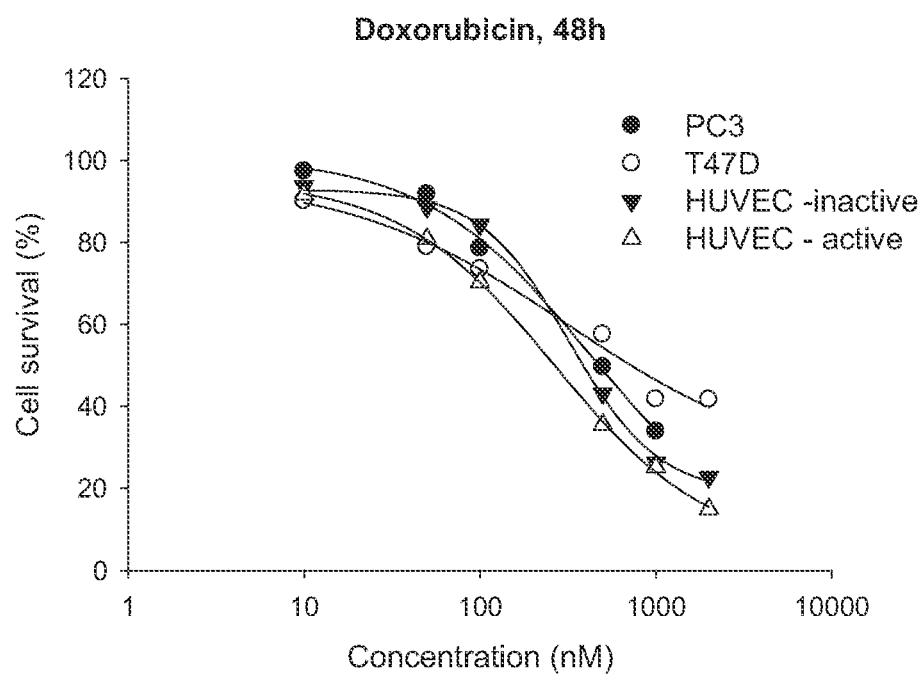
FIGS. 35A-B illustrate Compound 17ya showed potent endothelial cell growth inhibition. Cell growth inhibition of doxorubicin (FIG. 35A) and compound 17ya (FIG. 35B) was investigated in several cell lines by SRB study. The definitions HUVEC-active and HUVEC-inactive represent growth factor-supplemented and growth factor-deprived endothelial cell cultures, respectively.
Figure 35B:
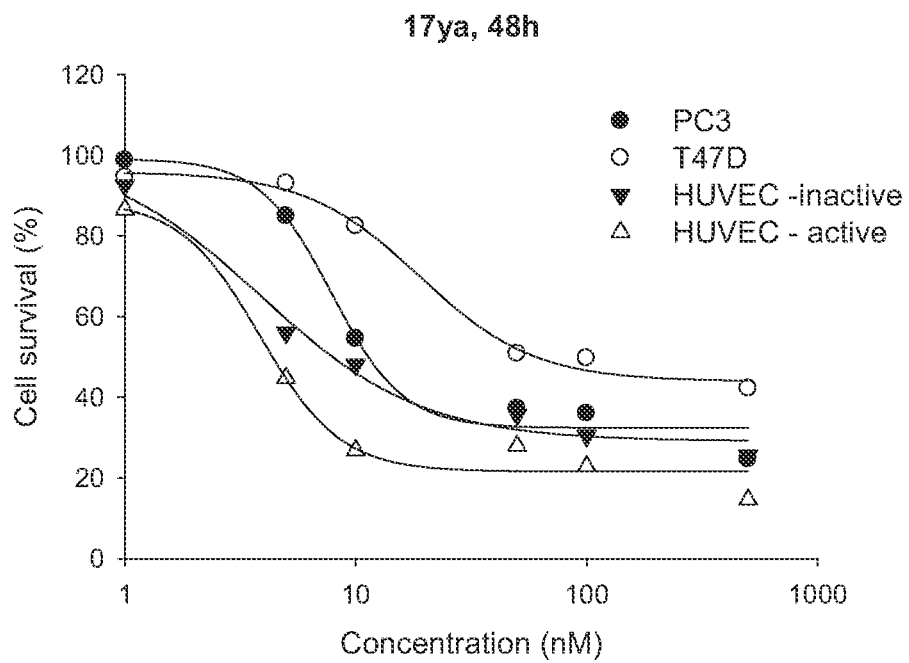
Figure 37A:
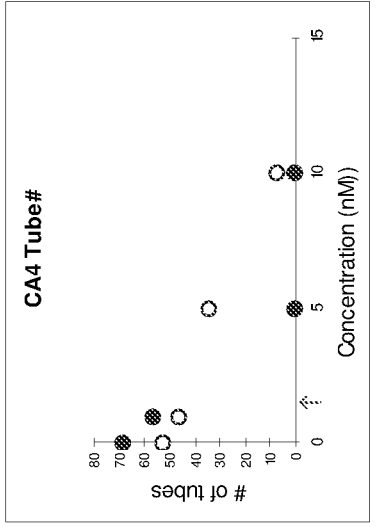
FIGS. 37A-F illustrate the inhibition of the endothelial capillary formation and disruption of preformed capillaries. Inhibition of capillary formation (●) and disruption of preformed capillary (O) were compared in vitro study using HUVEC cells after 15 h CA4 (Figure A and Figure D), DOX (Figure B and Figure E), and 17ya (Figure C and Figure F) treatment. Arrow shows the IC$_{50}$ value of each compound in HUVEC cell growth inhibition.
Figure 37B:
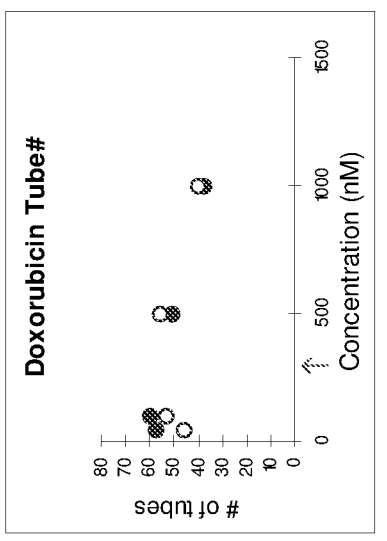
Figure 37C:
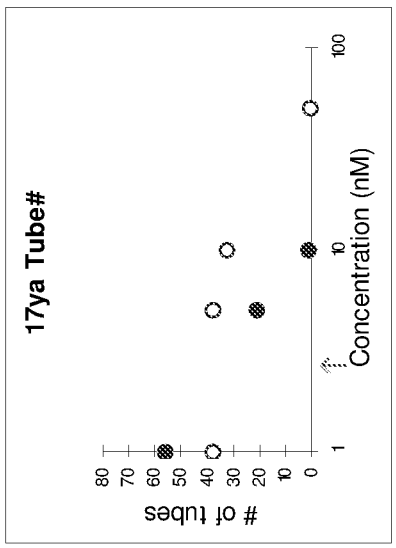
Figure 37D:
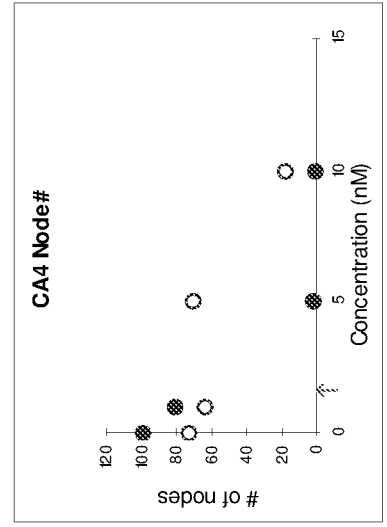
Figure 37E:
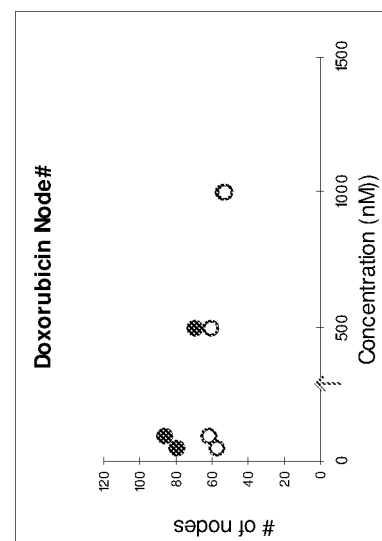
Figure 37F:
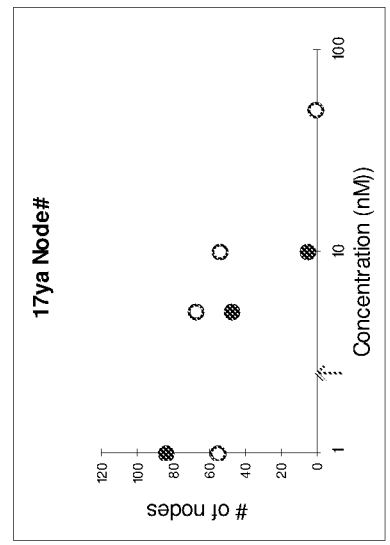

17ya and 55 exhibited high antiproliferative activity against endothelial cells. 17ya and 55 were evaluated for cytotoxic activity against growth factor-supplemented endothelial cells and growth factor-deprived endothelial cell cultures. Combretastatin A-4 (CA4) and doxorubicin were used as positive and negative control, respectively. Compound 17ya exhibited higher potency than compound 55 against actively proliferating endothelial cells (Table 24 and FIG. 35). Both 17ya and 55 exhibited selectivity for endothelial cells showing lower $IC_{50}$ values compared to one of the prostate cancer cells. CA4, 17ya and 55 were 8, 5 and 3 times more active against endothelial cells than against cancer cells, respectively, while doxorubicin was not specific to endothelial cells (Table 24 and FIG. 35). However, no selectivity was observed between quiescent and active endothelial cells with these compounds (data not shown).

TABLE 24

Endothelial cell growth inhibition of 17ya and 55. N = 3

| | CA4 | Doxorubicin |
|---|---|---|
| PC3 | 3.2 | 397.0 |
| T47D | 6.0 | 352.8 |
| HUVEC | 1.2 | 273.6 |
| Selectivity ratio*, cancer cells/HUVEC | 7.6 | 1.4 |

TABLE 24-continued

Endothelial cell growth inhibition of 17ya and 55. N = 3

| | 17ya | 55 |
|---|---|---|
| PC3 | 7.8 | 23.3 |
| T47D | 18.0 | 37.4 |
| HUVEC | 2.8 | 9.7 |
| Selectivity ratio*, cancer cells/ HUVEC | 4.6 | 3.1 |

*To obtain the selectivity ratio between cancer cells and HUVEC cells, the mean IC$_{50}$ (nM) values of test compounds in PC3 and T47D cells were used.

17ya disrupts the formation of endothelial capillaries but does not disrupt preformed capillaries. The activity of 17ya was investigated on endothelial cells engaged in capillary tube formation in vitro. Endothelial cells were placed on a Matrigel matrix and the formation and construction of capillary tubes in the presence or absence of compounds were observed (CA4, doxorubicin, and 17ya).

To avoid confusion between early stage of tube formation and disruption of tube construction, HUVEC cells on matrix in the presence of drug treatment were incubated for 15 h. Then disruption of capillary was determined by counting the number of tubes and nodes in each treatment group. On the other hand, to evaluate the effect of test compound in preformed capillaries, HUVEC cells on matrix were allowed to form capillary tube for 16 h and the capillaries were treated with test compounds.

As a result, the number of tubes and nodes was gradually decreased over time due to deficiency or consumption of nutrient by HUVEC cells (FIG. 36). This trend was observed in every drug treatment group (FIG. 36). In order to examine the difference between untreated and pretreated capillaries 15 h incubation groups were compared (FIG. 36).

Endothelial cells that were exposed to various concentrations of 17ya (0 to 50 µM) plated on Matrigel matrix resulted in inhibition of tube formation in a dose dependent manner. 17ya with approximate IC$_{50}$ value of 5 nM in cell growth inhibition studies inhibited more than 50% of tube formation compared to vehicle-control (FIG. 37). 17ya at 10 nM completely inhibited the tube formation (FIG. 37). However, in the preformed capillaries, the 10 nM 17ya treatment group did not disrupt the capillary structure by 15 h (FIG. 36). These results suggest that 17ya inhibits the formation of endothelial capillaries significantly but is less effective to disrupt preformed capillaries. Similar result was observed in CA4 treatment group (FIG. 37). However, doxorubicin did not affect the capillary construction at toxic concentration.

17ya and 55 increased the permeability of endothelial cell monolayers. Antitubulin agents could modify the integrity of endothelial cell layers lining blood vessels by targeting cytoskeleton of the endothelial cells. Thus, the vascular disruption effect of antitubulin agent is known to increase the permeability of blood vessel and thus could lead to protein leakage and high blood viscosity. This could result in reduction of blood flow, causing subsequent tumor death from hypoxia and nutrient deprivation.

Figure 38:
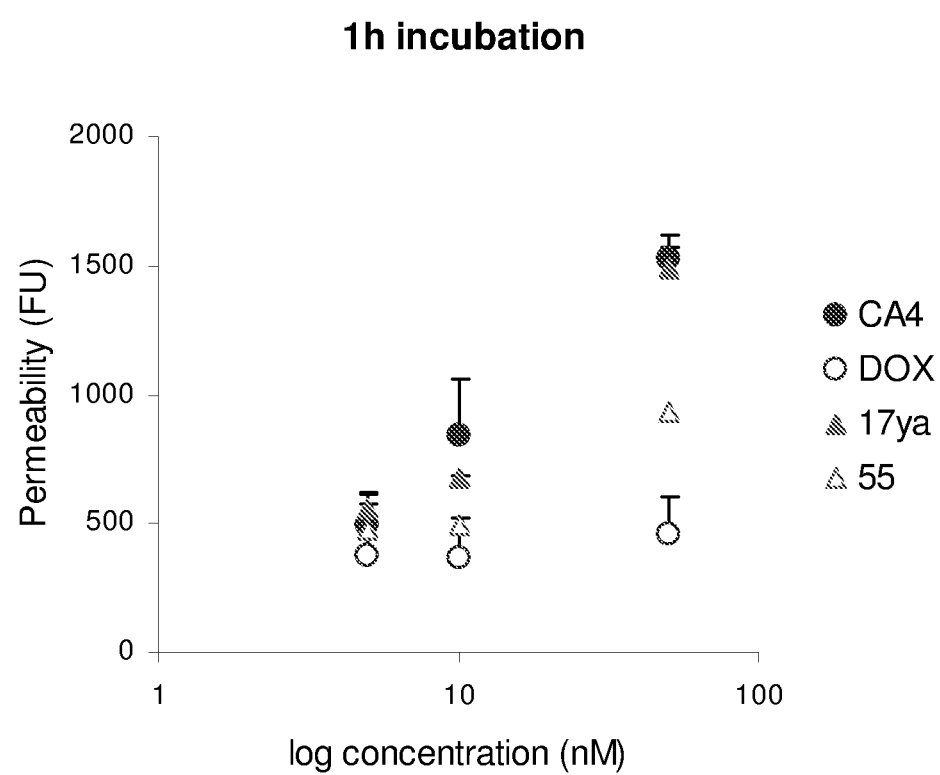

The effect of 17ya and 55 was evaluated on vascular permeability using in vitro study using transwell system with confluent HUVEC monolayers. The change in permeability by test compound was measured by the leakage of dextran (MW 40,000) after 1, 2, and 4 h of drug treatment. CA4 was used as a positive control. CA4, 17ya, and 55 resulted in increased permeability and the effect was more pronounced at 1 h incubation (data was not shown). 17ya showed a potency similar to CA4 (FIG. 38). Doxorubicin did not induce any change in the permeability of endothelial cell monolayer (FIG. 38).

Example 26

Synthesis of (benzofuranyl-1H-imidazol-4-yl)(3,4,5-trimethoxyphenyl)methanone (17ya(i)) and (benzothiophenyl-1H-imidazol-4-yl)(3,4,5-trimethoxyphenyl)methanones (17ya(ii))

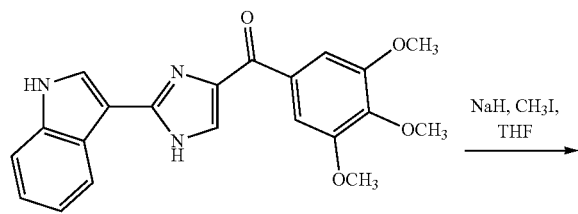

6a

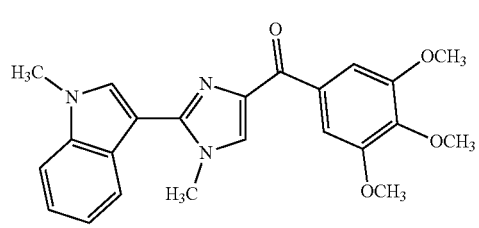

6c

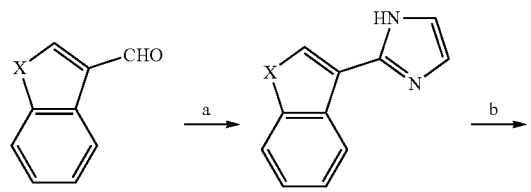

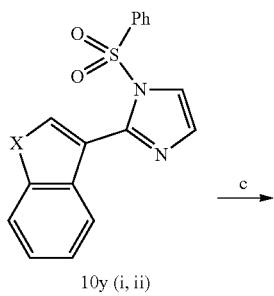

10y (i, ii)

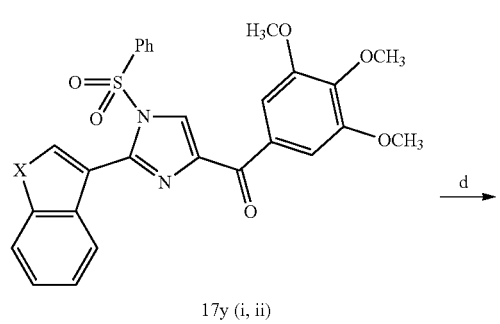

17y (i, ii)

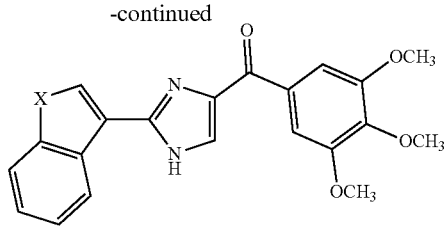

17ya (i, ii)

Reagents and conditions: (a) NH₄OH, glyoxal, ethanol, RT; (b) NaH, PhSO₂Cl, THF, 0° C.-RT; (c) t-BuLi (1.7M in Pentane), 3,4,5-trimethoxybenzoyl chloride, THF, -78° C.; (d) TBAF, THF, RT i: x = O
ii: x = S Synthesis of (2-(Benzofuran-3-yl)-1H-imidazol-4-yl)(3,4,5-trimethoxyphenyl)methanone (17ya(i)), and (2-(benzo[b]thiophen-3-yl)-1H-imidazol-4-yl)(3,4,5-trimethoxyphenyl)methanone (17ya(ii))

To a solution of compounds 10y (i, ii) (2.32 g, 5.0 mmol) in anhydrous THF (100 ml) at −78° C. was added 1.7 M tert-butyllithium in pentane (3.5 mL, 6.0 mmol) and stirred for 10 min. A solution of 3,4,5-trimethoxybenzoyl chloride (1.38 g, 6.0 mmol) in THF was added at −78° C. and stirred overnight. The reaction mixture was quenched with 100 ml of saturated NaHCO₃ solution (aqueous) and extracted by ethyl acetate (300 ml). The organic layer was dried over magnesium sulfate and concentrated. The residue was used for next step by adding 10 mL of 1.0 M tetrabutyl ammonium fluoride and stirred overnight. The reaction mixture was diluted by 200 ml of saturated NaHCO₃ solution (aqueous) and extracted by ethyl acetate (200 ml). The organic layer was dried over magnesium sulfate and concentrated. The residue was purified by flash column chromatography (hexane:ethyl acetate 3:1) to give a white solid. 17ya (i): 4.7% yield. Mp 208-210° C. $^1$H NMR (CDCl₃, 500 MHz) δ 8.77 (s, 1H), 8.12 (d, J=7.6 Hz, 1H), 7.90 (s, 1H), 7.632-7.65 (m, 1H), 7.44-7.49 (m, 2H), 7.29 (s, 2H), 3.99 (s, 3H), 3.93 (s, 6H). MS (ESI) calcd for $C_{21}H_{18}N_2O_5$ 378.1, found 377.1[M−H]⁻. HPLC1: $t_R$ 5.18 min, purity 98.8%. 17ya(ii): 3.2% yield. Mp 185-187° C. $^1$H NMR (CDCl₃, 500 MHz) δ 10.62 (s, 1H), 8.74 (d, J=5.0 Hz, 1H), 8.06 (s, 1H), 7.92-7.95 (m, 2H), 7.48-7.54 (m, 2H), 7.29 (s, 2H), 3.99 (s, 3H), 3.97 (s, 6H). MS (ESI) calcd for $C_{21}H_{18}N_2O_4S$ 394.1, found 392.8[M−H]⁻. HPLC: $t_R$ 5.38 min, purity 95.6%.

Example 27

Synthesis of Aryl Benzoyl Imidazole

Figure 40:
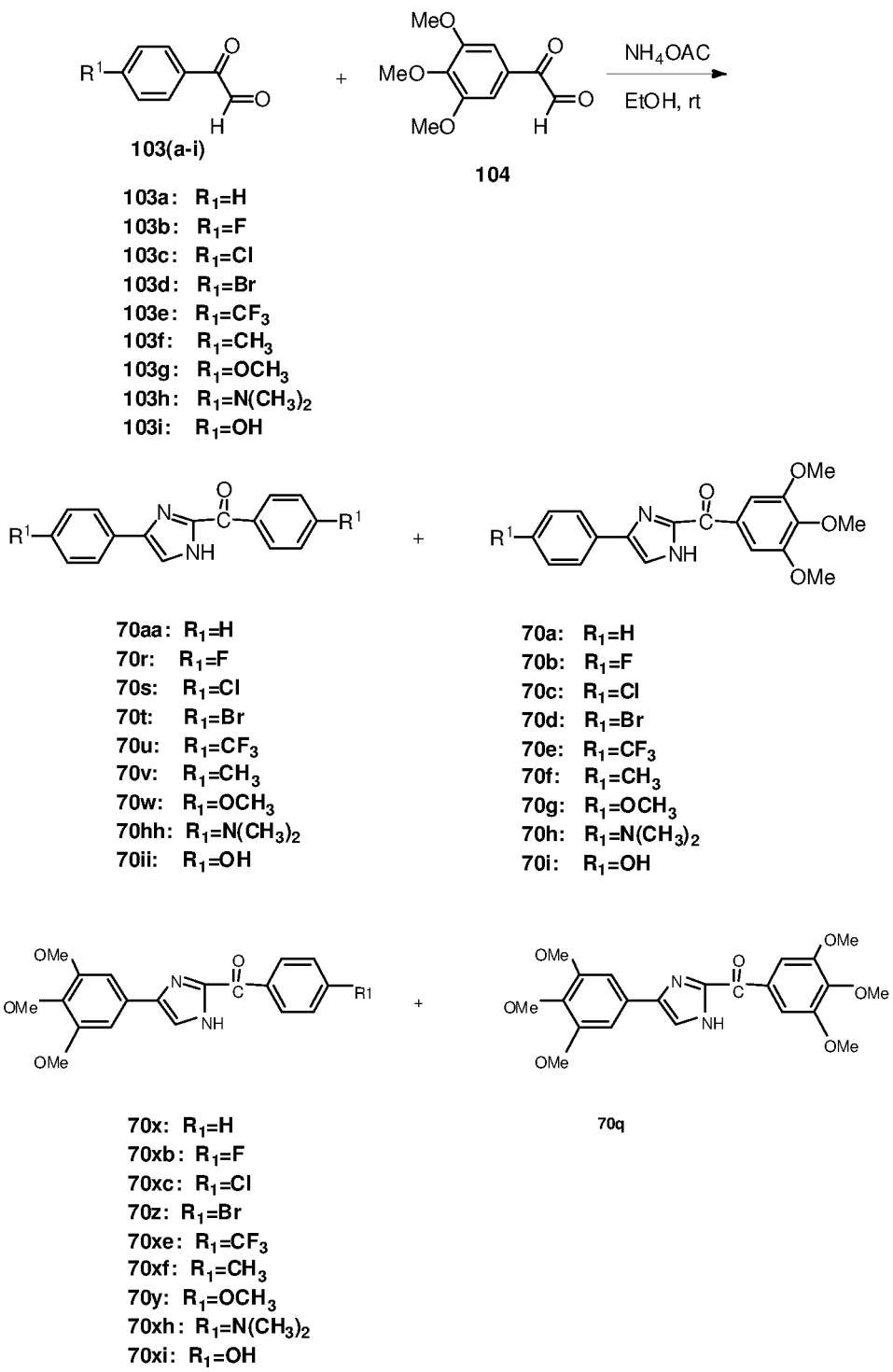
FIG. 40 depicts a synthetic scheme of aryl benzoyl imidazole compounds of this invention.

General Procedure for the Preparation of (4 or 5)-aryl-2-aryloyl-(1H)-Imidazole derivatives (FIG. 40)

To ammonium acetate (10 mmol) in ethanol (5 mL) and water (0.3 ml) was added arylglyoxal hydrate 103 (1 mmol) in ethanol (5 ml) and 3,4,5-trimethoxyphenyl glyoxal hydrate 104 (1 mmol) in ethanol (10 ml). The mixture was stirred at room temperature for 30-45 min. The reaction was stopped after the consumption of the starting material monitored by TLC. The mixture was then extracted with ethyl acetate. The organic layer was washed with brine, dried over anhydrous sodium sulfate and concentrated to get the crude product. The crude was purified by flash chromatography. (The two IUPAC names given below correspond to freely interconverting tautomers, not unresolved mixtures.)

Phenyl-(4-phenyl-1H-imidazol-2-yl)methanone and phenyl-(5-phenyl-1H-imidazol-2-yl)methanone (70aa): $^1$H NMR (500 MHz, DMSO-$d_6$): δ 13.80 (s, 0.25H), 13.63 (s, 1H), 8.60 (d, J=7.76 Hz, 2H), 8.47 (d, J=7.7 Hz, 0.5H,), 8.08 (s, 1H,), 7.97 (d, J=7.95 Hz, 0.5H), 7.94 (d, J=7.64 Hz, 2H), 7.79(s, 0.25H), 7.69 (t, J=7.1 Hz, 1H), 7.66 (t, J=7.6 Hz, 0.25H), 7.60 (t, J=7.6 Hz, 2H), 7.57 (t, J=8.1 Hz, 0.5H), 7.47 (t, J=7.55 Hz, 0.5H), 7.42 (t, J=7.7 Hz, 2H), 7.37 (t, J=7.1 Hz, 0.25H), 7.28 (t, J=7.3 Hz, 1H).

(4-Fluorophenyl)(4-(4-fluorophenyl)-1H-imidazol-2-yl)methanone and (4-fluorophenyl)(5-(4-fluorophenyl)-1H-imidazol-2-yl)methanone (70r): $^1$H NMR (400 MHz, chloroform-d) δ 10.68 (s, 1H), 10.52 (s, 1H), 8.93-8.82 (dd, J=5.89, 8.64 Hz, 2H), 8.72 (dd, J=5.60, 8.70 Hz, 0.39H), 7.89 (dd, J=5.39, 8.72 Hz, 2H), 7.63 (dd, J=5.05, 8.25 Hz, 0.46H), 7.59 (d, J=2.2 Hz, 0.29H), 7.55 (d, J=2.8 Hz, 1H) 7.25-7.20 (m, 2H), 7.20-7.13 (m, 2H).

(4-Chlorophenyl)(4-(4-chlorophenyl)-1H-imidazol-2-yl)methanone and (4-chlorophenyl)(5-(4-chlorophenyl)-1H-imidazol-2-yl)methanone (70s): $^1$H NMR (400 MHz, chloroform-d) δ 10.70 (s, 0.65H), 10.55 (s, 1H), 8.78 (d, J=8.65 Hz, 2H), 8.63 (s, 1H), 7.87 (s, 2H), 7.66-7.52 (m, 5H), 7.50-7.39 (m, 2H).

4-Bromophenyl-(4-(4-bromophenyl)-1H-imidazol-2-yl)ketone and 4-bromophenyl-(5-(4-bromophenyl)-1H-imidazol-2-yl)methanone (70t): $^1$H NMR (500 MHz, DMSO-$d_6$) δ 13.91(s, 0.16H), 13.73 (s, 1H), 8.51 (d, J=8.4 Hz, 2H), 8.42 (d, J=8.3 Hz, 0.32H), 8.16 (s, 1H), 7.93 (d, J=8.15 Hz, 0.32H), 7.89 (d, J=8.35 Hz, 2H), 7.83 (d, J=8.45 Hz, 2H), 7.80 (d, J=8.4 Hz, 0.32H), 7.79 (s, 0.16H), 7.67(d, J=8.05 Hz, 0.32H), 7.62 (d, J=8.35 Hz, 2H,).

p-Tolyl(4-p-tolyl-1H-imidazol-2-yl)methanone and p-tolyl(5-p-tolyl-1H-imidazol-2-yl)methanone (70v): $^1$H NMR (400 MHz, chloroform-d) δ 10.96 (s, 1H), 10.73 (s, 1H), 8.71 (d, J=8.26 Hz, 2H), 8.54 (d, J=8.23 Hz, 2H), 7.82 (d, J=8.11 Hz, 2H), 7.67-7.49 (m, 4H), 7.37 (t, J=7.62, 7.62 Hz, 4H), 7.30 (s, 1H), 7.28 (s, 2H), 7.26 (s, 1H), 2.49 (d, J=4.52 Hz, 6H), 2.42 (d, J=4.95 Hz, 6H).

(4-(Trifluoromethyl)phenyl)(4-(4-(trifluoromethyl)phenyl)-1H-imidazol-2-yl)methanone and (4-(trifluoromethyl)phenyl)(5-(4-(trifluoromethyl)phenyl)-1H-imidazol-2-yl)methanone (70u): $^1$H NMR (400 MHz, chloroform-d) δ 10.83 (s, 0.38H), 10.60 (s, 1H), 8.78 (d, J=8.19 Hz, 2H), 8.64 (d, J=8.13 Hz, 0.48H), 7.93 (d, J=8.34 Hz, 2H), 7.76 (d, J=8.56 Hz, 2H), 7.66-7.59 (m, 3H).

(4-Methoxyphenyl)(4-(4-methoxyphenyl)-1H-imidazol-2-yl)methanone and (4-methoxyphenyl)(5-(4-methoxyphenyl)-1H-imidazol-2-yl)methanone (70w): $^1$H NMR (400 MHz, chloroform-d) δ 10.50 (s, 1H), 10.38 (s, 1H), 8.77 (d, J=8.90 Hz, 2H), 8.60 (d, J=8.89 Hz, 2H), 7.77 (s, 1H), 7.75 (s, 1H), 7.48 (d, J=8.75 Hz, 1H), 7.45-7.36 (m, 2H), 7.03-6.87 (m, 5H), 3.86 (s, 2H), 3.85 (s, 2H), 3.84 (s, 2H), 3.80 (s, 2H), 3.79 (s, 2H).

(4-(Dimethylamino)phenyl)(4-(4-(dimethylamino)phenyl)-1H-imidazol-2-yl)methanone and (4-(dimethylamino)phenyl)(5-(4-(dimethylamino)phenyl)-1H-imidazol-2-yl)methanone (70hh): $^1$H NMR (500 MHz, DMSO-$d_6$) δ 13.17 (s, 0.35H), 13.12 (s, 1H), 8.64 (d, J=8.95 Hz, 2H), 8.50 (d, J=8.95 Hz, 1H), 7.80-7.69 (m, 4H), 7.50 (s, 1H), 6.82 (d, J=8.99 Hz, 2H), 6.76 (d, J=7.70, 7.70 Hz, 5H), 3.07 (s, 6H), 3.05 (s, 4H), 2.95 (s, 4H), 2.93 (s, 6H).

(4-Hydroxyphenyl)(4-(4-hydroxyphenyl)-1H-imidazol-2-yl)methanone and (4-hydroxyphenyl)(5-(4-hydroxyphenyl)-1H-imidazol-2-yl)methanone (70ii): $^1$H NMR (500 MHz, DMSO-$d_6$) δ 13.37 (s, 0.37H), 13.29 (s, 1H), 10.39 (s, 1H), 9.46 (s, 1H), 8.60 (d, J=7.88 Hz, 3H), 8.47 (s, 1H), 7.79 (s, 2H), 7.73 (d, J=7.48 Hz, 4H), 7.55 (s, 1H), 6.92 (d, J=8.02 Hz, 4H), 6.81 (d, J=8.03 Hz, 4H).

(4-Phenyl-1H-imidazol-2-yl)(3,4,5-trimethoxyphenyl)methanone and (5-phenyl-1H-imidazol-2-yl)(3,4,5-trimethoxyphenyl)methanone (70a): $^1$H NMR (400 MHz, chloroform-d) δ 10.63 (s, 0.48H), 10.47 (s, 1H), 8.19 (s, 2H), 7.98 (s, 1H), 7.82 (t, J=1.67, 1.67 Hz, 1H), 7.81 (t, J=1.11, 1.11 Hz, 1H), 7.60-7.53 (m, 11H), 7.51 (d, J=1.97 Hz, 11H), 7.46-7.30 (m, 3H), 7.29-7.22 (m, 11H), 3.95 (s, 5H), 3.91 (s, 3H), 3.91 (s, 3H), 3.89 (s, 11H).

(4-(4-Fluorophenyl)-1H-imidazol-2-yl)(3,4,5-trimethoxyphenyl)methanone and (5-(4-fluorophenyl)-1H-imidazol-2-yl)(3,4,5-trimethoxyphenyl)methanone (70b). $^1$H NMR (400 MHz, chloroform-d) δ 10.60 (s, 0.30H), 10.46 (s, 11H), 8.15 (s, 2H), 7.97 (s, 11H), 7.77 (dd, J=5.35, 8.90 Hz, 2H), 7.58-7.50 (dd, J=5.10, 8.20 Hz, 0.47H), 7.48 (s, 0.46H), 7.46 (s, 1H), 7.45 (s, 1H), 7.10-7.02 (m, 2H), 3.94 (s, 6H), 3.92 (s, 3H), 3.91 (s, 2H), 3.89 (s, 1H).

(4-(4-Chlorophenyl)-1H-imidazol-2-yl)(3,4,5-trimethoxyphenyl)methanone and (5-(4-chlorophenyl)-1H-imidazol-2-yl)(3,4,5-trimethoxyphenyl)methanone (70c): $^1$H NMR (400 MHz, chloroform-d) δ 10.57 (s, 0.33H), 10.45 (s, 1H), 8.15 (s, 2H), 7.97 (s, 0.49H), 7.81-7.68 (m, 2H), 7.51-7.47 (m, 1H), 7.36-7.30 (m, 2H), 3.94 (s, 6H), 3.91 (s, 3H), 3.89 (s, 0.75H).

(4-(4-Bromophenyl)-1H-imidazol-2-yl)(3,4,5-trimethoxyphenyl)methanone and (5-(4-bromophenyl)-1H-imidazol-2-yl)(3,4,5-trimethoxyphenyl)methanone (70d): $^1$H NMR (400 MHz, chloroform-d) δ 10.77 (s, 0.36H), 10.59 (s, 1H), 8.24 (s, 2H), 8.06 (s, 1H), 7.78 (d, J=1.86 Hz, 1H), 7.76 (d, J=1.98 Hz, 11H), 7.69-7.47 (m, 4H), 4.03 (s, 6H), 4.01 (s, 3H), 4.00 (s, 2H), 3.99 (s, 1H).

(4-p-Tolyl-1H-imidazol-2-yl)(3,4,5-trimethoxyphenyl)methanone and (5-p-tolyl-1H-imidazol-2-yl)(3,4,5-trimethoxyphenyl)methanone (70f): $^1$H NMR (400 MHz, chloroform-d) δ 10.57 (s, 0.77H), 10.44 (s, 1H), 8.18 (s, 2H), 7.96 (s, 1H), 7.71 (d, J=1.87 Hz, 1H), 7.69 (d, J=1.88 Hz, 1H), 7.47 (d, J=2.44 Hz, 2H), 7.22 (s, 1H), 7.16 (s, 1H), 3.94 (s, 6H), 3.92 (s, 3H), 3.90 (s, 3H), 3.89 (s, 2H).

(4-(4-(Trifluoromethyl)phenyl)-1H-imidazol-2-yl)(3,4,5-trimethoxyphenyl)methanone and (5-(4-(trifluoromethyl)phenyl)-1H-imidazol-2-yl)(3,4,5trimethoxyphenyl)methanone (70e): $^1$H NMR (400 MHz, chloroform-d) δ 10.90 (s, 0.16H), 10.67 (s, 1H), 8.26 (s, 2H), 8.08 (s, 0.36H), 8.01 (d, J=7.30 Hz, 2H), 7.80-7.88 (m, 0.79H), 7.76-7.62 (m, 3H), 4.08-3.95 (m, 111H).

(4-(4-Methoxyphenyl)-1H-imidazol-2-yl)(3,4,5-trimethoxyphenyl)methanone and (5-(4-methoxyphenyl)-1H-imidazol-2-yl)(3,4,5-trimethoxyphenyl)methanone (70g): $^1$H NMR (400 MHz, chloroform-d) δ 10.60 (s, 11H), 10.50 (s, 11H), 8.27 (s, 2H), 8.05 (s, 11H), 7.84 (s, 11H), 7.82 (s, 11H), 7.59 (d, J=8.87 Hz, 11H), 7.54 (d, J=1.90 Hz, 11H), 7.51 (d, J=2.31 Hz, 11H), 7.05-6.97 (m, 4H), 4.04 (s, 5H), 4.01 (s, 3H), 4.00 (s, 3H), 3.98 (s, 2H), 3.89 (s, 2H), 3.88 (s, 3H).

(4-(4-(Dimethylamino)phenyl)-1H-imidazol-2-yl)(3,4,5-trimethoxyphenyl)methanone and (5-(4-(dimethylamino)phenyl)-1H-imidazol-2-yl)(3,4,5-trimethoxyphenyl)methanone (70h): $^1$H NMR (500 MHz, chloroform-d) δ 10.67 (s, 1H), 10.54 (s, 0.49H), 8.28 (s, 1H), 8.03 (s, 2H), 7.78 (s, 1H), 7.76 (s, 1H), 7.53 (d, J=8.79 Hz, 2H), 7.50 (d, J=1.56 Hz, 1H), 6.78 (m, 4H), 4.03 (s, 4H), 3.99 (s, 8H), 3.97 (s, 3H), 3.04 (s, 6H), 3.02 (s, 4H).

(4-(4-Hydroxyphenyl)-1H-imidazol-2-yl)(3,4,5-trimethoxyphenyl)methanone and (5-(4-hydroxyphenyl)-1H-imidazol-2-yl)(3,4,5-trimethoxyphenyl)methanone) (70i): $^1$H NMR (500 MHz, chloroform-d) δ 11.19 (s, 1H), 10.75 (s, 1H), 8.23 (s, 2H), 7.98 (s, 2H), 7.77 (s, 1H), 7.75 (s, 1H), 7.54 (d, J=5.13 Hz, 3H), 7.49 (s, 1H), 6.90 (t, J=9.24, 9.24 Hz, 4H), 4.01 (s, 6H), 3.99 (s, 3H), 3.97 (s, 5H), 3.96 (s, 3H).

Phenyl(4-(3,4,5-trimethoxyphenyl)-1H-imidazol-2-yl)methanone and phenyl(5-(3,4,5-trimethoxyphenyl)-1H-imidazol-2-yl)methanone (70x): $^1$H NMR (400 MHz, chloroform-d) δ 10.67 (s, 0.69H), 10.51 (s, 1H), 8.74-8.61 (m, 2H), 8.56-8.43 (m, 11H), 7.63-7.54 (m, 1H), 7.53-7.43 (m, 4H), 7.04 (s, 2H), 6.75 (s, 1H), 3.89 (s, 6H), 3.89 (s, 3H), 3.83 (s, 1H), 3.82 (s, 2H).

4-Methoxyphenyl(4-(3,4,5-trimethoxyphenyl)-1H-imidazol-2-yl)methanone and 4-methoxyphenyl(5-(3,4,5-trimethoxyphenyl)-1H-imidazol-2-yl)methanone (70y): $^1$H NMR (400 MHz, chloroform-d) δ 10.79 (s, 1H), 10.66 (s, 1H), 8.83 (d, J=8.96 Hz, 2H), 8.70 (d, J=8.92 Hz, 11H), 7.56 (d, J=1.72 Hz, 11H), 7.53 (d, J=2.25 Hz, 11H), 7.14 (s, 2H), 7.06 (d, J=3.68 Hz, 1H), 7.04 (d, J=3.51 Hz, 1H), 6.83 (s, 1H), 3.99 (s, 5H), 3.96 (s, 4H), 3.95 (s, 3H), 3.94 (s, 2H), 3.92 (s, 2H), 3.91 (s, 2H).

4-Bromophenyl(4-(3,4,5-trimethoxyphenyl)-1H-imidazol-2-yl)methanone and 4-bromophenyl(5-(3,4,5-trimethoxyphenyl)-1H-imidazol-2-yl)methanone (70z): $^1$H NMR (400 MHz, chloroform-d) δ 10.66 (s, 0.54H), 10.57 (s, 1H), 8.68-8.63 (m, 2H), 8.56-8.51 (m, 1H), 7.80-7.75 (m, 1H), 7.73-7.69 (m, 2H), 7.61-7.55 (m, 2H), 7.12 (s, 2H), 6.82 (s, 1H), 4.02 (s, 3H), 3.98 (s, 6H), 3.93 (s, 1H), 3.92 (s, 2H).

3,4,5-Trimethoxyphenyl-(4-(3,4,5-trimethoxyphenyl)-1H-imidazol-2-yl)methanone and 3,4,5-trimethoxyphenyl-(5-(3,4,5-trimethoxyphenyl)-1H-imidazol-2-yl)methanone (70q)$^1$H NMR (400 MHz, chloroform-d) δ 10.76 (s, 0.40H), 10.61 (s, 1H), 8.20 (s, 2H), 7.95 (s, 11H), 7.48 (d, J=1.90 Hz, 0.40H), 7.47 (d, J=2.34 Hz, 11H), 7.06 (s, 2H), 6.75 (s, 1H), 3.93 (s, 5H), 3.91 (d, J=0.84 Hz, 4H), 3.89 (s, 1H), 3.87 (s, 2H), 3.86 (s, 5H) 3.83 (s, 1H), 3.82 (s, 2H).

Example 28

Synthesis of Aryl Benzoyl Imidazole

General Procedure for the Preparation of (4 or 5)-aryl-2-aryloyl-(1H)-Imidazole derivatives 70m, 70n and 70o

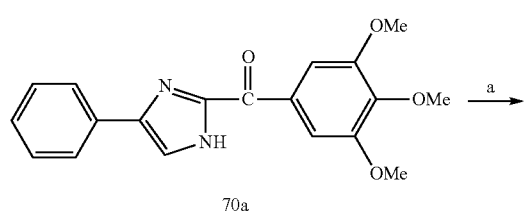

70a

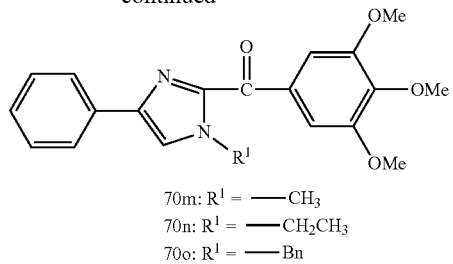

70m: R$^1$ = —CH$_3$
70n: R$^1$ = —CH$_2$CH$_3$
70o: R$^1$ = —Bn

Reagents and conditions: (a) NaH, CH$_3$I for 70m, CH$_3$CH$_2$Br for 70n and BnBr for 70o To a solution of 70a (135 mg, 0.4 mmol) in THF (10 mL) in ice-bath was added sodium hydride (60% dispersion in mineral oil, 28 mg, 0.60 mmol) followed by adding methyl iodide (85 mg, 0.60 mmol) (for 70m) or ethyl iodide (93 mg, 0.60 mmol) (for 70n) or benzyl bromide (102 mg, 0.60 mmol) (for 70o). The resulting reaction mixture was stirred overnight under reflux condition. After dilution by 50 ml of saturated NaHCO$_3$ solution (aqueous), the reaction mixture was extracted by ethyl acetate (100 ml). The organic layer was dried over magnesium sulfate and concentrated. The residue was purified by flash column chromatography.

(1-Methyl-4-phenyl-1H-imidazol-2-yl)(3,4,5-trimethoxyphenyl)methanone (70m): $^1$H NMR (500 MHz, chloroform-d) δ 7.97 (d, J=2.38 Hz, 2H), 7.85 (d, J=6.01 Hz, 2H), 7.46-7.39 (m, 3H), 7.28 (d, J=2.39 Hz, 1H), 4.16-4.10 (m, 3H), 3.99 (d, J=2.82 Hz, 9H).

(1-Ethyl-4-phenyl-1H-imidazol-2-yl)(3,4,5-trimethoxyphenyl)methanone (70n): $^1$H NMR (400 MHz, chloroform-d) δ 7.95 (s, 2H), 7.89-7.83 (m, 2H), 7.51 (s, 1H), 7.43 (t, J=7.61, 7.61 Hz, 2H), 7.36-7.31 (m, 1H), 4.56 (q, J=7.19, 7.19, 7.19 Hz, 2H), 3.99 (s, 6H), 3.98 (s, 3H), 1.30 (t, J=7.19, 7.19 Hz, 3H).

(1-Benzyl-4-phenyl-1H-imidazol-2-yl)(3,4,5-trimethoxyphenyl)methanone (70o):1H NMR (500 MHz, chloroform-d) δ 7.94 (d, J=1.70 Hz, 2H), 7.84 (d, J=7.73 Hz, 2H), 7.47-7.28 (m, 9H), 5.74 (s, 2H), 3.98 (s, 9H).

Synthesis of Compound 105

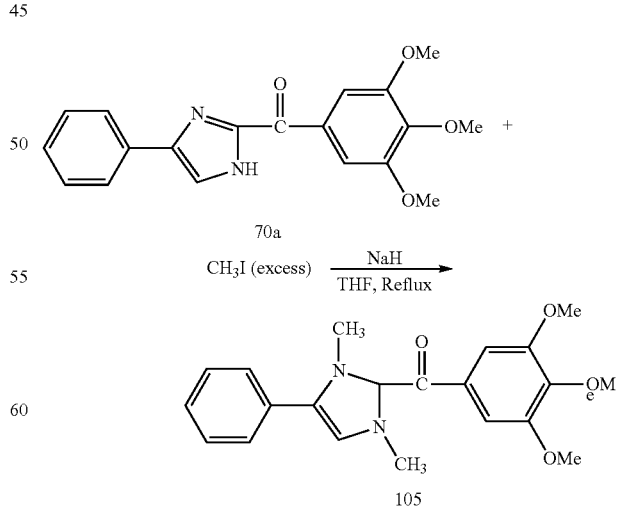

To a solution of 70a (135 mg, 0.4 mmol) in THF (10 mL) in ice-bath was added sodium hydride (60% dispersion in mineral oil, 28 mg, 0.60 mmol) followed by adding excessive methyl iodide. The resulting reaction mixture was stirred overnight under reflux condition. After dilution by 50 ml of saturated NaHCO$_3$ solution (aqueous), the reaction mixture was extracted by ethyl acetate (100 ml). The organic layer was dried over magnesium sulfate and concentrated. The residue was purified by flash column chromatography.

(1,3-Dimethyl-4-phenyl-2,3-dihydro-1H-imidazol-2-yl)(3,4,5-trimethoxyphenyl)methanone (105): $^1$H NMR (400 MHz, chloroform-d) δ 7.78-7.62 (m, 2H), 7.39-7.25 (m, 3H), 7.06 (s, 11H), 6.55 (d, J=0.78 Hz, 2H), 5.55 (s, 11H), 3.75 (d, J=9.74 Hz, 9H), 3.41 (d, J=1.10 Hz, 6H).

In vitro growth inhibitory effects (IC$_{50}$ (nM)) of compound 105 of LNCaP is 4235 nM; of PC3 is 3487 nM and of PPC1 is 5294 nM.

Example 29

Synthesis of Aryl Benzoyl Imidazole

Figure 41:
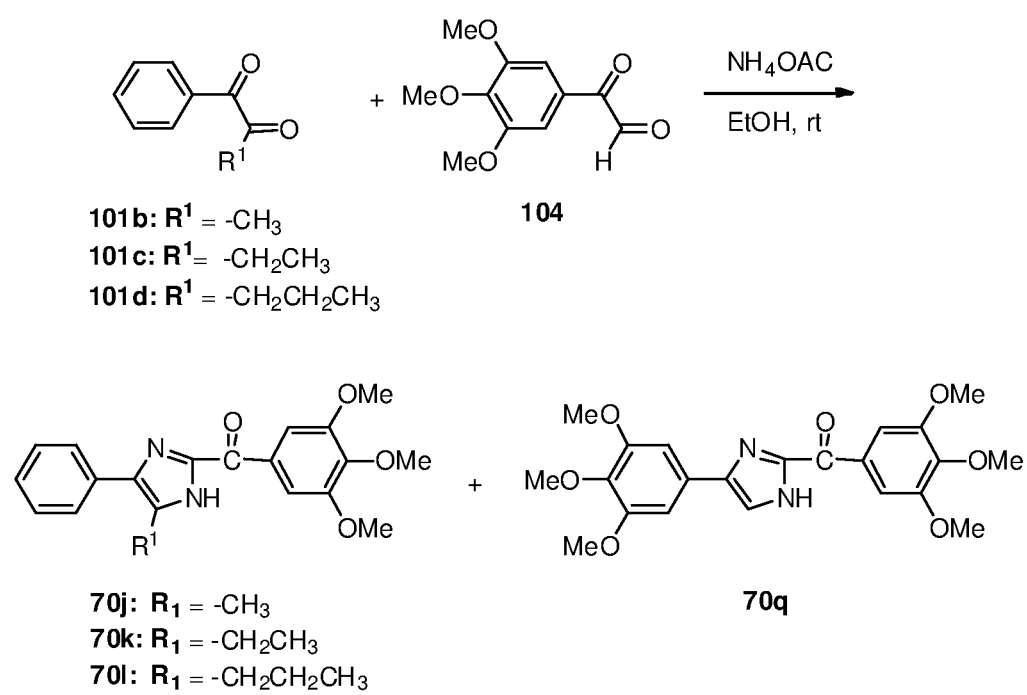
FIG. 41 depicts a synthetic scheme of aryl benzoyl substituted-imidazole compounds of this invention.

General Procedure for the Preparation of (4 or 5)-alkyl-(5 or 4)-aryl-2-aryloyl-(1H)-Imidazole derivatives (70j, 70k, 70l) (FIG. 41)

To ammonium acetate (10 mmol) in ethanol (5 ml) and water (0.3 ml) was added phenyl alkyl diones 101 (b-d) (1 mmol) in ethanol (5 ml) and 3,4,5-trimethoxyphenyl glyoxal hydrate 104 (1 mmol) in ethanol (10 ml). The mixture was stirred at room temperature for 30-45 min. The reaction was stopped after the consumption of the starting material monitored by TLC. The mixture was then extracted with ethyl acetate. The organic layer was washed with brine, dried over anhydrous sodium sulfate and concentrated to get the crude product. The crude was purified by flash chromatography.

(5-Methyl-4-phenyl-1H-imidazol-2-yl)(3,4,5-trimethoxyphenyl)methanone and (4-methyl-5-phenyl-1H-imidazol-2-yl)(3,4,5-trimethoxyphenyl)methanone (70j): $^1$H NMR (400 MHz, chloroform-d) δ 10.43 (s, 0.59H), 10.32 (s, 1H), 8.24 (s, 2H), 8.05 (s, 1H), 7.87-7.71 (m, 3H), 7.62-7.38 (m, 6H), 4.02 (s, 5H), 4.01 (s, 3H), 3.99 (s, 2H), 3.98 (s, 3H), 3.95 (s, 2H), 2.64 (s, 3H), 2.56 (s, 1H).

(5-Ethyl-4-phenyl-1H-imidazol-2-yl)(3,4,5-trimethoxyphenyl)methanone and (4-ethyl-5-phenyl-1H-imidazol-2-yl)(3,4,5-trimethoxyphenyl)methanone (70k): $^1$H NMR (400 MHz, chloroform-d) δ 10.85 (s, 1H), 8.28 (s, 2H), 8.15 (s, 1H), 7.75 (m, 1H), 7.45-7.30 (m, 5H), 4.00 (m, 9H), 3.05 (m, 2H), 1.40 (m, 3H).

(4-Phenyl-5-propyl-1H-imidazol-2-yl)(3,4,5-trimethoxyphenyl)methanone and (5-phenyl-4-propyl-1H-imidazol-2-yl)(3,4,5-trimethoxyphenyl)methanone (70l): $^1$H NMR (400 MHz, chloroform-d) δ 10.52 (s, 0.52H), 10.47 (s, 1H), 8.24 (s, 2H), 8.14 (s, 1H), 7.78 (d, J=7.39 Hz, 2H), 7.60-7.43 (m, 5H), 7.36 (t, J=7.40, 7.40 Hz, 1H), 4.01 (s, 5H), 4.00 (s, 3H), 3.99 (s, 4H), 3.00-2.93 (t, J=7.40, 7.40 Hz, 2H), 2.84 (t, J=7.50, 7.50 Hz, 1H), 1.94-1.87 (m, 1H), 1.87-1.78 (m, 2H), 1.07 (t, J=7.33, 7.33 Hz, 3H), 0.98-0.92 (t, J=7.10, 7.10 Hz, 1H).

Synthesis of Compound 70p

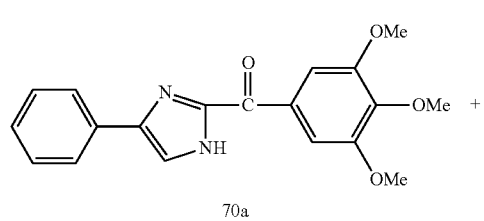

70a

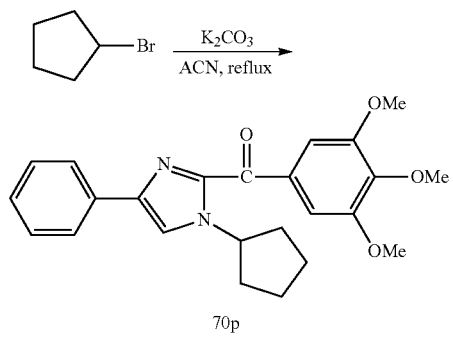

70p

To a solution of 70a (135 mg, 0.4 mmol) in ACN (10 mL) was added potassium carbonate (82 mg, 0.60 mmol) followed by cyclopentyl bromide (72 mg, 0.48 mmol). The resulting reaction mixture was stirred overnight under reflux condition. After dilution by 50 ml of saturated NaHCO$_3$ solution (aqueous), the reaction mixture was extracted by ethyl acetate (100 ml). The organic layer was dried over magnesium sulfate and concentrated. The residue was purified by flash column chromatography.

(1-cyclopentyl-4-phenyl-1H-imidazol-2-yl)(3,4,5-trimethoxyphenyl)methanone (70p): $^1$H NMR (500 MHz, chloroform-d) δ 7.90-7.82 (m, 4H), 7.61 (d, J=1.7 Hz, 1H), 7.42 (td, J=7.7, 1.7 Hz, 2H), 7.33-7.28 (m, 1H), 5.88-5.32 (m, 1H), 3.98 (t, J=1.9 Hz, 9H), 2.64-2.20 (m, 2H), 2.00-1.77 (m, 6H).

Synthesis of Compound 70ab

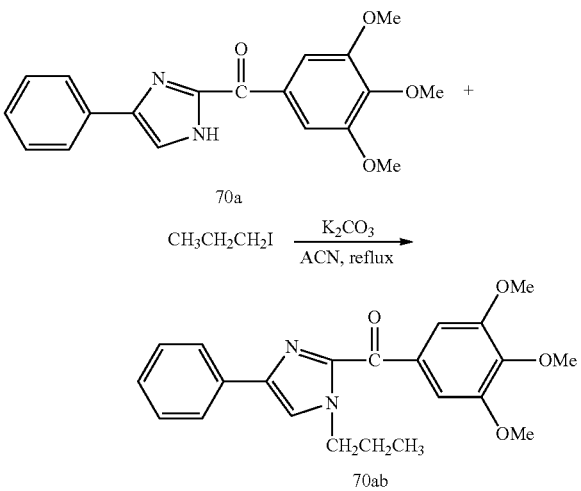

To a solution of 70a (135 mg, 0.4 mmol) in ACN (10 mL) was added potassium carbonate (82 mg, 0.60 mmol) followed by n-propyl iodide (82 mg, 0.48 mmol). The resulting reaction mixture was stirred overnight under reflux condition. After dilution by 50 ml of saturated NaHCO$_3$ solution (aqueous), the reaction mixture was extracted by ethyl acetate (100 ml). The organic layer was dried over sodium sulfate and concentrated. The residue was purified by flash column chromatography.

Synthesis of Compound 70ac

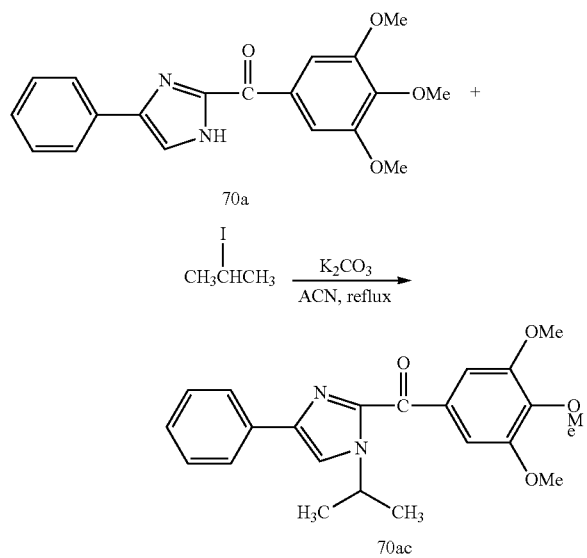

To a solution of 70a (135 mg, 0.4 mmol) in ACN (10 mL) was added potassium carbonate (82 mg, 0.60 mmol) followed by isopropyl iodide (82 mg, 0.48 mmol). The resulting reaction mixture was stirred overnight under reflux condition. After dilution by 50 ml of saturated NaHCO$_3$ solution (aqueous), the reaction mixture was extracted by ethyl acetate (100 ml). The organic layer was dried over sodium sulfate and concentrated. The residue was purified by flash column chromatography.

Synthesis of Compound 70ad

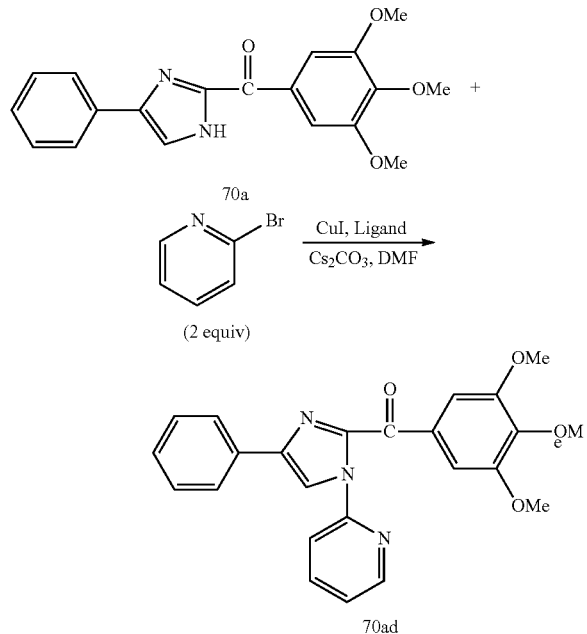

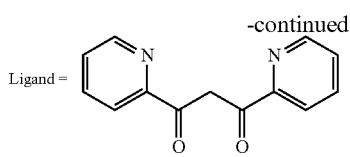

Under inert atmosphere, a Schlenk flask was charged with Cs$_2$CO$_3$ (260 mg, 0.8 mmol), CuI (76 mg, 0.4 mmol), ligand (0.4 mmol), compound 70a (135 mg, 0.4 mmol), 2-pyrimidyl bromide (124 mg, 0.8 mmol), and DMF (5 mL). The reactionmixture was stirred for 30 min at room temperature, and then heated to 110° C. for 2 days. The reaction mixture was monitored by TLC. After the starting material was completely consumed, the reaction was stopped and the mixture was cooled to room temperature. The reaction mixture was directly passed through a plug of silca gel. After being rinsed with ethyl acetate, the combined filtrate was washed with saturated brine. After the organic layer was dried by sodium sulfate, it was concentrated. The residue was purified by column chromatographyon silica gel to provide the desired product.

Example 30

Synthesis of Aryl Benzyl Imidazole

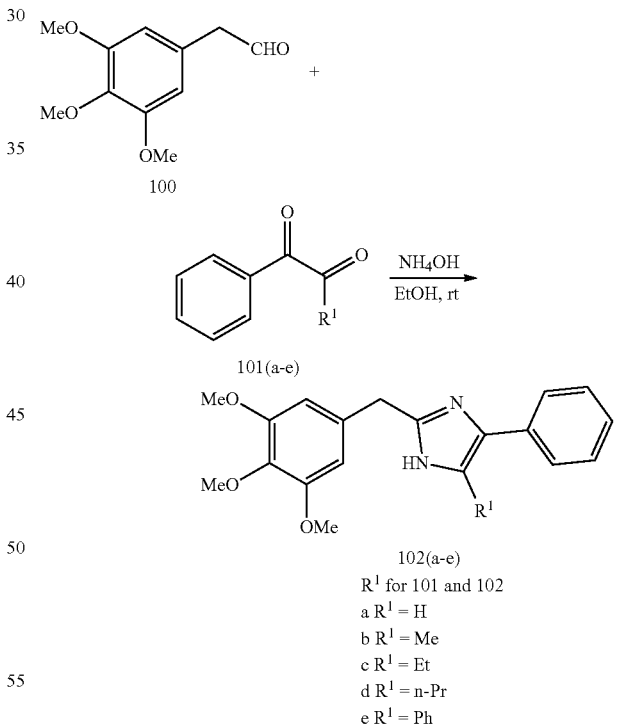

General procedure for the synthesis of 5-(alkyl or aryl)-4-phenyl-2-(3,4,5-trimethoxybenzyl)-1H-imidazole and 4-(alkyl or aryl)-5-phenyl-2-(3,4,5-trimethoxybenzyl)-1H-imidazole (102 (a-e). To a solution of the aldehyde 100 (5 mmol) in ethanol (20 mL) at 0° C. was added the phenyl alkyl dione 101 (5.5 mmol) and a solution of 29% ammonium hydroxide in water (50 mmol, 7 mL). After stirring for 2-3 days at room temperature, the reaction mixture was concentrated and the residue was subjected to flash column chromatography with dichloromethane as eluent to yield the titled compound as a yellow powder. Yield: 20-30%.

5-Phenyl-2-(3,4,5-trimethoxybenzyl)-1H-imidazole and 4-phenyl-2-(3,4,5-trimethoxybenzyl)-1H-imidazole (102a): 1H NMR (500 MHz, chloroform-d) δ 7.91-7.62 (m, 2H), 7.43-7.34 (m, 2H), 7.27-7.21 (m, 2H), 6.51 (s, 2H), 4.12 (s, 2H), 3.86 (s, 3H), 3.84 (s, 6H).

5-Methyl-4-phenyl-2-(3,4,5-trimethoxybenzyl)-1H-imidazole and 4-methyl-5-phenyl-2-(3,4,5-trimethoxybenzyl)-1H-imidazole (102b): 1H NMR (500 MHz, chloroform-d) δ 7.55 (d, J=7.6 Hz, 2H), 7.43-7.37 (m, 2H), 7.25 (d, J=6.7 Hz, 1H), 6.49 (s, 2H), 4.03 (s, 2H), 3.84 (d, J=1.3 Hz, 3H), 3.81 (d, J=1.2 Hz, 6H), 2.42 (s, 3H).

5-Ethyl-4-phenyl-2-(3,4,5-trimethoxybenzyl)-1H-imidazole and 4-ethyl-5-phenyl-2-(3,4,5-trimethoxybenzyl)-1H-imidazole (102c): 1H NMR (500 MHz, chloroform-d) δ 8.47 (s, 0.42H), 8.39 (s, 0.58H), 7.86-7.62 (m, 2H), 7.41 (m, 2H), 7.35-7.31 (m, 1H), 6.54 (m, 2H), 4.10 (m, 2H), 3.90-3.83 (m, 9H), 2.79 (m, 2H), 1.38-1.17 (m, 3H).

4-Phenyl-5-propyl-2-(3,4,5-trimethoxybenzyl)-1H-imidazole and 5-phenyl-4-propyl-2-(3,4,5-trimethoxybenzyl)-1H-imidazole (102d): 1H NMR (400 MHz, chloroform-d) δ 8.63 (s, 0.48H), 8.50 (s, 0.52H), 7.70-7.64 (m, 1H), 7.41 (m, 3H), 7.37-7.32 (m, 1H), 6.52 (d, J=1.3 Hz, 2H), 4.08 (d, J=5.1 Hz, 2H), 3.87 (m, 3H), 3.86-3.84 (m, 6H), 2.73 (m, 2H), 1.88-1.75 (m, 1H), 1.64 (m, 1H), 0.98 (m, 3H).

4,5-Diphenyl-2-(3,4,5-trimethoxybenzyl)-1H-imidazole (102e): 1H NMR (400 MHz, chloroform-d) δ 7.44-7.36 (m, 4H), 7.28-7.20 (m, 6H), 6.50 (s, 2H), 4.08 (s, 2H), 3.78 (m, 9H).

Example 31

Figure 42:
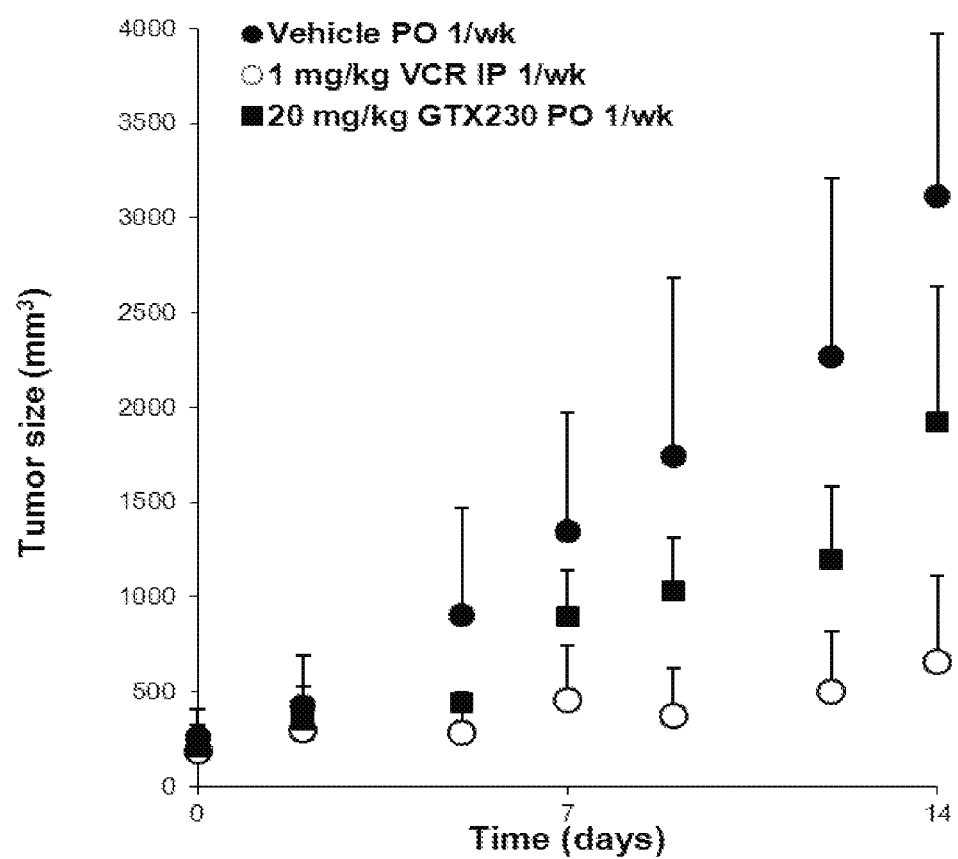
FIG. 42 depicts the in vivo anti-cancer efficacy of 17ya in HL60 leukemia cell xenografts.
Figure 43A:
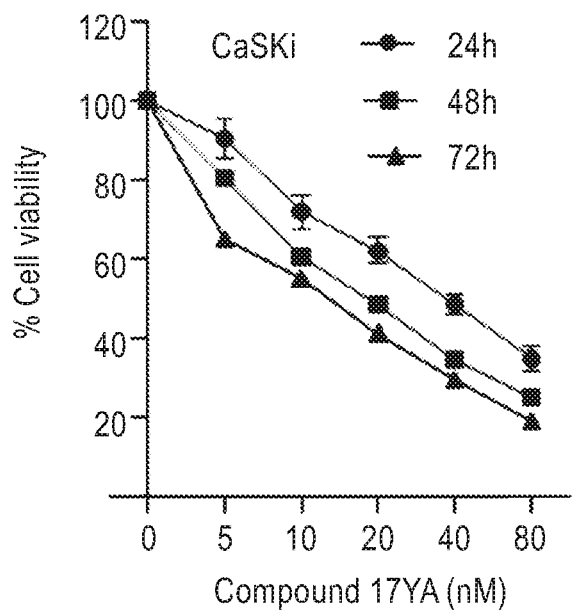
FIGS. 43A-D illustrate the effect of compound 17ya on cervical cancer cells lines CaSki, HeLa, SiHa, and C33s at various concentrations.
Figure 43B:
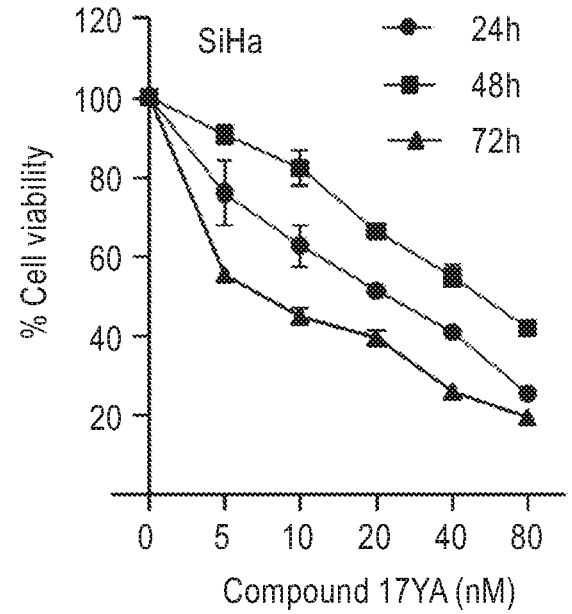
Figure 43C:
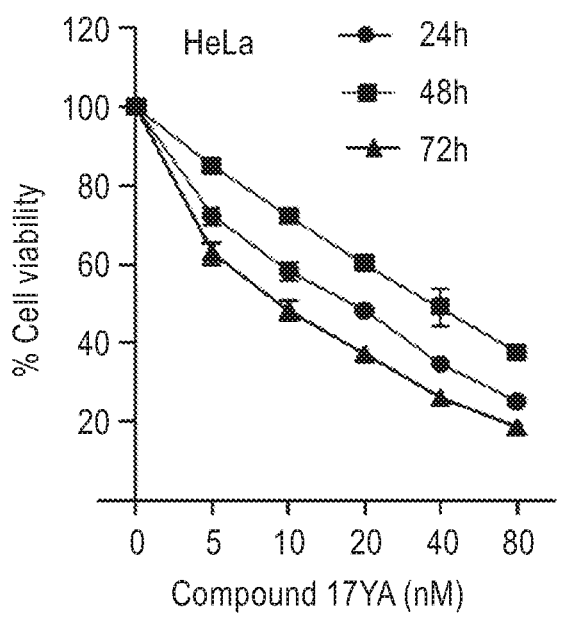
Figure 43D:
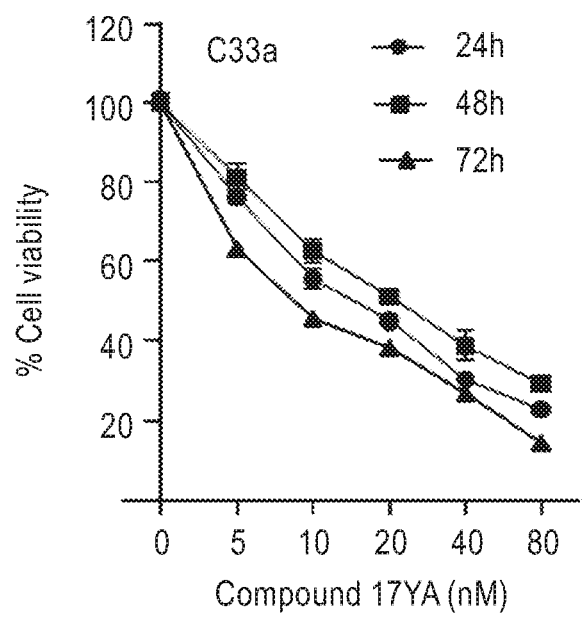
Figure 44A:
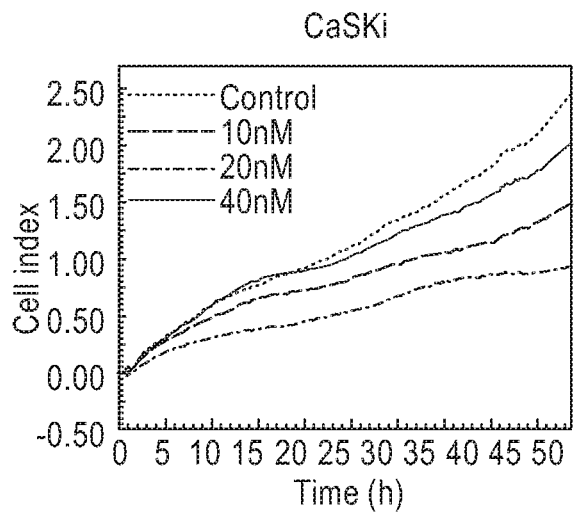
FIGS. 44A-D illustrate that compound 17ya inhibited the growth of all four cervical cell lines, CaSki, HeLa, SiHa, and C33s, in a dose dependent manner.
Figure 44B:
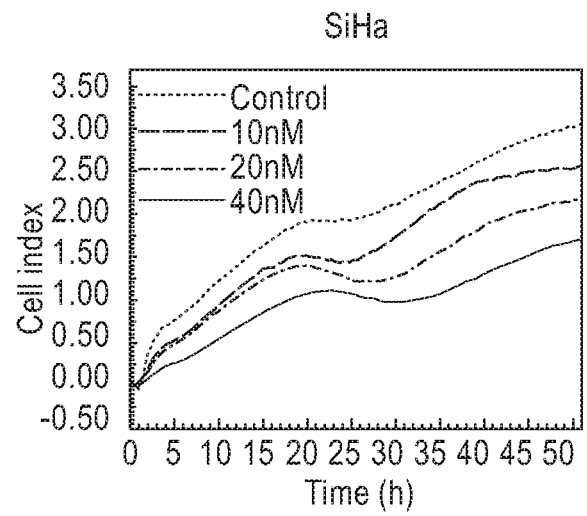
Figure 44C:
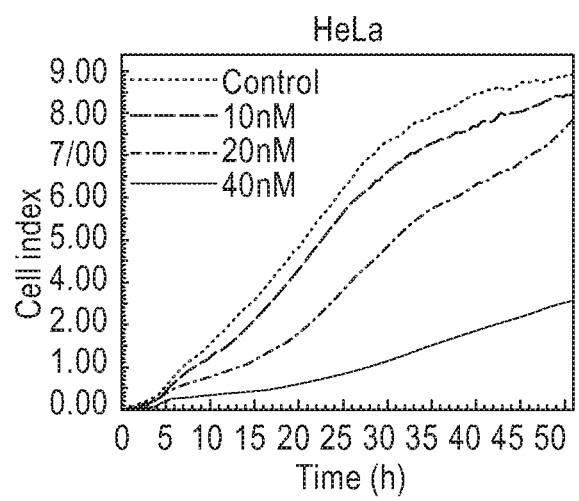
Figure 44D:
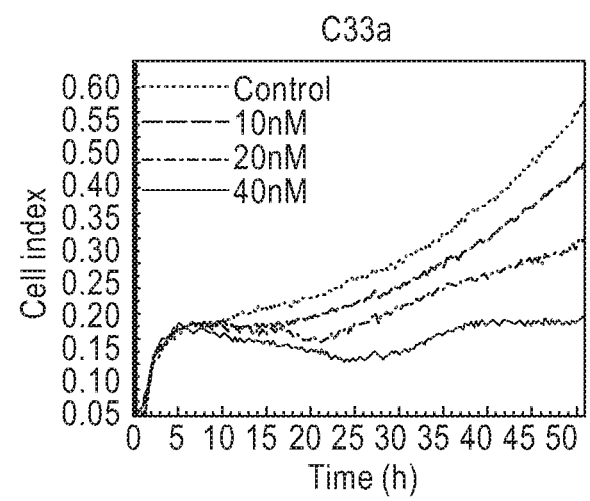
Figure 45A:
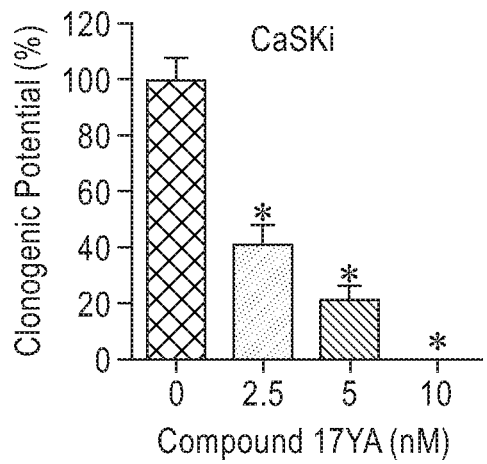
FIGS. 45A-D illustrate the effect of compound 17ya on four CxCa cell lines (CaSki, HeLa, SiHa, and C33s) treated at 1.25-10 nM concentration for 14 days where compound 17ya significantly (p<0.05) inhibited the number of cells formed in all four cervical cancers cell lines compared with respective controls.
Figure 45B:
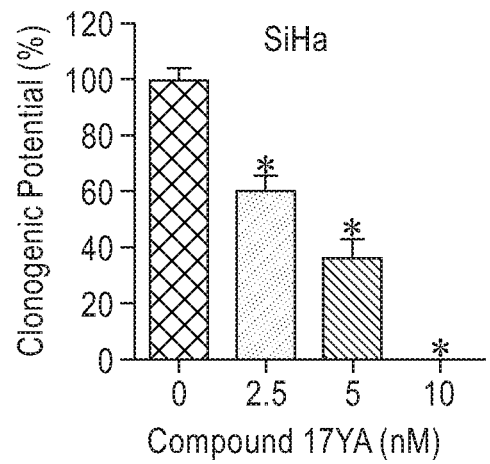
Figure 45C:
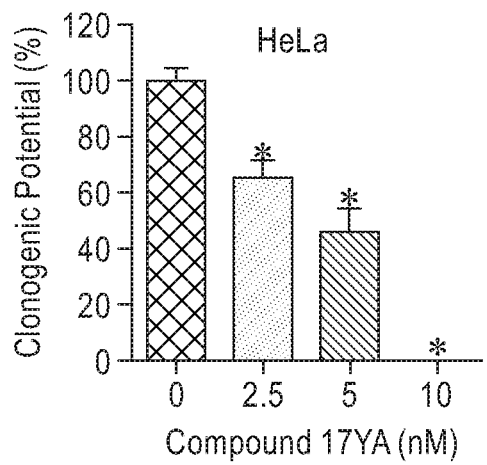
Figure 45D:
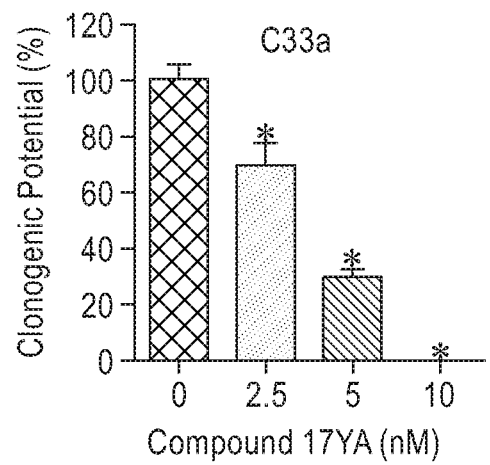

In Vivo Effacacy in Leukemia (HL60) Xenograft (FIG. 42)

HL60 cells (10×107 per mL) were prepared in RPMI1640 growth media containing 10% FBS, and mixed with Matrigel (BD Biosciences, San Jose, CA) at 1:1 ratio. Tumors were established by injecting 100 µL of the mixture (5×106 cells per animal) subcutaneously into the flank of 6-8-week-old male athymic nude mice. Length and width of tumors were measured and the tumor volume ($mm^3$) was calculated by the formula, $\pi/6 \times L \times W2$, where length (L) and width (W) were determined in mm. When the tumor volumes reached 200 $mm^3$ approximately, the animals bearing HL60 tumors were treated with vehicle [Tween80/DMSO/$H_2O$ (2/2/6)], or 17ya (20 mg/kg) orally. The dosing schedule was once a week for two weeks. Vincristine (1 mg/mL) was administrated via intraperitoneal injection once a week.

Results. Human promyelocytic leukemia cells, HL60 cells were inoculated in nude mice and the tumor volumes were allowed to reach about 200 $mm^3$. Vincristine (1 mg/kg), which is in clinic for hematological cancers including leukemia, was used to evaluate the response of this in vivo model against a positive control drug. The tumor volumes ($mm^3$) were plotted against time and are the means±SD from four to five animals. HL60 tumor was found to be fast-growing and the volume reached 2000-3000 $mm^3$ within two weeks. Though 1 mg/kg intraperitoneal injection of vincristine exhibited very potent tumor growth inhibitory effect (FIG. 42) and the tumor growth inhibition (TGI) was 84%. Orally administered 17ya (20 mg/kg) showed 40% tumor growth inhibition. The size of HL60 tumors was maintained up to 5 days after 17ya treatment without dramatic increase but during the next 2 days tumor sizes increased significantly (60-100%). It suggests that more a frequent dosing schedule could enhance the tumor growth inhibitory effect of 17ya.

Example 32

Cervical Cancer

Materials and Methods

Cell culture, growth conditions and treatment. The human CxCa cells (CaSki, HeLa, $C_{33}A$ and SiHa) that were obtained from American Type Culture Collection (ATCC; Manassas, VA, USA) were cytogenetically tested and authenticated. CxCa cells were cultured in an RPMI-1640 and DMEM medium, supplemented with 10% fetal bovine serum, and 1% antibiotic and antimycotic solution with 5% $CO_2$. Cells were growing in humidified atmosphere containing 5% $CO_2$ at 37° C.

Antibodies and Reagents. Antibodies against of p21 (cat. #2947), p53 (cat. #2524), PCNA (cat. #13110), JAK2 (cat. #3230), pJAK2 (cat. #3771), STAT3 (cat. #9139), pstat3Tyr (705) (cat. #9145), pstat3 ser (727) (cat #9134), (Bax (cat #2772), Bcl2 (cat #2872), PARP (cat. #9532), pcdk1 (cat #9111), $p^{34}$ (cat #), Cyclin B1 (cat #4138), Bid (cat #2002), Bim (cat #2819), Bcl-xl (cat #2764), Survivin (cat #2808) and GAPDH (cat #5174), were obtained from Cell Signaling Technology Inc (Danvers, MA, USA). HPV E6 (cat #SC-480) and HPVE7 (cat. #SC-698) antibodies where obtained from Santa Cruz Biotechnology, Dallas, TX, USA. HRP-conjugated anti-rabbit and anti-mouse antibodies were obtained from Promega Corp, Madison, WI, USA. The anti-mouse cy3 secondary antibody was purchased from Thermo Fisher Scientific, Carlsbad; CA, USA.

Cell Viability. The effect of Compound 17ya on cell viability was determined by the 3-(4,5-dimethylthiazole-2-yl)-2,5-biphenyl tetrazolium bromide (MTT) assay. CxCa cells were seeded in 96 well plates at a density of 5000 cells/well and incubated at 37° C. for 24 h. Afterwards, the medium was replaced with Compound 17ya (0-80 nM) for 24, 48 and 72h. After the respective time point, 20 microliters of MTT—were added in each well containing 100-µL media for 2h, formazan was dissolved in DMSO, absorbance was taken at 540 nm, and percentage (%) cell viability was calculated in term of $IC_{50}$.

Colony forming assay. To investigate the effect of Compound 17ya on clonogenic potentials of CxCa cells, colony formations assay was performed. Briefly, $2.5 \times 10^2$ CxCa cells were separately seeded in 12 well plate and allowed to grow for 2-3 days. Afterwards, the cells were treated with a different concentration of Compound 17ya with vehicle control. After 14 days, the cells were washed with Phosphate buffer saline (PBS), fixed with cold methanol, stained with crystal violet and counted.

Transient transfection. Small-interfering RNA (siRNA) targeted to STAT3, p53 and a non-targeting control was used in an interference assay (Santa Cruz). CaSki cells were seeded into 6 well plates ($2 \times 10^5$) in antibiotic-free media for at least 24 h before transfection until the cells were 30-40% confluent. CaSki, cells were transiently transfected with STAT3 siRNA (100 nM), p53 siRNA (50 nM) or control siRNA (50 nM) using Lipofectamine 2000 according to the manufacturer's protocol. Afterwards, 6h media was replaced with Compound 17ya (20 nM) or vehicle for 24 h and lysates were prepared for western blot analysis and mRNA analysis [53].

RNA isolation and real-time PCR (qRT-PCR). RNA was extracted from cell lines and tumor xenograft by using TRIzol (Invitrogen). The qRT-PCR was performed. The primers sequences are listed in supplementary Table. S1. The specific primers set for miR-23b, mi-R$_{34}$a, and U6 were purchased from (Applied Biosystems, Foster City, CA, USA). The expression of miRNA and mRNA was normalized with the expression of endogenous control, U6snRNA and GAPDH respectively.

Western blotting. Western blot analysis was performed as follows. Briefly, cells were lysed in lysis buffer supplemented with protease and phosphatase inhibitors (Thermo Scientific). The protein samples were resolved via SDS-PAGE according to size and then transferred to the polyvinylidene fluoride membrane (Millipore, Billerica, MA, USA) by electroblotting.

Molecular Docking. Molecular docking experiments were performed to know whether and where Compound 17ya binds in (HPV16 E6, E7 and STAT3. The crystal structure of STAT3 (PDB ID: 1bg1) and HPV16 E6 (PDB ID: 4xr81) were retrieved from the RCSB Protein Data Bank.

Cell migration and invasion. For Scratch assays, CxCa cells were seeded (2×10$^5$ cells/well) in 12-well culture plates and allowed to form a 80-90% confluent monolayer. A standardized wound was made by using 200-μl micropipette tip for −1 mm width. The cells were washed twice with PBS and replaced with serum-free medium containing various concentrations of VERU-111. After 24 h cells were washed with PBS. Images of the wounds were monitored under a phase-contrast microscope at ×100 magnification.

Migration assay was performed by using a cell migration 96 well, pore size, 8 μm; Corning plate. Briefly, overnight starved CxCa cells (1.5×10$^5$ cells per well) were seeded in a serum-free medium. The bottom chambers were filled with serum-containing medium and Compound 17ya (0-5 nM) was added to the upper side of the membrane. The plate was incubated for 24 h, and then the non-motile cells at the top of the filter were removed using a cotton swab. The migrating cells were fixed in 4% paraformaldehyde and stained with crystal violet (0.1%) for 15 min at room temperature. We also investigated the effect of Compound 17ya on cellular motility by an agarose bead-based cell motility assay as describe earlier. Briefly, CxCa cells were mixed into a low melting point agarose solution and drops of suspension were placed onto plates. At 24 h, the plates were photographed using a phase-contrast microscope.

The invasion assay was performed by using a cell invasion kit (BD Biocoat™ Matrigel Invasion Chambers; BD Biosciences, San Jose, CA, USA).

Real time cell proliferation and migration by xCELLigence assays. To further confirm the effect of Compound 17ya on migration, invasion, and proliferation of CxCa cells, real-time proliferation, migration and invasion assays were performed using the xCELLigence system as described. The CxCa cells (5×10$^3$) were seeded per chamber of cell proliferation or invasion and 7×10$^4$ cells/well for migration. Compound 17ya (0-15 nM) or the vehicle control (0.1% DMSO) was added and the experiment was allowed to run for 48 h. Average baseline cell index of Compound 17ya-treated cells was calculated and compared with vehicle-treated control cells.

Cell cycle analysis. For cell cycle analysis, approximately 70% confluent Caski and SiHa CxCa cells were synchronized by overnight starvation of cells in serum free media. Cells were exposed to different concentrations of Compound 17ya at (0-50 nM) for 24 h. Samples were analyzed with Accuri C$_6$ (BD Biosciences) flow cytometer in the FL2 channel as described.

Apoptosis analysis. The Annexin V-7AAD apoptosis kit (BD Biosciences, San Diego, CA) was utilized to determine Compound 17ya ability of inducing apoptosis in CxCa cells. To analyze the effect of Compound 17ya on mitochondrial membrane potential (APM), Tetramethyl rhodamine ethyl ester (TMRE) (Invitrogen) stain method was employed.

Orthotopic xenograft study. Six-week-old female athymic nude mice were used in accordance to protocol reviewed and approved by the UTHSC Institutional Animal Care and Use Committee (UTHSC-IACUC). Briefly, CaSki cells (4×10$^6$) were dispersed in 100 μL PBS (1×) and 100 μL Matrigel (BD Biosciences) and injected directly into the cervix of each mouse without any surgery. When tumor volume reached −200 mm$^3$, tumor-bearing mice were randomly divided into two groups (n=6 per group). Compound 17ya (50 μg/mice) and the vehicle control (1×PBS) were injected intra-tumorally three times per week for 4 weeks. The weight of mice as well as tumors volume were measured every week from the day when they were administered. The tumor volume was calculated according to the tumor volume (mm$^3$)=0.5× L×W×H, wherein L is length, W is width, and H is height. When tumors volume of the control mice reached 1000 mm$^3$, the mice were sacrificed and tumors were excised and used for tissue sectioning, histopathology RNA isolations and lysate preparations.

Immunofluorescence and immunohistochemistry analysis. Immunofluorescence analysis was performed to detect the expression p21 and p53 of CxCa cells treated with Compound 17ya. IHC analysis for PCNA, E6, E7, p21, p53, MMP-2, MMP-9, STAT3, pSTAT3tyr (705) and pSTAT3 Ser (727) was performed on xenograft tumor tissue (5-micron sections). Briefly the tumour tissues were deparaffinized, rehydrated, treated with 0.3% hydrogen peroxide and processed for antigen retrieval using a heat-induced technique.

Statistical analysis. The results are representative of at least three independent experiments performed in triplicate. All results are expressed as the means+SEs. Statistical analysis was processed using Graph Pad prism 5. The data were as analyzed by ANOVA, Newman-Keule's post hoc test, and two tailed student t test. P<0.05 was considered statistically significant.

Compound 17ya exhibited antiproliferative activity and clonogenic potential of CxCa cells. The cytotoxic effect of compound 17ya on cervical cancers cell lines, CaSki, HeLa, SiHa and C$_{33}$a was studied at various concentrations (5-80 nM). The results of the study are illustrated in FIG. 43A-D. Compound 17ya inhibited the growth of all four cervical cell lines in a dose dependent manner as illustrated in FIGS. 44A-D. The long-term treatment effect of compound 17ya on cell proliferations in cervical cancers was determined by colony formation assays. Four CxCa cell lines were treated with compound 17ya at 1.25-10 nM concentration for 14 days. The results demonstrated that compound 17ya significantly (p<0.05) inhibited the number of cells formed in all four cervical cancers cell lines compared with respective controls. The results are illustrated in FIG. 45A-D.

Figure 46A:
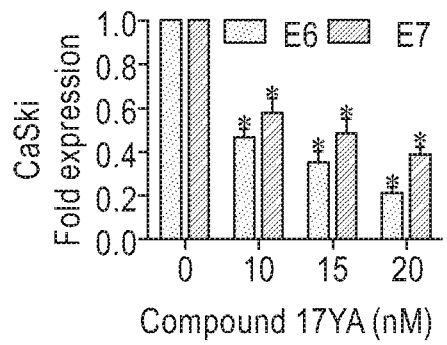
FIGS. 46A-B illustrate the effect of compound 17ya on HPV E6 and E7 oncogenes, p21 and p53 in CaSki and SiHa cells as investigated by qPCR, western blot analysis and confocal microscopy.
Figure 46B:
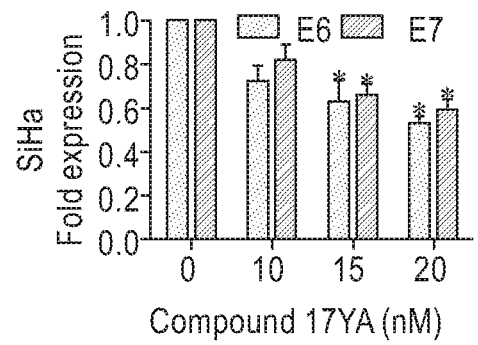
Figure 47A:
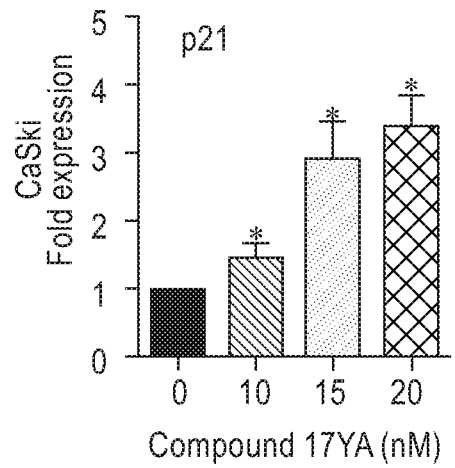
FIGS. 47A-D illustrate the effect of compound 17ya on the expression of p21 and p53.
Figure 47B:
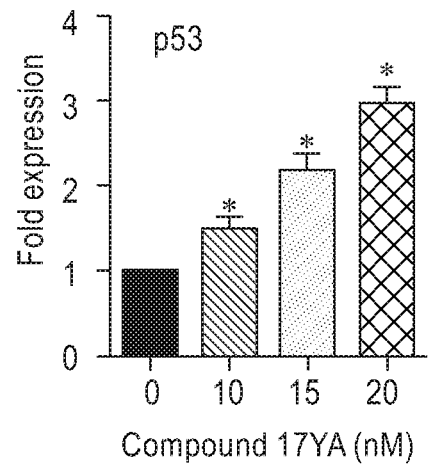
Figure 47C:
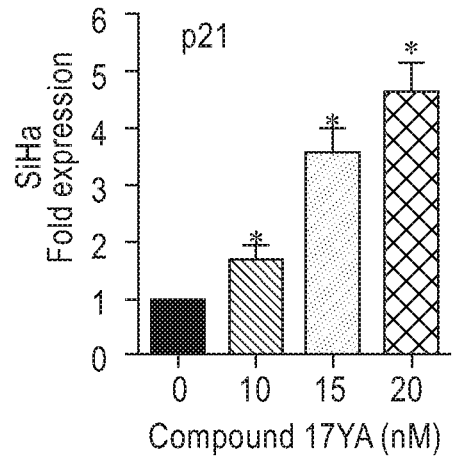
Figure 47D:
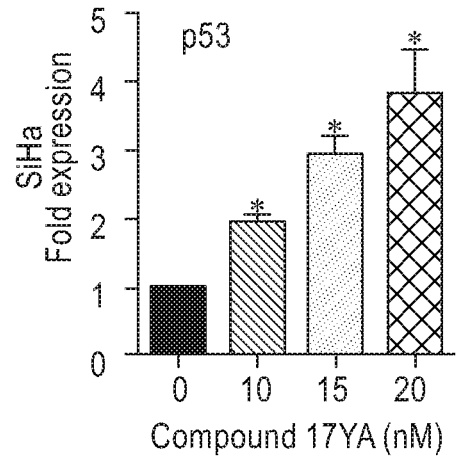

The effect of compound 17ya on HPV E6 and E7 oncogenes, p21 and p53 in CaSki and SiHa cells was investigated by qPCR, western blot analysis and confocal microscopy. The results indicated that compound 17ya had a significant downregulation of both HPV16 E6 and E7 transcripts in a dose dependent manner as illustrated in FIGS. 46A-B. Expression of p21 levels was significantly increased in both the mRNA (illustrated in FIGS. 47A-B) and protein level that indicated the involvement of p53 dependent apoptosis in these cells. Compound 17ya significantly induced the expression of p53 the at dose dependent manner on mRNA level (FIGS. 47C-D) and as western blot analysis confirmed functional restorations in p53. Confocal microscopic analysis further evidenced that compound 17ya led to a functional restoration of $p^{53}$ and p21 as confirmed through the increased nuclear translocation of p53 and p21 in CxCa cells. The results confirmed that compound 17ya repressed both transcription and translation of E6 and E7 oncogenes, thereby leading to the restoration of the vital tumor suppressor pathways.

Figure 48A:
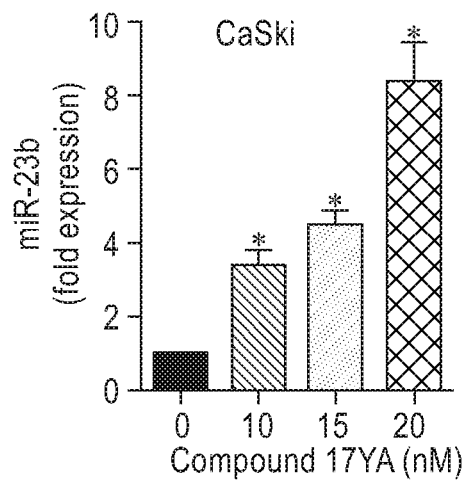
Figure 48B:
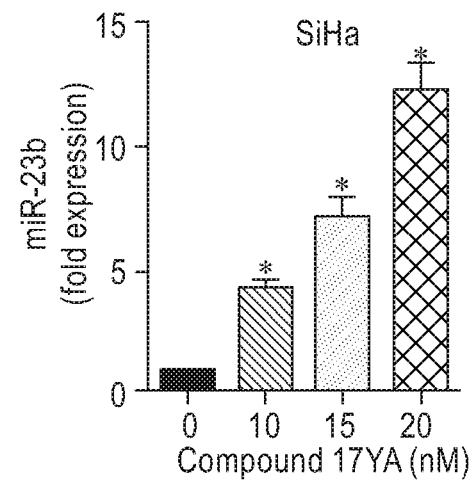
Figure 48C:
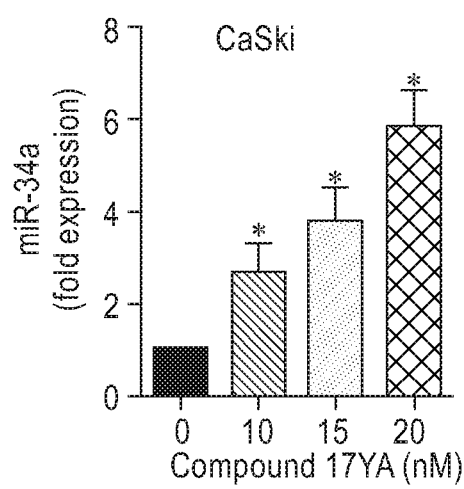
Figure 48D:
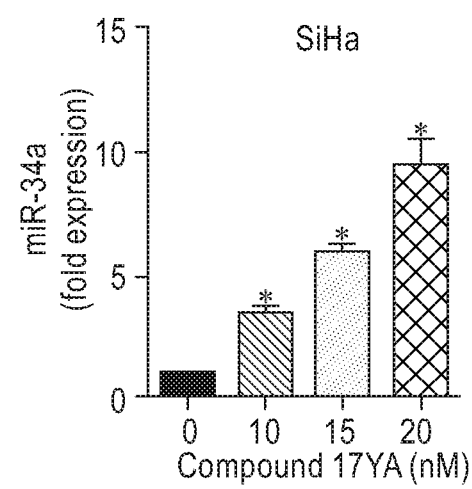

Compound 17ya treatment induced the expression of 23b and miR-34a in CxCa cells. The effect of compound 17ya on the expression of miR-23b and miR-34a by qRT-PCR in CxCa cells illustrated an 8- and 14-fold induction of miR-23b expression in treated (20 nM) CaSki and SiHa cells, respectively, as compared to the untreated control. The results are illustrated in FIGS. 48A-B. MiR-34a was also significantly upregulated in dose dependent compared to untreated cells as illustrated in FIGS. 48C-D.

Compound 17ya inhibited JAK2/STAT3 signalling pathways. The JAK2 kinases phosphorylate STAT3 (Signal transducers and activators of transcription 3) is known to contribute to oncogenesis in cervical cancer. The effect of compound 17ya on JAK2/STAT3 and regulations of p53 in CxCa cells demonstrated that the compound down regulated the expression of p-JAK2 dose dependently in CxCa cell lines as determine by western blot analysis. And compound 17ya decreased total STAT3 at a higher concentration while the levels of pSTAT (Ser727) and pSTAT (Tyr705) in a dose-dependent manner. Treatment with compound 17ya also restored the expression of p53 levels in part due to STAT3 silencing, suggesting STAT3 inactivation as one of the mechanisms of action. Compound 17 ya resulted in lower levels of STAT3 when p53 was knocked down that suggested the compound induced p53, which further caused decreases in STAT3 levels.

Figure 49A:
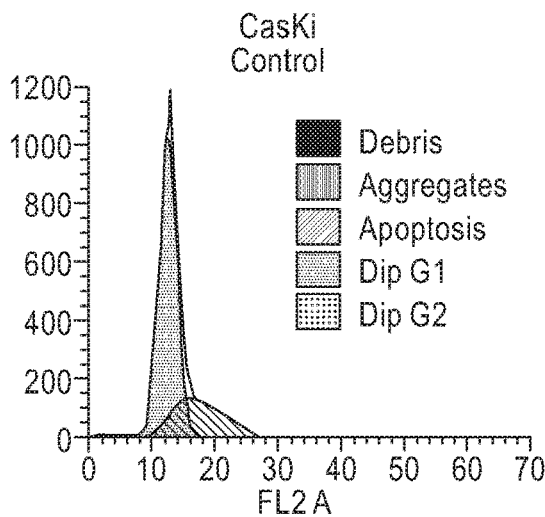
FIGS. 49A-C illustrate flow cytometer results determined that compound 17ya arrested cell cycle progression of CaSki in dose dependent manner in contrast to vehicle control.
Figure 49B:
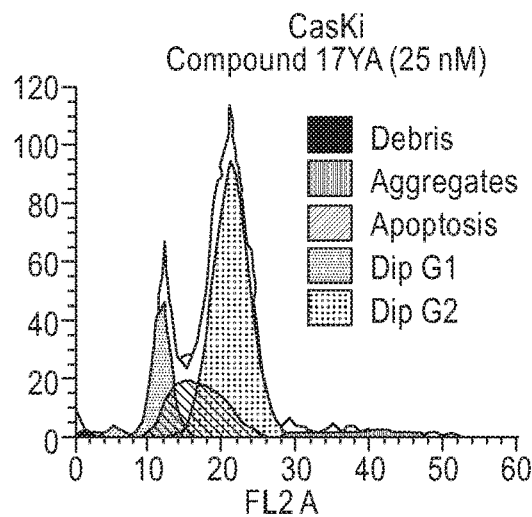
Figure 49C:
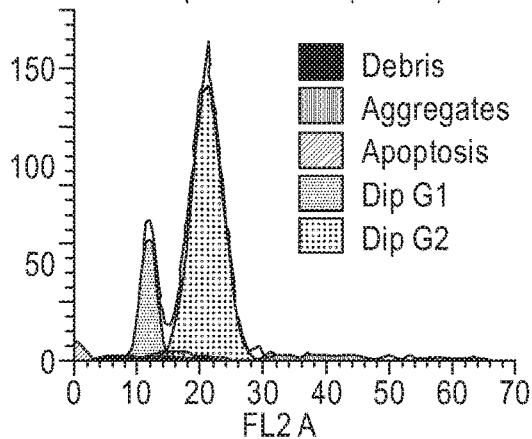

Compound 17ya arrested cell cycle at G2/M phase. The effects of compound 17ya on distributions of cells in different phase of the cell cycle by flow cytometry was determined by staining CaSki and SiHa cells with Propidium Iodide. Flow cytometer results determined that compound 17ya arrested cell cycle progression of CaSki (FIGS. 49A-C) and SiHa cells at G2/M phase in dose dependent manner in contrast to vehicle control. Western blot analysis demonstrated that an increase in cyclin B1 levels, suggesting a possible late G2 or M phase arrest in CxCa cells. The test indicated substantial dose-dependent reeducation in both p34cdc2 and phospho-Cdk1 levels that confirmed G2/M arrest by compound 17ya. Compound 17ya treatment upregulated p21cip1/waf1 and downregulated PCNA levels.

Compound 17ya induced apoptosis in CxCa cells. To determine the type of cell death induced by compound 17ya, Annexin V (stains early apoptotic cells)-7AAD (stains dead cells) based flow cytometry was used for detection of the percent apoptotic or necrotic cells. Compound 17ya increased the percentage of apoptotic cells in both early and late apoptotic phases in CaSki and SiHa cells in a dose dependent manner indicating apoptotic cell death. The study of compound 17ya on modulations of apoptotic proteins by western blot analysis demonstrated that treatment with compound 17ya markedly increased the protein levels of the pro-apoptotic Bid and Bim, whereas it decreased the protein levels of anti-apoptotic Bcl-xl and Survivin in CaSki and SiHa compared with the control group. The results suggested that compound 17ya significantly inhibited proliferation through apoptotic cell death in CxCa cells.

Compound 17ya was studied to determine the impact on the mitochondrial membrane potential of both CxCa cell lines. Flow cytometer and fluorescence microscope studies with a Tetramethylrhodamine ethyl ester (TMRE) stain was used to examine mitochondrial membrane potential. The results determined that compound 17ya significantly decreased the mitochondrial membrane potential of both CaSki and SiHa cells. Treatment with compound 17ya modulated p53-dependent apoptotic markers such as Bcl2 and Bax. PARP cleavage increased in a dose-dependent manner in both cell lines. The results demonstrated that compound 17ya induced apoptosis by altering the regulation of apoptotic genes, particularly through the upregulation of Bax and downregulation of Bcl-2.

Figure 50:
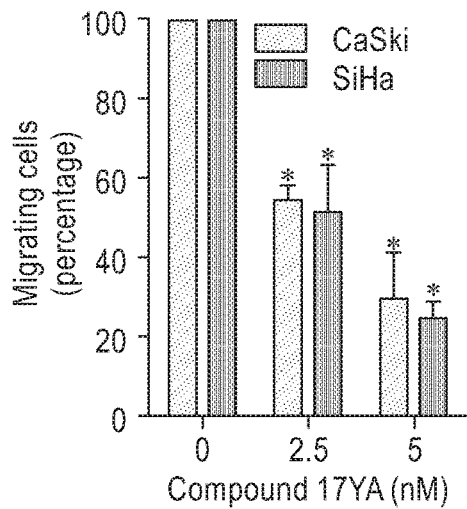
FIG. 50 illustrates the results of compound 17ya in Transwell assay coming plate for effectively inhibited cell migration in a dose-dependent manner.
Figure 51:
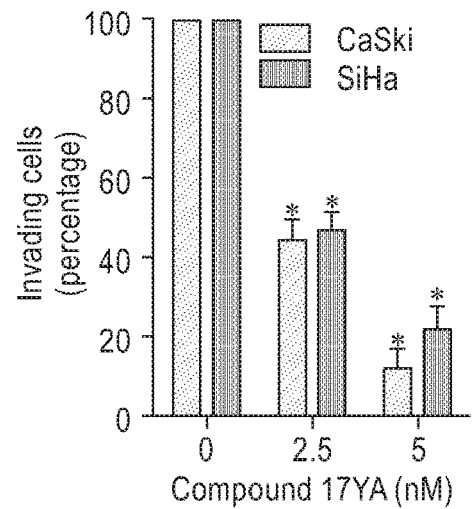
FIG. 51 illustrates an agarose bead assay experiment that showed that compound 17ya effectively inhibited cell migration in a dose-dependent manner.

Compound 17ya inhibited cell migration, invasion, and MMPs expression in CxCa. The effect of compound 17ya on human CxCa cell migration and invasion was studied using wound-healing assays, corning plate, bead assays, and cell invasion kit (BD Biocoat™ Matrigel) assays. Compound 17ya and wound healing assay at several concentrations (2.5-5 nM) for 24 h was studied. The results determined that wound gaps in the 2.5 and 5 nM concentration treated groups were significantly wider than those in the untreated (control) group. The cell migration was further analyzed by Transwell assay corning plate. Similar to the results of the wound healing assay, compound 17ya effectively inhibited cell migration in a dose-dependent manner as illustrated in FIG. 50. Agarose bead assay experiments showed a similar effect. See FIG. 51. These findings were confirmed by using the xCELLigence real time cell migration system in CxCa cell further verifying the effects on cellular motility.

The effect of compound 17ya on cell invasion was determined by treating CxCa cells with 2.5-5 nM compound 17ya followed by allowing cells to invade in Matrigel-coated Transwell for 24 h. The results demonstrated compound 17ya reduced the invaded cell in a dose dependent manner in CxCa cell as illustrated in FIGS. 52A-B. Compared to the control group, compound 17ya suppressed invasion by 44.70%, 12.34% in CaSki and 47.37%, and 22.34% in SiHa at 2.5 and 5 nM, respectively.

We determined the effect of compound 17ya on the expression of proteolytic enzymes matrix metalloproteinases (MMPs) MMP-2, MMP-9, uPA, uPAR, TIMP-1 and TIMP-2 in CxCa cells compared to the untreated group by use of RT-qPCR. The data illustrated that the mRNA level of MMP-2, MMP-9, UPA and uPAR were significantly ($p<0.05$) reduced and those of TIMP-1 and TIMP-2 were significantly ($p<0.05$) elevated at dose dependent manners in both CxCa cell as illustrated in FIGS. 53A-F. These data clearly demonstrate that compound 17ya inhibited CxCa cell migration, invasion and metastasis by downregulating the levels of uPA, uPAR, MMP-2 and MMP-9 proteolytic enzymes, and upregulating TIMP-1 and TIMP-2.

Compound 17ya inhibited CxCa cell-derived orthotopic xenograft tumors in athymic nude mice. The effect of compound 17ya treatment on inhibition of tumor growth in vivo, was performed by an orthotopic xenograft study as described in Materials and Methods. To determine an effective dose, mice were treated with compound 17ya (50 µg/mice, three times in week) intratumorally for 3 weeks. The results demonstrated that intra-tumoral administration of compound 17ya (50 µg/mice, three times in week) significantly ($p<0.01$) inhibited CaSki cell-derived orthotopic xenograft tumors in athymic nude mice compared to an untreated control. The results are illustrated in FIGS. 54A-C. Administration of compound 17ya significantly ($p<0.05$) reduced both tumor volume and weight compared to control groups. During experiments, no signs of toxicity were present as reflected by unaltered body weights compared with the control group. The effect of compound 17ya on the expression of E6 and E7 on mRNA level was determined by qRT-PCR and the results demonstrated that expression of E6 and E7 were down regulated in treated groups compared to the control group. The experiment also measured PCNA, E6, E7, p21, p53, MMP-2, MMP-9, STAT3, pSTAT3$^{ser727}$ and pSTAT3$^{tyr705}$ protein expression in xenograft tumor tissues. Compared to the control the expression of PCNA, E6, E7 MMP-2, MMP-9, STAT3, pSTAT3$^{ser727}$ and pSTAT3$^{tyr705}$ significantly decreased, while the expression of p53 and p21remarkably increased in the treatment group that correlated with the in vitro assessment.

All of the features described herein (including any accompanying claims, abstract and drawings), and/or all of the steps of any method or process so disclosed, may be combined with any of the above aspects in any combination, except combinations where at least some of such features and/or steps are mutually exclusive. Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A compound of Formula IX having the structure

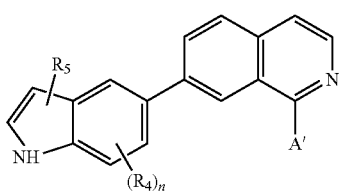

Formula IX wherein $R_4$ and $R_5$ are independently hydrogen, O-alkyl, O-haloalkyl, F, Cl, Br, I, haloalkyl, CN, —CH$_2$CN, NH$_2$, hydroxyl, —(CH$_2$)$_i$NHCH$_3$, —(CH$_2$)$_i$NH$_2$, —(CH$_2$)$_i$N(CH$_3$)$_2$, —OC(O)CF$_3$, C$_1$-C$_5$ linear or branched alkyl, alkylamino, aminoalkyl, —OCH$_2$Ph, —NHCO-alkyl, COOH, —C(O)Ph, C(O)O-alkyl, C(O)H, —C(O)NH$_2$ or NO$_2$;

A' is halogen; substituted or unsubstituted single-, fused- or multiple-ring, aryl or (hetero)cyclic ring systems; substituted or unsubstituted, saturated or unsaturated N-heterocycles; substituted or unsubstituted, saturated or unsaturated S-heterocycles; substituted or unsubstituted, saturated or unsaturated O-heterocycles; substituted or unsubstituted, saturated or unsaturated cyclic hydrocarbons; or substituted or unsubstituted, saturated or unsaturated mixed heterocycles;

wherein said A' ring is optionally substituted by 1-5 substituents which are independently O-alkyl, O-haloalkyl, F, Cl, Br, I, haloalkyl, CN, —CH$_2$CN, NH$_2$, hydroxyl, —(CH$_2$)$_i$NHCH$_3$, —(CH$_2$)$_i$NH$_2$, —(CH$_2$)$_i$N(CH$_3$)$_2$, —OC(O)CF$_3$, C$_1$-C$_5$ linear or branched alkyl, alkylamino, aminoalkyl, —OCH$_2$Ph, —NHCO-alkyl, COOH, —C(O)Ph, C(O)O-alkyl, C(O)H, —C(O)NH$_2$ or NO$_2$;

i is an integer between 1-5; and n is an integer between 1-3;

or its pharmaceutically acceptable salt, hydrate, polymorph, or isomer.

2. The compound according to claim 1, wherein the compound is at least one of 7-(3,4,5-trimethoxyphenyl)-1-(1H-indol-5-yl)isoquinoline (6a), 1,7-bis-(1H-indol-5-yl)isoquinoline (6b), 1-(4-fluorophenyl)-7-(1H-indol-5-yl)isoquinoline (6c), or 1-chloro-7-(1H-indol-5-yl)isoquinoline (6d).

3. The compound according to claim 1, wherein A' is 3,4,5-trimethoxyphenyl.

4. The compound according to claim 1, wherein A' is indolyl.

5. The compound according to claim 4, wherein A' is 2-indolyl.

6. The compound according to claim 4, wherein A' is a substituted or unsubstituted 3-indolyl.

7. The compound according to claim 4, wherein A' is 5-indolyl.

8. The compound according to claim 1, wherein A' is 4-fluorophenyl.

9. The compound according to claim 1, wherein A' is 3,4,5-trimethoxyphenyl and $R_4$ and $R_5$ are hydrogen.

10. The compound according to claim 1, wherein A' is indolyl and $R_4$ and $R_5$ are hydrogen.

11. The compound according to claim 1, wherein A' is 5-indolyl and $R_4$ and $R_5$ are hydrogen.

12. The compound according to claim 1, wherein A' is 4-fluorophenyl and and $R_4$ and $R_5$ are hydrogen.

13. The compound according to claim 1, wherein A' is a halogen.

14. The compound according to claim 1, wherein A' is phenyl.

15. The compound according to claim 1, wherein A' is a substituted phenyl.

16. A compound, wherein the compound is at least one of 1-chloro-7-(4-fluorophenyl)isoquinoline, 7-(4-fluorophenyl)-1-(1H-indol-5-yl)isoquinoline, 7-(4-fluorophenyl)-1-(3,4,5-trimethoxyphenyl)isoquinoline, 1,7-bis(4-fluorophenyl)isoquinoline, 1,7-bis(3,4,5-trimethoxyphenyl)isoquinoline, 1-(4-fluorophenyl)-7-(3,4,5-trimethoxyphenyl)isoquinoline, 1-(1H-indol-5-yl)-7-(3,4,5-trimethoxyphenyl)isoquinoline, or 1-chloro-7-(3,4,5-trimethoxyphenyl)isoquinoline.

* * * * *